US012668774B2

(12) United States Patent
Janousek et al.

(10) Patent No.: US 12,668,774 B2
(45) Date of Patent: Jun. 30, 2026

(54) PRODUCT, SYSTEM AND METHOD OF CELL CULTIVATION

(71) Applicant: BTL Healthcare Technologies a.s., Prague (CZ)

(72) Inventors: Jiri Janousek, Jilove u Prahy (CZ); Marek Sirl, Prague (CZ); Peter Gorilak, Nesvady (CZ); Matej Kubovcak, Kralova pri Senci (SK)

(73) Assignee: BTL Healthcare Technologies a.s., Prague (CZ)

( * ) Notice: Subject to any disclaimer, the term of this patent is extended or adjusted under 35 U.S.C. 154(b) by 0 days.

(21) Appl. No.: 19/028,930

(22) Filed: Jan. 17, 2025

(65) Prior Publication Data

US 2025/0270503 A1 Aug. 28, 2025

Related U.S. Application Data

(63) Continuation of application No. PCT/IB2024/059990, filed on Oct. 11, 2024, which is a continuation-in-part of application No. 18/763,199, filed on Jul. 3, 2024, and a continuation-in-part of application No. 18/731,896, filed on Jun. 3, 2024, and a continuation-in-part of application No. PCT/IB2024/053805, filed on Apr. 18, 2024.

(60) Provisional application No. 63/698,265, filed on Sep. 24, 2024, provisional application No. 63/654,493, filed on May 31, 2024, provisional application No. 63/570,973, filed on Mar. 28, 2024, provisional application No. 63/555,543, filed on Feb. 20, 2024, provisional application No. 63/589,661, filed on Oct. 12, 2023.

(51) Int. Cl.
| | |
|---|---|
| *C12N 5/07* | (2010.01) |
| *A23K 10/20* | (2016.01) |
| *A23K 20/195* | (2016.01) |
| *A23L 13/00* | (2016.01) |
| *C12N 15/85* | (2006.01) |

(52) U.S. Cl.
CPC ............... *C12N 5/06* (2013.01); *A23K 10/20* (2016.05); *A23K 20/195* (2016.05); *A23L 13/00* (2016.08); *C12N 15/85* (2013.01); *C12N 2510/04* (2013.01)

(58) Field of Classification Search
None
See application file for complete search history.

(56) References Cited

U.S. PATENT DOCUMENTS

| | | |
|---|---|---|
| 922,075 A | 5/1909 | Bates |
| 1,087,094 A | 2/1914 | Berrigan |
| 4,642,238 A | 2/1987 | Lin |
| 5,541,102 A | 7/1996 | Donis |
| 5,607,840 A | 3/1997 | Van Gorp |
| 5,607,854 A | 3/1997 | Prahl |
| 6,338,866 B1 | 1/2002 | Criggall |
| 6,403,142 B1 | 6/2002 | McDaniel, III |
| 6,537,597 B1 | 3/2003 | Nakamori |
| 6,537,782 B1 | 3/2003 | Shibuya |
| 6,783,792 B2 | 8/2004 | McDaniel, III |
| 6,821,534 B2 | 11/2004 | McDaniel, III |
| 6,855,365 B2 | 2/2005 | Short |
| 6,897,040 B2 | 5/2005 | Morris |
| 6,962,812 B2 | 11/2005 | Shibuya |
| 7,078,035 B2 | 7/2006 | Short |
| 7,115,385 B2 | 10/2006 | Breitschwerdt |
| 7,166,445 B2 | 1/2007 | Morris |
| 7,232,677 B2 | 6/2007 | Short |
| 7,416,874 B2 | 8/2008 | Short |
| 7,432,097 B2 | 10/2008 | Short |
| 7,432,098 B2 | 10/2008 | Short |
| 7,442,548 B2 | 10/2008 | Thomson |
| 7,449,334 B2 | 11/2008 | Thomson |
| 7,452,706 B2 | 11/2008 | Short |
| 7,456,019 B2 | 11/2008 | Goodwin |
| 7,465,470 B2 | 12/2008 | Saito |
| 7,553,665 B2 | 6/2009 | Aloni |
| 7,563,769 B2 | 7/2009 | Bogin |
| 7,592,175 B2 | 9/2009 | Amit |
| 7,604,829 B2 | 10/2009 | Schopf |
| 7,628,528 B2 | 12/2009 | Zeikus |
| 7,662,615 B2 | 2/2010 | Chang |
| 7,749,756 B2 | 7/2010 | Leonhartsberger |
| 7,807,176 B2 | 10/2010 | Nishikawa |
| 7,816,140 B2 | 10/2010 | Lau |
| 7,819,576 B2 | 10/2010 | Zeikus |
| 7,824,895 B2 | 11/2010 | Short |
| 7,863,031 B2 | 1/2011 | Short |
| 7,879,377 B2 | 2/2011 | Dahl |

(Continued)

FOREIGN PATENT DOCUMENTS

| | | |
|---|---|---|
| CA | 3231125 A1 | 4/2023 |
| CA | 3275968 A1 | 6/2024 |

(Continued)

OTHER PUBLICATIONS

Sommeregger et al., "Powerful expression in Chinese Hamster Ovary cells using bacterial artificial chromosomes: Parameters influencing productivity" 7 (Suppl. 6) BMC Proceedings p. 25, 1-2 (Year: 2013).*

(Continued)

*Primary Examiner* — Nancy J Leith

(74) *Attorney, Agent, or Firm* — Riverside Law LLP

(57) ABSTRACT

The present invention provides products, systems, and methods of cultivation of non-human metazoan cells.

30 Claims, 38 Drawing Sheets

Specification includes a Sequence Listing.

(56) References Cited

U.S. PATENT DOCUMENTS

| | | | |
|---|---|---|---|
| 7,897,379 B2 | 3/2011 | Kenney |
| 7,939,495 B2 | 5/2011 | Chung |
| 7,955,833 B2 | 6/2011 | Reiter |
| 7,955,851 B2 | 6/2011 | Amit |
| 7,977,096 B2 | 7/2011 | Nistor |
| 8,012,931 B2 | 9/2011 | Cujec |
| 8,034,770 B2 | 10/2011 | Belouski |
| 8,043,614 B2 | 10/2011 | Ahlfors |
| 8,067,171 B2 | 11/2011 | Khatibm |
| 8,076,300 B2 | 12/2011 | Presta |
| 8,080,265 B2 | 12/2011 | Kizoulis |
| 8,114,646 B2 | 2/2012 | Martin |
| 8,119,783 B2 | 2/2012 | Bogin |
| 8,158,424 B2 | 4/2012 | Thomson |
| 8,188,040 B2 | 5/2012 | Belouski |
| 8,211,697 B2 | 7/2012 | Sakurada |
| 8,222,034 B2 | 7/2012 | Amit |
| 8,236,527 B2 | 8/2012 | Chen |
| 8,252,557 B2 | 8/2012 | Katayama |
| 8,257,941 B2 | 9/2012 | Sakurada |
| 8,318,465 B2 | 11/2012 | Filho |
| 8,343,918 B2 | 1/2013 | Glass |
| 8,361,963 B2 | 1/2013 | Belouski |
| 8,383,365 B2 | 2/2013 | Cujec |
| 8,398,932 B2 | 3/2013 | Busujima |
| 8,410,051 B2 | 4/2013 | Belouski |
| 8,426,203 B2 | 4/2013 | Thomson |
| 8,440,408 B2 | 5/2013 | Grillberger |
| 8,470,552 B2 | 6/2013 | Croughan |
| 8,524,497 B2 | 9/2013 | Reiter |
| 8,563,311 B2 | 10/2013 | Amit |
| 8,569,050 B1 | 10/2013 | Ericsson |
| 8,569,061 B2 | 10/2013 | Nistor |
| 8,609,823 B2 | 12/2013 | Bogin |
| 8,618,053 B2 | 12/2013 | Belouski |
| 8,628,815 B2 | 1/2014 | Torney |
| 8,642,546 B2 | 2/2014 | Belouski |
| 8,672,245 B2 | 3/2014 | Finnigan |
| 8,722,621 B2 | 5/2014 | Glass |
| 8,748,156 B2 | 6/2014 | Grillberger |
| 8,759,299 B2 | 6/2014 | Dong |
| 8,771,988 B2 | 7/2014 | Goepfert |
| 8,772,571 B2 | 7/2014 | Lau |
| 8,790,913 B2 | 7/2014 | Zeikus |
| 8,795,985 B2 | 8/2014 | Belouski |
| 8,828,719 B2 | 9/2014 | Cain |
| 8,835,385 B2 | 9/2014 | Belouski |
| 8,835,604 B2 | 9/2014 | Hoegenhaug |
| 8,853,374 B2 | 10/2014 | Inouye |
| 8,859,280 B2 | 10/2014 | Gardner |
| 8,877,478 B2 | 11/2014 | Steer |
| 8,894,756 B2 | 11/2014 | Galliher |
| 8,916,522 B2 | 12/2014 | Bogin |
| 8,936,924 B2 | 1/2015 | Solbak |
| 8,940,860 B2 | 1/2015 | Dimarchi |
| 8,945,925 B2 | 2/2015 | Amit |
| 8,951,784 B2 | 2/2015 | Gould |
| 8,962,290 B2 | 2/2015 | Chen |
| 8,962,556 B2 | 2/2015 | Yayon |
| 8,980,844 B2 | 3/2015 | Chung |
| 8,998,793 B2 | 4/2015 | Oatley |
| 8,999,929 B2 | 4/2015 | Mohammadi |
| 9,005,942 B2 | 4/2015 | Chen |
| 9,006,400 B2 | 4/2015 | Boettcher |
| 9,012,192 B2 | 4/2015 | Chen |
| 9,018,010 B2 | 4/2015 | Amit |
| 9,045,733 B2 | 6/2015 | Chen |
| 9,079,971 B2 | 7/2015 | Cujec |
| 9,085,785 B2 | 7/2015 | Reed |
| 9,109,193 B2 | 8/2015 | Galliher |
| 9,127,242 B2 | 9/2015 | Guertin |
| 9,149,056 B2 | 10/2015 | Zhang |
| 9,157,058 B2 | 10/2015 | Dalla-Betta |
| 9,163,211 B2 | 10/2015 | Reiter |
| 9,169,309 B2 | 10/2015 | Jeong |
| 9,174,181 B2 | 11/2015 | Kocourek |
| 9,213,999 B2 | 12/2015 | Sakurada |
| 9,217,130 B2 | 12/2015 | Hashimoto |
| 9,234,210 B2 | 1/2016 | Famili |
| 9,266,935 B2 | 2/2016 | Boettcher |
| 9,272,251 B2 | 3/2016 | Jones |
| 9,273,106 B2 | 3/2016 | Belouski |
| 9,273,278 B2 | 3/2016 | Lee |
| 9,273,292 B2 | 3/2016 | Song |
| 9,279,103 B2 | 3/2016 | Chen |
| 9,279,107 B2 | 3/2016 | Chen |
| 9,315,565 B2 | 4/2016 | Cain |
| 9,321,995 B2 | 4/2016 | Liu |
| 9,332,779 B2 | 5/2016 | Marga |
| 9,340,814 B2 | 5/2016 | Sasaki |
| 9,345,254 B2 | 5/2016 | Samoto |
| 9,359,617 B2 | 6/2016 | Francky |
| 9,382,515 B2 | 7/2016 | Jaenisch |
| 9,388,375 B2 | 7/2016 | Brau |
| 9,410,121 B2 | 8/2016 | Amit |
| 9,428,727 B2 | 8/2016 | Leist |
| 9,428,766 B2 | 8/2016 | Goepfert |
| 9,434,778 B2 | 9/2016 | Morin |
| 9,434,922 B2 | 9/2016 | Oatley |
| 9,439,874 B2 | 9/2016 | Weng |
| 9,453,194 B2 | 9/2016 | Zeikus |
| 9,458,215 B2 | 10/2016 | Lau |
| 9,458,220 B2 | 10/2016 | Dimarchi |
| 9,464,126 B2 | 10/2016 | Mohammadi |
| 9,474,785 B2 | 10/2016 | Mohammadi |
| 9,476,081 B2 | 10/2016 | Cain |
| 9,480,809 B2 | 11/2016 | Guney |
| 9,487,568 B2 | 11/2016 | Bogin |
| 9,487,572 B2 | 11/2016 | Weiss |
| 9,493,530 B2 | 11/2016 | Belouski |
| 9,506,086 B2 | 11/2016 | Jannson |
| 9,517,273 B2 | 12/2016 | Cujec |
| 9,573,987 B2 | 2/2017 | Dimarchi |
| 9,585,412 B2 | 3/2017 | Corrigan |
| 9,593,156 B2 | 3/2017 | Dimarchi |
| 9,631,004 B2 | 4/2017 | Morin |
| 9,637,557 B2 | 5/2017 | Scheer |
| 9,637,717 B2 | 5/2017 | Lee |
| 9,643,133 B2 | 5/2017 | Goodwin |
| 9,644,186 B2 | 5/2017 | Chen |
| 9,657,075 B2 | 5/2017 | Mohammadi |
| 9,670,446 B2 | 6/2017 | Khan |
| 9,670,504 B2 | 6/2017 | Miller |
| 9,670,519 B2 | 6/2017 | Srivastava |
| 9,695,403 B2 | 7/2017 | Weiner |
| 9,714,411 B2 | 7/2017 | Grillberger |
| 9,714,414 B2 | 7/2017 | Jaenisch |
| 9,714,433 B2 | 7/2017 | Sakurada |
| 9,738,692 B2 | 8/2017 | Inouye |
| 9,745,359 B2 | 8/2017 | Qin |
| 9,758,568 B2 | 9/2017 | Grillberger |
| 9,783,771 B2 | 10/2017 | Khan |
| 9,803,168 B2 | 10/2017 | Nishimura |
| 9,809,630 B2 | 11/2017 | Ju |
| 9,809,796 B2 | 11/2017 | Gillberger |
| 9,862,753 B2 | 1/2018 | Yayon |
| 9,879,290 B2 | 1/2018 | Kurek |
| 9,883,689 B2 | 2/2018 | Perumalla |
| 9,901,631 B2 | 2/2018 | Degrace |
| 9,908,664 B2 | 3/2018 | Galliher |
| 9,925,241 B2 | 3/2018 | Suh |
| 9,926,355 B2 | 3/2018 | Mohammadi |
| 9,926,356 B2 | 3/2018 | Mohammadi |
| 9,932,553 B2 | 4/2018 | Brau |
| 9,943,545 B2 | 4/2018 | Rezner |
| 9,957,484 B2 | 5/2018 | Rana |
| 9,957,534 B2 | 5/2018 | Kurek |
| 9,969,965 B2 | 5/2018 | Tuohey |
| 9,969,966 B2 | 5/2018 | Asgari |
| 9,969,992 B2 | 5/2018 | Weiner |
| 9,975,936 B2 | 5/2018 | Cujec |
| 9,988,600 B2 | 6/2018 | Rayner-Brandes |
| 10,000,770 B2 | 6/2018 | Famili |
| 10,011,642 B2 | 7/2018 | Belouski |

(56) References Cited

U.S. PATENT DOCUMENTS

| | | | |
|---|---|---|---|
| 10,011,822 B2 | 7/2018 | Wu |
| 10,022,415 B2 | 7/2018 | Yoo |
| 10,030,225 B2 | 7/2018 | Von Hagen |
| 10,045,544 B2 | 8/2018 | Spierts |
| 10,059,915 B2 | 8/2018 | Lee |
| 10,066,000 B2 | 9/2018 | Vasu |
| 10,066,205 B2 | 9/2018 | Amit |
| 10,076,554 B2 | 9/2018 | Boettcher |
| 10,081,787 B2 | 9/2018 | Zeikus |
| 10,092,888 B2 | 10/2018 | Barksdale |
| 10,093,904 B2 | 10/2018 | Jaenisch |
| 10,098,368 B2 | 10/2018 | Nakase |
| 10,104,903 B2 | 10/2018 | Sunvold |
| 10,125,166 B2 | 11/2018 | Rothbauer |
| 10,138,284 B2 | 11/2018 | Weiss |
| 10,138,461 B2 | 11/2018 | Grillberger |
| 10,144,938 B2 | 12/2018 | Noguera |
| 10,179,898 B2 | 1/2019 | Khan |
| 10,179,920 B2 | 1/2019 | Jansson |
| 10,189,883 B2 | 1/2019 | Morin |
| 10,196,617 B2 | 2/2019 | Solbak |
| 10,222,387 B2 | 3/2019 | McGrane |
| 10,226,548 B2 | 3/2019 | Ahlfors |
| 10,227,559 B2 | 3/2019 | Shimoni |
| 10,233,225 B2 | 3/2019 | Dimarchi |
| 10,240,121 B2 | 3/2019 | Gevaert |
| 10,266,843 B2 | 4/2019 | Derosa |
| 10,273,265 B2 | 4/2019 | Rothbauer |
| 10,280,397 B2 | 5/2019 | Oatley |
| 10,294,289 B2 | 5/2019 | Gouze |
| 10,327,463 B2 | 6/2019 | Sheehan |
| 10,329,594 B1 | 6/2019 | Forman |
| 10,336,799 B2 | 7/2019 | Nolle |
| 10,336,983 B2 | 7/2019 | Popp |
| 10,350,554 B2 | 7/2019 | Goodwin |
| 10,364,278 B2 | 7/2019 | Mohammadi |
| 10,377,805 B2 | 8/2019 | Cujec |
| 10,377,806 B2 | 8/2019 | Morin |
| 10,385,113 B2 | 8/2019 | Thallapuranam |
| 10,392,429 B2 | 8/2019 | Weiss |
| 10,400,210 B2 | 9/2019 | Caracci |
| 10,428,340 B2 | 10/2019 | Weiner |
| 10,428,349 B2 | 10/2019 | Derosa |
| 10,429,378 B2 | 10/2019 | Eilertsen |
| 10,472,404 B2 | 11/2019 | Qin |
| 10,472,605 B2 | 11/2019 | Barry |
| 10,473,673 B2 | 11/2019 | McGrane |
| 10,519,413 B2 | 12/2019 | Brau |
| 10,544,395 B2 | 1/2020 | Hiller |
| 10,548,902 B1 | 2/2020 | Majeed |
| 10,563,169 B2 | 2/2020 | Von Hagen |
| 10,570,367 B2 | 2/2020 | Bruninghaus |
| 10,577,613 B1 | 3/2020 | Goel |
| 10,590,382 B2 | 3/2020 | Amit |
| 10,619,131 B2 | 4/2020 | Von Hagen |
| 10,633,424 B2 | 4/2020 | Mohammadi |
| 10,655,099 B2 | 5/2020 | Grillberger |
| 10,669,522 B2 | 6/2020 | Fike |
| 10,669,524 B2 | 6/2020 | Forgacs |
| 10,675,428 B2 | 6/2020 | Guney |
| 10,689,652 B2 | 6/2020 | Stampfer |
| 10,695,404 B2 | 6/2020 | Evans |
| 10,696,731 B2 | 6/2020 | Grillberger |
| 10,696,941 B2 | 6/2020 | Dalla-Betta |
| 10,703,788 B2 | 7/2020 | Mohammadi |
| 10,745,458 B2 | 8/2020 | Weiss |
| 10,768,184 B2 | 9/2020 | McGrane |
| 10,787,652 B2 | 9/2020 | Lotvin |
| 10,793,827 B2 | 10/2020 | Barrett |
| 10,801,003 B2 | 10/2020 | Jaques |
| 10,842,809 B2 | 11/2020 | Jackson |
| 10,843,141 B2 | 11/2020 | Goodwin |
| 10,870,851 B2 | 12/2020 | Stampfer |
| 10,883,076 B2 | 1/2021 | Khan |
| 10,920,196 B2 | 2/2021 | Genovese |
| 10,927,346 B2 | 2/2021 | Valamehr |
| 10,954,276 B2 | 3/2021 | Ju |
| 10,961,291 B2 | 3/2021 | Cujec |
| 10,961,556 B2 | 3/2021 | Ley |
| 10,973,242 B2 | 4/2021 | Shigeta |
| 10,973,244 B2 | 4/2021 | Jackson |
| 10,982,198 B2 | 4/2021 | Lotvin |
| 10,995,129 B2 | 5/2021 | Weiss |
| 11,001,810 B1 | 5/2021 | Lian |
| 11,008,138 B2 | 5/2021 | Galliher |
| 11,015,171 B2 | 5/2021 | Yamashita |
| 11,021,528 B2 | 6/2021 | Gouze |
| 11,028,361 B2 | 6/2021 | Fike |
| 11,046,931 B2 | 6/2021 | Caracci |
| 11,072,640 B2 | 7/2021 | Belouski |
| 11,077,165 B2 | 8/2021 | Zicker |
| 11,098,081 B2 | 8/2021 | Rothbauer |
| 11,102,993 B2 | 8/2021 | Stewart |
| 11,104,875 B2 | 8/2021 | Hiller |
| 11,110,488 B1 | 9/2021 | Frota |
| 11,111,471 B2 | 9/2021 | Galliher |
| 11,124,760 B2 | 9/2021 | Yang |
| 11,124,804 B2 | 9/2021 | Derosa |
| 11,129,874 B2 | 9/2021 | Boettcher |
| 11,135,244 B2 | 10/2021 | Rezner |
| 11,142,560 B2 | 10/2021 | Weiss |
| 11,147,300 B2 | 10/2021 | Leung |
| 11,154,077 B2 | 10/2021 | Corrigan |
| 11,162,062 B2 | 11/2021 | Brau |
| 11,174,459 B2 | 11/2021 | Forgacs |
| 11,203,738 B2 | 12/2021 | Dyson |
| 11,207,257 B2 | 12/2021 | Shin |
| 11,208,451 B2 | 12/2021 | Qin |
| 11,208,633 B2 | 12/2021 | Lotvin |
| 11,229,681 B2 | 1/2022 | Takada |
| 11,230,725 B2 | 1/2022 | Florin |
| 11,248,031 B2 | 2/2022 | Morin |
| 11,248,034 B2 | 2/2022 | Menting |
| 11,254,723 B2 | 2/2022 | Fang |
| 11,259,546 B2 | 3/2022 | Shigeta |
| 11,274,321 B2 | 3/2022 | Reed |
| 11,284,633 B2 | 3/2022 | Gross |
| 11,291,229 B2 | 4/2022 | Ingoglia |
| 11,292,999 B2 | 4/2022 | Paldus |
| 11,306,342 B2 | 4/2022 | Chin |
| 11,312,539 B2 | 4/2022 | Galliher |
| 11,324,233 B2 | 5/2022 | Ray |
| 11,332,771 B2 | 5/2022 | Oshodi |
| 11,344,050 B2 | 5/2022 | Leung |
| 11,352,407 B2 | 6/2022 | Lancaster |
| 11,357,244 B2 | 6/2022 | Leung |
| 11,365,389 B2 | 6/2022 | Barrett |
| 11,365,394 B2 | 6/2022 | Valamehr |
| 11,371,002 B2 | 6/2022 | Jaques |
| 11,391,725 B2 | 7/2022 | Wang |
| 11,419,358 B2 | 8/2022 | Akintoye |
| 11,427,802 B2 | 8/2022 | Mironov |
| 11,432,574 B2 | 9/2022 | Pattillo |
| 11,452,834 B2 | 9/2022 | Guney |
| 11,466,246 B2 | 10/2022 | Dyson |
| 11,466,290 B2 | 10/2022 | Breunig |
| 11,470,871 B2 | 10/2022 | Pattillo |
| 11,478,006 B2 | 10/2022 | Pattillo |
| 11,479,591 B2 | 10/2022 | Eveleth |
| 11,479,792 B2 | 10/2022 | Genovese |
| 11,484,879 B2 | 11/2022 | Hanyu |
| 11,498,949 B2 | 11/2022 | Vasu |
| 11,499,135 B2 | 11/2022 | Mironov |
| 11,504,651 B2 | 11/2022 | Varanasi |
| 11,505,784 B2 | 11/2022 | Clemens |
| 11,510,999 B2 | 11/2022 | Lee |
| 11,512,273 B2 | 11/2022 | Breemhaar |
| 11,555,058 B2 | 1/2023 | Lancaster |
| 11,555,170 B2 | 1/2023 | Flynn |
| 11,559,072 B2 | 1/2023 | Leung |
| 11,559,073 B2 | 1/2023 | Leung |
| 11,576,411 B2 | 2/2023 | Leung |
| 11,589,598 B2 | 2/2023 | Savir |
| 11,591,572 B2 | 2/2023 | Clevers |

(56)          References Cited

U.S. PATENT DOCUMENTS

| | | |
|---|---|---|
| 11,597,199 B2 | 3/2023 | Parfenov |
| 11,627,751 B2 | 4/2023 | Leung |
| 11,629,322 B2 | 4/2023 | Prabhudharwadkar |
| 11,642,484 B2 | 5/2023 | Guney |
| 11,649,449 B2 | 5/2023 | Lawrence |
| 11,650,159 B2 | 5/2023 | Renata |
| 11,660,415 B2 | 5/2023 | Guney |
| 11,680,237 B2 | 6/2023 | Castillo |
| 11,680,295 B2 | 6/2023 | Khatib |
| 11,685,899 B2 | 6/2023 | Simmons |
| 11,692,167 B2 | 7/2023 | Corbin |
| 11,697,624 B2 | 7/2023 | Blaney |
| 11,697,678 B2 | 7/2023 | Gouze |
| 11,702,629 B2 | 7/2023 | Walsh |
| 11,708,587 B2 | 7/2023 | Genovese |
| 11,714,081 B2 | 8/2023 | Eilertsen |
| 11,718,824 B2 | 8/2023 | Caracci |
| 11,725,290 B2 | 8/2023 | Reed |
| 11,738,510 B2 | 8/2023 | Kozlovski |
| 11,739,136 B2 | 8/2023 | Pu |
| 11,746,135 B2 | 9/2023 | Dvorak |
| 11,752,509 B2 | 9/2023 | Liu |
| 11,752,510 B2 | 9/2023 | Liu |
| 11,758,931 B2 | 9/2023 | Kayser |
| 11,760,964 B2 | 9/2023 | Muller-Aufferman |
| 11,771,112 B2 | 10/2023 | March |
| 11,779,033 B2 | 10/2023 | Scionti |
| 11,819,846 B2 | 11/2023 | Hanyu |
| 11,820,794 B2 | 11/2023 | Flynn |
| 11,827,677 B2 | 11/2023 | Wang |
| 11,834,643 B2 | 12/2023 | Galliher |
| 11,840,558 B2 | 12/2023 | Belouski |
| 11,859,161 B2 | 1/2024 | Paldus |
| 11,866,700 B2 | 1/2024 | Kang |
| 11,884,909 B2 | 1/2024 | Huang |
| 11,891,596 B2 | 2/2024 | Mueller-Auffermann |
| 11,898,127 B1 | 2/2024 | Leung |
| 11,912,967 B2 | 2/2024 | Tandikul |
| 11,912,972 B2 | 2/2024 | Huang |
| 11,944,664 B2 | 4/2024 | Boettcher |
| 11,952,597 B2 | 4/2024 | Lotvin |
| 11,970,724 B2 | 4/2024 | Oshodi |
| 11,976,302 B2 | 5/2024 | Genovese |
| 11,981,884 B2 | 5/2024 | Benton |
| 11,991,994 B2 | 5/2024 | Anderson-Baron |
| 11,992,029 B2 | 5/2024 | Peterson |
| 11,992,033 B2 | 5/2024 | Belt |
| 11,993,637 B2 | 5/2024 | Cujec |
| 12,031,152 B2 | 7/2024 | Johnson |
| 12,037,613 B2 | 7/2024 | Zhai |
| 12,041,949 B2 | 7/2024 | Ghotra |
| 12,089,615 B2 | 9/2024 | Ghotra |
| 12,102,102 B2 | 10/2024 | Kreamer |
| 12,127,575 B2 | 10/2024 | Pattillo |
| 12,168,019 B1 | 12/2024 | Andrews |
| 12,281,293 B1 | 4/2025 | Huang |
| 12,359,228 B2 | 7/2025 | Behkish |
| 12,391,773 B2 | 8/2025 | Mccurdy |
| 2004/0091968 A1 | 5/2004 | Short |
| 2005/0009161 A1 | 1/2005 | Streeter |
| 2005/0020814 A1 | 1/2005 | Rudolph |
| 2005/0037955 A1 | 2/2005 | Hooper |
| 2006/0094104 A1 | 5/2006 | Grillberger |
| 2006/0223155 A1 | 10/2006 | Streeter |
| 2007/0212332 A1 | 9/2007 | Baylink |
| 2007/0212770 A1 | 9/2007 | Grillberger |
| 2007/0212778 A1 | 9/2007 | Bramke |
| 2008/0009040 A1 | 1/2008 | Grillberger |
| 2008/0064080 A1 | 3/2008 | Grillberger |
| 2008/0064105 A1 | 3/2008 | Grillberger |
| 2008/0076158 A1 | 3/2008 | Dassler |
| 2008/0261299 A1 | 10/2008 | Zeikus |
| 2008/0313747 A1 | 12/2008 | Kern |
| 2009/0029465 A1 | 1/2009 | Thomson |
| 2009/0042253 A1 | 2/2009 | Hiller |
| 2009/0275128 A1 | 11/2009 | Thomson |
| 2009/0280217 A1 | 11/2009 | Katase |
| 2009/0304646 A1 | 12/2009 | Sakurada |
| 2010/0105100 A1 | 4/2010 | Sakurada |
| 2010/0120104 A1 | 5/2010 | Reed |
| 2010/0173409 A1 | 7/2010 | Gardner |
| 2010/0173839 A1 | 7/2010 | Glass |
| 2010/0178680 A1 | 7/2010 | Goodwin |
| 2010/0185047 A1 | 7/2010 | Khatib |
| 2010/0240090 A1 | 9/2010 | Sakurada |
| 2010/0267135 A1 | 10/2010 | Sakurada |
| 2010/0286042 A1 | 11/2010 | Imamura |
| 2011/0027417 A1 | 2/2011 | Corrigan |
| 2011/0039332 A1 | 2/2011 | Sakurada |
| 2011/0081680 A1 | 4/2011 | Grillberger |
| 2011/0081722 A1 | 4/2011 | Grillberger |
| 2011/0104754 A1 | 5/2011 | Bramke |
| 2011/0117603 A1 | 5/2011 | Piparia |
| 2011/0151512 A1 | 6/2011 | Grillberger |
| 2011/0262965 A1 | 10/2011 | Barrett |
| 2011/0306750 A1 | 12/2011 | Hoegenhaug |
| 2011/0312087 A1 | 12/2011 | Khan |
| 2012/0021094 A1 | 1/2012 | Sunvold |
| 2012/0052069 A1 | 3/2012 | Belouski |
| 2012/0135889 A1 | 5/2012 | Khatib |
| 2012/0156182 A1 | 6/2012 | Ahlfors |
| 2012/0190061 A1 | 7/2012 | Croughan |
| 2012/0214740 A1 | 8/2012 | Imamura |
| 2012/0308544 A1 | 12/2012 | Steinfeld |
| 2013/0078690 A1 | 3/2013 | Reed |
| 2013/0095062 A1 | 4/2013 | Chen |
| 2013/0149755 A1 | 6/2013 | Reed |
| 2013/0210707 A1 | 8/2013 | Chung |
| 2013/0236959 A1 | 9/2013 | Chen |
| 2013/0236962 A1 | 9/2013 | Thomson |
| 2013/0303573 A1 | 11/2013 | Boss |
| 2014/0094406 A1 | 4/2014 | Mohammadi |
| 2014/0107022 A1 | 4/2014 | Mohammadi |
| 2014/0134306 A1 | 5/2014 | Sakaji |
| 2014/0206083 A1 | 7/2014 | Sakurada |
| 2014/0273095 A1 | 9/2014 | Oshodi |
| 2014/0315280 A1 | 10/2014 | Ehwald |
| 2015/0017694 A1 | 1/2015 | Kurek |
| 2015/0031601 A1 | 1/2015 | Hoegenhaug |
| 2015/0076060 A1 | 3/2015 | Lee |
| 2015/0079238 A1 | 3/2015 | Marga |
| 2015/0099295 A1 | 4/2015 | Chen |
| 2015/0111821 A1 | 4/2015 | Suh |
| 2015/0132840 A1 | 5/2015 | Arnold |
| 2015/0140591 A1 | 5/2015 | Florin |
| 2015/0140640 A1 | 5/2015 | Reed |
| 2015/0183847 A1 | 7/2015 | Qin |
| 2015/0240219 A1 | 8/2015 | Baylink |
| 2015/0299280 A1 | 10/2015 | Nakayama |
| 2015/0315539 A1 | 11/2015 | Villanueva |
| 2016/0158317 A1 | 6/2016 | Hoegenhaug |
| 2016/0227830 A1 | 8/2016 | Genovese |
| 2016/0227831 A1 | 8/2016 | Marga |
| 2016/0244710 A1 | 8/2016 | Wood |
| 2016/0251625 A1 | 9/2016 | Genovese |
| 2016/0289633 A1 | 10/2016 | Yang |
| 2016/0312168 A1 | 10/2016 | Pizzi |
| 2017/0037421 A1 | 2/2017 | Blessing |
| 2017/0066808 A9 | 3/2017 | Glass |
| 2017/0095533 A1 | 4/2017 | Bogin |
| 2017/0143005 A1 | 5/2017 | Miyamoto |
| 2017/0172178 A1 | 6/2017 | Corrigan |
| 2017/0198258 A1 | 7/2017 | Jin |
| 2017/0218407 A1 | 8/2017 | Reed |
| 2017/0233447 A1 | 8/2017 | Qin |
| 2017/0327787 A1 | 11/2017 | Fukuda |
| 2017/0342371 A1 | 11/2017 | Barrett |
| 2018/0037867 A1 | 2/2018 | Simmons |
| 2018/0110240 A1 | 4/2018 | Mao |
| 2018/0127475 A1 | 5/2018 | Yayon |
| 2018/0148494 A1 | 5/2018 | Gouze |
| 2018/0179559 A1 | 6/2018 | Reed |
| 2018/0193418 A1 | 7/2018 | Suh |
| 2018/0237736 A1 | 8/2018 | Tuohey |

(56)        References Cited

U.S. PATENT DOCUMENTS

| | | | |
|---|---|---|---|
| 2018/0282431 | A1 | 10/2018 | Scheer |
| 2018/0298409 | A1 | 10/2018 | Reed |
| 2018/0346941 | A1 | 12/2018 | Kurek |
| 2019/0008186 | A1 | 1/2019 | Jackson |
| 2019/0014796 | A1 | 1/2019 | Jackson |
| 2019/0024079 | A1 | 1/2019 | Genovese |
| 2019/0040427 | A1 | 2/2019 | Kurek |
| 2019/0055513 | A1 | 2/2019 | Ng |
| 2019/0069575 | A1 | 3/2019 | Shigeta |
| 2019/0112572 | A1 | 4/2019 | Figueroa |
| 2019/0136173 | A1 | 5/2019 | Levinson |
| 2019/0144891 | A1 | 5/2019 | Jansson |
| 2019/0161733 | A1 | 5/2019 | Pijnappel |
| 2019/0169566 | A1 | 6/2019 | Gevaert |
| 2019/0185584 | A1 | 6/2019 | Scheer |
| 2019/0192630 | A1 | 6/2019 | Suh |
| 2019/0241874 | A1 | 8/2019 | Jaenisch |
| 2019/0292515 | A1 | 9/2019 | Phelps |
| 2019/0300393 | A1 | 10/2019 | Fleckner |
| 2019/0313666 | A1 | 10/2019 | Lignet |
| 2019/0338232 | A1 | 11/2019 | Breemhaar |
| 2019/0352676 | A1 | 11/2019 | Senaratne |
| 2019/0382808 | A1 | 12/2019 | Reed |
| 2019/0390161 | A1 | 12/2019 | Knaup |
| 2020/0002397 | A1 | 1/2020 | Qin |
| 2020/0005619 | A1 | 1/2020 | Emmons |
| 2020/0010796 | A1 | 1/2020 | Merz |
| 2020/0040303 | A1 | 2/2020 | Simmons |
| 2020/0080048 | A1 | 3/2020 | Popp |
| 2020/0080050 | A1 | 3/2020 | Nahmias |
| 2020/0115669 | A1 | 4/2020 | Bremer, Jr. |
| 2020/0140810 | A1 | 5/2020 | Ben-Arye |
| 2020/0140821 | A1 | 5/2020 | Elfenbein |
| 2020/0165569 | A1 | 5/2020 | Genovese |
| 2020/0172856 | A1 | 6/2020 | Reed |
| 2020/0181656 | A1 | 6/2020 | Kurek |
| 2020/0181664 | A1 | 6/2020 | Behkish |
| 2020/0205441 | A1 | 7/2020 | Cheison |
| 2020/0236971 | A1 | 7/2020 | Audibert |
| 2020/0239852 | A1 | 7/2020 | Hiller |
| 2020/0270320 | A1 | 8/2020 | Dvorak |
| 2020/0308579 | A1 | 10/2020 | Kang |
| 2020/0325441 | A1 | 10/2020 | Hiller |
| 2020/0377850 | A1 | 12/2020 | Bruninghaus |
| 2020/0385674 | A1 | 12/2020 | Ross |
| 2020/0392448 | A1 | 12/2020 | Goodwin |
| 2020/0392461 | A1 | 12/2020 | Mullen |
| 2020/0399603 | A1 | 12/2020 | Kishida |
| 2021/0002605 | A1 | 1/2021 | Murakami |
| 2021/0009657 | A1 | 1/2021 | Gouze |
| 2021/0017548 | A1 | 1/2021 | Behkish |
| 2021/0024959 | A1 | 1/2021 | Valamehr |
| 2021/0037870 | A1 | 2/2021 | Krieger |
| 2021/0068425 | A1 | 3/2021 | Ross |
| 2021/0069654 | A1 | 3/2021 | Goodwin |
| 2021/0076706 | A1 | 3/2021 | Herrmann |
| 2021/0079342 | A1 | 3/2021 | Amit |
| 2021/0084940 | A1 | 3/2021 | Schlebusch |
| 2021/0087521 | A1 | 3/2021 | Ikeda |
| 2021/0087525 | A1 | 3/2021 | Burridge |
| 2021/0087537 | A1 | 3/2021 | Valamehr |
| 2021/0092978 | A1 | 4/2021 | Xu |
| 2021/0102163 | A1 | 4/2021 | Lee |
| 2021/0123013 | A1 | 4/2021 | Feyeux |
| 2021/0130760 | A1 | 5/2021 | Castillo |
| 2021/0138219 | A1 | 5/2021 | Stankowski |
| 2021/0139843 | A1 | 5/2021 | Nahmias |
| 2021/0139858 | A1 | 5/2021 | Lian |
| 2021/0163895 | A1 | 6/2021 | Valamehr |
| 2021/0169802 | A1 | 6/2021 | Yun |
| 2021/0171662 | A1 | 6/2021 | Scheer |
| 2021/0171912 | A1 | 6/2021 | Genovese |
| 2021/0189317 | A1 | 6/2021 | Henry |
| 2021/0207080 | A1 | 7/2021 | Beauchesne |
| 2021/0222109 | A1 | 7/2021 | Yin |
| 2021/0222128 | A1 | 7/2021 | Chen |
| 2021/0235733 | A1 | 8/2021 | Kayser |
| 2021/0246480 | A1 | 8/2021 | Chin |
| 2021/0269767 | A1 | 9/2021 | Fike |
| 2021/0269797 | A1 | 9/2021 | Beigelman |
| 2021/0284971 | A1 | 9/2021 | Matsumoto |
| 2021/0307363 | A1 | 10/2021 | Wernimont |
| 2021/0309956 | A1 | 10/2021 | Pizzi |
| 2021/0317395 | A1 | 10/2021 | Hiller |
| 2021/0332326 | A1 | 10/2021 | Vodnala |
| 2021/0340570 | A1 | 11/2021 | Genovese |
| 2021/0345654 | A1 | 11/2021 | Krieger |
| 2021/0348108 | A1 | 11/2021 | Choi |
| 2021/0348129 | A1 | 11/2021 | Rebello |
| 2021/0371788 | A1 | 12/2021 | Huang |
| 2021/0380923 | A1 | 12/2021 | Coffman |
| 2021/0392908 | A1 | 12/2021 | Reed |
| 2021/0392920 | A1 | 12/2021 | Dyson |
| 2021/0393700 | A1 | 12/2021 | O'Heeron |
| 2021/0395677 | A1 | 12/2021 | Reed |
| 2021/0395690 | A1 | 12/2021 | Nahmias |
| 2022/0000154 | A1 | 1/2022 | Leung |
| 2022/0000826 | A1 | 1/2022 | Jewell |
| 2022/0002652 | A1 | 1/2022 | Patrick |
| 2022/0007695 | A1 | 1/2022 | Kayser |
| 2022/0007696 | A1 | 1/2022 | Lavon |
| 2022/0017859 | A1 | 1/2022 | Guehenneux |
| 2022/0023807 | A1 | 1/2022 | Damren |
| 2022/0025310 | A1 | 1/2022 | Chin |
| 2022/0033753 | A1 | 2/2022 | Brau |
| 2022/0041672 | A1 | 2/2022 | Misaghi |
| 2022/0041979 | A1 | 2/2022 | Forgacs |
| 2022/0053796 | A1 | 2/2022 | Bayle |
| 2022/0056394 | A1 | 2/2022 | Leung |
| 2022/0064217 | A1 | 3/2022 | Wehkamp |
| 2022/0064690 | A1 | 3/2022 | Florin |
| 2022/0071233 | A1 | 3/2022 | Kaplan |
| 2022/0071247 | A1 | 3/2022 | Kayser |
| 2022/0073856 | A1 | 3/2022 | Pitkänen |
| 2022/0073868 | A1 | 3/2022 | Cooper |
| 2022/0073870 | A1 | 3/2022 | Johnson |
| 2022/0073944 | A1 | 3/2022 | Derosa |
| 2022/0079194 | A1 | 3/2022 | Li |
| 2022/0079200 | A2 | 3/2022 | Krieger |
| 2022/0081475 | A1 | 3/2022 | Li |
| 2022/0089661 | A1 | 3/2022 | Li |
| 2022/0096598 | A1 | 3/2022 | Duan |
| 2022/0098546 | A1 | 3/2022 | Akcali |
| 2022/0110347 | A1 | 4/2022 | Leung |
| 2022/0145337 | A1 | 5/2022 | Reed |
| 2022/0154137 | A1 | 5/2022 | Ng |
| 2022/0154228 | A1 | 5/2022 | Reed |
| 2022/0162662 | A1 | 5/2022 | Chin |
| 2022/0168220 | A1 | 6/2022 | Levin |
| 2022/0169962 | A1 | 6/2022 | Takeuchi |
| 2022/0169973 | A1 | 6/2022 | Dehottay |
| 2022/0177818 | A1 | 6/2022 | Matuszczyk |
| 2022/0177823 | A1 | 6/2022 | Vila Juárez |
| 2022/0183316 | A1 | 6/2022 | Santo |
| 2022/0183317 | A1 | 6/2022 | Krieger |
| 2022/0184142 | A1 | 6/2022 | Valamehr |
| 2022/0185856 | A1 | 6/2022 | Morin |
| 2022/0186167 | A1 | 6/2022 | Vela |
| 2022/0195358 | A1 | 6/2022 | Tandikul |
| 2022/0195359 | A1 | 6/2022 | Lavon |
| 2022/0195368 | A1 | 6/2022 | Genovese |
| 2022/0195392 | A1 | 6/2022 | Rowat |
| 2022/0202759 | A1 | 6/2022 | Jackson |
| 2022/0204909 | A1 | 6/2022 | Alzate |
| 2022/0213427 | A1 | 7/2022 | Melchiorri |
| 2022/0213438 | A1 | 7/2022 | Lin |
| 2022/0220439 | A1 | 7/2022 | Lavon |
| 2022/0228097 | A1 | 7/2022 | White |
| 2022/0228121 | A1 | 7/2022 | Stout |
| 2022/0228187 | A1 | 7/2022 | Oshodi |
| 2022/0234012 | A1 | 7/2022 | Castan |
| 2022/0243192 | A1 | 8/2022 | Forman |
| 2022/0243193 | A1 | 8/2022 | Forman |
| 2022/0251487 | A1 | 8/2022 | Kubota |

(56) References Cited

U.S. PATENT DOCUMENTS

| | | |
|---|---|---|
| 2022/0251550 A1 | 8/2022 | Genovese |
| 2022/0275325 A1 | 9/2022 | Barrett |
| 2022/0282285 A1 | 9/2022 | Webber |
| 2022/0287331 A1 | 9/2022 | Schlebusch |
| 2022/0290090 A1 | 9/2022 | Ball |
| 2022/0298472 A1 | 9/2022 | Kober |
| 2022/0298480 A1 | 9/2022 | Chin |
| 2022/0306987 A1 | 9/2022 | Duthoit |
| 2022/0308042 A1 | 9/2022 | Wang |
| 2022/0315880 A1 | 10/2022 | Lang |
| 2022/0315953 A1 | 10/2022 | Langereis |
| 2022/0322703 A1 | 10/2022 | Van Eyk |
| 2022/0325212 A1 | 10/2022 | Toledano |
| 2022/0325220 A1 | 10/2022 | Vainikka |
| 2022/0325258 A1 | 10/2022 | Kogut |
| 2022/0330599 A1 | 10/2022 | Zahn |
| 2022/0333066 A1 | 10/2022 | Amit |
| 2022/0333148 A1 | 10/2022 | Chin |
| 2022/0340636 A1 | 10/2022 | Menting |
| 2022/0340864 A1 | 10/2022 | Shimizu |
| 2022/0369665 A1 | 11/2022 | Valenzuela |
| 2022/0372435 A1 | 11/2022 | Phelps |
| 2022/0372436 A1 | 11/2022 | Oshodi |
| 2022/0380712 A1 | 12/2022 | Sieck |
| 2022/0388725 A1 | 12/2022 | Galliher |
| 2022/0394997 A1 | 12/2022 | Legarth |
| 2022/0395001 A1 | 12/2022 | Jackson |
| 2022/0400716 A1 | 12/2022 | Rease |
| 2022/0408731 A1 | 12/2022 | Shah |
| 2022/0411734 A1 | 12/2022 | Pietras |
| 2022/0411742 A1 | 12/2022 | Namatame |
| 2022/0411824 A1 | 12/2022 | Genovese |
| 2023/0002718 A1 | 1/2023 | Haupt |
| 2023/0002739 A1 | 1/2023 | Newton |
| 2023/0012452 A1 | 1/2023 | Pereira-Taveres |
| 2023/0016607 A1 | 1/2023 | Lu |
| 2023/0017014 A1 | 1/2023 | Drugmand |
| 2023/0030915 A1 | 2/2023 | Jewell |
| 2023/0045226 A1 | 2/2023 | Jaques |
| 2023/0046426 A1 | 2/2023 | Hariharan |
| 2023/0049887 A1 | 2/2023 | Audibert |
| 2023/0050194 A1 | 2/2023 | Vogel |
| 2023/0054944 A1 | 2/2023 | Ben-Shitrit |
| 2023/0060907 A1 | 3/2023 | Gharibian |
| 2023/0067342 A1 | 3/2023 | Jackson |
| 2023/0067465 A1 | 3/2023 | Ju |
| 2023/0070582 A1 | 3/2023 | Nahmias |
| 2023/0071409 A1 | 3/2023 | Trassy |
| 2023/0073515 A1 | 3/2023 | Rezania |
| 2023/0073614 A1 | 3/2023 | Nahmias |
| 2023/0075095 A1 | 3/2023 | King |
| 2023/0077429 A1 | 3/2023 | Caplan |
| 2023/0081499 A1 | 3/2023 | Popp |
| 2023/0083026 A1 | 3/2023 | Moutsatsou |
| 2023/0091040 A1 | 3/2023 | Leung |
| 2023/0091231 A1 | 3/2023 | Nahmias |
| 2023/0093399 A1 | 3/2023 | West |
| 2023/0100306 A1 | 3/2023 | Engelmayr, Jr. |
| 2023/0101863 A1 | 3/2023 | Robertson |
| 2023/0105342 A1 | 4/2023 | Anderson-Baron |
| 2023/0108652 A1 | 4/2023 | Konrad |
| 2023/0108890 A1 | 4/2023 | Kawashima |
| 2023/0122678 A1 | 4/2023 | Dyson |
| 2023/0130038 A1 | 4/2023 | Vasu |
| 2023/0130851 A1 | 4/2023 | Eveleth |
| 2023/0132594 A1 | 5/2023 | Sathe |
| 2023/0132925 A1 | 5/2023 | Jane |
| 2023/0146879 A1 | 5/2023 | Röntgen |
| 2023/0149834 A1 | 5/2023 | Varanasi |
| 2023/0151330 A1 | 5/2023 | Faram |
| 2023/0151386 A1 | 5/2023 | Henry |
| 2023/0157316 A1 | 5/2023 | Rease |
| 2023/0159874 A1 | 5/2023 | Johannessen |
| 2023/0159879 A1 | 5/2023 | Henry |
| 2023/0159954 A1 | 5/2023 | Henry |
| 2023/0167394 A1 | 6/2023 | Gaertner |
| 2023/0172231 A1 | 6/2023 | Zaune-Figlar |
| 2023/0183762 A1 | 6/2023 | Reed |
| 2023/0203420 A1 | 6/2023 | Leung |
| 2023/0203446 A1 | 6/2023 | Múller-Auffermann |
| 2023/0203449 A1 | 6/2023 | Clemens |
| 2023/0210131 A1 | 7/2023 | Savir |
| 2023/0210132 A1 | 7/2023 | Savir |
| 2023/0210133 A1 | 7/2023 | Savir |
| 2023/0210134 A1 | 7/2023 | Savir |
| 2023/0210135 A1 | 7/2023 | Savir |
| 2023/0212498 A1 | 7/2023 | Bode |
| 2023/0220027 A1 | 7/2023 | Orvar |
| 2023/0220332 A1 | 7/2023 | Amit |
| 2023/0220347 A1 | 7/2023 | Hwang |
| 2023/0225361 A1 | 7/2023 | Nahmias |
| 2023/0225391 A1 | 7/2023 | Mandelik |
| 2023/0227760 A1 | 7/2023 | Vila |
| 2023/0227764 A1 | 7/2023 | Prabhudharwadkar |
| 2023/0240324 A1 | 8/2023 | Dikovsky |
| 2023/0240325 A1 | 8/2023 | Leune |
| 2023/0240334 A1 | 8/2023 | Marchal |
| 2023/0248020 A1 | 8/2023 | Chuang |
| 2023/0250148 A1 | 8/2023 | Lancaster |
| 2023/0255253 A1 | 8/2023 | Levin |
| 2023/0257711 A1 | 8/2023 | Roberts |
| 2023/0270965 A1 | 8/2023 | Guney |
| 2023/0272318 A1 | 8/2023 | Liu |
| 2023/0272324 A1 | 8/2023 | Castillo |
| 2023/0272346 A1 | 8/2023 | Genovese |
| 2023/0272347 A1 | 8/2023 | Clevers |
| 2023/0279320 A1 | 9/2023 | Flynn |
| 2023/0284662 A1 | 9/2023 | Kaplan |
| 2023/0287317 A1 | 9/2023 | Kaplan |
| 2023/0303646 A1 | 9/2023 | Boss |
| 2023/0303956 A1 | 9/2023 | Weissenbach |
| 2023/0313109 A1 | 10/2023 | Sieck |
| 2023/0320288 A1 | 10/2023 | Scully |
| 2023/0322904 A1 | 10/2023 | Sanctorum |
| 2023/0323287 A1 | 10/2023 | Daris |
| 2023/0332101 A1 | 10/2023 | Walsh |
| 2023/0340390 A1 | 10/2023 | Zheng |
| 2023/0348545 A1 | 11/2023 | Gasser |
| 2023/0354851 A1 | 11/2023 | Montelongo |
| 2023/0357445 A1 | 11/2023 | Scheer |
| 2023/0365639 A1 | 11/2023 | Wehkamp |
| 2023/0365919 A1 | 11/2023 | Barrett |
| 2023/0365920 A1 | 11/2023 | Hiller |
| 2023/0371552 A1 | 11/2023 | Jackson |
| 2023/0374432 A1 | 11/2023 | Goh |
| 2023/0383223 A1 | 11/2023 | Wang |
| 2023/0392120 A1 | 12/2023 | Dhadwar |
| 2023/0397633 A1 | 12/2023 | Davila |
| 2023/0399620 A1 | 12/2023 | Dhadwar |
| 2023/0404951 A1 | 12/2023 | Ephraim |
| 2023/0407224 A1 | 12/2023 | Lavon |
| 2023/0413856 A1 | 12/2023 | Padilla |
| 2023/0416674 A1 | 12/2023 | Figueroa |
| 2023/0416747 A1 | 12/2023 | Zheng |
| 2024/0000128 A1 | 1/2024 | Han |
| 2024/0002784 A1 | 1/2024 | Inada |
| 2024/0002803 A1 | 1/2024 | Savir |
| 2024/0008507 A1 | 1/2024 | Felke |
| 2024/0010983 A1 | 1/2024 | Weissenbach |
| 2024/0010984 A1 | 1/2024 | Cruz |
| 2024/0016185 A1 | 1/2024 | March |
| 2024/0034979 A1 | 2/2024 | Chen |
| 2024/0034987 A1 | 2/2024 | Kaplan |
| 2024/0041064 A1 | 2/2024 | Zotter |
| 2024/0041067 A1 | 2/2024 | Scionti |
| 2024/0043493 A1 | 2/2024 | Weiss |
| 2024/0043787 A1 | 2/2024 | Robertson |
| 2024/0052291 A1 | 2/2024 | Connon |
| 2024/0060191 A1 | 2/2024 | Reed |
| 2024/0066149 A1 | 2/2024 | Kinoshita |
| 2024/0074478 A1 | 3/2024 | Block |
| 2024/0076594 A1 | 3/2024 | Paldus |
| 2024/0084258 A1 | 3/2024 | Yamamoto |
| 2024/0090531 A1 | 3/2024 | Macqueen |

(56)                References Cited

U.S. PATENT DOCUMENTS

| | | |
|---|---|---|
| 2024/0093141 A1 | 3/2024 | Holmström |
| 2024/0093152 A1 | 3/2024 | Kaplan |
| 2024/0093153 A1 | 3/2024 | Chin |
| 2024/0101968 A1 | 3/2024 | Keophiphath |
| 2024/0108031 A1 | 4/2024 | Sagalowicz |
| 2024/0117287 A1 | 4/2024 | Mueller-Auffermann |
| 2024/0117401 A1 | 4/2024 | Balcarcel |
| 2024/0122222 A1 | 4/2024 | Ercili-Cura |
| 2024/0141268 A1 | 5/2024 | Tandikul |
| 2024/0148012 A1 | 5/2024 | Hosseini |
| 2024/0148022 A1 | 5/2024 | Davila |
| 2024/0148023 A1 | 5/2024 | Li |
| 2024/0148024 A1 | 5/2024 | Ong |
| 2024/0148025 A1 | 5/2024 | Nikinmaa |
| 2024/0148034 A1 | 5/2024 | Hosseini |
| 2024/0150723 A1 | 5/2024 | Forte |
| 2024/0150724 A1 | 5/2024 | Hosseini |
| 2024/0156127 A1 | 5/2024 | Häkämies |
| 2024/0156138 A1 | 5/2024 | Häkämies |
| 2024/0158449 A1 | 5/2024 | Flynn |
| 2024/0164404 A1 | 5/2024 | Frelka |
| 2024/0164406 A1 | 5/2024 | Häkämies |
| 2024/0165557 A1 | 5/2024 | Tervasmäki |
| 2024/0174957 A1 | 5/2024 | Dezfuli |
| 2024/0174963 A1 | 5/2024 | Huang |
| 2024/0182859 A1 | 6/2024 | Han |
| 2024/0191198 A1 | 6/2024 | Benson |
| 2024/0191200 A1 | 6/2024 | Simmons |
| 2024/0191206 A1 | 6/2024 | Amit |
| 2024/0196944 A1 | 6/2024 | Leung |
| 2024/0200033 A1 | 6/2024 | Banks |
| 2024/0200110 A1 | 6/2024 | Nissinen |
| 2024/0209033 A1 | 6/2024 | Chaung |
| 2024/0218311 A1 | 7/2024 | Nahmias |
| 2024/0218315 A1 | 7/2024 | Vainikka |
| 2024/0218319 A1 | 7/2024 | Ercili-Cura |
| 2024/0225047 A9 | 7/2024 | Stadler |
| 2024/0225060 A1 | 7/2024 | Walker |
| 2024/0228940 A1 | 7/2024 | Goral |
| 2024/0229096 A1 | 7/2024 | Bae |
| 2024/0240133 A1 | 7/2024 | Buchmann |
| 2024/0254419 A1 | 8/2024 | Castillo |
| 2024/0254435 A1 | 8/2024 | Jämsä |
| 2024/0254470 A1 | 8/2024 | Forman |
| 2024/0261371 A1 | 8/2024 | Xiao |
| 2024/0268422 A1 | 8/2024 | Hosseini |
| 2024/0277831 A1 | 8/2024 | King |
| 2024/0287463 A1 | 8/2024 | Chen |
| 2024/0287569 A1 | 8/2024 | Chen |
| 2024/0298678 A1 | 9/2024 | Hosseini |
| 2024/0301442 A1 | 9/2024 | Wang |
| 2024/0315306 A1 | 9/2024 | Larumbe Beramendi |
| 2024/0318133 A1 | 9/2024 | Johnson |
| 2024/0327771 A1 | 10/2024 | Yoshioka |
| 2024/0336895 A1 | 10/2024 | Pelling |
| 2024/0352423 A1 | 10/2024 | Hosseini |
| 2024/0397977 A1 | 12/2024 | Wernimont |
| 2024/0399431 A1 | 12/2024 | Balaban |
| 2024/0400960 A1 | 12/2024 | Thyden |
| 2025/0000123 A1 | 1/2025 | Matthew |
| 2025/0043228 A1 | 2/2025 | Mueller-Auffermann |
| 2025/0043240 A1 | 2/2025 | Ovissipour |
| 2025/0108072 A1 | 4/2025 | Silva |
| 2025/0179122 A1 | 6/2025 | Andrews |
| 2025/0215372 A1 | 7/2025 | Timmins |
| 2025/0280854 A1 | 9/2025 | Badri |
| 2025/0340821 A1 | 11/2025 | Boyce |

FOREIGN PATENT DOCUMENTS

| | | | |
|---|---|---|---|
| CN | 101463319 A | 6/2009 |
| CN | 101603026 B | 1/2011 |
| CN | 102603886 B | 8/2013 |
| CN | 103045636 B | 3/2014 |
| CN | 103113461 B | 6/2014 |
| CN | 102618440 B | 7/2014 |
| CN | 103320461 B | 4/2015 |
| CN | 103468673 B | 8/2015 |
| CN | 103757025 B | 10/2015 |
| CN | 103641903 B | 3/2016 |
| CN | 104292939 B | 4/2016 |
| CN | 103205453 B | 6/2016 |
| CN | 103960457 B | 6/2016 |
| CN | 205662385 U | 10/2016 |
| CN | 104582828 B | 11/2016 |
| CN | 106086041 A | 11/2016 |
| CN | 104445634 B | 3/2017 |
| CN | 104497119 B | 11/2017 |
| CN | 104387465 B | 12/2017 |
| CN | 106811473 B | 5/2018 |
| CN | 105985956 B | 9/2018 |
| CN | 105524158 B | 1/2019 |
| CN | 105731654 B | 2/2019 |
| CN | 105800886 B | 2/2019 |
| CN | 105348380 B | 3/2019 |
| CN | 105622763 B | 3/2019 |
| CN | 106635972 B | 3/2019 |
| CN | 109628533 A | 4/2019 |
| CN | 105199969 B | 5/2019 |
| CN | 106146088 B | 5/2019 |
| CN | 104404012 B | 6/2019 |
| CN | 110484487 A | 11/2019 |
| CN | 110583892 A | 12/2019 |
| CN | 105861594 B | 4/2020 |
| CN | 107176762 B | 6/2020 |
| CN | 107217069 B | 6/2020 |
| CN | 110128519 B | 6/2020 |
| CN | 107188944 B | 7/2020 |
| CN | 107267537 B | 7/2020 |
| CN | 108467426 B | 8/2020 |
| CN | 110257227 B | 8/2020 |
| CN | 111088282 B | 8/2020 |
| CN | 110241023 B | 9/2020 |
| CN | 106929547 B | 10/2020 |
| CN | 109336982 B | 10/2020 |
| CN | 111019881 B | 10/2020 |
| CN | 111808820 A | 10/2020 |
| CN | 106978390 B | 11/2020 |
| CN | 109321519 B | 1/2021 |
| CN | 106635953 B | 2/2021 |
| CN | 107686516 B | 2/2021 |
| CN | 108373510 B | 2/2021 |
| CN | 212488409 U | 2/2021 |
| CN | 112626013 A | 4/2021 |
| CN | 112717120 A | 4/2021 |
| CN | 111087449 B | 5/2021 |
| CN | 110468143 B | 6/2021 |
| CN | 112919718 A | 6/2021 |
| CN | 112941034 A | 6/2021 |
| CN | 107487841 B | 7/2021 |
| CN | 108771028 B | 8/2021 |
| CN | 109055085 B | 8/2021 |
| CN | 111620745 B | 8/2021 |
| CN | 112795531 B | 8/2021 |
| CN | 109021088 B | 9/2021 |
| CN | 109180794 B | 9/2021 |
| CN | 111269926 B | 9/2021 |
| CN | 113355354 A | 9/2021 |
| CN | 109287864 B | 10/2021 |
| CN | 109674023 B | 10/2021 |
| CN | 109467595 B | 11/2021 |
| CN | 108148875 B | 12/2021 |
| CN | 111333700 B | 12/2021 |
| CN | 111333716 B | 12/2021 |
| CN | 111500608 B | 1/2022 |
| CN | 110255699 B | 2/2022 |
| CN | 110697959 B | 2/2022 |
| CN | 114010525 A | 2/2022 |
| CN | 108752455 B | 3/2022 |
| CN | 109206475 B | 3/2022 |
| CN | 111560059 B | 3/2022 |
| CN | 111973805 B | 3/2022 |
| CN | 109536507 B | 4/2022 |
| CN | 111944823 B | 4/2022 |

(56) References Cited

FOREIGN PATENT DOCUMENTS

| | | | |
|---|---|---|---|
| CN | 114106103 | B | 4/2022 |
| CN | 114316017 | A | 4/2022 |
| CN | 114317303 | A | 4/2022 |
| CN | 111153982 | B | 5/2022 |
| CN | 109593630 | B | 6/2022 |
| CN | 110564772 | B | 7/2022 |
| CN | 110804091 | B | 7/2022 |
| CN | 111662370 | B | 7/2022 |
| CN | 110438027 | B | 8/2022 |
| CN | 112225793 | B | 8/2022 |
| CN | 113527513 | B | 8/2022 |
| CN | 114891733 | A | 8/2022 |
| CN | 114958716 | A | 8/2022 |
| CN | 217265341 | U | 8/2022 |
| CN | 111500590 | B | 9/2022 |
| CN | 114990055 | A | 9/2022 |
| CN | 217377581 | U | 9/2022 |
| CN | 115247180 | A | 10/2022 |
| CN | 115247188 | A | 10/2022 |
| CN | 115247189 | A | 10/2022 |
| CN | 109504680 | B | 11/2022 |
| CN | 114540123 | B | 11/2022 |
| CN | 113025563 | B | 12/2022 |
| CN | 115462435 | A | 12/2022 |
| CN | 115595296 | A | 1/2023 |
| CN | 115651891 | A | 1/2023 |
| CN | 112961833 | B | 3/2023 |
| CN | 115820372 | A | 3/2023 |
| CN | 115820564 | A | 3/2023 |
| CN | 115820607 | A | 3/2023 |
| CN | 112501126 | B | 4/2023 |
| CN | 114804533 | B | 4/2023 |
| CN | 115975806 | A | 4/2023 |
| CN | 116004520 | A | 4/2023 |
| CN | 218860500 | U | 4/2023 |
| CN | 111892646 | B | 5/2023 |
| CN | 114835824 | B | 5/2023 |
| CN | 115536711 | B | 5/2023 |
| CN | 116041478 | A | 5/2023 |
| CN | 116042681 | A | 5/2023 |
| CN | 116103166 | A | 5/2023 |
| CN | 116121174 | A | 5/2023 |
| CN | 219079145 | U | 5/2023 |
| CN | 110592004 | B | 6/2023 |
| CN | 112522205 | B | 6/2023 |
| CN | 114712485 | B | 6/2023 |
| CN | 116200372 | A | 6/2023 |
| CN | 116200420 | A | 6/2023 |
| CN | 116217681 | A | 6/2023 |
| CN | 116239702 | A | 6/2023 |
| CN | 116254220 | A | 6/2023 |
| CN | 116327884 | A | 6/2023 |
| CN | 219186467 | U | 6/2023 |
| CN | 114317330 | B | 7/2023 |
| CN | 114767757 | B | 7/2023 |
| CN | 116376951 | A | 7/2023 |
| CN | 113754784 | B | 8/2023 |
| CN | 115044541 | B | 8/2023 |
| CN | 116333075 | B | 8/2023 |
| CN | 116555389 | A | 8/2023 |
| CN | 116621643 | A | 8/2023 |
| CN | 113862277 | B | 9/2023 |
| CN | 114751991 | B | 9/2023 |
| CN | 115485367 | B | 9/2023 |
| CN | 115975002 | B | 9/2023 |
| CN | 116458565 | B | 9/2023 |
| CN | 116693650 | A | 9/2023 |
| CN | 116731120 | A | 9/2023 |
| CN | 116731148 | A | 9/2023 |
| CN | 116801725 | A | 9/2023 |
| CN | 113717973 | B | 10/2023 |
| CN | 115404222 | B | 10/2023 |
| CN | 116590225 | B | 10/2023 |
| CN | 116926014 | A | 10/2023 |
| CN | 116970548 | A | 10/2023 |
| CN | 114805534 | B | 11/2023 |
| CN | 116333159 | B | 11/2023 |
| CN | 116732099 | B | 11/2023 |
| CN | 117004555 | A | 11/2023 |
| CN | 117070381 | A | 11/2023 |
| CN | 117126894 | A | 11/2023 |
| CN | 114525304 | B | 12/2023 |
| CN | 116987200 | B | 12/2023 |
| CN | 117210386 | A | 12/2023 |
| CN | 117243262 | A | 12/2023 |
| CN | 117247886 | A | 12/2023 |
| CN | 117247897 | A | 12/2023 |
| CN | 117281134 | A | 12/2023 |
| CN | 117304334 | A | 12/2023 |
| CN | 117363577 | A | 1/2024 |
| CN | 117430685 | A | 1/2024 |
| CN | 113908252 | B | 2/2024 |
| CN | 116143899 | B | 2/2024 |
| CN | 116875476 | B | 2/2024 |
| CN | 117486981 | A | 2/2024 |
| CN | 117511861 | A | 2/2024 |
| CN | 117535349 | A | 2/2024 |
| CN | 117551693 | A | 2/2024 |
| CN | 117551694 | A | 2/2024 |
| CN | 117551729 | A | 2/2024 |
| CN | 117568267 | A | 2/2024 |
| CN | 117586424 | A | 2/2024 |
| CN | 117599112 | A | 2/2024 |
| CN | 117603902 | A | 2/2024 |
| CN | 115386541 | B | 3/2024 |
| CN | 117384275 | B | 3/2024 |
| CN | 117486996 | B | 3/2024 |
| CN | 117643791 | A | 3/2024 |
| CN | 117717503 | A | 3/2024 |
| CN | 117737103 | A | 3/2024 |
| CN | 117778468 | A | 3/2024 |
| CN | 111471644 | B | 4/2024 |
| CN | 114316031 | B | 4/2024 |
| CN | 114790237 | B | 4/2024 |
| CN | 114958761 | B | 4/2024 |
| CN | 114990056 | B | 4/2024 |
| CN | 117447580 | B | 4/2024 |
| CN | 117837749 | A | 4/2024 |
| CN | 117866883 | A | 4/2024 |
| CN | 114686438 | B | 5/2024 |
| CN | 116003541 | B | 5/2024 |
| CN | 116262781 | B | 5/2024 |
| CN | 116262782 | B | 5/2024 |
| CN | 116986758 | B | 5/2024 |
| CN | 117959819 | A | 5/2024 |
| CN | 117964154 | A | 5/2024 |
| CN | 117965599 | A | 5/2024 |
| CN | 117987355 | A | 5/2024 |
| CN | 118048371 | A | 5/2024 |
| CN | 118086050 | A | 5/2024 |
| CN | 118086356 | A | 5/2024 |
| CN | 118108545 | A | 5/2024 |
| CN | 220907314 | U | 5/2024 |
| CN | 116218695 | B | 6/2024 |
| CN | 117586842 | B | 6/2024 |
| CN | 118146312 | A | 6/2024 |
| CN | 118207231 | A | 6/2024 |
| CN | 118291386 | A | 7/2024 |
| CN | 118344490 | A | 7/2024 |
| CN | 118373892 | A | 7/2024 |
| CN | 118374440 | A | 7/2024 |
| CN | 118388055 | A | 7/2024 |
| CN | 116924844 | B | 8/2024 |
| CN | 118439747 | A | 8/2024 |
| CN | 118440883 | A | 8/2024 |
| CN | 118440891 | A | 8/2024 |
| CN | 118460420 | A | 8/2024 |
| CN | 118497116 | A | 8/2024 |
| CN | 118546864 | A | 8/2024 |
| CN | 116058444 | B | 9/2024 |
| CN | 118598338 | A | 9/2024 |
| CN | 118702786 | A | 9/2024 |
| CN | 116003512 | B | 10/2024 |
| CN | 118059163 | B | 10/2024 |

(56)        References Cited

FOREIGN PATENT DOCUMENTS

| | | | |
|---|---|---|---|
| CN | 118389446 | B | 10/2024 |
| CN | 118633673 | B | 10/2024 |
| CN | 118724315 | A | 10/2024 |
| CN | 118726142 | A | 10/2024 |
| CN | 118813529 | A | 10/2024 |
| CN | 221788804 | U | 10/2024 |
| CN | 116555266 | B | 11/2024 |
| CN | 117886893 | B | 11/2024 |
| CN | 118872847 | A | 11/2024 |
| CN | 118878701 | A | 11/2024 |
| CN | 118909950 | A | 11/2024 |
| CN | 118956737 | A | 11/2024 |
| CN | 118956911 | A | 11/2024 |
| CN | 119014506 | A | 11/2024 |
| CN | 119020438 | A | 11/2024 |
| CN | 119039392 | A | 11/2024 |
| CN | 117624382 | B | 12/2024 |
| CN | 118324849 | B | 12/2024 |
| CN | 118581048 | B | 12/2024 |
| CN | 119113034 | A | 12/2024 |
| CN | 119120354 | A | 12/2024 |
| CN | 119144663 | A | 12/2024 |
| CN | 119193265 | A | 12/2024 |
| CN | 119193355 | A | 12/2024 |
| CN | 119193471 | A | 12/2024 |
| CN | 119193472 | A | 12/2024 |
| CN | 118546228 | B | 1/2025 |
| CN | 119235703 | A | 1/2025 |
| CN | 119242709 | A | 1/2025 |
| CN | 119265260 | A | 1/2025 |
| CN | 119318609 | A | 1/2025 |
| CN | 119320777 | A | 1/2025 |
| CN | 119350464 | A | 1/2025 |
| CN | 114874978 | B | 2/2025 |
| CN | 118995825 | B | 2/2025 |
| CN | 118995826 | B | 2/2025 |
| CN | 119214214 | B | 2/2025 |
| CN | 119432767 | A | 2/2025 |
| CN | 119464267 | A | 2/2025 |
| CN | 119523087 | A | 2/2025 |
| CN | 119529034 | A | 2/2025 |
| CN | 119530146 | A | 2/2025 |
| CN | 118755665 | B | 3/2025 |
| CN | 119563773 | A | 3/2025 |
| CN | 119662526 | A | 3/2025 |
| CN | 119685251 | A | 3/2025 |
| CN | 119700624 | A | 3/2025 |
| CN | 116925199 | B | 4/2025 |
| CN | 119490567 | B | 4/2025 |
| CN | 119745714 | A | 4/2025 |
| CN | 119776473 | A | 4/2025 |
| CN | 119824043 | A | 4/2025 |
| CN | 119842678 | A | 4/2025 |
| CN | 119874939 | A | 4/2025 |
| CN | 116083350 | B | 5/2025 |
| CN | 119912542 | A | 5/2025 |
| CN | 119913201 | A | 5/2025 |
| CN | 119932079 | A | 5/2025 |
| CN | 119950382 | A | 5/2025 |
| CN | 119979470 | A | 5/2025 |
| CN | 120040325 | A | 5/2025 |
| CN | 120060399 | A | 5/2025 |
| CN | 118186038 | B | 6/2025 |
| CN | 119530102 | B | 6/2025 |
| CN | 120098096 | A | 6/2025 |
| CN | 120098904 | A | 6/2025 |
| CN | 120098929 | A | 6/2025 |
| CN | 120136978 | A | 6/2025 |
| CN | 120137844 | A | 6/2025 |
| CN | 120137888 | A | 6/2025 |
| CN | 120138095 | A | 6/2025 |
| CN | 118440172 | B | 7/2025 |
| CN | 118791576 | B | 7/2025 |
| CN | 119177256 | B | 7/2025 |
| CN | 119776442 | B | 7/2025 |
| CN | 119979551 | B | 7/2025 |
| CN | 120240570 | A | 7/2025 |
| CN | 120241960 | A | 7/2025 |
| CN | 120248133 | A | 7/2025 |
| CN | 120272479 | A | 7/2025 |
| CN | 120289658 | A | 7/2025 |
| CN | 120361192 | A | 7/2025 |
| CN | 116284346 | B | 8/2025 |
| CN | 119823285 | B | 8/2025 |
| CN | 120400160 | A | 8/2025 |
| CN | 120425015 | A | 8/2025 |
| CN | 120247599 | B | 9/2025 |
| CN | 120249193 | B | 9/2025 |
| CN | 120590479 | A | 9/2025 |
| CN | 120665174 | A | 9/2025 |
| CN | 120700159 | A | 9/2025 |
| CN | 117305394 | B | 10/2025 |
| CN | 118421739 | B | 10/2025 |
| CN | 120365401 | B | 10/2025 |
| CN | 120733036 | A | 10/2025 |
| CN | 120757608 | A | 10/2025 |
| CN | 120796498 | A | 10/2025 |
| CN | 120131528 | B | 11/2025 |
| CN | 118235848 | B | 12/2025 |
| EP | 0234773 | B1 | 4/1992 |
| EP | 1096017 | A2 | 5/2001 |
| EP | 2708232 | B1 | 11/2016 |
| EP | 2965745 | B1 | 8/2017 |
| EP | 2853584 | B1 | 3/2021 |
| EP | 4108307 | A3 | 2/2023 |
| EP | 4328296 | A1 | 2/2024 |
| EP | 4418882 | A1 | 8/2024 |
| EP | 4445745 | A1 | 10/2024 |
| EP | 4501443 | A1 | 2/2025 |
| EP | 4624571 | A1 | 10/2025 |
| GB | 2385767 | A | 9/2003 |
| IN | 201621025611 | A | 2/2018 |
| IN | 202421035535 | A | 5/2024 |
| IN | 202421103034 | A | 1/2025 |
| IN | 202521005363 | A | 3/2025 |
| JP | 4635196 | B2 | 2/2011 |
| JP | 4978913 | B2 | 7/2012 |
| JP | 6089189 | B2 | 3/2017 |
| JP | 6351952 | B2 | 7/2018 |
| JP | 6901091 | B2 | 7/2021 |
| JP | 2023039157 | A | 3/2023 |
| JP | 2023055867 | | 4/2023 |
| JP | 7475873 | B2 | 4/2024 |
| KR | 101033738 | B1 | 5/2011 |
| KR | 101121077 | B1 | 6/2012 |
| KR | 101434734 | B1 | 9/2014 |
| KR | 101754272 | B1 | 7/2017 |
| KR | 101956097 | B1 | 3/2019 |
| KR | 101970888 | B1 | 4/2019 |
| KR | 102040203 | B1 | 11/2019 |
| KR | 102200324 | B1 | 1/2021 |
| KR | 20210105789 | A | 8/2021 |
| KR | 102362988 | B1 | 2/2022 |
| KR | 102414754 | B1 | 6/2022 |
| KR | 20230057206 | A | 4/2023 |
| KR | 102529976 | B1 | 5/2023 |
| KR | 20230079340 | A | 6/2023 |
| KR | 20230109353 | A | 7/2023 |
| KR | 102581772 | B1 | 9/2023 |
| KR | 20240077718 | A | 6/2024 |
| KR | 20240164155 | A | 11/2024 |
| KR | 20250073874 | A | 5/2025 |
| KR | 20250100942 | A | 7/2025 |
| KR | 102882918 | B1 | 11/2025 |
| RU | 2755539 | C1 | 9/2021 |
| TW | 200533742 | A | 10/2005 |
| TW | 1715083 | B | 1/2021 |
| TW | 202111110 | A | 3/2021 |
| TW | 202239332 | | 10/2022 |
| TW | M638177 | U | 3/2023 |
| WO | 1995008630 | A1 | 3/1995 |
| WO | 1998037880 | A1 | 9/1998 |
| WO | 1999008539 | A1 | 2/1999 |
| WO | 1999063058 | A1 | 12/1999 |

(56) References Cited

FOREIGN PATENT DOCUMENTS

| | | | | | |
|---|---|---|---|---|---|
| WO | 2000071728 | A1 | 11/2000 | | |
| WO | 0114529 | A1 | 3/2001 | | |
| WO | 2001060166 | A1 | 8/2001 | | |
| WO | WO 01/62947 | * | 8/2001 | ............... | C12P 7/06 |
| WO | 0164047 | A1 | 9/2001 | | |
| WO | 0190333 | A2 | 11/2001 | | |
| WO | 0164047 | A9 | 6/2002 | | |
| WO | 0114529 | A9 | 9/2002 | | |
| WO | 2002067690 | A1 | 9/2002 | | |
| WO | 02095003 | A2 | 11/2002 | | |
| WO | 2002090527 | A1 | 11/2002 | | |
| WO | 0190333 | A3 | 1/2003 | | |
| WO | 03012058 | A2 | 2/2003 | | |
| WO | 2003045317 | A2 | 6/2003 | | |
| WO | 2003051908 | A1 | 6/2003 | | |
| WO | 03094835 | A2 | 11/2003 | | |
| WO | 03012058 | A3 | 12/2003 | | |
| WO | 2004005493 | A1 | 1/2004 | | |
| WO | 2004023887 | A1 | 3/2004 | | |
| WO | 2004055155 | A2 | 7/2004 | | |
| WO | 2004069298 | A1 | 8/2004 | | |
| WO | 02095003 | A3 | 9/2004 | | |
| WO | 2004055155 | A3 | 9/2004 | | |
| WO | 2004078924 | A3 | 5/2005 | | |
| WO | 2005083058 | A1 | 9/2005 | | |
| WO | 2005090564 | A1 | 9/2005 | | |
| WO | 2005120244 | A1 | 12/2005 | | |
| WO | 2005108617 | A3 | 2/2006 | | |
| WO | 2006028684 | A2 | 3/2006 | | |
| WO | 2006029197 | A1 | 3/2006 | | |
| WO | 2006029198 | A2 | 3/2006 | | |
| WO | 2006041429 | A2 | 4/2006 | | |
| WO | 2006029198 | A3 | 5/2006 | | |
| WO | 2006048783 | A2 | 5/2006 | | |
| WO | 2006053010 | A2 | 5/2006 | | |
| WO | 2006053010 | A3 | 7/2006 | | |
| WO | 2006048783 | A8 | 8/2006 | | |
| WO | 2006048783 | A3 | 11/2006 | | |
| WO | 2007005370 | A1 | 1/2007 | | |
| WO | 03094835 | A3 | 3/2007 | | |
| WO | 2006097110 | A3 | 4/2007 | | |
| WO | 2007049904 | A1 | 5/2007 | | |
| WO | 2006041429 | A3 | 6/2007 | | |
| WO | 2007042577 | A3 | 6/2007 | | |
| WO | 2007066694 | A1 | 6/2007 | | |
| WO | 2007079936 | A1 | 7/2007 | | |
| WO | 2007085412 | A1 | 8/2007 | | |
| WO | 2007085412 | B1 | 10/2007 | | |
| WO | 2007111105 | A1 | 10/2007 | | |
| WO | 2007141309 | A2 | 12/2007 | | |
| WO | 2007146689 | A2 | 12/2007 | | |
| WO | 2008036916 | A2 | 3/2008 | | |
| WO | 2007146689 | A3 | 4/2008 | | |
| WO | 2008038287 | A2 | 4/2008 | | |
| WO | 2007141309 | A3 | 5/2008 | | |
| WO | 2008051854 | A9 | 6/2008 | | |
| WO | 2008085879 | A2 | 7/2008 | | |
| WO | 2008106012 | A1 | 9/2008 | | |
| WO | 2008124133 | A1 | 10/2008 | | |
| WO | 2008128289 | A1 | 10/2008 | | |
| WO | 2008036916 | A3 | 11/2008 | | |
| WO | 2008085879 | A3 | 11/2008 | | |
| WO | 2008121563 | A3 | 11/2008 | | |
| WO | 2008134220 | A1 | 11/2008 | | |
| WO | 2008136398 | A1 | 11/2008 | | |
| WO | 2008141207 | A1 | 11/2008 | | |
| WO | 2009006930 | A1 | 1/2009 | | |
| WO | 2009006997 | A1 | 1/2009 | | |
| WO | 2009007852 | A2 | 1/2009 | | |
| WO | 2008033517 | A9 | 2/2009 | | |
| WO | 2009023562 | A2 | 2/2009 | | |
| WO | 2009036113 | A1 | 3/2009 | | |
| WO | 2009039001 | A1 | 3/2009 | | |
| WO | 2006028684 | A3 | 4/2009 | | |
| WO | 2008038287 | A3 | 4/2009 | | |
| WO | 2008133938 | A3 | 4/2009 | | |
| WO | 2009046978 | A1 | 4/2009 | | |
| WO | 2009047007 | A1 | 4/2009 | | |
| WO | 2009048119 | A1 | 4/2009 | | |
| WO | 2009023562 | A3 | 5/2009 | | |
| WO | 2009078333 | A1 | 6/2009 | | |
| WO | 2009007852 | A3 | 8/2009 | | |
| WO | 2009080912 | A3 | 8/2009 | | |
| WO | 2009114702 | A2 | 9/2009 | | |
| WO | 2009145875 | A1 | 12/2009 | | |
| WO | 2009149171 | A2 | 12/2009 | | |
| WO | 2009151541 | A1 | 12/2009 | | |
| WO | 2009152484 | A2 | 12/2009 | | |
| WO | 2009152485 | A2 | 12/2009 | | |
| WO | 2009156030 | A1 | 12/2009 | | |
| WO | 2009156413 | A1 | 12/2009 | | |
| WO | 2010009478 | A2 | 1/2010 | | |
| WO | 2008149353 | A3 | 2/2010 | | |
| WO | 2009114702 | A3 | 2/2010 | | |
| WO | 2009149171 | A3 | 3/2010 | | |
| WO | 2009152484 | A3 | 3/2010 | | |
| WO | 2010009478 | A3 | 3/2010 | | |
| WO | 2010022508 | A1 | 3/2010 | | |
| WO | 2010022509 | A1 | 3/2010 | | |
| WO | 2010033085 | A1 | 3/2010 | | |
| WO | 2009149171 | A4 | 5/2010 | | |
| WO | 2009152485 | A3 | 5/2010 | | |
| WO | 2010050448 | A1 | 5/2010 | | |
| WO | 2010072676 | A1 | 7/2010 | | |
| WO | 2010080826 | A1 | 7/2010 | | |
| WO | 2010086078 | A1 | 8/2010 | | |
| WO | 2010089151 | A1 | 8/2010 | | |
| WO | 2010092335 | A1 | 8/2010 | | |
| WO | 2010110767 | A1 | 9/2010 | | |
| WO | 2010080985 | A8 | 10/2010 | | |
| WO | 2010115185 | A1 | 10/2010 | | |
| WO | 2010089151 | A8 | 11/2010 | | |
| WO | 2010125006 | A1 | 11/2010 | | |
| WO | 2010129503 | A1 | 11/2010 | | |
| WO | 2010129600 | A2 | 11/2010 | | |
| WO | 2010135247 | A1 | 11/2010 | | |
| WO | 2010135588 | A2 | 11/2010 | | |
| WO | 2007146689 | A9 | 12/2010 | | |
| WO | 2010135588 | A3 | 1/2011 | | |
| WO | 2011008959 | A1 | 1/2011 | | |
| WO | 2011014363 | A1 | 2/2011 | | |
| WO | 2011014391 | A1 | 2/2011 | | |
| WO | 2010129600 | A3 | 4/2011 | | |
| WO | 2011011072 | A3 | 4/2011 | | |
| WO | 2011053281 | A1 | 5/2011 | | |
| WO | 2011056183 | A1 | 5/2011 | | |
| WO | 2011058558 | A2 | 5/2011 | | |
| WO | 2011060613 | A9 | 6/2011 | | |
| WO | 2011068526 | A1 | 6/2011 | | |
| WO | 2011073199 | A1 | 6/2011 | | |
| WO | 2011091111 | A1 | 7/2011 | | |
| WO | 2011058558 | A3 | 10/2011 | | |
| WO | 2011133902 | A2 | 10/2011 | | |
| WO | 2011134920 | A1 | 11/2011 | | |
| WO | 2011139804 | A2 | 11/2011 | | |
| WO | 2011133886 | A3 | 12/2011 | | |
| WO | 2011154525 | A1 | 12/2011 | | |
| WO | 2011159071 | A2 | 12/2011 | | |
| WO | 2011159359 | A2 | 12/2011 | | |
| WO | 2012019122 | A2 | 2/2012 | | |
| WO | 2012019160 | A1 | 2/2012 | | |
| WO | 2012027533 | A2 | 3/2012 | | |
| WO | 2012029909 | A1 | 3/2012 | | |
| WO | 2012040550 | A1 | 3/2012 | | |
| WO | 2011133902 | A3 | 4/2012 | | |
| WO | 2011139804 | A3 | 4/2012 | | |
| WO | 2011159895 | A2 | 5/2012 | | |
| WO | 2012019122 | A3 | 5/2012 | | |
| WO | 2011159071 | A3 | 6/2012 | | |
| WO | 2012078037 | A1 | 6/2012 | | |
| WO | 2012027209 | A3 | 7/2012 | | |
| WO | 2012097079 | A2 | 7/2012 | | |
| WO | 2012099279 | A1 | 7/2012 | | |
| WO | 2012099786 | A1 | 7/2012 | | |

(56) References Cited

FOREIGN PATENT DOCUMENTS

| | | | |
|---|---|---|---|
| WO | 2012106759 | A1 | 8/2012 |
| WO | 2012109279 | A2 | 8/2012 |
| WO | 2012109279 | A3 | 10/2012 |
| WO | 2012145682 | A1 | 10/2012 |
| WO | 2012147048 | A2 | 11/2012 |
| WO | 2012154738 | A1 | 11/2012 |
| WO | 2012158244 | A2 | 11/2012 |
| WO | 2012163368 | A1 | 12/2012 |
| WO | 2012166973 | A1 | 12/2012 |
| WO | 2012173078 | A1 | 12/2012 |
| WO | 2012147048 | A3 | 1/2013 |
| WO | 2012158244 | A3 | 1/2013 |
| WO | 2013010048 | A2 | 1/2013 |
| WO | 2013040688 | A1 | 3/2013 |
| WO | 2013010048 | A3 | 4/2013 |
| WO | 2013049247 | A1 | 4/2013 |
| WO | 2013049692 | A1 | 4/2013 |
| WO | 2012097079 | A3 | 6/2013 |
| WO | 2013082309 | A1 | 6/2013 |
| WO | 2013090769 | A2 | 6/2013 |
| WO | 2013090919 | A1 | 6/2013 |
| WO | 2013096386 | A1 | 6/2013 |
| WO | 2013106548 | A1 | 7/2013 |
| WO | 2013090769 | A3 | 8/2013 |
| WO | 2013116432 | A1 | 8/2013 |
| WO | 2013122864 | A1 | 8/2013 |
| WO | 2013148348 | A1 | 10/2013 |
| WO | 2013158312 | A1 | 10/2013 |
| WO | 2013166339 | A1 | 11/2013 |
| WO | 2013169802 | A1 | 11/2013 |
| WO | 2013170017 | A2 | 11/2013 |
| WO | 2013170636 | A1 | 11/2013 |
| WO | 2013172628 | A1 | 11/2013 |
| WO | 2013182553 | A2 | 12/2013 |
| WO | 2013184958 | A1 | 12/2013 |
| WO | 2013184960 | A2 | 12/2013 |
| WO | 2013184962 | A1 | 12/2013 |
| WO | 2013186294 | A1 | 12/2013 |
| WO | 2013182553 | A3 | 1/2014 |
| WO | 2013184962 | A4 | 1/2014 |
| WO | 2014010746 | A1 | 1/2014 |
| WO | 2013170017 | A3 | 2/2014 |
| WO | 2013184958 | A4 | 2/2014 |
| WO | 2013184960 | A3 | 3/2014 |
| WO | 2014037919 | A1 | 3/2014 |
| WO | 2014046293 | A1 | 3/2014 |
| WO | 2014060898 | A2 | 4/2014 |
| WO | 2014071419 | A2 | 5/2014 |
| WO | 2014074012 | A1 | 5/2014 |
| WO | 2014075807 | A1 | 5/2014 |
| WO | 2014052451 | A3 | 6/2014 |
| WO | 2014060898 | A3 | 6/2014 |
| WO | 2014084027 | A1 | 6/2014 |
| WO | 2014094386 | A1 | 6/2014 |
| WO | 2014110512 | A1 | 7/2014 |
| WO | 2014144198 | A1 | 9/2014 |
| WO | 2014145593 | A2 | 9/2014 |
| WO | 2014148361 | A1 | 9/2014 |
| WO | 2014152603 | A1 | 9/2014 |
| WO | 2014182242 | A1 | 11/2014 |
| WO | 2014199114 | A1 | 12/2014 |
| WO | 2014145593 | A3 | 1/2015 |
| WO | 2015003773 | A1 | 1/2015 |
| WO | 2015027209 | A2 | 2/2015 |
| WO | 2015038988 | A1 | 3/2015 |
| WO | 2015047298 | A1 | 4/2015 |
| WO | 2015057980 | A1 | 4/2015 |
| WO | 2015061361 | A1 | 4/2015 |
| WO | 2015027209 | A3 | 5/2015 |
| WO | 2015066377 | A1 | 5/2015 |
| WO | 2015070372 | A1 | 5/2015 |
| WO | 2015086783 | A1 | 6/2015 |
| WO | 2015095809 | A1 | 6/2015 |
| WO | 2015101510 | A1 | 7/2015 |
| WO | 2015102528 | A1 | 7/2015 |
| WO | 2015118233 | A1 | 8/2015 |
| WO | 2015120174 | A1 | 8/2015 |
| WO | 2015121471 | A1 | 8/2015 |
| WO | 2015140708 | A1 | 9/2015 |
| WO | 2015148515 | A1 | 10/2015 |
| WO | 2015165583 | A1 | 11/2015 |
| WO | 2015171644 | A1 | 11/2015 |
| WO | 2015188131 | A1 | 12/2015 |
| WO | 2015191462 | A1 | 12/2015 |
| WO | 2015194208 | A1 | 12/2015 |
| WO | 2015172002 | A3 | 1/2016 |
| WO | 2016010165 | A1 | 1/2016 |
| WO | 2016016894 | A1 | 2/2016 |
| WO | 2016023775 | A1 | 2/2016 |
| WO | 2016027850 | A1 | 2/2016 |
| WO | 2010042189 | A3 | 3/2016 |
| WO | 2015185691 | A9 | 3/2016 |
| WO | 2016033241 | A1 | 3/2016 |
| WO | 2016036275 | A1 | 3/2016 |
| WO | 2016065326 | A2 | 4/2016 |
| WO | 2016073858 | A1 | 5/2016 |
| WO | 2016076761 | A1 | 5/2016 |
| WO | 2016065326 | A3 | 6/2016 |
| WO | 2016087560 | A1 | 6/2016 |
| WO | 2016091349 | A1 | 6/2016 |
| WO | 2016099971 | A1 | 6/2016 |
| WO | 2016110786 | A1 | 7/2016 |
| WO | 2015171928 | A8 | 8/2016 |
| WO | 2016120594 | A1 | 8/2016 |
| WO | 2016025750 | A3 | 9/2016 |
| WO | 2016139340 | A1 | 9/2016 |
| WO | 2016143826 | A1 | 9/2016 |
| WO | 2016110786 | A8 | 10/2016 |
| WO | 2016156476 | A1 | 10/2016 |
| WO | 2016166310 | A1 | 10/2016 |
| WO | 2016168454 | A1 | 10/2016 |
| WO | 2016057529 | A3 | 11/2016 |
| WO | 2016176456 | A1 | 11/2016 |
| WO | 2016190394 | A1 | 12/2016 |
| WO | 2016195157 | A1 | 12/2016 |
| WO | 2017011598 | A1 | 1/2017 |
| WO | 2017025210 | A1 | 2/2017 |
| WO | 2017026462 | A1 | 2/2017 |
| WO | 2017042242 | A1 | 3/2017 |
| WO | 2017044864 | A1 | 3/2017 |
| WO | 2017049094 | A1 | 3/2017 |
| WO | 2017062517 | A1 | 4/2017 |
| WO | 2017066471 | A1 | 4/2017 |
| WO | 2017070303 | A1 | 4/2017 |
| WO | 2017075260 | A1 | 5/2017 |
| WO | 2017078176 | A1 | 5/2017 |
| WO | 2017081214 | A1 | 5/2017 |
| WO | 2017085086 | A1 | 5/2017 |
| WO | 2017089016 | A1 | 6/2017 |
| WO | 2017091943 | A1 | 6/2017 |
| WO | 2017097983 | A1 | 6/2017 |
| WO | 2017116449 | A1 | 7/2017 |
| WO | 2017117091 | A1 | 7/2017 |
| WO | 2017117559 | A1 | 7/2017 |
| WO | 2017124100 | A1 | 7/2017 |
| WO | 2016176456 | A9 | 8/2017 |
| WO | 2017132185 | A1 | 8/2017 |
| WO | 2017143071 | A1 | 8/2017 |
| WO | 2017146646 | A1 | 8/2017 |
| WO | 2017147216 | A1 | 8/2017 |
| WO | 2017149025 | A1 | 9/2017 |
| WO | 2017165244 | A1 | 9/2017 |
| WO | 2017174329 | A1 | 10/2017 |
| WO | 2017175086 | A1 | 10/2017 |
| WO | 2017177169 | A1 | 10/2017 |
| WO | 2017180669 | A1 | 10/2017 |
| WO | 2017189683 | A1 | 11/2017 |
| WO | 2017191691 | A1 | 11/2017 |
| WO | 2017193087 | A1 | 11/2017 |
| WO | 2017196175 | A1 | 11/2017 |
| WO | 2017207822 | A1 | 12/2017 |
| WO | 2017216620 | A1 | 12/2017 |
| WO | 2017223457 | A1 | 12/2017 |
| WO | 2018007597 | A1 | 1/2018 |

(56)  References Cited

FOREIGN PATENT DOCUMENTS

| | | | |
|---|---|---|---|
| WO | 2018011805 | A2 | 1/2018 |
| WO | 2018016814 | A1 | 1/2018 |
| WO | 2018017419 | A1 | 1/2018 |
| WO | 2017193087 | A8 | 2/2018 |
| WO | 2018011805 | A3 | 2/2018 |
| WO | 2018033542 | A1 | 2/2018 |
| WO | 2018034655 | A1 | 2/2018 |
| WO | 2018035158 | A1 | 2/2018 |
| WO | 2018038711 | A1 | 3/2018 |
| WO | 2018011805 | A9 | 4/2018 |
| WO | 2018049025 | A3 | 5/2018 |
| WO | 2018096343 | A1 | 5/2018 |
| WO | 2018102780 | A1 | 6/2018 |
| WO | 2018104197 | A1 | 6/2018 |
| WO | 2017100313 | A8 | 7/2018 |
| WO | 2018081476 | A9 | 7/2018 |
| WO | 2018125631 | A1 | 7/2018 |
| WO | 2018132494 | A1 | 7/2018 |
| WO | 2018138515 | A1 | 8/2018 |
| WO | 2018144965 | A1 | 8/2018 |
| WO | 2018146689 | A1 | 8/2018 |
| WO | 2018148376 | A1 | 8/2018 |
| WO | 2018155913 | A1 | 8/2018 |
| WO | 2018162346 | A1 | 9/2018 |
| WO | 2018162353 | A1 | 9/2018 |
| WO | 2018167621 | A1 | 9/2018 |
| WO | 2018185025 | A1 | 10/2018 |
| WO | 2018185634 | A1 | 10/2018 |
| WO | 2018187568 | A1 | 10/2018 |
| WO | 2018189738 | A1 | 10/2018 |
| WO | 2018204497 | A1 | 11/2018 |
| WO | 2018204847 | A2 | 11/2018 |
| WO | 2018205985 | A1 | 11/2018 |
| WO | 2018208628 | A1 | 11/2018 |
| WO | 2018208836 | A1 | 11/2018 |
| WO | 2017214709 | A8 | 12/2018 |
| WO | 2018227016 | A1 | 12/2018 |
| WO | 2018232750 | A1 | 12/2018 |
| WO | 2018234430 | A1 | 12/2018 |
| WO | 2019010116 | A1 | 1/2019 |
| WO | 2019014652 | A1 | 1/2019 |
| WO | 2019016795 | A1 | 1/2019 |
| WO | 2019018660 | A1 | 1/2019 |
| WO | 2019030069 | A2 | 2/2019 |
| WO | 2019032725 | A1 | 2/2019 |
| WO | 2019046782 | A2 | 3/2019 |
| WO | 2019032725 | A8 | 4/2019 |
| WO | 2019067966 | A1 | 4/2019 |
| WO | 2019046782 | A3 | 5/2019 |
| WO | 2019092054 | A1 | 5/2019 |
| WO | 2019098310 | A1 | 5/2019 |
| WO | 2019088496 | A3 | 6/2019 |
| WO | 2019108756 | A1 | 6/2019 |
| WO | 2019113556 | A1 | 6/2019 |
| WO | 2019115675 | A1 | 6/2019 |
| WO | 2019122239 | A1 | 6/2019 |
| WO | 2019126438 | A1 | 6/2019 |
| WO | 2019126748 | A1 | 6/2019 |
| WO | 2019088528 | A3 | 7/2019 |
| WO | 2019140260 | A1 | 7/2019 |
| WO | 2019144968 | A1 | 8/2019 |
| WO | 2019171298 | A1 | 9/2019 |
| WO | 2019178508 | A1 | 9/2019 |
| WO | 2019181999 | A1 | 9/2019 |
| WO | 2019182156 | A1 | 9/2019 |
| WO | 2019169233 | A9 | 10/2019 |
| WO | 2019191495 | A1 | 10/2019 |
| WO | 2019209892 | A1 | 10/2019 |
| WO | 2019210870 | A1 | 11/2019 |
| WO | 2019211189 | A1 | 11/2019 |
| WO | 2019212293 | A1 | 11/2019 |
| WO | 2019212973 | A1 | 11/2019 |
| WO | 2019224467 | A1 | 11/2019 |
| WO | 2019231848 | A1 | 12/2019 |
| WO | 2019234442 | A1 | 12/2019 |
| WO | 2019240221 | A1 | 12/2019 |
| WO | 2019245278 | A1 | 12/2019 |
| WO | 2019246066 | A1 | 12/2019 |
| WO | 2020006409 | A1 | 1/2020 |
| WO | 2020016655 | A2 | 1/2020 |
| WO | 2020023450 | A1 | 1/2020 |
| WO | 2020030628 | A1 | 2/2020 |
| WO | 2020036184 | A1 | 2/2020 |
| WO | 2020016655 | A3 | 3/2020 |
| WO | 2020047124 | A1 | 3/2020 |
| WO | 2020047300 | A1 | 3/2020 |
| WO | 2020049535 | A1 | 3/2020 |
| WO | 2020051042 | A1 | 3/2020 |
| WO | 2020056343 | A1 | 3/2020 |
| WO | 2019115675 | A9 | 4/2020 |
| WO | 2020067502 | A1 | 4/2020 |
| WO | 2020072125 | A1 | 4/2020 |
| WO | 2020072140 | A1 | 4/2020 |
| WO | 2020076776 | A1 | 4/2020 |
| WO | 2020077144 | A1 | 4/2020 |
| WO | 2020081097 | A1 | 4/2020 |
| WO | 2020081128 | A1 | 4/2020 |
| WO | 2020095305 | A1 | 5/2020 |
| WO | 2020097083 | A1 | 5/2020 |
| WO | 2020100143 | A1 | 5/2020 |
| WO | 2020104650 | A1 | 5/2020 |
| WO | 2020106743 | A1 | 5/2020 |
| WO | 2020116765 | A1 | 6/2020 |
| WO | 2020120251 | A2 | 6/2020 |
| WO | 2020123876 | A1 | 6/2020 |
| WO | 2020131661 | A1 | 6/2020 |
| WO | 2020120251 | A3 | 7/2020 |
| WO | 2020141236 | A1 | 7/2020 |
| WO | 2020144166 | A1 | 7/2020 |
| WO | 2020146368 | A1 | 7/2020 |
| WO | 2020146373 | A1 | 7/2020 |
| WO | 2020148480 | A1 | 7/2020 |
| WO | 2020150078 | A1 | 7/2020 |
| WO | 2020155807 | A1 | 8/2020 |
| WO | 2020167676 | A1 | 8/2020 |
| WO | 2020169703 | A1 | 8/2020 |
| WO | 2020160187 | A3 | 9/2020 |
| WO | 2020176224 | A1 | 9/2020 |
| WO | 2020176758 | A1 | 9/2020 |
| WO | 2020179257 | A1 | 9/2020 |
| WO | 2020182970 | A1 | 9/2020 |
| WO | 2020201296 | A1 | 10/2020 |
| WO | 2020206162 | A1 | 10/2020 |
| WO | 2020206470 | A1 | 10/2020 |
| WO | 2020210398 | A1 | 10/2020 |
| WO | 2020219755 | A1 | 10/2020 |
| WO | 2020222239 | A1 | 11/2020 |
| WO | 2020225709 | A1 | 11/2020 |
| WO | 2020230138 | A1 | 11/2020 |
| WO | 2020234425 | A1 | 11/2020 |
| WO | 2020237021 | A1 | 11/2020 |
| WO | 2020223381 | A3 | 12/2020 |
| WO | 2020238961 | A1 | 12/2020 |
| WO | 2020239807 | A1 | 12/2020 |
| WO | 2020243324 | A1 | 12/2020 |
| WO | 2020243695 | A1 | 12/2020 |
| WO | 2020245355 | A1 | 12/2020 |
| WO | 2020249544 | A1 | 12/2020 |
| WO | 2020251537 | A1 | 12/2020 |
| WO | 2020252388 | A1 | 12/2020 |
| WO | 2020264200 | A1 | 12/2020 |
| WO | 2021003188 | A1 | 1/2021 |
| WO | 2021013698 | A1 | 1/2021 |
| WO | 2021015571 | A1 | 1/2021 |
| WO | 2021016523 | A1 | 1/2021 |
| WO | 2021021968 | A1 | 2/2021 |
| WO | 2021028674 | A1 | 2/2021 |
| WO | 2021030412 | A1 | 2/2021 |
| WO | 2021032637 | A1 | 2/2021 |
| WO | 2021041461 | A1 | 3/2021 |
| WO | 2021044377 | A1 | 3/2021 |
| WO | 2021044379 | A1 | 3/2021 |
| WO | 2021046305 | A1 | 3/2021 |
| WO | 2021047495 | A1 | 3/2021 |

(56) References Cited

FOREIGN PATENT DOCUMENTS

| | | | |
|---|---|---|---|
| WO | 2021048325 | A1 | 3/2021 |
| WO | 2021051054 | A1 | 3/2021 |
| WO | 2021055366 | A1 | 3/2021 |
| WO | 2021055579 | A1 | 3/2021 |
| WO | 2021055592 | A1 | 3/2021 |
| WO | 2021055616 | A1 | 3/2021 |
| WO | 2021055841 | A1 | 3/2021 |
| WO | 2021061832 | A1 | 4/2021 |
| WO | 2021061900 | A1 | 4/2021 |
| WO | 2021066113 | A1 | 4/2021 |
| WO | 2021067641 | A1 | 4/2021 |
| WO | 2021069353 | A1 | 4/2021 |
| WO | 2021074556 | A1 | 4/2021 |
| WO | 2021084159 | A1 | 5/2021 |
| WO | 2021085637 | A1 | 5/2021 |
| WO | 2021087404 | A1 | 5/2021 |
| WO | 2021089355 | A1 | 5/2021 |
| WO | 2021089661 | A1 | 5/2021 |
| WO | 2021092049 | A1 | 5/2021 |
| WO | 2021092051 | A1 | 5/2021 |
| WO | 2021094500 | A1 | 5/2021 |
| WO | 2021094826 | A1 | 5/2021 |
| WO | 2021095034 | A1 | 5/2021 |
| WO | 2021102375 | A1 | 5/2021 |
| WO | 2021106697 | A1 | 6/2021 |
| WO | 2021107473 | A1 | 6/2021 |
| WO | 2021110712 | A1 | 6/2021 |
| WO | 2021110767 | A1 | 6/2021 |
| WO | 2021111196 | A1 | 6/2021 |
| WO | 2021111219 | A1 | 6/2021 |
| WO | 2021111263 | A1 | 6/2021 |
| WO | 2021111270 | A1 | 6/2021 |
| WO | 2021116361 | A1 | 6/2021 |
| WO | 2021126584 | A1 | 6/2021 |
| WO | 2020201296 | A8 | 7/2021 |
| WO | 2021133602 | A1 | 7/2021 |
| WO | 2021133939 | A1 | 7/2021 |
| WO | 2021134512 | A1 | 7/2021 |
| WO | 2021138482 | A1 | 7/2021 |
| WO | 2021138674 | A1 | 7/2021 |
| WO | 2021140656 | A1 | 7/2021 |
| WO | 2021142376 | A1 | 7/2021 |
| WO | 2021146627 | A1 | 7/2021 |
| WO | 2021148663 | A1 | 7/2021 |
| WO | 2021148955 | A1 | 7/2021 |
| WO | 2021148960 | A1 | 7/2021 |
| WO | 2021149906 | A1 | 7/2021 |
| WO | 2021150837 | A1 | 7/2021 |
| WO | 2021151025 | A1 | 7/2021 |
| WO | 2021152536 | A1 | 8/2021 |
| WO | 2021158103 | A1 | 8/2021 |
| WO | 2021158104 | A1 | 8/2021 |
| WO | 2021158105 | A1 | 8/2021 |
| WO | 2021158831 | A1 | 8/2021 |
| WO | 2021160301 | A1 | 8/2021 |
| WO | 2021161397 | A1 | 8/2021 |
| WO | 2021163203 | A1 | 8/2021 |
| WO | 2021163216 | A1 | 8/2021 |
| WO | 2021163438 | A1 | 8/2021 |
| WO | 2021163481 | A1 | 8/2021 |
| WO | 2021168042 | A1 | 8/2021 |
| WO | 2021141692 | A3 | 9/2021 |
| WO | 2021173974 | A1 | 9/2021 |
| WO | 2021178254 | A1 | 9/2021 |
| WO | 2021178928 | A2 | 9/2021 |
| WO | 2021181235 | A1 | 9/2021 |
| WO | 2021191443 | A1 | 9/2021 |
| WO | 2021191623 | A1 | 9/2021 |
| WO | 2021191624 | A1 | 9/2021 |
| WO | 2021191913 | A1 | 9/2021 |
| WO | 2021195259 | A1 | 9/2021 |
| WO | 2021178928 | A3 | 10/2021 |
| WO | 2021195718 | A1 | 10/2021 |
| WO | 2021198169 | A1 | 10/2021 |
| WO | 2021207293 | A1 | 10/2021 |
| WO | 2021207401 | A1 | 10/2021 |
| WO | 2021207755 | A1 | 10/2021 |
| WO | 2021211841 | A1 | 10/2021 |
| WO | 2021214345 | A1 | 10/2021 |
| WO | 2021216460 | A1 | 10/2021 |
| WO | 2021216583 | A1 | 10/2021 |
| WO | 2021219823 | A1 | 11/2021 |
| WO | 2021220004 | A1 | 11/2021 |
| WO | 2021224434 | A1 | 11/2021 |
| WO | 2021231372 | A1 | 11/2021 |
| WO | 2021231569 | A1 | 11/2021 |
| WO | 2021234348 | A1 | 11/2021 |
| WO | 2021239046 | A1 | 12/2021 |
| WO | 2021239908 | A2 | 12/2021 |
| WO | 2021245711 | A1 | 12/2021 |
| WO | 2021248141 | A1 | 12/2021 |
| WO | 2021248158 | A1 | 12/2021 |
| WO | 2021250292 | A1 | 12/2021 |
| WO | 2021250407 | A1 | 12/2021 |
| WO | 2021251387 | A1 | 12/2021 |
| WO | 2021255435 | A1 | 12/2021 |
| WO | 2021262783 | A1 | 12/2021 |
| WO | 2021263282 | A1 | 12/2021 |
| WO | 2022003700 | A1 | 1/2022 |
| WO | 2022004079 | A1 | 1/2022 |
| WO | 2022008424 | A1 | 1/2022 |
| WO | 2022011163 | A1 | 1/2022 |
| WO | 2022024119 | A1 | 2/2022 |
| WO | 2022026999 | A1 | 2/2022 |
| WO | 2022034092 | A1 | 2/2022 |
| WO | 2022034211 | A1 | 2/2022 |
| WO | 2022036370 | A1 | 2/2022 |
| WO | 2022036371 | A1 | 2/2022 |
| WO | 2022037481 | A1 | 2/2022 |
| WO | 2022038240 | A2 | 2/2022 |
| WO | 2022038241 | A1 | 2/2022 |
| WO | 2022039998 | A1 | 2/2022 |
| WO | 2022040375 | A1 | 2/2022 |
| WO | 2022020431 | A3 | 3/2022 |
| WO | 2022047263 | A1 | 3/2022 |
| WO | 2022049217 | A1 | 3/2022 |
| WO | 2022050733 | A1 | 3/2022 |
| WO | 2022052877 | A1 | 3/2022 |
| WO | 2022053706 | A1 | 3/2022 |
| WO | 2022067034 | A1 | 3/2022 |
| WO | 2021239908 | A3 | 4/2022 |
| WO | 2021263179 | A9 | 4/2022 |
| WO | 2022069613 | A1 | 4/2022 |
| WO | 2022079717 | A1 | 4/2022 |
| WO | 2022079718 | A1 | 4/2022 |
| WO | 2022081511 | A1 | 4/2022 |
| WO | 2022087509 | A1 | 4/2022 |
| WO | 2022038240 | A3 | 5/2022 |
| WO | 2022087750 | A1 | 5/2022 |
| WO | 2022093846 | A1 | 5/2022 |
| WO | 2022094418 | A1 | 5/2022 |
| WO | 2022096664 | A1 | 5/2022 |
| WO | 2022097139 | A1 | 5/2022 |
| WO | 2022097716 | A1 | 5/2022 |
| WO | 2022098213 | A1 | 5/2022 |
| WO | 2022104373 | A1 | 5/2022 |
| WO | 2022112593 | A1 | 6/2022 |
| WO | 2022114955 | A1 | 6/2022 |
| WO | 2022115033 | A1 | 6/2022 |
| WO | 2022115289 | A2 | 6/2022 |
| WO | 2022115609 | A1 | 6/2022 |
| WO | 2022117750 | A1 | 6/2022 |
| WO | 2022121509 | A1 | 6/2022 |
| WO | 2022122548 | A1 | 6/2022 |
| WO | 2022123519 | A2 | 6/2022 |
| WO | 2022125590 | A1 | 6/2022 |
| WO | 2022125793 | A1 | 6/2022 |
| WO | 2022125809 | A1 | 6/2022 |
| WO | 2022129862 | A1 | 6/2022 |
| WO | 2022132059 | A1 | 6/2022 |
| WO | 2022132983 | A1 | 6/2022 |
| WO | 2022139499 | A1 | 6/2022 |
| WO | 2022140185 | A1 | 6/2022 |
| WO | 2022140187 | A1 | 6/2022 |

(56) References Cited

FOREIGN PATENT DOCUMENTS

| | | | |
|---|---|---|---|
| WO | 2022140210 | A1 | 6/2022 |
| WO | 2022140389 | A1 | 6/2022 |
| WO | 2022114955 | A8 | 7/2022 |
| WO | 2022115289 | A3 | 7/2022 |
| WO | 2022115506 | A3 | 7/2022 |
| WO | 2022123519 | A3 | 7/2022 |
| WO | 2022125587 | A9 | 7/2022 |
| WO | 2022144434 | A1 | 7/2022 |
| WO | 2022147107 | A1 | 7/2022 |
| WO | 2022147184 | A1 | 7/2022 |
| WO | 2022153957 | A1 | 7/2022 |
| WO | 2022155578 | A1 | 7/2022 |
| WO | 2022156939 | A1 | 7/2022 |
| WO | 2022159959 | A1 | 7/2022 |
| WO | 2021222479 | A9 | 8/2022 |
| WO | 2022171696 | A1 | 8/2022 |
| WO | 2022172000 | A1 | 8/2022 |
| WO | 2022174030 | A1 | 8/2022 |
| WO | 2022178357 | A1 | 8/2022 |
| WO | 2021239908 | A9 | 9/2022 |
| WO | 2022187181 | A1 | 9/2022 |
| WO | 2022187745 | A1 | 9/2022 |
| WO | 2022189505 | A1 | 9/2022 |
| WO | 2022189704 | A1 | 9/2022 |
| WO | 2022192426 | A1 | 9/2022 |
| WO | 2022192429 | A1 | 9/2022 |
| WO | 2022192434 | A1 | 9/2022 |
| WO | 2022192441 | A1 | 9/2022 |
| WO | 2022192446 | A1 | 9/2022 |
| WO | 2022192448 | A1 | 9/2022 |
| WO | 2022192454 | A1 | 9/2022 |
| WO | 2022192455 | A1 | 9/2022 |
| WO | 2022192694 | A1 | 9/2022 |
| WO | 2022196710 | A1 | 9/2022 |
| WO | 2022197816 | A1 | 9/2022 |
| WO | 2022203513 | A1 | 9/2022 |
| WO | 2022204120 | A1 | 9/2022 |
| WO | 2022204166 | A1 | 9/2022 |
| WO | 2022204738 | A1 | 10/2022 |
| WO | 2022207963 | A1 | 10/2022 |
| WO | 2022208525 | A1 | 10/2022 |
| WO | 2022211461 | A1 | 10/2022 |
| WO | 2022212602 | A1 | 10/2022 |
| WO | 2022215055 | A1 | 10/2022 |
| WO | 2022216857 | A1 | 10/2022 |
| WO | 2022218413 | A1 | 10/2022 |
| WO | 2022221549 | A1 | 10/2022 |
| WO | 2022225593 | A1 | 10/2022 |
| WO | 2022225880 | A1 | 10/2022 |
| WO | 2022225974 | A1 | 10/2022 |
| WO | 2022149142 | A3 | 11/2022 |
| WO | 2022178357 | A8 | 11/2022 |
| WO | 2022221261 | A3 | 11/2022 |
| WO | 2022229500 | A1 | 11/2022 |
| WO | 2022229501 | A1 | 11/2022 |
| WO | 2022229502 | A1 | 11/2022 |
| WO | 2022229503 | A1 | 11/2022 |
| WO | 2022229504 | A1 | 11/2022 |
| WO | 2022229507 | A1 | 11/2022 |
| WO | 2022229508 | A1 | 11/2022 |
| WO | 2022232322 | A1 | 11/2022 |
| WO | 2022234586 | A1 | 11/2022 |
| WO | 2022235553 | A1 | 11/2022 |
| WO | 2022235688 | A1 | 11/2022 |
| WO | 2022238867 | A1 | 11/2022 |
| WO | 2022245844 | A1 | 11/2022 |
| WO | 2022246063 | A1 | 11/2022 |
| WO | 2022225943 | A3 | 12/2022 |
| WO | 2022248594 | A1 | 12/2022 |
| WO | 2022251580 | A1 | 12/2022 |
| WO | 2022259254 | A1 | 12/2022 |
| WO | 2022261434 | A1 | 12/2022 |
| WO | 2022261647 | A1 | 12/2022 |
| WO | 2022266648 | A1 | 12/2022 |
| WO | 2022268842 | A1 | 12/2022 |
| WO | 2022270598 | A1 | 12/2022 |
| WO | 2022270598 | A5 | 12/2022 |
| WO | 2022236080 | A3 | 1/2023 |
| WO | 2023002292 | A1 | 1/2023 |
| WO | 2023003470 | A1 | 1/2023 |
| WO | 2023003471 | A1 | 1/2023 |
| WO | 2023003804 | A1 | 1/2023 |
| WO | 2023004430 | A1 | 1/2023 |
| WO | 2023275356 | A1 | 1/2023 |
| WO | 2023277150 | A1 | 1/2023 |
| WO | 2023278117 | A1 | 1/2023 |
| WO | 2023278137 | A1 | 1/2023 |
| WO | 2023278301 | A1 | 1/2023 |
| WO | 2023278306 | A1 | 1/2023 |
| WO | 2023278317 | A1 | 1/2023 |
| WO | 2023278557 | A1 | 1/2023 |
| WO | 2023279983 | A1 | 1/2023 |
| WO | 2023281114 | A1 | 1/2023 |
| WO | 2023281512 | A1 | 1/2023 |
| WO | 2023282762 | A1 | 1/2023 |
| WO | 2023285813 | A1 | 1/2023 |
| WO | 2022241289 | A3 | 2/2023 |
| WO | 2023004515 | A1 | 2/2023 |
| WO | 2023006897 | A1 | 2/2023 |
| WO | 2023007050 | A1 | 2/2023 |
| WO | 2023012523 | A1 | 2/2023 |
| WO | 2023014712 | A1 | 2/2023 |
| WO | 2023015317 | A1 | 2/2023 |
| WO | 2023016357 | A1 | 2/2023 |
| WO | 2023017509 | A1 | 2/2023 |
| WO | 2023018995 | A1 | 2/2023 |
| WO | 2023019203 | A1 | 2/2023 |
| WO | 2023023857 | A1 | 3/2023 |
| WO | 2023034384 | A1 | 3/2023 |
| WO | 2023038547 | A1 | 3/2023 |
| WO | 2023049162 | A1 | 3/2023 |
| WO | 2023049537 | A1 | 3/2023 |
| WO | 2023054556 | A1 | 4/2023 |
| WO | 2023059044 | A1 | 4/2023 |
| WO | 2023062015 | A1 | 4/2023 |
| WO | 2023063468 | A1 | 4/2023 |
| WO | 2023066646 | A1 | 4/2023 |
| WO | 2023067595 | A1 | 4/2023 |
| WO | 2023069931 | A1 | 4/2023 |
| WO | 2023069991 | A1 | 4/2023 |
| WO | 2023074607 | A1 | 5/2023 |
| WO | 2023080894 | A1 | 5/2023 |
| WO | 2023081615 | A1 | 5/2023 |
| WO | 2023081618 | A1 | 5/2023 |
| WO | 2023086502 | A1 | 5/2023 |
| WO | 2023087033 | A1 | 5/2023 |
| WO | 2023089568 | A1 | 5/2023 |
| WO | 2023091821 | A1 | 5/2023 |
| WO | 2022174030 | A9 | 6/2023 |
| WO | 2023067081 | A3 | 6/2023 |
| WO | 2023094619 | A1 | 6/2023 |
| WO | 2023099413 | A1 | 6/2023 |
| WO | 2023104984 | A1 | 6/2023 |
| WO | 2023106300 | A1 | 6/2023 |
| WO | 2023112952 | A1 | 6/2023 |
| WO | 2023114918 | A1 | 6/2023 |
| WO | 2023118412 | A1 | 6/2023 |
| WO | 2023118414 | A1 | 6/2023 |
| WO | 2023118597 | A1 | 6/2023 |
| WO | 2023118872 | A1 | 6/2023 |
| WO | 2023122133 | A1 | 6/2023 |
| WO | 2023122688 | A1 | 6/2023 |
| WO | 2022232322 | A9 | 7/2023 |
| WO | 2023129418 | A1 | 7/2023 |
| WO | 2023129971 | A2 | 7/2023 |
| WO | 2023132371 | A1 | 7/2023 |
| WO | 2023139493 | A1 | 7/2023 |
| WO | 2023081816 | A3 | 8/2023 |
| WO | 2023133568 | A3 | 8/2023 |
| WO | 2023144148 | A1 | 8/2023 |
| WO | 2023144369 | A1 | 8/2023 |
| WO | 2023147288 | A1 | 8/2023 |
| WO | 2023148598 | A1 | 8/2023 |
| WO | 2023150293 | A2 | 8/2023 |

(56) References Cited

FOREIGN PATENT DOCUMENTS

| | | | |
|---|---|---|---|
| WO | 2023150555 | A1 | 8/2023 |
| WO | 2023152487 | A1 | 8/2023 |
| WO | 2023152488 | A1 | 8/2023 |
| WO | 2023152489 | A1 | 8/2023 |
| WO | 2023152492 | A1 | 8/2023 |
| WO | 2023152493 | A1 | 8/2023 |
| WO | 2023156933 | A1 | 8/2023 |
| WO | 2023164573 | A1 | 8/2023 |
| WO | 2023146852 | A3 | 9/2023 |
| WO | 2023150293 | A3 | 9/2023 |
| WO | 2023150503 | A3 | 9/2023 |
| WO | 2023170280 | A1 | 9/2023 |
| WO | 2023170287 | A1 | 9/2023 |
| WO | 2023170643 | A1 | 9/2023 |
| WO | 2023172323 | A1 | 9/2023 |
| WO | 2023172343 | A1 | 9/2023 |
| WO | 2023176862 | A1 | 9/2023 |
| WO | 2023180600 | A1 | 9/2023 |
| WO | 2023181040 | A1 | 9/2023 |
| WO | 2022240910 | A8 | 10/2023 |
| WO | 2023186698 | A1 | 10/2023 |
| WO | 2023187031 | A1 | 10/2023 |
| WO | 2023187771 | A1 | 10/2023 |
| WO | 2023192991 | A1 | 10/2023 |
| WO | 2023192995 | A2 | 10/2023 |
| WO | 2023194619 | A1 | 10/2023 |
| WO | 2023194620 | A1 | 10/2023 |
| WO | 2023196500 | A1 | 10/2023 |
| WO | 2023197883 | A1 | 10/2023 |
| WO | 2023200008 | A1 | 10/2023 |
| WO | 2023201027 | A1 | 10/2023 |
| WO | 2023201048 | A2 | 10/2023 |
| WO | 2023201349 | A1 | 10/2023 |
| WO | 2023205677 | A1 | 10/2023 |
| WO | 2023178084 | A3 | 11/2023 |
| WO | 2023192995 | A3 | 11/2023 |
| WO | 2023201048 | A3 | 11/2023 |
| WO | 2023205656 | A3 | 11/2023 |
| WO | 2023211696 | A1 | 11/2023 |
| WO | 2023211726 | A1 | 11/2023 |
| WO | 2023212122 | A1 | 11/2023 |
| WO | 2023212677 | A2 | 11/2023 |
| WO | 2023212722 | A1 | 11/2023 |
| WO | 2023215542 | A1 | 11/2023 |
| WO | 2023220002 | A1 | 11/2023 |
| WO | 2023223083 | A1 | 11/2023 |
| WO | 2023224484 | A1 | 11/2023 |
| WO | 2023225686 | A1 | 11/2023 |
| WO | 2023225687 | A1 | 11/2023 |
| WO | 2023225995 | A1 | 11/2023 |
| WO | 2023229973 | A1 | 11/2023 |
| WO | 2023225662 | A3 | 12/2023 |
| WO | 2023233340 | A1 | 12/2023 |
| WO | 2023235815 | A1 | 12/2023 |
| WO | 2023239640 | A1 | 12/2023 |
| WO | 2023239672 | A1 | 12/2023 |
| WO | 2023240152 | A1 | 12/2023 |
| WO | 2023242230 | A1 | 12/2023 |
| WO | 2023242231 | A1 | 12/2023 |
| WO | 2023243111 | A1 | 12/2023 |
| WO | 2023244712 | A1 | 12/2023 |
| WO | 2023249963 | A1 | 12/2023 |
| WO | 2024001184 | A1 | 1/2024 |
| WO | 2024002851 | A1 | 1/2024 |
| WO | 2024003117 | A1 | 1/2024 |
| WO | 2024005054 | A1 | 1/2024 |
| WO | 2024006931 | A1 | 1/2024 |
| WO | 2024007033 | A1 | 1/2024 |
| WO | 2024009084 | A1 | 1/2024 |
| WO | 2024009087 | A1 | 1/2024 |
| WO | 2024013740 | A1 | 1/2024 |
| WO | 2024013745 | A1 | 1/2024 |
| WO | 2024014956 | A1 | 1/2024 |
| WO | 2024015329 | A1 | 1/2024 |
| WO | 2024015365 | A1 | 1/2024 |
| WO | 2024020405 | A1 | 1/2024 |
| WO | 2024023524 | A1 | 2/2024 |
| WO | 2024024720 | A1 | 2/2024 |
| WO | 2024033928 | A1 | 2/2024 |
| WO | 2024038139 | A2 | 2/2024 |
| WO | 2024038281 | A1 | 2/2024 |
| WO | 2024038139 | A3 | 3/2024 |
| WO | 2024059358 | A1 | 3/2024 |
| WO | 2024064910 | A1 | 3/2024 |
| WO | 2023044100 | A8 | 4/2024 |
| WO | 2023086502 | A9 | 4/2024 |
| WO | 2024044689 | A3 | 4/2024 |
| WO | 2024069186 | A1 | 4/2024 |
| WO | 2024071109 | A1 | 4/2024 |
| WO | 2024074916 | A1 | 4/2024 |
| WO | 2024076759 | A1 | 4/2024 |
| WO | 2024081022 | A1 | 4/2024 |
| WO | 2024084082 | A1 | 4/2024 |
| WO | 2024085898 | A1 | 4/2024 |
| WO | 2024086370 | A1 | 4/2024 |
| WO | 2023172696 | A9 | 5/2024 |
| WO | 2024088255 | A1 | 5/2024 |
| WO | 2024097749 | A2 | 5/2024 |
| WO | 2024098059 | A2 | 5/2024 |
| WO | 2024100137 | A1 | 5/2024 |
| WO | 2024100227 | A1 | 5/2024 |
| WO | 2024100228 | A1 | 5/2024 |
| WO | 2024100229 | A1 | 5/2024 |
| WO | 2024100230 | A1 | 5/2024 |
| WO | 2024100401 | A1 | 5/2024 |
| WO | 2024107345 | A1 | 5/2024 |
| WO | 2024107348 | A1 | 5/2024 |
| WO | 2024112636 | A1 | 5/2024 |
| WO | 2023230578 | A9 | 6/2024 |
| WO | 2024084014 | A3 | 6/2024 |
| WO | 2024098059 | A3 | 6/2024 |
| WO | 2024117904 | A1 | 6/2024 |
| WO | 2024118522 | A1 | 6/2024 |
| WO | 2024119096 | A1 | 6/2024 |
| WO | 2024120482 | A1 | 6/2024 |
| WO | 2024123235 | A1 | 6/2024 |
| WO | 2024126712 | A1 | 6/2024 |
| WO | 2024130251 | A1 | 6/2024 |
| WO | 2024130392 | A1 | 6/2024 |
| WO | 2024133961 | A1 | 6/2024 |
| WO | 2024134176 | A1 | 6/2024 |
| WO | 2024134658 | A1 | 6/2024 |
| WO | 2024097749 | A3 | 7/2024 |
| WO | 2024141754 | A1 | 7/2024 |
| WO | 2024141918 | A1 | 7/2024 |
| WO | 2024145619 | A1 | 7/2024 |
| WO | 2024145977 | A1 | 7/2024 |
| WO | 2024148818 | A1 | 7/2024 |
| WO | 2024151321 | A2 | 7/2024 |
| WO | 2024153174 | A1 | 7/2024 |
| WO | 2024133770 | A3 | 8/2024 |
| WO | 2024168400 | A1 | 8/2024 |
| WO | 2024170148 | A1 | 8/2024 |
| WO | 2024170696 | A1 | 8/2024 |
| WO | 2024170702 | A1 | 8/2024 |
| WO | 2024163952 | A3 | 9/2024 |
| WO | 2024181235 | A1 | 9/2024 |
| WO | 2024186212 | A1 | 9/2024 |
| WO | 2024197243 | A1 | 9/2024 |
| WO | 2024080892 | A3 | 10/2024 |
| WO | 2024211655 | A1 | 10/2024 |
| WO | 2024213599 | A1 | 10/2024 |
| WO | 2024228448 | A1 | 11/2024 |
| WO | 2024242255 | A1 | 11/2024 |
| WO | 2024125824 | A3 | 12/2024 |
| WO | 2024151548 | A9 | 12/2024 |
| WO | 2024233991 | A3 | 12/2024 |
| WO | 2024245959 | A1 | 12/2024 |
| WO | 2024251858 | A1 | 12/2024 |
| WO | 2024253585 | A | 12/2024 |
| WO | 2024256710 | A3 | 1/2025 |
| WO | 2024259376 | A3 | 1/2025 |
| WO | 2025003498 | A1 | 1/2025 |
| WO | 2025005124 | A1 | 1/2025 |

(56)             References Cited

FOREIGN PATENT DOCUMENTS

| WO | 2025005124 A5 | 1/2025 |
| WO | 2025012442 A1 | 1/2025 |
| WO | 2025019473 A1 | 1/2025 |
| WO | 2025039158 A1 | 2/2025 |
| WO | 2025040524 A1 | 2/2025 |
| WO | 2025041145 A2 | 2/2025 |
| WO | 2025046586 A1 | 3/2025 |
| WO | 2025049891 A1 | 3/2025 |
| WO | 2025050066 A1 | 3/2025 |
| WO | 2025054345 A1 | 3/2025 |
| WO | 2025058807 A1 | 3/2025 |
| WO | 2024226461 A3 | 4/2025 |
| WO | 2025064822 A3 | 4/2025 |
| WO | 2025073942 A1 | 4/2025 |
| WO | 2025078824 A1 | 4/2025 |
| WO | 2025085759 A1 | 4/2025 |
| WO | 2025062138 A3 | 5/2025 |
| WO | 2025089214 A1 | 5/2025 |
| WO | 2025096916 A1 | 5/2025 |
| WO | 2025104748 A1 | 5/2025 |
| WO | 2025109112 A1 | 5/2025 |
| WO | 2025137123 A1 | 6/2025 |
| WO | 2025141177 A1 | 7/2025 |
| WO | 2025141178 A1 | 7/2025 |
| WO | 2025141193 A1 | 7/2025 |
| WO | 2025141211 A1 | 7/2025 |
| WO | 2025144762 A1 | 7/2025 |
| WO | 2025153091 A1 | 7/2025 |
| WO | 2025155925 A1 | 7/2025 |
| WO | 2025160262 A1 | 7/2025 |
| WO | 2025160324 A2 | 7/2025 |
| WO | 2025128722 A3 | 8/2025 |
| WO | 2025137439 A3 | 8/2025 |
| WO | 2025166336 A1 | 8/2025 |
| WO | 2025169198 A1 | 8/2025 |
| WO | 2025172423 A1 | 8/2025 |
| WO | 2025175069 A1 | 8/2025 |
| WO | 2025176874 A1 | 8/2025 |
| WO | 2025181349 A1 | 9/2025 |
| WO | 2025184567 A1 | 9/2025 |
| WO | 2025191562 A1 | 9/2025 |
| WO | 2025196762 A1 | 9/2025 |
| WO | 2025210630 A1 | 10/2025 |
| WO | 2025215354 A1 | 10/2025 |
| WO | 2025224346 A1 | 10/2025 |
| WO | 2025240521 A2 | 11/2025 |
| WO | 2025257695 A1 | 12/2025 |
| WO | 2025259382 A1 | 12/2025 |
| WO | 2026006386 A1 | 1/2026 |

OTHER PUBLICATIONS

Obaidi et al., "The role of protein hydrolysates in prolonging viability and enhancing antibody production of CHO cells" 105 Applied Microbiology and Biotechnology 3115-3129 (Year: 2021).*

Khan et al., "Akt Kinase Pohsphorylation of Inositol 1,4,5-Triphosphate Receptors" 281(6) The Journal of Biological Chamistry 3731-3737 (Year: 2006).*

Crea et al., "Over-expression of hTERT in Cho K1 results in decreased apoptosis and reduced serum dependency" 121 Journal of Biotechnology 109-123 (Year: 2006).*

Barakova et al. "The efficiency of phytase and impact-disintegrator-activator processing for reducing phytic acid in soy protein hydrolysates" 3 Processes and Food Production Equipment 3-10 (Year: 2023).*

Agustini, Rudiana, and Nuniek Herdyastuti. "The Study of Amylase's Reaction Kinetics From Soybean Sprouts (*Glycine max* L.) in Hydrolyzing Starch." International Joint Conference on Science and Engineering (IJCSE 2020). Atlantis Press, 2020. 6 pages.

Akita, Kiyomi, and Fumitake Yoshida. "Bubble size, interfacial area, and liquid-phase mass transfer coefficient in bubble columns." Industrial & Engineering Chemistry Process Design and Development 13.1 (1974): 84-91.

Akpapunam, M. A., S. O. Igbedioh, and I. Aremo. "Effect of malting time on chemical composition and functional properties of soybean and bambara groundnut flours." International journal of food sciences and nutrition 47.1 (1996): 27-33.

Alam, Mohd Nazrul Hisham Zainal, and Firdausi Razali. "Scaleup of Stirred and Aerated BioengineeringTM Bioreactor Based on Constant Mass Transfer Coefficient." Jurnal Teknologi (2005): 95â-110.

Alhuthali, Sakhr, Pavlos Kotidis, and Cleo Kontoravdi. "Osmolality effects on CHO cell growth, cell vol. antibody productivity and glycosylation." International journal of molecular sciences 22.7 (2021): 3290. 19 pages.

Ali, Haider, Sofia Zhu, and Jannike Solsvik. "Effects of geometric parameters on volumetric mass transfer coefficient of non-Newtonian fluids in stirred tanks." International Journal of Chemical Reactor Engineering 20.7 (2022): 697-711.

Alkhalidi, A., R. Amano, and M. Khawaja. "Estimation model of KLa constant using bubble release rate and bubble size." Sch. J. Eng. Tech. 7.2 (2019): 33-40.

Altamirano, Claudia, et al. "Considerations on the lactate consumption by CHO cells in the presence of galactose." Journal of biotechnology 125.4 (2006): 547-556.

Altamirano, Claudia, et al. "Strategies for fed-batch cultivation of t-PA producing CHO cells: substitution of glucose and glutamine and rational design of culture medium." Journal of biotechnology 110.2 (2004): 171-179.

ATCC hTERT-immortalized Cell Culture Guide, www.atcc.org, 2022, 32 pages.

Aznauryan, Erik, et al. "Discovery and validation of human genomic safe harbor sites for gene and cell therapies." Cell Reports Methods 2.1 (2022). 10.1016/j.crmeth.2021.100154. 20 pages.

Barlat, I., et al. "Loss of the G1-S control of cyclin A expression during tumoral progression of Chinese hamster lung fibroblasts." Cell Growth & Differentiation: The Molecular Biology Journal of the American Association for Cancer Research 4.2 (1993): 105-113.

Beiranvand, Fateme, Seyed Hesam Najibi, and Bahram Hashemi Shahraki. "Experimental measurement of equilibrium surface tension of an aqueous solution of polyethylene glycol and a surfactant." Iranian Journal of Oil and Gas Science and Technology 9.3 (2020): 26-43.

Białkowska, Kamila, et al. "Spheroids as a type of three-dimensional cell cultures-examples of methods of preparation and the most important application." International journal of molecular sciences 21.17 (2020): 6225. 17 pages.

Branda, Catherine S., and Susan M. Dymecki. "Talking about a revolution: The impact of site-specific recombinases on genetic analyses in mice." Developmental cell 6.1 (2004): 7-28.

Brose, Daniel J., and Paul Van Eikeren. "A membrane-based method for removal of toxic ammonia from mammalian- cell culture." Applied biochemistry and biotechnology 24 (1990): 457-468.

Buffo, M. M., et al. "Influence of dual-impeller type and configuration on oxygen transfer, power consumption, and shear rate in a stirred tank bioreactor." Biochemical Engineering Journal 114 (2016): 130-139.

Carina Villacres; Venkata S. Tayi;Michael Butler;. (2021). Strategic feeding of NS0 and CHO cell cultures to control glycan profiles and immunogenic epitopes of monoclonal antibodies. Journal of Biotechnology, doi: 10.1016/j. jbiotec.2021.04.005. 14 pages.

Castel, Christophe, Roda Bounaceur, and Eric Favre. "Membrane processes for direct carbon dioxide capture from air: possibilities and limitations." Frontiers in Chemical Engineering 3 (2021): 668867. 15 pages.

Chalmers, Jeffrey J. "Cells and bubbles in sparged bioreactors." Cell Culture Engineering IV: Improvements of Human Health (1995): 311-320.

Chen, Zhao-Lie, et al. "Temperature shift as a process optimization step for the production of pro-urokinase by a recombinant Chinese hamster ovary cell line in high-density perfusion culture." Journal of bioscience and bioengineering 97.4 (2004): 239-243.

Chung, Myung-Il, et al. "Reduction of ammonia accumulation and improvement of cell viability by expression of urea cycle enzymes in Chinese hamster ovary cells." Journal of microbiology and biotechnology 13.2 (2003): 217-224.

(56)        References Cited

OTHER PUBLICATIONS

Chusainow, Janet, et al. "A study of monoclonal antibody-producing CHO cell lines: What makes a stable high producer?. " Biotechnology and bioengineering 102.4 (2009): 1182-1196.
Clincke, Marie-Francoise, et al. "Very high density of CHO cells in perfusion by ATF or TFF in WAVE bioreactor™. Part I. Effect of the cell density on the process." Biotechnology progress 29.3 (2013): 754-767.
Conway, John, Hélène Gaudreau, and Claude P. Champagne. "The effect of the addition of proteases and glucanases during yeast autolysis on the production and properties of yeast extracts." Canadian journal of microbiology 47.1 (2001): 18-24.
Cudak, Magdalena. "The effect of vessel scale on gas hold-up in gas-liquid systems." Chemical and Process Engineering 41.4 (2020): 241-256.
Cunningham, John T., et al. "Protein and nucleotide biosynthesis are coupled by a single rate-limiting enzyme, PRPS2, to drive cancer." Cell 157.5 (2014): 1088-1103.
Curriden, Scott, and Ellis Englesberg. "Inhibition of growth of proline-requiring Chinese hamster ovary cells (CHO-K1) resulting from antagonism by a system amino acids." Journal of Cellular Physiology 106.2 (1981): 245-252.
Darrin Kuystermans; Mohamed Al-Rubeai. (2009). cMyc increases cell number through uncoupling of cell division from cell size in CHO cells. , 9(1), 76-0. doi: 10.1186/1472-6750-9-76.
Davies, Sarah L., et al. "Functional heterogeneity and heritability in CHO cell populations." Biotechnology and Bioengineering 110.1 (2013): 260-274.
De Zawadzki, Andressa et al., Increasing calcium phosphate aqueous solubility and spontaneous supersaturation combining citrate and gluconate with perspectives for functional foods, Journal of Food Chemistry. 10.1016/j.foodchem.2021.131701; Nov. 30, 2021. 9 pages.
Derouazi, Madiha, et al. "Genetic characterization of CHO production host DG44 and derivative recombinant cell lines." Biochemical and biophysical research communications 340.4 (2006): 1069-1077.
DeZengotita, Vivian M., et al. "Selected amino acids protect hybridoma and CHO cells from elevated carbon dioxide and osmolality." Biotechnology and bioengineering 78.7 (2002): 741-752.
DeZengotita, Vivian M., Roy Kimura, and William M. Miller. "Effects of CO 2 and osmolality on hybridoma cells: growth, metabolism and monoclonal antibody production." Cell Culture Engineering VI (1998): 213-227.
Dong, Q., & Saneoka, H. (2020). Physiological Characteristics, Phytase Activity, and Mineral Bioavailability of a Low-Phytate Soybean Line during Germination. Plant Foods for Human Nutrition, 75(3), 383-389. doi: 10.1007/s11130-020-00827-x.
Fan, Yuzhou, et al. "Amino acid and glucose metabolism in fed-batch CHO cell culture affects antibody production and glycosylation." Biotechnology and bioengineering 112.3 (2015): 521-535.
Faust, Christine, et al. "Impact of lipopolysaccharides on cultivation and recombinant protein expression in human embryonal kidney (HEK-293) cells." Engineering in Life Sciences 21.11 (2021): 778-785.
Folmsbee, "An explanation and evaluation of sterile connector soiling tests" PALL technical position paper, Oct. 19, 2021, 6 pages.
Fu, Bo, et al. "Competition between chemolithotrophic acetogenesis and hydrogenotrophic methanogenesis for exogenous H2/CO2 in anaerobically digested sludge: impact of temperature." Frontiers in Microbiology 10 (2019): 2418. 9 pages.
Gao, Yang, et al. "Constitutive activation of transforming growth factor Beta receptor 1 in the mouse uterus impairs uterine morphology and function." Biology of reproduction 92.2 (2015): 34-1.
Grein, Tanja A., et al. "Aeration and shear stress are critical process parameters for the production of oncolytic measles virus." Frontiers in bioengineering and biotechnology 7 (2019): 78. 11 pages.
Ha, Thanh Toan, Thi Phuong Lien Duong, and Thi Bich Tram Phan. "Effect of germination on antioxidant capacity and nutritional quality of soybean seeds (Glycinemax (L.) Merr.)." CTU Journal of Innovation and Sustainable Development 06 (2017): 93-101.

Harsini and Swartz, Trends in cultivated meat scale-up and bioprocessing; Good Food Institute, Mar. 20, 2024. 42 pages.
Hoeijmakers, Jan HJ, Hanny Odijk, and Andries Westerveld. "Differences between rodent and human cell lines in the amount of integrated DNA after transfection." Experimental cell research 169.1 (1987): 111-119.
Holmlund, A. C., et al. "Growth and metabolism of recombinant CHO cell-lines in serum free medium containing derivatives of glutamine." Animal Cell Technology. Butterworth-Heinemann, 1992. 176-179.
Huang, Zhuangrong, et al. "CHO cell productivity improvement by genome-scale modeling and pathway analysis: Application to feed supplements." Biochemical Engineering Journal 160 (2020): 107638. 34 pages.
Huang, Zhuangrong, et al. "Insights into the impact of rosmarinic acid on CHO cell culture improvement through transcriptomics analysis." Processes 10.3 (2022): 533. 12 pages.
Huntley, Nichole F., and John F. Patience. "Xylose: absorption, fermentation, and post-absorptive metabolism in the pig." Journal of Animal Science and Biotechnology 9 (2018): 1-9.
Zhang, Lili, et al. "An oncogenic role for the phosphorylated h-subunit of human translation initiation factor eIF3." Journal of Biological Chemistry 283.35 (2008): 24047-24060.
Zhao, Xinghui, et al. "Overexpression of survivin and cyclin D1 in CHO cells confers apoptosis resistance and enhances growth in serum-free suspension culture." Biotechnology letters 33 (2011): 1293-1300.
Zhu, Marie M., et al. "Effects of elevated pCO2 and osmolality on growth of CHO cells and production of antibody-fusion protein B1: A case study." Biotechnology progress 21.1 (2005): 70-77.
Jacob, Friedrich Felix, et al. "Spent yeast from brewing processes: a biodiverse starting material for yeast extract production." Fermentation 5.2 (2019): 51. 19 pages.
Jacob, Friedrich Felix, Mathias Hutzler, and Frank-Jürgen Methner. "Comparison of various industrially applicable disruption methods to produce yeast extract using spent yeast from top-fermenting beer production: influence on amino acid and protein content." European Food Research and Technology 245 (2019): 95-109.
Jang, Mi, Ellen Sofie Pete, and Per Bruheim. "The impact of serum-free culture on HEK293 cells: From the establishment of suspension and adherent serum-free adaptation cultures to the investigation of growth and metabolic profiles." Frontiers in Bioengineering and Biotechnology 10 (2022): 964397. 16 pages.
Jerabek, Tobias, et al. "Life at the periphery: what makes CHO cells survival talents." Applied Microbiology and Biotechnology 106.18 (2022): 6157-6167.
Jiang, Susu, Weixi Cai, and Baojun Xu. "Food quality improvement of soy milk made from short-time germinated soybeans." Foods 2.2 (2013): 198-212.
Kamachi, Yasuharu, and Takeshi Omasa. "Development of hyper osmotic resistant CHO host cells for enhanced antibody production." Journal of bioscience and bioengineering 125.4 (2018): 470-478.
Kim, Sung-Hyun, and Gyun-Min Lee. "Differences in optimal pH and temperature for cell growth and antibody production between two Chinese hamster ovary clones derived from the same parental clone." Journal of microbiology and biotechnology 17.5 (2007): 712-720.
Klepetsanis, Pavlos G., and Petros G. Koutsoukos. "Spontaneous precipitation of calcium sulfate at conditions of sustained supersaturation." Journal of colloid and interface science 143.2 (1991): 299-308.
Klöckner, Wolf, et al. "Correlation between mass transfer coefficient k L a and relevant operating parameters in cylindrical disposable shaken bioreactors on a bench-to-pilot scale." Journal of biological engineering 7 (2013): 1-14.
Kohli, Vinny, and Siddhartha Singha. "Protein digestibility of soybean: how processing affects seed structure, protein and non-protein components." Discover Food 4.1 (2024): 7. 16 pages.
Kraus, Barbara, et al. "Avian cell line-Technology for large scale vaccine production." BMC proceedings. vol. 5. BioMed Central, 2011. 3 pages.

(56) References Cited

OTHER PUBLICATIONS

Kurano, N., et al. "Growth behavior of Chinese hamster ovary cells in a compact loop bioreactor. 2. Effects of medium components and waste products." Journal of biotechnology 15.1-2 (1990): 113-128.

Lab 1st Bioreactor BR500-Series V.20221208, 11 pages.

Lee, Tsung-Yih, et al. "Inhibitory effect of excessive glucose on its biochemical pathway and the growth of Chinese hamster ovary (CHO) cells." Journal of Carbohydrate Chemistry 34.1 (2015): 1-11.

Leong, Dawn Sow Zong, et al. "Evaluation and use of disaccharides as energy source in protein-free mammalian cell cultures." Scientific reports 7.1 (2017): 45216. 10 pages.

Li, Jincai, et al. "Feeding lactate for CHO cell culture processes: impact on culture metabolism and performance." Biotechnology and bioengineering 109.5 (2012): 1173-1186.

Li, Xiao, et al. "Transcriptomic analysis reveals MAPK signaling pathways affect the autolysis in baker's yeast." FEMS yeast research 20.5 (2020): foaa036. 11 pages.

Lin, Hsiao-Hsien, et al. "High glucose enhances cAMP level and extracellular signal-regulated kinase phosphorylation in Chinese hamster ovary cell: Usage of Br-CAMP in foreign protein B-galactosidase expression." Journal of bioscience and bioengineering 124.1 (2017): 108-114.

Lobo and Borges, Protease activity during 72 hours germination of Soyabean (Glycine max var JS-355), Poster, Feb. 2013. 2 pages.

López-Martínez, Manuel Ignacio, Fidel Toldrá, and Leticia Mora. "Sequential Enzymatic Hydrolysis and Ultrasound Pretreatment of Pork Liver for the Generation of Bioactive and Taste-Related Hydrolyzates." Journal of agricultural and food chemistry 72.28 (2024): 15693-15703.

Lu, Subiao, Xiangming Sun, and Yuanxing Zhang. "Insight into metabolism of CHO cells at low glucose concentration on the basis of the determination of intracellular metabolites." Process biochemistry 40.5 (2005): 1917-1921.

Luo, Jun, et al. "Comparative metabolite analysis to understand lactate metabolism shift in Chinese hamster ovary cell culture process." Biotechnology and bioengineering 109.1 (2012): 146-156.

Major-Godlewska, Marta, and Magdalena Cudak. "Gas Hold-Up in Vessel with Dual Impellers and Different Baffles." Energies 15.22 (2022): 8685. 14 pages.

Majors, Brian S., et al. "E2F-1 overexpression increases viable cell density in batch cultures of Chinese hamster ovary cells." Journal of biotechnology 138.3-4 (2008): 103-106.

Martínez-Edo, Gabriel, et al. "Isothiocyanate-Functionalized mesoporous silica nanoparticles as building blocks for the design of nanovehicles with optimized drug release profile." Nanomaterials 9.9 (2019): 1219. 16 pages.

Martínez, Verónica S.; Dietmair, Stefanie; Quek, Lake-Ee; Hodson, Mark P.; Gray, Peter; Nielsen, Lars K. . (2013). Flux balance analysis of CHO cells before and after a metabolic switch from lactate production to consumption. Biotechnology and Bioengineering, 110(2), 660-666. doi: 10.1002/bit.24728.

Matsuo, Taisuke, et al. "The effects of vitamin B6 compounds on cell proliferation and melanogenesis in B16F10 melanoma cells." Oncology Letters 15.4 (2018): 5181-5184.

Mengke Yuan; Jingcheng Zhang; Yuanpeng Gao; Zikun Yuan; Zhenliang Zhu; Yongke Wei; Teng Wu; Jing Han; Yong Zhang;. (2021). HMEJ-based safe-harbor genome editing enables efficient generation of cattle with increased resistance to tuberculosis . Journal of Biological Chemistry, doi:10.1016/j.jbc.2021.100497. 12 pages.

Merten, O-W., S. Petres, and E. Couve. "A simple serum-free freezing medium for serum-free cultured cells." Biologicals 23.2 (1995): 185-189.

Michele Sadler, "Myco-protein—a new food", BNF Nutrition Bulletin, Sep. 1990. 11 pages.

Morrison, Carly et al., Improvement of growth rates through nucleoside media supplementation of CHO clones; Cytotechnology, 10.1007/s10616-019-00319-0(; May 21, 2019. 10 pages.

Mosser, Mathilde, et al. "Combination of yeast hydrolysates to improve CHO cell growth and IgG production." Cytotechnology 65.4 (2013): 629-641.

Mulukutla, Bhanu Chandra, et al. "Identification and control of novel growth inhibitors in fed-batch cultures of Chinese hamster ovary cells." Biotechnology and Bioengineering 114.8 (2017): 1779-1790.

Nayar, Gautam. Oxygen transport in animal cell biogreactors with vibrating-plate aerators. Diss. Massachusetts Institute of Technology, 1995. 270 pages.

Njoroge, B. NK, and Slade Gilbert Mwamachi. "Ammonia removal from an aqueous solution by the use of a natural zeolite." Journal of Environmental Engineering and Science 3.2 (2004): 147-154.

Nolan, Ryan P., and Kyongbum Lee. "Dynamic model of CHO cell metabolism." Metabolic engineering 13.1 (2011): 108-124.

Pan, Xiao, et al. "Metabolic characterization of a CHO cell size increase phase in fed-batch cultures." Applied microbiology and biotechnology 101 (2017): 8101-8113.

Papapetrou, Eirini P., and Axel Schambach. "Gene insertion into genomic safe harbors for human gene therapy." Molecular Therapy 24.4 (2016): 678-684.

Peksel, Begüm, et al. "Mild heat induces a distinct "eustress" response in Chinese Hamster Ovary cells but does not induce heat shock protein synthesis." Scientific reports 7.1 (2017): 15643. 12 pages.

Pennycook, Betheney R., et al. "E2F-dependent transcription determines replication capacity and S phase length." Nature communications 11.1 (2020): 3503. 10 pages.

Pereira, Sara, Helene Faustrup Kildegaard, and Mikael Rørdam Andersen. "Impact of CHO metabolism on cell growth and protein production: An overview of toxic and inhibiting metabolites and nutrients." Biotechnology Journal 13.3 (2018): 1700499. 40 pages.

Perillo, Matteo, et al. "The spontaneous immortalization probability of mammalian cell culture strains, as their proliferative capacity, correlates with species body mass, not longevity." biomedical journal 46.3 (2023): 100596. Supplementary Material. 1 page.

Petry, Florian, and Denise Salzig. "Large-scale production of size-adjusted B-cell spheroids in a fully controlled stirred-tank reactor." Processes 10.5 (2022): 861. 22 pages.

Podpora, Bartlomiej, et al. "Spent brewer's yeast extracts as a new component of functional food." Czech Journal of Food Sciences 34.6 (2016): 554. 10 pages.

Polacco, Joseph C., and Evelyn A. Havir. "Comparisons of soybean urease isolated from seed and tissue culture." Journal of Biological Chemistry 254.5 (1979): 1707-1715.

Prabhu, Anuja, and Mugdha Gadgil. "Nickel and cobalt affect galactosylation of recombinant IgG expressed in CHO cells." Biometals 32 (2019): 11-19.

Qian, Yueming; Sowa, Steven W.; Aron, Kathryn L.; Xu, Ping; Langsdorf, Erik; Warrack, Bethanne; Aranibar, Nelly; Tremml, Gabi; Xu, Jianlin; McVey, Duncan; Reily, Michael; Khetan, Anurag; Borys, Michael C .; Li, Zheng Jian. (2020). New insights into genetic instability of an industrial CHO cell line by orthogonal omics. Biochemical Engineering Journal, 107799—. doi: 10.1016/j.bej.2020.107799. 38 pages.

Qin, Jane Yuxia; Zhang, Li; Clift, Kayla L.; Hulur, Imge; Xiang, Andy Peng; Ren, Bing-Zhong; Lahn, Bruce T.; Hansen, Immo A. . (2010). Systematic Comparison of Constitutive Promoters and the Doxycycline-Inducible Promoter. PLoS ONE, 5(5), e10611—. doi:10.1371/journal.pone.0010611.

Rafacz-Livingston, K. A., C. M. Parsons, and R. A. Jungk. "The effects of various organic acids on phytate phosphorus utilization in chicks." Poultry Science 84.9 (2005): 1356-1362.

Rao, Potu N., and Joseph Engelberg. "Hela cells: effects of temperature on the life cycle." Science 148.3673 (1965): 1092-1094.

Rees, Byron, et al. "Characterization and performance of the Allegro™ STR 200 single-use stirred tank bioreactor." BMC Proceedings. vol. 9. No. Suppl 9. London: BioMed Central, 2015. 2 pages.

Renner, Wolfgang A., et al. "Recombinant cyclin E expression activates proliferation and obviates surface attachment of Chinese hamster ovary (CHO) cells in protein-free medium." Biotechnology and bioengineering 47.4 (1995): 476-482.

(56) References Cited

OTHER PUBLICATIONS

Roca, Berta Capella, et al. "An arginase-based system for selection of transfected CHO cells without the use of toxic chemicals." Journal of Biological Chemistry 294.49 (2019): 18756-18768.

Rochovansky, Olga. "Pyrimidine biosynthesis in the chick." Archives of Biochemistry and Biophysics 138.2 (1970): 574-581.

Romanova, Nadiya, et al. "Hyperosmolality in CHO cell culture: effects on the proteome." Applied microbiology and biotechnology 106.7 (2022): 2569-2586.

Sasaki, Masahiro, et al. "Development of a novel serum-free freezing medium for mammalian cells using the silk protein sericin." Biotechnology and applied biochemistry 42.2 (2005): 183-188.

Sciola and Yavorsky, Mycoplasm removal, Millipore ED, May 6, 2006. 3 pages.

Shang, Menglin, et al. "Investigating the influence of physiologically relevant hydrostatic pressure on CHO cell batch culture." Scientific Reports 11.1 (2021): 162. 9 pages.

Shin, Woo-Shik, et al. "Application of scale-up criterion of constant oxygen mass transfer coefficient (kLa) for production of itaconic acid in a 50 L pilot-scale fermentor by fungal cells of Aspergillus terreus." J. Microbiol. Biotechnol 23.10 (2013): 1445-1453.

Shrestha, Dewan, et al. "Genomics and epigenetics guided identification of tissue-specific genomic safe harbors." Genome biology 23.1 (2022): 199.

Sieck, Jochen B., et al. "Adaptation for survival: Phenotype and transcriptome response of CHO cells to elevated stress induced by agitation and sparging." Journal of biotechnology 189 (2014): 94-103.

Sigma Aldrich, Electrical Schematic for P&D Pilot 130L, Nov. 12, 2008.23 pages.

Sikdar, Subhas K., and Sudhir B. Sawant. "Ammonia removal from mammalian cell culture medium by ion- exchange membranes." Separation science and technology 29.12 (1994): 1579-1591.

Šom, Ondej et al., Investigation of poloxamer cell protective ability via shear sensitive aggregates in stirred aerated bioreactor, Biochemical engineering Journal, 10.1016/j.bej.2022. 108549; Jul. 21, 2022. 7 pages.

Šom, Ondej et al., Characterization of hydrodynamic stress in ambr250® bioreactor system and its impact on mammalian cell culture, Biochemical Engineering Journal, 10.1016/j.bej.2021. 108240; Oct. 19, 2021. 9 pages.

Stout, Andrew J., et al. "Engineered autocrine signaling eliminates muscle cell FGF2 requirements for cultured meat production." Cell Reports Sustainability 1.1 (2024). 9 pages.

Stout, Andrew J., et al. "Immortalized bovine satellite cells for cultured meat applications." ACS synthetic biology 12.5 (2023): 1567-1573.

Surve, Tanaya, and Mugdha Gadgil. "Manganese increases high mannose glycoform on monoclonal antibody expressed in CHO when glucose is absent or limiting: Implications for use of alternate sugars." Biotechnology Progress 31.2 (2015): 460-467.

Suzuki, Takahiro, Takeshi Sato, and Minoru Kominami. "A dense cell retention culture system using stirred ceramic membrane reactor." Biotechnology and bioengineering 44.10 (1994): 1186-1192.

Takagi, Yasuhiro, et al. "The enhancement of antibody concentration and achievement of high cell density CHO cell cultivation by adding nucleoside." Cytotechnology 69 (2017): 511-521.

Takalloo, Zeinab; Nikkhah, Mohsen; Nemati, Robabeh; Jalilian, Nezam; Sajedi, Reza H. . (2020). Autolysis, plasmolysis and enzymatic hydrolysis of baker's yeast (Saccharomyces cerevisiae): a comparative study. World Journal of Microbiology and Biotechnology, 36(5), 68—. doi: 10.1007/s11274-020-02840-3. 14 pages.

Takuma, Shinya, Chikashi Hirashima, and James M. Piret. "Effects of glucose and CO2 concentrations on CHO cell physiology." Animal Cell Technology: Basic & Applied Aspects: Proceedings of the Fifteenth Annual Meeting of the Japanese Association for Animal Cell Technology (JAACT), Fuchu, Japan, Nov. 11-15, 2002. Dordrecht: Springer Netherlands, 2003. 5 pages.

Tamaru, Shizuka, et al. "Dietary soybean peptides containing a low-molecular fraction can lower serum and liver triglyceride levels in rats." Journal of nutritional science and vitaminology 60.6 (2014): 436-442.

Tang, Ning, and Leif H. Skibsted. "Zinc bioavailability from phytate-rich foods and zinc supplements. Modeling the effects of food components with oxygen, nitrogen, and sulfur donor ligands." Journal of agricultural and food chemistry 65.39 (2017): 8727-8743.

Tao, Fangfang, et al. "Simulation study on gas holdup of large and small bubbles in a high pressure gas-liquid bubble column." Processes 7.9 (2019): 594. 16 pages.

Thompson, Larry H., and Raymond M. Baker. "Isolation of mutants of cultured mammalian cells." Methods in cell biology. vol. 6. Academic Press, 1973. 209-281.

Tihanyi, Borbála, and László Nyitray. "Recent advances in CHO cell line development for recombinant protein production." Drug Discovery Today: Technologies 38 (2020): 25-34.

Tomita, Kazunori. "How long does telomerase extend telomeres? Regulation of telomerase release and telomere length homeostasis." Current genetics 64.6 (2018): 1177-1181.

Torres, Mauro, et al. "Long term culture promotes changes to growth, gene expression, and metabolism in CHO cells that are independent of production stability." Biotechnology and Bioengineering 120.9 (2023): 2389-2402.

Vagadia, Brinda Harish, Sai Kranthi Vanga, and Vijaya Raghavan. "Inactivation methods of soybean trypsin inhibitor—A review." Trends in Food Science & Technology 64 (2017): 115-125.

Van Driessche, Alexander ES, T. M. Stawski, and M. Kellermeier. "Calcium sulfate precipitation pathways in natural and engineered environments." Chemical Geology 530 (2019): 119274. 29 pages.

Walls, Peter LL, et al. "Quantifying the potential for bursting bubbles to damage suspended cells." Scientific reports 7.1 (2017): 15102. 9 pages.

Watson, Pavinee E., et al. "Drivers of palatability for cats and dogs-What it means for pet food development." Animals 13.7 (2023): 1134. 22 pages.

Weidner, Tobias; Druzinec, Damir; Mühlmann, Martina; Buchholz, Rainer; Czermak, Peter . (2017). The components of shear stress affecting insect cells used with the baculovirus expression vector system. Zeitschrift für Naturforschung C doi: 10.1515/znc-2017-0066. 11 pages.

Weiss, Christine H., Corinna Merkel, and Aline Zimmer. "Impact of iron raw materials and their impurities on CHO metabolism and recombinant protein product quality." Biotechnology Progress 37.4 (2021): e3148. 14 pages.

Wlaschin, Katie F., and Wei-Shou Hu. "Engineering cell metabolism for high-density cell culture via manipulation of sugar transport." Journal of biotechnology 131.2 (2007): 168-176.

Wurm, Florian M., and Maria João Wurm. "Cloning of CHO cells, productivity and genetic stability—a discussion." Processes 5.2 (2017): 20. 13 pages.

Wurm, Maria J., and Florian M. Wurm. "Naming CHO cells for bio-manufacturing: Genome plasticity and variant phenotypes of cell populations in bioreactors question the relevance of old names." Biotechnology Journal 16.7 (2021): 2100165. 24 pages.

Xiao, Shang, et al. "Continuous feeding reduces the generation of metabolic byproducts and increases antibodies expression in Chinese hamster ovary-K1 cells." Life 11.9 (2021): 945. 12 pages.

Xu, Jianlin, et al. "Systematic development of temperature shift strategies for Chinese hamster ovary cells based on short duration cultures and kinetic modeling." MAbs. Vol. 11. No. 1. Taylor & Francis, 2019. 15 pages.

Xu, Sen, et al. "A practical approach in bioreactor scale-up and process transfer using a combination of constant P/V and vvm as the criterion." Biotechnology Progress 33.4 (2017): 1146-1159.

Xu, Sen, et al. "Impact of Pluronic® F68 on hollow fiber filter-based perfusion culture performance." Bioprocess and Biosystems Engineering 40 (2017): 1317-1326.

Yamanaka, Kumiko, et al. "Development of serum-free and grain-derived-nutrient-free medium using microalga-derived nutrients and mammalian cell-secreted growth factors for sustainable cultured meat production." Scientific Reports 13.1 (2023): 498. 13 pages.

(56) References Cited

OTHER PUBLICATIONS

Yamano-Adachi, Noriko, et al. "Establishment of fast-growing serum-free immortalised cells from Chinese hamster lung tissues for biopharmaceutical production." Scientific Reports 10.1 (2020): 17612. 12 pages.
Yehia, N. S., et al. "Effects of some parameters affecting the crystallization rate of calcium sulfate dihydrate in sodium chloride solution." Journal of American Science 7.6 (2011): 635-644.
Yuan, Mengke, et al. "HMEJ-based safe-harbor genome editing enables efficient generation of cattle with increased resistance to tuberculosis." Journal of Biological Chemistry 296 (2021). 10 pages.
Yuk, Inn H., et al. "Effects of copper on CHO cells: cellular requirements and product quality considerations." Biotechnology Progress 31.1 (2015): 226-238.
Zagari, Francesca, et al. "Lactate metabolism shift in CHO cell culture: the role of mitochondrial oxidative activity." New biotechnology 30.2 (2013): 238-245.
Zhang, Li-xiang, et al. "Responses of CHO-DHFR cells to ratio of asparagine to glutamine in feed media: cell growth, antibody production, metabolic waste, glutamate, and energy metabolism." Bioresources and Bioprocessing 3 (2016): 1-12.
Andreassen et al., (2020) Screening of by-products from the food industry as growth promoting agents in serum-free media for skeletal muscle growth. Food Funct, 11: pp. 2477-2488 (Year: 2020).
Deionized Water Conductivity. Datasheet [online]. Alpha Measurement Systems, 2024 [retrieved on 2025-08-05] Retrieved from the Internet: < https://alpha-measure.com/deionized-water-conductivity/> (Year: 2024) (pp. 1-5).
DMEM Formulation. Datasheet [online]. Sigma, 2025 [retrieved on 2025-08-05]. Retrieved from the Internet: (Year: 2025) (pp. 1-13).
Jiang et al. "Strategies for Sustainable Substitution of Livestock Meat" Foods Sept 3 2020 (Year: 2020) (pp. 1-20).
Marson et al., (2020) Proteolytic enzymes positively modulated the physiocochemical and antioxidant properties of spent yeast protein hydrolysates. Process biochemistry, 91: pp. 34-35 (Year: 2020).
Mattick et al., (2015) Anticipatory life cycle analysis of in vitro biomass cultivation for cultured meat production in the United States. Environ. Sci. Technol., 49: p. 11941-11949.
R. Ian Freshney, Scale-up and Automation. In: Culture of Animal Cell: A Manual of Basic Technique and Specialized Applications (Hoboken, NJ, John Wiley & Sons, Inc., 2010), pp. 497-515. QH585.2.F74 2010 (Year: 2010).
Romero et al. "Systems biology and metabolic modeling for cultivated meat: A promisingmedia optimization and cost reduction" Comprehensive Reviews in Food Science and Food(Year: 2023) (pp. 1-2).
Kook, Moo-Chang, et al. "Bacillus subtilis fermentation for enhancement of feed nutritive value of soybean meal." Journal of applied biological chemistry 57.2 (2014): 183-188. F74 2010 (Year: 2010).
R. Ian Freshney, "Defined Media and Supplements", "Serum-Free Media", "Preparation and Sterilization". In: Culture of Animal Cell: A Manual of Basic Technique and Specialized Applications. (Hoboken, NJ, John Wiley & Sons, Inc., 2010), pp. 99-132. QH585.2.
Pasitka, L., Cohen, M., Regenbaum, S. et al. Spontaneous immortalization of bovine fibroblasts following long-term expansion offers a non-transformed cell source for cultivated beef. Nat Food 6, 1079-1094 (2025). https://doi.org/10.1038/s43016-025-01255-3.
R. Ian Freshney, "Preparation and Sterilization", "Scale-up and Automation." In: Culture of Animal Cell: A Manual of Basic Technique and Specialized Applications. (Hoboken, NJ, John Wiley & Sons, Inc., 2010), pp. 133-162, 497-515. QH585.2.F74 2010 (Year: 2010).
United States Environmental Protection Agency, "Water: Monitoring & Assessment", Mar. 6, 2012. (Year: 2012).

* cited by examiner

PRODUCT, SYSTEM AND METHOD OF CELL CULTIVATION

CROSS-REFERENCE TO RELATED APPLICATIONS

This application is a continuation of PCT Patent Application No. PCT/IB2024/059990, which is a continuation in part of U.S. Non-Provisional patent application Ser. No. 18/731,896 filed on Jun. 3, 2024, and U.S. Non-Provisional patent application Ser. No. 18/763,199 filed on Jul. 3, 2024, and PCT Patent application No. PCT/IB2024/053805 filed Apr. 18, 2024, and claims priority to U.S. Provisional Patent Application No. 63/589,661 filed Oct. 12, 2023, and U.S. Provisional Patent Application No. 63/555,543 filed Feb. 20, 2024, and U.S. Provisional Patent Application No. 63/570, 973 filed Mar. 28, 2024, and U.S. Provisional Patent Application No. 63/654,493 filed May 31, 2024, and U.S. Provisional Patent Application No. 63/698,265 filed Sep. 24, 2024, and wherein all the listed applications are also incorporated herein by reference and in their entireties. U.S. Provisional Patent Application No. 63/497,051 is also incorporated herein by reference.

FIELD OF THE INVENTION

The present invention relates to the field of food science, cell biology, biochemistry and chemistry. The present invention is also related to an alternative protein source solving arising climatic and ecological problems.

REFERENCE TO SEQUENCE LISTING SUBMITTED ELECTRONICALLY

The Sequence Listing written in the XML text file: "206448-0038-02US_SequenceListing.xml"; created on May 1, 2025, and 47,516 bytes in size, is hereby incorporated by reference.

BACKGROUND OF THE INVENTION

The cultivated cell industry offers a transformative solution to some of the most pressing global challenges, including environmental degradation, ethical concerns over animal welfare, and health issues associated with conventional animal-based products. This invention provides a comprehensive system designed to cultivate non-human metazoan cells for a range of applications, including food production, pharmaceuticals, and other sectors. To address the growing demand for sustainable protein sources, the invention introduces scalable, energy-efficient cultivation methods, alongside an optimized culture medium that is animal-free, uniform, and reproducible. These methods are critical for ensuring high-density cell growth and consistent quality over time, thus overcoming current limitations such as reliance on costly inputs and inconsistent yields. The cultivation system integrates advanced techniques to support efficient biomass production, enabling the manufacture of high-quality, cultivated meat products for both human and animal consumption, as well as biologically active substances for pharmaceutical use. By providing a unified, adaptable system for large-scale production, this invention promises to meet the specific demands of diverse industries while significantly reducing environmental impact and contributing to global food security and public health.

The cultivated cell industry is a rapidly growing field, offering the potential for more sustainable, efficient, and innovative products that can benefit various aspects of our lives. These cultivated products, or components of them, have applications across a wide range of industries, including pharmaceuticals, healthcare, biotechnology, food, cosmetics, beauty care, construction, textiles, and agriculture.

With the world's population expected to surge in the coming decades, the demand for food is set to rise exponentially, putting immense pressure on the agricultural sector. The meat industry, being a crucial component of the human and pet diet, faces a daunting challenge in meeting the increasing requirements for food availability and proper quality. However, in order to preserve the availability of food globally at an acceptable level, the expansion and intensification of the meat industry over the years have taken a severe toll on the environment, contributing significantly to the ongoing climatic crisis. As the population grows, so does the need for more land and resources to produce livestock and feed crops, leading to widespread deforestation and habitat loss. This rapid land conversion not only diminishes biodiversity but also exacerbates carbon emissions, as forests play a vital role in sequestering carbon from the atmosphere. Consequently, climate change intensifies, affecting weather patterns and exacerbating natural disasters, posing further challenges for food production. In response to these pressing environmental concerns, innovative solutions are emerging within the meat industry to promote sustainability and reduce its ecological footprint.

Alternative protein sources, such as plant-based and lab-grown meat alternatives, have gained traction as potential solutions to meet the increasing demand for protein sources without further straining the environment. These innovations not only reduce greenhouse gas emissions but also mitigate land and water use issues associated with traditional animal agriculture.

While addressing the environmental impact of the meat industry is crucial, it is essential not to overlook the dietary needs of other members of our households-our beloved pets. The pet food industry is a substantial and integral part of our lives. Like the human food industry, it is constantly innovating to provide sustainable protein alternatives. While the recommended human diet may emphasize more plant-based proteins, the diets of our feline and canine companions, who evolved from carnivorous species, require more animal protein for proper nutrition. However, meat production is responsible for approximately 15% of global greenhouse gas emissions, and it accounts for 60% of all emissions generated by the global food industry.

Currently, the main focus of the cultured meat industry (as one of potential solutions to the environmental crisis) is to provide texturized whole-cut meat products that are designed for satisfactory consumption by humans. However, it was found that there may be many difficulties to be overcome accompanying the production of pet food products also, including dry kibble, dry snack, meaty chunks, meaty chunks with gravy and/or any other products that are not addressed in the prior art yet. Usual methods of dry pet food production such as extrusion, cold-pressing and other usual methods for making pet food are in need of improvement in order to produce pet food products that do not require the use of any products that originated from animal products. There is a need to provide methods for producing pet food products from cell biomass that look visually appealing, appetizing and are nutritionally designed for every dog and cat.

Pets, including dogs and cats and other animals, form an integral part of our lives and have their own dietary requirements. The global pet food industry is substantial, and like the human food industry, it faces the challenge of sustainability in the face of a growing pet population. With respect to carnivorous animals, the conventional pet food industry stands on the production of pet food from meat by-products from conventional meat processing, often in the form of mechanically separated meat that is usually of a poor quality or in the form of low quality internal organs that often comprise high levels of selenium. These types of animal sources are not suitable for human consumption according to standards in the majority of the countries, and often the animal sources are not suitable for human consumption, for example animals that suffered serious disease or have even died before slaughtering. This naturally leads to a variety of potentially harmful ways to worsen the condition of the pet after the pet consumes such pet food products, specifically with meat components that often contains pathogens like *Salmonella, Escherichia coli. Staphylococcus aureus* and other undesirable microorganisms due to insufficient quality of processing the meat. Additionally, the above mentioned pathogens create metabolites that are also potentially harmful.

Mechanically separated meat in a pet food also has a higher risk of physical harm from the meat by-products that comes from mechanically separated meat and bones in a form of sharp residues from bones that could potentially cause severe problems while consuming the food. Also, these meat by-products or rendered meat components have to be processed in very high temperatures in order to ensure the sterility of the components and this is done at the cost of further decreasing the quality and nutritional value of the end product. Conventional meat by-products further result in relatively high ash content in the final pet food composition, which may further result in many health issues. On top of that, conventional livestock breeding is in a vast majority of cases linked with constant doping with pharmaceuticals comprising antibiotics, hormones, growth promoters and other substances that stay in meat products after slaughter in amounts which are potentially harmful to a consumer, regardless of whether it is a meat by-product or higher quality meat. Constant doping with pharmaceuticals of animals predestined to be slaughtered is bringing many issues on a global level. For example, frequent and continuous use of antibiotics in animal farming leads to the development of antibiotic-resistant bacteria in animals. These resistant bacteria can be transmitted to humans through consumption of contaminated meat, leading to antibiotic-resistant infections that are difficult to treat. This poses a significant public health risk, as common infections could become untreatable. Animals raised in conditions with constant exposure to antibiotics may have weakened immune systems. This can make them more susceptible to diseases, and the immune-suppressed animals can act as reservoirs for pathogens, potentially facilitating their transmission to humans. Overuse of antibiotics in animal farming can create an environment where viruses and bacteria are constantly exposed to selective pressure. This pressure can drive the development of mutations that make these microorganisms more virulent or harder to control. This increases the risk of disease outbreaks among animals and potentially humans as well, as was witnessed during the COVID outbreak in 2019. The widespread use of antibiotics in animal farming contributes to the release of these drugs into the environment through animal waste runoff. This can lead to the contamination of soil and water sources, potentially affecting aquatic ecosystems and even entering the human food chain indirectly through crops irrigated with contaminated water. Also, in most slaughterhouses, the conditions of animal welfare are not sufficient. Animals are forced to live in squalid conditions, where they often cannot even turn around or move freely, not to mention the unsanitary environment. Poor quality animal feed directly translates into low-quality meat. Advocating for improved animal nutrition standards is crucial for both animal welfare and the quality of the meat or their products that humans or animals are consuming.

FEDIAF (European Pet Food Industry Federation) annually publishes the Nutritional Guidelines for Complete and Complementary Pet Food for Dogs and Cats. These nutritional guidelines are widely adopted and followed by major pet food manufacturers across Europe and other parts of the world. These guidelines serve as a reference point for formulating pet food products that meet the nutritional requirements of pets. By adhering to FEDIAF's recommendations, major producers ensure that their pet food offerings are well-balanced and provide the necessary nutrients to support the health and vitality of pets. These guidelines also state that indeed, there is an alternative to meat components of pet food such as plant-based sources of protein and fat, however, it is also shown as not adequate for the vast majority of carnivorous animals, specifically dogs and cats. Plant-derived alternatives also contain many anti-nutritional factors that limit digestion and absorption of the nutrient, while many vegetable protein sources do not contain certain essential amino acids or contain insufficient levels of them.

For these and many other reasons, this complex issue is in need of a solution that does not contribute to the climate crisis and at the same time is sustainable, relatively cheap, available, and designed for each animal taking into account their species, age, breed, and health condition.

The processes of cell cultivation with the goal of gaining pure and stable cell lines face many different challenges. For example, a tightly regulated form of programmed cell death (e.g. apoptosis) triggers cells to self-destruct without any external influence. It is a mechanism used to eliminate unnecessary or damaged cells in organisms. It is an essential part of life, particularly for multicellular organisms that must control the growth, development, and turnover of cells in order to maintain homeostasis.

Cell cultivation processes, according to the state of the art, have many disadvantages such as high energy consumption at different stages of the whole process which needs to be optimized for sustainability, economic parameters and availability. Low number of cell cycles, low yield of a cell biomass after cultivation, usage of ethically problematic components, problematic suspension cultivation of cells, and the complicated process of harvesting cell biomass represent challenges for optimization. Other disadvantages that may accompany the cultivation processes are the use of ethically problematic Fetal Bovine Serum (FBS), even in very low concentrations or only in some steps of the cultivation, and economic parameters of cultivation media caused mainly by the high price of individual components, especially proteins.

Apoptosis is mediated by proteolytic enzymes called caspases, which trigger cell death by cleaving specific proteins in the cytoplasm and nucleus. Caspases exist in all cells as inactive precursors, or procaspases, which are usually activated by cleavage by other caspases, producing a proteolytic caspase cascade. The activation process is initiated by either extracellular or intracellular death signals, which cause intracellular adaptor molecules to aggregate and activate procaspases. Caspase activation is regulated by members of the B-cell lymphoma 2 (Bcl-2) and Inhibitor of Apoptosis (IAP) protein families.

Other challenges and issues of these cell cultivation processes include for example an appropriate supply of nutrients, oxygen, carbon dioxide, and other substances in a cultivation environment; appropriate mixing; cell biomass transfer; maintaining the pH and temperature within the optimal range for cell growth; maintaining a sterile environment with the usage of either very little or no antibiotics; presence or formation of toxins; foam formation; shear stress; and other problems.

For the above-mentioned reasons, there is a need in the art for improved processes of cell cultivation that provide sufficient yield of the cultivated cell biomass, without the use of ethically problematic components in any quantity and at any step of production. An improved process of cell biomass harvesting that minimizes the risk of contamination and ensures that the final food product meets safety and quality standards is also needed.

Cell culture cultivation systems are essential for the production of various cell products in the dynamic fields of pharmaceuticals and food industry. In particular, the emerging sector of cultivated meat production requires efficient cultivation of non-human metazoan cells in a sufficient quantity and quality, while simultaneously the production process must also meet the demands for safety from all points of view considered, not surpass the bearable capital requirements, ensure the availability of the food products for everyone and not significantly magnify climate crisis issues. Nowadays, the cultivated meat industry struggles to strike the equilibrium between all of the requirements mentioned above, as the field of the invention is extraordinarily complex. For this and many other reasons, there is a need for providing a cultivation system and methods for the cultivation of non-human metazoan cells using features that contribute to increasing efficiency.

Scaling up the production of cultured cells, whether for food products like cultured meat or for pharmaceutical applications, presents numerous significant challenges. A key issue in this process is the culture medium, which is essential for the proliferation and differentiation of non-human metazoan cells. A substantial part of the culture medium is an amino acid source. In one aspect of the invention, the amino acid source is derived from a hydrolyzed protein hydrolysate usually originating from a source such as soy, pea, *faba* beans, mung beans or any other appropriate source of protein. The products of the hydrolysis reaction, the source of protein with an enzyme capable of hydrolysing the bonds between the amino acid units are amino acids and short peptides which can be consumed by the cells. However, the hydrolysate may contain compounds such as inositol hexaphosphate and other undesired substances naturally found in the source of protein. Such compounds are not desired in the culture medium because they can interfere with cell growth and can lead to the formation of precipitates, which decreases the performance of filtration (a common method of sterilization of cell culture media). In addition, such compounds precipitate with minerals, salts and other compounds that form a substantial part of the culture medium, thus also increasing the resource requirements. The resulting frequent clogging of filtration systems not only hinders scalability but also significantly drives up production costs. This is particularly problematic when producing high amounts of cultured cells used for pharmacy or food production.

Therefore, there is a need for culture medium treatment to resolve such drawbacks of using protein hydrolysate as the source of protein.

BRIEF SUMMARY OF THE INVENTION

The drawbacks described above are solved by this invention and provides new aspect of cultivating non-human metazoan cells system and method of its production and methods providing products from the cell biomass of the non-human metazoan cells.

In order to address the above-mentioned drawbacks the present invention refers to solutions and subject-matters which provide for the following:

A food composition prepared from metazoan cells (e.g. non-human metazoan cells) cultivated in a culture media that influences the nutritional level of human or animal. The food product comprises metazoan cells cultivated from at least one metazoan cell population derived from at least one animal species. The metazoan cells are cultivated in a culture vessel of a cultivation device in a culture media environment. The cultivated cells, cell line or cell population may be chosen according to the detailed description below. With respect to animal needs, it is provided here tailoring the nutritional profile of the pet food or human food to meet the specific dietary requirements of the individual companion animals and individual humans considering their species, gender, age, breed, activity factor and health condition. This novel pet food composition is beneficial for the companion animals in many ways, for example, the novel pet food composition does not comprise antibiotics, exogenous hormones, or may comprise only trace amounts that are naturally found in meat products. Also, this pet food composition does not comprise any sharp residues or any xenobiotic that could potentially be in conventional pet food products, which is directly related to the method of preparing such pet food composition and the differences between conventional pet food products made by conventional methods and the novel pet food composition presented here. Moreover, the methods of preparing such pet food compositions are more green, healthy, more trackable and ethical than conventional processing of pet food because the animal components are cultivated ex vivo instead of slaughtering animals and using extreme amounts of resources such as water and land. Furthermore, the methods described herein address many negative externalities associated with the animal husbandry and meat industries.

An alternative aspect to the production of pet food products is presented. This document provides a pet food composition, along with its components and the methods used to prepare them, with a special focus on how the primary component is made. The primary component is prepared by processing a cell biomass comprising at least one non-human metazoan cell line. The cell biomass may be prepared by a cultivation system. The primary component prepared by processing the cell biomass may be combined with at least one other component selected from the secondary and tertiary component. The secondary component may comprise at least one source of saccharides and/or at least one source of fats. The tertiary component may comprise vitamins, minerals, binders, palatants, antioxidants, colorants and/or preservatives. The combination of the components may be then used as an input into an extrusion system, mold-injection system, cold-press system and/or cannery system.

In one aspect of the invention, a method of producing a food composition may comprise:

providing a primary component comprising at least one cultivated non-human metazoan cell line; and at least one of:

a secondary component comprising at least one source of saccharides or source of fats; or a tertiary component comprising at least one of vitamins, minerals, binders, palatants, antioxidants, colorants, or preservatives.

In one aspect of the invention, the food composition may comprise:

a primary component comprising a harvested non-human metazoan cell biomass of at least one cultivated non-human metazoan cell line; and at least one of:

a secondary component comprising at least one source of saccharides or source of fats; or a tertiary component comprising at least one substance of vitamins, minerals, binders, palatants, antioxidants, colorants and preservatives.

In one aspect of the invention, a method of producing dry pet food may comprise:

mixing a non-human metazoan cell biomass comprising at least one non-human metazoan cell line with a solidifying agent to obtain a primary component;

mixing the primary component with at least one of a secondary component or tertiary component;

extruding the combination of components to provide an extrudate; and drying the extrudate to obtain a dry pet food product.

In one aspect of the invention, a dry pet food product may comprise:

a primary component comprising a cell biomass of at least one non-human metazoan cell line and a solidifying agent; and at least one of a secondary component and a tertiary component;

wherein the secondary component comprises at least one source of fats or at least one source of saccharides, wherein the tertiary component comprises at least one of vitamins, minerals, binders, palatants, antioxidants, colorants or preservatives, and wherein the dry pet food product comprises an extruded combination of the primary component and at least one of the secondary component and the tertiary component.

In one aspect of the invention, a method of producing wet pet food product may comprise:

mixing a cell biomass comprising at least one non-human metazoan cell line with a solidifying agent to obtain a primary component;

mixing the primary component with at least one of a secondary or a tertiary component;

filling the combination of components into packaging to obtain a wet pet food product; and sterilizing the wet pet food product.

In one aspect of the invention, a wet pet food product may comprise:

a primary component comprising a cell biomass of at least one non-human metazoan cell line and solidifying agent; and at least one of a secondary component and a tertiary component, wherein the secondary component comprises at least one source of fats or at least one source of saccharides, wherein the tertiary component comprises at least one of vitamins, minerals, binders, palatants, antioxidants, colorants or preservatives, and wherein the wet pet food product is sterilized.

The disadvantages of the current cell cultivation processes according to state of the art are solved as described herein. As presented, processes for cell cultivation for preparing cultured products that may be used as food product for human consumption or as a pet food product are presented. An example of the food product is cultured meat. A cell cultivation system for carrying out these processes and food products provided by said processes are also provided. The cultivation system comprises a cultivation device that may further comprise at least one of the following devices: a seeding tank, a harvesting device, a control unit, sensors, analytical instruments, any other appropriate device, or a combination thereof. Optionally the cultivation system may further comprise a device for preparing a food product.

The cell cultivation processes comprise the step of cell cultivation in the cultivation device, for example, formed by a bioreactor. The processes may further comprise at least one step of obtaining the metazoan cells; modification of cells; providing gain of function to cells; inoculation of cells to the cultivation device; harvesting the cultured cells; processing harvested cells into the final product; any other appropriate step, and/or combination thereof.

In one aspect of the invention, a method of non-human metazoan cell cultivation may comprise:

preparing a non-human metazoan cell line by at least one of:

a. cell immortalization by affecting the TERT gene or modified TERT gene;

b. genetic modification aimed to reduce the exogenous growth factor requirements in the culture environment, wherein the genetic modification is:

i. modification of the level of expression of at least one of CDK4, Transferrin receptor, HRas, TGF receptor, FGF-5, FGF-2, FGF-1, or FGF-8, Insulin, FGF, myr-Akt, Myostatin, MyoD, Pax7, SREBP, PPARy, or genes involved in the regulation of iron metabolism ii. transferrin receptor (gene TRFC) overexpression and a consequent transferrin reduction, iii. TGF-beta receptors overexpression (TGF-beta1 reduction)

iv. Insulin overexpression (insulin reduction), or v. FGF-2 overexpression (FGF-2 reduction);

c. genetic modification aimed to endogenously express at least one antimicrobial compound, wherein the antimicrobial compound is allicin, nisin, surfactin, defensin, a lysozyme, a cathelicidin, a histidine, bioactive peptide derived from Abalone Viscera, lactoferrin, a C-type lectin, or a host defense-related ribonuclease;

d. cell cycle shortening; or e. affecting suspension growth, and cultivating at least one non-human metazoan cell line prepared by at least one of steps a), b), c), d) or e).

In one aspect if the invention, a method of cultivating non-human metazoan cells may comprise genetic modification comprising inactivation of PRNP protein.

In one aspect of the invention, a method of cultivating non-human metazoan cells may comprise genetic modification comprising inactivation of endogenous retroviruses.

In one aspect of the invention, a cultivated non-human metazoan cell line having genetic modification may comprise inactivation of PRNP protein.

In one aspect of the invention, a cultivated non-human metazoan cell line having genetic modification may comprise an inactivation of endogenous retroviruses.

In one aspect of the invention, a food composition may comprise cell line having genetic modification comprising inactivation of PRNP protein.

In one aspect of the invention, a food composition may comprise cell line having genetic modification comprising inactivation of endogenous retroviruses.

In one aspect of the invention, a cultivated non-human metazoan cells may comprise:

a non-human metazoan cell line having at least one modification selected from:

a. cell immortalization provided by affecting the TERT gene or modified TERT gene;

b. genetic modification aimed to reduce the exogenous growth factor requirements in culture environment, wherein the genetic modification is provided by i. modification of the level of expression of at least one of genes selected from CDK4, Transferrin receptor, TGF receptor, FGF-5, FGF-2, FGF-1, or FGF-8, Insulin, FGF, myr-Akt, Myostatin, MyoD, Pax7, SREBP, PPARy, or genes involved in the regulation of iron metabolism, ii. transferrin receptor (gene TFRC) overexpression and a consequent transferrin reduction, iii. TGF-beta receptors overexpression (TGF-beta1 reduction), iv. insulin overexpression (insulin reduction), or v. FGF-2 overexpression (FGF-2 reduction);

c. genetic modification aimed to endogenously express at least one antimicrobial compound, wherein the antimicrobial compound is allicin, nisin, surfactin, defensin, a lysozyme, a cathelicidin, a histidine, a bioactive peptide derived from Abalone Viscera, lactoferrin, a C-type lectin, or a host defense-related ribonucleases d. cell cycle shortening; or e. a modification affecting suspension growth.

In one aspect of the invention, a method of cell cultivation may comprise:

introducing at least one polynucleotide sequence into a targeted locus, wherein the targeted locus is genomic safe harbor, wherein the safe harbor is PGRandom or ROSA26.

In one aspect of the invention, a method of cell modification may comprise introducing polynucleotide sequence into a safe harbor of the non-human metazoan cell line located on chromosome 20 at the position 1953300019532739±100 0000 bps.

In one aspect of the invention, a non-human metazoan cell line may be created by introducing polynucleotide sequence into a safe harbor of the non-human metazoan cell line located on chromosome 20 at the position 1953300019532739±100 0000 bps.

In one aspect of the invention, a method of cell cultivation may comprise:

providing at least one antimicrobial compound in the culture medium;

wherein the antimicrobial compound is provided by endogenously or exogenously.

In one aspect of the invention, a method of cell cultivation comprising a non-genetic modification may comprise:

adapting subpopulation of the non-human metazoan cells by gradual adaptation or long term adaptation, and selecting the adapted subpopulations of the non-human metazoan cells that have uniform phenotype behavior from the original population, wherein the subpopulation is adapted to at least one of:

a) growing on scaffolds, growing on micro carriers, growing on macro carriers, growing in spheroids or growing in suspension b) growing in low-oxygen conditions, high-oxygen or in a high cell density c) growing in the absence of at least one of L-proline or L-glutamine growing in the culture medium d) growing in serum-free, protein-free or low-protein culture medium e) growing in a mechanically stressful environment f) growing in a culture medium comprising protein hydrolysate wherein the non-human metazoan cells are used in the production of products.

In one aspect of the invention, a method of cell cultivation comprising a non-genetic modification may comprise:

introducing a stress treatment to a non-human metazoan cell population to a induce stress response, wherein the stress treatment is at least one of UV radiation, gamma radiation or chemical stress factor; and selecting a subpopulation responding to such stress treatment, wherein the subpopulation is characterized by having at least one uniform phenotype behavior of:

a) homogenous doubling time b) absence of senescence markers c) Hayflick limit overcome.

In one aspect of the invention, a method of cell cultivation in the cultivation system may comprise:

preparing a culture medium;

inoculating the non-human metazoan cells to a cultivation device;

cultivating the non-human metazoan cells in the cultivation device;

harvesting the non-human metazoan cells; and optionally preparing a food product.

A method of externally stimulating of the non-human metazoan cells may comprise:

at least one external physical stimulation mechanism applied locally or globally to the non-human metazoan cells;

wherein the at least one external physical stimulation mechanism provides electromagnetic energy, mechanical energy or both.

Disclosed herein is a cultivation system and methods for the cultivation of non-human metazoan cells to solve the problems depicted in the background of the invention. The cultivation system is designed to maximize the efficiency of the cultivation from the view of the cell quality and cell biomass yield, while also decreasing the energy and resource requirements of the processes. The cultivation system may comprise the utilities, instruments and devices for culture medium preparation and the cultivation of the non-human metazoan cells. The culture medium may be prepared using a water purification method to remove at least one type of ion and/or other substances potentially contained in water. The culture medium may be recycled to not further increase the consumption of the resources. The cultivation device within the cultivation system may comprise a gas sparging system to provide gaseous nutrients to the cells, wherein similarly to medium recycling, exhaust gas from the cultivation device may be recycled to not further increase the resources consumption. In addition, the exhaust gas may be rejuvenated and/or recycled by cultivating converting organisms. Converting organisms are capable of converting the exhaust gas to other gas. The converting organism itself may be further used as a source of amino acids and nutritional peptides for the cultivation of the non-human metazoan cells. In order to further increase the efficiency, the heat exchange system may be applied within the cultivation system configured to save the heat from the culture medium tank that consumes a substantial portion of the heat, thus decreasing the energy consumption. The cultivation system may comprise other features used for dynamic loading of the medium according to measurement of various parameters of the culture medium, cultivation system and/or non-human metazoan cells, as well as a multimodal regime of sparging of the gas and/or external physical stimulation to increase well-being of the non-human metazoan cells. As presented, the combination of the features in the cultivation system conclusively improving the cultivation of the non-human metazoan cells that may be used in the pharmaceutical industry and/or to produce comestible products with satis-factory properties compared to conventional meat products. The comestible product may be a meat-like product, which means product including cultivated non-human metazoan cells. The term comestible product includes a food product, pet food product, food product component, and pet food product component. Food products may include pet food or food product for human consumption. A food product com-ponent may be any component included in a food product. A pet food product component is any component included in a pet food product.

In one aspect of the invention, the cultivation system for cultivating a cell biomass may comprise:

a cultivation device and a gas sparging system, wherein the cultivation device is configured to cultivate non-human metazoan cells and to produce a non-human metazoan cell biomass.

In one aspect of the invention, the cultivation system may provide non-human metazoan cell biomass, waste medium, and solid residues resulting from the purification of protein hydrolysate.

In one aspect of the invention, the cultivation system may comprise at least one harvesting device.

In one aspect of the invention, the cultivation system may comprise at least one water purification unit, which may be used to purify water from the water source.

In one aspect of the invention, the cultivation system may comprise at least one hydrolysis tank.

In one aspect of the invention, the cultivation system may comprise at least one loading tank.

In one aspect of the invention, the loading tank may be configured to load at least one of the following: antimicro-bial compounds, pH modifying agents, water, amino acids and nutritional peptides, sugars, salts, proteins, and vita-mins.

In one aspect of the invention, the cultivation system may comprise at least one pump.

In one aspect of the invention, the cultivation system may comprise at least one filtration unit or centrifuge unit.

In one aspect of the invention, the cultivation system may comprise a heat exchange system.

In one aspect of the invention, the cultivation system may comprise a gas recycling system.

In one aspect of the invention, the cultivation system may comprise a medium recycling system.

In one aspect of the invention, the cultivation system may comprise a control unit that is communicatively and opera-tively coupled to the cultivation system.

In one aspect of the invention, the cultivation system may comprise a collateral cultivation device.

In one aspect of the invention, a non-human metazoan cell biomass may comprise:

a harvested non-human metazoan cell biomass provided by at least one cell cycle of a non-human metazoan cell line cultivated in a cultivation system.

Disclosed herein are methods for a culture medium pro-duction, including a process of proteolysis by proteolytic enzymes in hydrolysis tank to provide a protein hydrolysate comprising amino acids and peptides with different molecu-lar weight higher than 17 kDa, ranging from 6.7 kDa to 17 kDa, ranging from 1.7 kDa to 6.7 kDa, ranging from 1 kDa to 1.7 kDa and/or with molecular weight less than 1 kDa. Disclosed herein are aspects for the modification of the resulting protein hydrolysate in the hydrolysis tank and addition of nutritional additives in the mixing tank.

Disclosed herein are three aspects utilized for the modi-fication of protein hydrolysate to remove inositol hexaphos-phates, its derivatives and/or their salts and/or any other related form of those compounds. The first aspect comprise the use of enzymes having phytase activity to cleave the phosphate ester bonds of inositol molecules and under certain pH and temperature conditions. This process is performed to provide free phosphate groups as nutrition for the cultivation of non-human metazoan cells and to prevent clogging of filters by inositol hexaphosphates and its deriva-tives.

The second aspect comprise the use of precipitating agents to generate precipitates of inositol hexaphosphate and/or its derivatives and their removal by filtration unit to prevent the clogging of filters by inositol hexaphosphate and its derivatives.

The third aspect comprise the use of a combination of both enzymes having phytase activity and precipitating agents in one of two orders.

This disclosure relates to methods for preparing a purified protein hydrolysate from modified protein hydrolysate by filtration, centrifugation, or a combination of both methods, or by any other suitable method. For these purposes, the filtration unit and/or centrifugation techniques may be implemented. During the filtration obtained sediment or solid residues, with unutilized nutrients, may be further processed for the production of food products. For steril-ization of the culture medium, the sterile barrier may be used.

As described herein, the purified protein hydrolysate is mixed with nutritional additives to provide a culture medium suitable for the cultivation of the non-human metazoan cells in the cultivation system. The cultivation system may com-prise at least one of: culture medium tanks for the prepara-tion of the culture medium, and cultivation device for the cell cultivation and features to produce a product. The cultivation system may further comprise at least one of the following features: at least one filtration unit; a plurality of sterile barriers; a plurality of pumps; a plurality of analytical instruments and sensors; a gas sparging system comprising a plurality of gas tanks; a gas recycling system; at least one culture medium tank comprising a hydrolysis tank, a mixing tank, a loading tank, a storage tank and a waste medium tank; a water purification unit; a medium recycling system; a heat exchange system; a collateral cultivation device; at least one harvesting device; a control unit (the term "control unit" and "control device" may be interchangeable); an external physical stimulation mechanisms; and a product processing device.

This disclosure also relates to the harvested cell biomass, which may be utilized in the production of food products for human and/or animal consumption. Additionally, the present invention also pertains to the use of harvested cell-free culture medium, from which signaling compounds and/or compounds having therapeutic effect produced by genetically modified non-human metazoan cells may be isolated.

In one aspect of the invention, a method for producing a protein hydrolysate may comprise:

providing a source of the protein;

mixing the source of the protein with at least one proteolytic enzyme to cleave peptide bonds of the source of the protein; and mixing the source of the protein with at least one enzyme having phytase activity to cleave inositol hexaphosphate and its derivatives.

In one aspect of the invention, protein hydrolysate may comprise:

a protein hydrolysate generated by the reaction of a source of protein with at least one proteolytic enzyme and at least one enzyme having phytase activity in an aqueous environment.

All of the advantages and technical effects being described in the context of each of the different subjects, e.g. the food and pet food, the cultivation, the cultivation system, the culture medium production, etc., can also be applied, individually or commonly, for the remaining subjects according to the present invention.

BRIEF DESCRIPTION OF THE DRAWINGS

All of the advantages and technical effects being described in the context of each of the different subjects, such as the food products including pet food products, the cultivation and its methods, the cultivation system and its methods of use, the culture medium and its methods of production, etc., can also be applied, individually or commonly, for the remaining subjects according to the present invention.

Various aspects of the invention and examples of said aspects will be described and explained through the use of the accompanying drawings, which are summarized below.

DETAILED DESCRIPTION OF THE INVENTION

The present disclosure provides a product comprising non-human metazoan cells and production methods of various products, e.g. food products or pet food products. The pet food products are designed to provide nutrition, care, beauty effect and/or health benefits to a subject, wherein the subject is subjected to an oral consumption of such pet food products. The exemplary subject subjected to an oral consumption may be a big breed dog, a small breed dog, a cat and/or any other animal having at least partially carnivorous diet. The exemplary subjects mentioned above are not limiting and the subjects subjected to an oral consumption may comprise any metazoan species, including human.

Figure 1:
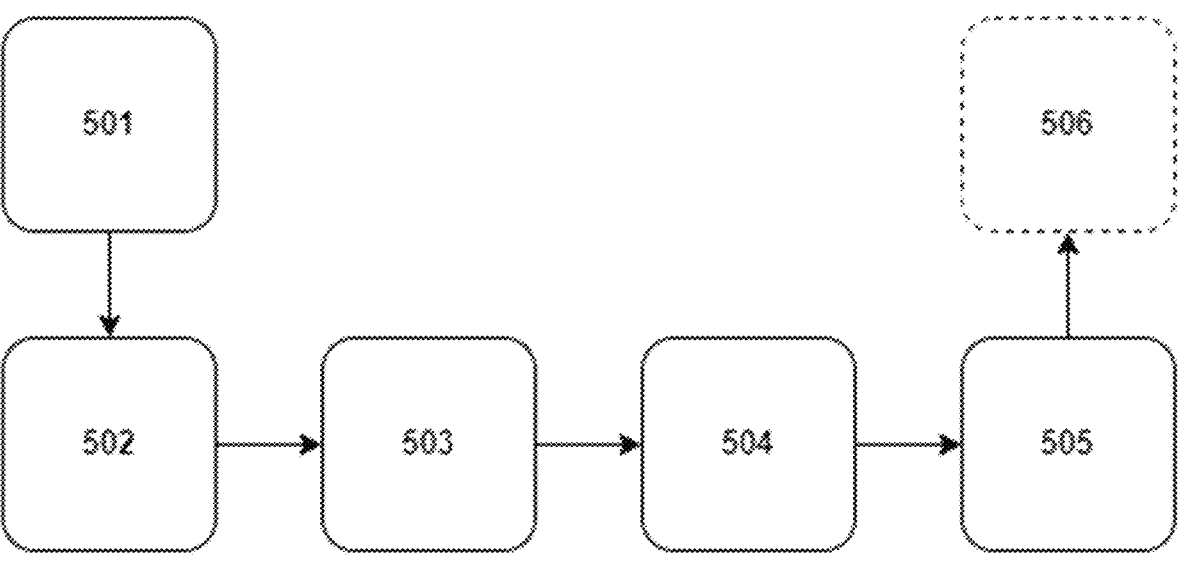
FIG. 1—illustrates the production methods of pet food products.

The production methods of pet food products may comprise the following steps as depicted in FIG. 1:

501 preparing a non-human metazoan cell line; and

502 cultivating the non-human metazoan cells in a cultivation system to obtain cell biomass; and

503 processing cell biomass to obtain a primary component; and

504 combining primary component with at least one component selected from the group of:

a secondary component, wherein the secondary component may comprise at least one source of saccharides and/or source of fats; and a tertiary component, wherein the tertiary component may comprise at least one auxiliary compound selected from the group of vitamins, minerals, binders, palatants, antioxidants, colorants and/or preservatives;

505 processing the combined components from the step 504 into a pet food product;

and optionally;

506 packaging and sterilizing the pet food product.

The production methods of pet food products in a step 505 as depicted in the FIG. 1 may comprise extrusion, cold-pressing, mold-injection and/or canning.

The pet food composition comprises at least one metazoan cell derived from at least one animal species and is cultivated within the same culture vessel or multiple culture vessels, in order to ensure the varied and balanced food most natural and convenient to the animals, while optionally improving their health conditions by providing the present pet food composition. In order to at least partially mitigate the drawbacks of the conventional pet food described above, the pet food composition according to at least one aspect of the invention may comprise animal meat with at least a small amount of cultivated metazoan cells.

Figure 2:
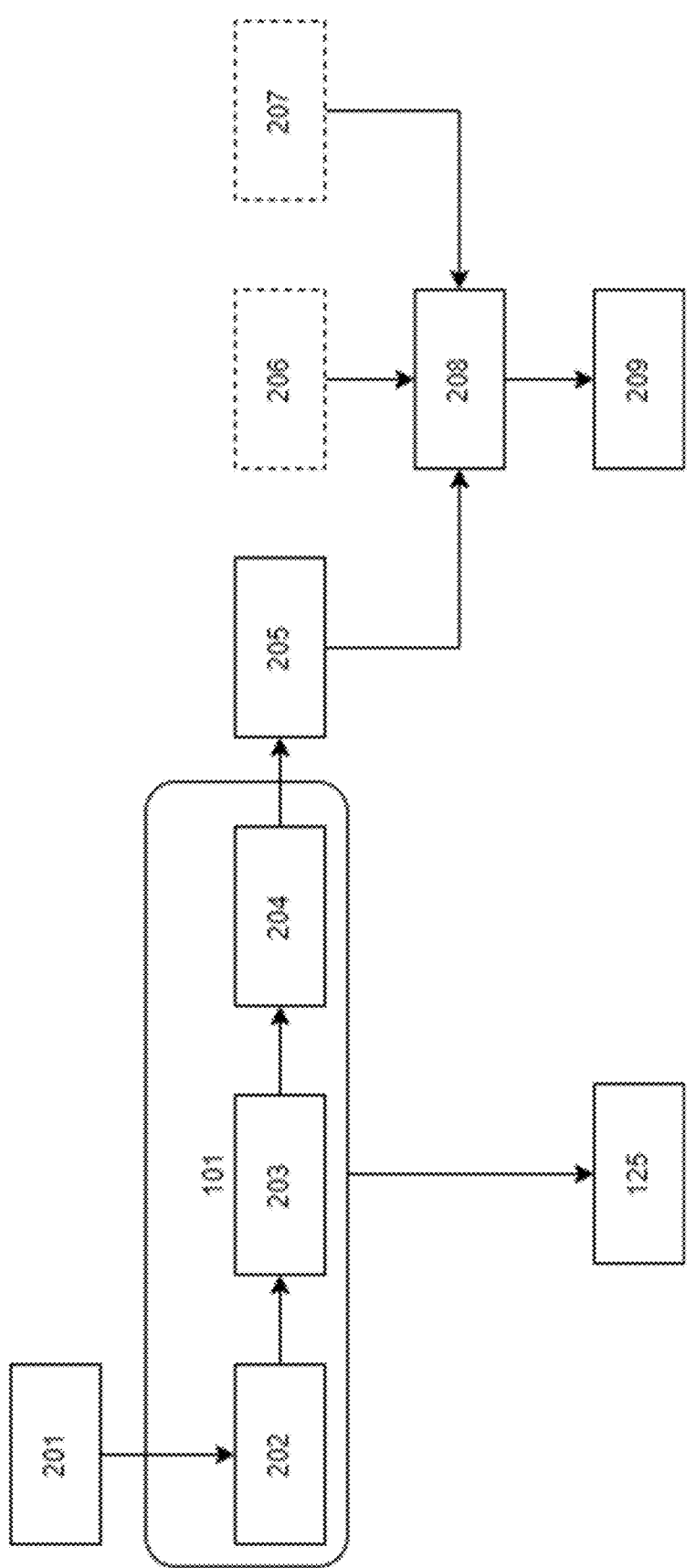
FIG. 2—illustrates an exemplary preparation scheme of pet food composition.

FIG. 2 is an exemplary preparation scheme of a pet food composition comprising the steps of: 201 obtaining metazoan cells, 202 inoculation in the culture vessel within the cultivation device 101, 203 cultivating the metazoan cells in the culture vessel within the cultivation device 101, 204 harvesting the metazoan cells from the culture vessel within the cultivation device 101; providing 205 primary component, 206 secondary component (optional), 207 tertiary component (optional), 208 processing the pet food composition, 209 processed pet food composition; the cultivation device 101 is controlled by the control unit 125.

The pet food composition may comprise a primary component, or a combination of a primary component with at least one of a secondary component and/or a tertiary component. The primary component may comprise at least one cultivated metazoan cell. In one aspect, the primary component may comprise at least one cell line, and/or cell population of cultivated metazoan cells. The secondary component may comprise at least one source of saccharides and/or fats. In one aspect of the invention, the secondary component may comprise a non-animal source of saccharides and/or fats. In another aspect, the secondary component may comprise at least one plant-originated source of saccharides and/or fats. In another aspect of the invention, the secondary component may comprise a metazoan cell source of saccharides and/or fats. A tertiary component may comprise at least one auxiliary compound selected from the group of vitamins, minerals, binders, palatants, antioxidants, colorants and/or preservatives.

The secondary component may comprise a non-animal source of saccharides and/or fats, preferably a plant-originated source.

The source of saccharides of the secondary component may comprise at least one of saccharide sources that comprise rice, corn, potatoes, sweet potatoes, barley, oats, peas, tapioca, lentils, chickpeas, sorghum, *quinoa*, millet, wheat, cassava, yams, pumpkin, carrots, beet pulp, apples, bananas, blueberries, cranberries, apricots, butternut squash, chia seeds, flaxseed, sunflower seeds, pumpkin seeds, carrageenan and/or any combination thereof;

The source of fats of the secondary component may comprise at least one of olive oil, coconut oil, avocado oil, canola oil, sunflower oil, flaxseed oil, sesame oil, almonds, walnuts, cashews, pecans, macadamia nuts, hazelnuts, flaxseeds, sunflower seeds, pumpkin seeds, hemp seeds, sesame seeds, avocado, olives, almond butter, cashew butter, seaweed, tahini, hummus and/or any combination thereof.

The tertiary component may comprise at least one of vitamins, minerals, binders, palatants, antioxidants, colorants and/or preservatives.

The tertiary component from the group of vitamins may comprise at least one of ascorbic acid, ascorbic acid phosphate, biotin, choline chloride, D-calcium pantothenate, folic acid, i-inositol, niacinamide, para-aminobenzoic acid, pyridoxal hydrochloride, pyridoxine hydrochloride, riboflavin, thiamine hydrochloride, vitamin B12 and/or any combination thereof.

The tertiary component from the group of binders may comprise at least one of guar gum, carrageenan, xanthan gum, pectin, cellulose, egg product, potato starch, rice flour, soy protein Isolate, corn starch, wheat gluten, gelatin, inulin or pea fiber and/or from the group of preservatives vitamin E, rosemary extract, citric acid, mixed tocopherols, ascorbic acid, green tea extract, cranberry extract, clove oil, oregano oil, neem extract and synthetic preservatives such as butylated hydroxyanisole, butylated hydroxytoluene, ethoxyquin, propyl gallate, sorbic acid, calcium propionate, potassium sorbate, sodium benzoate, tert-butylhydroquinone, natamycin or any combination thereof.

The tertiary component from the group of colorants may comprise at least one of beta-carotene, beet juice powder, turmeric, caramel color, spinach powder, *spirulina* extract, paprika extract, annatto extract, annatto seeds, chlorophyll, saffron, *gardenia* extract, red beet powder, carrot juice concentrate, purple sweet potato, hibiscus extract, cochineal extract, curcumin, cabbage extract, paprika, grape skin, caramelized onion, anthocyanins or any combination thereof.

The tertiary component from the group of preservatives may comprise at least one of vitamin E, rosemary extract, citric acid, mixed tocopherols, ascorbic acid, green tea extract, cranberry extract, clove oil, oregano oil, butylated hydroxyanisole, butylated hydroxytoluene, ethoxyquin, propyl gallate, sorbic acid, calcium propionate, potassium sorbate, sodium benzoate, tert-butylhydroquinone or any combination thereof.

The tertiary component from the group of antioxidants may comprise at least one of butylated hydroxyanisole, ethoxyquin, tert-butylhydroquinone, vitamin C, vitamin E, lycopene or any combination thereof;

The tertiary component from the group of palatants, wherein the palatants may comprise any compound or mixture that can increase the palatability of the pet food composition. The palatants may be animal-derived or plant-derived and may comprise artificial and natural flavors, hydrolyzed proteins, fat sprays, Maillard's reaction products or any combination thereof The tertiary component from the group of minerals may comprise at least one of the minerals may be a compound having at least one element selected from the group Ca, Cl, Cr, Cu, F, Fe, I, K, Mn, Co, Na, Ni, Se, Sn, Zn or any combination thereof.

In one aspect of the invention, the prepared pet food composition may further comprise beneficial microorganisms, emulsifiers, sweeteners, acidity regulators and digestibility enhancers.

The cell line may comprise a culture selected for uniformity from a cell population derived from a homogeneous tissue source. The cell line may include CHO, C2C12, MDBK, MDCK, CHO-K1 or CHO-DG44.

The cell population may comprise at least one of the following: one cell line suitable for growth in an artificial environment, a mixture of cell lines suitable for growth in an artificial environment, cells derived from at least one cell line suitable for growth in an artificial environment and/or cells derived from at least one tissue and suitable for growth in an artificial environment. The cells derived from at least one cell line may include cells derived through at least one passage and various genetic changes. The cells derived from at least one cell tissue may include cells isolated from living tissue and grown and/or multiplicated in the artificial environment. The artificial environment may comprise growth in an artificial culture medium.

Metazoan cells may be obtained through a biopsy and/or necropsy of animal tissue or from commercially available metazoan cell sources. Obtained metazoan cells may be inoculated in at least one culture vessel within a cultivation device. The culture vessel contains a culture medium in which the metazoan cells are cultivated. The cultivation process may comprise proliferation, differentiation and any genetic or non-genetic modification.

The non-human metazoan cells may comprise bovine, avian, porcine, equine, piscine, *cervine* or cricetine cell lines. In another aspect of the invention, the non-human metazoan cells may comprise any other non-human metazoan cell line.

The non-human metazoan cells may have the characteristics and/or properties of: hepatocytes, myocytes, myoblasts, osteoblasts, fibroblasts, lipoblasts, odontoblasts, keratinocytes, mesenchymal stem cells, multipotent progenitor cells, embryonic stem cells, myofibroblasts, myosatellite cells and/or any combinations thereof.

The cultivated metazoan cells further include nucleic acids, including DNA and RNA, from which it was derived. For example, the cell line of CHO-K1 cells comprises DNA of the Chinese hamster (*Cricetulus griseus*). For another example, the cell population derived from CHO-K1 comprises DNA of the Chinese hamster (*Cricetulus griseus*). For yet another example, a cell culture derived from bovine tissue includes DNA of cattle (*Bos taurus*).

The cell population may therefore include nucleic acids (e.g. DNA) of the species from which it was derived. In another words, the primary component comprising the cultivated cells, cultivated cell population and/or cultivated cell line may therefore include nucleic acids (e.g. DNA) of the species from which it was derived and/or obtained.

The nucleic acids (e.g. DNA) of the primary component may be analyzed by various methods to determine the species from which the primary component was derived. Further, the mixture of the primary component, secondary component and/or tertiary component may be analyzed by various methods to determine the species from which the primary component was derived. Furthermore, any form of the pet food composition originating from the primary component, secondary component and/or tertiary component may be analyzed by various methods to determine the species from which the primary component was derived. Such analysis may provide information about one species or more, for example if more than one species was used for preparation of the pet food composition.

The analysis of nucleic acid may comprise isolation of the sample, homogenization of the sample, isolation of the nucleic acid, polymerase chain reaction, sequencing of DNA and/or sequencing of RNA and comparing to databases of nucleic acids.

However, the cultivated cell lines may undergo specific or non-specific mutation in their DNA, due to the process of cell culture or targeted mutation of their genome.

Therefore, the pet food composition may include a primary component comprising cultured cells with nucleic acids having a maximal 99% of similarity with the DNA of the species from which it was derived.

However, it can be expected that DNA may be damaged due to preparation of the pet food composition. Therefore, the pet food composition may include a primary component comprising cultured cells with sequence of nucleic acid having a maximal 99% similarity with the DNA of the species from which it was derived.

In one aspect of the invention, the prepared food composition comprises at least one of animal cells, wherein the animal cells may be derived from any animal (non-human).

Examples of species from which the metazoan cells may be derived from at least one of:

cattle (*Bos taurus*), chicken (*Gallus domesticus*), domestic pig (*Sus domesticus*), house cricket (*Acheta domesticus*), garden snail (*Helix pomatia*), common carp (*Cyprinus carpio*), horse (*Equus ferus*), edible crab (*Cancer pagurus*), marsh frog (*Pelophylax ridibundus*), common *octopus* (*Octopus vulgaris*), gilt-head bream (*Sparus aurata*), roe deer (*Capreolus capreolus*), common sea urchin (*Echinus esculentus*), harbor seal (*Phoca vitulina*), European stag beetle (*Lucanus cervus*), African bush elephant (*Loxodonta africana*), house mouse (*Mus musculus*), green sea turtle (*Chelonia mydas*). Therefore, primary component may comprise cultivated metazoan cells that are derived, for example, from bovine, avian, porcine, equine, piscine, *cervine* or cricetine cell lines. Also, the metazoan cells in a primary component may have characteristics of fibroblasts, myoblasts, adipocytes, myocytes or hepatocytes.

The cell population used may be primary (non-immortalized) cells, or an immortalized cell line. Commercially available immortalized cell lines may be used, for example MDBK, MDCK, CHO or C2C12.

In the evaluation of cultured non-human metazoan cells within a composition, it is important to assess the degree of similarity between nucleic acid sequences obtained from the sample and reference genomes or reference cell lines. For example, when comparing a sequence of 100 nucleobases from the sample to a reference genome, a 99% similarity (i.e., 99 out of 100 nucleobases identical) may be considered a strong indication that the cultured cells share a common origin with the reference species or cell line. However, lower thresholds, such as 98%, 97%, or even 80%, may also be relevant, depending on the required by the analysis and the biological context.

Similarity thresholds can be adjusted based on the nature of the genomic regions analyzed. A high similarity (e.g. 99% to 100%) might indicate that the cultured cells likely originate from the reference species or cell line, particularly when analyzing conserved regions of the genome. On the other hand, a similarity of 90% to 98% may still suggest a close relationship but could reflect natural genetic variation, sequencing errors, or the influence of less conserved regions. Further, a similarity range as low as 80% to 90% may indicate that the cells originate from a related species or are subject to higher variability in the genomic regions being compared.

When evaluating samples, ranges of similarity can be implemented depending on the sensitivity of the analysis. For example, a range of 97% to 100% similarity may be sufficient for determining a close genetic match to the reference species or cell line, while 80% to 96% similarity may suggest further investigation to confirm the origin of the cultured cells. In cases where the similarity is below 80%, it may indicate that the sample contains cells from a different or unknown source.

The choice of similarity threshold may depend on the method of analysis. For instance, highly conserved genomic regions may require a 99% to 100% match to confirm identity, while more variable regions may allow for a broader range, such as 80% to 95%. Additionally, the type of nucleic acid analyzed (e.g., DNA or RNA) and the specific genomic markers used (e.g., single nucleotide polymorphisms or larger structural variations) may influence the expected degree of similarity. Empirical data and statistical validation can help define appropriate thresholds to ensure accurate and reliable identification.

In some aspects of the invention, the composition of the final product is intrinsically linked to the methods by which it is derived from cultivated non-human metazoan cells. The process of cultivating non-human metazoan cells to form cell biomass, and subsequently processing this cell biomass into pet food or products for human consumption, ensures that the characteristics of the composition (e.g., cellular content, molecular markers) are a direct result of the specific steps taken in development of the cell line, cultivation, harvesting, and processing. This interconnection between the methods and the composition plays a critical role in determining the nature and functionality of the final food product.

The composition produced from non-human metazoan cell biomass may vary depending on the precise methodologies applied during cultivation and harvesting. For instance, the conditions under which the non-human metazoan cells are cultivated (e.g., culture media, growth factors, temperature) may influence the yield and quality of the biomass, including its molecular composition (e.g., protein, lipid, and nucleic acid profiles). The subsequent steps, such as cell disruption, extraction, and purification, further modify the final composition. Thus, the specific methods employed in these stages may be closely tied to the structural and functional properties of the resulting food product.

In cases where multiple methods can be applied to similar cell types, the resulting products may exhibit certain common features due to the use of non-human metazoan cells as the base material. However, variations in methodology (e.g., different techniques for biomass isolation, purification, or formulation) may lead to distinctions in the final product, which can be assessed by evaluating compositional markers. These markers may include specific protein or lipid profiles, nucleic acid sequences, or any other molecular signatures indicative of the production method used.

To accurately evaluate the relationship between the composition and the methods used to derive it, compositional analysis can be employed to detect residual markers or characteristics unique to the specific methods of cultivation and processing. For instance, the detection of specific proteins, lipids, or nucleic acids that result from the particular processing conditions can serve as indicators of the method employed, even when the base material (non-human metazoan cells) remains consistent. Such analysis provides a comprehensive way to link the final product back to the methods applied in its production, ensuring that both the composition and the methods used to create it are considered as part of the overall evaluation.

The connection between the composition and the methods of production may be especially important in ensuring that the food product derived from non-human metazoan cells meets predefined functional or safety standards. Since different methods may alter the composition in subtle but significant ways, the selection of specific cultivation and processing techniques can influence not only the biochemical properties of the final product but also its performance, usability, and safety profile. This emphasizes the need to consider both the composition and the methods of production together when evaluating the product.

For example, when the analysis of the pet food comprising cultured cells reveals a sequence of the 100 nucleobases and the comparison with DNA databases identifies 99 nucleobases identical in the genome of Chinese hamster, such analysis should be assumed as positive. In such a case, it should be assumed that the analyzed pet food comprises cultured cells from the Chinese hamster.

In another aspect, analysis of nucleic acid of the pet food composition may comprise isolation of the sample, homogenization of the sample, isolation of the nucleic acid, polymerase chain reaction, sequencing of DNA and/or sequencing of RNA and comparing to the databases of genes. In case a specific gene of the particular animal is found in the sample of the pet food composition, it should be assumed that the analyzed pet food comprises cultured cells from the particular animal. In one case, when the pet food composition prepared from the cultured cells includes a gene and/or another representative sequence of the Chinese hamster, it should be assumed that the pet food is prepared from the CHO cell line and/or cells derived from the CHO cells.

In yet another aspect, analysis of nucleic acid of the pet food composition may include homogenization of the pet food sample (e.g. pulverization), isolation of total nucleic acids, using real-time polymerase chain reaction (called also qPCR) with primers targeted to specific gene of the reference animal and quantification of the detected gene (e.g. by fluorescent probes).

In case of cell population comprising cell line CHO-K1 and/or cells derived from cell line CHO-K1, the primers may be targeted against the genes of the Chinese hamster. The reference gene and/or specific gene may comprise Chinese hamster genes EIF3K, AKR1A1, RPS16, and/or others.

Therefore, the pet food composition from the CHO-K1 cells may include a nucleic acid sequence of gene of a Chinese hamster. Further the pet food composition from the CHO-K1 cells may include a nucleic acid sequence in any part of the genome of the Chinese hamster.

For another example, when the analysis of the pet food comprising cultured cells reveals a sequence of the 20 nucleobases and the comparison with the DNA databases identifies 19 nucleobases identical in the genome of *Bos taurus*, such analysis should be assumed as positive. In such a case, it should be assumed that the analyzed pet food comprises cultured cells from the *Bos taurus*.

As depicted in the FIG. 1, the step 503 of production methods is a crucial step of cell biomass processing into primary component, which may be used in further steps. The step 503 of production methods may comprise processing cell biomass to obtain a primary component. The cell biomass may be processed by at least one process of:

washing to flush out culture medium residues to obtain primary component; and/or homogenizing to obtain primary component in a form of even more homogenous mixture; and/or centrifuging, sieving and/or filtering to remove the portion of water to obtain primary component in a form of even more concentrated paste; and/or dried, vacuum dried, lyophilized and/or IR dried to obtain a powderous primary component; and/or solidifying with at least one solidifying agent to obtain a primary component in a more solid form, i. e. mixed with at least one plasticizer, stabilizer, emulsifying agent, gelling agent and/or any other suitable additive to obtain a primary component in a form of viscoelastic material, or in another words, to obtain a primary component in a more solid form; and chemically lysing, hydrolysing and/or autolysing to obtain primary component that is more digestible and/or hypoallergenic; and/or thermally treating and/or combining with thermally activated substances to perform at least one of Maillard reaction, denaturation, caramelization, lipid oxidation, gelatinization, enzymatic reaction and/or change of texture to obtain a primary component that is more digestible, tender, aromatic, flavorful, palatable and/or resistant to harmful microorganisms; and/or inactivating to stop the proliferation phase of the non-human metazoan cells to obtain a primary component that is stable and safe for consumption.

The cell biomass may be processed with at least one process described in the previous paragraph to obtain the primary component. The processes may be performed in any order.

The cell biomass may be processed by at least one product processing device selected from the group of:

a mixer, a grinder, a chopper, a lyophilizer, a steamer, a blender, a cooker, a boiler, a dryer, a vacuum dryer, a grill, a roaster, a washing device, a reaction vessel, a bioreactor; a filtration device, a centrifuge, a sieve, a grill, a heater, UV lamp, IR lamp, extruder, chiller, freezer;

and/or any other product processing device.

The cell biomass may be washed to improve the texture, flavor, and aroma of the cell biomass. The washing of the cell biomass may flush out remaining culture media, metabolites and other undesired compounds. The washing of the cell biomass may also dilute the cell biomass if needed. The washing of the cell biomass may also rinse the cell biomass with a solution comprising various nutrients.

The cell biomass may be mechanically and/or chemically homogenized to disrupt any clumps, aggregates, and lumps that may form during the cultivation process.

The cell biomass may be centrifuged, sieved, filtered, dried and/or evaporated to remove a portion of water from the cell biomass. The cell biomass before centrifuging, sieving, filtering, drying and/or evaporating may be characterized by having a total water content in a range of 75 wt. % to 99 wt. %, in a range of 76 wt. % to 98 wt. %, in a range of 77 wt. % to 97 wt. %, in a range of 78 wt. % to 96 wt. %, in a range of 79 wt. % to 95 wt. %, in a range of 80 wt. % to 94 wt. %, in a range of 81 wt. % to 93 wt. %, in a range of 82 wt. % to 92 wt. %, in a range of 83 wt. % to 91 wt. %, in a range of 84 wt. % to 90 wt. %, in a range of 85 wt. % to 89 wt. %, in a range of 86 wt. % to 88 wt. %.

The portion of water removed from the cell biomass may be in a range of 1 wt. % to 5 wt. % of the cell biomass, in a range of 10 wt. % to 15 wt. % of the cell biomass, in a range of 20 wt. % to 25 wt. % of the cell biomass, in a range of 30 wt. % to 35 wt. % of the cell biomass, in a range of 40 wt. % to 45 wt. % of the cell biomass, in a range of 50 wt. % to in a range of 55 wt. % of the cell biomass, in a range of 60 wt. % to 65 wt. % of the cell biomass, in a range of 70 wt. % to 75 wt. % of the cell biomass, in a range of 80 wt. % to 85 wt. % of the cell biomass or in a range of 90 wt. % to 95 wt. % of the cell biomass. In one aspect of the invention, the cell biomass after centrifuging, sieving, filtering, drying and/or evaporating may be characterized by having lower total water content than before at least one of said processes. In yet another aspect of the invention, the cell biomass may have only intracellular water, i. e. the water inside the cells of the cell biomass.

The cell biomass may have the mass density in the range of 900 to 1200 kg·m$^{-3}$, in the range of 930 kg·m$^{-3}$ to 1170 kg·m$^{-3}$, in the range of 960 kg·m$^{-3}$ to 1140 kg·m$^{-3}$, in the range of 990 kg·m$^{-3}$ to 1110 kg·m$^{-3}$ or in the range of 1020 kg·m$^{-3}$ to 1080 kg·m$^{-3}$.

The cell biomass may be solidified using at least one solidifying agent. The solidifying agents may perform solidifying, emulsifying, gelling, stiffening or any other process that changes the texture of the cell biomass.

The textural and/or viscoelastic properties of the cell biomass may be enhanced using at least one solidifying agent selected from the group of xanthan gum, sodium alginate, potassium alginate, locust bean gum, carrageenan, guar gum, glycerol monooleate, glycerol monostearate, glycerol distearate, glyceryl dioleate, glyceryl dicaprylate, soy lecithin, cellulose gum, whey protein concentrate, tragacanth gum, arabic gum, konjac, acacia, gellan gum, gelatin, pectin, agar, glucomannan, carboxymethylcellulose, methylcellulose, potato starch, corn starch, tapioca starch, transglutaminase, polyphosphate and/or any other solidifying agent to obtain the primary component in more solid form. The solidifying agent may further comprise any saccharide, protein and/or any other compound capable of solidifying the cell biomass, i. e. capable of increasing the dynamic viscosity of the cell biomass. The said amount of solidifying agent may vary depending on the characteristics of the cell biomass.

The solidifying agent may be added to the cell biomass in an amount in a range of 0.01 wt. % to 15 wt. %, in a range of 0.1 wt. % to 15 wt. %, in a range of 1 wt. % to 14 wt. %, in a range of 2 wt. % to 13 wt. %, in a range of 3 wt. % to 12 wt. %, in a range of 4 wt. % to 11 wt. %, in a range of 5 wt. % to 10 wt. %, in a range of 6 wt. % to 9 wt. %, in a range of 7 wt. % to 8 wt. % of the cell biomass and/or any other amount of solidifying agent depending on the properties of the solidifying agent. The said amount of solidifying agent may vary depending on the characteristics of the cell biomass.

In one aspect of the invention, the solidifying agent may be different from the secondary component.

The cell biomass may be inactivated (i. e. the cell biomass is killed) to stop proliferation, differentiation, maturation, any cell metabolic processes or any other phase of the non-human metazoan cell cycle. The cell biomass may be inactivated using drying, chemical detergent induced lysis, cooling and/or any other kind of thermal treatment. The cell biomass may be also inactivated using an osmotic shock, wherein the osmotic shock may be performed by exposing the cell biomass to an hypertonic or hypotonic solution.

The thermal treatment of the cell biomass may comprise exposing the cell biomass to a heating environment having a temperature in a range of 80° C. to 150° C., in a range of 85° C. to 145° C., in a range of 90° C. to 140° C., in a range of 95° C. to 135° C., in a range of 100° C. to 130° C., in a range of 105° C. to 125° C. or in a range of 110° C. to 120° C. The duration of exposure of the cell biomass to a heating environment may be in a range of 30 seconds to 600 seconds, in a range of 60 seconds to 540 seconds, in a range of 90 seconds to 510 seconds, in a range of 120 seconds to 480 seconds, in a range of 150 seconds to 450 seconds, in a range of 180 seconds to 420 seconds, in a range of 210 seconds to 390 seconds, in a range of 240 seconds to 360 seconds or in a range of 270 seconds to 330 seconds. The heating environment may comprise a plurality of heating elements configured to provide heat to an environment. The heating elements may comprise electrical heater, ceramic heater, autoclave, infrared heater, induction heater, steam heater and/or any other appropriate device.

The cell biomass may be dried using a thermal treatment described in the previous paragraph. The cell biomass may be dried by a thermal treatment using air drier, oven, heater or any other appropriate device capable of reducing water content of the cell biomass. The cell biomass may be also lyophilized to reduce the water content of the cell biomass.

The osmotic shock of the cell biomass may comprise exposing the cell biomass to a hypotonic or hypertonic solution capable of inducing osmotic stress. The hypertonic solution may increase the osmotic pressure outside the cell that draws intracellular water out of the cell, which may cause cells to shrink, disrupt its structure and restrict its function. The exposure to the hypotonic solution may result in an influx of water into the cell, which may lead to the swelling of the cells, rupture of the cell membrane, disruption of cellular integrity, leakage of cellular contents and eventual cell lysis. The hypertonic and hypotonic solution is tailored and chosen according to the cell biomass characteristics such that undesirable effects are minimized. The concentration of such solutions is also calculated according to the cell biomass characteristics. The exemplary hypertonic and hypotonic solution may be an aqueous solution of sodium chloride, magnesium chloride, potassium chloride, ammonium chloride, EDTA and/or any other appropriate solution.

The cell biomass may be characterized by a cell density in a range of $10^6$ to $10^{13}$ cells per 1 g of the cell biomass, $10^7$ to $10^8$ cells per 1 g of the cell biomass, $10^8$ to $10^9$ cells per 1 g of the cell biomass, $10^9$ to $10^{10}$ cells per 1 g of the cell biomass or $10^{10}$ to $10^{11}$ cells per 1 g of the cell biomass.

The cell biomass may have the characteristics of a suspension, wherein the suspension may have the cells evenly distributed throughout a dispersion medium without settling out or joining together into aggregates, clumps and/or lumps. In another aspect, the cells may join together into larger aggregates, clumps and/or lumps and may settle over time. In yet another aspect, the cell biomass may be processed to remove a portion of extracellular and/or intracellular water. Such processed cell biomass may have the characteristics of a concentrated paste. The cell biomass in a form of concentrated paste may be characterized by its rheological parameters and/or properties. Such rheological parameters and/or properties may comprise dynamic (shear) viscosity, kinematic viscosity, storage modulus and loss modulus.

The dynamic viscosity of the cell biomass in ambient temperature at 20° C. may be in a range of 500 mPa·s to 3000 mPa·s, in a range of 550 mPa·s to 2950 mPa·s, in a range of 600 mPa·s to 2900 mPa·s, in a range of 650 mPa·s to 2850 mPa·s, in a range of 700 mPa·s to 2800 mPa·s, in a range of 750 mPa·s to 2750 mPa·s, in a range of 800 mPa·s to 2700 mPa·s, in a range of 850 mPa·s to 2650 mPa·s, in a range of 900 mPa·s to 2600 mPa·s, in a range of 950 mPa·s to 2550 mPa·s, in a range of 1000 mPa·s to 2500 mPa·s, in a range of 1050 mPa·s to 2450 mPa·s, in a range of 1100 mPa·s to 2400 mPa·s, in a range of 1150 to 2350 mPa·s, 1200 mPa·s to 2300 mPa·s, in a range of 1250 mPa·s to 2550 mPa·s, in a range of 1300 mPa·s to 2500 mPa·s, in a range of 1350 mPa·s to 2450 mPa·s, in a range of 1400 mPa·s to 2400 mPa·s, in a range of 1450 mPa·s to 2350 mPa·s, in a range of 1500 mPa·s to 2300 mPa·s, in a range of 1550 mPa·s to 2250 mPa·s, in a range of 1600 mPa·s to 2200 mPa·s, in a range of 1650 mPa·s to 2150 mPa·s, in a range of 1700 mPa·s to 2100 mPa·s, in a range of 1750 mPa·s to 2050 mPa·s, in a range of 1800 mPa·s to 2000 mPa·s or in a range of 1850 mPa·s to 1950 mPa·s.

The storage modulus of the cell biomass may be in a range of 0.5 Pa to 10.0 Pa, in a range of 0.6 Pa to 9.9 Pa, in a range of 0.7 Pa to 9.8 Pa, in a range of 0.8 Pa to 9.7 Pa, in a range of 0.9 Pa to 9.6 Pa, in a range of 1.0 Pa to 9.5 Pa, in a range of 1.1 Pa to 9.4 Pa, in a range of 1.2 Pa to 9.3 Pa, in a range of 1.3 Pa to 9.2 Pa, in a range of 1.4 Pa to 9.1 Pa, in a range of 1.5 Pa to 9.0 Pa, in a range of 1.6 Pa to 8.9 Pa, in a range of 1.7 Pa to 8.8 Pa, in a range of 1.8 Pa to 8.7 Pa, in a range of 1.9 Pa to 8.6 Pa, in a range of 2.0 Pa to 8.5 Pa, in a range of 2.1 Pa to 8.4 Pa, in a range of 2.2 Pa to 8.3 Pa, in a range of 2.3 Pa to 8.2 Pa, in a range of 2.4 Pa to 8.1 Pa, in a range of 2.5 Pa to 8.0 Pa, in a range of 2.6 Pa to 7.9 Pa, in a range of 2.7 Pa to 7.8 Pa, in a range of 2.8 Pa to 7.7 Pa, in a range of 2.9 Pa to 7.6 Pa, in a range of 3.0 Pa to 7.5 Pa, in a range of 3.1 Pa to 7.4 Pa, in a range of 3.2 Pa to 7.3 Pa, in a range of 3.3 Pa to 7.2 Pa, in a range of 3.4 Pa to 7.1 Pa, in a range of 3.5 Pa to 7.0 Pa, in a range of 3.6 Pa to 6.9 Pa, in a range of 3.7 Pa to 6.8 Pa, in a range of 3.8 Pa to 6.7 Pa, in a range of 3.9 Pa to 6.6 Pa, in a range of 4.0 Pa to 6.5 Pa, in a range of 4.1 Pa to 6.4 Pa, in a range of 4.2 Pa to 6.3 Pa, in a range of 4.3 Pa to 6.2 Pa, in a range of 4.4 Pa to 6.1 Pa, in a range of 4.5 Pa to 6.0 Pa, in a range of 4.6 Pa to 5.9 Pa, in a range of 4.7 Pa to 5.8 Pa, in a range of 4.8 Pa to 5.7 Pa, in a range of 4.9 Pa to 5.6 Pa, in a range of 5.0 Pa to 5.5 Pa, in a range of 5.1 Pa to 5.4 Pa, in a range of 5.2 Pa to 5.3 Pa. The measurement conditions were approximately 20° C., relative humidity in a range of 70% to 85%, operating frequency 1 Hz and shear strain amplitude about 0.9%.

The loss modulus of the cell biomass may be in a range of 0.1 Pa to 7 Pa, in a range of 0.2 Pa to 6.9 Pa, in a range of 0.3 Pa to 6.8 Pa, in a range of 0.4 Pa to 6.7 Pa, in a range of 0.5 Pa to 6.6 Pa, in a range of 0.6 Pa to 6.5 Pa, in a range of 0.7 Pa to 6.4 Pa, in a range of 0.8 Pa to 6.3 Pa, in a range of 0.9 Pa to 6.2 Pa, in a range of 1.0 Pa to 6.1 Pa, in a range of 1.1 Pa to 6.0 Pa, in a range of 1.2 Pa to 5.9 Pa, in a range of 1.3 Pa to 5.8 Pa, in a range of 1.4 Pa to 5.7 Pa, in a range of 1.5 Pa to 5.6 Pa, in a range of 1.6 Pa to 5.5 Pa, in a range of 1.7 Pa to 5.4 Pa, in a range of 1.8 Pa to 5.3 Pa, in a range of 1.9 Pa to 5.2 Pa, in a range of 2.0 Pa to 5.1 Pa, in a range of 2.1 Pa to 5.0 Pa, in a range of 2.2 Pa to 4.9 Pa, in a range of 2.3 Pa to 4.8 Pa, in a range of 2.4 Pa to 4.7 Pa, in a range of 2.5 Pa to 4.6 Pa, in a range of 2.6 Pa to 4.5 Pa, in a range of 2.7 Pa to 4.4 Pa, in a range of 2.8 Pa to 4.3 Pa, in a range of 2.9 Pa to 4.2 Pa, in a range of 3.0 Pa to 4.1 Pa, in a range of 3.1 Pa to 4.0 Pa, in a range of 3.2 Pa to 3.9 Pa, in a range of 3.3 Pa to 3.8 Pa, in a range of 3.4 Pa to 3.7 Pa, in a range of 3.5 Pa to 3.6 Pa. The measurement conditions were approximately 20° C., relative humidity in a range of 70% to 85%, operating frequency 1 Hz and shear strain amplitude about 0.9%.

The rheological parameters described in the preceding paragraphs may be measured using at least one analytical instrument and/or method selected from the group of capillary rheometer, cone rheometer, plate rheometer, oscillatory viscometer, rolling ball viscometer, vibrational viscometer, microfluidic viscometer, rotational viscometer, micro rheometer, extensional rheometer and/or any other analytical instrument/method capable of measuring such parameters.

Examples of bovine cell lines may be Madin-Darby Bovine kidney (MDBK) cell line, bovine lung cells, bovine microvascular endothelial cell line or bovine mammary epithelial cell line (bMECs). These examples are not limiting and the piscine cell lines may be originated in any metazoan species categorized under *Bos* Genus. Another metazoan species in the *Bos* genus from which the cell line may have originated are *Bison bison* (American *Bison*), *Bos taurus* (Cattle), *Bos indicus* (*Zebu*) and/or *Bos grunniens* (Yak).

Examples of avian cell lines may be chicken embryonic fibroblast-1 (CEF-1) cell line, quail myoblast 7 (QM7) cell line, chicken embryonic kidney (CEK) cell line or chicken macrophage (HD11) cell line. These examples are not limiting and the avian cell lines may be originated in any metazoan species categorized under Aves (Class). Other metazoan species in the Aves class from which the cell line may have originated are *Columba livia* (Rock Pigeon), *Gallus gallus domesticus* (Domestic Chicken), Anas platyrhynchos (Mallard Duck), and/or *Meleagris gallopavo* (Wild Turkey).

Examples of equine cell lines may be horse dermal fibroblast (NBL-6) cell line, equine fibroblast (EFC) cell line, equine progenitor (EPC) cell line or equine endometrial (EEC) cell line. These examples are not limiting and the equine cell lines may be originated in any metazoan species categorized under *Equus* (Genus). Other metazoan species in the *Equus* genus from which the cell line may have originated are *Equus caballus* (Horse), *Equus ferus przewalskii* (Przewalski's Horse), *Equus africanus asinus* (Donkey), and/or *Equus zebra* (Zebra).

Examples of piscine cell lines may be rainbow trout gonad 2 (RTG-2) cell line, chinook salmon embryo 214 (CHSE-214) cell line, epithelioma papulosom *cyprini* (EPC) cell line, grass carp tail (GCT) cell line or rainbow trout gill W1 (RTGill-W1) cell line. These examples are not limiting and the piscine cell lines may be originated in any metazoan species categorized under Pisces (Superclass). Other metazoan species in the Cerividae family from which the cell line may have originated are *Alces alces* (Moose), *Odocoileus virginianus* (White-Tailed Deer), *Rangifer tarandus* (Reindeer), *Axis axis* (*Axis* Deer) and/or *Capreolus capreolus* (Roe Deer).

Examples of *cervine* cell lines may be *cervus elaphus* lung cells 1 (CCL-1) cell line or *cervus elaphus* fibroblast (CFC) cell line. These examples are not limiting and the *cervine* cell lines may be originated in any metazoan species categorized under Cervidae (Family). Other metazoan species in the Rodentia order from which the cell line may have originated are *Mus musculus* (House Mouse), *Rattus norvegicus* (Brown Rat), *Cavia porcellus* (Guinea Pig), *Meriones unguiculatus* (Mongolian Gerbil) and/or *Mesocricetus auratus* (Golden Hamster).

Examples of cricetine cell lines may be chinese hamster ovary (CHO) cell line, chinese hamster ovary K1 (CHO-K1)

cell line, chinese hamster lung (CHLN) cell line or baby hamster kidney 21 (CHK-21) cell line. These examples are not limiting and the cricetine cell lines may be originated in any metazoan species categorized under Rodentia (Order). Other metazoan species in the Rodentia order from which the cell line may have originated are *Mus musculus* (House Mouse), *Rattus norvegicus* (Brown Rat), *Cavia porcellus* (Guinea Pig), *Meriones unguiculatus* (Mongolian Gerbil) and/or *Mesocricetus auratus* (Golden Hamster) *Meriones unguiculatus* (Mongolian Gerbil) and/or *Mesocricetus auratus* (Golden Hamster).

Other examples of such non-human metazoan cell lines may be originated in any non-human metazoan specie such as *Sus domesticus* (Domestic pig), *Acheta domesticus* (House Cricket), *Helix pomatia* (Garden snail), *Cyprinus carpio* (Common carp), *Cancer pagurus* (Edible crab), *Pelophylax ridibundus* (Marsh frog), *Octopus vulgaris* (Common *octopus*), *Sparus aurata* (Gilt-head bream), *Capreolus capreolus* (Roe deer), *Echinus esculentus* (Common sea urchin), *Phoca vitulina* (Harbor seal), *Lucanus cervus* (European stag beetle) and/or *Mus musculus* (House mouse).

The cell biomass may comprise at least one non-human metazoan cell line. Therefore, the cell biomass may comprise, for example, at least two non-human metazoan cell lines, at least three non-human metazoan cell lines or any other quantity of different non-human metazoan cell lines higher than one. Combining non-human metazoan cell lines may be beneficial to provide a high-quality source of nutrients within the primary component.

An exemplary combination may be:

a first cell line having characteristics of fibroblasts, wherein the first cell line may accumulate a relatively high amount of amino acids and proteins; and a second cell line having characteristics of adipocytes, wherein the second cell line may accumulate a relatively high amount of fatty acids and fats;

thus providing a cell biomass rich in both protein and fats while preserving the animal origin of said nutrients;

wherein the cell biomass is prepared for being processed into the primary component.

Another exemplary combination may be:

a first cell line having characteristics of fibroblasts, wherein the first cell line may accumulate a relatively high amount of amino acids and proteins; and a second cell line having characteristics of adipocytes, wherein the second cell line may accumulate a relatively high amount of fatty acids and fats; and a third cell line having characteristics of myoblasts, wherein the third cell line may improve the textural properties of the cell biomass comprising said three different cell lines;

thus providing a cell biomass rich in both protein and fats while preserving animal origin of said nutrients with improved textural properties;

wherein the cell biomass is prepared for being processed into the primary component.

In one aspect of the invention, the combination of the non-human metazoan cell lines may comprise a combination of at least two different non-human metazoan cell lines from the same metazoan species. The primary component prepared from only one non-human metazoan species may be considered as the pure primary component. For example, the bovine fibroblasts and bovine adipocytes may be combined, which will result in a pure bovine primary component.

In another aspect of the invention, the combination of the non-human metazoan cell lines may comprise a combination of cell lines from at least two different non-human metazoan species. The primary component prepared from at least two different non-human metazoan species may be considered as the hybrid primary component. For example, the CHO-K1 (Chinese Hamster Ovaries—K1 cells) cells and embryonic chicken fibroblasts may be combined, which will result in a hybrid primary component.

The cell biomass may be further processed by any other process to obtain the primary component suitable for further processing into pet food products.

The pet food product may be produced by using the primary component. The pet food product may be produced by combining the primary component with at least one component selected from the secondary component and the tertiary component described herein. Therefore, the pet food product may be made:

from the primary component; and/or from a combination of the primary component with the secondary component; and/or from a combination of the primary component with the tertiary component; and/or from a combination of the primary component with the secondary component and the tertiary component.

The primary component may comprise at least one non-human metazoan cell line. Therefore, the primary component may comprise, for example, two non-human metazoan cell lines. For another example, the primary component may comprise three non-human metazoan cell lines. For yet another example, the primary component may comprise four non-human metazoan cell lines.

The secondary component may comprise at least one source of saccharides and/or fats, wherein:

at least one of the sources of saccharides may be glucose and fructose, chicory root extract, inulin, resistant starch, maltodextrin, lactose, maltose, sucrose and saccharose, rice, corn, potatoes, sweet potatoes, barley, oats, peas, soy, tapioca, lentils, chickpeas, sorghum, *quinoa*, millet, wheat, cassava, yams, pumpkin, carrots, beet pulps, apples, bananas, blueberries, cranberries, apricots, butternut squash, carrageenan, *spirulina*, pectin, pineapple, tomatoes, elderberries, rosehips, beets, celery, resistant starch, inulin, xanthan gum, cereals, grains, beta-glucans, *psyllium*, oat bran, what bran, cellulose, broccoli, cauliflower, guar gums, chicory roots, cranberries, squash, beans, group of waxy rice starch, waxy barley starch, waxy maize starch, waxy wheat starch, waxy potato starch, oat starch, gluten, sorbitol, spinach, grape, glycerol, soybean hulls, whole grain oat, grape, celery and/or any other appropriate source of saccharides and/or combination thereof; and at least one of the sources of fats may be olive oil, coconut oil, avocado oil, canola oil, sunflower oil, flaxseed oil, sesame oil, rapeseed oil, flaxseed oil, vegetable oils, corn oil, soy oil, cottonseed oil, palm oil, linseed oil, menhaden oil, peanut oil, olestra, almonds, walnuts, cashews, pecans, macadamia nuts, hazelnuts, flaxseeds, sunflower seeds, pumpkin seeds, hemp seeds, sesame seeds, avocado, olives, almond butter, cashew butter, seaweed, tahini, hummus, lauric acid, linoleic acid, babassu oil, palmitoleic acid, cohune oil, palm kelner oil, tucum oil, soybean oil and/or any other appropriate source of fats and/or combination thereof;

and wherein the secondary component may serve as a source of nutrition, as a source of digestibility enhancer, and/or as a source of palatability enhancers.

In one aspect of the invention, the secondary component may comprise at least one source of saccharides and at least one source of fats. Therefore, the secondary component may comprise, for example, two sources of saccharides and one source of fat. For another example, the secondary component may comprise three sources of saccharides and two sources of fats. For yet another example, the secondary component may comprise one source of saccharides and two sources of fats. A more specific example of one such aspect of the invention may be a secondary component comprising:

a first source of saccharides, for example a potato that has been boiled in an amount of 5 wt. % of the product; and a second source of saccharides, for example a soybean that has been mashed and boiled in an amount of 40 wt. % of the product; and a first source of fats, for example sunflower oil in an amount of 1 wt. % of the product; and a second source of fats, for example flaxseeds in an amount of 0.5 wt. % of the product.

The tertiary component may comprise at least one auxiliary compound selected from the group of vitamins, minerals, binders, palatants, antioxidants, colorants and/or preservatives, wherein:

at least one of the vitamins may be ascorbic acid, ascorbic acid phosphate, biotin, choline chloride, D-calcium pantothenate, folic acid, i-inositol, niacinamide, para-aminobenzoic acid, pyridoxal hydrochloride, pyridoxine hydrochloride, riboflavin, thiamine hydrochloride, vitamin B12, choline, taurine and/or any combination thereof; and at least one of the minerals may be a compound having at least one element selected from the group Ca, Cl, Cr, Cu, F, Fe, I, K, Mn, Co, Na, Ni, Se, Sn, Zn or any combination thereof; and at least one of the binders may be guar gum, carrageenan, xanthan gum, pectin, cellulose, potato starch, rice flour, soy protein isolate, corn starch, wheat gluten, gelatin, inulin or pea fiber;

and at least one of the preservatives vitamin E, rosemary extract, citric acid, mixed tocopherols, ascorbic acid, green tea extract, cranberry extract, clove oil, oregano oil, neem extract and synthetic preservatives such as butylated hydroxyanisole, butylated hydroxytoluene, ethoxyquin, propyl gallate, sorbic acid, calcium propionate, potassium sorbate, sodium benzoate, tert-butyl-hydroquinone, natamycin or any combination thereof; wherein the binders are different to solidifying agents; and at least one of the palatants may be animal-derived or plant-derived and may comprise artificial and natural flavors, hydrolyzed proteins, fat sprays, Maillard's reaction product, probiotics, prebiotics or any other appropriate palatants and/or any combination thereof; and at least one of the antioxidants may be butylated hydroxyanisole, ethoxyquin, tert-butylhydroquinone, vitamin C, vitamin E, lycopene or any other appropriate antioxidant and/or any combination thereof; and at least one of the colorants may be beta-carotene, beetjuice powder, turmeric, caramel color, spinach powder, *spirulina* extract, paprika extract, annatto extract, annatto seeds, chlorophyll, saffron, *gardenia* extract, red beet powder, carrot juice concentrate, purple sweet potato, hibiscus extract, cochineal extract, curcumin, cabbage extract, paprika, grape skin, caramelized onion, anthocyanins or any combination thereof; and at least one of the preservatives may be vitamin E, rosemary extract, citric acid, mixed tocopherols, ascorbic acid, green tea extract, cranberry extract, clove oil, oregano oil, butylated hydroxyanisole, butylated hydroxytoluene, ethoxyquin, propyl gallate, sorbic acid, calcium propionate, potassium sorbate, sodium benzoate, tert-butylhydroquinone or any combination thereof;

wherein the tertiary component may serve as a source of nutrition; and/or may serve as a quality enhancer of the pet food product; and/or may contribute to treat, ameliorate and/or prevent health problems of the subjected pet; and/or may improve the well-being of the subjected pet.

The step 504 of production methods as depicted in the FIG. 1 may comprise combining the primary component with at least one component selected from the group of a secondary component, wherein the secondary component may comprise at least one source of saccharides and/or fats; and a tertiary component, wherein the tertiary component may comprise at least one auxiliary compound selected from the group of vitamins, minerals, binders, palatants, antioxidants, colorants and/or preservatives.

Step 504 of the production methods as depicted in the FIG. 1 may be performed using a mixer, homogenizer, blender, shredder, slicer and/or any other instrument capable of mixing the components.

Step 505 of the production methods as depicted in the FIG. 1 may comprise processing the combined components from the step 504 into a pet food product by the following production systems:

an extrusion system, wherein the extrusion system may comprise at least one mixer unit, at least one extruder, at least one die, at least one cutter, at least one drying unit, at least one cooler, at least one finishing station, at least one packaging station and at least one conveyor; and/or a mold-injection system, wherein the mold-injection system may comprise at least one mixer unit, at least one extruder, at least one mold, at least one drying unit, at least one cooler, at least one finishing station, at least one packaging station and at least one conveyor; and/or a cold-press system, wherein the cold-press system may comprise at least one mixer unit, at least one cold-press, at least one finishing station, at least one packaging station and at least one conveyor; and/or a cannery system, wherein the cannery system at least one mixer unit, at least one extruder, at least one die, at least one cutter, at least one filling station, at least one sterilizing unit and at least one conveyor; and/or may be processed manually; and/or any combination thereof.

Step 506 of the production methods as depicted in the FIG. 1 may comprise packaging and sterilizing the pet food product. The pet food products may be packaged in bag, can, jar, tetra pak, pouch and/or any other appropriate packaging. The pet food products may be sterilized by thermal treatment, chemical treatment, irradiation, UV irradiation and/or high-pressure processing. The packaging may be transparent, opaque, tinted or any combination thereof.

Figure 3:
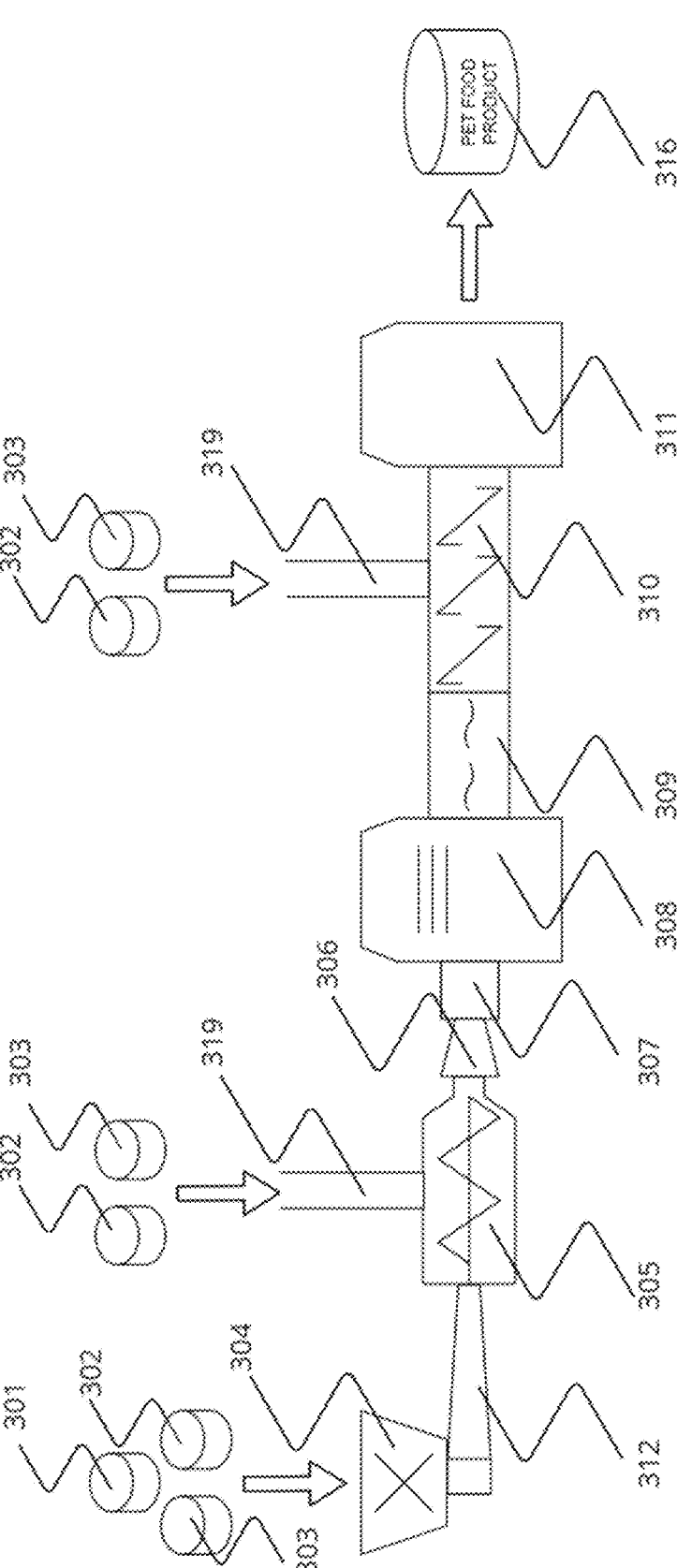
FIG. 3—illustrates the exemplary aspect of the extrusion system.

In one aspect of the invention, the pet food products may be produced by an extrusion method using an extrusion system as depicted in the FIG. 3. The extrusion system may comprise at least one of the following members:

a mixer unit 304, wherein the mixer unit 304 may be configured to combine at least one component selected from the group of primary component 301, secondary component 302 and tertiary component 303 to obtain a combination of components; and an extruder 305, wherein the extruder 305 may comprise a single screw or twin screw and may be configured to process a combination of components from the mixer unit 304 to obtain an extrudate; and wherein the extruder 305 may comprise at least one feeder 319 for adding at least one other component selected from the group of secondary component 302 and tertiary component 303; and a die 306, wherein the shape of the die 306 determines the shape of the extrudate; and a cutter 307, wherein the cutter 307 may be configured to periodically cut the extrudate at the end of the die 306 to obtain cut extrudate; and a drying unit 308, wherein the drying unit 308 may comprise a heating environment with a plurality of heating elements and exhaust system and may be configured to dry the cut extrudate; and a cooler 309, wherein the cooler 309 may comprise an air blower, counterflows cooler, fluidized bed cooler, rotary drum cooler and/or freezer and may be configured to decrease the temperature of the cut extrudate; and a finishing station 310, wherein the finishing station 310 may comprise a single drum coater, double drum coater, wing type coater, silt coater, spray coater, powder coater or any other appropriate mechanism and may be configured to coat the cut extrudate and/or to separate the cut extrudate from the residues to obtain the pet food product; and wherein the finishing station 310 may comprise at least one feeder 319 for adding at least one other component selected from the group of secondary component 302 and tertiary component 303; and a packaging station 311, wherein the packaging station 311 may be configured to pack the pet food product into bag, can, jar, tetra pak, pouch and/or into any other suitable packaging; and at least one conveyor 312, wherein the conveyor 312 may be configured to transfer a combination of components within the extrusion system;

wherein the extrusion system may provide at least one pet food product selected from the group of wet or dry meat-like chunk, dry snack, dry kibble or soft kibble.

The exemplary aspect of the extrusion system according to the previous description may be configured as depicted in the FIG. 3.

The mixer unit may be configured to combine at least one component selected from the group of primary component, secondary component and tertiary component. The mixer unit may be a pressure homogenizer, ultrasonic homogenizer, planetary mixer, blender, uniflow static mixer and/or any other mixer capable of homogenizing the combination of the components.

The conveyor may be configured to transfer components within the extrusion system. The conveyor may be configured to transfer at least one component from the mixer unit to the extruder, to transfer the extrudate from the extruder to a drying unit, to transfer the extrudate from the drying unit to a cooler, to transfer the extrudate from the cooler to the finishing station and/or to transfer the extrudate from the finishing station to the packaging station. The conveyor may be a tubular conveyor, screw conveyor, belt conveyor, chain conveyor, slat conveyor and/or air conveyor.

The extruder may comprise a plurality of propellers regularly positioned in a longitudinal axis of the extruder, thus creating a screw configured to extrude the combination of components. The extruder may comprise a single screw extruder and twin screw extruder and may be configured to process a combination of components from the mixer unit to obtain the extrudate. The extruder may further comprise at least one feeder, at least one air inlet and/or at least one heating element.

The heating element of the extruder may comprise an electrical heater, ceramic heater, infrared heater, induction heater and/or steam heater. The temperature of the heating environment made by the heating element may have the temperature in a range of 50° C. to 55° C., in a range of 60° C. to 65° C. in a range of 70° C. to 75° C. in a range of 80° C. to 85° C. in a range of 90° C. to 95° C. in a range of 100° C. to 105° C., in a range of 110° C. to 115° C., in a range of 120° C. to 125° C., in a range of 130° C. to 135° C., in a range of 140° C. to 145° C. or in a range of 150° C. to 155° C.

The die may have the shape of a rectangle, square, triangle, circle, bone, star, fish, heart, moon, flower, propeller and/or any other regular or irregular shape. The die may be also configured to provide the extrudate with a hollow. The die may comprise at least one orifice.

The cutter may comprise at least one knife or slicer that may be configured to periodically separate the extrudate in the vicinity of the die to provide a cut extrudate with uniform size and volume.

The drying unit may comprise at least one of oven, air blower, lyophilizer and electrical heater and may be configured to dry the extrudate. The drying of the extrudate may comprise removing a portion of the water from the extrudate, wherein said portion of water may be in a range of 1 wt. % to 15 wt. % of the total water content, in a range of 2 wt. % to 14 wt. % of the total water content, in a range of 3 wt. % to 13 wt. % of the total water content, in a range of 4 wt. % to 12 wt. % of the total water content, in a range of 5 wt. % to 11 wt. % of the total water content, in a range of 6 wt. % to 10 wt. % of the total water content or in a range of 7 wt. % to 9 wt. % of the total water content.

The cooler may comprise an air blower, counterflows cooler, fluidized bed cooler, rotary drum cooler and/or freezer and may be configured to decrease the temperature of the extrudate.

The finishing station may comprise rotary drum, rotary double-drum and/or vacuum coater and may be configured to coat the extrudate and/or to separate the extrudate from the residues to obtain the pet food product. The extrudate may be coated using spraying, dipping, splashing, sprinkling or soaking to obtain a coating. The coating may comprise fat, spices, palatants, moisturizers, enzymatic digest, yeast extract and/or any other appropriate substance capable of increasing the palatability of the product. In another aspect of the invention, the extrudate may be coated by a primary component comprising at least one non-human metazoan cell line.

The packaging station may be configured to package the pet food product into bag, can, jar, tetra pak, pouch and/or into any other suitable packaging. The materials of the packaging may comprise at least one material selected from the group of PVC, PET, PE, AL (aluminum foil), paperboard, nylon, polypropylene, biodegradable plastics and/or any other suitable material. The packaging station may also be configured to label the pet food products. In another aspect of the invention, the packaging station may be configured to sterilize, wherein the method of sterilization may be selected according to the package of the pet food product and its material. The sterilization may be performed using at least one method from the group of heat sterilization, high-pressure processing, irradiation and/or chemical treatment. The sterilization processes may preserve nutritional values. The sterilization of the pet food products may serve to extend the shelf-life of the pet food product, preserve nutritional quality and/or to comply with regulations.

The pet food products may be sterilized using a heat sterilization, wherein the packed pet food product may be heated to a specific temperature for a set portion of time to eliminate bacteria, viruses, pathogens and/or other undesired microorganisms. The heat sterilization methods may comprise pasteurization, hot-steaming, dipping in a hot boiling water and/or sous-vide cooking.

The pet food products may be sterilized using a high-pressure processing, wherein the packed pet food products may be exposed to a high-pressure environment for a set portion of time to eliminate bacteria, viruses, pathogens and/or other microorganisms.

The pet food products may be sterilized using irradiation, wherein the packed pet food products may be exposed to ionizing radiation for a set portion of time to eliminate bacteria, viruses, pathogens and/or other microorganisms.

The pet food products may be sterilized using chemical agents, wherein the packed pet food products may comprise a tertiary component in the form of antioxidants and/or preservatives. The pet food products may comprise a tertiary component in an amount capable of eliminating the bacteria, viruses, pathogens and/or other microorganisms.

In one aspect of the invention, the extrusion system may comprise a steaming unit, which may be configured to solidify the product while at the same time it may cause the extrudate to bind the water, thus increasing the volume of the extrudate. The steaming unit may comprise a steam chamber, steam tunnel or any other environment capable of providing the environment with the hot vapor.

Figure 4:
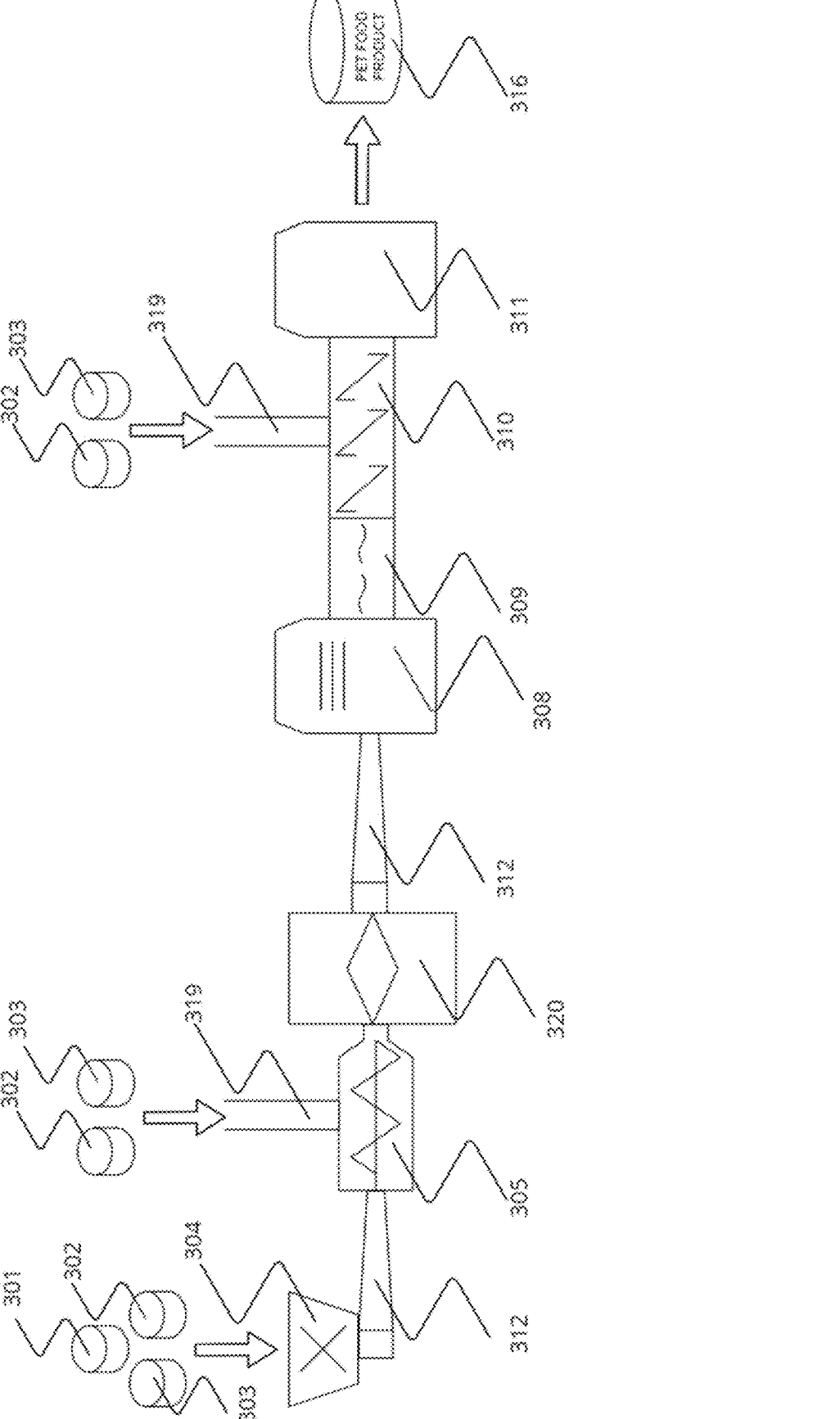
FIG. 4—illustrates the exemplary aspect of the mold-injection system.

In one aspect of the invention, the pet food products may be produced by a mold-injection method using a mold-injection system as depicted in the FIG. 4 The mold-injection system may comprise at least one of the following members:

a mixer unit 304, wherein the mixer unit 304 may be configured to combine at least one component selected from the group of primary component 301, secondary component 302 and tertiary component 303 to obtain a combination of components; and an extruder 305, wherein the extruder 305 may comprise a single screw extruder or twin screw extruder and may be configured to process a combination of components from the mixer unit 304 to obtain an extrudate; and wherein the extruder 305 may comprise at least one feeder 319 for adding at least one other component selected from the group of secondary component 302 and tertiary component 303; and a mold 320, wherein the mold 320 may have the various shape and may be configured to shape the extrudate; and wherein the mold 320 may have a heating environment capable of thermally treating and solidifying the extrudate; and a drying unit 308, wherein the drying unit 308 may comprise a heating environment with a plurality of heating elements and exhaust system and may be configured to dry the molded extrudate; and a cooler 309, wherein the cooler 309 may comprise an air blower, counterflows cooler, fluidized bed cooler, rotary drum cooler and/or freezer and may be configured to decrease the temperature of the molded extrudate; and a finishing station 310, wherein the finishing station 310 may comprise a single drum coater, double drum coater, wing type coater, silt coater, spray coater, powder coater or any other appropriate mechanism and may be configured to coat the molded extrudate and/or to separate the molded extrudate from the residues to obtain the pet food product; and wherein the finishing station 310 may comprise at least one feeder 319 for adding at least one other component selected from the group of secondary component 302 and tertiary component 303; and a packaging station 311, wherein the packaging station 311 may be configured to pack the pet food product into bag, can, jar, tetra pak, pouch and/or into any other suitable packaging; and at least one conveyor 312, wherein the conveyor 312 may be configured to transfer a combination of components within the mold-injection system;

wherein the mold-injection system may provide at least one pet food product 316 selected from the group of a dry snack and a wet snack.

The exemplary aspect of the mold-injection system according to the previous description may be configured as depicted in the FIG. 4.

Figure 5:
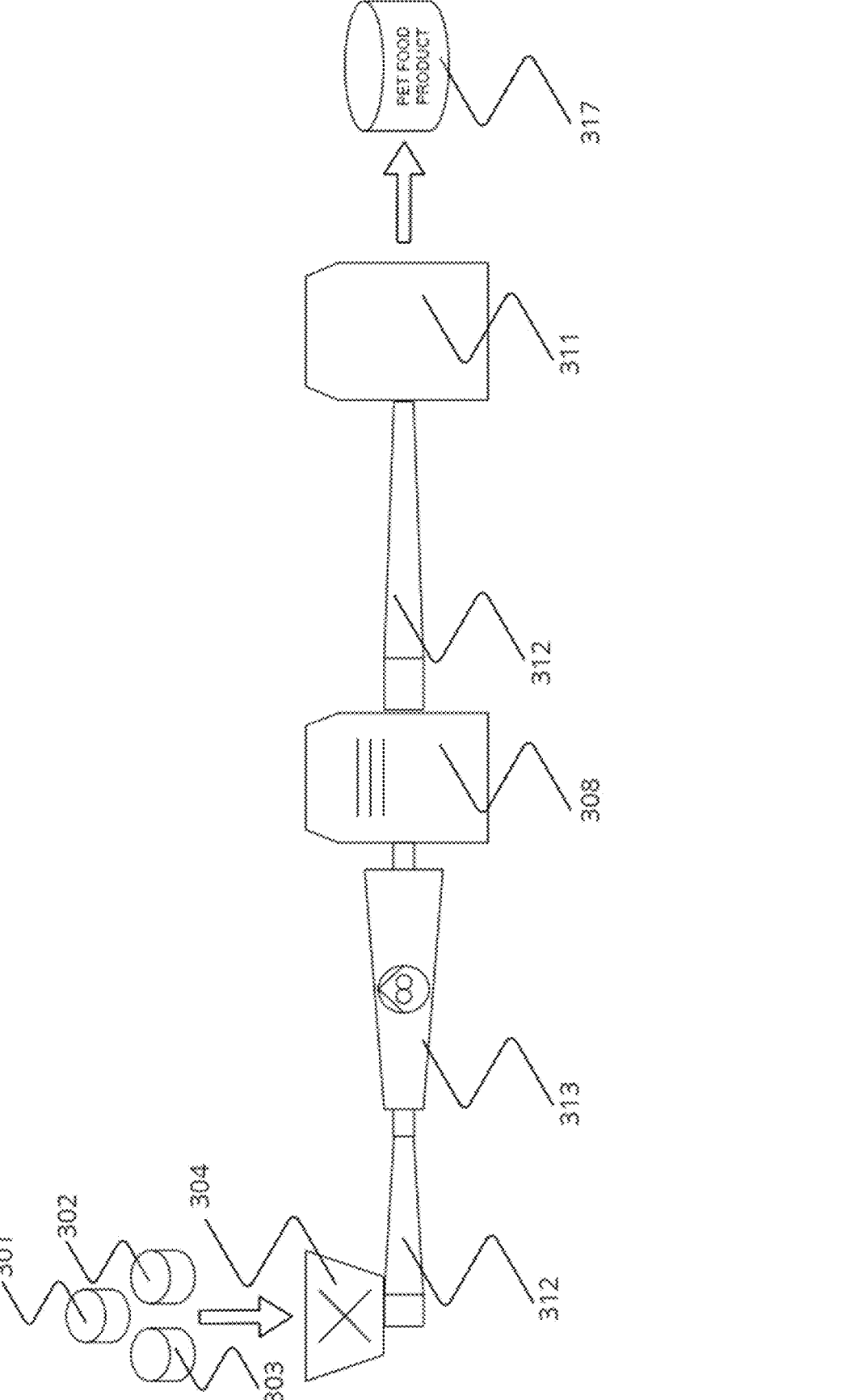
FIG. 5—illustrates the exemplary aspect of the cold-press system.

In one aspect of the invention, the pet food products may be produced by a cold-pressing method using a cold-press system in the FIG. 5. The cold-press system may comprise at least one of the following members:

a mixer unit 304, wherein the mixer unit 304 may be configured to combine at least one component selected from the group of primary component 301, secondary component 302 and tertiary component 303 to obtain a combination of components; and a cold-press 313, wherein the cold-press 313 may be configured to process a combination of components from the mixer unit 304 to obtain a pellet; and a finishing station 310, wherein the finishing station 310 may comprise a single drum coater, double drum coater, wing type coater, silt coater, spray coater, powder coater or any other appropriate mechanism and may be configured to coat the pellet and/or to separate the pellet from the residues to obtain the pet food product; and a packaging station 311, wherein the packaging station 311 may be configured to pack the pet food product into a bag, can, jar, tetra pak, pouch and/or into any other suitable packaging; and at least one conveyor 312, wherein the conveyor 312 may be configured to transfer a combination of components within the cold-press system;

wherein the cold-press system may provide at least one pet food product 317 selected from the group of cold-pressed pellets or cold-pressed rolls.

The exemplary aspect of the cold-press system according to the previous description may be configured as depicted in the FIG. 5.

Figure 6:
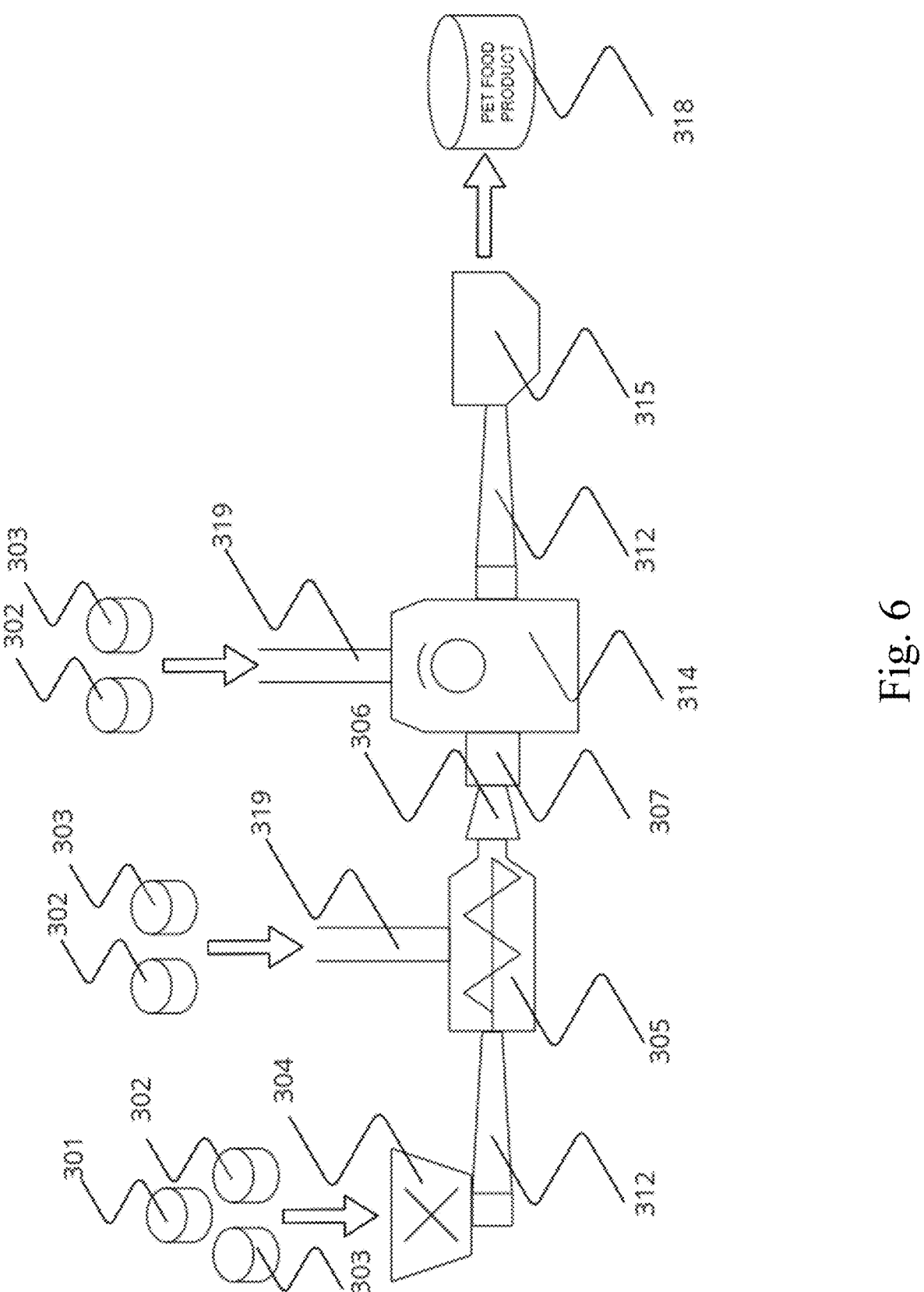
FIG. 6—illustrates the exemplary aspect of the cannery system.

In one aspect of the invention, the pet food products may be produced by cannery method using a cannery system as depicted in the FIG. 6. The cannery system may comprise at least one of the following members:

a mixer unit 304, wherein the mixer unit 304 may be configured to combine at least one component selected from the group of primary component 301, secondary component 302 and tertiary component 303 to obtain a combination of components; and an extruder 305, wherein the extruder 305 may comprise a single screw extruder or twin screw extruder and may be configured to process a combination of components from the mixer unit 304 to obtain an extrudate; and a die 306, wherein the shape of the die 306 determines the shape of the extrudate; and a cutter 307, wherein the cutter 307 may be configured to periodically cut the extrudate at the end of the die 306 to obtain cut extrudate; and a filling station 314, wherein the filling station 314 may be configured to fill any other components selected from the group of primary component 301, secondary component 302 and tertiary component 303 and to fill the cut extrudate from the extruder into a can, jar and/or pouch;

a sterilizing unit 315, wherein the sterilizing unit 315 may be configured to sterilize packed pet food products using heat sterilization by an autoclave; and at least one conveyor 312, wherein the conveyor 312 may be configured to transfer a combination of components within the cannery system, wherein the cannery system may provide at least one pet food product 318 selected from the group of pâté, meaty chunks, meaty chunks with gravy or wet snack.

The exemplary aspect of the cannery system according to the previous description may be configured as depicted in the FIG. 6.

The filling station may comprise a plurality of dispensers, nozzles, jets and/or orifices for adding at least one from the primary component, secondary component and tertiary component. The filling station may be used to fill the packaging with cut extrudate, secondary component and tertiary component. The filling station may also be configured to enclose the packaging so it may be ready for sterilization using the sterilization unit.

The sterilization unit may comprise a heat sterilization by an autoclave, wherein the heat sterilization may be performed by at least one of the following steps:

transporting at least one pet food product to an autoclave by a transporting mechanism; and wherein the transporting mechanism may comprise a positionable basket, rack, tray, cup or any other suitable mechanism capable of transporting at least one pet food product from the conveyor to the sterilization unit; and exposing the pet food product to an heating environment inside of said autoclave for a portion of time, wherein the said heating environment has a temperature in a range of 100° C. to 180° C., in a range of 110° C. to 170° C., in a range of 120° C. to 160° C., in a range of 130° C. to 150° C., in a range of 135° C. to 145° C.; and said portion of time is in a range of 1 second to 1500 seconds, in a range of 90 seconds to 900 seconds, in a range of 120 seconds to 60 seconds, in a range of 180 seconds to 480 seconds, in a range of 240 seconds to 420 seconds, in a range of 300 seconds to 360 seconds; wherein the said environment may have a pressure higher than atmospheric pressure (approximately 101,325 Pa) to increase the temperature of the heating environment;

wherein the said environment comprises a water medium, a heating element, an insulation divisive to the outer environment; and wherein the heating element may comprise an electric boiler, a gas boiler, pressure boiler or any other appropriate heating element capable of heating a water medium to obtain a boiling point; and wherein the water medium above the boiling point may provide the heating environment in the form of boiling water or hot steam.

The heat sterilization process may be provided according to the description in the preceding paragraphs, wherein the process described may be considered as one sterilization cycle. The pet food products may undergo at least one sterilization cycle. The heat sterilization unit may provide the sterilized product after performing the heat sterilization process described in the preceding paragraphs. The rate of the heat sterilization process may be optimized to provide the proper sterilization, i. e. to stop the growth of microorganisms in the pet food product in the shortest time possible, while not disrupting any textural properties of the pet food product. The balance between the portion of time that the pet food product may be exposed to the heating environment and the temperature may vary depending on the properties of the pet food product produced by the cannery system.

The exemplary aspects of the production methods depicted in the FIG. 3, FIG. 4, FIG. 5 and FIG. 6 are exemplary and are not limiting to the aspects of the invention. Aspects of the production methods may comprise at least one member from the list of the members in the description of each production method.

In one aspect of the invention, all production methods including extrusion method, mold-injection method, cold-pressing method and/or cannery method may be combined. All members of the production system using said production methods may be interchangeable and may be combined, i. e. the members of one production system may be used in another production system. Each member of the production system may be included within one production system at least once. The properties of the pet food product may depend on the primary, secondary and tertiary component selected. The properties of the pet food product may depend on the configuration of the production system, wherein the production system may be using extrusion method, mold-injection method, cold-pressing method, cannery method and/or the combination thereof having members of at least two different production methods.

For example, the pet food product may be made using a sterilizing unit from the cannery system for sterilizing the cold-pressed product from the cold-press system, even though the cold-press system usually does not comprise a sterilizing unit. For another example, the cannery system may use the mold from the mold-injection system if the aimed product is a molded product with higher moisture content preferably packaged in a can, pouch and/or jar.

In one aspect of the invention, the sterilized pet food products may be labeled and wrapped in a plastic foil or any other foiling to increase the durability of said products.

In one aspect of the invention, the pet food products may be produced manually. The manual production may comprise the production of complementary products, preferably dry snacks and/or wet snacks. The manual production may comprise folding, drying, blanching, rolling, kneading, baking and/or any other appropriate process to produce the pet food product.

In one aspect of the invention, the extrusion system, mold-injection system, the cold-press system and/or cannery system may comprise a labeling system to provide the pet food product with a label on the outer surface of the packaging. The label may be made from plastic, paper or a combination thereof. The material for the label may further comprise a printing.

The pet food products may comprise protein originated from at least one component selected from the primary component, secondary component and tertiary component. Preferably, the pet food products may comprise protein which originates from the primary component. Even more preferably, the pet food products may comprise protein originated from a primary component, which is originated from a cell biomass, wherein the cell biomass may comprise at least one non-human metazoan cell line. The non-human metazoan cell line may comprise bovine, avian, porcine, equine, piscine, *cervine*, cricetine cell lines, or any appropriate cell line, wherein the cell lines may be modified by at least one genetic or non-genetic modification to enhance its nutritional properties. The genetic or non-genetic modification may be also oriented to provide more resilient cell lines, immortalized cell lines, cell lines with a specific phenotype, cell lines with a homogenous double time, cell lines with a homogenous cell cycle, cell lines with enhanced metabolism processes and/or any other cell line having any appropriate attribute.

Both hybrid primary component and pure primary component may have its benefits. The primary component is designed according to the desired final pet food product with respect to the optional addition of secondary component and primary component. The final pet food product may be designed using at least one of these three approaches:

the first approach of a designed pet food product of complete diet is oriented towards meeting the demands of subject subjected to oral digestion of said pet food product on regular daily basis, wherein such pet food products may provide complete nutrition to a subject; and the second approach of a designed pet food product of complementary diet is oriented towards treating, mitigating, preventing or ameliorating any health issue of a subject subjected to oral digestion of said pet food product; and the third approach of a designed pet food product of complementary diet is oriented towards rewarding said subject subjected to oral digestion of said pet food product on an irregular basis, wherein such pet food product may be used as a snack or treat for said subject to train the subject.

The cell biomass made from the cell lines described in the preceding paragraphs may be characterized by its nutritional profile, i. e. content of amino acids, peptides, proteins, saccharides, fatty acids, fats, minerals and vitamins.

The cell biomass made from the cell lines listed in the preceding paragraphs may comprise:

arginine in a range of 0.5 g to 5 g per 100 g of dry matter; and histidine in a range of 0.2 g to 4 g per 100 g of dry matter; and isoleucine in a range of 0.5 g to 5 g per 100 g of dry matter; and leucine in a range of 1 g to 8 g per 100 g of dry matter; and lysine in a range of 1 g to 8 g per 100 g of dry matter; and methionine in a range of 0.2 g to 3 g per 100 g of dry matter; and cysteine in a range of 0.1 g to 3 g per 100 g of dry matter; and phenylalanine in a range of 0.5 g to 4 g per 100 g of dry matter; and tyrosine in a range of 0.4 g to 4 g per 100 g of dry matter; and threonine in a range of 0.1 g to 4 g per 100 g of dry matter; and tryptophan in a range of 0.1 g to 0.7 g per 100 g of dry matter; and valine in a range of 1 g to 4 g per 100 g of dry matter; and proline in a range of 0.1 g to 4.5 g per 100 g of dry matter; and alanine in a range of 1 g to 6 g per 100 g of dry matter; and glutamic acid and glutamine in a range of 2 g to 12 g per 100 g of dry matter; and aspartic acid and asparagine in a range of 2 g to 9 g per 100 g of dry matter; and glycine in a range of 1 g to 6 g per 100 g of dry matter; and serine in a range of 1 g to 7 g per 100 g of dry matter; and proteins in a range of 40 g to 70 g per 100 g of dry matter; and saturated fatty acids in a range of 0.01 to 0.2 g per 100 g of dry matter; and monounsaturated fatty acids in a range of 0.01 g to 0.2 g per 100 g of dry matter; and polyunsaturated fatty acids in a range of 0.01 g to 0.2 g per 100 g of dry matter; and fats in a range of 5 g to 25 g per 100 g of dry matter; and saccharides in a range of 0.1 g to 2 g per 100 g of dry matter; and minerals in a range of 1 g to 5 g per 100 g of dry matter; and calcium in a range of 10 mg to 100 mg per 100 g of dry matter; and phosphorus in a range of 300 mg to 1500 mg per 100 g of dry matter; and potassium in a range of 600 mg to 1500 mg per 100 g of dry matter; and sodium in a range of 100 mg to 300 mg per 100 g of dry matter; and magnesium in a range of 30 mg to 150 mg per 100 g of dry matter; and copper in a range of 0.01 mg to 3 mg per 100 g of dry matter; and iron in a range of 0.01 mg to 20 mg per 100 g of dry matter; and manganese in a range of 0.01 mg to 6 mg per 100 g of dry matter; and zinc in a range of 0.01 mg to 40 mg per 100 g of dry matter; and vitamins in a range of 0.01 mg to 350 mg per 100 g of dry matter; and vitamin A in a range of 0.01 mg to 0.1 mg per 100 g of dry matter; and vitamin D in a range of 0.01 mg to 0.1 mg per 100 g of dry matter; and vitamin E in a range of 1 mg to 50 mg per 100 g of dry matter; and vitamin B1 in a range of 0.1 mg to 2.5 mg per 100 g of dry matter; and vitamin B2 in a range of 0.1 mg to 2.5 mg per 100 g of dry matter; and vitamin B5 in a range of 1 mg to 40 mg per 100 g of dry matter; and vitamin B6 in a range of 0.01 mg to 2 mg per 100 g of dry matter; and vitamin B12 in a range of 0.01 mg to 0.1 mg per 100 g of dry matter; and vitamin B3 in a range of 1 mg to 20 mg per 100 g of dry matter; and vitamin B9 in a range of 0.01 mg to 0.1 mg per 100 g of dry matter; and vitamin B7 in a range of 0.01 mg to 0.1 mg per 100 g of dry matter; and choline in a range of 10 mg to 150 mg per 100 g of dry matter; and vitamin K in a range of 0.0001 mg to 0.05 mg per 100 g of dry matter.

The nutritional profile in the preceding paragraph is an exemplary nutritional profile of the cell biomass comprising at least one non-human metazoan cell line described above. The nutritional profile of each cell biomass may vary according to the characteristics of cell lines in the cell biomass, cell cultivation conditions and/or culture medium composition.

Dry Products

In one aspect of the invention, the pet food products may be dry pet food products, i.e., pet food products having water content in a range of 4 wt. % to 14 wt. %, in a range of 5 wt. % to 14 wt. %, in a range of 6 wt. % to 14 wt. %, in a range of 7 wt. % to 14 wt. %, in a range of 8 wt. % to 14 wt. %, in a range of 9 wt. % to 14 wt. %, in a range of 10 wt. % to 14 wt. %, in a range of 11 wt. % to 14 wt. %, in a range of 12 wt. % to 14 wt. %, or in a range of 13 wt. % to 14 wt. %.

In one aspect of the invention, the pet food products may be wet pet food products, i.e., pet food products having water content in a range of 14 wt. % to 99 wt. %, in a range of 16 wt. % to 99 wt. %, in a range of 18 wt. % to 99 wt. %, in a range of 20 wt. % to 99 wt. %, in a range of 22 wt. % to 99 wt. %, in a range of 24 wt. % to 99 wt. %, in a range of 26 wt. % to 99 wt. %, in a range of 28 wt. % to 99 wt. %, in a range of 30 wt. % to 99 wt. %, in a range of 32 wt. % to 99 wt. %, in a range of 34 wt. % to 99 wt. %, in a range of 36 wt. % to 99 wt. %, in a range of 38 wt. % to 99 wt. %, in a range of 40 wt. % to 99 wt. %, in a range of 42 wt. % to 99 wt. %, in a range of 44 wt. % to 99 wt. %, in a range of 46 wt. % to 99 wt. %, in a range of 48 wt. % to 99 wt. %, in a range of 50 wt. % to 99 wt. %, in a range of 52 wt. % to 99 wt. %, in a range of 54 wt. % to 99 wt. %, in a range of 56 wt. % to 99 wt. %, in a range of 58 wt. % to 99 wt. %, in a range of 60 wt. % to 99 wt. %, in a range of 62 wt. % to 99 wt. %, in a range of 64 wt. % to 99 wt. %, in a range of 66 wt. % to 99 wt. %, in a range of 68 wt. % to 99 wt. %, in a range of 70 wt. % to 99 wt. %, in a range of 72 wt. % to 99 wt. %, in a range of 74 wt. % to 99 wt. %, in a range of 76 wt. % to 99 wt. %, in a range of 78 wt. % to 99 wt. %, in a range of 80 wt. % to 99 wt. %, in a range of 82 wt. % to 99 wt. %, in a range of 84 wt. % to 99 wt. %, in a range of 86 wt. % to 99 wt. %, in a range of 88 wt. % to 99 wt. %, in a range of 90 wt. % to 99 wt. %, in a range of 92 wt. % to 99 wt. %, in a range of 94 wt. % to 99 wt. % or in a range of 96 wt. % to 99 wt. %.

For the purpose of this aspect of the invention, the term "proteins" may comprise amino acids and/or any other biopolymer having more than one amino acid unit.

For the purpose of this aspect of the invention, the term "fats" may comprise fatty acids, fats and any ester of fatty acids. In one aspect of the invention, the pet food products may comprise omega-3 and omega-6 fatty acids.

For the purpose of this aspect of the invention, the term "saccharides" may comprise sugars, starch, cellulose and/or any other derivative of monosaccharides, disaccharides, oligosaccharides or polysaccharides.

In one aspect of the invention, all pet food products, i.e. dry pet food products and wet pet food products, may comprise ash in a range of 0.01 wt. % to 15 wt. %, or in a range of 1 wt. % to 15 wt. %, or in a range of 2 wt. % to 15 wt. %, or in a range of 3 wt. % to 15 wt. %, or in a range of 4 wt. % to 15 wt. %, or in a range of 5 wt. % to 15 wt. %, or in a range of 6 wt. % to 15 wt. %, or in a range of 7 wt. % to 15 wt. %, or in a range of 8 wt. % to 15 wt. %, or in a range of 9 wt. % to 15 wt. %, or in a range of 10 wt. % to 15 wt. %, or in a range of 11 wt. % to 15 wt. %, or in a range of 12 wt. % to 15 wt. %, or in a range of 13 wt. % to 15 wt. %, or in a range of 14 wt. % to 15 wt. %. For the purpose of this aspect of the invention, the term "ash" may comprise any organic or inorganic substances that persist in the sample of the pet food product after heating the sample at high temperature higher than 600° C. until it reaches a constant weight and every organic material is removed.

In another aspect of the invention, the dry pet food products may comprise the dry kibble and dry snacks having a water content in a range of 0.01 wt. % to 14 wt. %, in a range of 2 wt. % to 12 wt. %, in a range of 4 wt. % to 10 wt. %, in a range of 6 wt. % to 8 wt. %.

The dry pet food product may further include a crude fat in a range of 5 wt. % to 25 wt. %, in a range of 8 wt. % to 22 wt. %, in a range of 11 wt. % to 19 wt. %, in a range of 14 wt. % to 16 wt. %.

The dry pet food product may further include a crude fiber in a range of 1 wt. % to 10 wt. %, in a range of 3 wt. % to 8 wt. %, or in a range of 5 wt. % to 6 wt. %.

The dry pet food product may further include a crude protein in a range of 20 wt. % to 80 wt. %, in a range of 25 wt. % to 75 wt. %, in a range of 30 wt. % to 70 wt. %, in a range of 35 wt. % to 65 wt. %, in a range of 40 wt. % to 60 wt. %, in a range of 45 wt. % to 55 wt. %.

The dry pet food product may further include a crude ash in a range of 0.01 wt. % to 10 wt. %, in a range of 1 wt. % to 9 wt. %, in a range of 3 wt. % to 7 wt. %, or in a range of 4.5 wt. % to 5.5 wt. %.

Dry Kibble

The dry pet food products may comprise the dry kibble, wherein the dry kibble may include the primary component in a range of 4 wt. % to 70 wt. % of the dry kibble, in a range of 8 wt. % to 64 wt. % of the dry kibble, in a range of 12 wt. % to 60 wt. % of the dry kibble, in a range of 16 wt. % to 56 wt. % of the dry kibble, in a range of 20 wt. % to 52 wt. % of the dry kibble, in a range of 24 wt. % to 48 wt. % of the dry kibble, in a range of 28 wt. % to 44 wt. % of the dry kibble, in a range of 32 wt. % to 40 wt. % of the dry kibble or in a range of 34 wt. % to 36 wt. % of the dry kibble, wherein the primary component comprises processed non-human metazoan cell biomass of at least one non-human metazoan cell line.

The primary component of the dry kibble may be processed by removing a portion of water from the cell biomass, combining the non-human metazoan cell biomass with the solidifying agent or any other appropriate process capable of increasing the dynamic viscosity of the cell biomass, wherein the portion of water removed from the cell biomass may be in a range of 5 wt. % to 90 wt. % of the cell biomass, in a range of 10 wt. % to 85 wt. % of the cell biomass, in a range of 15 wt. % to 80 wt. % of the cell biomass, in a range of 20 wt. % to 75 wt. % of the cell biomass, in a range of 25 wt. % to 70 wt. % of the cell biomass, in a range of 30 wt. % to 65 wt. % of the cell biomass, in a range of 35 wt. % to 60 wt. % of the cell biomass, in a range of 40 wt. % to 55 wt. % of the cell biomass, in a range of 45 wt. % to 50 wt. % of the cell biomass.

The primary component of the dry kibble may be processed by removing a portion of water from the cell biomass, combining the non-human metazoan cell biomass with the solidifying agent or any other appropriate process capable of increasing the dynamic viscosity of the cell biomass, wherein the solidifying agent may be in a range of 0.01 wt. % to 15 wt. % of the cell biomass, in a range of 0.1 wt. % to 15 wt. % of the cell biomass, in a range of 1 wt. % to 14 wt. % of the cell biomass, in a range of 2 wt. % to 13 wt. % of the cell biomass, in a range of 3 wt. % to 12 wt. % of the cell biomass, in a range of 4 wt. % to 11 wt. % of the cell biomass, in a range of 5 wt. % to 10 wt. % of the cell biomass, in a range of 6 wt. % to 9 wt. % of the cell biomass or in a range of 7 wt. % to 8 wt. % of the cell biomass.

The crude protein of the primary component may be in a range of 3 wt. % to 55 wt. %, in a range of 7 wt. % to 41 wt. %, in a range of 11 wt. % to 37 wt. %, in a range of 15 wt. % to 34 wt. %, in a range of 19 wt. % to 30 wt. % or in a range of 23 wt. % to 26 wt. %.

The crude fat of the primary component may be in a range of 0.01 wt. % to 30 wt. %, in a range of 0.1 wt. % to 30 wt. %, in a range of 1 wt. % to 30 wt. %, in a range of 3 wt. % to 30 wt. %, in a range of 6 wt. % to 27 wt. %, in a range of 9 wt. % to 24 wt. %, in a range of 12 wt. % to 21 wt. % or in a range of 15 wt. % to 18 wt. %.

The dry kibble may further include a secondary component, wherein the secondary component may be in a range of 1 wt. % to 65 wt. %, in a range of 5 wt. % to 60 wt. % in a range of 10 wt. % to 55 wt. %, in a range of 15 wt. % to 50 wt. %, in a range of 20 wt. % to 45 wt. %, in a range of 25 wt. % to 40 wt. %, in a range of 30 wt. % to 35 wt. %.

The crude fat of the secondary component may be in a range of 0.01 wt. % to 30 wt. %, in a range of 0.1 wt. % to 30 wt. %, in a range of 1 wt. % to 30 wt. %, in a range of 3 wt. % to 30 wt. %, in a range of 6 wt. % to 27 wt. %, in a range of 9 wt. % to 24 wt. %, in a range of 12 wt. % to 21 wt. %, in a range of 15 wt. % to 18 wt. %.

The saccharides of the secondary component may be in a range of 20 wt. % to 90 wt. %, in a range of 30 wt. % to 80 wt. %, in a range of 40 wt. % to 70 wt. % or in a range of 50 wt. % to 60 wt. %.

The source of saccharides of the secondary component may be in a range of 50 wt. % to 85 wt. % of the secondary component, in a range of 55 wt. % to 80 wt. % of the secondary component or in a range of 60 wt. % to 80 wt. % of the secondary component, wherein the secondary component is different from the solidifying agent.

The source of fats of the secondary component may be in a range of 15 wt. % to 50 wt. % of the secondary component, in a range of 20 wt. % to 45 wt. % of the secondary component, in a range of 25 wt. % to 40 wt. % of the secondary component, wherein the secondary component is different from the solidifying agent.

The dry kibble may further include a tertiary component, wherein the tertiary component may be in a range of 0.01 wt. % to 15 wt. %, in a range of 0.1 wt. % to 15 wt. %, in a range of 1 wt. % to 15 wt. %, in a range of 2 wt. % to 14 wt. %, in a range of 3 wt. % to 13 wt. % or in a range of 4 wt. % to 12 wt. %, in a range of 5 wt. % to 11 wt. %, in a range of 6 wt. % to 10 wt. %, in a range of 7 wt. % to 9 wt.

The tertiary component may include vitamins, wherein the vitamins may be in a range of 0.01 wt. % to 15 wt. % of the tertiary component, in a range of 3 wt. % to 13 wt. % of the tertiary component or from 5 wt. % to 11 wt. % of the tertiary component or in a range of 7 wt. % to 9 wt. % of the tertiary component.

The tertiary component may include minerals, wherein the minerals may be in a range of 1 wt. % to 50 wt. % of the tertiary component, in a range of 5 wt. % to 45 wt. % of the tertiary component or from 10 wt. % to 40 wt. % of the tertiary component, in a range of 15 wt. % to 35 wt. % of the tertiary component or in a range of 20 wt. % to 30 wt. % of the secondary component.

The tertiary component may include binders, wherein the binders may be in a range of 1 wt. % to 80 wt. % of the tertiary component, in a range of 15 wt. % to 60 wt. % of the tertiary component or from 30 to 40 wt. % of the tertiary component.

The tertiary component may include palatants, wherein the palatants may be in a range of 1 wt. % to 50 wt. % of the tertiary component, in a range of 5 wt. % to 45 wt. % of the tertiary component or from 10 wt. % to 40 wt. % of the tertiary component, in a range of 15 wt. % to 35 wt. % of the tertiary component or in a range of 20 wt. % to 30 wt. % of the secondary component.

The tertiary component may include antioxidants, wherein the antioxidants may be in a range of 1 wt. % to 15 wt. % of the tertiary component, in a range of 3 wt. % to 13 wt. % of the tertiary component or from 5 wt. % to 11 wt. % of the tertiary component or in a range of 7 wt. % to 9 wt. % of the tertiary component.

The tertiary component may include colorants, wherein the colorants may be in a range of 1 wt. % to 10 wt. % of the tertiary component, in a range of 3 wt. % to 10 wt. % of the tertiary component, in a range of 5 wt. % to 10 wt. % of the tertiary component or in a range of 7 wt. % to 10 wt. %.

The tertiary component may include preservatives, wherein the preservatives may be in a range of in a range of 1 wt. % to 10 wt. % of the tertiary component, in a range of 3 wt. % to 10 wt. % of the tertiary component, in a range of 5 wt. % to 10 wt. % of the tertiary component or in a range of 7 wt. % to 10 wt. %.

The dry kibble may be the small sized breed pet dry kibble, which may have the size in a range of 0.6 cm to 1.1 cm, in a range of 0.62 cm to 1.05 cm, in a range of 0.64 cm to 0.95 cm, in a range of 0.66 cm to 0.88 cm or in a range of 0.68 cm to 0.84 cm.

The dry kibble may be the small sized breed pet dry kibble, which may have the volume in a range of 0.15 $cm^3$ to 0.5 $cm^3$, or in a range of 0.25 $cm^3$ to 0.45 $cm^3$, or in a range of 0.30 $cm^3$ to 0.40 $cm^3$.

The dry kibble may be the medium size breed pet dry kibble, which may have the size in a range of 1.1 cm to 1.6 cm, in a range of 1.25 cm to 1.45 cm, in a range of 1.3 cm to 1.4 cm.

The dry kibble may be the medium size breed pet dry kibble, which may have the volume in a range of 0.5 $cm^3$ to 3 $cm^3$, in a range of 1.0 $cm^3$ to 2.5 $cm^3$, in a range of 1.5 $cm^3$ to 2 $cm^3$.

The dry kibble may be the big size breed pet dry kibble, which may have the size in a range of 1.6 cm to 2 cm, in a range of 1.7 cm to 1.9 cm, in a range of 1.75 cm to 1.85 cm.

The dry kibble may be the big size breed pet dry kibble, which may have the volume in a range of 3 $cm^3$ to 4 $cm^3$, in a range of 3.15 $cm^3$ to 3.85 $cm^3$, in a range of 3.3 $cm^3$ to 3.7 $cm^3$, in a range of 3.45 $cm^3$ to 3.55 $cm^3$.

Dry Snack

The dry pet food products may comprise the dry snack, wherein the dry snack may include the primary component in a range of 2 wt. % to 95 wt. % of the dry snack, in a range of 5 wt. % to 90 wt. % of the dry snack, in a range of 10 wt. % to 85 wt. % of the dry snack, in a range of 15 wt. % to 80 wt. % of the dry snack, in a range of 20 wt. % to 75 wt. % of the dry snack, in a range of 25 wt. % to 70 wt. % of the dry snack, in a range of 30 wt. % to 65 wt. % of the dry snack, in a range of 35 wt. % to 60 wt. % of the dry snack, in a range of 40 wt. % to 55 wt. % of the dry snack, wherein the primary component comprises processed non-human metazoan cell biomass of at least one non-human metazoan cell line.

The primary component may be processed by removing a portion of water from the cell biomass, combining the non-human metazoan cell biomass with the solidifying agent or any other appropriate process capable of increasing the dynamic viscosity of the cell biomass, wherein the portion of water removed from the cell biomass may be in a range of 5 wt. % to 90 wt. % of the cell biomass, in a range of 10 wt. % to 85 wt. % of the cell biomass, in a range of 15 wt. % to 80 wt. % of the cell biomass, in a range of 20 wt. % to 75 wt. % of the cell biomass, in a range of 25 wt. % to 70 wt. % of the cell biomass, in a range of 30 wt. % to 65 wt. % of the cell biomass, in a range of 35 wt. % to 60 wt. % of the cell biomass, in a range of 40 wt. % to 55 wt. % of the cell biomass, in a range of 45 wt. % to 50 wt. % of the cell biomass.

The primary component of the dry snack may be processed by removing a portion of water from the cell biomass, combining the non-human metazoan cell biomass with the solidifying agent or any other appropriate process capable of increasing the dynamic viscosity of the cell biomass, wherein the solidifying agent may be in a range of 0.01 wt. % to 15 wt. % of the cell biomass, in a range of 0.1 wt. % to 15 wt. % of the cell biomass, in a range of 1 wt. % to 14 wt. % of the cell biomass, in a range of 2 wt. % to 13 wt. % of the cell biomass, in a range of 3 wt. % to 12 wt. % of the cell biomass, in a range of 4 wt. % to 11 wt. % of the cell biomass, in a range of 5 wt. % to 10 wt. % of the cell biomass, in a range of 6 wt. % to 9 wt. % of the cell biomass or in a range of 7 wt. % to 8 wt. % of the cell biomass.

The crude protein of the primary component of the dry snack may be in a range of 10 wt. % to 85 wt. %, in a range of 15 wt. % to 80 wt. %, in a range of 20 wt. % to 75 wt. %, in a range of 25 wt. % to 70 wt. %, in a range of 30 wt. % to 65 wt. %, in a range of 35 wt. % to 60 wt. %, in a range of 40 wt. % to 55 wt. % or in a range of 45 wt. % to 50 wt. %.

The crude fat of the primary component of the dry snack may be in a range of 0.01 wt. % to 25 wt. %, in a range of 0.1 wt. % to 25 wt. %, in a range of 1 wt. % to 25 wt. %, in a range of 3 wt. % to 25 wt. %, in a range of 6 wt. % to 22 wt. %, in a range of 9 wt. % to 20 wt. % kibble, in a range of 12 wt. % to 18 wt. % or in a range of 14 wt. % to 16 wt. %.

The dry snack may further include a secondary component, wherein the secondary component may be in a range of 5 wt. % to 65 wt. %, in a range of 10 wt. % to 60 wt. %, in a range of 15 wt. % to 55 wt. %, in a range of 20 wt. % to 50 wt. %, in a range of 25 wt. % to 45 wt. % or in a range of 30 wt. % to 40 wt. %.

The crude fat of the secondary component may be in a range of 0.01 wt. % to 30 wt. %, in a range of 0.1 wt. % to 30 wt. %, in a range of 1 wt. % to 30 wt. %, in a range of 3 wt. % to 30 wt. %, in a range of 6 wt. % to 27 wt. %, in a range of 9 wt. % to 24 wt. %, in a range of 12 wt. % to 21 wt. % or in a range of 15 wt. % to 18 wt. %.

The saccharides of the secondary component may be in a range of 20 wt. % to 90 wt. %, in a range of 30 wt. % to 80 wt. %, in a range of 40 wt. % to 70 wt. % or in a range of 50 wt. % to 60 wt. %.

The source of saccharides of the secondary component may be in a range of 1 wt. % to 85 wt. %, in a range of 5 wt. % to 85 wt. %, in a range of 10 wt. % to 80 wt. %, in a range of 15 wt. % to 75 wt. %, in a range of 20 wt. % to 70 wt. %, in a range of 25 wt. % to 65 wt. %, in a range of 30 wt. % to 60 wt. %, in a range of 35 wt. % to 55 wt. % or in a range of 40 wt. % to 50 wt. %, wherein the secondary component is different from the solidifying agent.

The source of fats of the secondary component may be in a range of 10 wt. % to 80 wt. %, in a range of 15 wt. % to 70 wt. %, in a range of 20 wt. % to 60 wt. %, wherein the secondary component is different from the solidifying agent.

The dry snack may further include a tertiary component, wherein the tertiary component may be in a range of 0.01 wt. % to 15 wt. %, in a range of 0.1 wt. % to 15 wt. %, in a range of 1 wt. % to 15 wt. %, in a range of 2 wt. % to 14 wt. %, in a range of 3 wt. % to 13 wt. % or in a range of 4 wt. % to 12 wt. %, in a range of 5 wt. % to 11 wt. %, in a range of 6 wt. % to 10 wt. %, in a range of 7 wt. % to 9 wt. %.

The tertiary component may include vitamins, wherein the vitamins may be in a range of 0.01 wt. % to 15 wt. % of the tertiary component, in a range of 3 wt. % to 13 wt. % of the tertiary component or from 5 wt. % to 11 wt. % of the tertiary component or in a range of 7 wt. % to 9 wt. % of the tertiary component.

The tertiary component may include minerals, wherein the minerals may be in a range of 1 wt. % to 50 wt. % of the tertiary component, in a range of 5 wt. % to 45 wt. % of the tertiary component or from 10 wt. % to 40 wt. % of the tertiary component, in a range of 15 wt. % to 35 wt. % of the tertiary component or in a range of 20 wt. % to 30 wt. % of the secondary component.

The tertiary component may include binders, wherein the binders may be in a range of 1 wt. % to 80 wt. % of the tertiary component, in a range of 15 wt. % to 60 wt. % of the tertiary component or from 30 to 40 wt. % of the tertiary component.

The tertiary component may include palatants, wherein the palatants may be in a range of 1 wt. % to 50 wt. % of the tertiary component, in a range of 5 wt. % to 45 wt. % of the tertiary component or from 10 wt. % to 40 wt. % of the tertiary component, in a range of 15 wt. % to 35 wt. % of the tertiary component or in a range of 20 wt. % to 30 wt. % of the secondary component.

The tertiary component may include antioxidants, wherein the antioxidants may be in a range of 1 wt. % to 15 wt. % of the tertiary component, in a range of 3 wt. % to 13 wt. % of the tertiary component or from 5 wt. % to 11 wt. % of the tertiary component or in a range of 7 wt. % to 9 wt. % of the tertiary component.

The tertiary component may include colorants, wherein the colorants may be in a range of 1 wt. % to 10 wt. % of the tertiary component, in a range of 3 wt. % to 10 wt. % of the tertiary component, in a range of 5 wt. % to 10 wt. % of the tertiary component or in a range of 7 wt. % to 10 wt. %.

The tertiary component may include preservatives, wherein the preservatives may be in a range of in a range of 1 wt. % to 10 wt. % of the tertiary component, in a range of 3 wt. % to 10 wt. % of the tertiary component, in a range of 5 wt. % to 10 wt. % of the tertiary component or in a range of 7 wt. % to 10 wt. %.

The wet pet food products may comprise meaty chunks, meaty chunks with gravy, wet snack or pâtéhaving a water content in a range of 14 wt. % to 99 wt. %, in a range of 15 wt. % to 99 wt. %, in a range of 15 wt. % to 85 wt. %, in a range of 20 wt. % to 75 wt. %, in a range of 25 wt. % to 70 wt. %, in a range of 30 wt. % to 65 wt. %, in a range of 35 wt. % to 60 wt. %, in a range of 40 wt. % to 55 wt. % or in a range of 45 wt. % to 50 wt. %.

The wet pet food product may further include a crude fat in a range of 0.01 wt. % to 30 wt. %, in a range of 1 wt. % to 30 wt. %, in a range of 3 wt. % to 30 wt. %, in a range of 6 wt. % to 27 wt. %, in a range of 9 wt. % to 24 wt. %, in a range of 12 wt. % to 21 wt. %, in a range of 15 wt. % to 18 wt. %.

The wet pet food product may further include a crude fiber in a range of 0.01 wt. % to 15 wt. %, in a range of 3 wt. % to 12 wt. %, or in a range of 5 wt. % to 10 wt. %, in a range of 7 wt. % to 8 wt. %.

The wet pet food product may further include a crude protein in a range of 20 wt. % to 80 wt. %, in a range of 25 wt. % to 75 wt. %, in a range of 30 wt. % to 70 wt. %, in a range of 35 wt. % to 65 wt. %, in a range of 40 wt. % to 60 wt. %, in a range of 45 wt. % to 55 wt.

The wet pet food product may further include a crude ash in a range of 0.01 wt. % to 10 wt. %, in a range of 1 wt. % to 9 wt. %, in a range of 3 wt. % to 7 wt. %, or in a range of 4.5 wt. % to 5.5 wt. %.

Wet Products

Meaty Chunks

The wet pet food products may comprise meaty chunks, wherein the meaty chunks may include the primary component in a range of 35 wt. % to 85 wt. % of the meaty chunks, in a range of 40 wt. % to 80 wt. % of the meaty chunks, in a range of 45 wt. % to 75 wt. % of the meaty chunks, in a range of 50 wt. % to 70 wt. % of the meaty chunks, in a range of 55 wt. % to 65 wt. % of the meaty chunks, wherein the primary component comprises processed non-human metazoan cell biomass of at least one non-human metazoan cell line.

The primary component of the meaty chunks may be processed by removing a portion of water from the cell biomass, combining the non-human metazoan cell biomass with the solidifying agent or any other appropriate process capable of increasing the dynamic viscosity of the cell biomass, wherein the portion of water removed from the cell biomass may be in a range of 0.01 wt. % to 45 wt. % of the cell biomass, in a range of 1 wt. % to 45 wt. % of the cell biomass, in a range of 5 wt. % to 40 wt. % of the cell biomass, in a range of 10 wt. % to 35 wt. % of the cell biomass, in a range of 15 wt. % to 30 wt. % of the cell biomass, in a range of 20 wt. % to 25 wt. %.

The primary component of the meaty chunks may be processed by removing a portion of water from the cell biomass, combining the non-human metazoan cell biomass with the solidifying agent or any other appropriate process capable of increasing the dynamic viscosity of the cell biomass, wherein the solidifying agent may be in a range of 0.01 wt. % to 15 wt. %, in a range of 0.1 wt. % to 15 wt. %, in a range of 1 wt. % to 14 wt. %, in a range of 2 wt. % to 13 wt. %, in a range of 3 wt. % to 12 wt. %, in a range of 4 wt. % to 11 wt. %, in a range of 5 wt. % to 10 wt. %, in a range of 6 wt. % to 9 wt. %, in a range of 7 wt. % to 8 wt. %.

The crude protein of the primary component in a range of 10 wt. % to 60 wt. %, in a range of 15 wt. % to 55 wt. %, in a range of 20 wt. % to 50 wt. %, in a range of 25 wt. % to 45 wt. %, in a range of 30 wt. % to 40 wt. %.

The crude fat of the primary component in a range of 0.01 wt. % to 25 wt. %, in a range of 0.1 wt. % to 25 wt. %, in a range of 1 wt. % to 25 wt. %, in a range of 3 wt. % to 25 wt. %, in a range of 6 wt. % to 22 wt. %, in a range of 9 wt. % to 20 wt. %, in a range of 12 wt. % to 18 wt. %, in a range of 14 wt. % to 16 wt. %.

The meaty chunks may further include a secondary component, wherein the secondary component may be in a range of 5 wt. % to 60 wt. %, in a range of 10 wt. % to 55 wt. %, in a range of 15 wt. % to 50 wt. %, in a range of 20 wt. % to 45 wt. %, in a range of 25 wt. % to 40 wt. %, in a range of 30 wt. % to 35 wt. %.

The crude fat of the secondary component may be in a range of 0.01 wt. % to 60 wt. % of, in a range of 5 wt. % to 55 wt. %, in a range of 10 wt. % to 50 wt. %, in a range of 15 wt. % to 45 wt. %, in a range of 20 wt. % to 40 wt. % or in a range of 25 wt. % to 35 wt. %.

The saccharides of the secondary component in a range of 0.5 wt. % to 25 wt. %, in a range of 1 wt. % to 25 wt. %, in a range of 5 wt. % to 25 wt. %, in a range of 10 wt. % to 20 wt. %, in a range of 12.5 wt. % to 17.5 wt. %, in a range of 14 wt. % to 16 wt. %.

The source of saccharides of the secondary component may be in a range of 50 wt. % to 85 wt. % of the secondary component, in a range of 55 wt. % to 80 wt. % of the secondary component or in a range of 60 wt. % to 80 wt. % of the secondary component, wherein the secondary component is different from the solidifying agent.

The source of fats of the secondary component may be in a range of 15 wt. % to 50 wt. % of the secondary component, in a range of 20 wt. % to 45 wt. % of the secondary component, in a range of 25 wt. % to 40 wt. % of the secondary component, wherein the secondary component is different from the solidifying agent.

The meaty chunks may further include a tertiary component, wherein the tertiary component may be in a range of 0.01 wt. % to 15 wt. %, in a range of 0.1 wt. % to 15 wt. %, in a range of 1 wt. % to 15 wt. %, in a range of 2 wt. % to 14 wt. %, in a range of 3 wt. % to 13 wt. % or in a range of 4 wt. % to 12 wt. %, in a range of 5 wt. % to 11 wt. %, in a range of 6 wt. % to 10 wt. %, in a range of 7 wt. % to 9 wt. %.

The tertiary component may include vitamins, wherein the vitamins may be in a range of 0.01 wt. % to 15 wt. % of the tertiary component, in a range of 3 wt. % to 13 wt. % of the tertiary component or from 5 wt. % to 11 wt. % of the tertiary component or in a range of 7 wt. % to 9 wt. % of the tertiary component.

The tertiary component may include minerals, wherein the minerals may be in a range of 1 wt. % to 50 wt. % of the tertiary component, in a range of 5 wt. % to 45 wt. % of the tertiary component or from 10 wt. % to 40 wt. % of the tertiary component, in a range of 15 wt. % to 35 wt. % of the tertiary component or in a range of 20 wt. % to 30 wt. % of the secondary component.

The tertiary component may include binders, wherein the binders may be in a range of 1 wt. % to 80 wt. % of the tertiary component, in a range of 15 wt. % to 60 wt. % of the tertiary component or from 30 to 40 wt. % of the tertiary component.

The tertiary component may include palatants, wherein the palatants may be in a range of 1 wt. % to 50 wt. % of the tertiary component, in a range of 5 wt. % to 45 wt. % of the tertiary component or from 10 wt. % to 40 wt. % of the tertiary component, in a range of 15 wt. % to 35 wt. % of the tertiary component or in a range of 20 wt. % to 30 wt. % of the secondary component.

The tertiary component may include antioxidants, wherein the antioxidants may be in a range of 1 wt. % to 15 wt. % of the tertiary component, in a range of 3 wt. % to 13 wt. % of the tertiary component or from 5 wt. % to 11 wt. % of the tertiary component or in a range of 7 wt. % to 9 wt. % of the tertiary component.

The tertiary component may include colorants, wherein the colorants may be in a range of 1 wt. % to 10 wt. % of the tertiary component, in a range of 3 wt. % to 10 wt. % of the tertiary component, in a range of 5 wt. % to 10 wt. % of the tertiary component or in a range of 7 wt. % to 10 wt. %.

The tertiary component may include preservatives, wherein the preservatives may be in a range of in a range of 1 wt. % to 10 wt. % of the tertiary component, in a range of 3 wt. % to 10 wt. % of the tertiary component, in a range of 5 wt. % to 10 wt. % of the tertiary component or in a range of 7 wt. % to 10 wt. %.

Meaty Chunks with Gravy

The wet pet food products may comprise the meaty chunks with gravy, wherein the meaty chunks with gravy may include the primary component in a range of 25 wt. % to 85 wt. %, in a range of 30 wt. % to 80 wt. %, in a range of 35 wt. % to 75 wt. %, in a range of 40 wt. % to 70 wt. %, in a range of 45 wt. % to 65 wt. % or in a range of 50 wt. % to 60 wt. %, wherein the primary component comprises processed non-human metazoan cell biomass of at least one non-human metazoan cell line.

The primary component of the meaty chunks with gravy may be processed by removing a portion of water from the cell biomass, combining the non-human metazoan cell biomass with the solidifying agent or any other appropriate process capable of increasing the dynamic viscosity of the cell biomass, wherein the portion of water removed from the cell biomass may be in a range of 0.01 wt. % to 45 wt. % of the cell biomass, in a range of 1 wt. % to 45 wt. % of the cell biomass, in a range of 5 wt. % to 40 wt. % of the cell biomass, in a range of 10 wt. % to 35 wt. % of the cell biomass, in a range of 15 wt. % to 30 wt. % of the cell biomass, in a range of 20 wt. % to 25 wt. %.

The primary component of the meaty chunks with gravy may be processed by removing a portion of water from the cell biomass, combining the non-human metazoan cell biomass with the solidifying agent or any other appropriate process capable of increasing the dynamic viscosity of the cell biomass, wherein the solidifying agent may be in a range, wherein the solidifying agent may be in a range of 0.01 wt. % to 15 wt. %, in a range of 0.1 wt. % to 15 wt. %, in a range of 1 wt. % to 14 wt. %, in a range of 2 wt. % to 13 wt. %, in a range of 3 wt. % to 12 wt. %, in a range of 4 wt. % to 11 wt. %, in a range of 5 wt. % to 10 wt. %, in a range of 6 wt. % to 9 wt. %, in a range of 7 wt. % to 8 wt. %.

The crude protein of the primary component in a range of 10 wt. % to 60 wt. %, in a range of 15 wt. % to 55 wt. %, in a range of 20 wt. % to 50 wt. %, in a range of 25 wt. % to 45 wt. %, in a range of 30 wt. % to 40 wt. %.

The crude fat of the primary component in a range of 0.01 wt. % to 25 wt. %, in a range of 0.1 wt. % to 25 wt. %, in a range of 1 wt. % to 25 wt. %, in a range of 3 wt. % to 25 wt. %, in a range of 6 wt. % to 22 wt. %, in a range of 9 wt. % to 20 wt. %, in a range of 12 wt. % to 18 wt. % or in a range of 14 wt. % to 16 wt. %.

The meaty chunks with gravy may further include a secondary component in a range of 5 wt. % to 60 wt. %, in a range of 10 wt. % to 55 wt. %, in a range of 15 wt. % to 50 wt. %, in a range of 20 wt. % to 45 wt. %, in a range of 25 wt. % to 40 wt. %, in a range of 30 wt. % to 35 wt. %.

The crude fat of the secondary component may be in a range of 0.01 wt. % to 60 wt. % of, in a range of 5 wt. % to 55 wt. %, in a range of 10 wt. % to 50 wt. %, in a range of 15 wt. % to 45 wt. %, in a range of 20 wt. % to 40 wt. % or in a range of 25 wt. % to 35 wt. %.

The saccharides of the secondary component in a range of 0.5 wt. % to 25 wt. %, in a range of 1 wt. % to 25 wt. %, in a range of 5 wt. % to 25 wt. %, in a range of 10 wt. % to 20 wt. %, in a range of 12.5 wt. % to 17.5 wt. %, in a range of 14 wt. % to 16 wt. %.

The source of saccharides of the secondary component may be in a range of 50 wt. % to 85 wt. % of the secondary component, in a range of 55 wt. % to 80 wt. % of the secondary component or in a range of 60 wt. % to 80 wt. % of the secondary component, wherein the secondary component is different from the solidifying agent.

The source of fats of the secondary component may be in a range of 15 wt. % to 50 wt. % of the secondary component, in a range of 20 wt. % to 45 wt. % of the secondary component, in a range of 25 wt. % to 40 wt. % of the secondary component, wherein the secondary component is different from the solidifying agent.

The meaty chunks with gravy may further include a tertiary component, wherein the tertiary component may be in a range of 0.01 wt. % to 15 wt. %, in a range of 0.1 wt. % to 15 wt. %, in a range of 1 wt. % to 15 wt. %, in a range of 2 wt. % to 14 wt. %, in a range of 3 wt. % to 13 wt. % or in a range of 4 wt. % to 12 wt. %, in a range of 5 wt. % to 11 wt. %, in a range of 6 wt. % to 10 wt. %, in a range of 7 wt. % to 9 wt. %.

The tertiary component may include vitamins, wherein the vitamins may be in a range of 0.01 wt. % to 15 wt. % of the tertiary component, in a range of 3 wt. % to 13 wt. % of the tertiary component or from 5 wt. % to 11 wt. % of the tertiary component or in a range of 7 wt. % to 9 wt. % of the tertiary component.

The tertiary component may include minerals, wherein the minerals may be in a range of 1 wt. % to 50 wt. % of the tertiary component, in a range of 5 wt. % to 45 wt. % of the tertiary component or from 10 wt. % to 40 wt. % of the tertiary component, in a range of 15 wt. % to 35 wt. % of the tertiary component or in a range of 20 wt. % to 30 wt. % of the secondary component.

The tertiary component may include binders, wherein the binders may be in a range of 1 wt. % to 80 wt. % of the tertiary component, in a range of 15 wt. % to 60 wt. % of the tertiary component or from 30 to 40 wt. % of the tertiary component.

The tertiary component may include palatants, wherein the palatants may be in a range of 1 wt. % to 50 wt. % of the tertiary component, in a range of 5 wt. % to 45 wt. % of the tertiary component or from 10 wt. % to 40 wt. % of the tertiary component, in a range of 15 wt. % to 35 wt. % of the tertiary component or in a range of 20 wt. % to 30 wt. % of the secondary component.

The tertiary component may include antioxidants, wherein the antioxidants may be in a range of 1 wt. % to 15 wt. % of the tertiary component, in a range of 3 wt. % to 13 wt. % of the tertiary component or from 5 wt. % to 11 wt. % of the tertiary component or in a range of 7 wt. % to 9 wt. % of the tertiary component.

The tertiary component may include colorants, wherein the colorants may be in a range of 1 wt. % to 10 wt. % of the tertiary component, in a range of 3 wt. % to 10 wt. % of the tertiary component, in a range of 5 wt. % to 10 wt. % of the tertiary component or in a range of 7 wt. % to 10 wt. %.

The tertiary component may include preservatives, wherein the preservatives may be in a range of in a range of 1 wt. % to 10 wt. % of the tertiary component, in a range of 3 wt. % to 10 wt. % of the tertiary component, in a range of 5 wt. % to 10 wt. % of the tertiary component or in a range of 7 wt. % to 10 wt. %.

pâté

In one aspect of the invention, the wet pet food products may comprise the pâté, wherein the pâté may include the primary component in a range of 25 wt. % to 85 wt. % of the pâté, in a range of 30 wt. % to 80 wt. % of the pâté, in a range of 35 wt. % to 75 wt. % of the pâté, in a range of 40 wt. % to 70 wt. % of the pâté, in a range of 45 wt. % to 65 wt. % of the pâté, in a range of 50 wt. % to 60 wt. % of the pâté, wherein the primary component comprises processed non-human metazoan cell biomass of at least one non-human metazoan cell line.

The primary component of the pâté may be processed by removing a portion of water from the cell biomass, combining the non-human metazoan cell biomass with the solidifying agent or any other appropriate process capable of increasing the dynamic viscosity of the cell biomass; wherein the portion of water removed from the cell biomass may be in a range of 0.01 wt. % to 40 wt. % of the cell biomass, in a range of 1 wt. % to 40 wt. % of the cell biomass, in a range of 5 wt. % to 35 wt. % of the cell biomass, in a range of 10 wt. % to 30 wt. % of the cell biomass, in a range of 15 wt. % to 25 wt. % of the cell biomass, in a range of 18 wt. % to 22 wt. %.

The primary component of the pâté may be processed by removing a portion of water from the cell biomass, combining the non-human metazoan cell biomass with the solidifying agent or any other appropriate process capable of increasing the dynamic viscosity of the cell biomass, wherein the solidifying agent may be in a range of 0.01 wt. % to 15 wt. %, in a range of 0.1 wt. % to 15 wt. %, in a range of 1 wt. % to 14 wt. %, in a range of 2 wt. % to 13 wt. %, in a range of 3 wt. % to 12 wt. %, in a range of 4 wt. % to 11 wt. %, in a range of 5 wt. % to 10 wt. %, in a range of 6 wt. % to 9 wt. %, in a range of 7 wt. % to 8 wt. %.

The crude protein of the primary component in a range of 5 wt. % to 65 wt. %, in a range of 10 wt. % to 60 wt. %, in a range of 15 wt. % to 55 wt. %, in a range of 20 wt. % to 50 wt. %, in a range of 25 wt. % to 45 wt. %, in a range of 30 wt. % to 40 wt. %.

The crude fat of the primary component in a range of 0.01 wt. % to 25 wt. %, in a range of 0.1 wt. % to 25 wt. %, in a range of 1 wt. % to 25 wt. %, in a range of 3 wt. % to 25 wt. %, in a range of 6 wt. % to 22 wt. %, in a range of 9 wt. % to 20 wt. %, in a range of 12 wt. % to 18 wt. % or in a range of 14 wt. % to 16 wt. %.

The pâté may further include a secondary component, wherein the secondary component may be in a range of 0.1 wt. % to 75 wt. %, in a range of 5 wt. % to 70 wt. %, in a range of 10 wt. % to 65 wt. %, in a range of 15 wt. % to 60 wt. %, in a range of 20 wt. % to 55 wt. %, in a range of 25 wt. % to 50 wt. %, in a range of 30 wt. % to 45 wt. %, in a range of 35 wt. % to 40 wt. %.

The saccharides of the secondary component in a range of 0.5 wt. % to 25 wt. %, in a range of 1 wt. % to 25 wt. %, in a range of 5 wt. % to 25 wt. %, in a range of 10 wt. % to 20 wt. %, in a range of 12.5 wt. % to 17.5 wt. %, in a range of 14 wt. % to 16 wt. %.

The source of saccharides of the secondary component may be in a range of 50 wt. % to 85 wt. % of the secondary component, in a range of 55 wt. % to 80 wt. % of the secondary component or in a range of 60 wt. % to 80 wt. % of the secondary component, wherein the secondary component is different from the solidifying agent.

The source of fats of the secondary component may be in a range of 15 wt. % to 50 wt. % of the secondary component, in a range of 20 wt. % to 45 wt. % of the secondary component, in a range of 25 wt. % to 40 wt. % of the secondary component, wherein the secondary component is different from the solidifying agent.

The pâté may further include a tertiary component, wherein the tertiary component may be in a range of 0.01 wt. % to 15 wt. %, in a range of 0.1 wt. % to 15 wt. %, in a range of 1 wt. % to 15 wt. %, in a range of 2 wt. % to 14 wt. %, in a range of 3 wt. % to 13 wt. % or in a range of 4 wt. % to 12 wt. %, in a range of 5 wt. % to 11 wt. %, in a range of 6 wt. % to 10 wt. %, in a range of 7 wt. % to 9 wt. %.

The tertiary component may include vitamins, wherein the vitamins may be in a range of 0.01 wt. % to 15 wt. % of the tertiary component, in a range of 3 wt. % to 13 wt. % of the tertiary component or from 5 wt. % to 11 wt. % of the tertiary component or in a range of 7 wt. % to 9 wt. % of the tertiary component.

The tertiary component may include minerals, wherein the minerals may be in a range of 1 wt. % to 50 wt. % of the tertiary component, in a range of 5 wt. % to 45 wt. % of the tertiary component or from 10 wt. % to 40 wt. % of the tertiary component, in a range of 15 wt. % to 35 wt. % of the tertiary component or in a range of 20 wt. % to 30 wt. % of the secondary component.

The tertiary component may include binders, wherein the binders may be in a range of 1 wt. % to 80 wt. % of the tertiary component, in a range of 15 wt. % to 60 wt. % of the tertiary component or from 30 to 40 wt. % of the tertiary component.

The tertiary component may include palatants, wherein the palatants may be in a range of 1 wt. % to 50 wt. % of the tertiary component, in a range of 5 wt. % to 45 wt. % of the tertiary component or from 10 wt. % to 40 wt. % of the tertiary component, in a range of 15 wt. % to 35 wt. % of the tertiary component or in a range of 20 wt. % to 30 wt. % of the secondary component.

The tertiary component may include antioxidants, wherein the antioxidants may be in a range of 1 wt. % to 15 wt. % of the tertiary component, in a range of 3 wt. % to 13 wt. % of the tertiary component or from 5 wt. % to 11 wt. % of the tertiary component or in a range of 7 wt. % to 9 wt. % of the tertiary component.

The tertiary component may include colorants, wherein the colorants may be in a range of 1 wt. % to 10 wt. % of the tertiary component, in a range of 3 wt. % to 10 wt. % of the tertiary component, in a range of 5 wt. % to 10 wt. % of the tertiary component or in a range of 7 wt. % to 10 wt. %.

The tertiary component may include preservatives, wherein the preservatives may be in a range of in a range of 1 wt. % to 10 wt. % of the tertiary component, in a range of 3 wt. % to 10 wt. % of the tertiary component, in a range of 5 wt. % to 10 wt. % of the tertiary component or in a range of 7 wt. % to 10 wt. %.

Wet Snack

The wet pet food products may comprise wet snack, wherein the wet snack may include the primary component in a range of 35 wt. % to 85 wt. % of the wet snack, in a range of 40 wt. % to 80 wt. % of the wet snack, in a range of 45 wt. % to 75 wt. % of the wet snack, in a range of 50 wt. % to 70 wt. % of the wet snack, in a range of 55 wt. % to 65 wt. % of the wet snack, wherein the primary component comprises processed non-human metazoan cell biomass of at least one non-human metazoan cell line.

The primary component of the wet snack may be processed by removing a portion of water from the cell biomass, combining the non-human metazoan cell biomass with the solidifying agent or any other appropriate process capable of increasing the dynamic viscosity of the cell biomass, wherein the portion of water removed from the cell biomass may be in a range of 0.01 wt. % to 45 wt. % of the cell biomass, in a range of 1 wt. % to 45 wt. % of the cell biomass, in a range of 5 wt. % to 40 wt. % of the cell biomass, in a range of 10 wt. % to 35 wt. % of the cell biomass, in a range of 15 wt. % to 30 wt. % of the cell biomass, in a range of 20 wt. % to 25 wt. %.

The primary component of the wet snack may be processed by removing a portion of water from the cell biomass, combining the non-human metazoan cell biomass with the solidifying agent or any other appropriate process capable of increasing the dynamic viscosity of the cell biomass, wherein the solidifying agent may be in a range of 0.01 wt. % to 15 wt. %, in a range of 0.1 wt. % to 15 wt. %, in a range of 1 wt. % to 14 wt. %, in a range of 2 wt. % to 13 wt. %, in a range of 3 wt. % to 12 wt. %, in a range of 4 wt. % to 11 wt. %, in a range of 5 wt. % to 10 wt. %, in a range of 6 wt. % to 9 wt. %, in a range of 7 wt. % to 8 wt. %.

The crude protein of the primary component in a range of 10 wt. % to 60 wt. %, in a range of 15 wt. % to 55 wt. %, in a range of 20 wt. % to 50 wt. %, in a range of 25 wt. % to 45 wt. %, in a range of 30 wt. % to 40 wt. %.

The crude fat of the primary component in a range of 0.01 wt. % to 25 wt. %, in a range of 0.1 wt. % to 25 wt. %, in a range of 1 wt. % to 25 wt. %, in a range of 3 wt. % to 25 wt. %, in a range of 6 wt. % to 22 wt. %, in a range of 9 wt. % to 20 wt. %, in a range of 12 wt. % to 18 wt. %, in a range of 14 wt. % to 16 wt. %.

The wet snack may further include a secondary component, wherein the secondary component may be in a range of 5 wt. % to 60 wt. %, in a range of 10 wt. % to 55 wt. %, in a range of 15 wt. % to 50 wt. %, in a range of 20 wt. % to 45 wt. %, in a range of 25 wt. % to 40 wt. %, in a range of 30 wt. % to 35 wt. %.

The crude fat of the secondary component may be in a range of 0.01 wt. % to 60 wt. % of, in a range of 5 wt. % to 55 wt. %, in a range of 10 wt. % to 50 wt. %, in a range of 15 wt. % to 45 wt. %, in a range of 20 wt. % to 40 wt. % or in a range of 25 wt. % to 35 wt. %.

The saccharides of the secondary component in a range of 0.5 wt. % to 25 wt. %, in a range of 1 wt. % to 25 wt. %, in a range of 5 wt. % to 25 wt. %, in a range of 10 wt. % to 20 wt. %, in a range of 12.5 wt. % to 17.5 wt. %, in a range of 14 wt. % to 16 wt. %.

The source of saccharides of the secondary component may be in a range of 50 wt. % to 85 wt. % of the secondary component, in a range of 55 wt. % to 80 wt. % of the secondary component or in a range of 60 wt. % to 80 wt. % of the secondary component, wherein the secondary component is different from the solidifying agent.

The source of fats of the secondary component may be in a range of 15 wt. % to 50 wt. % of the secondary component, in a range of 20 wt. % to 45 wt. % of the secondary component, in a range of 25 wt. % to 40 wt. % of the secondary component, wherein the secondary component is different from the solidifying agent.

The tertiary component may include minerals, wherein the minerals may be in a range of 1 wt. % to 50 wt. % of the tertiary component, in a range of 5 wt. % to 45 wt. % of the tertiary component or from 10 wt. % to 40 wt. % of the tertiary component, in a range of 15 wt. % to 35 wt. % of the tertiary component or in a range of 20 wt. % to 30 wt. % of the secondary component.

The wet snack may further include a tertiary component, wherein the tertiary component may be in a range of 0.01 wt. % to 15 wt. %, in a range of 0.1 wt. % to 15 wt. %, in a range of 1 wt. % to 15 wt. %, in a range of 2 wt. % to 14 wt. %, in a range of 3 wt. % to 13 wt. % or in a range of 4 wt. % to 12 wt. %, in a range of 5 wt. % to 11 wt. %, in a range of 6 wt. % to 10 wt. %, in a range of 7 wt. % to 9 wt.

The tertiary component may include vitamins, wherein the vitamins may be in a range of 0.01 wt. % to 15 wt. % of the tertiary component, in a range of 3 wt. % to 13 wt. % of the tertiary component or from 5 wt. % to 11 wt. % of the tertiary component or in a range of 7 wt. % to 9 wt. % of the tertiary component.

The tertiary component may include binders, wherein the binders may be in a range of 1 wt. % to 80 wt. % of the tertiary component, in a range of 15 wt. % to 60 wt. % of the tertiary component or from 30 to 40 wt. % of the tertiary component.

The tertiary component may include palatants, wherein the palatants may be in a range of 1 wt. % to 50 wt. % of the tertiary component, in a range of 5 wt. % to 45 wt. % of the tertiary component or from 10 wt. % to 40 wt. % of the tertiary component, in a range of 15 wt. % to 35 wt. % of the tertiary component or in a range of 20 wt. % to 30 wt. % of the secondary component.

The tertiary component may include antioxidants, wherein the antioxidants may be in a range of 1 wt. % to 15 wt. % of the tertiary component, in a range of 3 wt. % to 13 wt. % of the tertiary component or from 5 wt. % to 11 wt. % of the tertiary component or in a range of 7 wt. % to 9 wt. % of the tertiary component.

The tertiary component may include colorants, wherein the colorants may be in a range of 1 wt. % to 10 wt. % of the tertiary component, in a range of 3 wt. % to 10 wt. % of the tertiary component, in a range of 5 wt. % to 10 wt. % of the tertiary component or in a range of 7 wt. % to 10 wt. %.

The tertiary component may include preservatives, wherein the preservatives may be in a range of in a range of 1 wt. % to 10 wt. % of the tertiary component, in a range of 3 wt. % to 10 wt. % of the tertiary component, in a range of 5 wt. % to 10 wt. % of the tertiary component or in a range of 7 wt. % to 10 wt. %.

In one aspect of the invention, the pet food products may be a part of a complementary diet to provide health benefits alongside nutrition to a subject.

In one aspect of the invention, the pet food products may be designed to improve gastrointestinal system and/or help to treat, ameliorate or prevent health issues of the gastrointestinal system (e.g. digestion problems, stool quality, stool odor, inflammatory bowel disease). The pet food products which may improve gastrointestinal system may comprise at least one of the following:

a primary component comprising at least one metazoan cell line; and a secondary component comprising a source of saccharides, more specifically at least one source of saccharides selected from the group of resistant starch, inulin, glucose, oligosaccharides, xanthan gum, maltodextrin, cereals, grains, corn, wheat, rice, oats, and/or beta-glucans; and a secondary component comprising a source of saccharides, more specifically at least one source of fiber selected from the group of *psyllium*, oat bran, barley, wheat bran, cellulose, broccoli, cauliflower, beet pulp, chicory root extract, pectin, guar gum, chicory root, blueberry, cranberry, squash, and/or beans; and a secondary component comprising a source of fats, more specifically at least one source of fats selected from the group of vegetable oils, corn oil, soy oil, cottonseed oil, palm oil, linseed oil, canola oil, rapeseed oil, menhaden oil, coconut oil, and/or olestra; and a tertiary component comprising probiotics which may improve and/or maintain the normal microflora in the gastrointestinal system, more specifically at least one probiotic selected from the group of *Lactobacillus*

*acidophilus, Enterococcus faecium, Bifidobacterium lactis, Lactobacillus casei, Bifidobacterium breve*, and/or *Yucca schidigera*; and a tertiary component comprising palatants that may improve the flavor of the pet food product, more specifically at least one palatant compound selected from the group of ginger, yeast extract, vegetable broth, seaweed extract, herb extract, vitamin C, and/or curcumin; and a tertiary component comprising minerals that may inhibit a gastric acid and protect gastric mucosa, more specifically at least one mineral substance source selected from the group of zinc salt, calcium salt, magnesium and/or selenium.

The pet food products designed to improve the gastrointestinal system and/or help to treat, ameliorate or prevent health issues of the gastrointestinal system may be in the form of dry pet food products and wet pet food products.

In one aspect of the invention, the pet food products may be designed to treat, ameliorate and/or prevent inflammation (e. g. inflammation of bowel, ears, eyes, genitals and/or skin). The pet food products which may remediate the inflammatory processes may comprise at least one of the following:

a primary component comprising at least one metazoan cell line; and a secondary component comprising at least one source of saccharides, more specifically at least one source of saccharides selected from the group of dextrins, sucrose, lactose, maltose, glucose, fructose, guar gum, chicory gum, *psyllium*, pectin, blueberry, and/or raspberry; and a secondary component comprising at least one source of fats, more specifically at least one source of fats selected from the group of flaxseed oil, algae, medium chain triglycerides, coconut oil, palm oil, palm kernel oil, canola oil, soybean oil, peanuts, corn oil, cottonseed oil, rapeseed oil, and/or linseed oil; and a tertiary component comprising a source of antioxidants, more specifically at least one source of antioxidant selected from the group of quercetin, curcumin, green tea, *boswellia serrata*, ginger, quercetin, pomegranate, lime peel, tulsi, cinnamon, coumarin, vitamin A, vitamin K, niacin, pantothenic acid, calcium, and/or glycyrrhizin; and wherein such pet food products designed to treat, ameliorate and/or prevent inflammation may further comprise at least one compound selected from the group of cytokines, chemokines, prostaglandins, glucosamine, eicosapentanoic acid (EPA), docosahexaenoic acid (DHA), and/or chondroitin.

In one aspect of the invention, the pet food products may be designed to improve the quality of fur, skin and/or claws of the pet (e. g. prevent or provide at least supportive therapy in case of fungal, parasitic or bacterial infections, dull claws, brittle skin, fur loss). The pet food product which may improve the quality of fur, skin and/or claws may comprise at least one of the following:

a primary component comprising at least one metazoan cell line; and a secondary component comprising source of saccharides, more specifically at least one source of saccharides selected from the group of starch, xanthan gum, glycogen, glucose, fructose, saccharose, lactose, maltose, oligosaccharides, cellulose, hemicellulose, and/or lignin; and a secondary component comprising a source of fiber, more specifically at least one source of fiber selected from the group of beet pulp, guar gum, chicory root, *psyllium*, pectin, blueberry, cranberry, squash, apples, oat, beans, citrus, barley, and/or peas; and a secondary component comprising source of fats, more specifically at least one source of fats selected from the group of coconut oil, lauric acid, linoleic acid, babassu oil, palmitoleic acid, cohune oil, palm kelner oil, and/or tucum oil; and a tertiary component comprising minerals which may maintain the integrity and barrier function of the skin, more specifically at least one mineral compound selected from the group of zinc, and/or sulfur; wherein such pet food products designed to improve the quality of fur, skin and/or claws may further comprise at least one compound selected from the group of vitamin A, vitamin E, chlorhexidine, and/or benzoyl peroxide.

In one aspect of the invention, the pet food products may be designed to improve the quality of vision apparatus (e. g. to prevent or provide at least supportive therapy in case of age-related macular degeneration, progressive retinal atrophy, keratoconjunctivitis sicca, glaucoma) and hearing apparatus (e. g. age-related hearing loss, noise-induced hearing loss, otitis interna). The pet food product which may improve the quality of vision apparatus and hearing apparatus may comprise at least one of the following:

a primary component comprising at least one metazoan cell line; and a secondary component comprising a source of saccharides, more specifically at least one source of saccharides selected from the group of monosaccharides, oligosaccharides and/or polysaccharides; and a secondary component comprising a source of fats, more specifically at least one source of fats selected from the group of soybean oil, corn oil, canola oil, and/or sunflower oil; and a tertiary component comprising antioxidants, more specifically at least one source of antioxidants selected from the group of polyphenols, lutein, zeaxanthin, ascorbic acid and/or vitamin E, wherein such pet food products designed to improve the quality of vision apparatus and hearing apparatus may further comprise at least one compound selected from the group of zinc, taurine, eicosapentaenoic acid, docosahexaenoic acid and/or β-carotene.

In one aspect of the invention, the pet food products may be designed to reduce any risk of triggering an allergic reaction by the subject, i. e. may be designed as hypoallergenic. The pet food product that may reduce any risk of triggering any allergic reaction may comprise at least one of the following:

a primary component comprising at least one metazoan cell line, wherein the primary component may be hydrolysed; and a secondary component comprising a source of saccharides, more specifically at least one source of saccharides selected from the group of rice, potato, tapioca, sweet potato, barley, and/or oats; and a secondary component comprising a source of saccharides, more specifically at least one source of saccharides selected from the group of crude fiber, peas, lentils, chickpeas, and/or pumpkin; and a secondary component comprising a source of fats, more specifically at least one source of fats selected from the group of coconut oil, canola oil, sunflower oil, and/or olive oil; and a tertiary component comprising antioxidant, more specifically at least one antioxidant selected from the group of α-lipoic acid, caprylic acid, vitamin E, rosemary extract, green tea extract, and/or turmeric;

wherein such pet food products designed to reduce any risk of triggering an allergic reaction by the subject may further comprise at least one compound selected from the group of hydrolyzed proteins, omega-3 fatty acids, glucosamine, and/or chondroitin.

In one aspect of the invention, the pet food products may be designed to treat and/or prevent dental issues. The pet food products designed for treatment and/or prevention of dental issues may comprise at least one of the following:

a primary component comprising at least one metazoan cell line; and a secondary component comprising a source of saccharides, more specifically at least one source of saccharides selected from the group of waxy potato starch, waxy rice starch, waxy barley starch, waxy maize starch, waxy sorghum starch, waxy wheat starch, waxy potato starch, oat starch, peas, tapioca, gluten, glucose, sorbitol, algae, spinach, grape, tomatoes, and/or glycerol; and a secondary component comprising a source of fiber, more specifically at least one source of fiber selected from the group of cellulose, beet pulp, soybean hulls, wheat bran, chicory, corn, rice bran, whole grain oat, grape, celery, and/or flaxseed; and a secondary component comprising a source of fats, more specifically at least one source of fats selected from the group of corn oil, olive oil, sunflower oil, peanut oil, rapeseed oil, soybean oil, cottonseed oil, coconut oil, canola oil, fish oil, and/or rice kernel oil; and a tertiary component comprising a source of antioxidant, more specifically at least one source of antioxidant selected from the group of green tea extract, rice bran, curcumin, marine oils, yeast, algae extract, rosemary extract, and/or aloe vera extract; and wherein such pet food products designed to treat and/or prevent dental issues may further comprise at least one other compound selected from the group of glycerol, taurine, glycyrrhizin, and/or quercetin.

In order to provide proper nutrition to dogs, cats and other carnivorous animals, the nutritional profile of every pet food composition according to the invention may be tailored according to their needs.

For example, cats need taurine, which is crucial for cats because they cannot synthesize it in sufficient quantities on their own. As an essential amino acid for cats, it must be obtained from their diet, while a plant-based diet does not provide this amino acid at all. Taurine plays a vital role in maintaining the proper function of a cat's eyes, heart, and is particularly important for pregnant cats to ensure healthy kitten births and overall health. In one aspect of the invention, taurine may be included in a pet food composition through a primary component prepared and does not need to be subsequently added. In another aspect of the invention, taurine can be added subsequently to ensure proper nutrition of the animal.

For another example, both dogs and cats require essential amino acids such as methionine and cysteine, which play crucial roles in various processes. These amino acids naturally occur in plant-based sources of nutrition in significantly lower amounts than in meat products. The pet food composition in the as disclosed herein may represent a more proper diet, because the cultivated metazoan cell nutritional profile may be tailored through cultivation in a designed, richer in methionine and cysteine culture medium. Alternatively, other essential or non-essential compounds may be obtained like this and improve the final pet food composition.

In one aspect of the invention, the pet food products may be designed specifically for dogs and/or specifically for cats.

The pet food products designed specifically for dogs may comprise:

- a primary component in a range of 5 wt. % to 55 wt. % of the pet food product;
- a secondary component in a range of 20 wt. % to 50 wt. % of the pet food product, wherein the source of saccharides is in a range of 50 wt. % to 75 wt. % of the secondary component and source of fats is in a range of 25 wt. % to 50 wt. % of the secondary component;
- a tertiary component in a range of 0.01 wt. % to 15 wt. % of the pet food product;
- crude fat in a range of 5 wt. % to 20 wt. % of the pet food product;
- crude fiber in a range of 1 wt. % to 10 wt. % of the pet food product;
- crude protein in a range of 5 wt. % to 55 wt. %;
- crude ash in a range of 1 wt. % to 8 wt. % of the pet food product.

In one aspect of the invention, the pet food products may be specifically designed for growing puppies and may comprise:

- a primary component in a range of 5 wt. % to 55 wt. % of the pet food product;
- a secondary component in a range of 20 wt. % to 50 wt. % of the pet food product, wherein the source of saccharides is in a range of 50 wt. % to 75 wt. % of the secondary component and source of fats is in a range of 25 wt. % to 50 wt. % of the secondary component;
- a tertiary component in a range of 0.01 wt. % to 15 wt. % of the pet food product;
- crude fat in a range of 5 wt. % to 20 wt. % of the pet food product;
- crude fiber in a range of 1 wt. % to 10 wt. % of the pet food product;
- crude protein in a range of 5 wt. % to 55 wt. %;
- crude ash in a range of 1 wt. % to 8 wt. % of the pet food product.

The pet food products designed specifically for cats may comprise:

- a primary component in a range of 15 wt. % to 65 wt. % of the pet food product;
- a secondary component in a range of 20 wt. % to 50 wt. % of the pet food product, wherein the source of saccharides is in a range of 40 wt. % to 65 wt. % of the secondary component and source of fats is in a range of 35 wt. % to 60 wt. % of the secondary component;
- a tertiary component in a range of 0.01 wt. % to 15 wt. % of the pet food product;
- crude fat in a range of 5 wt. % to 25 wt. % of the pet food product;
- crude fiber in a range of 1 wt. % to 9.5 wt. % of the pet food product;
- crude protein in a range of 15 wt. % to 75 wt. %;
- crude ash in a range of 1 wt. % to 8 wt. % of the pet food product.

In one aspect of the invention, the pet food products may be specifically designed for growing kittens and may comprise:

- a primary component in a range of 20 wt. % to 75 wt. % of the pet food product;

- a secondary component in a range of 20 wt. % to 50 wt. % of the pet food product, wherein the source of saccharides is in a range of 40 wt. % to 65 wt. % of the secondary component and source of fats is in a range of 35 wt. % to 60 wt. % of the secondary component;
- a tertiary component in a range of 0.01 wt. % to 15 wt. % of the pet food product;
- crude fat in a range of 15 wt. % to 35 wt. % of the pet food product;
- crude fiber in a range of 1 wt. % to 15 wt. % of the pet food product;
- crude protein in a range of 35 wt. % to 75 wt. %;
- crude ash in a range of 1 wt. % to 8 wt. % of the pet food product.

In one aspect of the invention, the pet food products may be prepared by lyophilizing, i. e. freeze-drying. The process of freeze-drying may be performed on at least one component selected from the group of primary component, secondary component, tertiary component and/or their combination thereof, wherein the lyophilizer may be used.

The lyophilizer may be coupled with at least one pump capable of decreasing pressure to a range of 1000 Pa to 50 Pa, in a range of 800 Pa to 100 Pa, in a range of 600 Pa to 200 Pa or in a range of 500 Pa to 300 Pa. The lyophilizer may have a cooling system capable of providing an environment having temperature in a range of −100° C. to −50° C. at a pressure in a range of 50 Pa to 1000 Pa.

The cooling system of the lyophilizer may be set for at least one operating regime. The first regime may comprise a gradual decreasing of the temperature from an ambient temperature in a range of 20° C. to 25° C. to a temperature of −100° C., wherein the temperature gradient for the temperature decrease is at least 1° C./minute, at least 2° C./minute, at least 3° C./minute, at least 4° C./minute or at least 5° C./minute. The second regime of decreasing the temperature may comprise decrease of the temperature from an ambient temperature to a first temperature in a range of 0° C. to −50° C. and then after a portion of time decrease of the temperature to a second temperature in a range of −50° C. to −100° C. Analogically, the third regime may comprise decrease to a first, second and third temperature, wherein the first temperature may be in a range of −0° C. to −40° C., second temperature may be in a range of −40° C. to −75° C. and third temperature is in a range of −75° C. to −100° C. Each decrease to a first, second or a third temperature represents a respective drying cycle, i. e. first drying cycle, second drying cycle and/or third drying cycle. In another aspect of the invention, the cooling system of the lyophilizer may be set for 4 or more drying cycles, wherein the drying cycles may cover a range of temperature from 0° C. to −100° C. In yet another aspect of the invention, the lyophilizer may be configured to perform a heating cycle after at least one drying cycle. The heating cycle may perform strengthening of at least one component or combination thereof, wherein the components or their combination thereof have been freeze-dried during at least one drying cycle.

The lyophilizer may have the inner working volume, i. e. the volume that may be loaded with at least one tray carrying at least one component selected from the group of primary component, secondary component, tertiary component and/ or their combination thereof. The inner working volume may be in a range of 10 liters to 5000 liters, in a range of 100 liters to 4000 liters, in a range of 500 liters to 3500 liters, in a range of 1000 liters to 3000 liters, in a range of 1500 liters to 2500 liters or in a range of 1800 liters to 2000 liters. The inner working volume may be configured to hold a plurality of shelves and/or trays, wherein the plurality shelves and/or trays along with the lyophilizer may be configured to hold material having weight in a range of 10 kg to 5000 kg, in a range of 100 kg to 4500 kg, in a range of 500 kg to 4000 kg, in a range of 1000 kg to 3500 kg, in a range of 1500 kg to 3000 kg or in a range of 2000 kg to 2500 kg.

The lyophilizer may be configured to automatically sanitize the inner volume and its surfaces without major disassembly. In another aspect of the invention, the lyophilizer may be sanitized by using at least one of UV sterilization, steam sterilization or by using at least one chemical agent.

The freeze-dried pet food product may be a dry pet food product in the form of a dry snack or a dry kibble; or semi-moist pet food product in the form of a meaty chunks or meaty chunks with gravy.

The freeze-dried pet food products may be in a form of semi-moist pet food, wherein:

the solid parts of the pet food product may be freeze-dried and its composition may be a combination of at least one of primary component, secondary component and tertiary component; and the liquid parts of the pet food product may be a secondary component and/or a combination of secondary component with a tertiary component; or the solid parts of the pet food product may be freeze dried and its composition may be a secondary component and/or a combination of secondary component with a tertiary component;

the liquid parts of the pet food product may be a primary component and/or a combination of at least one of primary component, secondary component and tertiary component.

The freeze-dried pet food products in a form of a dry snack or dry kibble may have the following characteristics:

a primary component in a range of 30 wt. % to 60 wt. % of the pet food product;

a secondary component in a range of 20 wt. % to 50 wt. % of the pet food product, wherein the source of saccharides is in a range of 25 wt. % to 50 wt. % of the secondary component and source of fats is in a range of 50 wt. % to 75 wt. % of the secondary component;

a tertiary component in a range of 0.01 wt. % to 15 wt. % of the pet food product;

crude fat in a range of 15 wt. % to 40 wt. % of the pet food product;

crude fiber in a range of 1 wt. % to 10 wt. % of the pet food product;

crude protein in a range of 20 wt. % to 40 wt. % of the pet food product;

crude ash in a range of 1 wt. % to 8 wt. % of the pet food product;

water in a range of 1 wt. % to 14 wt. % of the pet food product.

The pet food products in a form of a freeze-dried meaty chunks or freeze-dried meaty chunks with gravy may have the following characteristics:

a primary component in a range of 20 wt. % to 40 wt. % of the pet food product;

a secondary component in a range of 30 wt. % to 60 wt. % of the pet food product, wherein the source of saccharides is in a range of 25 wt. % to 50 wt. % of the secondary component and source of fats is in a range of 50 wt. % to 75 wt. % of the secondary component;

a tertiary component in a range of 0.01 wt. % to 15 wt. % of the pet food product;

crude fat in a range of 20 wt. % to 45 wt. % of the pet food product;

crude fiber in a range of 1 wt. % to 10 wt. % of the pet food product;

crude protein in a range of 15 wt. % to 45 wt. % of the pet food product;

crude ash in a range of 1 wt. % to 8 wt. % of the pet food product;

water in a range of 14 wt. % to 90 wt. % of the pet food product.

In one aspect of the invention, the culture medium that has been separated from the cell biomass may be used for the production of pet food products. The culture medium that has been used and was separated from the cell biomass during harvesting may be further processed to avoid any metabolites and potentially undesired compounds to be a part of the pet food product. The culture medium may be analyzed after harvesting to determine the nutritional values of the culture medium, which may be considered as a byproduct of the cell cultivation. The culture medium may comprise all nutrients essential for cell cultivation, including amino acids, which may originate from a protein hydrolysate. Such medium may be referred to as waste medium.

The protein hydrolysate may be produced by performing hydrolysis reaction on a proteinous substrate, wherein the byproducts of the reaction may be a sediment, filtrate and/or any other part of the hydrolysate not used further for the culture medium production. Such byproducts of the culture medium preparation may be further used for production of the pet food. The byproducts of the culture medium preparation may comprise saccharides, proteins, amino acids, fats and/or minerals.

The used culture medium, i. e. the waste medium after the cell cultivation after at least one cell cultivation cycle may be used. The waste medium may be made during harvesting of the cells performed by a centrifugation or filtration, wherein the cell biomass is separated from the waste medium. The waste medium may comprise saccharides, proteins, amino acids, fats, minerals and/or vitamins.

The waste medium may be modified to remove any undesired substances. The undesired substances may be metabolites and salts. The metabolites may comprise, for example, lactic acid, ammonia or glutamine. The salts may comprise any dissociated salts composed of the following ions:

cations $Na^+$, $K^+$, $Mg^{2+}$, $Ca^{2+}$, $Cu^{2+}$, $Fe^{3+}$, $Fe^{2+}$, $Zn^{2+}$; and/or anions $Cl^-$, $SO_4^{2-}$, $NO^{3-}$, $CO_3^{2-}$, $HCO^{3-}$, $H_2PO_4^-$, $HPO_4^{2-}$, $PO_4^{3-}$, $SeO_3^{2-}$.

The waste medium may be modified using precipitation, reverse osmosis, coagulation, filtration, ultrafiltration and/or any other appropriate process capable of removing undesired substances from the waste medium.

The cell biomass may comprise at least one type of non-human metazoan cell line. The cell biomass may comprise water and/or residues of the culture medium.

The waste medium may comprise saccharides, amino acids, ions of respective salts and/or minerals from the culture medium, and/or other trace compounds or elements. The waste medium may be characterized by and/or may have the following composition:

saccharides in amount in a range of 0.001 g/100 g to 10 g/100 g, wherein examples of such saccharides may be glucose, fructose, lactose and/or galactose;

amino acids in amount in a range of 0.001 wt. % to 1 wt. %, wherein examples of such amino acids may be alanine, arginine, asparagine, aspartic acid and/or glutamine;

crude fat in amount in a range of 0.001 wt. % to 0.1 wt. %;

total sulphur in amount in a range of 10 mg/kg to 300 mg/kg;

total phosphorus in amount in a range of 10 mg/kg to 400 mg/kg;

total nitrogen in amount in a range of 100 mg/l to 1200 mg/l, chlorides in amount in a range of 250 mg/kg to 3000 mg/kg;

urea in amount in a range of 0.001 g/kg to 1 g/kg;

vitamins in amount in a range of 0.001 g/100 g to 1 g/100 g;

lactate in amount in a range of 0.001 g/100 g to 1 g/100 g;

ammonium and its ammonium cations in amount in a range of 50 mg/l to 300 mg/l;

organic amines in amount in a range of 0.001 g/kg to a 1 g/kg, wherein the examples of such organic amines may be ethanolamine, ornithine and/or arginine;

water in amount in a range of 90 wt. % to 99.99 wt. %, wherein the waste medium is an aqueous solution of compounds and/or substances mentioned above.

Therefore, the waste medium may be used as an ingredient providing nutrition. The waste medium may be used for the production of wet pet food products in the form of nutritional drink, smoothie, meaty chunks, meaty chunks with gravy, pâté and/or wet snack. In one aspect of the invention, the waste medium may be used as an alternative to water in case water would be added in a final product. The waste medium may be used as an ingredient providing minerals, amino acids, peptides, vitamins and/or saccharides.

In one aspect of the invention, the waste medium may be processed to remove undesired parts of the waste medium to provide only suitable nutrition in proper concentration when used as an ingredient in the pet food products. The waste medium may be processed by at least one of the following processes:

a) the waste medium may comprise toxins, their residues, metabolic waste, and/or any other toxic substances that may be removed by adsorption process on porous material such as charcoal, active char, ion-exchange resin; and/or filtration techniques such as ultrafiltration and/or nanofiltration; and/or chemical treatment that neutralize or precipitate toxic substances.

b) the waste medium may comprise excess salt amounts that may be removed through dialysis, electrodialysis and/or reverse osmosis.

c) the waste medium may be concentrated by removing water, which may be done through evaporation, lyophilization, reverse osmosis and/or distillation, wherein the concentrating of the waste medium may comprise reducing water content up to 10 times.

d) the waste medium may be enriched by at least one of the substances selected from the group of fats, proteins, saccharides, colorants, antioxidants, preservatives, enzymes, solidifying agents, vitamins, minerals and/or any other additive.

In one aspect of the invention, the pet food product may be in the form of a nutritional drink and/or smoothie. In one aspect of the invention, the pet food product in the form of a nutritional drink and/or smoothie may be homogenous without any visible solid parts. In another aspect of the invention, the pet food product may comprise visible solid parts, wherein the visible solid parts may be primary component, secondary component and/or their combination. The solid parts may be produced by extruding at least one of said components or by lyophilization of said components or their combination thereof.

The pet food products in the form of nutritional drink and/or smoothie may be low in protein and high in fat and may have the following characteristics and/or may have the following composition:

a primary component in a range of 1 wt. % to 25 wt. %;

a secondary component in a range of 1 wt. % to 35 wt. %, wherein the source of saccharides may be in a range of 0 wt. % to 30 wt. % of the secondary component and source of fats is in a range of 70 wt. % to 100 wt. % of the secondary component;

a tertiary component in a range of 0.01 wt. % to 15 wt. % of the pet food product;

crude fat in a range of 5 wt. % to 25 wt. % of the pet food product;

crude fiber in a range of 0.1 wt. % to 5 wt. % of the pet food product;

crude protein in a range of 5 wt. % to 35 wt. % of the pet food product;

crude ash in a range of 0.1 wt. % to 8 wt. % of the pet food product;

water in a range of 50 wt. % to 95 wt. % of the pet food product.

The pet food products in the form of nutritional drink and/or smoothie may be high in protein and low in fat and may have the following characteristics:

a primary component in a range of 1 wt. % to 35 wt. %;

a secondary component in a range of 1 wt. % to 25 wt. %, wherein the source of saccharides may be in a range of 70 wt. % to 100 wt. % of the secondary component and source of fats is in a range of 0 wt. % to 30 wt. % of the secondary component;

a tertiary component in a range of 0.01 wt. % to 15 wt. % of the pet food product;

crude fat in a range of 1 wt. % to 10 wt. % of the pet food product;

crude fiber in a range of 0.1 wt. % to 5 wt. % of the pet food product;

crude protein in a range of 10 wt. % to 25 wt. % of the pet food product;

crude ash in a range of 0.1 wt. % to 8 wt. % of the pet food product;

water in a range of 50 wt. % to 95 wt. % of the pet food product.

In one aspect of the invention, the pet food product in the form of the nutritional drink and/or smoothie may be stored in the freezer to decrease the temperature of the pet food product, thus solidifying the pet food product to provide a pet food product in the form of ice cream.

In one aspect of the invention, the pet food products in the form of a dry snack and/or dry kibble may be characterized by its water activity. The water activity refers to the amount of free water available in the food that may support microbial growth. According to the present aspect of the invention, the water activity of the dry pet food products in the form of a dry snack and/or dry kibble may be in a range of 0.40 to 0.70, in a range of 0.41 to 0.69, in a range of 0.42 to 0.68, in a range of 0.43 to 0.67, in a range of 0.44 to 0.66, in a range of 0.45 to 0.65, in a range of 0.46 to 0.64, in a range of 0.47 to 0.63, in a range of 0.48 to 0.62, in a range of 0.49 to 0.61, in a range of 0.50 to 0.60, in a range of 0.51 to 0.69, in a range of 0.52 to 0.68, in a range of 0.53 to 0.57 or in a range of 0.54 to 0.56. The water activity may be regulated by the conditions of the extrusion process and/or by the selection of the components within the pet food product composition.

In one aspect of the invention, the main source of protein of all herein described pet food products may have originated from the primary component, wherein the primary component may comprise at least one cultivated non-human metazoan cell biomass.

In one aspect of the invention, the secondary component of the pet food products may comprise source of saccharides and/or source of fats, whereas the secondary component may comprise protein, whereas the main source of protein in the pet food products does not originate from the secondary component. In another aspect of the invention, the primary component has higher protein content than the secondary component. In yet another aspect of the invention, the secondary component is protein-free.

In one aspect of the invention, the tertiary component may comprise plant-originated protein to enhance nutrition and rheologic properties of the pet food product. The tertiary component containing plant-originated protein may comprise pea protein, peanut protein, soy protein, rice protein, potato protein, chickpea protein and/or any other plant-originated protein.

In one aspect of the invention, the pet food products may comprise shanta catnip, valerian root, silvervine, tartarian honeysuckle, cat thyme, lemongrass and/or any other palatant to enhance aroma and palatability of the pet food products.

In one aspect of the invention, the primary component, the secondary component and the tertiary component that may be filled by the filling station are not extruded. In another aspect of the invention, the primary component that is extruded may not be the same as the primary component filled by the filling station.

In one aspect of the invention, the heating element of the extruder may be configured to remove at least a portion of the water from the extruded components. The heating element may be implemented in the single screw or twin screw of the extrusion system. In another aspect of the invention, the heating element of the extruder may comprise at least one heating zone, wherein each zone may be configured to provide a different heating environment.

The pet food products may have the following parameters, which may be measured, calculated and/or determined by the following means:

size, wherein the size may be measured by any measuring ruler or any digital tool capable of measuring length; and shape, wherein the shape may be determined by visual inspection and may be compared to any known shape of any animal or human foodstuff; and volume, wherein the volume may be measured according to the properties of particular pet food product using the container with a scale, wherein the dry pet food may be measured by submerging the dry pet food to the container filled with water and comparing the initial and final volume on the scale; and weight, wherein the weight may be measured by any weight scale, more preferably an analytical scale; and mass density, wherein the mass density may be calculated by the ratio of weight and volume; and water content, wherein the water content may be measured using any thermogravimetric method, more preferably a dynamic thermogravimetry; and crude fat, wherein the crude fat may be measured by the extraction using any suitable non-polar solvent and then measuring the weight of the crude fat; and crude fiber, wherein the crude fiber may be measured using the Weende method; and crude protein, wherein the crude protein may be measured using the Kjeldahl method; and crude ash, wherein the crude ash content may be measured using any thermogravimetric method, more preferably a dynamic thermogravimetry; and gross energy (GE), wherein the gross energy may be calculated according to the equation below $$GE = (5.7 \times x_{protein}) + (9.4 \times x_{fat}) + [4.1 \times (x_{nitrogen\ free\ extract} + x_{fiber})];$$

wherein the $x_{protein}$ represents the crude protein in a wt. %; and wherein the $x_{fat}$ represents the crude fat in a %; and wherein $x_{fiber}$ represents the crude fiber in a %; and wherein $x_{nitrogen\ free\ extract}$ represents nitrogen free extract in a %, which may be calculated according to the equation below $$x_{nitrogen\ free\ extract} = 100 - (x_{water} + x_{protein} + x_{fat} + x_{ash} + x_{fiber});$$

wherein $x_{water}$ represents the water content in a %

Energy digestibility (ED), wherein the energy digestibility may be calculated according to the equation designed for dogs and cats below $$ED_{dogs} = 91.2 - (1.43 \times x_{fiber});$$

and $$ED_{cats} = 87.9 - (0.88 \times x_{fiber}).$$

Digestible energy (DE), wherein the digestible energy for dogs and cats may be calculated according to equations below $$DE_{dogs} = \frac{GE \times ED_{dogs}}{100};$$

and $$DE_{cats} = \frac{GE \times ED_{cats}}{100}.$$

Metabolizable energy (ME), wherein the metabolizable energy for dogs and cats may be calculated according to equation below $$ME_{dogs} = DE_{dogs} - (1.04 \times x_{protein});$$

and $$ME_{cats} = DE_{cats} - (1.04 \times x_{protein}).$$

The exemplary calculation of GE, $ED_{dogs}$, $ED_{cats}$, $DE_{dogs}$, $DE_{cats}$, $ME_{dogs}$, $ME_{cats}$ according to the previous paragraph are demonstrated below:

$$x_{protein} = 31\%; x_{fat} = 5.5\%; x_{fiber} = 0.6; x_{ash} = 2\%; x_{water} = 42\%$$

$$x_{nitrogen\ free\ extract} = 100 - (x_{water} + x_{protein} + x_{fat} + x_{ash} + x_{fiber}) = 18.9\%$$

$$GE =$$

$$(5.7 \times x_{protein}) + (9.4 \times x_{fat}) + [4.1 \times (x_{nitrogen\ free\ extract} + x_{fiber})] = 308.4\ kcal$$

$$ED_{dogs} = 91.2 - (1.43 \times x_{fiber}) = 89.7\%$$

$$ED_{cats} = 87.9 - (0.88 \times x_{fiber}) = 87.0\%$$

$$DE_{dogs} = \frac{GE \times ED_{dogs}}{100} = 276.7\ kcal$$

$$DE_{cats} = \frac{GE \times ED_{cats}}{100} = 268.2\ kcal$$

$$ME_{dogs} = DE_{dogs} - (1.04 \times x_{protein}) = 244.4\ kcal/100\ g$$

$$ME_{cats} = DE_{cats} - (1.04 \times x_{protein}) = 244.4\ kcal/100\ g$$

All equations mentioned in the previous paragraphs were published by the FEDIAF (European Pet Food Industry Federation) in their respective guidelines. All measurements are considered as the commonly used analytical methods in the food science and pet food industry. In one aspect of the invention, parameters and/or properties of the pet food products described in the previous paragraph may be measured by any appropriate analytical method or any other method capable of measuring these parameters reliably.

The exemplary dry pet food products may comprise dry snacks, dry kibble and/or any other dry pet food products that may be produced using the extrusion system.

Example 1: The Culture Hamster Dry Snack

The cultured hamster dry snack may be used as a part of a complementary diet and may be produced followingly:

the cell biomass comprising a CHO-K1 cell line (originated from the ovaries of *Cricetulus Griseus*, Chinese Hamster) in a form of a single cell suspension was washed with the water to flush out the remaining culture medium. The cell biomass was centrifuged to devoid the water used for flushing out the remaining culture medium. The cell biomass was mixed with the solidifying agent, wherein the solidifying agent was composed from the soy lecithin, flaxseed oil and potato starch in a ratio of 1:2:10. The solidifying agent was added in the cell biomass in an amount of 7 wt. % of the cell biomass to prepare the primary component, which had the dynamic viscosity of 2100 mPa·s.

The primary component in an amount of 63 wt. % of the dry snack was mixed with the:

secondary component in an amount of 35 wt. % of the dry snack, wherein the secondary component is composed of:

the source of saccharides in an amount of 60 wt. % of the secondary component composed from chickpeas, potato, oats, sweet potato, peas, plain beet pulp, *quinoa*, dried apples, carrots in a ratio of 1:1.5:1:1:1:1:1:2 and the source of fats in an amount of 40 wt. % of the secondary component composed from sunflower oil, safflower oil, rapeseed oil tocopherols, marine microalgal oil, flaxseeds, in a ratio of 3:1.5:1:1:1.5; and tertiary component in an amount of 2 wt. % of the dry snack, wherein the tertiary component comprises:

the vitamin mix 4 wt. % of the tertiary component composed from vitamin B12, vitamin D, vitamin B9, vitamin E, vitamin B6, vitamin A, vitamin B1; and the mineral mix 41 wt. % of the tertiary component composed from dicalcium phosphate, calcium carbonate, potassium phosphate, ferrous sulphate, zinc sulphate; and the palatant mix 45 wt. % of the tertiary component composed from green tea extract, citric acid, rosemary extract, turmeric, brewers dried yeast; and the antioxidant mix 10 wt. % of the tertiary component composed from ethoxyquin and lycopene.

The primary component, secondary component and tertiary component was mixed in a mixer unit. The combination of components was extruded using the extruder having the die in the shape of a square. The size of the die was 2 cm×2 cm and the cutter regularly cut the extrudate every 2 cm of the extruded combination of components, thus the extrudate has the size of about 2 cm×2 cm×2 cm. The extrudate was conveyed to the drying unit to dry to a water content of 10 wt. %. The extrudate was further conveyed to the cooler to cool the extrudate to an ambient temperature of approximately 20° C. The cooled extrudate was conveyed through the fishing station, where the residues were separated from the extrudate. The extrudate that was finished may be packed in the suitable packaging, for example the bag.

The exemplary hamster dry snack prepared according to the previous paragraph had the following properties:

shape of cube having a size of 2 cm×2 cm×2 cm; and
volume approximately 8 cm³; and
weight 3.2 g; and
mass density 0.4 g·cm⁻³; and
water content 10 wt. %; and
crude fat 10 wt. %; and
crude fiber 3 wt. %; and
crude protein 30 wt. %; and
crude ash 5 wt. %; and
gross energy 449.0 kcal; and
the energy digestibility for dogs 86.4% and the energy digestibility for cats 85.0%; and
the digestible energy for dogs 388.5 kcal and the digestible energy for cats 381.9 kcal; and
the metabolizable energy for dogs 357.3 kcal/100 g and the metabolizable energy for cats 358.8 kcal/100 g.

Example 2: The Cultured Beef Dry Kibble

The cultured beef dry kibble may be used as a complete diet and may be made using the extrusion system and may be produced followingly:

the cell biomass comprising a bovine fibroblast cell line originated from the muscle of Czech Fleckvieh Cattle (Red Pied, Spotted) was obtained by a biopsy of living tissue. The fibroblast cell line was modified to be cultivated in the form of spheroids. The cell biomass was washed with water to flush out the remaining culture medium. The cell biomass was centrifuged to remove the water used for flushing out the remaining culture medium. The cell biomass was homogenized to reduce any clumps. The cell biomass was inactivated by heating it for 120 seconds in an autoclave at a temperature of approximately 80° C. The inactivated cell biomass was mixed with the solidifying agent, which was composed of carrageenan, sesame oil, and potato starch in a ratio of 2:1:9. The solidifying agent was added to the cell biomass in an amount of 6 wt. % of the cell biomass, and the primary component was prepared, which had a dynamic viscosity of 2200 mPa·s.

The primary component in an amount of 25 wt. % of the dry kibble was then mixed with the:

secondary component in an amount of 71 wt. % of the dry kibble, which is composed of:

the source of saccharides in an amount of 74 wt. % of the secondary component composed of chickpeas, rice, *spirulina*, sweet potatoes, potatoes, pectin, barley, pineapple, dried apple, carrots, peas, beet pulp in a ratio of 1:1:1:2:1:1.5:1.5:2:2:1:1.5:1; and the source of fats in an amount of 26 wt. % of the secondary component composed of olive oil, tocopherols, safflower oil, rapeseed oil in a ratio of 1:1:1:1; and the tertiary component in an amount of 4 wt. %, which is composed of:

the vitamin mix in an amount of 14 wt. % of the tertiary component composed of vitamin B12, vitamin D, vitamin B9, vitamin E, vitamin C, vitamin B2, vitamin B6, vitamin A, vitamin B5; and the mineral mix in an amount of 12 wt. % of the tertiary component composed of calcium carbonate, potassium phosphate, ferrous sulphate, ferric citrate, zinc sulphate, zinc oxide, sodium selenite, iron sulphate, anhydrous calcium iodate, potassium iodide, copper sulphate; and the palatant mix in an amount of 50 wt. % of the tertiary component composed of thyme extract, raspberry extract, short-chain triglycerides, *Enterococcus faecium*; and the antioxidant mix in an amount of 14 wt. % of the tertiary component composed of lycopene; and the binder mix in an amount of 10 wt. % of the tertiary component composed of inulin and carrageenan.

The primary component and secondary component were mixed in a mixer unit. The combination of components was extruded using an extruder with a die in the shape of a star. The size of the die was approximately 1.2×1.2 cm, and the cutter regularly cut the extrudate every 1.6 cm of the extruded combination of components, resulting in an extrudate of about 1.2 cm×1.2 cm×1.6 cm. The extrudate was conveyed to the drying unit to dry to water content of 10 wt. %. The extrudate was further conveyed to the cooler to cool it to an ambient temperature of approximately 20° C. The cooled extrudate was then conveyed to a finishing station and passed through it, where the residues were separated from the extrudate. The cooled extrudate was also coated in the finishing station with a tertiary component, which comprised turmeric. The finished extrudate could be packed in suitable packaging, for example, a bag.

The exemplary beef dry kibble produced according to the previous paragraph had the following properties:

shape of star having a size of 1.2 cm×1.2 cm×1.6 cm; and volume 2.3 cm³; and weight 0.95 g; and mass density 0.41 g·cm⁻³; and water content 10 wt. %; and crude fat 13 wt. %; and crude fiber 3.5 wt. %; and crude protein 23.5 wt. %; and crude ash 7 wt. %; and gross energy 446.8 kcal; and the energy digestibility for dogs 85.6% and the energy digestibility for cats 84.5%; and the digestible energy for dogs 382.6 kcal and the digestible energy for cats 377.4 kcal; and the metabolizable energy for dogs 358.2 kcal/100 g and the metabolizable energy for cats 359.4 kcal/100 g.

66

Example 3: The Cultured Chicken Soft Kibble

The cultured chicken soft kibble may be used as a complete diet or complementary diet and may be made using the extrusion system and may be produced followingly:

the cell biomass comprising embryonic chicken fibroblasts UMNSAH/DF-1 (originated from the embryo of *Gallus Gallus*, Domestic Chicken) was washed with water to flush out the remaining culture medium. The washed cell biomass was homogenized to reduce any aggregates, clumps, or lumps during cultivation. The washed and homogenized cell biomass was filtered to remove the water used for flushing out the remaining culture medium. The washed, homogenized, and filtered biomass was inactivated by heating the cell biomass for 120 seconds in an autoclave at a temperature of approximately 80° C. The cell biomass was chemically lysed to disrupt the cell walls. The cell biomass was mixed with the solidifying agent comprising mashed soybean and agar in a 1:1. The solidifying agent was added in an amount of 10 wt. % of the cell biomass. The cell biomass mixed with the solidifying agent provided a primary component with a dynamic viscosity of 2620 mPa·s.

The primary component in an amount of 40 wt. % of the soft kibble was mixed with:

the secondary component in an amount of 57 wt. %, which was composed of:

the source of saccharides in an amount of 85 wt. % of the secondary component composed of sweet potatoes, peas, dried apples, dried tomatoes, pumpkin, chickpeas, beet pulps, blueberries, elderberries, rosehips, *spirulina* in a ratio of 1:1.2:1.5:1:2:3:1:1.5:2:1.7:2; and the source of fats in an amount of 15 wt. % of the secondary component composed of sunflower oil, soybean oil, flaxseed oil, tocopherols in a ratio of 1:1:1:1; and the tertiary component in an amount of 3 wt. % of the soft kibble, which is composed from:

the vitamin mix in an amount of 16 wt. % of the tertiary component composed of vitamin B12, vitamin B6, vitamin C, vitamin E, vitamin A, vitamin D; and the mineral mix in an amount of 44 wt. % of the tertiary component composed of zinc sulphate, zinc oxide, calcium chloride, potassium chloride, magnesium oxide, potassium iodide, copper sulphate, anhydrous calcium iodate, ferrous carbonate, manganese oxide; and the palatant mix in an amount of 35 wt. % of the tertiary component composed of brewers dried yeast and *Yucca schidigera*; and the colorant mix in an amount of 5 wt. % of the tertiary component composed of *chlorella* extract and saffron.

The primary component and secondary component were mixed in a mixer unit. The combination of components was extruded using an extruder with a die in the shape of a rectangle. The size of the die was 0.4 cm×1.2 cm, and the cutter regularly cut the extrudate every 2 cm of the extruded combination of components, resulting in an extrudate of about 0.4 cm×1.2 cm×2 cm. The secondary component was added to the extruder through the feeder, where the secondary component was a mix of guar gum and glycerol. The extrudate was conveyed through the drying unit for 10 seconds and then subsequently cooled to an ambient temperature of 20° C. in the cooler using a rotary drum cooler. The coated extrudate was a soft kibble, which could be vacuum-packed in a bag.

The exemplary cultured chicken soft kibble produced according to the previous paragraph had the following properties:

shape of little block having a size of 0.4 cm×1.2 cm×2 cm; and volume 0.96 cm³; and weight 0.6 g; and mass density 0.63 g·cm⁻³; and water content 30 wt. %; and crude fat 13 wt. %; and crude fiber 7 wt. %; and crude protein 21.5 wt. %; and crude ash 3 wt. %; and gross energy 378 kcal; and the energy digestibility for dogs 76.9% and the energy digestibility for cats 79.1%; and the digestible energy for dogs 290.7 kcal and the digestible energy for cats 299.0 kcal; and the metabolizable energy for dogs 268.3 kcal/100 g and the metabolizable energy for cats 282.4 kcal/100 g.

In one aspect of the invention, the pet food products may be mold-injected. The exemplary mold-injected pet food products may comprise dry snacks.

Example 4: The Cultured Mouse Dry Snack

The exemplary cultured mouse dry snack product may be used as a complementary diet and may be made using the mold-injection system and may be produced followingly:

the cell biomass comprising mouse myoblast cell line C2C12 (originated from the muscle of mouse, *Mus musculus*) was washed with a hypertonic solution of sodium chloride to inactivate the cell biomass and wash out the waste medium. The cell biomass was then centrifuged to remove the residual water. The cell biomass was mixed with a solidifying agent comprising alginate and soy lecithin in a ratio of 1:2 to obtain a primary component, which had a dynamic viscosity of 2100 mPa·s.

The primary component in an amount of 60 wt. % of the dry snack was mixed with:

the secondary component in an amount of 35 wt. % of the dry snack, which was composed of:

the source of saccharides in an amount of 60 wt. % of the secondary component composed of potatoes, rice, carrageenan, raspberries, barley, carrots, spinach in a ratio of 3:3:1:0.5:4:2:1; and the source of fats in an amount of 40 wt. % of the secondary component composed of linseed oil, olive oil, sunflower oil, long-chain triglycerides in a ratio of 1:1:1:1; and the tertiary component in an amount of 5 wt. % of the dry snack, which comprised:

the vitamin mix in an amount of 14 wt. % of the tertiary component composed of vitamin A, vitamin E, vitamin D, vitamin B6; and the mineral mix in an amount of 46 wt. % of the tertiary component composed of sodium glycinate, magnesium lactate, potassium chloride, calcium carbonate; and the colorant mix in an amount of 5 wt. % of the tertiary component composed of blueberry extract, *spirulina* extract; and the binder mix in an amount of 35 wt. % of the tertiary component composed of potato starch, guar gum and inulin.

The primary component, secondary component, and tertiary component were mixed in a mixer unit. The combination of components was extruded using an extruder, and the extrudate was injected into a mold in the shape of a bone. The size of the mold was approximately 0.4 cm×1.2 cm. The molded extrudate was released from the mold, conveyed through the drying unit to dry to a water content of less than 14 wt. %. The molded extrudate was then cooled to an ambient temperature of 20° C. and packaged into a vacuum-bag.

The exemplary cultured mouse dry snack produced according to the previous paragraph had the following properties:

shape of bone having a size of 0.4 cm×1.2 cm×2 cm; and volume 0.96 cm³; and weight 0.46 g; and mass density 0.48 g·cm⁻³; and water content 20 wt. %; and crude fat 10 wt. %; and crude fiber 11.7 wt. %; and crude protein 45 wt. %; and crude ash 3 wt. %; and gross energy 440.7 kcal; and the energy digestibility for dogs 70.3% and the energy digestibility for cats 75%; and the digestible energy for dogs 309.8 kcal and the digestible energy for cats 330.7 kcal; and the metabolizable energy for dogs 263.0 kcal/100 g and the metabolizable energy for cats 296.0 kcal/100 g.

In one aspect of the invention, the pet food products may be wet pet food. The exemplary wet pet food products may comprise of meaty chunks with gravy, pâté, wet snack, and/or any other wet pet food product. The wet pet food products may be made using the cannery system.

Example 5: The Cultured Quail Gravy with Cultured Horse Chunks

The exemplary cultured quail gravy with a cultured horse chunks wet pet food product may be used as a complete diet or complementary diet and may be made using the cannery system and may be produced followingly:

a first cell biomass comprising horse fibroblast cell line (originated from the muscle tissue of *Equus caballus*, Horse) was obtained by a biopsy of living tissue. The cell biomass was homogenized to reduce any aggregates, clumps, or lumps during cultivation. The cell biomass was mixed with a solidifying agent comprising gelatin; and a second cell biomass comprising a fibroblast cell line (originated from the muscle of Cotumix cotumix *japonica*, Japanese Quail) was obtained by a biopsy of living tissue. The cell biomass was homogenized to reduce any aggregates, clumps, or lumps during cultivation. The primary component was prepared by combining the first cell biomass and second cell biomass.

The primary component in an amount 30 wt. % of the meaty chunks with gravy was then mixed with:

the secondary component in an amount of 68 wt. %, which was composed of:

the source of saccharides in an amount of 79 wt. % of the secondary component composed of carrots, celery, tomatoes, sorghum, guar gum in a ratio of 1:2:1:1:0.3; and the source of fats in an amount of 21 wt. % of the secondary component composed of flaxseed oil, sunflower oil in a ratio of 1:1; and the tertiary component in an amount of 2 wt. %, which was composed of:
the vitamin mix in an amount of 14 wt. % of the tertiary component composed of vitamin A, vitamin E, vitamin D, vitamin C; and
the mineral mix in an amount of 46 wt. % of the tertiary component composed of zinc sulphate, zinc oxide, manganese sulphate, potassium iodide, sodium selenite; and
the binder mix in an amount of 40 wt. % of the tertiary component composed of potato starch and carrageenan.

The primary component, secondary component, and tertiary component were mixed together in a mixer unit. The combination of components was extruded using an extruder with a die in the shape of a cube. The size of the die was 2 cm×2 cm, and the cutter regularly cut the extrudate every 2 cm of the extruded combination of components, resulting in an extrudate of about 2 cm×2 cm×2 cm. The extrudate was filled into packaging with the first cell biomass and water was added to produce the meaty chunks in gravy having the total water content about 50 wt. %. The product was packed and the packed product was sterilized using a sterilizing unit in the form of an autoclave for 240 seconds at a temperature of at least 100° C.

The exemplary cultured quail gravy with a cultured horse chunks produced according to the previous paragraph had the following properties:
shape of meat chunks with a gravy, wherein the meat chunks had the size of approximately 2 cm×2 cm×2 cm cubes; and
water content 50 wt. %; and
crude fat 12 wt. %; and
crude fiber 5 wt. %; and
crude protein 22.5 wt. %; and
crude ash 6 wt. %; and
gross energy 280 kcal; and
the energy digestibility for dogs 76.9% and the energy digestibility for cats 79.1%; and
the digestible energy for dogs 215.3 kcal and the digestible energy for cats 221.5 kcal; and
the metabolizable energy for dogs 191.9 kcal/100 g and the metabolizable energy for cats 854.2 kcal/100 g.

Example 6: The Cultured Chicken pâté

The exemplary cultured chicken pats may be made using the cannery system and may be produced followingly:
the cell biomass comprising embryonic chicken fibroblasts UMNSAH/DF-1 (originated from the embryo of *Gallus Gallus*, Domestic Chicken) was inactivated by heating the cell biomass for 120 seconds in an autoclave having temperature approximately 80° C. The cell biomass was mixed with a solidifying agent in an amount of 3 wt. % of the cell biomass composed of soy lecithin to prepare the primary component. The primary component in an amount of 45 wt. % of chicken pâté was then mixed with:
the secondary component in an amount of 55 wt. %, which was composed of:
the source of saccharides in an amount of 38 wt. % of the secondary component composed of pectin, guar gum in a ratio of 1:2; and
the source of fats in an amount of 62 wt. % of the secondary component composed of olive oil, sunflower seeds, short-chain triglycerides and gelatin in a ratio of 1:1:2:4.

The primary component and secondary component was homogenized to obtain a pâté.

The exemplary cultured chicken pâté produced according to the previous paragraph had the following properties:
water content 10 wt. %; and
crude fat 25.5 wt. %; and
crude fiber 2 wt. %; and
crude protein 35.5 wt. %; and
crude ash 6 wt. %; and
gross energy 536.4 kcal; and
the energy digestibility for dogs 88% and the energy digestibility for cats 85.9%; and
the digestible energy for dogs 472.1 kcal and the digestible energy for cats 461.0 kcal; and
the metabolizable energy for dogs 435.2 kcal/100 g and the metabolizable energy for cats 433.6 kcal/100 g.

Example 7: The Cultured Pork Wet Snack

The exemplary cultured pork wet snack may be made using the cannery system and may be produced followingly:
the cell biomass comprising porcine PK13 epithelial kidney cells (originated from the kidney of *Sus scrofa*, pig) was inactivated by heating it for 150 seconds in an autoclave at a temperature of approximately 80° C. The cell biomass was mixed with a solidifying agent in an amount of 3 wt. % of the cell biomass comprising tapioca starch and transglutaminase to provide a primary component. The primary component in an amount of 40 wt. % of the wet snack was mixed with:
the secondary component in an amount of 60 wt. %, which was composed of:
the sources of saccharides in an amount of 58 wt. % of the secondary component composed of fava beans, dried tomatoes, and kale in a ratio of 1:3:2
the sources of fats in an amount of 42 wt. % of the secondary component composed of flaxseed oil, sunflower oil, and medium-chain triglycerides in a ratio of 1:3:3.

The primary and secondary components were homogenized. The combination of components was then filled by a filling station of the cannery system, where the combination of components took the shape of a packaging, preferably a can. The can was sterilized using an autoclave for 280 seconds in a temperature of 100° C.

The exemplary cultured pork wet snack produced according to the previous paragraph had the following properties:
water content 42 wt. %; and
crude fat 5.5 wt. %; and
crude fiber 0.6 wt. %; and
crude protein 31 wt. %; and
crude ash 2 wt. %; and
gross energy 308.4 kcal; and
the energy digestibility for dogs 89.7% and the energy digestibility for cats 7%; and
the digestible energy for dogs 276.7 kcal and the digestible energy for cats 268.2 kcal; and
the metabolizable energy for both dogs and cats 244.4 kcal/100 g.

Example 8: The CHO Pet Food Composition

The pet food composition and its components may have following properties:
the primary component was prepared from modified CHO-K1 cells. The CHO-K1 cells originate from the Chinese Hamster Ovary. The culture medium further comprise at least one of following compounds in following concentration:

glycine 18.28 mg/l, hydroxy L-proline 0.37 mg/l, L-alanine 18.28 mg/l, L-arginine hydrochloride 136.92 mg/l, L-asparagine-H2O 19.02 mg/l, L-aspartic acid 20.58 mg/l, L-cysteine hydrochloride H2O 15.96 mg/l, L-cysteine 2HCl 42.82 mg/l, L-glutamic acid 41.52 mg/l, L-glutamine 344.15 mg/l, L-histidine hydrochloride H2O 31.06 mg/l, L-isoleucine 51.19 mg/l, L-leucine 55.54 mg/l, L-lysine hydrochloride 86.45 mg/l, L-methionine 16.09 mg/l, L-ornithine HCl 0.86 mg/l, L-phenylalanine 33.78 mg/l, L-proline 34.42 mg/l, L-serine 24.84 mg/l, L-taurine 0.38 mg/l, L-threonine 50.31 mg/l, L-tryptophan 9.79 mg/l, L-tyrosine disodium salt dihydrate 52.73 mg/l, L-valine 50.32 mg/l, biotin 0.01 mg/l, choline chloride 8.3 mg/l, D-calcium pantothenate 2.05 mg/l, folic acid 2.41 mg/l, menadione (vitamin K3) 0.0023 mg/l, niacinamide 1.84 mg/l, nicotinic acid (niacin) 0.01 mg/l, para-aminobenzoic acid 0.01 mg/l, pyridoxal hydrochloride 0.03 mg/l, pyridoxine hydrochloride 0.03 mg/l, riboflavin 0.2 mg/l, thiamine hydrochloride 1.96 mg/l, vitamin A (acetate) 0.02 mg/l, vitamin B12 1.55 mg/l, vitamin D2 (calciferol) 0.02 mg/l, alpha tocopherol sodium phosphate 0.0023 mg/l, i-inositol 11.47 mg/l, calcium chloride anhydrous 108.28 mg/l, cupric sulphate (CuSO4·5H2O) 0.0011 mg/l, ferric sulphate (FeSO4·7H2O) 0.38 mg/l, ferric citrate 122.47 mg/l, ethanolamine 3.05 mg/l, magnesium chloride anhydrous 26.01 mg/l, magnesium sulphate anhydrous 53.27 mg/l, potassium chloride 288 mg/l, potassium nitrate 0.03 mg/l, sodium bicarbonate 2109.09 mg/l, sodium chloride 6120 mg/l, sodium phosphate monobasic (NaH2PO4·H2O) 69.55 mg/l, sodium phosphate dibasic (Na2HPO4) anhydrous 64.55 mg/l, zinc sulphate (ZnSO4·7H2O) 0.39 mg/l, sodium selenite (Na2SeO3·5H2O) 0.04 mg/l, 5-Methylcytosine 0.01 mg/l, 2'Deoxyadenosine 0.91 mg/l, 2'Deoxycytidine HCl 0.91 mg/l, 2'Deixyguanosine 0.91 mg/l, Thymidine 1.23 mg/l, Coenzyme A (CoA) 0.23 mg/l, diphosphopyridine nucleotide (DPN) 0.64 mg/l, flavin adenine nucleotide (FAD), 0.09 mg/l, triphosphopyridine nucleotide sodium 0.09 mg/l, triphosphopyridine nucleotide sodium 0.09 mg/l, thiamine pyrophosphate co-carboxylase (TPP) 0.09 mg/l, uridine triphosphate sodium (UTP) 0.09 mg/l, ascorbic acid 4.55 mg/l, glutathione monosodium 0.91 mg/l, D-glucosamine HCl 0.35 mg/l, D-glucose (dextrose) 2955.45 mg/l, sodium hypoxanthine 2.17 mg/l, Linoleic acid 0.04 mg/l, lipoic acid 0.1 mg/l, D-glucuronolactone 0.16 mg/l, HEPES 2708.18 mg/l, L-alpha-amino-n-butyric acid 0.5 mg/l, phenol red 9.18 mg/l, putrescine 2HCl 0.07 mg/l, sodium pyruvate 100 mg/l, sodium acetate 4.55 mg/l, sodium glucuronate monohydrate 0.16 mg/l, polysorbate 80 (Tween 80®) 1.14 mg/l.

The culture medium in an amount of 1,500 litres was put into a culture vessel of the inner volume 2000 litres. The CHO-K1 cells were inoculated into a culture medium through the inlet and were proliferated for 82 hours. The CHO-K1 cells were then separated from the culture medium and harvested. The cells were then dried to get rid of the 75% water content.

The nutritional profile of dried CHO-K1 cells cultured in a culture medium described above was analyzed. The typical results of analysis is shown below:

peptides and proteins in a range of 46 to 48 g/100 g of dry matter; wherein the amino acid profile comprises arginine in a range of 2.8 to 3 g/100 g of dry matter; histidine in a range of 0.4 to 0.5 g/100 g of dry matter; isoleucine in a range of 2.5 to 3 g/100 g of dry matter; leucine in a range of 6.5 to 7 g/100 g of dry matter; lysine in a range of 6 to 7 g/100 g of dry matter; methionine in a range of 1.3 to 1.5 g/100 g of dry matter; cysteine in a range of 1.9 to 2.1 g/100 g of dry matter; phenylalanine in a range of 2.8 to 3 g/100 g of dry matter; tyrosine in a range of 2.9 to 3.1 g/100 g of dry matter; threonine in a range of 2.7 to 2.9 g/100 g of dry matter; tryptophan in a range of 0.45 to 0.55 g/100 g of dry matter; valine in a range of 2.4 to 2.6 g/100 g of dry matter; proline in a range of 3.8 to 4 g/100 g of dry matter; alanine in a range of 4.5 to 4.8 g/100 g of dry matter; glutamic acid in a combination with glutamine in a range of 10.5 to 11 g/100 g of dry matter; aspartic acid in a combination with asparagine in a range of 6.7 to 7 g/100 g of dry matter; glycine in a range of 4.5 to 4.6 g/100 g of dry matter; serine in a range of 4.5 to 4.8 g/100 g of dry matter; and fats and fatty acids in a range of 11 to 13 g/100 g of dry matter; and saccharides in a range of 1 to 10 g/100 g of dry matter; and vitamins in a range of 150 to 300 mg/100 of dry matter; wherein the vitamin profile is vitamin D in a range of 0.001 to 0.01 mg/100 g of dry matter; vitamin A in a range of 0.001 to 0.01 mg/100 g of dry; vitamin E in a range of 0.9 to 40 mg/100 g of dry; vitamin B1 (thiamine) in a range of 0.5 to 2.5 mg/100 g; vitamin B2 (riboflavin) in a range of 0.1 to 1 mg/100 g of dry matter; vitamin B5 (pantothenic acid) in a range of 1 to 5 mg/100 g of dry matter; vitamin B6 (pyridoxine) in a range of 10 to 20 mg/100 g of dry matter; vitamin B12 (cyanocobalamin) in a range of 0.1 to 1 mg/100 g of dry matter; vitamin B3 (niacin) in a range of 10 to 20 mg/100 g of dry matter; vitamin B9 (folic acid) in a range of 1 to 5 mg/100 g of dry matter; vitamin B7 (biotin) in a range of 0.001 to 5 mg/100 g of dry matter; vitamin K in a range of 0.1 to 50 μg/100 g of dry matter; and minerals in a range of 2000 to 2300 mg/100 g of dry matter; wherein the mineral profile is calcium in a range of 37 to 42 mg/100 g of dry matter; phosphorus in a range of 960 to 1110 mg/100 g of dry; potassium in a range of 1150 to 1300 mg/100 g of dry matter; sodium in a range of 235 to 245/100 g of dry matter; magnesium in a range of 50 to 70 mg/100 g of dry matter; copper in a range of 0.5 to 0.6 mg/100 g of dry matter; iron in a range of 11 to 15 mg/100 g of dry matter; manganese in a range of 4.2 to 5 mg/100 g of dry matter; zinc in a range of 12 to 15 mg/100 g of dry matter; iodine in a range of 8 to 11 mg/100 g of dry matter; selenium in a range of 8 to 12 mg/100 g of dry matter; chloride in a range of 7 to 11 mg/100 g of dry matter.

According to the determined nutritional profile of the metazoan cell, the primary, the secondary and tertiary component is designed. The primary component comprises dried CHO-K1 cells in an amount of 30 g/100 g of dry matter. The secondary component comprises tapioca starch in an amount of 10 g/100 g of dry matter, corn in an amount of 30 g/100 g of dry matter and glycerol in amount 5 g/100 g of dry matter. The tertiary component comprises binders in a form of peanut paste in an amount 5 g/100 g of dry matter.

The pet food composition is then dried and the bone-shaped protein snack treat is extruded. The protein snack treat has about 50% protein, 40% saccharides, 5% fats and the remaining 5% corresponds to auxiliary compounds.

This pet food product may be used as a complementary pet food or as a complete pet food, which is usually used for dogs that are in a need of high protein intake and relatively low fat intake, e.g. professional dogs or agility sport dogs. This particular pet food has a proper amount of fiber to ensure good digestion and also high protein content for building muscle tissue. The higher protein intake may be also beneficial for the puppies below 1 year to fully develop their muscular system.

According to worldwide usual standards, the protein, fat, fiber and ash content must be determined. The recommended ash content from the FEDIAF guidelines and others are about 8% or less. The usual pet food products, however, contain significantly more than 8% due to animal separate by-products from the meat industry or bones, which has a negative impact on the nutrition and health of the animal. Although minerals are essential for the various functionality of the organism, it is beneficial for the companion animals that these essential compounds are from quality sources such as high-quality meat products or vegetables. Also, there is a space to vary the levels between the minerals through adding them in a form of tertiary component, which will always result in a content of the minerals that specific animals need, as in the present example, wherein the ash content is about 5%, due to an addition of calcium as one part of the tertiary component.

The nutritional profile of prepared pet food composition is summarized below in the Table 1:

TABLE 1

| Nutritional profile of protein snack treat | | | |
|---|---|---|---|
| Component | Dry weight [wt. %] | Nutritional ratio [%] | |
| CHO-K1 cells, dried | 30% | Protein | 50.0% |
| Tapioca starch | 10% | Fat | 5.0% |
| Glycerol | 5% | Fiber | 20.0% |
| Corn | 30% | Humidity | 20.0% |
| Peanuts | 5% | Ash | <2.0% |
| Water | 20% | | |

| | Nutrition energy per 100 g [kcal] |
|---|---|
| Protein | 160 |
| Fat | 50 |
| Saccharide | 155 |

Example 9: The Bovine Pet Food Simple

In another aspect of the invention, the example pet food composition may have following properties:

The primary component was prepared from bovine fibroblast cells and bovine adipocytes. The both metazoan cell populations have been selected to provide protein and fat to the pet food composition through primary component. The nutritional profile of obtained bovine fibroblast and adipocytes may be determined in the same way as the cells in the exemplary determination of example 8.

The primary component comprises bovine fibroblasts in an amount of 30 g/100 g of the dry mass and bovine adipocytes in an amount of 10 g/100 g of dry matter. According to the determined nutritional profile of the bovine fibroblasts and adipocytes, the secondary component is designed. The secondary component comprises a carrot in an amount of 15 g/100 g of dry matter. The bovine fibroblasts and bovine adipocytes cells are dried and then subsequently mixed with the secondary component comprising a chopped carrot, which was thermally treated by a boiling process in water. The tertiary component comprises rosemary extract, wheat gluten and gelatin in an amount of 5 g/100 g of dry matter. Also, the water is added in an amount of 40 g/100 g of dry matter, thus creating a saucy chunk product, which is packed in a can. The saucy chunk product has about 30% protein, 15% saccharides, 5% fats, 5% auxiliary compounds and the remaining 40% corresponds to water. This pet food product may be used as a complete pet food, which is usually used for dogs or cats that are in a need of moderate protein and fat intake. The pet food has a proper amount of fiber to ensure good digestion and also proper amount of protein and fat for basic nutrition.

The nutritional profile of prepared pet food composition is summarized below in the Table 2:

TABLE 2

| Beef saucy chunks pet food | | | |
|---|---|---|---|
| Component | Dry weight | Nutritional ratio | |
| Bovine fibroblasts | 30% | Protein | 30% |
| Bovine adipocytes | 10% | Fat | 5% |
| Carrot | 15% | Fiber | 3% |
| Rosemary extract | 0.5% | Ash | <2% |
| Wheat gluten | 2.5% | Water | 40% |
| Gelatin | 2% | | |
| Water | 40% | | |

| | Nutrition energy per 100 g [kcal] |
|---|---|
| Protein | 160 |
| Fat | 90 |
| Saccharide | 120 |

In another aspect, the pet food composition according to the invention may include a primary component including cultivated metazoan cells and a secondary component including metazoan cells. Optionally, a tertiary component may be added into the pet food composition.

Preparation of pet food partially from the cultivated metazoan cells is useful for limiting the number of slaughtered animals and mitigating the impact of the meat industry on the environment. Also, it may be seen by the customer as the first and more conservative option to a common pet food having a meat component originating only from animal meat.

Possible ratios of the primary component, secondary component and tertiary component are provided in Table 3 below:

TABLE 3

| Exemplary ratios of primary/secondary/tertiary components | | | |
|---|---|---|---|
| Exemplary ratios | Primary component (wt. %) | Secondary component (wt. %) | Tertiary component (wt. %) |
| Ratio 1 | 1-10 | 0-100 | 0-100 |
| Ratio 2 | 10-20 | 0-90 | 0-90 |
| Ratio 3 | 20-30 | 0-80 | 0-80 |
| Ratio 4 | 30-40 | 0-70 | 0-70 |
| Ratio 5 | 40-50 | 0-60 | 0-60 |
| Ratio 6 | 50-60 | 0-50 | 0-50 |
| Ratio 7 | 60-70 | 0-40 | 0-40 |
| Ratio 8 | 70-80 | 0-30 | 0-30 |
| Ratio 9 | 80-90 | 0-20 | 0-20 |
| Ratio 10 | 90-100 | 0-10 | 0-10 |

Another possible ratios of the primary component, secondary component and tertiary component are provided in Table 3b below:

TABLE 3b

| Exemplary ratios of primary/secondary/tertiary components | | | |
|---|---|---|---|
| Exemplary ratios | Primary component (wt. %) | Secondary component (wt. %) | Tertiary component (wt. %) |
| Ratio 1 | 1-10 | 0-100 | 5-55 |
| Ratio 2 | 10-20 | 0-90 | 5-50 |
| Ratio 3 | 20-30 | 0-80 | 5-45 |
| Ratio 4 | 30-40 | 0-70 | 5-40 |
| Ratio 5 | 40-50 | 0-60 | 5-35 |
| Ratio 6 | 50-60 | 0-50 | 5-30 |
| Ratio 7 | 60-70 | 0-40 | 5-25 |
| Ratio 8 | 70-80 | 0-30 | 5-20 |
| Ratio 9 | 80-90 | 0-20 | 5-15 |
| Ratio 10 | 90-100 | 0-10 | 5-10 |

Example 10: The Combination with Animal Meat

The primary component comprises cultivated metazoan cells in an amount of 10 wt. % of the pet food composition. The animal meat used as a secondary component comprises meat of at least one of the species mentioned in this disclosure. The secondary component comprising the animal meat was added in an amount of 90 wt. % of the pet food composition.

Example 11: Pet Food Composition Design

The primary component comprises cultivated metazoan cells in an amount of 75 wt. %. The animal meat used as a secondary component comprises meat of at least one of the species mentioned below in this disclosure. The secondary component was added in an amount of 20 wt. % of the pet food composition. The tertiary component comprises binders in an amount of 5 wt. %.

Protein, fat, fiber, water and ash content may be determined according to worldwide or other standards. The recommended ash content from the FEDIAF guidelines and others is about 8% or less. Usual pet food products, however, contain significantly more than 8% due to animal by-products from the meat industry or bones, which has a negative impact on the nutrition and health of the animal. Although minerals are essential for the various functions of the organism, it is beneficial for companion animals that these essential compounds are from quality sources such as high-quality meat products or vegetables. Also, there is an opportunity to vary the levels of different minerals by adding them in the form of a tertiary component, which will always result in levels of the minerals that specific animals need.

In one aspect of the invention, the petfood composition may comprise a primary component comprising at least one cultivated metazoan cell population in an amount in a range of in a range 0.001 wt. % to 99.99 wt. % or 10 wt. % to 90 wt. % or 30 wt. % to 70 wt. % or 40 wt. % to 60 wt. %.

In one aspect of the invention, the pet food composition may comprise a primary component comprising at least one cultivated metazoan cell population.

In another aspect of the invention, the pet food composition may comprise a primary component comprising at least one cultivated metazoan cell population in an amount in a range of in a range 0.001 wt. % to 99.99 wt. % or 10 wt. % to 90 wt. % or 30 wt. % to 70 wt. % or 40 wt. % to 60 wt. %, a secondary component comprising at least one source of saccharides or fats in an amount in a range 1 wt. % to 99 wt. % or 10 wt. % to 90 wt. % or 25 wt. % to 75 wt. % or 40 wt. % to 60 wt. %; and a tertiary component comprising at least one substance selected from a group consisting of vitamins, minerals, binders, palatants, antioxidants, colorants and preservatives.

In another aspect, the pet food composition may comprise a primary component comprising at least one cultivated metazoan cell population, a secondary component comprising at least one source of saccharides or fats and a tertiary component comprising at least one substance selected from a group consisting of vitamins, minerals, binders, palatants, antioxidants, colorants and preservatives.

In another aspect, the pet food composition may comprise a primary component comprising at least one cultivated metazoan cell population in an amount in a range of in a range 0.001 wt. % to 99.99 wt. % or 10 wt. % to 90 wt. % or 30 wt. % to 70 wt. % or 40 wt. % to 60 wt. %, a secondary component comprising at least one source of saccharides or fats in an amount in a range 1 wt. % to 99 wt. % or 10 wt. % to 90 wt. % or 25 wt. % to 75 wt. % or 40 wt. % to 60 wt. %.

In another aspect, the pet food composition may comprise a primary component comprising at least one cultivated metazoan cell population and a secondary component comprising at least one source of saccharides or fats.

In another aspect, the pet food composition may comprise
a primary component comprising at least one cultivated
    metazoan cell population in an amount in a range of
    0.001 wt. % to 99.99 wt. % or 10 wt. % to 90 wt. % or
    30 wt. % to 70 wt. % or 40 wt. % to 60 wt. %, and
at least one of a secondary component or a tertiary
    component;
wherein the secondary component comprises at least one
    source of saccharides and/or fats in a range of 1 wt. %
    to 99 wt. % or 10 wt. % to 90 wt. % or 25 wt. % to 75
    wt. % or 40 wt. % to 60 wt. %; and
wherein the tertiary component comprises at least one
    compound selected from the group consisting of vitamins, minerals, binders and preservatives in an a range
    of 1 wt. % to 90 wt. % or 10 wt. % to 90 wt. % or 20
    wt. % to 80 wt. % or 35 wt. % to 65 wt. %.

In another aspect, the pet food composition may comprise
a primary component comprising at least one cultivated
    metazoan cell population and
at least one of a secondary component or a tertiary
    component;
wherein the secondary component comprises at least one
    source of saccharides and/or fats; and
wherein the tertiary component comprises at least one
    compound selected from the group consisting of vitamins, minerals, binders and preservatives.

In another aspect, the pet food composition may comprise
a primary component comprising at least one cultivated
    metazoan cell population and
at least one of a secondary component or a tertiary
    component;
wherein the secondary component comprises at least one
    source of saccharides and/or fats; and
wherein the tertiary component comprises at least one
    compound selected from the group consisting of vitamins, minerals, binders and preservatives; and
wherein the metazoan cells in the primary component are
    derived from bovine, avian, porcine, equine, piscine,
    cervine or cricetine cell lines.

In another aspect, the pet food composition may comprise a primary component comprising at least one cultivated metazoan cell population and at least one of a secondary component or a tertiary component;

wherein the secondary component comprises at least one source of saccharides and/or fats; and wherein the tertiary component comprises at least one compound selected from the group consisting of vitamins, minerals, binders and preservatives, wherein the metazoan cells of the primary component have at least one of fibroblasts, myoblasts, adipocytes, myocytes or hepatocytes.

In another aspect, the pet food composition may comprise a primary component comprising at least one cultivated metazoan cell population and at least one of a secondary component or a tertiary component;

wherein the secondary component comprises at least one source of saccharides and/or fats; and wherein the tertiary component comprises at least one compound selected from the group consisting of vitamins, minerals, binders and preservatives, wherein the non-animal sources of saccharides and/or fats in the secondary component are originated from plants.

In another aspect, the pet food composition may comprise a primary component comprising at least one cultivated metazoan cell population; and at least one of a secondary component or a tertiary component;

wherein the secondary component comprises at least one source of saccharides and/or fats; and wherein the tertiary component comprises at least one compound selected from the group consisting of vitamins, minerals, binders and preservatives, wherein the saccharides in the secondary component are derived from rice, corn, potatoes, sweet potatoes, barley, oats, peas, tapioca, lentils, chickpeas, sorghum, *quinoa*, millet, wheat, cassava, yams, pumpkin, carrots, beet pulp, apples, bananas, blueberries, cranberries, apricots, butternut squash, chia seeds, flaxseed, sunflower seeds, or pumpkin seeds.

In another aspect, the pet food composition may comprise a primary component comprising at least one cultivated metazoan cell population and at least one of a secondary component or a tertiary component;

wherein the secondary component comprises at least one animal source of saccharides and/or fats; and wherein the tertiary component comprises at least one compound selected from the group consisting of vitamins, minerals, binders and preservatives, wherein the fats in the secondary component are derived from olive oil, coconut oil, avocado oil, canola oil, sunflower oil, flaxseed oil, sesame oil, almonds, walnuts, cashews, pecans, macadamia nuts, hazelnuts, flaxseeds, sunflower seeds, pumpkin seeds, hemp seeds, sesame seeds, avocado, olives, almond butter, cashew butter, seaweed, tahini, hummus or any other lipid, phospholipid, triacylglyceride sources or any combination thereof.

In another aspect, the pet food composition may comprise a primary component comprising at least one cultivated metazoan cell population and at least one of a secondary component or a tertiary component;

wherein the secondary component comprises at least one animal source of saccharides and/or fats; and wherein the tertiary component comprises at least one compound selected from the group consisting of vitamins, minerals, binders and preservatives, that is free from hormones, antibiotics and growth factors.

In another aspect, the pet food composition may comprise a primary component comprising at least one cultivated metazoan cell population and at least one of a secondary component or a tertiary component;

wherein the secondary component comprises at least one source of saccharides and/or fats; and wherein the tertiary component comprises at least one compound selected from the group consisting of vitamins, minerals, binders and preservatives;

wherein the pet food composition comprising proteins, polypeptides, oligopeptides and amino acids in a range of 1 wt. % to 90 wt. % or 10 wt. % to 90 wt. % or 20 wt. % to 80 wt. % or 35 wt. % to 65 wt. %.

In another aspect, the pet food composition may comprise a primary component comprising at least one cultivated metazoan cell population and at least one of a secondary component or a tertiary component;

wherein the secondary component comprises at least one source of saccharides and/or fats; and wherein the tertiary component comprises at least one compound selected from the group consisting of vitamins, minerals, binders and preservatives;

wherein the pet food composition comprising fats in an amount in a range of 1 wt. % to 40 wt. % or 10 wt. % to 40 wt. % or 15 wt. % to 35 wt. % or 20 wt. % to 30 wt. %.

In another aspect, the pet food composition may comprise a primary component comprising at least one cultivated metazoan cell population and at least one of a secondary component or a tertiary component;

wherein the secondary component comprises at least one source of saccharides and/or fats; and wherein the tertiary component comprises at least one compound selected from the group consisting of vitamins, minerals, binders and preservatives;

wherein the pet food composition comprising saccharides in an amount in a range of 1 wt. % to 90 wt. % or 10 wt. % to 90 wt. % or 20 wt. % to 80 wt. % or 35 wt. % to 65 wt. %.

In another aspect, the pet food composition may comprise a primary component comprising at least one cultivated metazoan cell population and at least one of a secondary component or a tertiary component;

wherein the secondary component comprises at least one source of saccharides and/or fats; and wherein the tertiary component comprises at least one compound selected from the group consisting of vitamins, minerals, binders and preservatives, comprising ash in an amount less than 15 wt. % or less than 12 wt. % or less than 10 wt. % or less than 8 wt. % or less than 4 wt. %.

In another aspect, the pet food composition may comprise a primary component comprising at least one cultivated metazoan cell population in an amount in a range of 0.001 wt. % to 99.99 wt. % or 1 wt. % to 90 wt. % or 30 wt. % to 70 wt. % or 40 wt. % to 60 wt. %; and at least one of a secondary component or a tertiary component;

wherein the secondary component comprises at least one animal source of saccharides and fats in an amount in a range of 1 wt. % to 90 wt. % or 10 wt. % to 90 wt. % or 25 wt. % to 75 wt. % or 40 wt. % to 60 wt. %; and wherein the tertiary component comprises at least one compound selected from the group of vitamins, minerals, binders and preservatives in an amount in a range of 1 wt. % to 90 wt. % or 10 wt. % to 90 wt. % or 25 wt. % to 75 wt. % or 40 wt. % to 60 wt. %.

In another aspect, the pet food composition may comprise a primary component comprising at least one cultivated metazoan cell population and at least one of a secondary component or a tertiary component;

wherein the secondary component comprises at least one animal source of saccharides and fats; and wherein the tertiary component comprises at least one compound selected from the group of vitamins, minerals, binders and preservatives, wherein the metazoan cells in the primary component are derived from bovine, avian, porcine, equine, piscine, cervine or cricetine cell lines.

In another aspect, the pet food composition may comprise a primary component comprising at least one cultivated metazoan cell population and at least one of a secondary component or a tertiary component;

wherein the secondary component comprises at least one animal source of saccharides and fats; and wherein the tertiary component comprises at least one compound selected from the group of vitamins, minerals, binders and preservatives, wherein the metazoan cells in the primary component comprise at least one of fibroblasts, myoblasts, adipocytes, myocytes or hepatocytes.

In another aspect, the pet food composition may comprise a primary component comprising at least one cultivated metazoan cell population and at least one of a secondary component or a tertiary component;

wherein the secondary component comprises at least one animal source of saccharides and fats; and wherein the tertiary component comprises at least one compound selected from the group of vitamins, minerals, binders and preservatives, wherein the animal source of saccharides and fats in the secondary component is derived from any animal meat product.

In another aspect, the pet food composition may comprise a primary component comprising at least one cultivated metazoan cell population and at least one of a secondary component or a tertiary component;

wherein the secondary component comprises at least one animal source of saccharides and fats; and wherein the tertiary component comprises at least one compound selected from the group of vitamins, minerals, binders and preservatives that is free from hormones, antibiotics and growth factors.

In another aspect, the pet food composition may comprise a primary component comprising at least one cultivated metazoan cell population and at least one of a secondary component or a tertiary component;

wherein the secondary component comprises at least one animal source of saccharides and fats; and wherein the tertiary component comprises at least one compound selected from the group of vitamins, minerals, binders and preservatives;

wherein the pet food composition comprising about 10 wt. % to 90 wt. % or 20 wt. % to 80 wt. % or 35 wt. % to 65 wt. % of proteins, polypeptides, oligopeptides and amino acids.

In another aspect, the pet food composition may comprise a primary component comprising at least one cultivated metazoan cell population and at least one of a secondary component or a tertiary component;

wherein the secondary component comprises at least one animal source of saccharides and fats; and wherein the tertiary component comprises at least one compound selected from the group of vitamins, minerals, binders and preservatives;

wherein the pet food composition comprising about 10 wt. % to 40 wt. % or 15 wt. % to 35 wt. % or 20 wt. % to 30 wt. % of fats.

In another aspect, the pet food composition may comprise a primary component comprising at least one cultivated metazoan cell population and at least one of a secondary component or a tertiary component;

wherein the secondary component comprises at least one animal source of saccharides and fats; and wherein the tertiary component comprises at least one compound selected from the group of vitamins, minerals, binders and preservatives;

wherein the pet food composition comprising about 1 wt. % to 90 wt. % or 10 wt. % to 90 wt. % or 20 wt. % to 80 wt. % or 35 wt. % or 65 wt. % of the saccharides.

In another aspect, the pet food composition may comprise a primary component comprising at least one cultivated metazoan cell population and at least one of a secondary component or a tertiary component;

wherein the secondary component comprises at least one animal source of saccharides and fats; and wherein the tertiary component comprises at least one compound selected from the group of vitamins, minerals, binders and preservatives, comprising less than 15 wt. % or less than 12 wt. % or less than 10 wt. % or less than 8 wt. % or less than 4 wt. %.

In another aspect, the method for preparing a pet food composition may comprise preparing a primary component by cultivating metazoan cells; and processing the primary component to create the pet food composition.

In another aspect, the method for preparing a pet food composition may comprise: preparing a primary component by cultivating metazoan cells; providing at least one of a secondary or a tertiary component; combining the primary component with at least one of the secondary and the tertiary component; and processing the pet food composition after combining the primary component with at least one of the secondary and the tertiary component.

In another aspect, the method of preparing a pet food composition may comprise: a) determining the desired nutritional needs for a group of animals; b) selecting and culturing a metazoan cell population to create a primary component; c) selecting a culture medium composition to obtain a desired nutritional profile of the metazoan cell; d) designing a nutritional profile of the metazoan cell including at least two of: proteins, amino acids, fats and fatty acids, minerals, vitamins or saccharides; e) selecting the secondary and/or tertiary component to provide a desired nutritional profile of the pet food composition; and f) preparing the pet food composition after combining the primary component with at least one of the secondary and the tertiary component.

In another aspect, the method of preparing a pet food composition, wherein a primary component comprises at least first and second metazoan cell populations, comprising the steps of: a) preparing the first metazoan cell population; b) preparing the second metazoan cell population; c) combining the first and second metazoan cell populations to create the primary component; d) combining the primary component with at least one of a secondary and a tertiary component; and e) processing the pet food composition after combining the primary component with the at least one of the secondary and the tertiary component.

In another aspect, the method for preparing a dry pet food composition may comprise the steps of: a) preparing a primary component comprising metazoan cells; b) combining the primary component with a secondary and/or a tertiary component to create a wet pet food composition; c) drying the wet pet food composition to a water content lower than 14 wt. % and creating the dry pet food composition; and d) processing the dry pet food composition into a desired shape of a kibble or snack treat.

In another aspect, the method for preparing a semi-moist pet food composition may comprise the steps of: a) preparing a primary component comprising metazoan cells; b) incorporating the primary component with a secondary and/or a tertiary component to create a wet pet food composition; c) processing the wet pet food composition to a water content in a range of 14 wt. % to 60 wt. % by drying or adding water to create a semi-moist pet food composition; and d) processing the semi-moist pet food composition to a desired shape of soft kibble, chewy chunks, or pouches.

In another aspect, the method for preparing a wet pet food composition may comprise the steps of: a) preparing a primary component comprising metazoan cells; b) incorporating the primary component with a secondary and/or a tertiary component to create the wet pet food composition; c) processing the wet pet food composition to a water content higher than 60 wt. % by adding water; and d) processing the wet pet food composition to a desired form of saucy chunks, minced meat chunks, or pâté.

In another aspect, the pet food composition for dogs, the pet food composition may comprise: a) a primary component comprising metazoan cells; b) fat and protein in a ratio in a range of 1:3 to 1:4; c) at least 1 wt. % or 2 wt. % or 3 wt. % of choline; and d) at least 0.5 wt. % or 1 wt. % or 1.5 wt. % of eicosapentaenoic acid (EPA) and at least 0.5 wt. % or 1 wt. % or 1. wt. % of docosahexanoic acid (DHA).

In another aspect, the pet food composition for cats, the pet food composition may comprise a) a primary component comprising metazoan cells, b) protein and fat in a ratio in a range of 1:3 to 1:4; c) at least 1 wt. % or 2 wt. % or 3 wt. % of taurine; and d) at least 0.5 wt. % or 1 wt. % or 1.5 wt. % of eicosapentaenoic acid (EPA) and at least 0.5 wt. % or 1 wt. % or 1. wt. % of docosahexanoic acid (DHA).

In another aspect, the pet food composition may comprise: a) a primary component comprising cultured metazoan cells; b) a secondary component comprising a source of saccharides and/or fats; and c) a tertiary component comprising at least one substance selected from the group consisting of vitamins, minerals, binders, palatants, antioxidants, colorants and preservatives.

In another aspect, the pet food composition may comprise: a) a primary component consisting of cultured metazoan cells; b) a secondary component comprising a source of saccharides and/or fats; and c) a tertiary component comprising at least one substance selected from the group consisting of vitamins, minerals, binders, palatants, antioxidants, colorants and preservatives.

In another aspect of the invention, the pet food composition may comprise:

a primary component comprising cultivated metazoan cells derived from the Chinese hamster; wherein the nucleic acid sequence of the metazoan cells may have sequence identity at least 60% or at least 70% or at least 80% or at least 90%.

In another aspect of the invention, the pet food composition may comprise:

a primary component comprising cultivated metazoan cells, wherein the pet food composition comprises a nucleic acid comprising at least one sequence of nucleobases of the Chinese Hamster.

In another aspect of the invention, the pet food composition may comprise:

a primary component comprising cultivated metazoan cells, wherein the pet food composition comprises a nucleic acid comprising at least one gene of the Chinese Hamster.

In another aspect of the invention, the pet food composition may comprise:

a primary component comprising cultivated metazoan cells, wherein the pet food composition comprises at least one gene of the Chinese Hamster.

The cell cultivation processes according to the invention may comprise at least one step of:

obtaining and processing of the metazoan cells;

modification of cells such as providing a gain of function to the cells;

inoculation of cells to the cultivation device;

cultivation of cells in the cultivation device;

harvesting the cultured cells;

processing harvested cells into the food product;

or a combination thereof.

The step of obtaining and processing the metazoan cells may comprise optionally cell isolation, separation, purification or any other similarly appropriate processes, preparing primary cell bank, preparing a production cell bank, and/or any other appropriate processes.

The processes according to the invention may further optionally comprise other steps, such as the step of mixing different cell lines before or after the harvesting. Optionally, the processes according to the invention may comprise the step of differentiation of cells.

The processes according to the invention may optionally comprise the step of preparing food product for human or animal consumption. The food product may be, for example, in the form of pet food or cultured meat product for human consumption, with the desired shape and sensoric properties.

In one aspect of the invention, the cell cultivation processes may comprise steps of:

obtaining and processing the metazoan cells;

preparing primary cell bank;

modification of cells such as providing a gain of function to the cells;

preparing production cell bank;

inoculation of cells to the seeding tank or to the cultivation device;

cultivation of cells in the cultivation device;

harvesting the cultured cells; and/or preparing the food product.

An explant may be taken for the purpose of isolation of cells. The explant may be taken post-mortem, by biopsy from a live animal or from the tissue that was previously frozen. The tissue may be frozen in pieces of various sizes ranging from 0.1 mm$^2$ to 5 cm$^2$, 1 cm$^3$ to 5 cm$^3$, or 1 mm$^3$ to 5 mm$^3$ and kept under constant conditions, for example, at temperature in the range of –20° C. to –196° C., in the range of –80° C. to –110° C., or in the range of –85° C. to –100° C.

In the case of a post-mortem explant collection, the tissue from suitable animal species may be taken, for example, from *Bos taurus*, various breeds may be used, for example, Czech Fleckvieh Cattle (Red Pied, Spotted), Charolais, Angus Aberdeen, Holstein, Belgian blue, from any other appropriate pedigree species, or other non-pedigree animal species. The anatomical location of explants may be for example muscle: semimembranosus, sternomandibularis; connective tissue: connective tissue under the skin above the main muscle at the hind leg, connective fascia cover of muscle segments of the hind leg; fat tissue: above sternum under the skin, or any other appropriate location. The explant samples may be taken, for example, in the range of 1 minute to 60 minutes, in the range of 3 minutes to 45 minutes, or in the range of 5 minutes to 20 minutes after the animal is slaughtered. Sample size may be in the range of 0.5 g to 30 g, in the range of 2 g to 15 g, in the range of 3 g to 10 g, or in the range of 2 g to 15 g. Immediately after extraction the samples may be sprayed with ethanol and transferred to Phosphate-Buffered Saline (PBS) with antibiotics and/or antimycotics (e.g. Penicilin, Streptomycin, Amphotericin, and/or any other suitable antibiotics and antimycotics). Samples may be placed, for example, into glass containers with a volume of 200 ml to 1 liter, with 100 ml to 500 ml of PBS, and then transported for further processing, while maintaining a constant temperature. The temperature may be, for example, in the range of 2° C. to 6° C.

In case of biopsy from live animal, the tissue from suitable animal species may be taken, for example, from *Bos taurus*, various breeds (e.g. Czech Fleckvieh Cattle [Red Pied, Spotted], Charolais, Angus Aberdeen, Holstein, Belgian blue) or from any other appropriate animal species. The amount of explant sample may be in the range of 0.1 g to 5 g, in the range of 0.2 g to 2 g, or in the range of 0.3 g to 1 g. The sample may be taken, for example, from the hind leg with a bioptic needle, which is valid for muscle tissue, connective tissue, and fat tissue as well.

The samples may be then transferred to colder environments, for example, at 2° C. to 6° C., for further processing and proceeded to isolation.

The sample of explant tissue may be mechanically homogenized, and subsequently, the homogenized tissue may be subjected to enzymatic dissociation in order to obtain dissociated single cells. The enzyme used for dissociation of cells from the tissue may be, for example, collagenase, trypsin, or any other appropriate enzyme. The homogenized tissue may be placed on a shaker at, for example 0.1 RCF to 3 RCF; maintained at a temperature in the range of, for example, 34° C. to 38° C. for the time required for enzyme digestion such as 10 minutes to 60 minutes. The cells may be filtered from tissue residues. The cells may be selected on adherent surfaces (passage 1) and multiplicated. The cells may be then collected (tissue based) and sorted. The sorted cell types may be multiplicated (passage 2). The cell stocks may be frozen, for example, at –75° C. to –196° C., in order to obtain a primary cell bank. The frozen, uniform cells may be stored in cryovials, wherein each cryovial may contain an amount of cells in the range of 200 000 to 4 million, or in the range of 0.5 million to 3 million, or in the range of 0.7 million to 2 million. The volume of cryovials may be, for example, in the range of 1 ml to 5 ml, or any other appropriate volume.

Cells may be stored for example in cryovials or in other appropriate containers in liquid nitrogen or in a freezer, while maintaining a constant temperature, for example, in the range of –75° C. to –196° C.

The cell types used for cultivation processes according to the invention may comprise many types of non-human metazoan cells such as: stem cells comprising embryonic stem cells (ESCs) and other cell types derived from blastocyst or other early-stage embryos; muscle stem cells such as myosatellite cells, mesenchymal stem cells or cells derived from the bone marrow, fat tissue, subcutaneous tissue or other tissues; or cells where the stemness character is induced or established afterwards such as induced pluripotent stem cells (iPSCs). Other used cell types may be myoblasts, myocytes, fibroblasts, fibro-adipogenic progenitors, preadipocytes, adipocytes, epithelial cells, cartilage cells and tendon-derived cells such as chondroblasts and chondrocytes, macrophages, keratinocytes, hepatocytes, testicular cells, Sertoli cells, or any other appropriate cells.

The cell lines used in the processes according to the invention may include for example Chinese hamster ovary (CHO) cells such as CHO-K1 or CHO-DG44; C2C12; Madin-Darby bovine kidney cells (MDBKs); Madin-Darby canine kidney (MDCK) cells; UMNSAH/DF-1; or any other appropriate cell lines.

The cultivated cells used in the processes may be any appropriate non-human metazoan cells. The cells may be for example bovine, porcine, fish (piscine), game (*cervine*), avian, rodent (cricetine, murine), equine, or any other appropriate cells.

The cells for cultivation may be selected, without limitation, for example from at least one of the following animals: cattle (*Bos taurus*), chicken (*Gallus domesticus*), domestic pig (*Sus domesticus*), house cricket (*Acheta domesticus*), garden snail (Helixpomatia), common carp (*Cyprinus carpio*), horse (*Equus ferus*), edible crab (*Cancer pagurus*), marsh frog (*Pelophylax ridibundus*), common *octopus* (*Octopus vulgaris*), gilt-head bream (*Sparus aurata*), roe deer (*Capreolus capreolus*), common sea urchin (*Echinus esculentus*), harbor seal (*Phoca vitulina*), European stag beetle (*Lucanus cervus*), African elephant (*Loxodonta africana*), house mouse (*Mus musculus*), green sea turtle (*Chelonia mydas*), or from any other appropriate animals.

In one aspect of the invention the cultivated cells may be bovine cells. The bovine cells may be selected from the group of: stem cells comprising embryonic stem cells and other cell types derived from blastocyst or other early-stage embryos; muscle stem cells such as myosatellite cells, mesenchymal stem cells or derived from bone marrow; fat tissue; subcutaneous tissue or other tissues; or cells where the stemness character is induced or established afterward such as induced pluripotent stem cells. Other used bovine cell types may be bovine myoblasts, myocytes, fibroblasts, fibro-adipogenic progenitors, preadipocytes, adipocytes, epithelial cells cartilage and tendon-derived cells such as chondroblasts and chondrocytes, macrophages, keratinocytes, hepatocytes, testicular cells, Sertoli cells, mesenchymal stem cells, myosatellite cells, or a combination thereof.

According to the present invention, the cells may be modified in various ways to improve their properties. For example, the cells may be genetically modified, may be subjected to non-genetic modification, or adapted to different conditions and environments.

The cells that are cultivated after the isolation from a source tissue, without modifications, usually do not grow uniformly, behave erratically, lose their properties over time, or are fragile. Their properties may be determined, for example by isolation conditions and other factors.

Post isolation, the bulk of multiplicated cells and a population of high numbers of cells is established. The subpopulations of cells with uniform common phenotype behavior (cell lines) are further selected from those populations. The main common phenotype traits of a given cell type are determined by specific characteristics and their preservation over time, homogenous doubling time, and speed of the cell cycle. To create cell lines with such characteristics, clonal populations originating from single cells are established and further cultivated under conditions of a continuous selection pressure. The selection pressure could be applied with repetitive steps during growth of the cell line with selection for further growth of only cells that fulfilled the selection criteria. An example of selection criteria for the derivation of spontaneously immortalized cell line is the selection of cells that undergo cell division in time-specific time intervals, such as 24 hours to 30 hours or 10 hours to 24 hours, and do not exhibit any marker of cell senescence. The result is a subpopulation (cell line) of selected cells that does not enter senescence and continues to grow with a constant doubling time. To support the spontaneous tendency of cells in isolated populations to undergo such selection criteria and be stably modified to maintain their characteristics, various treatments could be performed. Stress treatments that do not kill the cells but induce stress responses could result in more stable and resilient cell lines. Such stress treatment may comprise exposure to UV radiation, gamma radiation and/or chemical stress factors.

Various culture media components or treatments may be used to keep cells with the desired cell type characteristics under the described selection processes. Components may be for example proteins with signaling function and/or oligonucleotides of both deoxyribonucleic acid (DNA) and ribonucleic acid (RNA) that may affect the native transcription regulation. Specifically, oligonucleotides with a complementary sequence to a functional element of either DNA or RNA functional elements (antisense oligonucleotides, AONs) native in the cell and/or nucleotides with the sequence allowing them to bind to specific binding sites of a protein structure (e.g. aptamers) may be used. One of the key functions may be the regulation of the corresponding sequences in the genetic material of cells to modulate gene expression or further process genetic information relating to a cell life regulatory process. Specifically, the use of these components may lead to an upregulation or downregulation of the expression of specific genes or gene families, the nature of these regulations being transient and relying on the activity of the given oligonucleotide.

Single-stranded DNA or RNA oligonucleotide sequences complementary to the target sequences of mRNA in cultured cells may be used as regulating components in the culture media. AONs could alter or silence mRNA expression of target genes or modulate mRNA exon linkage in pre-mRNA splicing which results in the modulation of the number of protein-splicing variants in target genes. Examples of target genes for AONs silencing may be for example miR-140-5p or Ferroportin. Examples of target genes for modulation of splicing variants may be various receptors and/or other transmembrane or membrane proteins such as Fibroblast growth factor (FGF) receptor or Transforming growth factor (TGF) receptor. AONs may be added into media separately and/or together with other nucleotides. AONs could penetrate through the membrane of the target cell unassisted or accompanied by a carrier structure. Transport may be supported with chemical or physical methods for cellular delivery. Oligonucleotides may be used freely as a culture media compound or intracellular delivery may be facilitated with a delivery agent. Examples of those agents may be various lipid nanoparticles (LNPs) vesicles or transfection reagents. Concentration of AONs in media may be in the range of 0.002 μM/l to 5 μM/l, or in the range of 0.01 to 2 μM/l, or in the range of 0.1 to 1 μM/l.

Aptamers are short sequences of nucleic acids capable of binding specific sites of a protein structure. Aptamers may be used as regulating components in the culture media. Specifically, aptamers forming a complement ligand structure to specific receptors on the cell plasma membrane thereby serving as receptor agonists may be used. Examples of such receptors may be Transferrin receptor, Insulin receptor, TGF receptor, or FGF receptor.

The obtained metazoan cells may undergo various combinations of adaptation steps, which may include adaptation to grow in a suspension; adaptation to grow on scaffolds; adaptation to form spheroids; adaptation to grow in the absence of at least one of L-proline or L-glutamine; adaptation to a higher cell density level (for example, in the range of $5 \cdot 10^6$ cells/ml to $100 \cdot 10^6$ cells/ml, or in the range of $5 \cdot 10^6$ to $30 \cdot 10^7$); adaptation to cryopreservation; adaptation to low-oxygen or high-oxygen conditions; adaptation to serum-free, protein-free or low-protein culture medium; adaptation to mechanical stress or others.

In one aspect of the invention, the low-oxygen conditions may comprise conditions of less than 3 mg/l of oxygen in the culture medium, less than 2.5 mg/l of oxygen in the culture medium, less than 2 mg/l of oxygen in the culture medium, or less than 1.5 mg/l of oxygen in the culture medium.

In one aspect of the invention, the high-oxygen conditions may comprise conditions of more than 7 mg/l of oxygen in the culture medium, more than 8 mg/l of oxygen in the culture medium, more than 9 mg/l of oxygen in the culture medium, or more than 10 mg/l of oxygen in the culture medium.

The momentary concentration of oxygen in the culture medium is determined by the equilibrium between oxygen consumption by the cells and its dissolution into the culture medium from the sparging and overhead gas, and wherein the maximum achievable oxygen concentration is determined by the solubility of oxygen in the culture medium at the given temperature and oxygen partial pressure in the sparging gas.

In one aspect of the invention, the ability to grow in the absence of at least one of L-proline or L-glutamine in the culture medium may comprise gradual adaptation to low content of L-proline or L-glutamine in the culture medium.

In one aspect of the invention, the aforementioned adaptations may be achieved through the cultivation of cells in an environment where they are under selection pressure to undergo said adaptation or otherwise selecting cells with a desirable phenotype from the variability resulting from random mutations.

The cells used in processes according to the described herein may be genetically modified in order to introduce a certain gain/loss of functions into primary cells which are unable or hardly doable with GM-free methods, for example cell lines adaptation. The genetic modification output may be a stable cell line with the desired characteristics, for example: capability of continuous homogenous growth, shortened G1 phase of cell cycle in their proliferation phase, cell cycle around 24 hours in general, less than 24 hours in the proliferation phase, no structural genomic changes during lifetime of population, minimal impact of the epigenetic changes, consistent expression profile of cells correlating with their cell type, keeping differentiation potential with ability of induced differentiation, reduced requirements for media composition in terms of need for signaling factors, reduced requirements of resources for culture media composition in terms of need for nutrition components (e.g. amino acids), maintaining their endogenous signalization, or any other desired and appropriate characteristics.

The properties of cell lines could vary depending on used aspects to achieve a specific desired function.

The main goal of GM of cells used in processes according to the invention is to improve their ability to be used to create food product, for example cultivated meat. Examples of those improved attributes may be immortalization, reduced telomeres shortening and their preservation, maintaining the ability to differentiate in every or any step of cultivation, suspension growth capabilities, preservation of the epigenetic profile, temporary or permanent loss of contact inhibition, temporary or permanent maintenance of cell divisions, enhanced nutrition metabolism (e.g. enhanced sugar metabolism, shortening of the cell cycle, switching off the methylation in general or at the specific genomic loci), ability to fuse with other cells, various independence on nutritional or signaling compounds, or any other appropriate attributes.

The process of improving cell attributes may be represented by the gain of a specific function where the effect of the specific function could be an addition or reduction of functions or traits. The process of gain of function may comprise thawing of the primary cells of the desired type from the primary cell bank and performing the desired GM.

The methods used for the cell modification may comprise permanent and/or transient GM. Introduction of new genomic and transcriptomic elements include for example: the introduction of new sequences as well as genome editing mediated via Clustered regularly interspaced short palindromic repeats (CRISPR) combined with Caspase 9 (Cas9), Zinc finger nucleases, transcription activator-like effector nucleases (TALEN), or other genome editing tools. Even the generation of single or few nucleotide indels or substitutions may be sufficient to achieve the desired GM.

To achieve permanent or transient GM, a nucleic acid (NA) sequence may be introduced into the cells and/or their genomes by various means. These means may comprise viral vectors based on adenoviruses, adeno-associated viruses, retro/lentiviruses, or vectors derived and built on the above-mentioned. Other non-viral means may comprise use of NA carriers such as cationic polymers or proteins, liposomes, non-cationic polymers, nanoparticles, etc.

Both permanent and transient GM may be achieved by introduction of NA consisting of one or more specific functional coding or noncoding elements, such as promoter, coding DNA sequence, selection marker, or reporter marker. The insertion of functional elements may alter the endogenous gene expression or drive the expression of the inserted DNA per se. The recombinant NA introduced into the target cells might be of cisgenic or transgenic origin (in this document we use single-letter abbreviations defining the species of the particular DNA element, for example, "bTERT" stands for bovine telomerase reverse transcriptase). The introduced recombinant NA of the cisgenic origin might code for the amino acid sequence identical to its native counterpart or might code for a specific allelic variant, modified native protein by addition of specific linkers, signaling peptides, or other functional elements. To further increase the expression levels of the recombinant NA, codon-optimized NA sequence might be used.

Stable GM may be mediated via the introduction of NA into the specific or random locus of the target genome. The targeted locus might be a specific functional element regulating the expression of the gene of interest such as its promoter or DNA sequences transcribed into the untranslated region (UTR). Another specific targeted locus might be the so-called genomic safe harbor, offering a long-term stable expression of the inserted DNA sequence, while not interfering with any endogenous coding or noncoding elements. According to the invention, the genomic safe harbors used in the process may be defined as orthologues of previously described genomic safe harbors based on sequence similarity or genomic positions, namely bROSA26, bovine Adeno-associated virus integration site 1 (bAAVS1), bovine C-C motif chemokine receptor 5 (bCCR5), bovine Hipp11 locus (bH11), bovine Glyceraldehyde-3-phosphate dehydrogenase (bGAPDH), bovine Engorgement factor aplha (bEFalpha), bovine myosine heavy chain (bMYH9).

In one aspect of the invention, the introns or other non-coding parts of specific genes may be used as genomic safe harbors. These genes may be ubiquitously expressed across the cell types of different tissues and may have at least one long (>10,000 bp) span of noncoding DNA with no gene or chromatin regulatory function. The insertion itself (of even large approximately 10,000 bp long DNA fragments) into these loci does not directly affect the expression of any endogenous genes.

In one aspect of the invention, one such genomic safe harbor called PGrandom, located within the bovine gene Phosphodiesterase 4D (bPDE4D) on chromosome 20, specifically the interval from Ch20:19513000 to Ch20:19553000 may be used. This also applies to orthologous sequences of PGrandom in other species, while excluding the known coding and regulatory DNA elements. The area of the safe harbor according to the invention in the bPDE4D gene located on chromosome 20 may be in the range of 100,000 bp in both directions from the position Ch20:19533000, or in the range of 50,000 bp, or in the range of 25,000 bp, or in the range of 20,000 bp, or in the range of 10,000 bp, or in the range of 5,000 bp in both directions from the position Ch20:19533000. The bovine PGrandom (bPGrandom), similarly to other genomic safe harbors, may serve for knock-ins of any coding or regulatory DNA elements and may also be used for multiple tandem insertions.

The insertion cassettes may comprise one or more of the following exemplary genes: TERT, Cyklin-dependent kinase 4 (CDK4), E2F, Transferrin receptor (TFRC), Transforming growth factor receptor beta 1 (TGFBR1), TGFBR2, FGF-2 FGF-5, FGF-1, FGF-8, Insulin (INS), Protein kinase B (PKB) or its fusion version Myristoylation signal-attached Akt (myr-Akt), Myoblast determination protein (MyoD), Pair box protein 7 (Pax7), Sterol regulatory element binding protein (SREBP), Peroxisome proliferator-activated receptor gamma (PPARy), Solute carrier family 40 member 1 (SLC40A1), sodium leak channel (NALCN), Cluster of differentiation 2 (CD2), Focal adhesion kinase (FAK), Myogenin (MyoG), Myostatin (MSTN), Myogenic factor 5 (Myf5), or any other appropriate gene.

Precise regulation of expression levels of target genes of a particular GM is an inevitable step of a successful GM and a crucial part of the present invention. In order to fine-tune the expression levels and to decrease the risk of silencing the expression of the target gene in the modified cells, the species-specific promoters of housekeeping genes may be used. For cells of bovine origin, such examples may include the promoter of glyceraldehyde-3-phosphate dehydrogenase (bGAPDH), the promoter of eukaryotic translation Elongation factor 1 α (bEF1a; SEQ ID NO: 6), or the promoter of Phosphoglycerate kinase 1 (bPGK1; SEQ ID NO: 5), or any other appropriate promoter.

The inducible promoter system may be used in the genetic modification processes according to the invention. To control the expression of desired target genes used in gain of function genetic modification, inducible promoter systems may be used. Expression of accompanied target genes in an inducible promoter-target gene complex may be controlled in terms of switching on and switching off the target gene expression. Ongoing expression might be dependent on a continuous signal delivery or, alternatively, it could be stopped by signal delivery. Small interacting molecules of protein, saccharide, nucleic acid and/or other various compounds in the culture medium may serve as signal. Examples of those signaling compounds might be, for example, rapamycin, abscisic acid, auxin or auxin derivatives or auxin-like analogues, various antibiotics such as tetracycline or corticoid hormones or glucocorticoids or combination of the above mentioned compounds, or any other appropriate signaling compounds. Physical conditions optimized for a specific promoter may also be used as an induction trigger, starting or stopping expression of a target gene. Examples might be promoters whose ability to regulate expression of accompanied target genes is dependent on a specific temperature condition or exposure to a physical condition such as light stream of specific wavelength, exposure of a magnetic or electromagnetic field, ultrasonic application or other external stimulation.

The bovine Growth hormone polyadenylation signal (bGH-PolyA) is a specialized termination sequence for protein expression in eukaryotic cells. The bGH-polyA may be used in all expression constructs intended for knock-in mediated by, for instance, CRISPR/Cas9, Zinc finger nucleases, transcription activator-like effector nucleases (TALEN) or other genome editing tool. The signal may regulate termination of transcription, stabilize the transcripts and/or increase the expression.

One of the targets suitable for genetic modifications of cell lines according to the invention are endogenous retroviruses (ERVs). ERVs are gamma retroviruses found in the genome of all bovine strains or strains of other mammalian species and can be vertically transferred amongst the cells in in vitro culture. ERVs are known to affect cell behavior in general, and they may have a notable impact on the behavior of cell lines as well. There are more than 242 bovine ERVs identified in the bovine genome which may be used to create bovine ERV-inactivated cell lines for cultivated meat production. Although current evidence does not claim that ERV transcription and activity is crucial problem in the cultivated meat production, cells with reduced ERV transcription and activity and/or cells with modulated release of retroviral or retroviral like particles in the culture supernatant may be used to prevent potential harm in the future. This could happen if epigenetically silenced ERVs become temporarily or fully active and expressed. From a safety point of view, this mentioned gain of function may bring cell-based sources of nutrients with enhanced features that make the cultivated meat safer for human consumption in comparison with the conventional meat.

Inactivating the activity of known ERV loci in the genome of desired cell line is one aspect of the mentioned invention. ERV inactivation/gain of function may comprise independently or simultaneously targeting one or more ERV loci in the genome. According to the invention, the inactivation of ERVs through genome editing via CRISPR or other genome editing methods may be used. Inactivation of endogenous retroviruses (ERVs) may comprise deletion of ERVs sequences from genome or inactivation of their function by altering expression of genes ERV pol or ERV env or altering sequence to create inactive variant of ERVs. For example, use of Cas9 gRNA specific to the catalytic core of the ERV pol gene may be used. Other methods which may be used to modulate the transcriptional activity of ERVs in cell lines comprise the regulation of ERV env gene or other gene targets which regulate the expression of ERVs.

Another aspect of invention aimed at the enhanced food safety of cultivated meat is to use cell lines with gained resistance to the prion disease, known as Transmissible spongiform encephalopathies (TSE). Among cows, this disease is known as bovine spongiform encephalopathy, BSE. This disease is caused by a pathogenic, alternative form of a prion protein. In Europe, it is highly unlikely that the donor of the cells, the given cow, is infected a priori of the biopsy/slaughter. However, the cell culture can get infected via working with cattle-derived chemicals, such as FBS.

In one aspect of the invention, the genetic modification of genes responsible for prion multiplication via CRISPR or other genome editing methods may be used. For example, the knock-out of Cluster of differentiation 230 (CD230), also known as PRNP gene, or post-transcriptional modifications that modulate the translation of PRNP protein may be used for the desired gain of function. This will ensure that the food product is prion-free and safe for human consumption.

One of the inevitable steps toward the generation of the cell line used for food product, for example cultivated meat, production is the immortalization of the primary cells. This may be achieved via GM. The cell line may have spontaneously overcome the Hayflick limit or the subpopulation that immortalized spontaneously has been selected. The cell line may have undergone stress treatment which may have led to the selection of a subpopulation that became immortalized.

In one aspect of the invention, a stable long-term expression of bTERT might be used to prevent cells from gradually shortening telomeres concomitant with aging. The expression levels of bTERT may or may not match the levels of gene expression in the native bTERT-positive cells. This is an important modification usable for all cell types. The TERT gene may be truncated such that its stability and expression levels are improved.

In one aspect of the invention, the gene used for cell immortalization may be at least one of the bovine telomerase reverse transcriptase gene (bTERT), truncated rbTERT variant with deletion of the bases 1228-1287 characterized by coding sequence SEQ ID NO: 4 resulting in protein characterized by SEQ ID NO: 03 with deletion of amino acids 410-429, a coding sequence having at least 80%, at least 85%, at least 90%, 95%, or at least 99% sequence identity to SEQ ID NO: 4.

In this aspect of the invention, the product of rbTERT results in a truncated protein variant with the deletion of twenty amino acids (410-429) characterized by SEQ ID NO: 3, or a protein having at least 80%, or at least 85%, or at least 90%, or at least 95%, or at least 99% sequence identity to SEQ ID NO: 3.

In other aspects of the invention, the gene used for cell immortalization may be bTERT gene with at least 80%, at least 85%, at least 90%, at least 95%, or at least 99% sequence identity to SEQ ID NO: 2. In other aspects of the invention, the gene used for cell immortalization may be bTERT gene with the sequence of SEQ ID NO: 2.

In this aspect of the invention, the product of the bTERT may be a protein with at least 80%, at least 85%, at least 90%, at least 95%, or at least 99% sequence identity to SEQ ID NO: 1. In this aspect of the invention, the product of the bTERT may be a protein with the sequence of SEQ ID NO: 1.

The abovementioned TERT constructs may be introduced into the cells via both viral and non-viral means. The expression of the coding sequence may be driven by endogenous or by recombinant introduced promoter such as bGAPDH promoter, bEF1a promoter (SEQ ID NO: 6), or bPGK1 promoter (SEQ ID NO: 5). The genome editing may be done via CRISPR/Cas9, Zinc finger nucleases, transcription activator-like effector nucleases (TALEN) or another genome editing tool.

Introduction of full-length bovine telomerase gene sequence and/or introduction of full-length telomerase gene sequence from other mammals may be one of the approaches used to immortalize cells according to the invention. The introduction of a codon-optimized sequence of telomerase gene or a coding sequence or reduced coding sequence may be another method used to immortalize cells. These sequences of NA introduced into the genome result in the translation of bTERT or its allelic or species-specific allelic variation. The sequences may be inserted at random sites of the genome or safe harbors or may be in specific safe harbor PGrandom. Introduction of an alternative promoter, additional regulatory DNA element or modification of the native bTERT promoter may be performed to induce native TERT expression.

Alternatively, various modified sequences of bTERT may be used, including recombinant sequences fulfilling native bTERT protein function. Alternatively, different promoters may be used. Alternatively, different safe harbors may be used.

In one aspect of the invention GM of native bTERT promoter or respective orthologs in other species may be used. This GM may comprise indels or substitutions of the native TERT promoter.

In one aspect of the invention, the cell cultivation process may comprise the introduction of TERT gene sequence or modified TERT gene sequence into the safe harbor PGrandom located in gene bPDE4D on chromosome 20 in order to immortalize cells. The process may comprise introduction of full-length telomerase gene sequence, for example bovine full length telomerase gene sequence, or full-length telomerase gene sequence from other mammals. Introduction of allelic or species-specific allelic variation of TERT gene sequence, codon optimized telomerase gene sequence or coding sequence, or reduced coding sequence, may be used and introduced into the gene bPDE4D in order to immortalize cells. GM (indels, substitutions) of native TERT promoter may be used to induce native TERT expression. Examples of those genetic modifications may be introduction of transcription factors or regulation cis-elements. Any other appropriate variant or modification of TERT gene introduction may be used to immortalize cells. The safe harbor according to the invention may be PGrandom. Other target genes for immortalization may be, for example, Bcl-2, p53, p21, SV40LT, or any other appropriate target genes.

In one aspect of the invention, introduction of a modification comprising an insertion cassette coding one of the existing splicing variants of a target gene and, therefore, changing the balance between the transcribed splicing variants may be performed. Example of this target gene may be Bcl-2.

In one aspect of the invention, the immortalized cells may be kept in a production cell bank and the immortalization cassette may be removed at the point of inoculation to the cultivation device, for example formed by a production bioreactor. This would serve the purpose of eliminating risks associated with the new genetic structures in the genome, as the cells would be genetically identical to their wild-type counterparts found in the animal. Those cells can survive for many passages after TERT expression ceases, as the cultivation with the overexpressed TERT having elongated their telomeres substantially.

A genetic modification aimed to reduce the growth factor requirements in combination with the immortalization may be used in the processes according to the invention. The method may provide reduced or null demands for the presence of growth factors in the culture media. In bovine cell lines, bovine target gene coding sequences may be used. In other metazoan species, analogous target gene coding sequences from respective species may be used. Therefore, only sequences which are natively present in the genome of respective species are used. Resulting modification may be considered as cisgenic, where only transcription context is modulated or allelic version is introduced but no transgenic sequence is introduced in the genome. In another aspect of the invention, transgenic sequences (which are occurring in other species than in the species used for cell line cultivation) or artificial sequences (which do not have a described analogue in nature) may be used.

According to the invention, modification of iron metabolism in cells may be used in order to make them more sensitive to the transferrin present in the culture medium. Transferrin receptor (gene TFRC) overexpression, a consequent transferrin reduction, and changes in iron metabolism which lead to reduced iron export from cells may significantly lower the requirement for transferrin in culture media. In bovine cell lines, bovine target gene coding sequences may be used. In other metazoan species, respective orthologous coding sequences may be used.

In the case of *Bos taurus*, an example of such GM may comprise knock-in of a bEF1a promoter (or any other appropriate promoter) with the coding sequence of bovine TFRC into the genomic safe harbor PGrandom or any other safe harbor. The knock-in may be mediated by CRISPR/Cas9, Zinc finger nucleases, transcription activator-like effector nucleases (TALEN) or other genome editing tool.

In other aspect of the invention, the gene used for overexpression of transferrin receptor may be TFRC receptor gene characterized by SEQ ID NO: 7, or the TFRC receptor gene having a sequence identity of at least 80%, at least 85%, at least 90%, at least 95%, or at least 99% identical to SEQ ID NO: 7.

In other aspect of the invention, the protein product of a gene used for overexpression of transferrin receptor may be TFRC receptor protein characterized by SEQ ID NO: 12, or the TFRC receptor gene having a sequence identity of at least 80%, at least 85%, at least 90%, at least 95%, or at least 99% to SEQ ID NO: 12.

In other aspect of the invention, the regulation of iron metabolism (i.e. modification of iron forms and their export from the cells) may be used. One of the target genes involved in this regulation may be SLC40A1, encoding the ferroportin protein. The activity, expression of a gene and/or synthesis of a functional protein form may be affected. An SLC40A1 knockout resulting in a reduced requirement for transferrin may be used. Alternatively, hepcidin may be used for ferroportin activity inhibition. Expression and/or induced expression of hepcidin may be introduced into the cells.

In one aspect of the invention, the requirement of TGF-beta signaling needed from culture media may be substituted via overexpression of TGF-beta receptors in cells. In bovine cell lines, a bovine target gene coding sequences may be used. In other metazoan species, analogous target gene coding sequences may be used. Introduction of an insertion cassette expressing TGF-beta receptor type-1 (TGFBR1 gene) and/or type-2 (TGFBR2 gene) may be used. These targets may be overexpressed and/or constitutively expressed. The coding sequence of one or more of the genes in the cassette may be modified in a way that codes for phospho-mimetic amino acids that are critical for activation of the downstream signaling pathway. This would result in an active signaling pathway irrespective of ligand presence in the culture media. The insertion cassette may also contain appropriate promoters that control the precise level of target gene expression and may also contain other regulatory elements. An example of those promoters may be PGK. The method of introducing insertion cassettes may be CRISPR/Cas9, Zinc finger nucleases, transcription activator-like effector nucleases (TALEN) or other genome editing tools and may be targeted into the safe harbor areas of the genome of the respective species. Examples of those safe harbor may be ROSA26 or PGrandom site.

In one aspect of the invention, miR-140-5p downregulation aimed towards increased TGF-beta ligand family signaling may be used in the cell cultivation processes.

In other aspects of the invention, the gene used for overexpression of TGF receptor may be TGFBR1 gene characterized by SEQ ID NO: 13 or a TGF-beta1 receptor gene having a sequence identity at least 80%, at least 85%, at least 90%, at least 95%, or at least 99% identical to SEQ ID NO: 13.

In other aspect of the invention, the protein product of the gene used for overexpression of TGFBR1 is characterized by SEQ ID NO: 14 or a sequence having at least 80%, at least 85%, at least 90%, at least 95%, or at least 99% sequence identity to SEQ ID NO: 14.

In one aspect of the invention, the requirements of exogenous insulin signaling in the media may be reduced and substituted via endogenous overexpression of insulin in cells. In bovine cell lines, a bovine target gene coding sequence may be used. In other metazoan species, analogous target gene coding sequences may be used. Introduction of insertion cassettes expressing insulin and/or a constitutively active Akt kinase variant developed by fusion with the myr domain may be used. These two targets may be overexpressed and/or constitutively expressed. Insertion cassettes may contain appropriate promoters which control the precise level of target gene expression and may also contain other regulatory elements. Example of those promoters may be PGK. Methods of introducing insertion cassette may, for example, use CRISPR/Cas9, Zinc finger nucleases, transcription activator-like effector nucleases (TALEN) or other genome editing tools and may be targeted into the safe harbor areas of the genome of the respective species. Examples of the appropriate safe harbors may be for example ROSA26 or PGrandom site.

In other aspects of the invention, the gene used for overexpression of insulin may be the INS gene characterized by SEQ ID NO: 8 or genes having nucleotide sequences having at least 80%, at least 85%, at least 90%, at least 95%, or at least 99% sequence identity to SEQ ID NO: 8.

In other aspect of the invention, the protein product of a gene used for overexpression of insulin may be the protein characterized by SEQ ID NO: 9 or proteins having an amino acid sequence at least 80%, at least 85%, at least 90%, at least 95%, or at least 99% sequence identity to SEQ ID NO: 9.

In one aspect of the invention, the requirement of external FGF signaling needed from culture media may be substituted via overexpression of FGF ligand in cells. In bovine cell lines, bovine target gene coding sequences may be used. In other metazoan species, analogous target gene coding sequences may be used. Introduction of insertion cassette for at least one of FGF-2, FGF-5, FGF-1 or FGF-8 as target gene of desired gain of function may be used. These targets may be overexpressed and/or constitutively expressed. Insertion cassettes may contain appropriate promoters which control the precise level of target gene expression and may also contain other regulatory elements. An example of such a promoter may be the PGK1 promoter. Method of introduction of insertion cassette may, for example, use CRISPR/Cas9, Zinc finger nucleases, transcription activator-like effector nucleases (TALEN) or other appropriate genome editing tool. The introduction of insertion cassette may be targeted into the safe harbor areas of the genome of the respective species. Examples of the appropriate safe harbors may be ROSA26 or PGrandom site.

In other aspect of the invention, the gene used for overexpression of an FGF ligand may be an FGF2 gene characterized by SEQ ID NO: 10 or nucleic acid sequences having at least 80%, at least 85%, at least 90%, at least 95%, or at least 99% sequence identity to SEQ ID NO: 10.

In other aspect of the invention, the protein product of the gene used for overexpression of FGF2 may be characterized by SEQ ID NO: 11 or amino acid sequences having at least 80%, at least 85%, at least 90%, at least 95%, or at least 99% sequence identity to SEQ ID NO: 11.

As mentioned above, the cultivated cells may be for example bovine cells, or any other appropriate cells. In bovine cell lines, bovine HRas gene coding sequences may be used. In other metazoan species, analogous target gene coding sequences may be used.

Modification of endogenous expression of the HRas gene as well as insertion of a construct containing the HRas gene sequence or sequence with sequence similarity to the HRas gene sequence may be used. The HRas gene encodes a protein that plays a crucial role in the regulation of cell growth, differentiation, and apoptosis. The sequence of the modified HRas protein may have at least 80%, or at least 85%, or at least 90%, or at least 95%, or at least 97% or at least 98%, or at least 99% identity to the naturally occurring bovine HRas protein.

The bovine HRas protein is characterized by sequence SEQ ID NO: 15. The bovine nucleotide sequence encoding the HRas protein is characterized by sequence SEQ ID NO: 17.

In one aspect of the invention, modification of endogenous HRas may be defined as insertion, deletion or substitution of the amino acid at position 61 of the amino acid sequence of SEQ ID NO: 15. The resulting mutation may be for example, but without limitation, a Q61L mutation characterized by substitution of glutamine at position 61 of the HRas amino acid sequence by leucine (SEQ ID NO: 16). Any other appropriate amino acid may be used for substitution of amino acid at position 61.

Alternatively, this modified version of HRas may be overexpressed by introducing it into the genome in a cassette with a strong promoter or by introducing a plasmid with said cassette into the cells, wherein the plasmid gets diluted over time.

In one aspect of the invention, the modified nucleotide sequence of the HRas gene characterized by SEQ ID NO: 18, which encodes the HRas protein with Q61L substitution characterized by sequence SEQ ID NO: 16, may be used for reducing the requirement of the presence of at least one exogenous signaling compound in the culture media.

In one aspect of the invention, a protein characterized by sequence SEQ ID NO: 16 may be used in a method of reducing the requirement of the presence of exogenous signaling compounds in the culture media, the method comprising genetic modification, wherein the endogenous expression of the HRas gene is modified. The signaling compound may be FGF-2 growth factor, or any other appropriate signaling compound.

The cells with above mentioned modification of the HRas gene may be used in the cell cultivation processes for preparing food products for human or animal consumption. The food product may be for example cultured meat.

In the cell cultivation processes according to the invention, antimicrobial compounds (antimicrobials), for example, antimicrobial peptides (AMPs), or any other appropriate compounds with antimicrobial activity, may be used to provide protection against microbial contamination. Described herein provides a novel approach of controlling microbial contamination in cultivation systems by incorporating antimicrobials into the culture media. The cultivation system may comprise at least one bioreactor.

Also provided are methods of reducing requirements of the antimicrobial compounds in the culture media by altering their endogenous expression, as well as methods of using antimicrobial compounds, for example antimicrobial peptides, in the food products.

AMPs are a class of naturally occurring, small, cationic peptides that exhibit a broad-spectrum of antimicrobial activity against a wide range of microorganisms, including bacteria, fungi, and viruses.

Antimicrobial compounds that, may be used according to the invention, may include, for example, allicin, nisin, surfactin, defensins (e.g. α-defensins, β-defensins, for example HD5, HBD3, or BBD123 defensins), gingerol, lysozyme, kurkumin, berberin, thymol, eugenol, cathelicidins and histidines, bioactive peptides derived from abalone viscera (*Haliotis fulgens* and *Haliotis corrugata*), lactoferrin, phospholipases, C-type lectins, Host defense-related ribonucleases, or any other appropriate antimicrobial compound.

In one aspect of the invention, the culture medium does not comprise a compound selected from a group of antibiotics, such as penicillin, penicillin V, penicillin G, streptomycin, penicillin-streptomycin (Pen-Strep), ampicillin, gentamicin, tetracycline, or the salts thereof, or any other antibiotic.

At least one selected AMP or any other appropriate antimicrobial compound may be incorporated into the cultivation media used in the cell cultivation device. The cultivation device may comprise at least one bioreactor. The incorporation may occur either during the media preparation or may be added directly into the cultivation device during the cultivation process. The concentration of antimicrobials in the culture media may be adjusted to ensure effective antimicrobial activity while maintaining the growth and productivity of the desired cells. The antimicrobials may be added to the culture media continuously or intermittently at least at one specific time point during the cultivation process. The concentration of antimicrobial compound in the culture medium may be in a range of 0.01 µM to 100 µM, or in the range of 0.1 µM to 50 µM, or in the range of 0.2 µM to 25 µM, or in the range of 0.5 µM to 10 µM.

In one aspect of the invention, the antimicrobial compound may be an antimicrobial peptide characterized by an amino acid sequence selected from SEQ ID NO: 19 to SEQ ID NO: 32.

In another aspect of the invention, the antimicrobial compound may be an antimicrobial peptide with at least 80%, or at least 85%, or at least 90%, or at least 95%, or at least 98%, or at least 99% sequence identity to a sequence selected from SEQ ID NO: 19 to SEQ ID NO: 32.

In one aspect of the invention, the requirement of compounds with antimicrobial activities, such as antibiotics or antimicrobial peptides (AMPs), in the culture media may be reduced or substituted by altering the endogenous expression of antimicrobial compounds in cells.

The endogenous expression of AMPs may be regulated by:
    expression of genes encoding AMPs natively present in the genome in their native loci by insertion of a cassette containing a promoter sequence and/or transcription enhancer sequence and insertion of this cassette into the genome at a location directly preceding the site of native loci of these genes and/or
    insertion of a cassette containing an element for transcriptional regulation in the genome selected from transcription enhancers or promoters followed by one or more gene sequences encoding the AMPs.

In bovine cells, endogenous expression of AMPs may be regulated by expression of bovine genes encoding AMPs. In other metazoan species analogous species-dependent sequences of target genes encoding the AMPs may be used. Introduction of an insertion cassette expressing AMPs may be used. These targets may be overexpressed and/or constitutively expressed. The level of expression may be regulated using a promoter, an enhancer, the location of the insertion site, and/or the number of copies of target genes present in the genome. For example, the sequence for target gene (AMPs) may be present in the insertion cassette in multiple copies with or without a linker or transcription co-expression enhancer. An example of this transcription enhancer may be the IRES site. Another example may be the presence of one or more copies of the target gene in multiple sites in the genome. Insertion cassettes may comprise appropriate promoters that control the level of target gene expression and/or any other appropriate regulation elements. The promoters may have high relative expression potential for the gene following the promoter. Examples of promoters may include PGK, EF1a, CMV (e.g. CMV EF alpha), or any other appropriate promoters. Methods used for incorporation of the insertion cassette into the genome may include CRISPR/Cas9, Zinc finger nucleases, transcription activator-like effector nucleases (TALEN), or any other appropriate genome editing tool, and may be targeted into the safe harbor areas of the genome of the respective species. Examples of appropriate safe harbor may include ROSA26 or PGrandom site, or any other appropriate safe harbor.

The gene used for overexpression of AMPs according to the invention may be, for example, HBD3, HD5, DEFB1, DEFB2, DEFB3, DEFB4, DEFB5, DEFB6, DEFB7, DEFB8, DEFB9, DFB10, DFB11, or DFB12, or any other appropriate gene.

In another aspect of the invention, the protein product of a gene used for overexpression of antimicrobial peptide may comprise one of SEQ ID NO: 19 to SEQ ID NO: 32.

In another aspect of the invention, the protein product of a gene used for overexpression of antimicrobial peptide may have at least 80%, or at least 85%, or at least 90%, or at least 95%, or at least 98%, or at least 99% sequence identity to one of SEQ ID NO: 19 to SEQ ID NO: 32.

In one aspect of the invention, two or more gene sequences encoding antimicrobial peptides may be inserted sequentially into the genome to enhance the yield and extracellular secretion of AMPS by endogenous expression. The inserted gene sequences may be combined with a promoter and/or a transcription co-expression enhancer, such as, for example, the IRES site. In another aspect of the invention, the number of inserted gene sequences encoding antimicrobial peptides may be in a range from one to five. This aspect, which combines serial, repetitive insertion of target genes into the genome may be called "multiple copies insertion cassette". Multiple copies insertion cassettes may contain copies of the target gene encoding antimicrobials, for example, antimicrobial peptides characterized by sequences SEQ ID NO: 19 to SEQ ID NO: 32, in the range from one to five copies. The multiple copies insertion cassettes may contain multiple copies of the same gene or their combinations. The multiple copies insertion cassette may be inserted into the genome at random sites of the genome or safe harbors or may be in specific safe harbors (e.g. ROSA26 or PG random).

A cell line may be transformed with various numbers of multiple copies insertion cassettes in the range from one to fifty to enhance artificial endogenous AMPs production. The insertion site may or may not be the same in the genome. For example, each multiple copies insertion cassette integrated into the independent insertion site in the genome may contain as a target gene in the cassette the copies of the same gene or various genes encoding proteins, e.g. proteins characterized by sequences SEQ ID NO: 19 to SEQ ID NO: 32, or any other appropriate AMPs.

In one aspect of the invention, the antimicrobial compounds, for example antimicrobial peptides, according to the description above may be used in the final food product. The food product may be in the form of pet food or a product for human consumption, with the desired shape and sensory properties. The food product may be cultured meat. The final food product may comprise one or more cultivated cell types or one or more cultivated cell types mixed with other non-cellular compounds. As used herein, the term "non-cellular compound" may be an edible compound and may bring additional sensory and structural properties as well as additional nutritional value. The concentration of antimicrobial compounds, for example antimicrobial peptides, in the food product may be in a range of 0.01 mg/kg to 250 mg/kg, or in the range of 0.1 mg/kg to 200 mg/kg, or in the range of 1 mg/kg to 100 mg/kg, or in the range of 10 mg/kg to 50 mg/kg of the food product.

The antimicrobial compounds, for example antimicrobial peptides, according to the invention may be used in cosmetic products.

The culture medium for cell cultivation according to the invention may comprise:
  a source of amino acids;
  at least one additional component selected from vitamins, sugars, minerals, organic amines, or shear protectants; and
  at least one antimicrobial compound, wherein the antimicrobial compound is not a compound selected from a group of antibiotics.

The culture medium for cell cultivation according to the invention may comprise a protein hydrolysate as a source of amino acids. The total input of amino acids from the hydrolysate, including amino acids in the form of short peptides or suitable bioavailable derivatives, may be at least 75% by weight of the total input of all amino acids in the culture medium.

The culture medium for cell cultivation according to the invention may comprise an antimicrobial compound selected from a group of defensins. The antimicrobial compound may be a compound selected from compounds characterized by at least one sequence selected from sequences SEQ ID NO: 19 to SEQ ID NO: 32, or a compound having at least 80%, or at least 85%, or at least 90%, or at least 95%, or at least 98%, or at least 99% sequence identity with at least one sequence selected from sequences SEQ ID NO: 19 to SEQ ID NO: 32.

The method of cell cultivation according to the invention may comprise a step of altering the endogenous expression of antimicrobial compounds in cells. The altering the endogenous expression of antimicrobial compounds in cells may be performed by
  expression of genes encoding AMPs natively present in the genome in their native loci by insertion of a cassette containing a promoter sequence and/or transcription enhancer sequence and insertion of this cassette into the genome at a location directly preceding the site of native loci of these genes; and/or
  insertion of a cassette containing an element for transcriptional regulation in the genome selected from the group of transcription enhancers or promoters followed by one or more gene sequences encoding the AMPs.

The food product for human or animal consumption according to the invention may comprise cultivated cells and at least one antimicrobial compound. The antimicrobial compound may be a defensin. The antimicrobial compound may be a compound selected from compounds characterized by at least one of SEQ ID NO: 19 to SEQ ID NO: 32, or a compound having at least 80%, or at least 85%, or at least 90%, or at least 95%, or at least 98%, or at least 99% sequence identity with at least one sequence selected from sequences SEQ ID NO: 19 to SEQ ID NO: 32.

In the proliferation phase of cell culture, the duration of cell cycle is one of the parameters which affects final yield of a cell biomass. It's shortening towards the homogenic proliferation and uniform production of cell biomass for further use for food products may be one of the aspects of the invention. The cell cycle shortening may be achieved by shortening each cell cycle phase duration. For example the duration of S phase may be reduced by overexpression of EF2 factor. Proper timing of cell cycle phases transition may be driven by altering expression of cyclins and/or cyclin dependent kinases. As cyclin or cyclin dependent kinase may be used for example cyclin D or CDK4, or any other appropriate cyclin or cyclin dependent kinase. Altering expression of Cyclin D may accelerate the G1 phase, allowing faster progression to the S phase (DNA synthesis). General start of rapid proliferation of cells may be enhanced by leading cells to enter mitosis, this may be driven by starting the M phase for example via altering expression of cyclin A and CDK1. The above mentioned targets may be overexpressed, constitutively expressed, or a combination thereof may be used. Insertion cassettes may contain appropriate promoters which control the precise level of target gene expression and may also contain other regulatory elements. An example of the promoter may be PGK. Methods of introducing the insertion cassette may, for example, use CRISPR/Cas9, Zinc finger nucleases, transcription activator-like effector nucleases (TALEN) or other genome editing tool and may be targeted into the safe harbor areas of the genome of respective species. Examples of the appropriate safe harbors may be ROSA26 or PGrandom site.

For example, CDK4 overexpression provided by trans-duction of cell lines with a lentiviral vector containing CDK4 may be used, resulting in cells with maintained constitutive expression of CDK4 gene and shorter popu-lation doubling time. The expression of CDK4 may not be lowered and terminated during the lifetime of daughter cells. Alternatively, a different promoter, safe harbor and/or modi-fication of native CDK4 promoter locus may be used.

An example of a gain of function modification that the cells may acquire via genome editing according to the invention is the ability to grow in a suspension culture. Growth in a suspension culture may be defined as growth without a requirement for any attachment to the solid surface of the cultivation vessel or flask or bioreactor, in effect floating in the culture medium. The suspension growth may be supported with other factors such as dynamic cultivation conditions (e.g. stirring, mixing or circulation of the culti-vation environment, or other physical parameters). The ability of cells to grow under such conditions may be achieved via genetic modifications comprising knockout or knockdown of specific genes or insertion of nucleotide sequences into the genome leading to the same effect. Knock-out or knock-down of a gene may be performed permanently via editing the gene region in the genome or temporarily via antisense oligonucleotide-facilitated silenc-ing. The ability of cells to grow in a suspension culture may be achieved by altering expression bNACLN gene or alter-ing expression of CD2 gene and/or altering expression of FAK gene and/or expression of their fusion variant CD2-FAK.

In one aspect of the invention, endogenous differentiation factors determining the change of cell fate may be used. The differentiation driven by these factors may turn the various cell types into the desired cell types. Examples of the driven differentiation may be differentiation into a myoblast or adipocyte or any other suitable differentiation. Examples of myogenic differentiation factors may be MyoD, MyoG, Myf5, Pax7, MSTN, any other appropriate myogenic dif-ferentiation factors, or a combination thereof. Examples of adipogenic differentiation factors may be SRBEP, PPARy, any other appropriate adipogenic differentiation factors, or a combination thereof. In bovine cell lines, a bovine target gene coding sequence may be used. In other metazoan species, analogous target gene coding sequences may be used. These targets may be overexpressed, constitutively expressed, or a combination thereof. Insertion cassettes may contain appropriate promoters which control the precise level of target gene expression and may also contain other regulatory elements. An example of the promoter may be a PGK; any other appropriate promoter may be used. Methods of introducing insertion cassettes may use, for example, CRISPR/Cas9, Zinc finger nucleases, transcription activa-tor-like effector nucleases (TALEN), or other genome edit-ing tools and may be targeted into the safe harbor areas of the genome of respective species. Examples of the safe harbors may be ROSA26 or PGrandom site; any other appropriate safe harbor may be used.

In one aspect of the invention, the introduction of inser-tion cassette containing myostatin gene or its allelic or splicing variant may be used to enhance the myogenic differentiation effect. This gene may be regulated with a respective promoter which could ensure its constitutive expression or may be driven by an inducible promoter system to ensure its controlled expression.

Another method of cell line gain of function according to the invention may be the use of a marker system for successfully modified cells, followed with its consecutive targeted deletion from the genome of host cells. Marker systems may comprise genes commonly used as markers in cells. Examples of those genes and respective proteins may be genes encoding Green fluorescent protein (GFP), proteins from mFruits family of monomeric red fluorescent proteins (mRFPs) (e.g. mCherry), yellow fluorescent protein (YFP), or other genes for fluorescent proteins. Another example may be genes which provide the target cells resistance to antibiotics or other treatments. Examples of those genes may be the puromycin N-acetyltransferase (PAC) gene which facilitates resistance to the puromycin, the beta lactamase (BLA) gene which facilitates resistance to the ampicillin antibiotic, or any other gene with the antibiotic resistance gain of function.

After transformation with genes of interest, the cells may be further cultivated to a cell density allowing for selection of successfully transformed individual cells. Selected popu-lations may then be additionally modified. The other modi-fication may result in cells free of accessory or accompa-nying sequences introduced in the genome of the target cell line, which are only residues of the gene transfer technology and do not bring any direct effect to the cell.

The selection may be performed via a marker gene, for example fluorescent protein, associated with the target gene. Cells may be screened for the presence of marker genes and through fluorescence activated cell sorting (FACS) sorted accordingly to select for the desired subpopulation. The selection may be performed with marker genes of antibiotic resistance associated with the target gene; cells may be selected via antibiotic treatment. Only successfully trans-formed cells survive antibiotic treatment. Another method may comprise the excision of all marker and selection genes used in gene transfer technology. The Cre-lox system may be used to excise target sequences from the genome.

Another method described herein may comprise single cell sorting and clonal population selection. Cells may be multiplicated after target gene transformation, selection of successfully transformed cells and/or postprocessing of residual sequences. Single cells may be sorted into separate vessels, where every single cell may start to establish a uniform and homogenous cell population. Cells may be then passed to further cultivation where the desired gain of function is tested at the level of phenotype and/or genotype. The result is a population with a new cell type.

Optionally, repetition of above-mentioned points for addi-tional gain of function is possible.

The cell stocks may be frozen to obtain a production cell bank.

The cells may be modified in order to improve their cultivation properties and properties affecting the final food product. The cells may be modified by at least one of the following methods: cell immortalization provided by affect-ing the TERT gene or modified TERT gene; cell immortal-ization provided by other target genes for immortalization, such as Bcl-2, p53, p21, SV40LT, or any other appropriate target genes; genetic modification aimed to reduce the growth factor requirements in culture environment; genetic modification aimed to reduce requirements of FGF, TGF, transferrin or insulin in culture environment, wherein the genetic modification aimed to reduce the growth factor requirements may be provided by modification of the level of expression of at least one of genes selected from genes encoding CDK4, Transferrin receptor, TGF receptor, FGF-2, FGF-5, FGF-2, FGF-1, or FGF-8, Insulin, FGF, myr-Akt, Myostatin, MyoD, Pax7, SREBP, or PPARy, transferrin receptor (gene TFRC) overexpression and a consequent transferrin reduction, genes involved in a regulation of iron metabolism, TGF-beta receptors overexpression (TGF-beta1 reduction), insulin overexpression (insulin reduction), FGF-2 overexpression (FGF-2 reduction); cell cycle shortening; or affecting suspension growth, or any other appropriate method.

The cells may be modified or adapted to grow in protein free culture media, where the need of signaling protein may be substituted with their aptamer analogue. The aptamer ligand may be at least one of FGF, TGF, transferrin, or insulin analogue.

In one aspect of the invention the cells may be modified by at least two of the following methods:
  cell immortalization provided by affecting the TERT gene or modified TERT gene;
  cell immortalization provided by other target genes for immortalization, such as Bcl-2, p53, p21, SV40LT, or any other appropriate target genes for immortalization;
  genetic modification aimed to reduce the growth factor requirements in culture environment, such as genetic modification aimed to reduce requirements of FGF, TGF, transferrin or insulin in culture environment, wherein the genetic modification aimed to reduce the growth factor requirements may be provided by modification of the level of expression of at least one of genes selected from genes encoding CDK4, Transferrin receptor, TGF receptor, FGF-2, FGF-5, FGF-2, FGF-1, or FGF-8, Insulin, FGF, myr-Akt, Myostatin, MyoD, Pax7, SREBP, or PPARy, transferrin receptor (gene TFRC) overexpression and a consequent transferrin reduction, genes involved in a regulation of iron metabolism, TGF-beta receptors overexpression (TGF-beta1 reduction), insulin overexpression (insulin reduction), FGF-2 overexpression (FGF-2 reduction);
  cell cycle shortening;
  or affecting suspension growth.

In one aspect of the invention the cells may be modified by at least three of the following methods:
  cell immortalization provided by affecting the TERT gene or modified TERT gene;
  cell immortalization provided by other target genes for immortalization, such as Bcl-2, p53, p21, SV40LT, or any other appropriate target genes for immortalization;
  genetic modification aimed to reduce the growth factor requirements in culture environment, such as genetic modification aimed to reduce requirements of FGF, TGF, transferrin or insulin in culture environment, wherein the genetic modification aimed to reduce the growth factor requirements may be provided by modification of the level of expression of at least one of genes selected from CDK4, Transferrin receptor, TGF receptor, FGF-2, FGF-5, FGF-2, FGF-1, or FGF-8, Insulin, FGF, myr-Akt, Myostatin, MyoD, Pax7, SREBP, or PPARy, transferrin receptor (gene TFRC) overexpression and a consequent transferrin reduction, genes involved in a regulation of iron metabolism, TGF-beta receptors overexpression (TGF-beta1 reduction), insulin overexpression (insulin reduction), FGF-2 overexpression (FGF-2 reduction);
  cell cycle shortening;
  or affecting suspension growth.

In one aspect of the invention the cells may be modified by at least four of the following methods:
  cell immortalization provided by affecting the TERT gene or modified TERT gene;

cell immortalization provided by other target genes for immortalization, such as Bcl-2, p53, p21, SV40LT, or any other appropriate target genes for immortalization;
genetic modification aimed to reduce the growth factor requirements in culture environment, such as genetic modification aimed to reduce requirements of FGF, TGF, transferrin or insulin in culture environment, wherein the genetic modification aimed to reduce the growth factor requirements may be provided by modification of the level of expression of at least one of genes selected from CDK4, Transferrin receptor, TGF receptor, FGF-2, FGF-5, FGF-2, FGF-1, or FGF-8, Insulin, FGF, myr-Akt, Myostatin, MyoD, Pax7, SREBP, or PPARy, transferrin receptor (gene TFRC) overexpression and a consequent transferrin reduction, genes involved in a regulation of iron metabolism, TGF-beta receptors overexpression (TGF-beta1 reduction), insulin overexpression (insulin reduction), FGF-2 overexpression (FGF-2 reduction);
  cell cycle shortening;
  or affecting suspension growth.

In one aspect of the invention the cells may be modified by the following five methods:
  cell immortalization provided by affecting the TERT gene or modified TERT gene;
  cell immortalization provided by other target genes for immortalization, such as Bcl-2, p53, p21, SV40LT, or any other appropriate target genes for immortalization;
  genetic modification aimed to reduce the growth factor requirements in culture environment, such as genetic modification aimed to reduce requirements of FGF, TGF, transferrin or insulin in culture environment, wherein the genetic modification aimed to reduce the growth factor requirements may be provided by modification of the level of expression of at least one of genes selected from CDK4, Transferrin receptor, TGF receptor, FGF-2, FGF-5, FGF-2, FGF-1, or FGF-8, Insulin, FGF, myr-Akt, Myostatin, MyoD, Pax7, SREBP, or PPARy, transferrin receptor (gene TFRC) overexpression and a consequent transferrin reduction, genes involved in a regulation of iron metabolism, TGF-beta receptors overexpression (TGF-beta1 reduction), insulin overexpression (insulin reduction), FGF-2 overexpression (FGF-2 reduction);
  cell cycle shortening;
  and affecting suspension growth.

In one aspect of the invention the method of cell cultivation may comprise at least one method of:
  modification of the cellular TERT gene level expression;
  modification aimed to reduce the growth factor requirements;
  cell cultivation in protein free culture medium;
  or cell cultivation in culture medium comprising at least one aptamer analogue of signaling protein, wherein aptamer analogue of signaling protein may be at least one of FGF, TGF, transferrin or insulin, wherein modification aimed to reduce the growth factor requirements may comprise genetic modification aimed to reduce requirements of FGF, TGF, transferrin or insulin in culture environment.

In one aspect of the invention the method of cell cultivation may comprise at least two methods of:
  modification of the cellular TERT gene level expression;
  modification aimed to reduce the growth factor requirements;
  cell cultivation in protein free culture medium;

or cell cultivation in culture medium comprising at least one aptamer analogue of signaling protein, wherein aptamer analogue of signaling protein may be at least one of FGF, TGF, transferrin or insulin, wherein modification aimed to reduce the growth factor requirements may comprise genetic modification aimed to reduce requirements of FGF, TGF, transferrin or insulin in culture environment.

In one aspect of the invention the method of cell cultivation may comprise at least three methods of:

modification of the cellular TERT gene level expression;

modification aimed to reduce the growth factor requirements;

cell cultivation in protein free culture medium;

or cell cultivation in culture medium comprising at least one aptamer analogue of signaling protein, wherein aptamer analogue of signaling protein may be at least one of FGF, TGF, transferrin or insulin, wherein modification aimed to reduce the growth factor requirements may comprise genetic modification aimed to reduce requirements of FGF, TGF, transferrin or insulin in culture environment.

In one aspect of the invention the method of cell cultivation may comprise four following methods:

modification of the cellular TERT gene level expression;

modification aimed to reduce the growth factor requirements;

cell cultivation in protein free culture medium;

and cell cultivation in culture medium comprising at least one aptamer analogue of signaling protein, wherein aptamer analogue of signaling protein may be at least one of FGF, TGF, transferrin or insulin, wherein modification aimed to reduce the growth factor requirements may comprise genetic modification aimed to reduce requirements of FGF, TGF, transferrin or insulin in culture environment.

In one aspect of the invention the method of cell cultivation may comprise modification of the cellular TERT gene level expression and modification aimed to reduce the growth factor requirements, wherein modification aimed to reduce the growth factor requirements may comprise genetic modification aimed to reduce requirements of FGF, TGF, transferrin or insulin in culture environment.

In one aspect of the invention the method of cell cultivation may comprise modification of the cellular TERT gene level expression and cell cultivation in protein free culture medium.

In one aspect of the invention the method of cell cultivation may comprise modification of cells aimed to reduce the growth factor requirements and cell cultivation in protein free culture medium.

The non-human metazoan cells may be modified in various ways to improve their properties. The non-human metazoan cells may be genetically modified, may be subjected to a non-genetic modification and/or may be adapted to different conditions and environments The genetic modifications may comprise permanent and/or transient genetic modifications, wherein such genetic modifications may be an introduction of new genomic and transcriptomic elements and an introduction of new nucleic acid sequences. Such gene editing may be performed using methods such as CRISPR/Cas9, ZFNs, TALENs and/or other genome editing tools. Other methods for gene editing may comprise introduction by viral vectors based on adeno-viruses, adeno-associated viruses, retro/lentiviruses and/or vectors derived on the above mentioned.

The non-genetic modifications and/or adaptation processes may comprise selecting subpopulations with uniform common phenotypes based on specific characteristics such as their preservation over time, homogenous doubling time and/or speed of the cell cycle. To create cell lines with such characteristics, clonal populations originating from single cells may be established and may be further cultivated under conditions of a continuous selection pressure. The cells may be exposed to stress treatment, wherein the stress treatment may comprise exposure to UV radiation, gamma radiation and/or chemical stress factors.

The result of such improvement by any modification methods described above may be a gain of function and/or a loss of function, which may comprise:

at least one non-genetic modification and/or adaptation selected from the group of: an adaptation to grow in a suspension, adaptation to grow on scaffolds, adaptation to form spheroids, adaptation to grow in the absence of at least one of L-proline or L-glutamine, adaptation to higher cell density level, adaptation to cryopreservation, adaptation to low-oxygen conditions, adaptation to serum-free culture medium, adaptation to protein-free culture medium, adaptation to low-protein culture medium, adaptation to mechanical stress; and/or at least one genetic modification selected from the group of: shortening G1 phase in their proliferation phase, shortening cell cycle, capability of homogenous growth, immortalization, reduced telomeres shortening and their preservation, maintaining the ability to differentiate, ability to grow in a suspension, various changes of epigenetic profile, loss of contact inhibition, maintenance of cell divisions, enhanced nutrition metabolism, enhanced sugar metabolism, methylation switching off, cassettes insertion;

and any combination of genetic modification, non-genetic modification and/or adaptation.

The thawed cells with gain of function or cells from primary cell bank may be used in the production cell bank. The suitable cells for production cell bank may be thawed and multiplicated.

Multiplication is caused by cell division under controlled circumstances. Cells may be maintained in incubators where the temperature, humidity and carbon dioxide levels are regulated to mimic the physiological environment. Cells may be passaged regularly to prevent over-confluence and to maintain the health of the culture. Passaging may involve detaching the cells from the surface of the vessel used, counting them, and seeding a new culture with a defined cell density.

Cells with any genetic modification may be then passed to further cultivation where the desired gain of function is confirmed with a phenotype behavior. This may be then confronted with their genomic and transcriptomic analysis through whole genome sequencing. Original cells from primary cell bank, which were used as source cells for genetic modifications, may be used as a control for the state of origin. The results may be a dataset confirming that all genetic modifications used were performed as requested and are present in the genome in designed sites, appropriate number of copies, and did not cause any unintended changes.

The cell-freezing culture medium may be serum free. The production of serum-free culture medium may be supplemented with a cryostabilizer. The cryostabilizer may be selected from the group comprising of soy hydrolysate, rice hydrolysate, methylcellulose (MC), dimethylsulfoxide (DMSO), a combination thereof, or any other appropriate cryostabilizer. The serum-free culture medium may be used (commercially available Dulbecco's Modified Eagle Medium (DMEM)) or any other appropriate serum free culture medium.

The cultivation of cells may be optionally under gradual adaptation to desired conditions. Further cultivation of cells may be performed in specific conditions, where one or more parameters are varying and cells are gradually adapted to these conditions.

The varying conditions may be, for example, concentration of nutritional or signaling compounds in culture medium, physical conditions, type of cultivation, or any other suitable conditions.

For example, varying conditions may be concentration of amino acids, specific hydrolysate types, and their ratio in culture medium; concentrations of signaling factors in culture medium; or their complete absence. Varying physical conditions may be, for example, temperature or atmosphere concentration. The varying type of cultivation may be, for example, types of suspension conditions or any other suitable conditions. The result of cell cultivation in varying conditions may be a cell line of uniform behavior and properties with unique cell type which is ready to be used in further phases of the process.

The cells from Production cell bank may be thawed, for example, in laboratory conditions and gradually transferred from standard adherent cultivation, for example, in flasks to 50 ml erlenmeyer flask in suspension condition and further into 1l seed tank. In suspension cultivation, the cells that may be used for a cell cultivation may be in a form of a single cell; in a form of cell clumps such as aggregates, spheroids and/or organoids; in a form of cells connected to carriers such as microcarriers, macrocarriers or microfragments; or in any other appropriate form of cells.

In one aspect of the invention, cells may be cultivated in a bioreactor or in other suitable cultivation devices in the form of single cell suspension. Examples of those cells may be bovine embryonic stem cells, conventional single-cell, cultured cell lines such as C6, S2, or CHO cell lines; or other single cell suspension adapted cell lines. Another form of cultivation may be small clumps comprising two or more cells. To achieve better growth in suspension cultivation, bigger clumps and spheroids may be formed. Examples of cells in which cultivation form of spheroids may be used are bovine fibroblasts or myoblasts adapted for suspension cultivation.

The spheroids are cell aggregates self-assembling into three-dimensional (3D) structure. The size of spheroids may be from several cells to the size up to approximately 1 mm in diameter. Spheroids, cellular clumps, or cellular aggregates may be formed spontaneously, under certain conditions without need of any aggregate-inducing agents, formative surface, or any special well.

The spheroids, cellular clumps, or cellular aggregates may be inoculated into the cultivation device.

A culture medium for suspension cultivation of cells in the form of spheroids may be a basal medium that comprises essential compounds for cell survival and growth. The basal medium may comprise amino acids, saccharides (e.g. simple saccharides, complex saccharides, or polysaccharides such as glucose), and ions (e.g. calcium, magnesium, potassium, sodium or phosphate ions). The basal medium may be modified and/or supplemented. The basal medium may be supplemented with amino acids (e.g. L-glutamine), with antibiotics (e.g. penicillin and/or streptomycin), with anti-mycotics, with anti-clumping agents (e.g. dextran sulfate), or with any other appropriate supplements. L-glutamine is an amino acid that is essential for protein and nucleic acid synthesis and energy production in cell culture.

In the cell cultivation processes according to the invention, the additives, for example, polymers, proteins or polysaccharides, or any other appropriate additives, may be used in order to impact the size of spheroids, cell clumps or aggregates. Controlling the size of these formations is advantageous and may result in enhanced cell cultivation.

Shear protectants (for example, polyethylene glycol (PEG) or methylcellulose) may be used to mitigate shear stress, thus being beneficial for maintaining high cell viability and improving cell doubling time in high shear stress conditions.

Anti-clumping agents (for example, dextran sulfate) may be used to decrease the formation of cell clumps. This effect contributes to improved cell viability and a reduction in doubling time.

Size-control additives (for example, polyvinyl alcohol (PVA), PEG, MC or Pluronics, may be used to regulate cell clump sizes within cultures. By managing the size of the clumps, a homogenous spheroid population may be achieved.

The size of spheroids may be in the range of 10 $\mu m$ to 5 mm, in the range of 20 $\mu m$ to 3 mm, in the range of 30 $\mu m$ to 1 mm, in the range of 50 $\mu m$ to 500 $\mu m$, or in the range of 100 $\mu m$ to 300 $\mu m$.

In one aspect of the invention, optimal spheroid formation and cultivation may be achieved under given physical conditions. The given temperature may be for example in the range of 20° C. to 50° C., in the range of 25° C. to 45° C., or in the range of 30° C. to 40° C. The optimal agitation of the cultivation mixture during the cultivation process is necessary. That may be provided by stirring, mixing, or shaking, ensuring that the cells are aerated and nutrients are available to help the cells grow uniformly.

The optimal shaking, mixing, or stirring prevents the cultivated cell from sedimentation at the bottom of the cultivation device, which may result in cell death. Shaking/mixing/stirring speed may be in the range of 0.01 RCF to 500 RCF, or in the range of 0.1 RCF to 3 RCF, or in the range of 0.2 RCF to 2 RCF, or in the range of 0.3 RCF to 1.5 RCF. The shaking speed may be subjected to dynamic changes during the cultivation process. That may be in various time intervals for various lengths of time and/or shaking/mixing speed.

In one aspect of the invention, the cultivation atmosphere may comprise a mixture of oxygen, carbon dioxide, and nitrogen. The volume percentage of carbon dioxide in this cultivation atmosphere may be in the range of 1% to 20% of $CO_2$, in the range of 2% to 10% of $CO_2$, or in the range of 3% to 7% of $CO_2$ In one aspect of the invention, the volume percentage of oxygen in this cultivation atmosphere may be in the range of 1% to 30% of $O_2$, in the range of 1% to 20% of $O_2$, or in the range of 2% to 7% of $O_2$ In one aspect of the invention the volume percentage of nitrogen in this cultivation atmosphere may be in the range of 1% to 99% and could be substituted with any other inert gas, for example argon, helium, xenon.

The cultivation atmosphere may comprise air and/or may comprise air mixed with oxygen, carbon dioxide and nitrogen in concentration ranges mentioned above.

In one aspect of the invention the cell cultivation in spheroids may be performed, for example, in 12-well plates (2 ml/well to 3 mL/well) non-adherent—PVA coated/Ultra non-adherent, or in 6-well plates (3 ml/well to 5 ml/well) non-adherent—PVA coated/Ultra non-adherent, or in Erlenmeyer flask (25 mL) non-adherent—Polyethylene tereph-thalate glycol (PETG), or in any other appropriate cell cultivation vessel. The culture media may be changed, for example % volume in every 2 to 3 days. The seeding density may be in the range of 5 000 cells/ml to 10 000 000 cells/ml, in the range of 100 000 cells/ml to 1 000 000 cells/ml, in the range of 200 000 cells/ml to 800 000 cells/ml, or in the range of 400 000 cells/ml to 600 000 cells/ml. After seeding of single cell suspension (after trypsinization from adherent culture) there may be a static phase without shaking or mixing for the duration of 10 hours to 72 hours, 15 hours to 40 hours, or 18 hours to 35 hours.

The cell cultivation time from the inoculation to the cultivation device to the end of cultivation process may last, for example, in the range of 2 days to 30 days, in the range 3 days to 14 days, or 5 days to 10 days.

The passaging of the cells provided by the above-mentioned process may comprise transfer of suspension. It may also comprise adherence to any suitable cultivation vessel for a suitable time frame (for example, 2 hours, or in a range of 1 hour to 12 hours), and afterwards, the adherent cells may be subjected to enzymatic treatment (for example trypsin) to dissociate the cells back to suspension.

For freezing cells in spheroids, a serum-free cryo medium may be used.

The spheroids may be centrifuged at Relative Centrifugal Force (RCF) in the range of 10 G to 1000 G, in the range of 80 G to 600 G, or in the range of 100 G to 300 G for a time period in the range of 1 min. to 20 min, or in the range of 2 min. to 10 min, and resuspended in serum-free cryo medium. The cell amount may be, for example, in the range of 0.5 million cells to 20 million or 1 million cells to 10 million cells per one 1 ml of the freezing stock. The stock may be then transferred into a suitable freezing container at a temperature, for example, in the range of −80° C. to −196° C., for example −86° C.

For the cell quantification, methods such as flow cytometry, quantification of DNA of the cells (for example, cell lysis and fluorescence dyes), and measurement of lactate accumulation in media (for example, analyzed by HPLC) may be used. Image analysis of spheroids may be used for cell quantification, for example, by using neural networks to estimate the area covered by the spheroids and inferring population characteristics such as size, area, and a diameter distribution.

The cultured cells in the form of spheroids from any appropriate cultivation device (for example, 11 bioreactor) may be used as inoculum for any other appropriate cultivation device (for example, 10 1 bioreactor).

In one aspect of the invention, the cultivation of cells may be carried out in a suspension environment. The carriers or microcarriers may be used in this process.

The carriers may comprise a core and a coating. The material used for the core may be water insoluble material or biomaterial such as polysaccharide, protein, polymer (e.g. cellulose or microcrystalline cellulose), or any other appropriate material. The material for the coating may be non-toxic, cell adherent, water insoluble material or biomaterial such as polymer (e.g. poly-lactic acid (PLA), polycaprolactone (PCL), poly(lactic-co-glycolic acid) (PLGA), poly-caprolactone-co-lactic acid (PCLA), polyhydroxybutyrate (PHB)), protein (e.g. soy protein, pea protein, kidney bean protein, potato protein, or zein), or polysaccharide (e.g. methyl cellulose (MC), hydroxypropyl methylcellulose (HPMC), carboxymethyl cellulose (CMC), ethyl cellulose (EC), chitosan, carrageenan, xanthan gum, alginate, pectin, gellan gum, curdlan, polydextrose, pullulan, a polylysine, and/or any other appropriate material).

The process of fluidized bed spray coating may be used for preparing the carriers for cell cultivation to create a thin layer of polymer, protein, or polysaccharide on the core comprising, for example, microcrystalline cellulose and/or other suitable material. This technique may involve, for example, the use of a fluidized bed reactor, which suspends the particles in an upward flow of air and/or any other gas to ensure uniform coating.

The first step in the process of carrier formation may be the preparation of the microcrystalline cellulose in its appropriate size and purity. Once prepared, the microcrystalline cellulose may be then introduced into the fluidized bed reactor.

In order to create the coating solution, the desired polymer, protein, or polysaccharide may be dissolved or dispersed in a suitable solvent or culture medium for suspension cultivation. The concentration and viscosity of the solution are carefully controlled to ensure optimal coating performance.

The next step may involve the atomization of the coating solution where it is sprayed onto the suspended microcrystalline cellulose particles. This may be achieved using a spray nozzle or atomizer which breaks up the solution into small droplets.

As the droplets come into contact with the microcrystalline cellulose particles, the solvent or culture medium for suspension cultivation evaporates, leaving behind a thin layer of the desired coating material. The air or gas flow within the fluidized bed reactor may ensure that the particles remain in constant motion and allow for even distribution of the coating across the surface of the microcrystalline cellulose.

Once the coating process is complete, the coated microcrystalline cellulose particles may then be separated from the fluidized bed reactor and subjected to further processing, if necessary. This may involve drying, curing, or additional treatments to enhance the properties or stability of the coated particles.

The purpose of applying a thin layer onto the cellulose core may be to improve the effectiveness of cell attachment to carrier materials and facilitate cell collection without the need for costly enzyme treatments. Cells may be harvested by either dissolving the thin layer or mechanically separating them from the core if the layer can remain in the final product. Cells may be seeded as single cell suspension or as spheroids. Spheroids may require a longer period of static cultivation to allow for disintegration from 3D organoids to cover the 2D surface of the carriers. The transfer process from carrier to carrier is achieved by physical semi-dynamic cultivation with occasional static gaps in mixing.

Polymer-coated microfragments may be used in the cultivation processes according to the invention. There is the possibility of formation of bigger particles than in the case of spheroids without carriers while eliminating the necrotic core of spheroids because there is a better distribution of nutrients and oxygen. A better distribution of nutrients and oxygen may lead to a higher number of dividing cells and to higher efficiency of the processes.

The spheroids may consist of cells that are closely adjacent to each other. In a certain size of the spheroids, being in such a dense grouping, there may be an insufficient supply of oxygen and nutrients; and the formation of a necrotic core may occur. During the formation of the spheroids, the microfragments may get incorporated in the structure of the spheroid and the spheroids formed may not be so dense and may contain microvoids which help the distribution of nutrients and oxygen.

The microfragments may, for example, consist of poly-lactic acid (PLA) polymers. PLA fragments are hydrophilic, so they may help transport the culture medium to the cells in the spheroids. Other polymers may be used as well such as polyethylene terephthalate (PET), polycaprolactone (PCL), polytrimethylene terephthalate (PTT), polybutylene terephthalate (PBT), polyhydroxybutyrate (PHB), polyethylene naphthalate (PEN), poly(ethylene adipate) (PEA), poly(valerolactone) (PVL), poly(glycolic acid) (PGA), poly-hydroxyalkanoate (PHA), polybutylene adipate terephthalate (PBAT), polybutylene succinate (PBS), polyhydroxy-butyrate (PHB), polyethylene glycol (PEG), polyvinylpyrrolidone (PVP), or any other appropriate poly-mer. The polymer may be water soluble.

The size of aggregates formed by cells and microfragments may be in the range of 10 μm to 1 mm, or in the range of 50 μm to 600 μm, or in the range of 100 μm to 300 μm.

Raw material may be used such as a felt composed of fibers prepared, for example, by the electrospinning method. These fibers may be split into smaller fragments, for example, to the size in the range of 10 μm to 200 μm, in the range of 20 μm to 100 μm, or in the range of 50 μm to 70 μm. Cleavage may take place, for example, by aminolysis. Ethanolamine may be used for this purpose. The felt may be placed into a solution of ethanol and ethanolamine, heated, for example, at 37° C., and aminolysis may occur with constant stirring. The resulting fragments may be washed with ethanol and distilled water and then sterilized. The resulting fragments may be used for cell cultivation.

Polydopamine may be used in these processes to coat the microfragments used in the cell cultivation process according to the invention. Polydopamine may serve to increase the hydrophilicity of the fragments, to prevent the wrapping of fibers on each other and to improve the adhesion of cells to the fragments.

Serum free culture medium without any components of animal origin may be used for large scale cultivation of cells.

The hydrolysates of plant protein isolates may be used as amino acid sources in culture media according to the invention. The recombinant protein production may be used in culture medium components preparation.

The culture medium according to the invention may comprise macronutrients and micronutrients, other components adjusting the properties of the basal medium (osmo-lality and availability of micronutrients), and signaling com-ponents. The components may be dissolved, for example, in purified water or in water with inorganic salts such as phosphate buffer saline (PBS), water, or PBS with Bovine serum albumin (BSA) with a concentration of, for example, 1% BSA in total.

The signaling compounds may vary according to the specific cell type used in the cultivation in the bioreactor. Examples of those cells may be fibroblasts, myoblasts, adipocytes, their precursors, or a combination of thereof.

The signaling compounds may or may not induce specific change in the cell fate. Examples of these changes may be stimulation of proliferation and/or stimulation of differen-tiation. The signaling compounds may be used in a certain order during a certain time period. Examples may be the usage of a signaling compound for stimulation of prolifera-tion which is then substituted with the signaling compound for differentiation induction. The precise order of dosing of signaling compounds may or may not be correlated or crosslinked with other tools which affect the cell fate during cultivation.

Signaling compounds for various cell types aimed for stimulation of proliferation may comprise at least one of the following signaling proteins: FGF family ligands, insulin, Insulin like growth factor 1 (IGF-1), TGF family ligands, transferrin, or any other appropriate signaling compound.

Signaling compounds for various cell types aimed for myogenic differentiation may comprise at least one of FGF, insulin, TGF, Transferrin, IGF, Epidermal growth factor (EGF), Bone morphogenic protein (BMP), Interleukin 6 (IL-6), Interleukin 13 (IL-13), or any other appropriate signaling compound.

The culture medium according to the invention may comprise amino acids (AA) or their sources in combination with at least one type of compounds that may be selected from a group comprising: saccharides, fatty acids, vitamins and organic micronutrients, mineral compounds (e.g. inor-ganic salts), supplements (e.g. iron supplementation) com-pounds, organic amines, signaling compounds (e.g. growth factors, signaling proteins, or oligonucleotides), shear pro-tectants, additional compounds, compounds for manipula-tion, any other appropriate compounds, or a combination thereof. The media may also contain other compounds, like phospholipids or nucleic acids for example. The amino acids may be sourced, for example, from a protein hydrolysate.

The amino acids and their derivatives that may be sup-plied to the media are, for example: glycine, L-alanine, L-arginine, L-asparagine L-aspartic acid, L-cystine L-gluta-mic acid, L-glutamine, L-histidine, L-hydroxyproline, L-or-nithine, L-citrulline, L-isoleucine, L-leucine, L-lysine, L-methionine, L-phenylalanine, L-proline, L-serine, L-threonine, L-pyroglutamic acid, L-phosphoserine, L-tryp-tophan, L-tyrosine or L-valine. For the preparation of the culture medium, the given amino acid may be added in the pure form, as part of a complex mixture of compounds (for example a hydrolysate), or the hydrates or salts (for example hydrochlorides or sodium salts) of amino acids may be used.

The culture media may comprise protein hydrolysate as a main source of amino acids. The protein hydrolysate may serve as a source of all important amino acids in culture media according to the invention for the purpose of cell cultivation, or some amino acids may be supplied to the media separately such as L-methionine which is found in very low concentrations in most scalable protein sources. Other different individual amino acids may be supplied separately from a different source than a protein hydrolysate.

The term "protein hydrolysate" according to this patent application may be, for example, plant proteins, enzymatic hydrolysates, various types of yeast extracts or lysates (such as whole yeast autolysate), or algae acidic hydrolysate. Methods of protein hydrolysis may include acidic hydroly-sis, basic hydrolysis, enzymatic hydrolysis, or autolysis.

The culture medium according to the invention may comprise soy protein enzymatic hydrolysate, or any other appropriate scalable hydrolysate. For example, the suitable industrially scalable protein sources for hydrolysate prepa-ration may include soy, pea, rice, wheat, wheat gluten, corn, fava beans, alfalfa, hemp, chickpea, potato, pumpkin, rape-seed, red lentil, rice, *Spirulina, Chlorella,* sunflower, water lentil, duckweed, mungbean, bean, yeast, or any other appropriate protein source.

The total dry weight of hydrolysate added to the culture media may be for example in the range of 1 g/l to 200 g/l, or in the range of 3 g/l to 100 g/l, or in the range of 10 g/l to 50 g/l.

The culture medium according to the invention may comprise amino acids added separately, like L-methionine, for example. The total amount of amino acids added in addition to the amino acids from hydrolysate may be in the range of 0.02 g/l to 30 g/l, in the range of 0.05 g/l to 10 g/l, or in the range of 0.1 g/l to 5 g/l.

In one aspect of the invention, the culture medium may comprise at least one of the amino acids listed in the Table 4. There is also disclosed in the Table 4 the possible exemplary, but not limiting concentration of at least one amino acid that may be used in the culture medium according to the invention

TABLE 4

Culture medium composition

| Amino Acids | Concentration mg/l |
| --- | --- |
| Glycine | 0-1875 |
| L-Alanine | 0-445 |
| L-Arginine hydrochloride | 0-14750 |
| L-Asparagine-H2O | 0-750 |
| L-Aspartic acid | 0-665 |
| L-Cysteine hydrochloride-H2O | 0-1756 |
| L-Cystine-2HCI | 0-3129 |
| L-Glutamic acid | 0-735 |
| L-Glutamine | 0-36500 |
| L-Histidine hydrochloride-H2O | 0-3148 |
| L-Isoleucine | 0-5447 |
| L-Leucine | 0-5905 |
| L-Lysine hydrochloride | 0-9125 |
| L-Methionine | 0-1724 |
| L-Phenylalanine | 0-3548 |
| L-Proline | 0-1725 |
| L-Serine | 0-2625 |
| L-Threonine | 0-5345 |
| L-Tryptophan | 0-902 |
| L-Tyrosine disodium salt dihydrate | 0-5579 |
| L-Valine | 0-5285 |

The culture medium may comprise at least one saccharide used, for example, as a source of carbon. The saccharide to be used may be selected from the group: glucose, fructose, galactose, sucrose, lactose, maltose, any other appropriate saccharide, or a combination thereof. The saccharides may be used in the culture media, for example, in an amount in the range of 1 g/l to 350 g/l, in the range of 2 g/l to 100 g/l, or in the range of 3 g/l to 20 g/l.

In one aspect of the invention, glucose (dextrose) may be used in the culture medium in amounts in the range of 0 g/l to 315 g/l, in the range of 10 g/l to 200 g/l, or in the range of 50 g/l to 100 g/l.

The culture media may contain a fatty acid, for example linoleic acid, lipoic acid, stearic acid, or any other appropriate fatty acid. Linoleic acid may be used in the culture medium for example in amount in the range of 0 mg/l to 4.2 mg/l, in the range of 0.2 mg/l to 3 mg/l, or in the range of 0.5 mg/l to 2 mg/l. The lipoic acid may be used in the culture medium, for example in amount for example in the range of 0 mg/l to 10.5 mg/l, in the range of 0.2 mg/l to 8 mg/l, or in the range of 0.5 mg/l to 5 mg/l.

The culture media may contain at least one of or any combination of the following ions as a mineral compound: $Ca^{2+}$, $Cl^-$, $Cu^{2+}$, $SO_4^{2-}$, $Fe^{3+}$, $NO_3^-$, $Fe^{2+}$, $Mg^{2+}$, $K^+$, $Na^+$, $CO_3^{2-}$, $HCO_3^-$, $H_2PO_4^-$, $HPO_4^2$, $PO_4^{3-}$, $Zn^{2+}$, and $SeO_3^{2-}$. The media may also contain trace amounts of other mineral compounds and elements such as cobalt, iodine or manganese. The media may be prepared by dissolving different constituent compounds in water; any appropriate chemical compound may be used as long as it dissociates to the desired ions in aqueous solution. The total amount of mineral compounds added to the culture media may be, for example, in the range of 0.1 g/l to 50 g/l, or in the range of 1 g/l to 20 g/l, or in the range of 3 g/l to 10 g/l.

The culture media may contain a vitamin, for example, at least one compound selected from: alpha-tocopherol (vitamin E), ascorbic acid (vitamin C), pyridoxine (B6), pyridoxal (B6), cyanocobalamin (B12), hydroxocobalamin (vitamin B12), biotin, choline, pantothenic acid, folic acid, niacinamide, pyridoxine, riboflavin, thiamine, i-inositol, or a combination thereof. Any appropriate bioactive derivatives or precursors of these compounds may be used. For example, cyanocobalamin may be used instead of vitamin B12 as it can be readily converted to bioactive vitamin B12 by the cells. As another example, thiamine hydrochloride (chloride salt form of thiamine) may be used instead of thiamine. The total amount of vitamins added to the media may be, for example, in the range of 0.001 mg/l to 1000 mg/l, in the range of 0.1 mg/l to 100 mg/l, or in the range of 1 mg/l to 20 mg/l.

The culture medium may comprise at least one of the following organic micronutrient compounds: spermine, spermidine, putrescine, thymidine, L-Ornithine, Ethanolamine, myo-inositol, choline and/or any other appropriate organic micronutrient compounds.

The culture media may contain an organic amine, for example at least one compound selected from: putrescine, ethanolamine, any other appropriate amine, or a combination thereof. Organic amines may be added to the culture media, for example, in an amount in the range of 0.01 mg/l to 1000 mg/l, in the range of 0.1 mg/l to 100 mg/l, or in the range of 0.5 mg/l to 20 mg/l.

The culture media may contain a source of iron, for example, in a form of ferric citrate or any other appropriate source of iron. Ferric citrate, or another iron supplementation compound, may be added to the culture media in an amount in the range of 1 mg/l to 10000 mg/l, in the range of 10 mg/l to 1000 mg/l, or in the range of 50 mg/l to 200 mg/l.

The signaling compounds, for example, growth factors, may be used in the culture medium according to the invention. For example, at least one of transferrin, insulin, FGF (e.g. FGF-1 and FGF-2), TGF (e.g. TGF beta 1), IGF, or any other appropriate compounds may be used as a signaling compound.

In one aspect of the invention, the content of signaling compounds (e.g. growth factors such as FGF, TGF beta 1, insulin or transferrin or other signaling compounds) may be reduced. The concentration of TGF beta 1 may be in the range of 0 mg/l to 0.002 mg/l. The concentration of transferrin in the culture medium according to the invention may be in the range of 0 mg/l to 10 mg/l, in the range of 0.1 mg/l to 8 mg/l, or in the range of 0.5 mg/l to 5 mg/l. In one aspect of the invention, the reduced amount of transferrin may be in the range of 0 mg/l to 0.01 mg/l.

The concentration of insulin in the culture medium may be in the range of 0 to 2 g/l, in the range of 0.1 mg/l to 1 g/l, or 0.5 mg to 500 mg/l. In one aspect of the invention, the reduced amount of insulin may be in the range of 0 mg/l to 0.1 mg/l The concentration of FGF-2 in the culture medium may be in the range of 0 mg/l to 1 mg/l, in the range of 0.1 mg/l to 0.8 mg/l, or 0.2 mg/l to 0.5 mg/l. In one aspect of the invention, the reduced amount of FGF-2 may be in the range of 0 mg/l to 0.01 mg/l.

The concentration of TGF beta 1 in the culture medium may be in the range of 0 to 0.2 mg/l, in the range of 0.01 mg/l to 0.15 mg/l, or 0.05 mg/l to 0.1 mg/l. In one aspect of the invention, the reduced amount of TGF beta 1 may be in the range of 0 mg/l to 0.001 mg/l.

In one aspect of the invention, the culture medium may be without any signaling compounds, for example, growth factors. The culture medium according to the invention may be serum free and/or protein free.

In one aspect of the invention, the culture medium may comprise at least one stabilizing agent, wherein the stabilizing agents may be selected from shear protectants and/or anti-foaming agents.

The culture medium may comprise a shear protectant to provide minimum stress for metazoan cells. Shear protectants that may be used include but are not limited to, for example, any cellulose derivative (e.g. methylcellulose, ethylcellulose, carboxymethylcellulose (CMC)), poloxamer 188, polyethylene glycol, polypropylene glycol, dextran, dextran sulfate, polyvinyl alcohol, any other appropriate shear protectant, or their combination. The shear protectant concentration in the culture medium may be in the range of 0% to 5%, 0.01% to 2%, or 0.02% to 1% by weight.

The culture medium may comprise anti-foaming agent (e.g. silicone-based anti-foaming agents), polyethylene glycol (PEG), poly vinyl alcohol (PVA), polydimethylsiloxane, polysorbate 80, vegetable oils, any other appropriate anti-foaming agent, or the combination thereof. The concentration of the anti-foaming agent in the culture medium may be in the range of 0.001% to 5%, in the range of 0.01% to 1%, or in the range of 0.1% to 0.5% by weight. In one aspect of the invention, the content of culture medium components may be in the ranges according to the Table 5.

TABLE 5

| ranges of concentrations of culture medium components | |
| --- | --- |
| Media Component | Concentration (mg/l) |
| Supplement | |
| Transferrin | 0-10 |
| Insulin | 0-2000 |
| FGF2 | 0-1 |
| TGF beta 1 | 0-0.2 |
| Sodium selenium | 0-1.4 |
| Ascorbate | 0-6400 |
| Sugars | |
| D-Glucose (dextrose) | 0-315100 |
| Fatty Acids | |
| Linoleic acid | 0-4.2 |
| Lipoic acid | 0-10.5 |
| Amino Acids | |
| Glycine | 0-1875 |
| L-Alanine | 0-445 |
| L-Arginine hydrochloride | 0-14750 |
| L-Asparagine-H2O | 0-750 |
| L-Aspartic acid | 0-665 |
| L-Cysteine hydrochloride-H2O | 0-1756 |
| L-Cystine-2HCl | 0-3129 |
| L-Glutamic acid | 0-735 |
| L-Glutamine | 0-36500 |
| L-Histidine hydrochloride-H2O | 0-3148 |
| L-Isoleucine | 0-5447 |
| L-Leucine | 0-5905 |
| L-Lysine hydrochloride | 0-9125 |
| L-Methionine | 0-1724 |
| L-Phenylalanine | 0-3548 |
| L-Proline | 0-1725 |
| L-Serine | 0-2625 |
| L-Threonine | 0-5345 |
| L-Tryptophan | 0-902 |

TABLE 5-continued

| ranges of concentrations of culture medium components | |
| --- | --- |
| Media Component | Concentration (mg/l) |
| L-Tyrosine disodium salt dihydrate | 0-5579 |
| L-Valine | 0-5285 |
| Vitamins | |
| Biotin | 0-0.35 |
| Choline chloride | 0-898 |
| D-Calcium pantothenate | 0-224 |
| Folic acid | 0-265 |
| i-Inositol | 0-1260 |
| Niacinamide | 0-202 |
| Pyridoxine hydrochloride | 0-201.3 |
| Riboflavin | 0-21.9 |
| Thiamine hydrochloride | 0-217 |
| Vitamin B12 | 0-68 |
| Inorganic Salts | |
| Calcium chloride (CaCl2) (anhyd.) | 0-11660 |
| Cupric sulphate (CuSO4—5H2O) | 0-0.13 |
| Ferric nitrate (Fe(NO3)3—9H2O) | 0-5 |
| Ferric sulphate (FeSO4—7H2O) | 0-41.7 |
| Magnesium chloride (anhyd.) | 0-2864 |
| Magnesium sulphate (MgSO4) (anhyd.) | 0-4884 |
| Potassium chloride (KCl) | 0-31180 |
| Sodium bicarbonate (NaHCO3) | 0-243800 |
| Sodium chloride (NaCl) | 0-699550 |
| Sodium phosphate dibasic (Na2HPO4) (anhyd.) | 0-7102 |
| Sodium phosphate monobasic (NaH2PO4—H2O) | 0-6250 |
| Zinc sulphate (ZnSO4—7H2O) | 0-43.2 |
| Additional compounds | |
| Hypoxanthine Na | 0-239 |
| Putrescine 2HCl | 0-8.1 |
| Sodium pyruvate | 0-5500 |
| Thymidine | 0-36.5 |

In other aspects of the invention, the culture medium may comprise signaling molecules or nucleic acids.

In one aspect of the invention, oligonucleotides may be used as the constituent components of a culture medium for a cultivation of cells. Oligonucleotides may be with single or double stranded chains of nucleic acids containing 10 nucleotides to 70 nucleotides, 10 nucleotides to 120 nucleotides, or 1 nucleotide to 1000 nucleotides.

In one aspect of the invention, the oligonucleotides may be added to the culture medium in molar concentration in the range of 5 nM/l to 100 nM/l, in the range of 5 nM/l to 500 nM/l, or in the range of 50 nM/l to 50 mM/l or the concentration may vary during the cultivation when a peak of higher concentration may be followed with the lower concentration. The peak of high concentration may be from 1 hour to 10 hours or 10 hours to 72 hours of the cultivation.

In one aspect of the invention, oligonucleotides may be a one of the components of a cell type specific signaling compound or may be added to the culture medium independently to the other components.

Examples of oligonucleotides serving as AONs may be oligonucleotides whose target are mRNA of target genes. Examples of those target genes may be ferroportin, myostatin, p53, miRNA140, or others.

Examples of oligonucleotides serving as ligand to the suitable protein (aptamers) may be oligonucleotides able to bind the target proteins such as FGF-2 receptor, TGF-beta receptor, TrF receptor, insulin receptor, or others.

Additional compounds may be used, for example, hypoxanthine, putrescine, pyruvate, thymidine, ethanolamine, their salts or derivatives thereof (e.g. sodium hypoxanthine, or putrescine dihydrochloride), or any other appropriate additional compounds.

The hypoxanthine, for example, hypoxanthine sodium, may be used in the culture medium according to the invention in the concentration in the range of 0 mg/l to 239 mg/l, or in the range of 10 mg/l to 200 mg/l, or in the range of 50 mg/l to 100 mg/l.

The putrescine, for example, putrescine dihydrochloride, may be used in the culture medium according to the invention in the concentration in the range of 0 mg/l to 8.1 mg/l, in the range of 1 mg/l to 6 mg/l, or in the range of 2 mg/l to 5 mg/l.

The pyruvate, for example, pyruvate sodium, may be used in the culture medium according to the invention in the concentration in the range of 0 mg/l to 5.5 g/l, in the range of 100 mg/l to 3 g/l, or in the range of 500 mg/l to 1 g/l.

The thymidine may be used in the culture medium according to the invention in the concentration in the range of 0 mg/l to 36.5 mg/l, in the range of 5 mg/l to 25 mg/l, or in the range of 10 mg/l to 20 mg/l.

The recombinantly prepared signaling compounds may be used in the culture medium according to the invention. The signaling compounds may be stabilized to prevent degradation, for example, thermal degradation or proteolytic degradation. The signaling compounds may be secreted into the culture medium or accumulated in the cellular or subcellular compartment. Then, in the process of harvesting, they may be or may not be collected, purified, and separated or whole culture may be collected. From the whole cultivated culture, various fractions (parts) may be divided and collected in the form of pellets that are easy to handle. Those pellets may be further processed and may serve as a direct compound to be added to the culture medium. Pellets may be dissolved, lysed, or reconstituted prior to the application into the culture medium in an appropriate solvent.

In one aspect of the invention, production of recombinant signaling compounds for use as culture medium components may be used. The recombinant protein production may comprise the following expression systems: bacterial (example e.g. *Escherichia* coliand *Bacillus subtilis*), Brewer's yeast (e.g. *Saccharomyces cerevisiae*), non-conventional yeast (e.g. *Pichia pastoris, Hansenula polymorpha*, or *Yarrowia lipolytica*), filamentous fungi (e.g. *Aspergillus* spp. or *Trichoderma reesei*), plants (e.g. *Nicotiana tabacum, Hordeum vulgare*, or *Zea* May), insect cells or mammalian cell lines (e.g. HEK293 or CHO-K1), or any other appropriate expression systems. The recombinant protein production followed by the cellular lysis and derivation of the pellets or other recombinant protein rich derivatives may be used, for example, in *Streptococcus thermophilus, S. cerevisiae, P. pastoris* and various strains of species *Lactobacillus* spp. such as *Lactobacillus acidophilus, Lactobacillus plantarum, Lactobacillus casei*.

The differentiation of one or more cell types or part of cells may be achieved before the inoculation of cells to the seeding tank 128 or to the cultivation device 101 prior to their further multiplication. The cells from the production cell bank 132 may be allowed to differentiate to acquire desired properties. The differentiation onset may be spontaneous or natural or an induced reaction to the cell cultivation environment. The cultivation environment induced differentiation onset may be in response to the physical and chemical cultivation conditions such as media composition and the characteristics of used signaling compounds in media, extent and dimension of cultivation the cultivation vessel, the form and parameters of dynamic cultivation, external stimulation to the cells during cell cultivation and others. The result of differentiation may be the cell population in part or in the whole content of a bioreactor with a changed cell type. Examples of these changed cell types may be transition from myosatellite cell to the myoblast or to the myoblast syncytium or a myotube. Another example may be transition from mesenchymal stem cell to the preadipocyte or to the adipocyte. Yet another example may transition from a fibroblast to the adipocyte.

In one aspect of the invention the differentiation onset may be triggered via induced genetic expression. These induced genetic expressions may be started with an inducible promoter which may be a part of gain of function genetic modification. The promoter, for example a thermosensitive or photosensitive promoter, that triggers cell expression based on a change in a temperature or a light may be used. Another example may be an inducible promoter responding to the specific chemical compound. Example of this compound may be cumate. The differentiation may be used also for a part of the cells only. The resulting product may be made up of a mixture of different types of cells that may be intergrown with each other or with the other nutritional and structural compounds of a final product.

The differentiation may take place also after harvesting, for example the differentiation of wet cell biomass, and may be performed in other cultivation device 101 and/or in the cultivation bioreactor.

In one aspect of the invention, a part of the cell cultivation processes may be cellular inactivation where, for example, reproduction, metabolic, and other processes in the cells are stopped. The inactivation may be carried out, for example, by drying, heating, chemical inactivation, or by other appropriate processes required by food standards.

In one aspect of the invention, the raw wet cell biomass may be used in order to form the final food product and may be used as one component of a final food product. The final food product may be prepared using device for preparing food product 105. Examples of the raw cell biomass may be the concentrated cell biomass; the concentrated cell biomass with additional structural polysaccharides; or the concentrated cell biomass with all potential texturizers, plasticizers, fortifiers, flavors, or other food additives and additional structural polysaccharides and oils.

The raw cell biomass may then undergo inactivation of cellular processes which result in immortalized, nonviable cells. Examples of these processes may be inactivation with heat, where raw cell biomass or final food product is heated at least to 95° C. Another example may be autoclaving or pasteurization. Other appropriate processes may be used.

As mentioned, the cultivation system according to the invention may optionally comprise the device for preparing food product 105. The device for preparing food product 105 may be able to perform at least one of the following processes: receiving, storage, grinding, mixing, conveying, extrusion, cooking, drying, cooling, pumping, coating, dividing, packaging, or any other requested processes. The device for preparing food product 105 may be formed, for example, by an extruder. The extruder may comprise, for example, a bin, a feeder, a preconditioner, an extrusion, cooker, die/knife assembly, or any other appropriate components. The operating conditions may be adjusted to vary the characteristics of the finished food product as requested.

The processes for preparing the food product for human consumption or the pet food product may comprise the following steps:

a) preparing cultured metazoan cell biomass; and b) combining the metazoan cell biomass with at least one additional component in order to prepare the food product with a desired shape and other requested properties, wherein the step may comprise adjusting the water content of the food product provided, for example, by drying, creating the requested shape of the final food product, or any other appropriate processes.

The final food product may comprise one or more cultivated cell types or one or more cultivated cell types with other non-cellular compounds. Non-cellular compounds may be edible and may bring additional sensoric and structural properties as well as additional nutritional values.

The step of preparing the food product may optionally comprise mixing of the cultured cells with other non-cellular additional compounds (for example, compounds for making scaffold structure). The food product may comprise one or more cell types, one or more scaffold type material, and/or other additional materials and substances, such as sources of fat, proteins, saccharides, derivatives of crop plants, food grade ingredients, or any other appropriate additional compounds according to the description below. Cells may be co-cultivated with each other and use scaffold type material and/or any other additional materials and substances. The cultivation time may be for a time period, for example, in the range of 1 hour to 7 days, in the range of 2 hours to 3 days, or in the range of 10 to 48 hours. Cells may or may not continue to grow, multiplicate, or differentiate in the form of the food product. The processes of preparing the food product may comprise homogenization, chopping of the tissue from cultivated cells, formation of cell comprising aggregates, or filtering of the cells through a net with a size limit, a formation of blocks, or any other appropriate process according to the description below. Formation of blocks of the food product may comprise 3D print formation of requested shape including layering of various mixtures of cells with additional components. The food product may be defined as a mixture of cells and additives with a desired structure, cohesion, moisture, and nutritional parameters able to be formed into the final shape (block) which may be then passed to product packing.

The food product according to the invention intended for human consumption or as a pet food may comprise a different amount of cultured metazoan cells. The amount of cultured metazoan cells in the food product may be in the range of 1% to 90% by weight, in the range of 5% to 80%, or in the range of 10% to 60%.

The food product according to the invention may further comprise at least one additional component. The additional component that may be added to the mass of cultured metazoan cells, may be, for example, a source of amino acid, protein, saccharide, fat, or a combination thereof. The additional component may be, for example, a compound selected from the group of vitamins, sources of minerals, binders, palatants, antioxidants, colorants, preservatives, any other additional components, or a combination thereof.

The product according to the invention may comprise a non-animal source of saccharides and/or fats, for example a plant-originated source.

The non-animal source of saccharides may comprise at least one selected from the group comprising: rice, corn, potatoes, sweet potatoes, barley, oats, peas, tapioca, lentils, chickpeas, sorghum, *quinoa*, millet, wheat, cassava, yams, pumpkin, carrots, beet pulp, apples, bananas, blueberries, cranberries, apricots, butternut squash, chia seeds, flaxseed, sunflower seeds, pumpkin seeds or carrageenan, any other appropriate plant-originated source of saccharide or fats, or any combination thereof.

The non-animal source of fats may be at least one selected from the group of olive oil, coconut oil, avocado oil, canola oil, sunflower oil, tea tree oil, flaxseed oil, sesame oil, almonds, walnuts, cashews, pecans, macadamia nuts, hazelnuts, flaxseeds, sunflower seeds, pumpkin seeds, hemp seeds, sesame seeds, avocado, olives, almond butter, cashew butter, seaweed, tahini, hummus, any other non-animal fat, or a combination thereof.

The binder may be at least one ingredient selected from the group comprising: guar gum, carrageenan, xanthan gum, pectin, cellulose, egg product, peanut paste, potato starch, rice flour, soy protein isolate, corn starch, wheat gluten, gelatin, inulin or pea fiber, any other appropriate binder, or a combination thereof, or.

As the preservative may be at least one ingredient selected from the group comprising: vitamin E, rosemary extract, citric acid, mixed tocopherols, ascorbic acid, green tea extract, cranberry extract, clove oil, oregano oil, neem extract and synthetic preservatives such as butylated hydroxyanisole, butylated hydroxytoluene, propyl gallate, sorbic acid, calcium propionate, potassium sorbate, sodium benzoate, natamycin, any other appropriate preservative, or a combination thereof.

The colorant may be at least one ingredient selected from the group comprising: beta-carotene, beet juice powder, turmeric, caramel color, spinach powder, *spirulina* extract, paprika extract, annatto extract, annatto seeds, chlorophyll, saffron, *gardenia* extract, red beet powder, carrot juice concentrate, purple sweet potato, hibiscus extract, cochineal extract, curcumin, cabbage extract, paprika, grape skin, caramelized onion, anthocyanins, any other appropriate colorant, or a combination thereof.

The antioxidant may be at least one ingredient selected from the group comprising: butylated hydroxyanisole, ethoxyquin, tert-butylhydroquinone, vitamin C, vitamin E, lycopene, or a combination thereof, or any other appropriate antioxidant.

The palatant may be any compound or mixture that may increase the palatability of the food product. The palatant may be animal-derived or plant-derived and may be selected from the group comprising: artificial flavors, natural flavors, hydrolyzed proteins, fat sprays, any other appropriate palatant, or a combination thereof.

In one aspect of the invention, the prepared food product may further comprise beneficial microorganisms, emulsifiers, sweeteners, acidity regulators and digestibility enhancers, or any other appropriate ingredients.

The food product may be, for example, in the form of a cell biomass used for human or animal consumption. The product may be in at least one form selected from: minced meat in various forms, nuggets, meat for hamburgers, meatballs, sausages, granulated meat, sliced meat, meat cubes, meat noodles, steak, canned meat, or any other appropriate product comprising cultured cells.

The cultured food product may comprise a different content of water. The product may be for example dry food, semi-moist food, or wet food. The wet product may comprise more than 60% by weight water content in the product. The cultured product with water content in a range of 14% to 60% may be defined as semi-moist, and the product with a water content less than 14% may be defined as dry.

The dry cultured food product may be in the form of the kibble or snack treat. The cultured product in a form of a kibble may have a shape such as pellets, granules, rings, balls, tubes, pebbles, sticks, cubes, heart-shapes, star-shaped, bone-shaped, discs, diamonds, tetrahedrons, pyramids, spheres, cylinders, cones, triangles, rectangles, or any other irregular shape. The diameter of the kibble may be, for example, in a range of 5 mm to 9 mm for a small size, in a range of 10 mm to 14 mm for a medium size, and in a range of 15 mm to 20 mm for large size. The same dimension relates also to a snack treat form of a dry cultured product. The semi-moist cultured food product may be in the form of chewy chunks, soft kibble, or pouches; and the wet product may be in the form of a pâté, saucy chunks, or minced meat chunks.

Cells cultured in a large bioreactor may be harvested and concentrated to the desired moisture content of the cell biomass. At least one binder, plasticizer, or other food additives may be added to the cell biomass. The components may be combined and subsequently cut or molded into the desired food product in a blender, extruder, or other apparatus suitable for processing. In a further step, the product may be deactivated by heat. The final food product may be then packed in a food-grade packing.

The non-human metazoan cells in the created culture medium may be cultivated under optimal conditions. The optimal conditions may comprise temperature, in a range of 30° C. to 40° C., in a range of 32° C. to 39° C., or in a range of 33° C. to 42° C., which can be measured by various devices including a resistance temperature detector, thermocouple, digital thermometer with insertion probe, infrared thermometer with fiber optic probe or any other appropriate device.

Additionally, the optimal conditions may comprise pH, in a range of 3 to 8, in a range of 4 to 7, in a range of 3 to 9, which may be measured by various methods and devices including potentiometry, colorimetry, spectrophotometry, ion-selective electrodes, conductometry or any other measuring technique and/or device.

Additionally, the optimal conditions may comprise addition of antimicrobial agents, in a range of 500 mg/l to 10000 mg/l, in a range of 1000 mg/l to 8000 mg/l, in a range of 1000 mg/l to 5000 mg/l. The antimicrobial agents may comprise antibiotics, antimicrobial peptides or any other antimicrobial agent for deactivation and/or inhibition of bacteria, viruses, or fungi. For example, antimicrobial peptides from the group of defensin, nisin, fowlicidin, bacitracin or any other appropriate antimicrobial peptide may be used.

In one aspect of the invention, the loading tank 126 used for addition of antimicrobial agents and/or pH modifying agents may be composed of various materials and specific volumes, wherein the loading tank 126 may be connected to the cultivation device 101.

The non-human metazoan cells may be cultivated in the cultivation system. The cultivation takes place in a cultivation environment of culture medium. The cultivation may comprise all cultivation processes that take place in the cultivation device starting from the inoculation of the cells into a cultivation device and ending with the harvesting of the cell biomass. The cultivation processes may comprise phases such as growth, maintenance, differentiation and/or proliferation of the non-human metazoan cells.

The cultivation system may comprise at least one culture medium tank for the preparation of the culture medium and a cultivation device 101 for the cell cultivation and features to produce a cell biomass. The cultivation device 101 may comprise at least one culture vessel.

The cultivation system may further comprise at least one of the following features: at least one filtration unit; a plurality of sterile barriers; a plurality of pumps; a plurality of analytical instruments and sensors; a gas sparging system comprising a plurality of gas tanks; a gas recycling system; at least one culture medium tank comprising a hydrolysis tank, a mixing tank, a loading tank, a storage tank and a waste medium tank; a water purification unit; a medium recycling system; a heat exchange system; a collateral cultivation device; at least one harvesting device; a control unit (the term "control unit" and "control device" may be interchangeable); an external physical stimulation mechanisms; and a product processing device.

The cultivation system may comprise at least one harvesting device. The harvesting device may be used to separate the cell biomass from the culture medium. The cell biomass may be harvested after at least one cultivation cycle, wherein the cultivation cycle varies according to the chosen cell line to be cultivated. The cultivation cycle may be at least as long as the length of time needed to perform more than one cell doubling of the non-human metazoan cells, wherein the cell doubling corresponds to one cycle of the cell. The cultivation cycle may be in a range of 1 hour to 336 hours, in a range of 4 hours to 168 hours, in a range of 12 hours to 168 hours, in a range of 24 hours to 144 hours, in a range of 36 hours to 120 hours, in a range of 36 hours to 96 hours or in a range of 48 hours to 72 hours.

The cultivation device 101, preferably a bioreactor, may comprise at least one culture vessel made from food-grade stainless steel, stainless steel, glass, or any other suitable material that is not toxic to said metazoan cells and at the same time is inert to the culture medium, cell metabolites and other substances considered. The culture vessel may be cylindrical, cubic, rounded cubic, round-bottom cylindrical, or another suitable shape, and may comprise a stirred tank, bubble column tank, airlift tank, packed bed tank, rotating-wall tank, wheel-tank, fixed-bed tank, perfusion tank or hollow fiber tank.

The inner volume of a culture vessel in a device may be in a range of 1 l to 100,000 l, or in a range of 10 l to 10,000 l, or in the range of 100 l to 1000 l. The maximum working volume of the culture vessel may be in a range of ½ to $^{19}\!/_{20}$ of the whole volume of the culture vessel. For example, the culture vessel dimensions ratio of height to width may be in a range of 20:1 to 1:20, for example 1:1, 1:2, 1:3. The culture vessel may be able to withstand an internal pressure of at least 0.1 kPa compared to atmospheric pressure. The culture vessel may be able to withstand a ratio of internal pressure atmospheric pressure in a range of 0.01 to 5, wherein the ratio may be defined as the ratio between the internal pressure and atmospheric pressure. The internal pressure may be determined and/or measured by a pressure sensor positioned within the cultivation device. The culture vessel may further comprise a plurality of gas and fluid inlets/outlets to keep an optimal environment; the gas inlets may be formed by spargers, which are used to sparge a gas mixture in order to deliver O2 into the culture vessel, which may be designed as a membrane, sinter, ring, tube, mesh or any other similar design compatible with the cultivation device and gas outlets, which release gas from the culture vessel in order to dispose of CO2 from the cultivation environment; the exchange of gasses with the culture medium can occur inside of the cell culture vessel.

Optionally, at least one impeller and/or at least one baffle may be located inside the culture vessel of preferred shape to obtain optimal aeration of the mixture.

The cultivation device 101 may further comprise a plurality of sensors and analytical instruments located inside or outside the culture vessel to provide real-time data about the metazoan cell processes and the parameters, such as pH, total pressure in the culture vessel, concentrations, or partial pressures of important gasses such as O2 and CO2, temperature, nutrient concentration, and cell density.

Optionally, an external stimulation device stimulating the cell population may be positioned inside the culture vessel and/or proximate to the culture vessel, configured to provide radiofrequency, optical, magnetic or microwave radiation. The stimulation device may be positioned inside or outside the culture vessel to increase the effectiveness of metazoan cell processes.

The cultivation device 101 may further comprise a control device, preferably a PC unit with a specifically designed software, which can be operated by a skilled operator to ensure total control of all processes.

In one aspect of the invention, the cultivation device may have a gas recycling system, which ensures that the overhead gas from the culture vessel may be controllably exhausted or returned to the gas inlets; optionally, the gas composition may be changed, for example by removing $CO_2$ or moisture or adding $O_2$, before it is returned to the gas inlet.

In one aspect of the invention, the culture vessel may be sterilized using chemical agents, thermal sterilization or UV-radiation.

In one aspect of the invention, the parameters in the culture vessel may be measured by these analytical methods: (1) the temperature of the culture medium and culture vessel may be measured in real time using thermometers or thermal cameras; (2) the nutrient and metabolite concentrations in the culture medium may be measured in real time by probes inserted directly into the culture vessel, or off-line via a sample taken from the culture vessel; (3) preferably, measurements may be performed by electrochemical probes (for example glucose or ammonia probes), UV-Vis spectroscopy, mass spectrometry or polarimetry or other suitable methods; (4) optionally, extraction and/or separation methods may be employed before the analysis, such as capillary electrophoresis or HPLC; (5) cell density may be measured in real time using optical methods, such as turbidimetry, electromagnetic methods, such as the measurement of permittivity, or it may be inferred indirectly from parameters such as $O_2$ consumption, glucose consumption or $CO_2$ production.

In one aspect of the invention, the culture medium that has been separated from grown cell biomass may be used for the production of human or pet food products. The culture medium that has been used and was separated from the cell biomass during harvesting may be further processed to avoid potentially undesired compounds to be a part of the pet food product. The culture medium may be analyzed after harvesting to determine the nutritional values of the culture medium, which may be considered as a by-product of the cell cultivation. The culture medium may comprise all nutrients essential for cell cultivation, including amino acids, which may originate from a protein hydrolysate.

The cell biomass may comprise at least one type of non-human metazoan cell line. The cell biomass may comprise water and/or residues of the culture medium.

The portion of water removed from the cell biomass may be in a range of 1 wt. % to 5 wt. % of the cell biomass, in a range of 10 wt. % to 15 wt. % of the cell biomass, in a range of 20 wt. % to 25 wt. % of the cell biomass, in a range of 30 wt. % to 35 wt. % of the cell biomass, in a range of 40 wt. % to 45 wt. % of the cell biomass, in a range of 50 wt. % to in a range of 55 wt. % of the cell biomass, in a range of 60 wt. % to 65 wt. % of the cell biomass, in a range of 70 wt. % to 75 wt. % of the cell biomass, in a range of 80 wt. % to 85 wt. % of the cell biomass or in a range of 90 wt. % to 95 wt. % of the cell biomass. In one aspect of the invention, the cell biomass after centrifuging, sieving, filtering, drying and/or evaporating may be characterized by having lower total water content than before at least one of said processes. The harvested cell biomass may have only intracellular water, i. e. the water inside the cells of the harvested cell biomass.

The cultivation of the cell biomass may be characterized by a cell density achieved in continuous cultivation mode with yield in a range of $3.8 \cdot 10^8$ to $1.2 \cdot 10^{11}$ cells per 1 l of cultivation media per 1 day of cultivation, $1.9 \cdot 10^9$ to $7.6 \cdot 10^{10}$ cells per 1 l of cultivation media per day of cultivation, $3.8 \cdot 10^9$ to $3.8 \cdot 10^{10}$ cells per 1 l of cultivation media per day of cultivation.

The cell biomass may be centrifuged, sieved, filtered, dried and/or evaporated to remove a portion of water from the cell biomass, thereby obtaining harvested cell biomass. The cell biomass before centrifuging, sieving, filtering, drying and/or evaporating may be characterized by having a total water content in a range of 75 wt. % to 99 wt. %, in a range of 76 wt. % to 98 wt. %, in a range of 77 wt. % to 97 wt. %, in a range of 78 wt. % to 96 wt. %, in a range of 79 wt. % to 95 wt. %, in a range of 80 wt. % to 94 wt. %, in a range of 81 wt. % to 93 wt. %, in a range of 82 wt. % to 92 wt. %, in a range of 83 wt. % to 91 wt. %, in a range of 84 wt. % to 90 wt. %, in a range of 85 wt. % to 89 wt. %, in a range of 86 wt. % to 88 wt. %.

The harvested cell biomass may have the characteristics of a suspension, wherein the suspension may have the cells evenly distributed throughout a dispersion medium without settling out or joining together into aggregates, clumps and/or lumps. In another aspect, the cells may join together into larger aggregates, clumps and/or lumps and may settle over time. In yet another aspect, the cell biomass may be processed to remove a portion of extracellular and/or intracellular water. Such processed cell biomass may have the characteristics of a concentrated paste. i. e. the harvested cell biomass. The harvested cell biomass in a form of concentrated paste may be characterized by its rheological parameters and/or properties. Such rheological parameters and/or properties may comprise dynamic (shear) viscosity, kinematic viscosity, storage modulus and loss modulus.

The harvested cell biomass may have the mass density in the range of 900 $kg \cdot m^{-3}$ to 1200 $kg \cdot m^{-3}$, in the range of 930 $kg \cdot m^{-3}$ to 1170 $kg \cdot m^{-3}$, in the range of 960 $kg \cdot m^{-3}$ to 1140 $kg \cdot m^{-3}$, in the range of 990 $kg \cdot m^{-3}$ to 1110 $kg \cdot m^{-3}$ or in the range of 1020 $kg \cdot m^{-3}$ to 1080 $kg \cdot m^{-3}$.

The harvested cell biomass may be characterized by a cell density in a range of $10^7$ to $10^{10}$ cells per 1 g of the cell biomass, in a range of $10^8$ to $10^{10}$ cells per 1 g of the cell biomass, in a range of $10^9$ to $10^{10}$ cells per 1 g of the cell biomass.

The dynamic viscosity of the harvested cell biomass in ambient temperature at 20° C. may be in a range of 500 mPa·s to 3000 mPa·s, in a range of 550 mPa·s to 2950 mPa·s, in a range of 600 mPa·s to 2900 mPa·s, in a range of 650 mPa·s to 2850 mPa·s, in a range of 700 mPa·s to 2800 mPa·s, in a range of 750 mPa·s to 2750 mPa·s, in a range of 800 mPa·s to 2700 mPa·s, in a range of 850 mPa·s to 2650 mPa·s, in a range of 900 mPa·s to 2600 mPa·s, in a range of 950 mPa·s to 2550 mPa·s, in a range of 1000 mPa·s to 2500 mPa·s, in a range of 1050 mPa·s to 2450 mPa·s, in a range of 1100 mPa·s to 2400 mPa·s, in a range of 1150 to 2350 mPa·s, 1200 mPa·s to 2300 mPa·s, in a range of 1250 mPa·s to 2550 mPa·s, in a range of 1300 mPa·s to 2500 mPa·s, in a range of 1350 mPa·s to 2450 mPa·s, in a range of 1400 mPa·s to 2400 mPa·s, in a range of 1450 mPa·s to 2350 mPa·s, in a range of 1500 mPa·s to 2300 mPa·s, in a range of 1550 mPa·s to 2250 mPa·s, in a range of 1600 mPa·s to 2200 mPa·s, in a range of 1650 mPa·s to 2150 mPa·s, in a range of 1700 mPa·s to 2100 mPa·s, in a range of 1750 mPa·s to 2050 mPa·s, in a range of 1800 mPa·s to 2000 mPa·s or in a range of 1850 mPa·s to 1950 mPa·s.

The storage modulus of the harvested cell biomass may be in a range of 0.5 Pa to 10.0 Pa, in a range of 0.6 Pa to 9.9 Pa, in a range of 0.7 Pa to 9.8 Pa, in a range of 0.8 Pa to 9.7 Pa, in a range of 0.9 Pa to 9.6 Pa, in a range of 1.0 Pa to 9.5 Pa, in a range of 1.1 Pa to 9.4 Pa, in a range of 1.2 Pa to 9.3 Pa, in a range of 1.3 Pa to 9.2 Pa, in a range of 1.4 Pa to 9.1 Pa, in a range of 1.5 Pa to 9.0 Pa, in a range of 1.6 Pa to 8.9 Pa, in a range of 1.7 Pa to 8.8 Pa, in a range of 1.8 Pa to 8.7 Pa, in a range of 1.9 Pa to 8.6 Pa, in a range of 2.0 Pa to 8.5 Pa, in a range of 2.1 Pa to 8.4 Pa, in a range of 2.2 Pa to 8.3 Pa, in a range of 2.3 Pa to 8.2 Pa, in a range of 2.4 Pa to 8.1 Pa, in a range of 2.5 Pa to 8.0 Pa, in a range of 2.6 Pa to 7.9 Pa, in a range of 2.7 Pa to 7.8 Pa, in a range of 2.8 Pa to 7.7 Pa, in a range of 2.9 Pa to 7.6 Pa, in a range of 3.0 Pa to 7.5 Pa, in a range of 3.1 Pa to 7.4 Pa, in a range of 3.2 Pa to 7.3 Pa, in a range of 3.3 Pa to 7.2 Pa, in a range of 3.4 Pa to 7.1 Pa, in a range of 3.5 Pa to 7.0 Pa, in a range of 3.6 Pa to 6.9 Pa, in a range of 3.7 Pa to 6.8 Pa, in a range of 3.8 Pa to 6.7 Pa, in a range of 3.9 Pa to 6.6 Pa, in a range of 4.0 Pa to 6.5 Pa, in a range of 4.1 Pa to 6.4 Pa, in a range of 4.2 Pa to 6.3 Pa, in a range of 4.3 Pa to 6.2 Pa, in a range of 4.4 Pa to 6.1 Pa, in a range of 4.5 Pa to 6.0 Pa, in a range of 4.6 Pa to 5.9 Pa, in a range of 4.7 Pa to 5.8 Pa, in a range of 4.8 Pa to 5.7 Pa, in a range of 4.9 Pa to 5.6 Pa, in a range of 5.0 Pa to 5.5 Pa, in a range of 5.1 Pa to 5.4 Pa, or in a range of 5.2 Pa to 5.3 Pa in measurement conditions of approximately 20° C., relative humidity in a range of 70% to 85%, operating frequency 1 Hz and shear strain amplitude about 0.9%.

The loss modulus of the harvested cell biomass may be in a range of 0.1 Pa to 7 Pa, in a range of 0.2 Pa to 6.9 Pa, in a range of 0.3 Pa to 6.8 Pa, in a range of 0.4 Pa to 6.7 Pa, in a range of 0.5 Pa to 6.6 Pa, in a range of 0.6 Pa to 6.5 Pa, in a range of 0.7 Pa to 6.4 Pa, in a range of 0.8 Pa to 6.3 Pa, in a range of 0.9 Pa to 6.2 Pa, in a range of 1.0 Pa to 6.1 Pa, in a range of 1.1 Pa to 6.0 Pa, in a range of 1.2 Pa to 5.9 Pa, in a range of 1.3 Pa to 5.8 Pa, in a range of 1.4 Pa to 5.7 Pa, in a range of 1.5 Pa to 5.6 Pa, in a range of 1.6 Pa to 5.5 Pa, in a range of 1.7 Pa to 5.4 Pa, in a range of 1.8 Pa to 5.3 Pa, in a range of 1.9 Pa to 5.2 Pa, in a range of 2.0 Pa to 5.1 Pa, in a range of 2.1 Pa to 5.0 Pa, in a range of 2.2 Pa to 4.9 Pa, in a range of 2.3 Pa to 4.8 Pa, in a range of 2.4 Pa to 4.7 Pa, in a range of 2.5 Pa to 4.6 Pa, in a range of 2.6 Pa to 4.5 Pa, in a range of 2.7 Pa to 4.4 Pa, in a range of 2.8 Pa to 4.3 Pa, in a range of 2.9 Pa to 4.2 Pa, in a range of 3.0 Pa to 4.1 Pa, in a range of 3.1 Pa to 4.0 Pa, in a range of 3.2 Pa to 3.9 Pa, in a range of 3.3 Pa to 3.8 Pa, in a range of 3.4 Pa to 3.7 Pa, or in a range of 3.5 Pa to 3.6 Pa in measurement conditions of approximately 20° C., relative humidity in a range of 70% to 85%, operating frequency 1 Hz and shear strain amplitude about 0.9%.

The rheological parameters described in the preceding paragraphs may be measured using at least one analytical instrument and/or method selected from the group of capillary rheometer, cone rheometer, plate rheometer, oscillatory viscometer, rolling ball viscometer, vibrational viscometer, microfluidic viscometer, rotational viscometer, micro rheometer, extensional rheometer and/or any other analytical instrument/method capable of measuring such parameters.

Example 12: Explant Sourcing, Isolation of Cells, Primary Cell Bank

At a local slaughterhouse, a 5 g size sample of semimembranosus muscle tissue was taken from the male cow breed, Charolais. From muscle explant on sterile petri dish, all remains of connective or nerves tissue were removed, and the sample was cut by scissors till paste. The paste was then digested with Collagenase 2 to final concentration 2 mg/ml in DMEM medium for 60 minutes. The minced muscle tissue was passed through a 18 G syringe needle several times followed by separation through a 70 um strainer, and the homogenate was centrifuged for 5 min at 1600 G. Resuspended pellet in GM medium {for 50 ml: pure DMEM (39.45 ml)+20% FBS (10 ml)+10 ng/ml FGF (50 µl)+100 units/ml Penicillin and 100 µg/ml Streptomycin (combined antibiotics 0.5 ml)} and plated into 175 cm2 tissue-culture treated cultivation flask. After 3 days, the supernatant with debris was discarded, and cells were washed two times with PBS+ATB. Cells were then expanded for another 3 days, then cells were sorted based on criteria of expression of CD29+, CD56+ and CD29+CD56−. Cells were then further cultivated and frozen in stocks of 1 million cells in the Primary cell bank 131.

Example 13: GM Again of Function bTERT Immortalization

The primary bovine fibroblasts were immortalized in order to provide the cell line the ability to divide more than 40-60 times. An expression of telomerase reverse-transcriptase (TERT) that replicates the ends of chromosomes (telomeres), which would otherwise be naturally shortened by each cell cycle, was used.

Figure 7:
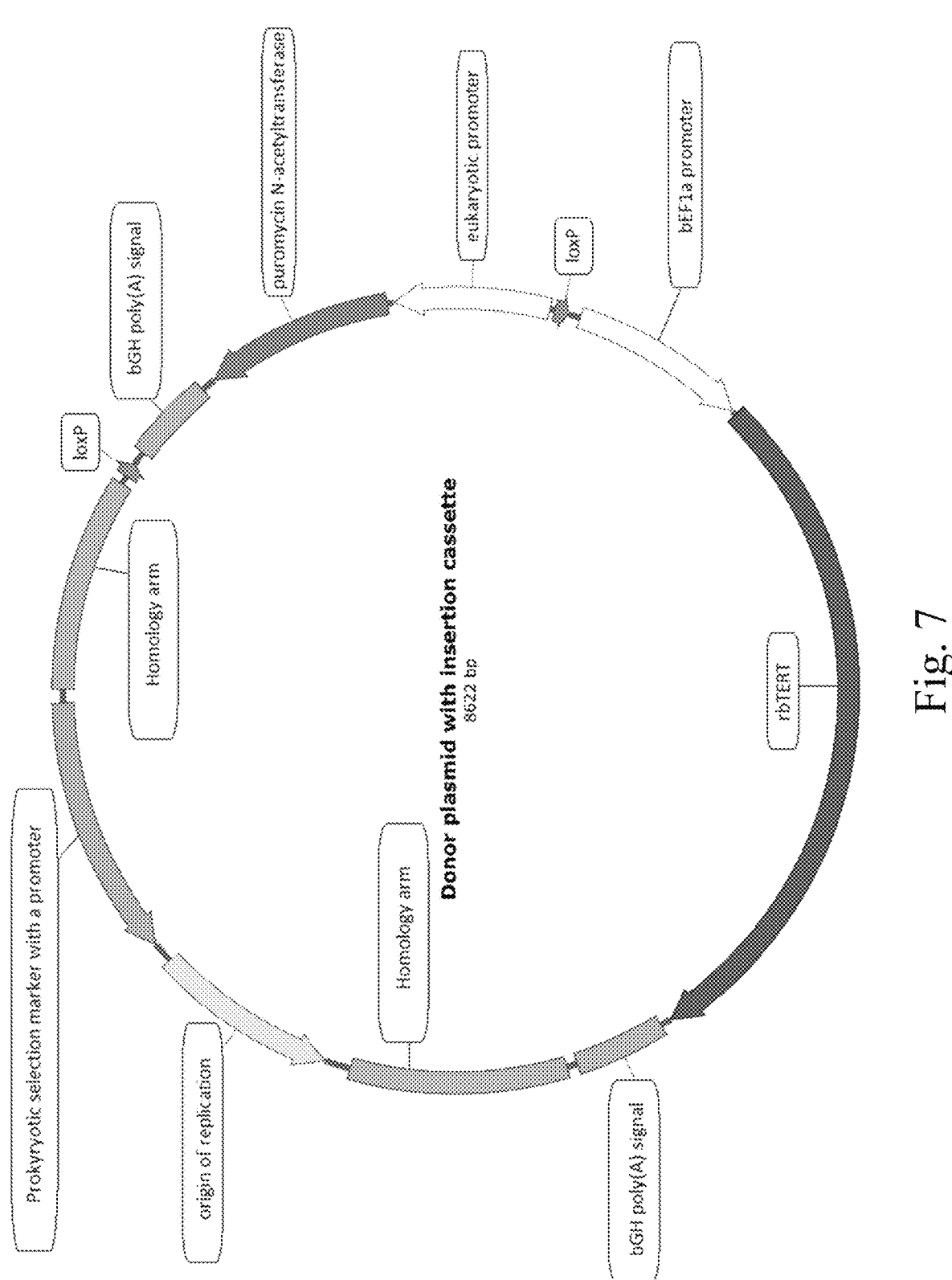
FIG. 7—illustrates the donor plasmid with immortalization cassette for the insertion to bPGrandom locus.
Figure 8:
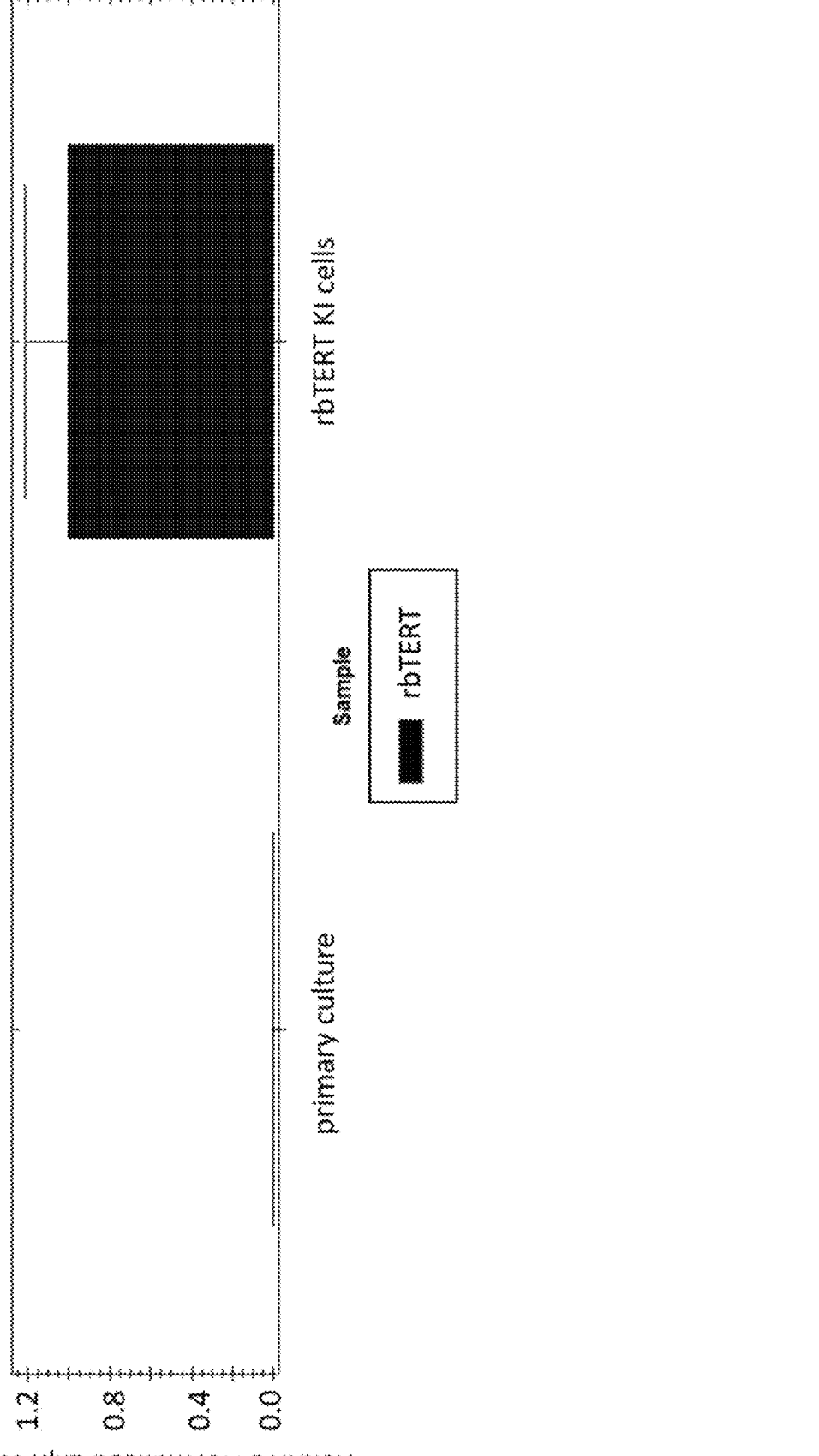
FIG. 8—illustrates the qPCR analysis of the stable expression of rbTERT.
Figure 9:
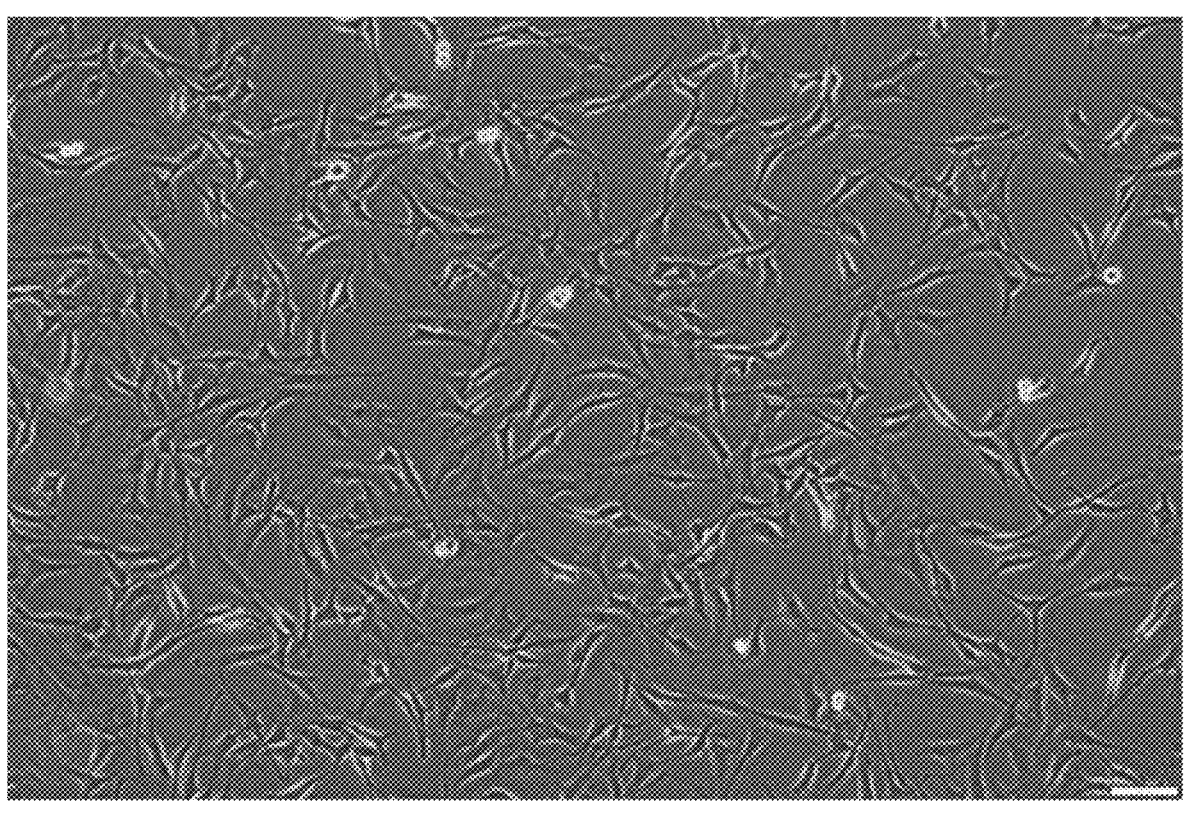
FIG. 9—illustrates the immortalized bTERT fibroblasts, passage 3 according to example 13
Figure 10:
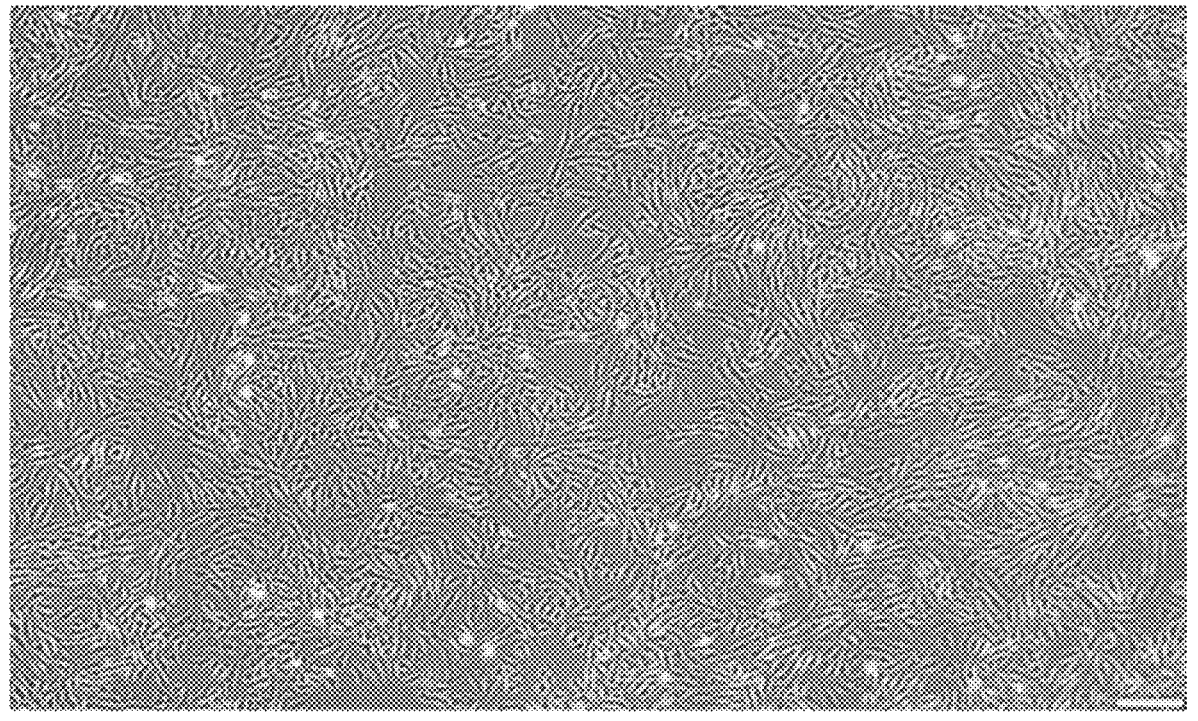
FIG. 10—illustrates the immortalized bTERT fibroblasts, passage 80 according example 13

Low passage (<5) primary bovine fibroblasts were trypsinized and 200,000 cells were seeded per well in a 6-well plate. Upon their appropriate adhesion (3 hours later), cells were subjected to transfection using Lipofectamine 3000 transfection reagent according to the manufacturer's instructions. The culture medium was exchanged for 2 ml of DMEM+10% FBS. Two plasmid vectors were co-transfected. A plasmid comprising a genome editing tool directing insertion to the bPGrandom locus and a second plasmid with an immortalization cassette comprising rbTERT gene corresponding to the SEQ ID NO: 4 (FIG. 7) was used. The transfection mixture was prepared in 250µ of Opti-MEM. 500 ng/ml of each plasmid was used with 5 µl of Lipofectamine 3000 reagent and 4 µl of P3000 reagent. The media was changed after overnight transfection. To enhance the population of transfected cells, the culture was subjected to two consecutive rounds of Puromycin selection treatments with a final concentration of 2 µg/mL, yielding only cells with the incorporated immortalization cassette. The culture was regularly passaged until it reached passage 50. The stable expression of rbTERT corresponding to the SEQ ID NO: 4 was validated via qPCR (FIG. 8). In addition, whole genome sequencing (with minimal coverage of 30×) confirmed the correct integration with no off-target integrations. The immortalized cell line was further tested by passaging until it reached passage 100. The passages 3 and 80 are shown on FIG. 9 and FIG. 10, wherein the magnification and/or resolution is 100 µm for FIG. 9 and 200 µm for FIG. 10. Karyotyping showed no structural or ploidy chromosomal changes compared to the initial primary culture. Finally, a production cell line bank 9 was established.

The bovine variants of widely used PGK1 and EF1a promoters were determined upon alignments of human, mouse, and cow promoter regions of the respective genes. In the case of PGK1, there are 45.7% identical sites. In case of EF1a, there were 51% identical sites among the three species. Selected sequences were cloned from the genomic DNA of bovine fibroblast culture. Cloning a fluorescent reporter marker downstream of the respective promoter sequences allowed for verification of their ability to drive expression in both human and bovine cells.

Figure 11:
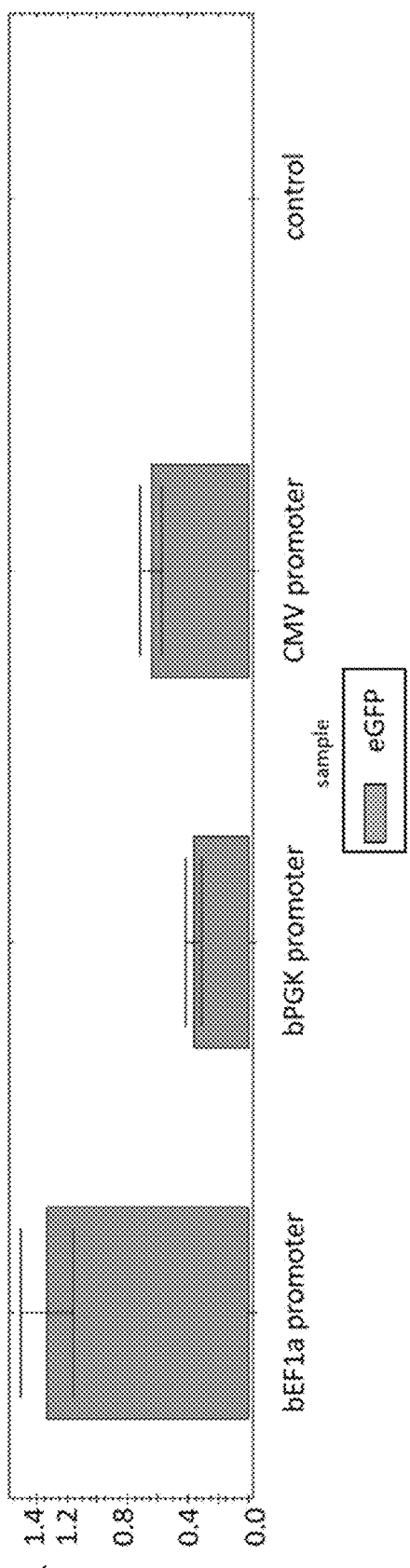
FIG. 11—illustrates the qPCR analysis of the transgene expression of Cytomegalovirus promoter, the bPGK1 promoter and bEF1a promoter.

The impact of the introduction of another copy of the aforementioned promoters into the genome on the expression of their native counterparts was tested via qPCR. Measurement of the expression levels of PGK1 and EF1a before and after the insertion of the extra copy showed no significant changes in the respective mRNA levels. Compared to the widely used Cytomegalovirus promoter, the bPGK1 promoter showed lower transgene (reporter gene) expression, while bEF1a promoter showed higher transgene expression (FIG. 11).

Example 14: Production Cell Bank

In order to create cell lines for up-scale production of cultivated meat, referred to as production cell lines, the cells from gain of function experiments were further cultivated, characterized, and frozen into inoculation stocks.

In step one, cells after the last selection step in gain of function experiment were multiplicated, cryopreserved in cryovials in 1 million cell stocks, and stored in liquid nitrogen. Cells were tested for the negative presence of pathogens (several strains of *mycoplasma* sp. And common bacteria and viruses) prior to cryopreservation. The stocks were labeled, and representative samples for each cell line were characterized via whole genome sequencing.

Example 15: Cultivation in Bioreactor, Cell Harvesting

Figure 12:
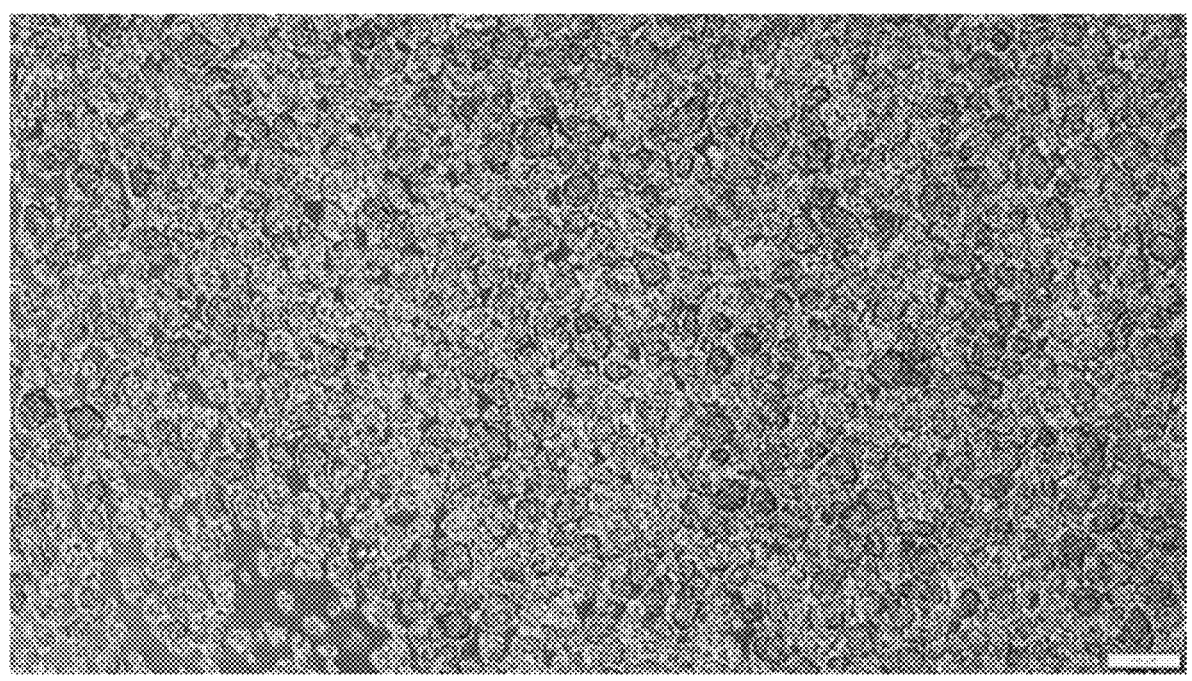
FIG. 12—illustrates the cell culture in the form of spheroids according to example 15

A cultivation device 101 formed by 400 ml stirred tank bioreactor was initialized with cell cultures of immortalized bovine fibroblasts formed into spheroids. These cultures were introduced from inoculation stocks containing 0.5% anti-clumping agent dextran sulfate. The cells were seeded at a density of approximately 400 cells/μl, which amounted to a total of roughly 160 million cells. The culture medium utilized for this process was bovine serum free medium (bSFM), which was further enriched with 0.1% polyethylene glycol (PEG) serving as a shear protectant. The cell culture from this example is depicted on FIG. 12, wherein the magnification and/or resolution is 200 μm.

For the mixing within the bioreactor, a Rushton impeller was deployed. Controlled environmental conditions included:

Aeration rate: Maintained at 0.0625 WM

Agitation speed: Fixed at 0.315 RCF

The continuous cultivation was performed over 7 days following a batch operation protocol, with no additional feeding regimen.

Cell density was monitored on a daily basis via flow cytometry.

At the end of the 7-day cultivation period, the final product was harvested and weighed using analytical scales resulting in a final yield of 5 grams per liter.

Example 16: The Culture Medium Composition

The culture medium for cultivation of cells was prepared and included the following media components:

signaling compounds basal medium compounds nutritional compounds.

The concentrated stock solutions of these three types of media components were prepared and stored individually.

Final culture medium was prepared by mixing them together prior to the cultivation of cells in the final concentration per liter according to desired concentration.

One example of the culture media composition is shown in Table 6. This culture medium composition comprises nutritional mixture of soy protein hydrolysate, fatty acids and saccharides combined with vitamins, inorganic salts, growth factors, and additional compounds.

Another example of the culture media composition is shown in Table 7. This culture medium composition comprises nutritional mixture of raw, food-grade amino acids, fatty acids, and saccharide D-glucose combined with vitamins, inorganic salts, growth factors, and additional compounds.

TABLE 6

| Example of culture media composition | |
|---|---|
| Media Component | Concentration (mg/l) |
| Growth factors | |
| Transferrin | 0.100 |
| Insulin | 20.000 |
| FGF2 | 0.100 |
| TGF beta 1 | 0.002 |
| Saccharides | |
| D-Glucose (dextrose) | 3 151.000 |
| Fatty Acids | |
| Linoleic acid | 0.042 |
| Lipoic acid | 0.105 |
| Nutritional mix | |
| soy hydrolysate | 10 000 |
| Vitamins | |
| Biotin | 0.004 |
| Choline chloride | 8.980 |
| D-Calcium pantothenate | 2.240 |
| Folic acid | 2.650 |
| i-Inositol | 12.600 |
| Niacinamide | 2.020 |
| Pyridoxine hydrochloride | 2.013 |
| Riboflavin | 0.219 |
| Thiamine hydrochloride | 2.170 |
| Vitamin B12 | 0.680 |
| Ascorbate | 64.000 |
| Inorganic Salts | |
| Sodium selenium | 0.014 |
| Calcium chloride (CaCl2) (anhyd.) | 116.600 |
| Cupric sulfate (CuSO4—5H2O) | 0.001 |
| Ferric nitrate (Fe(NO3)3—9H2O) | 0.050 |
| Ferric sulfate (FeSO4—7H2O) | 0.417 |
| Magnesium chloride (anhyd.) | 28.640 |
| Magnesium sulfate (MgSO4) (anhyd.) | 48.840 |
| Potassium chloride (KCl) | 311.800 |
| Sodium bicarbonate (NaHCO3) | 2 438.000 |
| Sodium chloride (NaCl) | 6 995.500 |
| Sodium phosphate dibasic (Na2HPO4) (anhyd.) | 71.020 |
| Sodium phosphate monobasic (NaH2PO4—H2O) | 62.500 |
| Zinc sulfate (ZnSO4—7H2O) | 0.432 |
| Additional compounds | |
| Hypoxanthine Na | 2.390 |
| Putrescine 2HCl | 0.081 |
| Sodium pyruvate | 55.000 |
| Thymidine | 0.365 |

TABLE 7

| Example of culture media composition | |
|---|---|
| Media Component | Concentration (mg/l) |
| Growth factors | |
| Transferrin | 0.100 |
| Insulin | 20.000 |
| FGF2 | 0.100 |
| TGF beta 1 | 0.002 |
| LIF | 0.050 |
| Saccharides | |
| D-Glucose (dextrose) | 1 000.000 |
| Amino Acids | |
| Glycine | 18.750 |
| L-Alanine | 4.450 |
| L-Arginine hydrochloride | 147.500 |
| L-Asparagine-H2O | 7.500 |
| L-Aspartic acid | 6.650 |
| L-Cysteine hydrochloride-H2O | 17.560 |
| L-Cystine-2HCl | 31.290 |
| L-Glutamic acid | 7.350 |
| L-Glutamine | 365.000 |
| L-Histidine hydrochloride-H2O | 31.480 |
| L-Isoleucine | 54.470 |
| L-Leucine | 59.050 |
| L-Lysine hydrochloride | 91.250 |
| L-Methionine | 17.240 |
| L-Phenylalanine | 35.480 |
| L-Proline | 17.250 |
| L-Serine | 26.250 |
| L-Threonine | 53.450 |
| L-Tryptophan | 9.020 |
| L-Tyrosine disodium salt dihydrate | 55.790 |
| L-Valine | 52.850 |
| Fatty Acids | |
| Linoleic acid | 0.042 |
| Lipoic acid | 0.105 |
| Vitamins | |
| Biotin | 0.004 |
| Choline chloride | 8.980 |
| D-Calcium pantothenate | 2.240 |
| Folic acid | 2.650 |
| i-Inositol | 12.600 |
| Niacinamide | 2.020 |
| Pyridoxine hydrochloride | 2.013 |
| Riboflavin | 0.219 |
| Thiamine hydrochloride | 2.170 |
| Vitamin B12 | 0.680 |
| Ascorbate | 64.000 |
| Inorganic Salts | |
| Sodium selenium | 0.014 |
| Calcium chloride (CaCl2) (anhyd.) | 116.600 |
| Cupric sulfate (CuSO4—5H2O) | 0.001 |
| Ferric nitrate (Fe(NO3)3—9H2O) | 0.050 |
| Ferric sulfate (FeSO4—7H2O) | 0.417 |
| Magnesium chloride (anhyd.) | 28.640 |
| Magnesium sulfate (MgSO4) (anhyd.) | 48.840 |
| Potassium chloride (KCl) | 311.800 |
| Sodium bicarbonate (NaHCO3) | 2 438.000 |
| Sodium chloride (NaCl) | 6 995.500 |
| Sodium phosphate dibasic (Na2HPO4) (anhyd.) | 71.020 |
| Sodium phosphate monobasic (NaH2PO4—H2O) | 62.500 |
| Zinc sulfate (ZnSO4—7H2O) | 0.432 |
| Additional compounds | |
| Hypoxanthine Na | 2.390 |
| Putrescine 2HCl | 0.081 |
| Sodium pyruvate | 55.000 |
| Thymidine | 0.365 |

Example 17: Inactivation and Final Food Product Preparation

The bovine fibroblast cells in a form of spheroids cultivated in 200 l bioreactor were harvested. The resulting 2 kg cell biomass was then transferred into ten pieces of one liter Erlenmeyer flasks and centrifuged at 200 G. The rest of the culture medium was filtered from the cell biomass using a water vacuum pump. The concentrated cell biomass was then washed with a washing medium comprising a phosphate saline buffer. The concentrated cell biomass, with maximum content of residual washing medium of up to 5% and moisture content in the range of 90% to 95%, was homogeneously mixed with oat grain-based plasticizer in a blender. The mixture was then molded into a form of nuggets. The product was deactivated by heat in the autoclave at 120° C. for 60 minutes and packed in a food-grade packing.

Figure 13:
FIG. 13—illustrates the food product in the form of a nugget.

The exemplary food product according to the invention in the form of a nugget is depicted on FIG. 13.

The disclosure relates to processes of cell cultivation for preparing food products that may be used for human consumption or as pet food. The cultivation system 100 for carrying out these processes and cell-based food products provided by said processes are also provided.

The cultivation system 100 comprises a cultivation device 101, formed for example by a bioreactor. The cultivation system 100 may further comprise at least one of the following devices: a seeding tank 128, a harvesting device 104, a control unit 125, or sensors and analytical instruments 129, or any other appropriate device, or a combination thereof. Optionally the system may further comprise a device 105 for preparing food product.

The process of cell cultivation using the culture media, especially the process of preparing the culture media and its composition is described below.

The invention relates to a culture media based on a protein hydrolysate suitable for cell cultivation and a process for preparation thereof. The culture media according to the invention may be used, for example, for cell cultivation for the purpose of using the cell biomass for animal or human nutrition.

Mammalian cells are composed of a variety of chemical compounds. A major component of cell biomass is protein, which usually makes up 60% to 70% of dry mass of cells. Proteins are long polymers of amino acids. There are 20 proteinogenic amino acids, 9 of which are dietary essential in mammals, meaning that they cannot be synthesized by the organism and must be sourced from food, or, in the case of cultivated cells, from the culture media.

Cell-line specific mutations may cause cells to become unable to synthesize one or more amino acids (auxotrophy), and therefore need to be provided in the culture media. Cells may also exhibit better growth characteristics and metabolic efficiency when fed non-essential amino acids, even if they are not strictly dependent on them. Generally, amino acids are consumed in media in proportion to the amino acid composition of the cellular protein. However, some amino acids, especially glutamine, may be overconsumed as they are also used in metabolism as well as in synthesizing other compounds like nucleic acid precursors. To provide cells in culture with adequate amino acids for protein synthesis, commonly used culture media formulations contain individual amino acids at different ratios of concentration. These amino acids are usually produced by fermentation processes with microorganisms engineered to produce a specific amino acid. Some amino acids can also be synthesized chemically, but this is generally more expensive than microbial production. However, while microbial production works well for the needs of cell cultivation in research and therapeutic protein production applications, it is too expensive for larger scale cell production, like for cultivated meat production.

Therefore, there is a need for culture media with an alternative and more economically advantageous source of amino acids. This culture media should be suitable for cell cultivation and economically favorable.

The disadvantages of the solutions according to state of the art are solved by the presented and which provides culture media suitable for cell cultivation and the processes for preparation thereof.

The culture media may be prepared by dissolving the individual media components in water or in a suitable aqueous buffer when components are solid. Liquid media components may be mixed with water or aqueous buffer at any time relative to the time of addition of solid media components. The important step of media preparation is the step of sterilization.

The culture media may comprise protein hydrolysate as a source of amino acids. The protein hydrolysate may serve as a source of all important amino acids in culture media according to the invention for the purpose of cell cultivation, or some amino acids may be supplied to the media separately, for example methionine, which is found in very low concentrations in most scalable protein sources. Typically, methionine is commercially available in wholesale at prices compatible with use in industrial-scale cell cultivation.

The advantageous process of protein hydrolysis into shorter peptide chains and/or single amino acids is also provided by the disclosed herein.

The culture media according to the invention may be used, for example, for cell cultivation for the purpose of using the cell biomass for animal or human nutrition. The culture media according to the invention may be used for cultivated meat production.

When individual media components are solid at room temperature, the culture medium may be prepared by dissolving the individual media components in water or a suitable aqueous buffer. The resulting solutions are then sterilized by a suitable sterilization method in order to remove fungi, bacteria, viruses and other possible contaminating agents. Sterilization methods may include thermal sterilization, sterilization by ionizing radiation, sterilization by filtration or sterilization by chemical compounds, for example chlorine dioxide or ethylene oxide. Advantageously, physical methods of sterilization may be used, as they minimize the risk of contamination of the final product with the residues of chemical disinfectants. For liquid media components, such as ethanolamine, sterilization may occur before dissolving the compound in water or aqueous buffer. Some solid media components, for example sodium chloride, may also be sterilized before dissolving them in water or an aqueous buffer (in this case, filtration may not be used as a sterilization method). Advantageously, some chemical compounds or their solutions may be mixed together before sterilization, therefore reducing the number of compounds which need to be sterilized separately. The media may be prepared at the final desired concentration or as a concentrate that will later be diluted to the final desired concentration. The media may also be desiccated to be stored as a dry powder. The media may be added to the culture vessel at the final desired concentration or as concentrated feedstock. In the case of feedstock, the ratios of some components may be changed, or some components may be omitted or added to prevent undesirable changes in media pH, osmolarity or composition when adding the feedstock, as well as to ensure that certain chemical compounds do not accumulate to a level which would be harmful to the cultivated cells.

The media components may be mixed in a mixing vessel, which may be made for example of stainless steel or a glass. The mixing vessel may be equipped with a stirrer, for example impeller and may have inputs from storage tanks with media components and outputs for emptying the vessel.

The volume of the mixing vessel may be in the range of 500 ml to 10 $m^3$, or in the range of 2 l to 5 $m^3$, or in the range of 500 l to 3 $m^3$.

The storage tanks may be made for example of stainless steel or glass. The volume of the storage tank may be in the range of 100 ml to 5 $m^3$, or in the range of 2 l to 3 $m^3$, or in the range of 500 l to 1 $m^3$.

The media components may be dosed into the mixing vessel through sterilization filter, or may be sterilized prior to the placement to the mixing vessel or may be sterilized in the mixing vessel.

The mixing vessel may be equipped with different types of sensors, such as for example thermal sensor, pH probe, conductometer, or any other type of appropriate sensor according to the needs of the process.

The system for culture media preparation may be equipped with pipes, pumps, control unit, programmable logic controller and the like.

The protein source for hydrolysis may be selected from an industrially scalable protein source. Industrially scalable protein sources include phototrophic organisms, such as land plants, green algae, red algae, brown algae, or other phototrophic eukaryotes, phototrophic prokaryotes such as cyanobacteria, or cultivated heterotrophic prokaryotes or eukaryotes, such as bacteria or yeast. The organism used as a protein source may be able to synthesize all amino acids from inorganic nitrogen sources, such as ammonia ions, nitrate ions or molecular nitrogen. The hydrolysis may be performed on a protein isolate from the source organism, or on the whole biomass of the source organism. The source organism may be mechanically or chemically pretreated to improve the speed and efficiency of the hydrolysis process. Saccharides, fats or other compounds may be removed from the biomass of the source organism to facilitate easier processing. Examples of suitable industrially scalable protein sources may include soy, pea, rice, wheat, wheat gluten, corn, fava beans, alfalfa, hemp, chickpea, potato, pumpkin, rapeseed, red lentil, rice, *Spirulina, Chlorella*, sunflower, water lentil, mung bean or yeast. The present invention is not limited to the listed exemplary protein sources.

The protein hydrolysate or multiple hydrolysates from the same or different source organisms may serve as a source of all important amino acids in culture media for the purpose of cell cultivation or some amino acids may be supplied separately, for example methionine, which is found in very low concentrations in most scalable protein sources. Other different individual amino acids may be supplied separately from a different source than a protein hydrolysate. Typically, methionine and some non-essential amino acids such as asparagine or glutamic acid, are commercially available in wholesale at prices compatible with use in industrial-scale cell cultivation. However, the majority of essential amino acid content of the media according to the invention may be sourced from hydrolysates. The approach may be more economically feasible at large scale than using individual free amino acids, as is commonly done in the biopharmaceutical industry or basic research.

The process of hydrolysis entails breaking the original protein molecule into shorter peptide chains and/or single amino acids. For the purposes of this document, including patent claims, the term "protein hydrolysate" is understood to be a mix of amino acids, that may contain peptides and other molecules prepared from a suitable protein source by any suitable method, including acidic, basic, or enzymatic hydrolysis, autolysis or lysis by fermentation with a suitable microorganism which is able to break down the protein. The "protein hydrolysate" according to this patent application may be for example plant protein enzymatic hydrolysates, various types of yeast extracts or lysates (such as whole yeast autolysate), or algae acidic hydrolysate.

Methods of protein hydrolysis may include acidic hydrolysis, basic hydrolysis, enzymatic hydrolysis, or autolysis. Acidic hydrolysis subjects the protein source to a very low pH, usually at an elevated temperature. The duration of reaction may be hours or days. Acidic hydrolysis unfortunately leads to significant degradation of several amino acids, most notably tryptophan, which would then have to be sourced separately at significant costs. Significant degradation of some amino acids also occurs during basic hydrolysis, which subjects the protein source to a very high pH, usually at an elevated temperature. Additionally, the acid or base used for the hydrolysis would have to be removed from the hydrolysate before it could be used to cultivate cells, presenting further complications. For example, when acidic hydrolysis is performed using hydrochloric acid, the acid may be removed by neutralization or evaporation. However, both processes are economically unfavorable because: i) neutralization process results in unfavorably high concentration of salts, which also need to be removed, and ii) evaporation is energy-intensive and the resulting HCl vapors pose a health and environmental hazard that would need to be solved. The process of autolysis relies on the activity of the endogenous enzymes of the source organism to break down the protein source, and this process is usually not very efficient and does not generally result in sufficient hydrolysis of the source protein. Additionally, proteins can be broken down by fermentation with organisms such as *Bacillus licheniformis* or *Aspergillus oryzae*, which produce a large amount of proteolytic enzymes. However, with this approach, some of the amino acids from the source protein may be consumed by the organism that was used to break down the protein during the process of fermentation. Also, metabolic waste products and other compounds from the fermenting organism may contaminate the resulting lysate and adversely affect its properties in respect to mammalian cell cultivation.

The hydrolysate according to the invention may be obtained by enzymatic hydrolysis of a suitable protein source. The industrially scalable protein source is advantageous. In one aspect of the invention soy protein isolate may be used as the protein source for enzymatic hydrolysis. Advantageously, soy protein isolate has a favorable ratio of most amino acids for the purpose of mammalian cell cultivation, with the exception of methionine which is present at a relatively low concentration. However, methionine may be added to the media separately as mentioned above.

The method of enzymatic hydrolysis uses a so called protease, an enzyme that catalyzes the breakdown of peptide bonds in order to achieve protein hydrolysis at much milder conditions than acidic or basic hydrolysis, therefore preserving all of the amino acids of the original protein.

In one aspect of the invention, the enzyme used for hydrolysis may be immobilized on a solid support. This aspect sterically prevents the molecules of the enzyme from breaking each other down and allows the enzyme to be separated from the substrate after the reaction and used again. The solid support may be present in the form of solid carriers suspended in the reaction mixture, or a solid structure with a large surface area, such as a sponge or fibrous structure, through which the reaction mixture is perfused. The enzyme may also be added in soluble (free) form. After hydrolysis is complete, the resulting hydrolysate is separated from the solid support with immobilized enzyme by simply draining the reaction vessel (in the case of large solid structure) or removing the enzyme on solid support by filtration or sedimentation (in the case of suspended carriers). The filtration step may also remove any solid residues from the source protein, such as cell wall debris. Free enzymes may be removed from the hydrolysate by ultrafiltration or deactivated with elevated temperature when hydrolysis is complete. Ultrafiltration of the hydrolysate may additionally remove any larger peptide chains which were not digested by the enzyme; these peptide chains may be harmful to the cells and therefore their removal may be beneficial. The temperature elevation used to deactivate the enzyme may also sterilize the resulting hydrolysate. If the enzyme is removed by ultrafiltration, it may retain at least partial catalytic activity and thus may be recycled for another round of hydrolysis. Ultrafiltration or thermal deactivation may also be used to remove active enzyme molecules from hydrolysates prepared by immobilized enzymes, in the event that some of the enzyme detaches from the solid support and dissolves into the reaction mixture.

The solid support may be formed by, for example, silica, epoxide resin, cellulose, chitosan, glass wool, alginate, or by other appropriate materials. The solid support may be in the form of porous or solid beads, sponge, fibers, or other suitable configuration. The solid support may have a large surface area to volume ratio to allow the binding of a large amount of enzyme. For example, beads of porous silica or any other suitable material with a diameter in the range of 1 $\mu$m to 10000 $\mu$m, or in the range of 10 $\mu$m to 1000 $\mu$m, or in the range of 20 $\mu$m to 500 $\mu$m, may be used as a solid support for enzyme immobilization. Immobilization may be achieved, for example, by functionalizing the silica bead surface with amino groups and using a crosslinking agent, such as glutaraldehyde, to bind the enzyme to the solid support. Other functional groups, like aldehyde or epoxy groups, may be also used for enzyme immobilization. The amino groups in this aspect of the invention are covalently bonded to glutaraldehyde, after which excess glutaraldehyde is removed and the enzyme is added. The amino groups on the surface of the enzyme then bind the remaining free aldehyde groups of the glutaraldehyde molecules on the silica bead surface. The immobilization may be performed in water or a suitable aqueous buffer. Thanks to the porous nature and large surface area of the silica beads, a relatively high amount of enzyme may be immobilized relative to the weight of the solid support.

The enzymes according to the invention may be, for example, ALCALASE® serine endopeptidase enzyme (protease from *Bacillus licheniformis*), FLAVOURZYME® proteolytic enzyme blend (protease from *Aspergillus oryzae*) or PROTAMEX® enzyme preparation, or their combination. Any other appropriate proteolytic enzymes or their combinations may be used.

Water, or a suitable aqueous buffer, may be used to dissolve the protein source for the hydrolysis. Some proteins may require a buffer to adjust the pH to a level where they have better solubility. The pH may be in the range of 2 to 12, or in the range of 6 to 10, or in the range of 7.5 to 8.5. A very dilute buffer, or no buffer at all, may be used so that the resulting hydrolysate may be added to the final culture media at high concentrations while minimizing its impact on media osmolarity.

The buffer may include, for example, potassium phosphate, sodium bicarbonate, or any other appropriate buffer.

The concentration of protein may be in the range of 1 g/l to 100 g/l, or in the range of 2 g/l to 30 g/l, or in the range of 3 g/l to 20 g/l.

In one aspect of the invention, the concentration of potassium phosphate buffer in the range of 10 mM to 100 mM, or in the range of 20 mM to 40 mM, or in the range of 25 mM to 35 mM may be used for pH adjustment to dissolve the soy protein to a concentration in the range of 3 g/l to 50 g/l, or in the range of 4 g/l to 40 g/l, or in the range of 5 g/l to 20 g/l. In another aspect of the invention, the soy protein is dissolved in distilled water to a concentration in the range of 1 g/l to 100 g/l, or in the range of 3 g/l to 50 g/l, or in the range of 6 g/l to 20 g/l.

Other concentrations of the source protein may be used, however very high concentrations of source protein lead to incomplete dissolving of the protein and formation of a highly viscous colloidal solution, presenting problems for the hydrolysis and further processing, while low concentrations of protein may limit the speed of the hydrolysis reaction.

In one aspect of the invention, the source protein may be added at a higher concentration than the maximum soluble concentration. This additional protein may be dissolved after the protein concentration in solution is decreased due its hydrolysis by the enzyme. This results in high concentration of available substrate during the entire process, potentially improving hydrolysis efficiency. Multiple cycles of substrate addition into the same reaction mixture may be performed. In one aspect of the invention a base or a suitable buffer may be added to counteract the change and keep the enzyme in its pH optimum.

The key parameter for efficient conversion of the hydrolysate into cell biomass is the degree of hydrolysis, defined as the percentage of peptide bonds in the source protein that are hydrolyzed during the reaction. A higher degree of hydrolysis corresponds to a larger percentage of the source protein converted into free amino acids or short peptides, which are usable by mammalian cells as nutrition. Mammalian cells are incapable of absorbing and digesting proteins and longer peptides. Peptides longer than four amino acids, or in other words heavier than approximately 500 Daltons, have very poor absorption by mammalian cells. In various aspects of the invention, the amount of the source protein in the range of 20% to 100%, in the range of 30% to 70%, or in the range of 40% to 60% may be converted into free amino acids and short peptides smaller than 500 Da.

Enzymes used for hydrolysis may fall into two general categories: exoproteases and endoproteases. Exoproteases cleave the protein or peptide chains at the ends, whereas endoproteases can cleave peptide bonds in the middle of the chain. In one aspect of the invention, a combination of endoproteases and exoproteases may be used, since endoproteases may create more free ends of peptide chains, increasing the efficiency of exoproteases, and exoproteases are more efficient in hydrolyzing the protein to single amino acids. In one aspect of the invention, endoproteases and exoproteases may be used sequentially in this order to maximize hydrolysis efficiency.

In one aspect of the invention, additional enzymes may be added to the reaction mixture after the beginning of hydrolysis. This may be done with the same enzyme, mainly in order to counteract the gradual decrease in its enzymatic activity due to degradation of the enzyme molecule. In one aspect of the invention, enzymes with a higher pH optimum may be added at the start of the hydrolysis, when pH is higher, and enzymes with a lower pH optimum may be added later, when the pH is lower, thus maximizing the efficiency of the respective enzymes. pH tends to decrease naturally during hydrolysis due to the increase in the amount of carboxylic groups.

Regardless of whether immobilized or free enzyme is used, sufficient mixing of the reaction mixture is important to achieve high efficiency. In the case of immobilized enzymes, this applies to both the enzyme immobilization and protein hydrolysis steps. In one aspect of the invention, in the case of immobilized enzymes, mixing methods which minimize mechanical damage to the solid carriers should be used. These may include roller mixing, shaking, or low-shear impellers such as hydrofoil or elephant ear impellers. In the case of enzymes immobilized to a large solid support, sufficient perfusion of the support with the reaction mixture must be assured.

The mixing of the protein source, e.g. protein isolate, with water, or with a suitable aqueous buffer, dissolving the protein source and the process of hydrolysis itself may be performed in appropriate reaction vessel or a tank, for example in a laboratory or industrial reactor.

The reactor for hydrolysis may be for example a batch reactor, continuous stirred tank reactor, or plug flow reactor. The reactor volume may be in the range of 0.1 l to 100 000 l, or in the range of 0.3 l to 15,000 l, or in the range of 1 l to 5 000 l.

The mixing may be provided by the appropriate stirrer, for example paddle impeller. The elephant-ear impeller may be used. The outer diameter of stirrer or impeller may be in the range of $\frac{1}{10}$ to $\frac{9}{10}$ of the inner reactor diameter, or in the range of $\frac{3}{10}$ to $\frac{8}{10}$ of the inner reactor diameter, or in the range of $\frac{4}{10}$ to $\frac{7}{10}$ of the inner reactor diameter, for example $\frac{2}{3}$ of the inner reactor diameter. Stirrer or impeller may be located in the center of the reactor or outside of the center of the reactor.

The reaction components may be added to the reactor manually, or based on gravity from the storage vessel connected to the reactor, or using a pumping system. The source protein may be in a liquid solution or in a form of powder and may be added to the reactor manually or automatically.

The storage tanks may be made for example of stainless steel or glass. The volume of the storage tank may be in the range of 100 ml to 5 m, or in the range of 2 l to 3 m, or in the range of 500 l to 1 m$^3$.

The reactor may be equipped with different types of sensors, such as for example thermal sensor, pH probe, conductometer, or any other type of appropriate sensor according to the needs of the process of hydrolysis. The pH may be monitored during the whole procedure by a pH electrode. The reactor temperature may be regulated for example with a reactor thermal jacket, which may be equipped with a heating coil and/or heating/cooling medium.

For precise monitoring of the degree of hydrolysis a sampling system may be used. The degree of hydrolysis may be monitored by titration and/or by absorbance measurement, for example at a wavelength in the range of 190 nm to 350 nm, or 190 nm to 230 nm.

The system for protein source hydrolysis may be equipped with pipes, pumps, control unit, programmable logic controller and the like.

For the purpose of filtration, for example for removing impurities, for separation of enzyme immobilized on a carrier from the reaction solution, or for separation of larger peptides from hydrolysate, may be used appropriate filtration device equipped with filtration materials. The filtration material may be, for example, filtration fabrics, ceramics, glass, membranes or other suitable materials. The size of pores in filtration material may be for example, but not limited to, 500 μm to 10 μm for filtration, 10 μm to 0.1 μm for microfiltration, 0.1 μm to 1 nm for ultrafiltration and 1 nm to 0.1 nm for nanofiltration. The membranes characterized with the range of 60 kDa to 500 Da may be used.

In one aspect of the invention, hydrolysis by free enzymes may be performed by dissolving the protein substrate. This protein substrate may be, for example, whole biomass, protein concentrate or protein isolate from soy, pea, rice, wheat, wheat gluten, corn, fava beans, alfalfa, hemp, chickpea, potato, pumpkin, rapeseed, red lentil, rice, *spirulina, chlorella*, sunflower, water lentil, mung bean or yeast, or another suitable protein source. The concentration of protein solution may be in the range of 3 g/l to 50 g/l, or in the range 10 g/l to 30 g/l, or in the range of 15 g/l to 25 g/l. For a given volume of the protein solution, the ALCALASE® serine endopeptidase enzyme may be added in concentration in the range of 0.0001 g/l to 5 g/l, or in the range of 0.001 g/l to 2 g/l, or in the range of 0.01 g/l to 0.5 g/l. The resulting solution has a basic pH, allowing for a high activity of ALCALASE® serine endopeptidase enzyme. The temperature may be in the range of 50° C. to 70° C., or in the range 55° C. to 65° C., or in the range of 58° C. to 62° C. Over a period of constant mixing, which may be in the range of 30 minutes to 24 hours, or in the range of 1 hour to 12 hours, or in the range of 2 hours to 8 hours, the pH of the solution decreases as the results of the hydrolysis of peptide bonds and increased number of carboxylic groups. This allows for a high activity of FLAVOURZYME® proteolytic enzyme blend, which may be added at a concentration in the range 0.0002 g/l to 10 g/l, or in the range 0.003 g/l to 6 g/l, or in the range of 0.01 g/l to 0.5 g/l to the reaction mixture. The resulting mixture may then be incubated for an additional time period in the range of 1 hour to 48 hours, or in the range of 5 hours to 24 hours, or in the range of 8 hours to 12 hours at temperature in the range of 30° C. to 80° C., or in the range of 40° C. to 70° C., or in the range of 50° C. to 60° C., with constant mixing, after which the residual enzyme is thermally deactivated. With this procedure, 20% to 100%, 30% to 70%, or 40% to 60% of the source protein may be converted into free amino acids.

The ratio of enzyme to substrate may be optimized to decrease the amount of enzyme, which is the most expensive component. For example, the total amount of enzyme used may be in the range 20% to 0.0002%, or in the range 6% to 0.05%, or in the range of 1% to 0.1% of the total amount of source protein used.

The protein hydrolysis may be carried out with immobilized enzyme in an amount in the range of 0.01 g to 10 g, or in the range of 0.25 g to 1.8 g, or in the range of 0.5 g to 1.5 g on 10 grams of enzyme carrier. The enzyme carrier may be made from glass, porous silica, alginate, epoxy methacrylate, chitosan, or from any other suitable material, in the form of beads, wool, sponge, fibers, or in any other suitable form. The enzyme carrier may be, for example, formed by glass beads, porous silica beads, alginate beads, epoxy methacrylate beads, glass wool, chitosan, or any other suitable enzyme carrier. Suitable enzyme carriers are described in more detail in the chapter "Hydrolysate preparation—general description". For example, 1 gram of immobilized enzyme on 10 grams of porous silica beads may be used.

The immobilized enzymes may be prepared by suspending a setweight of $NH_2$-functionalized porous silica microbeads in the setweight of distilled water. The ratio of set weight of $NH_2$-functionalized porous silica microbeads versus distilled water may be in the range of 1:1 to 1:10000, or in the range of 1:10 to 1:1000, or in the range of 1:20 to 1:100. Silica beads are further activated with the addition of glutaraldehyde. The amount of glutaraldehyde added to the reaction mixture may be in the range of 0.01 mmol to 70 mmol, or in the range of 0.05 mmol to 40 mmol, or in the range of 0.1 mmol to 10 mmol of glutaraldehyde per 1 g of silica beads. The excess glutaraldehyde is washed away, and the silica beads are resuspended, for example, in half the original volume. ALCALASE® serine endopeptidase enzyme is then added to a final concentration with constant stirring. This procedure may immobilize 10% to 100%, 60% to 90%, or 70% to 80% of the used enzyme on the silica beads. This may correspond to 10 gram to 100 grams, 30 grams to 60 grams, or 40 grams to 50 grams of enzyme immobilized per 1 kilogram of silica beads.

In one aspect of the invention, silica beads with immobilized ALCALASE® serine endopeptidase enzyme may be added to a soy protein solution in distilled water. The amount of silica beads with immobilized ALCALASE® serine endopeptidase enzyme may be, for example, in the range of 10 g/l to 20 g/l, or in the range of 12 g/l to 18 g/l, or in the range of 14 g/l to 16 g/l, or any other appropriate amount. After hydrolysis, for 2 hours at 62° C. with constant mixing for example, the beads bound to ALCALASE® serine endopeptidase enzyme may be removed by centrifugation. Silica beads with immobilized FLAVOURZYME® proteolytic enzyme blend are added in the amount, for example, in the range of 4 g/l to 40 g/l, or in the range of 5 g/l to 30 g/l, or in the range of 10 g/l to 20 g/l. The appropriate time of hydrolysis may be, for example, in the range of 10 minutes to 24 hours, or in the range of 30 minutes to 12 hours, or in the range of 1 hour to 6 hours. The temperature of hydrolysis may be in the range of 10° C. to 90° C., or in the range of 25° C. to 80° C., or in the range of 50° C. to 70° C. In another aspect of the invention, ALCALASE® serine endopeptidase enzyme beads may not be removed at this step and may instead be removed at the end of the process. In yet another aspect of the invention, ALCALASE® serine endopeptidase enzyme and FLAVOURZYME® proteolytic enzyme blend beads may have different sizes, facilitating their separation after removal from the solution. In another aspect of the invention, FLAVOURZYME® proteolytic enzyme blend beads may be added at the start of hydrolysis or at any other point during the hydrolysis. After further hydrolysis, for a time period which may be in the range of 1 hour to 24 hours, or in the range of 6 hours to 20 hours, or in the range of 10 hours to 14 hours, at a temperature which may be in the range of 20° C. to 90° C., or in the range of 30° C. to 80° C., or in the range of 40° C. to 60° C., for example 55° C. with constant mixing, the FLAVOURZYME® proteolytic enzyme blend beads are removed by centrifugation and the resulting hydrolysate is thermally sterilized, which also deactivates any enzyme which could have detached from the solid support. After filtration to remove solid debris, the hydrolysate can be used to prepare culture media. With this method, the amount of source protein in the range of 20% to 100%, or in the range of 30% to 95%, or in the range of 40% to 90%, may be converted into cell-usable products, meaning free amino acids or peptides of 500 Da or less.

Since ALCALASE® serine endopeptidase enzyme and FLAVOURZYME® proteolytic enzyme blend are quite stable in their immobilized form, they may be recycled in the hydrolysate production process according to the invention. In one aspect of the invention, the silica beads with immobilized ALCALASE® serine endopeptidase enzyme may be used for 2 to 50, 5 to 40, or 10 to 30 cycles of hydrolysis while maintaining around half of their original catalytic activity. In another aspect of the invention, silica beads with immobilized FLAVOURZYME® proteolytic enzyme blend can be used for 2 to 50, 5 to 40, or 10 to 30 hydrolysis cycles while maintaining sufficient catalytic activity. Generally, even though immobilized enzymes tend to be more stable than free enzymes, their enzymatic activity decreases with use. Therefore, in later cycles, duration of the reaction or enzyme to substrate ratio may be changed to maintain a consistent quality of the resulting hydrolysate.

The culture medium according to the invention may comprise an optimized ratio of amino acids, sourced from a protein hydrolysate for example, in combination with at least one type of compounds selected from a group comprising: sugars, vitamins and organic micronutrients, mineral compounds, iron supplementation compounds, organic amines, and shear protectants, or a combination thereof. The media may also contain other compounds, like fatty acids, phospholipids, or nucleic acids, for example. Media according to the invention with an optimized ratio of amino acids and other nutrients may facilitate a lower production of harmful waste metabolites, such as ammonia or lactate, by the cells.

An optimized ratio of amino acids is such that essential amino acids may be present in any ratio, where the highest possible conversion efficiency for essential amino acids is in the range of 5% to 100%, or in the range of 20% to 90%, or in the range of 30% to 80%. The term "highest possible conversion efficiency" determines what percent of the essential amino acids provided to the cells can be converted into cellular protein, assuming no loss of amino acids to catabolism, conversion to other compounds (nucleic acids, for example), or spontaneous degradation. The highest possible conversion efficiency is determined by the essential amino acid that is the most limiting to the cells. It is calculated such as that for all individual essential amino acids added to the medium in any form at any time point during the cultivation process, the content of that particular essential amino acid in the culture media as a fraction of total essential amino acid content added in any form at any time point to the culture media is divided by the content of that individual amino acid in cellular protein as a fraction of total content of essential amino acids in the lowest obtained ratio, in other words the ratio for the essential amino acid which forms the lowest percentage of the amino acids added to the medium in comparison to the percentage of that particular amino acid in cellular biomass, is then multiplied by 100 to obtain the highest possible conversion efficiency of the provided essential amino acids into cellular protein. All percentages in the calculation of highest possible conversion efficiency are percentages by weight. The amino acids in the culture media may be present in the form of free amino acids or peptides. Non-essential amino acids are omitted in this calculation, as they can be synthesized by the cells and thus are not limiting in terms of the highest possible conversion efficiency. An example of possible essential amino acid content in cellular protein can be seen in the Table 8 below.

The above description may be summarized by the following equation:

$$H_{EAA} = \frac{\dfrac{A_{EAAM}}{\sum A_{EAAM}}}{\dfrac{A_{EAAC}}{\sum A_{EAAC}}} * 100,$$

where $H_{EAA}$ is the highest conversion efficiency for a particular amino acid, $A_{EAAM}$ is the content of that particular essential amino acid in media, $\Sigma A_{EAAM}$ is the total content of all essential amino acids in culture media, $A_{EAAC}$ is the content of that particular essential amino acid in cellular protein and $\Sigma A_{EAAC}$ is the total content of all essential amino acids in cellular protein.

An example calculation for the essential amino acid tryptophan would proceed as follows: let's assume that the total amount of tryptophan added to the culture media over the period of cultivation was 2 grams, and the total amount essential amino acids added to the media over the same time period was 100 grams. From Table 8, we know that in 100 grams of cellular protein, out of 44.7 grams of total essential amino acids, 1.6 grams are tryptophan.

We calculate:

$$H_{EAA} = \frac{\dfrac{2}{100}}{\dfrac{1.6}{44.7}} * 100 = 55.875\%$$

We have calculated that the highest conversion efficiency for tryptophan is 55.875%. Now, we repeat this process for each of the nine individual essential amino acid. The lowest of nine numbers we obtain is the final highest conversion efficiency.

If the amino acid content in the example in Table 1 is used, the resulting amounts used in the media over the whole cultivation process for each essential amino acid given as grams per 100 grams of total essential amino acids used in the media over the whole cultivation process may be in the ranges summarized in the Table 9.

TABLE 8

| example of possible essential amino acid content in the cellular protein | |
|---|---|
| Amino acid | content [g/100 g cellular protein] |
| His | 2.7 |
| Ile | 5.1 |
| Leu | 8.9 |
| Lys | 8.2 |
| Met | 2.9 |
| Phe | 4.7 |
| Thr | 4.8 |
| Trp | 1.6 |
| Val | 5.8 |
| Sum | 44.7 |

TABLE 9

| ranges of concentrations of amino acids in grams per 100 grams of total essential amino acids used in the media | | | |
|---|---|---|---|
| Amino acid | range 1 | range 2 | range 3 |
| His | 0.30 to 6.04 | 1.21 to 5.44 | 1.81 to 4.83 |
| Ile | 0.57 to 11.41 | 2.28 to 10.27 | 3.42 to 9.13 |
| Leu | 1.00 to 19.91 | 3.98 to 17.92 | 5.97 to 15.93 |
| Lys | 0.92 to 18.34 | 3.67 to 16.51 | 5.50 to 14.68 |
| Met | 0.32 to 6.49 | 1.30 to 5.84 | 1.95 to 5.19 |
| Phe | 0.53 to 10.51 | 2.10 to 9.46 | 3.15 to 8.41 |
| Thr | 0.54 to 10.74 | 2.15 to 9.66 | 3.22 to 8.59 |
| Trp | 0.18 to 3.58 | 0.72 to 3.22 | 1.07 to 2.86 |
| Val | 0.65 to 12.98 | 2.60 to 11.68 | 3.89 to 10.38 |

However, the composition of cell biomass is somewhat variable, and therefore the values for each essential amino acid in terms of weight percentage of total essential amino acids used in the media may also be in the ranges summarized in the Table 10.

TABLE 10

| ranges of weight percentage concentration of total essential amino acids used in the media | | | |
|---|---|---|---|
| Amino acid | range 4 | range 5 | range 6 |
| His | 0.2 to 7.9 | 0.8 to 7.1 | 1.2 to 6.3 |
| Ile | 0.3 to 14.9 | 1.5 to 13.4 | 2.3 to 11.9 |
| Leu | 0.7 to 25.9 | 2.7 to 23.3 | 4.1 to 20.8 |
| Lys | 0.6 to 23.9 | 2.5 to 21.5 | 3.8 to 19.1 |
| Met | 0.2 to 8.5 | 0.9 to 7.6 | 1.3 to 6.8 |
| Phe | 0.3 to 13.7 | 1.4 to 12.3 | 2.2 to 11.0 |
| Thr | 0.3 to 14.0 | 1.5 to 12.6 | 2.2 to 11.2 |
| Trp | 0.1 to 4.7 | 0.5 to 4.2 | 0.7 to 3.8 |
| Val | 0.4 to 16.9 | 1.8 to 15.2 | 2.7 to 13.5 |

The culture medium according to the invention may comprise soy protein enzymatic hydrolysate, or any other appropriate scalable hydrolysate according to the description of hydrolysates and preparation thereof, as mentioned above. For example, the suitable industrially scalable protein sources for hydrolysate preparation may include soy, pea, rice, wheat, wheat gluten, corn, fava beans, alfalfa, hemp, chickpea, potato, pumpkin, rapeseed, red lentil, rice, *Spirulina, Chlorella*, sunflower, water lentil, mung bean or yeast. The present invention is not limited to the listed exemplary protein sources.

The total dry weight of hydrolysate added to the culture media may be in the range of 1 g/l to 200 g/l, or in the range of 3 g/l to 100 g/l, or in the range of 10 g/l to 50 g/l.

The culture medium according to the invention may comprise amino acids added separately, like methionine, for example. The total amount of amino acids added in addition to the amino acids from hydrolysate may be in the range of 0.02 g/l to 30 g/l, or in the range of 0.05 g/l to 10 g/l, or in the range of 0.1 g/l to 5 g/l.

As a sugar may be used at least one compound selected from the group: glucose, fructose, galactose, sucrose, lactose, maltose, or a combination thereof, or any other appropriate saccharide. Sugars may be added to the culture media in an amount in the range of 1 g/l to 200 g/l, or in the range of 3 g/l to 100 g/l, or in the range of 10 g/l to 50 g/l.

The media may contain at least one of or any combination of the following ions as a mineral compound: $Ca^{2+}$, $Cl^-$, $Cu^{2+}$, $SO_4^{2-}$, $Fe^{3+}$, $NO_{3-}$, $Fe^{2+}$, $Mg^{2+}$, $K^+$, $Na^+$, $CO_3^{2-}$, $HCO_{3-}$, $H_2PO_{4-}$, $HPO_4^{2-}$, $PO_4^{3-}$, $Zn^{2+}$, $SeO_3^{2-}$. The media may also contain trace amounts of other mineral compounds and elements, such as cobalt, iodine or manganese. As the media is prepared by dissolving different constituent compounds in water, any appropriate chemical compound may be used as long as it dissociates to the desired ions in aqueous solution. For example, NaCl and KCl both produce a $Cl^-$ ion when dissolved. As another example, $CuSO_4$ and $MgCl_2$ or $MgSO_4$ and $CuCl_2$ may be used to produce $Cu^{2+}$, $Mg^{2+}$, $SO_4^{2-}$ and $Cl^-$ ions. Assuming equimolar amounts, the resulting aqueous solution will have the same composition for both combinations of compounds used. The total amount of mineral compounds added to the culture media may be in the range of 0.1 g/l to 50 g/l, or in the range of 1 g/l to 20 g/l, or in the range of 3 g/l to 10 g/l.

As a vitamin may be used at least one compound selected from: vitamin B12, biotin, choline, pantothenic acid, folic acid, niacinamide, pyridoxine, riboflavin, thiamine, i-inositol, or a combination thereof. Any appropriate bioactive derivatives or precursors of these compounds may be used. For example, cyanocobalamin may be used instead of vitamin B12, as it can be readily converted to bioactive vitamin B12 by the cells. As another example, thiamine hydrochloride (chloride salt form of thiamine) may be used instead of thiamine. The total amount of vitamins added to the media, in terms of vitamins added separately and omitting the vitamins present in lysate or extracts, may be in the range of 0.001 mg/l to 1000 mg/l, or in the range of 0.1 mg/l to 100 mg/l, or in the range of 1 mg/l to 20 mg/l.

As an organic amine may be used at least one compound selected from: putrescine, ethanolamine, or a combination thereof, or any other appropriate amine. Organic amines may be added to the culture media in an amount in the range of 0.01 mg/l to 1000 mg/l, or in the range of 0.1 mg/l to 100 mg/l, or in the range of 0.5 mg/l to 20 mg/l.

Vitamins and organic amines or their respective precursors or derivatives may be supplied in the form of a lysate or extract, for example autolysed yeast extract or any other appropriate lysate or extract. Extract or lysate for supplementation of micronutrients may be added to the culture media in an amount in the range of 0.01 g/l to 20 g/l, or in the range of 0.1 g/l to 10 g/l, or in the range of 0.5 g/l to 5 g/l.

Iron may be supplemented by, for example, ferric citrate or any other appropriate source of iron. Ferric citrate, or another iron supplementation compound, may be added to the culture media in an amount in the range of 1 mg/l to 10000 mg/l, or in the range of 10 mg/l to 1000 mg/l, or in the range of 50 mg/l to 200 mg/l.

As a shear protectant may be used for example polyethylene glycol (PEG), carboxymethyl cellulose (CMC), dextran sulfate, or any other appropriate shear protectant or their combination. The shear protectant may be added to the culture media in an amount in the range of 0% to 5%, 0.01% to 2%, or 0.02% to 1% by weight.

In one aspect of the invention, the culture medium may comprise composition as described in Table 13.

In one aspect of the invention hydrolysis by free enzyme was performed by dissolving soy protein isolate in distilled water to a concentration of 10 g/l and the addition of ALCALASE® serine endopeptidase enzyme to a concentration of 0.05 g/l. The ALCALASE® serine endopeptidase enzyme used was supplied by Novozymes company. The resulting solution had a basic pH, allowing for a high activity of ALCALASE® serine endopeptidase enzyme at 62° C. Over 2 hours with constant mixing, the pH of the solution decreased as the results of the hydrolysis of peptide bonds and increased number of carboxylic groups. These conditions allowed for a high activity of-FLA-VOURZYME® proteolytic enzyme blend, which was added to a concentration of 0.15 g/l. The resulting mixture was then incubated for additional 20 hours at 62° C. with constant mixing, after which the residual enzyme was thermally deactivated. With this procedure, 43% of the source protein was converted into free amino acids.

Results of HPLC analysis of amino acid content using UV detection (cysteine was not measured in this analysis) are summarized in Table 11.

TABLE 11

HPLC analysis of amino acid content in hydrolysate

| Amino acid | mg/l |
|---|---|
| Asp | 136.45 |
| Glu | 253.40 |
| Asn | 388.74 |
| Ser | 248.59 |
| Gln | 170.42 |
| His | 147.57 |
| Gly | 80.27 |
| Thr | 226.47 |
| Arg | 426.90 |
| Ala | 138.12 |
| Tyr | 210.82 |
| Met | 56.30 |
| Val | 286.39 |
| Cystine | 8.46 |
| Trp | 60.30 |
| Phe | 296.79 |
| Ile | 260.56 |
| Leu | 469.37 |
| Lys | 381.21 |
| Pro | 31.25 |
| Sum | 4288.91 |

In one aspect of the invention the immobilized enzymes were prepared by suspending a 600 mg of $NH_2$-functionalized porous silica microbeads in 50 ml of distilled water. Silica beads were further activated with the addition of 0.003% by volume of glutaraldehyde.

After 30 minutes, excess glutaraldehyde was washed away with distilled water and the silica beads were suspended in half the original volume. The ALCALASE® serine endopeptidase enzyme, supplied by Novozymes company, was then added to a final concentration of 0.1% with constant stirring. This procedure immobilized 80% of the used enzyme on the silica beads, corresponding to 4 grams of enzyme immobilized per 1 kilogram of silica beads.

The silica beads with immobilized ALCALASE® serine endopeptidase enzyme were added to a soy protein solution of 13 g/l in distilled water at a density of 10 grams of beads per liter. After hydrolysis for 2 hours at 62° C. with constant mixing, the beads with ALCALASE® serine endopeptidase enzyme were removed by centrifugation and 40 grams of silica beads with immobilized FLAVOURZYME® proteolytic enzyme blend were added. After further hydrolysis for 20 hours at 62° C. with constant mixing, the FLA-VOURZYME® proteolytic enzyme blend beads were removed by centrifugation and the resulting hydrolysate was thermally sterilized for 20 minutes at 130° C. and pressure of 2.5 atmospheres, which also deactivated any enzyme that may have detached from the solid support. After filtration to remove solid debris, the hydrolysate was used to prepare culture media. With this method, 5% of the source protein was converted into free amino acids.

Results of HPLC (UV detection) analysis of amino acid content (cysteine was not measured in this analysis) are summarized in Table 12.

TABLE 12

HPLC analysis of amino acid content in hydrolysate

| Amino acid | Soy, water (mg/l) |
|---|---|
| Asp | 15.33 |
| Glu | 0.00 |
| Asn | 1.51 |
| Ser | 5.86 |
| Gln | 10.57 |
| His | 14.04 |
| Gly | 68.39 |
| Thr | 0.00 |
| Arg | 21.31 |
| Ala | 32.71 |
| Tyr | 36.01 |
| Met | 11.58 |
| Val | 36.01 |
| Cystine | 4.33 |
| Trp | 8.08 |
| Phe | 123.73 |
| Ile | 33.87 |
| Leu | 204.85 |
| Lys | 51.05 |
| Pro | 1.35 |
| Sum | 680.59 |

TABLE 13 example content of relevant compounds in the culture media according to the invention

| Compound | Category | Concentration in media [mg/l] |
|---|---|---|
| Biotin | vitamins and low-abundance organic compounds | 0.0035 |
| Choline chloride | vitamins and low-abundance organic compounds | 8.9800 |
| D-Calcium pantothenate | vitamins and low-abundance organic compounds | 2.2400 |
| Folic Acid | vitamins and low-abundance organic compounds | 2.6500 |
| Niacinamide | vitamins and low-abundance organic compounds | 2.0200 |
| Pyridoxine hydrochloride | vitamins and low-abundance organic compounds | 2.0130 |
| Riboflavin | vitamins and low-abundance organic compounds | 0.2190 |

TABLE 13-continued

| | example content of relevant compounds in the culture media according to the invention | |
|---|---|---|
| Compound | Category | Concentration in media [mg/l] |
| Thiamine hydrochloride | vitamins and low-abundance organic compounds | 2.1700 |
| Vitamin B12 | vitamins and low-abundance organic compounds | 0.6800 |
| i-Inositol | vitamins and low-abundance organic compounds | 12.6000 |
| Calcium Chloride (CaCl$_2$) (anhydrous) | mineral compounds | 116.6000 |
| Cupric sulfate (CuSO$_4$•5H$_2$O) | mineral compounds | 0.0800 |
| Ferric Nitrate (Fe(NO$_3$)$_3$•9H$_2$O) | mineral compounds | 0.0500 |
| Ferrous sulfate (FeSO$_4$•7H$_2$O) | mineral compounds | 0.4170 |
| Magnesium Chloride (anhydrous) | mineral compounds | 28.6400 |
| Magnesium Sulfate (MgSO$_4$) (anhydrous) | mineral compounds | 48.8400 |
| Potassium Chloride (KCl) | mineral compounds | 311.8000 |
| Sodium Bicarbonate (NaHCO$_3$) | mineral compounds | 2,438.0000 |
| Sodium Chloride (NaCl) | mineral compounds | 6,995.5000 |
| Sodium Phosphate dibasic (Na$_2$HPO$_4$) (anhydrous) | mineral compounds | 71.0200 |
| Sodium Phosphate monobasic (NaH$_2$PO$_4$•H$_2$O) | mineral compounds | 62.5000 |
| Zinc sulfate (ZnSO$_4$•7H$_2$O) | mineral compounds | 0.4320 |
| Sodium selenite | mineral compounds | 0.0300 |
| Soy protein enzymatic hydrolysate | amino acids | 1,000.0000 |
| Ferric citrate | iron supplementation | 120.0000 |
| Glucose | sugars | 3150.0000 |
| Putrescine | organic amines | 1.0000 |
| Ethanolamine | organic amines | 3.0000 |

The cultivation system may comprise features that decrease energy consumption and resource usage while maximizing the cell biomass yield. Cell biomass yield may be characterized by a maximum operative cell density, i. e. the maximum yield obtained by the cultivation of the non-human metazoan cells in a cell density approaching its allowable value considering respective non-human metazoan cells.

At least part of the process of cell cultivation may take place in a device with a smaller volume than the volume of the cultivation device, for example in a seeding tank. Optionally, the seeding tank may be used in order to multiply cells before their inoculation into the cultivation device.

Figure 14:
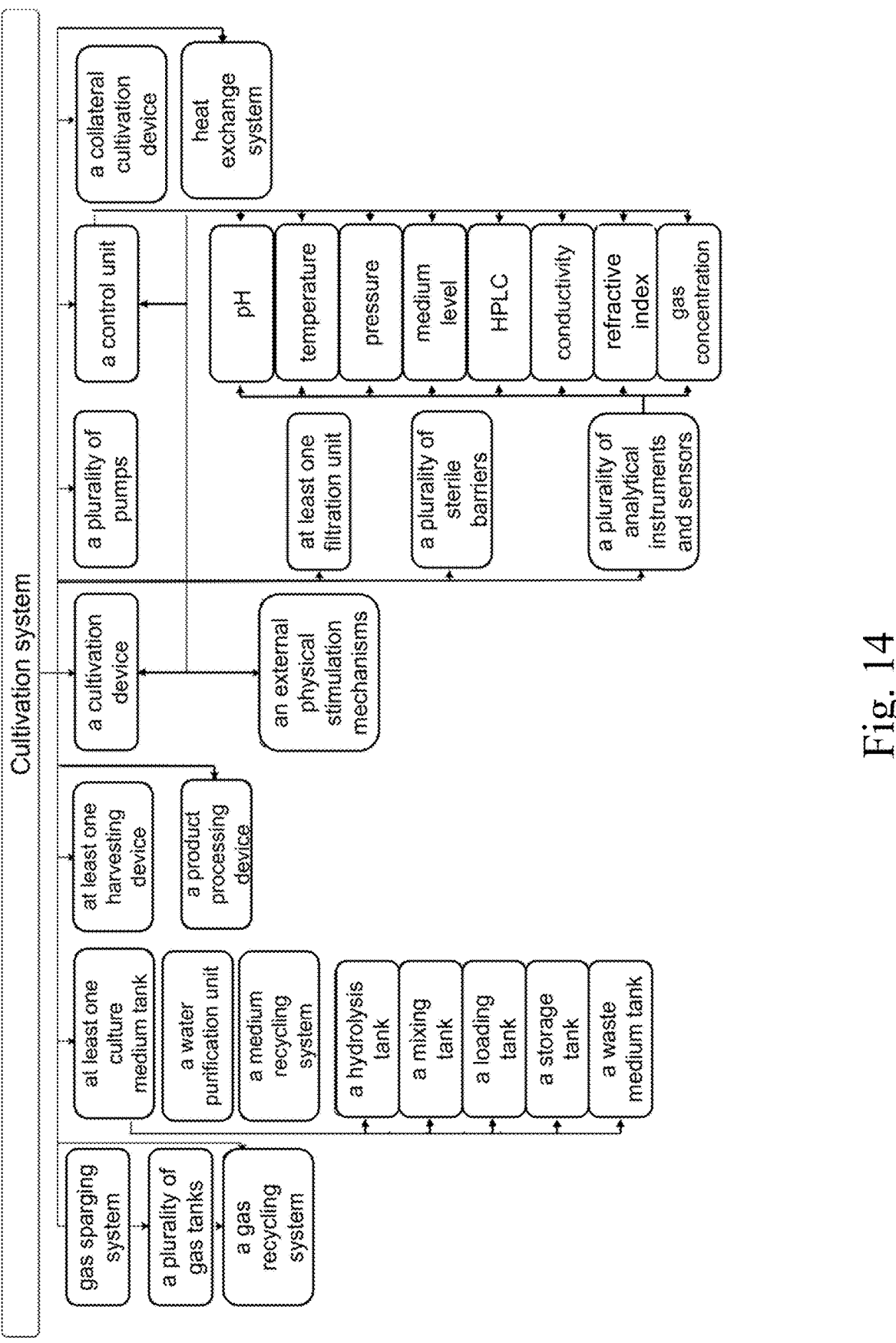
FIG. 14—illustrates the cultivation system and all component of the cultivation system FIG. 15—illustrates the cultivation steps FIG. 16—illustrates one aspect of the invention comprising a gas sparging system.

The cultivation system may comprise at least one of: culture medium tanks for the preparation of the culture medium, and cultivation device for the cell cultivation and features to produce a product as depicted in FIG. 14. The cultivation system may further comprise at least one of the following features: at least one filtration unit; a plurality of sterile barriers; a plurality of pumps; a plurality of analytical instruments and sensors; a gas sparging system comprising a plurality of gas tanks; a gas recycling system; at least one culture medium tank comprising a hydrolysis tank, a mixing tank, a loading tank, a storage tank and a waste medium tank; a water purification unit; a medium recycling system; a heat exchange system; a collateral cultivation device; at least one harvesting device; a control unit (the term "control unit" and "control device" may be interchangeable); an external physical stimulation mechanisms; and a product processing device.

In one aspect of the invention, the filtration unit may be configured to filter solid parts of the protein hydrolysate or the culture medium. The cultivation system may comprise at least one filtration unit or at least one pump. The filtration unit may comprise at least one filter selected from the group of membrane filters, depth filters, mesh filters, activated carbon filters, ceramic filters, centrifugal filters, ultrafiltration filters, nanofiltration filters, ion exchange filters, cross-flow (tangential flow) filters, adsorption filters or fiber filters. The filter of the filtration unit may comprise at least one material selected from the group of cellulose, glass fiber, polyethersulfone (PES), polyvinylidene fluoride (PVDF), nylon, polypropylene, polyethylene terephthalate (PET), polytetrafluoroethylene (PTFE), polyacrylonitrile (PAN), polyvinyl chloride (PVC), stainless steel, silica, alumina, silicon carbide, titanium dioxide, zeolites, or synthetic polymers. The filter may be housed in a housing configured to cover the whole filter, wherein the housing may comprise at least one material selected from the group of stainless steel, polycarbonate, polyethylene, or other suitable biocompatible and sterilizable materials. The pore size of the filter may be in a range of 0.001 μm to 1 μm, in a range of 0.01 μm to 1 μm, in a range of 0.1 μm to 1 μm, in a range of 0.2 μm to 1 μm, in a range of 0.3 μm to 1 μm, in a range of 0.4 μm to 1 μm, in a range of 0.5 μm to 1 μm, in a range of 0.6 μm to 1 μm, in a range of 0.7 μm to 1 μm, in a range of 0.8 μm to 1 μm or in a range of 0.9 μm to 1 μm. The size of the pore may vary according to the selected type of filter and the specific requirements of the filtration. The configuration of the filtration unit may be configured according to the scale of the cultivation system, according to the flow rate of the filtered protein hydrolysate or the culture medium and according to the composition of the protein hydrolysate or the culture medium. The filtration unit may further include sealing mechanisms such as O-rings, gaskets, clamps or any other sealing mechanisms capable of preventing leakage and maintaining a sterile environment. The sealing mechanisms of the filtration unit may comprise materials such as silicone, ethylene propylene diene monomer, or polytetrafluoroethylene. The filtration unit may further comprise auxiliary components selected from the group of pumps, pressure sensors, flow meters, valves and means for monitoring the filtration process.

The product processing device may be a mixer, grinder, press, cold-press, extruder, chopper, power heater, lyophilizer, steamer, blender, cooker, boiler, dryer, vacuum dryer, grill, roaster and/or any other product processing device.

The cultivation device may comprise at least one bioreactor e.g. culture vessel, which is an apparatus connected to the control unit of the cultivation device in which a set of biological, biochemical and chemical reactions and/or cultivation processes are carried out in the culture medium using cultivation methods. The terms "culture vessel" and "cultivation vessel" may be interchangeable.

The culture medium refers to a solution (e.g. aqueous solution) that may comprise at least one type of compound selected from the group of sugars, amino acids, peptides, organic amines, minerals, vitamins, fats, fatty acids, growth factors, and/or shear protectants. The culture medium may be prepared in at least one culture medium tank. The culture medium tanks may comprise at least one tank from the group of mixing tank, hydrolysis tank, storage tank, loading tank and/or waste medium tank.

In one aspect of the invention, the hydrolysis tank may be configured to provide an environment for the hydrolysis reaction. The cultivation system may comprise at least one hydrolysis tank. The hydrolysis tank may comprise a main body constructed from at least one material selected from stainless steel, glass-lined steel, titanium, polyethylene, polypropylene, polytetrafluoroethylene or any other suitable materials. The main body may comprise various shapes, such as cylindrical or rectangular or any other suitable geometries. The hydrolysis tank may comprise insulation configured as an outer jacket of the hydrolysis tank, wherein the space between the outer jacket and the wall of the hydrolysis tank may be filled with an appropriate insulation material or medium. The hydrolysis tank may further comprise at least one input and at least one output for loading and unloading the ingredients. The input of the hydrolysis tank may be configured as a shaft, wherein the shaft may be used for loading the ingredients. The hydrolysis tank may further comprise a heating system configured to heat the inner environment of the hydrolysis tank. The hydrolysis tank may comprise mixing mechanisms comprising at least one stirrer, paddle or any other instrument capable of mixing the protein hydrolysate. The sealing mechanisms of the hydrolysis tank may comprise materials such as silicone, ethylene propylene diene monomer, and polytetrafluoroethylene. The hydrolysis tank may be configured to withstand a maximum temperature of at least 100° C. The hydrolysis tank may further comprise auxiliary components selected from the group of pumps, pressure sensors, flow meters, valves and means for monitoring the hydrolysis reaction.

In one aspect of the invention, the cultivation system may comprise at least one storage tank for storing the culture medium. The storage tank may provide a sterile environment. The storage tank may comprise a main body constructed from at least one material selected from stainless steel, glass-lined steel, titanium, polyethylene, polypropylene, polytetrafluoroethylene or any other suitable materials. The storage tank may further comprise auxiliary components selected from the group of pumps, pressure sensors, flow meters, valves and means for monitoring the state of the culture medium. The storage tank may further comprise at least one input and at least one output for loading and unloading the ingredients. The storage tank may further comprise mixing mechanisms comprising at least one stirrer, paddle or any other instrument capable of mixing the culture medium. The sealing mechanisms of the storage tank may comprise materials such as silicone, ethylene propylene diene monomer, or polytetrafluoroethylene. The storage tank may comprise a heating system configured to heat the inner environment of the storage tank or may comprise a cooling system configured to cool the inner environment of the storage tank.

The cultivation processes comprise all processes that take place in the cultivation device, starting from the inoculation of the cells into a cultivation device and ending with the harvesting of the cell biomass. The cultivation processes may comprise the phases such as growth, maintenance and/or proliferation of the cultured non-human metazoan cells.

The cultivation device may have the inner volume of culture vessel in a range of 1 l to 1,000,000 l, or in a range of 10 l to 50,000 l, or in a range of 20 l to 30,000 l, or in the range of 100 l to 5,000 l, or in the range of 1,000 l to 4,000 l, or in the range of 1,500 l to 3,500 l, or in the range of 2,000 l to 3,000 l. The maximum working volume of the culture vessel may be in a range of $\frac{1}{2}$ to $\frac{19}{20}$ of the whole volume of the culture vessel. The culture vessel dimensions ratio of width to height may be in a range of 20:1 to 1:20, or a range of 15:1 to 1:15, or a range of 10:1 to 1:10 or a range of 5:1 to 1:5, for example 1:1, 1:2, 1:3 or 1:4.

The methods for sterilization of the cultivation device may comprise hot steam sterilization, UV sterilization, chemical sterilization, irradiation or any combination thereof Materials used for the cultivation device may comprise at least one of: AISI 304 stainless steel, AISI 316 stainless steel, AISI 309 stainless steel, AISI 310 stainless steel, AISI 430 stainless steel, Inconel® 600, Monel® 400, Nickel 200, Hastelloy® C276, Hastelloy® C22, Hastelloy® X, titanium, ceramics, polylactic acid, polyvinyl acetate, polycaprolactone, polystyrene, polyvinylchloride, glass and/or any other suitable material that is not toxic to said metazoan cells and at the same time is inert to the culture medium, cell metabolites and other substances considered.

The inner surface of the cultivation device may be modified so the cells do not adhere to the inner surface of the cultivation device. The inner surface of the cultivation device may be modified by a coating with at least one substance selected from the group of proteins e.g. extracellular matrix proteins, glycoproteins, laminins (e.g. laminin 111, laminin 121, laminin 211, laminin 221), collagens (e.g. collagen I, collagen II, collagen III, collagen IV), nidogen, entactin, PIPAAm (Poly(N-isopropylacrylamide), gelatin (synthetic, porcine, salmon) and/or any other appropriate coating.

The cultivation device may comprise a heating system and cooling system configured to increase and decrease the temperature in the cultivation device. The heating system may comprise an electrical heater, infrared heater and/or a heat pump. All aforementioned may be configured to transfer heat to an outer jacket of the cultivation device. Analogically, the cooling system may be used to decrease the temperature by chiller, cool air and/or cold water. Both heating system and cooling system may be coupled with the control unit and may be a part of heat exchange system.

The gas sparging system comprises a plurality of gas tanks and spargers. The gas tanks comprise at least one gas selected from the group of the following: hydrogen, carbon dioxide, oxygen, nitrogen, and air. The sparger may be used to deliver gas into a cultivation device and may be designed as a tube, ring, frittage, mesh and/or any other design compatible with the cultivation device. The gas sparging system may comprise 1 to 15 spargers per 1,000 Ll of the cultivation device, or preferably 2 to 10 spargers per 1,000 l of the cultivation device volume, or more preferably 4 to 8 spargers per 1,000 l of the cultivation device volume, or even more preferably 5 to 6 spargers per 1,000 l of the cultivation device volume. The spargers may be positioned within the cultivation device 101. More specifically, spargers may be positioned in the middle, in the bottom and/or on the side of the culture vessel. The gas flow of all the gasses may be controlled by a plurality of mass flow controllers and/or rotameters connected between the cultivation device and the gas sparging system. The gas sparging system may be coupled with the control unit.

The sparger may have a pore size in the range of 0.1 mm to 6 mm, or in the range of 1 mm to 5 mm, or in the range of 2 mm to 4 mm. The spargers may have the ability to provide the gas exit velocity in the range of 0.01 m/s to 3 m/s, or in the range of 0.1 m/s to 2.5 m/s, or in the range of 0.5 m/s to 2.5 m/s, or in the range of 1 m/s to 2 m/s or in the range of 1.5 m/s to 2 m/s. The size of the bubbles sparged into the cultivation device may be uniform for all bubbles and may be in a range of 0.1 mm to 6 mm.

In another aspect of the invention, the gas sparging system may be configured to produce the bubbles with at least two different sizes, i.e. in a multimodal regime, wherein sparged gas bubbles have a multimodal distribution. The gas sparging system may be configured to sparge both small and large bubbles, which may be beneficial to sufficiently aerate the mixture inside the cultivation device while sufficiently providing the gas to the non-human metazoan cells and not mechanically disrupting and/or damaging the cells due to bubble burst caused by energy dissipation.

The small bubbles may have a size in the range of 0.1 mm to 2 mm, or in the range of 0.2 mm to 1.9 mm, or in the range of 0.3 mm to 1.8 mm, or in the range of 0.4 mm to 1.7 mm, or in the range of 0.5 mm to 1.6 mm, or in the range of 0.6 mm to 1.5 mm, or in the range of 0.7 mm to 1.4 mm, or in the range of 0.8 mm to 1.3 mm, or in the range of 0.9 mm to 1.2 mm, or in the range of 1.0 mm to 1.1 mm;
and the big bubbles,
which may have a size in the range of 2.0 mm to 6.0 mm, or in the range of 2.1 mm to 5.9 mm, or in the range of 2.2 mm to 5.8 mm, or in the range of 2.3 mm to 5.7 mm, or in the range of 2.4 mm to 5.6 mm, or in the range of 2.5 mm to 5.5 mm, or in the range of 2.6 mm to 5.4 mm, or in the range of 2.7 mm to 5.3 mm, or in the range of 2.8 mm to 5.2 mm, or in the range of 2.9 mm to 5.1 mm, or in the range of 3.0 mm to 5.0 mm, or in the range of 3.1 mm to 4.9 mm, or in the range of 3.2 mm to 4.8 mm, or in the range of 3.3 mm to 4.7 mm, or in the range of 3.4 mm to 4.6 mm, or in the range of 3.5 mm to 4.5 mm, or in the range of 3.6 mm to 4.4 mm, or in the range of 3.7 mm to 4.3 mm, or in the range of 3.8 mm to 4.2 mm, or in the range of 3.9 mm to 4.1 mm.
Having both small and large bubbles sparged together may be beneficial, because the smaller bubbles have higher capability of transferring into liquid (higher mass transfer coefficient) and tend to coalesce into larger bubbles, which causes less mechanical damage to the cells due to a bubble burst than a plurality of small bubble bursting. The large bubbles also tend to form less foam above the liquid phase inside the cultivation device.

Foam may be produced during cultivation processes by dispersing the non-human metazoan cells in the liquid medium, which is forming above the liquid phase in the gaseous phase. The foam may be removed, or at least partially removed, or disrupted or at least partially disrupted. The foam may be eliminated with anti-foaming agents, foam breakers, foam traps and/or ultrasound. The anti-foaming agents used to mitigate the effects of the foam forming above the liquid phase may comprise at least one substance of the following: methylcellulose, ethoxyethylcellulose, carboxymethylcellulose (CMC), poloxamer 188, polyethylene glycol (PEG), polypropylene glycol, dextran, dextran sulfate, polyvinyl alcohol, or any other appropriate shear protectant, their derivatives and/or their combination.

The operation of the cultivation device may be divided into two groups. First—productive operation comprising cultivation of the non-human metazoan cells. Second—non-productive operation comprising cleaning and sterilizing. Those operations from the second group may be performed using a unit for cleaning in place and a unit for sterilization in place. The cultivation device 101 and the components of the cultivation system may be sanitized and/or cleaned using at least one cleaning agent selected from the group of: sodium hydroxide, potassium hydroxide, ethanol, isopropanol, detergents, ionic surfactants and/or tenzides.

The cultivation device may comprise a plurality of ports for various functions. One of the ports may be an inoculation port used for inoculating the non-human metazoan cells into the cultivation device and/or to the culture medium. The cultivation device may further comprise a sampling port used for obtaining the samples from the cultivation device used for further analysis. Other ports within the cultivation device may be used for real-time instrumental analysis. In another aspect of the invention, the cultivation device may comprise a plurality of inputs and outputs for the removal of cell biomass. The inputs and outputs may be used for any other transfer from and to the cultivation device. The cultivation device may further comprise safety features, such as safety valves, sudden stop mechanism, protection barrier, decontamination shower and/or any other safety measures needed for safe operation.

In one aspect of the invention, the cultivation system may comprise an external physical stimulation mechanism, which is capable of influencing the biological, biochemical and chemical reactions inside the cultivation device. The exposure of cultivated non-human metazoan cells to an external physical stimulation may influence cell proliferation, differentiation, cell cycle progression, growth rate, enzyme activities, membrane structure and cellular transformation. The external physical influence is capable of permeating through cells and changing the electric field of the cell membrane, which can cause biological changes, especially changes in the ion efflux between the inner and outer space of the cells. The external physical stimulation mechanisms are based on exposure to at least one source of energy selected from the group of acoustic waves, electromagnetic waves, electric current, magnetic fields and/or any other energy source. The external physical stimulation mechanisms may be positioned inside and/or outside the cultivation device and may be applied globally or locally to a cultivated non-human metazoan cell population, wherein local application refers to application to a volume of the cultivation device that is smaller than the volume of the whole cultivation device. In addition, ultrasound may be used to externally stimulate the cultivated non-human metazoan cell population and may also mitigate the formation of foam above the liquid phase in the cultivation device, i. e. in the non-working volume of the cultivation device.

The cells may be stimulated using magnetic fields comprising impulses in monophasic, biphasic or polyphasic shape. The impulse duration may be in a range of 1 microseconds to 1000 microseconds, 10 microseconds to 1000 microseconds, 15 microseconds to 950 microseconds, 100 microseconds to 900 microseconds. The impulses may be assembled in the train. The impulses within the train may be modulated in amplitude or frequency to create various envelopes e.g. rectangular, triangle, trapeze and/or staircase. The train duration may be in the range of 0.1 seconds to 120 seconds, or in a range of 0.5 seconds to 50 seconds, or in a range of 1 seconds to 20 seconds. The repetition rate of impulses may be in a range of 1 Hz to 300 Hz and the intensity of the field may be in the range of 0.01 mT to 7 T, or in the range of 0.1 mT to 6 T, or in the range of 0.5 mT to 5 T, or in the range of 0.8 mT to 4 T. The intensity is measured on the coil surface.

The cells may also be stimulated using acoustic waves having characteristics of ultrasound, infrasound and/or audible sound. The acoustic waves, infrasound and/or ultrasound may have the frequency in the range of 0.01 Hz to 2,000 kHz and power density in the range of 1 mW/cm$^2$ to 10 W/cm$^2$.

The cells may also be stimulated by radio waves and/or microwaves having a frequency in the range of 3 kHz to 300 GHz.

The cells may also be stimulated using light stimulation having wavelengths in a range of 500 nm to 1,200 nm and the intensity in the range of 1 J/cm$^2$ to 20 J/cm$^2$. The light stimulation mechanism may be laser, LED, bulb and/or lamp.

The cells may also be stimulated electrically by applying DC voltage. In addition, the cells may be exposed to the biphasic, sinusoidal, saw tooth, square wave, pulsed and/or continuous mode of electrical stimulation. The frequency of electrical stimulation may be in the range of 5 Hz to 600 kHz. The strength of the electric field applied may be in the range of 0.5 µV/mm to 10 V/mm. The electric current density of said electric fields may be in the range of 0.001 A/m$^2$ to 10 A/m$^2$.

All above mentioned parameters of the external physical stimulation are measured at the surface of the source, for example, at the coil surface, or at the light source surface (e. g. LED surface, lamp surface, or bulb surface).

External physical stimulation may be used periodically or independently during every phase of the cultivation processes. The external physical stimulation may be repeated in a period of 1 second, 5 seconds, 10 seconds, 15 seconds, 20 seconds, 30 seconds, 45 seconds, 1 minute, 2 minutes, 5 minutes, 10 minutes, 15 minutes, 20 minutes, 30 minutes, 45 minutes, 1 hour, 2 hours, 3, hours, 4 hours, 8 hours, 16 hours, 24 hours, 32 hours, 48 hours, 72 hours, 96 hours, 120 hours, 144 hours and/or 168 hours. The external physical stimulation may be repeated at least once during the cultivation cycle.

In order to provide the proper transport of the nutrients inside the cultivation device, aeration of the mixture inside the cultivation device may be applied, where no so-called "dead zones" form. The cultivation device may comprise a plurality of aeration utilities selected from the group of baffles, impellers and/or agitators. The proper aeration is crucial to safely distribute the nutrients to the cells while not mechanically damaging the cells or negatively affecting the cell processes. The control unit of the cultivation device may be configured to regulate the aeration of the culture medium. The aeration may be dynamically changed according to the rheological properties of the mixture. The control unit may be configured to regulate the aeration of the culture medium. The rheological properties of the mixture considered may comprise the density, kinematic, dynamic viscosity, shear stress, shear rate, surface tension and/or elasticity. Said rheological properties of the mixture may be measured by a rheometer using sample obtained from the cultivation device.

The cultivation system may comprise at least one impeller. The impeller may have a radial shape, axial-rushton shape, leaf shape, pitched-blade shape, marine shape, angled shape, flat blade shape, curved blade shape, tilted blade shape, shrouded shape, pitched curved blade shape, reversed pitch shape, gate shape, finger shape, double motion shape, helix shape, anchor shape, elephant ear shape, spin filter shape, packed-bed basket shape and/or toroid shape.

The baffles may be positioned on the inner wall of the cultivation device and may be perpendicular or substantially (e.g. from 70° to 110°) to the wall or may be pointing from the inner wall of the cultivation device. There may be at least 2 baffles in the cultivation vessel and maximum 10 baffles, wherein the baffles are usually in even quantity 2, 4, 6 and 8; or may be in odd quantity evenly distributed to obtain regular aeration and/or transport processes within the cultivation device.

The cultivation device may comprise at least one sensor or analytical instrument that is connected to a control unit of the cultivation system. The values sensed by sensors and analytical instruments may comprise pH, total and partial pressure, temperature, refractive index, osmolality, osmolarity, conductivity, liquid level density, foam level, total cell density, live cell density (viability), optical density, dissolved gas concentration, lactate concentration and/or concentration of any substance within the cultivation device. The control unit may comprise a PCB and/or microprocessor that may be configured to run a software.

The pH may be measured using a glass electrode probe, a calomel electrode probe, a ion-sensitive field-effect transistor (ISFET) and/or may be measured by conductivity measurement. The aforementioned probes and/or instruments may be positioned within the cultivation device, or the measurement may be performed using samples obtained from the sampling port. Accordingly, the measurement may be real-time if the pH analysis is performed using the instrumentalization within the cultivation device. The optimal pH value inside the cultivation device may be in a range of 4.0 to 10; in a range of 4.1 to 10; in a range of 4.2 to 10; in a range of 4.3 to 10; in a range of 4.4 to 10; in a range of 4.5 to 10; in a range of 4.6 to 10; in a range of 4.7 to 10; in a range of 4.8 to 10; in a range of 4.9 to 10; in a range of 5.0 to 10; in a range of 5.1 to 10; in a range of 5.2 to 10; in a range of 5.3 to 10; in a range of 5.4 to 10; in a range of 5.5 to 10; in a range of 5.6 to 10; in a range of 5.7 to 10; in a range of 5.8 to 10; in a range of 5.9 to 10; in a range of 6.0 to 10; in a range of 6.1 to 10; in a range of 6.2 to 10; in a range of 6.3 to 10; in a range of 6.4 to 10; in a range of 6.5 to 10; in a range of 6.6 to 10; in a range of 6.7 to 10; in a range of 6.8 to 10; in a range of 6.9 to 10; in a range of 7.0 to 10; in a range of 7.1 to 10; in a range of 7.2 to 10; in a range of 7.3 to 10; in a range of 7.4 to 10; in a range of 7.5 to 10; in a range of 7.6 to 10; in a range of 7.7 to 10; in a range of 7.8 to 10; in a range of 7.9 to 10; in a range of 8.0 to 10; in a range of 8.1 to 10; in a range of 8.2 to 10; in a range of 8.3 to 10; in a range of 8.4 to 10; in a range of 8.5 to 10; in a range of 8.6 to 10; in a range of 8.7 to 10; in a range of 8.8 to 10; in a range of 8.9 to 10; in a range of 9.0 to 10; in a range of 9.1 to 10; in a range of 9.2 to 10; in a range of 9.3 to 10; in a range of 9.4 to 10; in a range of 9.5 to 10; in a range of 9.6 to 10; in a range of 9.7 to 10; in a range of 9.8 to 10; in a range of 9.9 to 10; in a range of 4.0 to 4.1; in a range of 4.1 to 4.2; in a range of 4.2 to 4.3; in a range of 4.3 to 4.4; in a range of 4.4 to 4.5; in a range of 4.5 to 4.6; in a range of 4.6 to 4.7; in a range of 4.7 to 4.8; in a range of 4.8 to 4.9; in a range of 4.9 to 5.0; in a range of 5.0 to 5.1; in a range of 5.1 to 5.2; in a range of 5.2 to 5.3; in a range of 5.3 to 5.4; in a range of 5.4 to 5.5; in a range of 5.5 to 5.6; in a range of 5.6 to 5.7; in a range of 5.7 to 5.8; in a range of 5.8 to 5.9; in a range of 5.9 to 6.0; in a range of 6.0 to 6.1; in a range of 6.1 to 6.2; in a range of 6.2 to 6.3; in a range of 6.3 to 6.4; in a range of 6.4 to 6.5; in a range of 6.5 to 6.6; in a range of 6.6 to 6.7; in a range of 6.7 to 6.8; in a range of 6.8 to 6.9; in a range of 6.9 to 7.0; in a range of 7.0 to 7.1; in a range of 7.1 to 7.2; in a range of 7.2 to 7.3; in a range of 7.3 to 7.4; in a range of 7.4 to 7.5; in a range of 7.5 to 7.6; in a range of 7.6 to 7.7; in a range of 7.7 to 7.8; in a range of 7.8 to 7.9; in a range of 7.9 to 8.0; in a range of 8.0 to 8.1; in a range of 8.1 to 8.2; in a range of 8.2 to 8.3; in a range of 8.3 to 8.4; in a range of 8.4 to 8.5; in a range of 8.5 to 8.6; in a range of 8.6 to 8.7; in a range of 8.7 to 8.8; in a range of 8.8 to 8.9; in a range of 8.9 to 9.0; in a range of 9.0 to 9.1; in a range of 9.1 to 9.2; in a range of 9.2 to 9.3; in a range of 9.3 to 9.4; in a range of 9.4 to 9.5; in a range of 9.5 to 9.6; in a range of 9.6 to 9.7; in a range of 9.7 to 9.8; in a range of 9.8 to 9.9; in a range of 9.9 to 10.0.

The pH inside the cultivation device may be regulated by at least one way of the following:

adding $CO_2$ in the cultivation device;

adding at least one basic substance selected from the group of sodium bicarbonate, sodium carbonate, sodium hydroxide, potassium hydroxide and/or any other basic substance;

adding at least one acidic substance selected from the group of hydrochloric acid, sulfuric acid, formic acid; wherein the amount of added substance may be in an amount that would decrease the pH value by at least 0.1, 0.2, 0.3, 0.4 and/or 0.5.

The pH inside the culture vessel may be regulated also using buffer solutions selected from the group of phosphate buffers, bicarbonate buffers, Good's buffers, McIlvaine Buffer and/or Britton-Robinson buffer.

The temperature may be monitored and controlled in each part of the cultivation system. The temperature may be measured using a thermometer, thermal conductivity detector (TCD), resistance temperature detector (RTD), infrared thermometer, and/or thermographic camera. Said instruments for the temperature measurement may be positioned within the cultivation device or outside the cultivation device. The optimal temperature in the cultivation system varies throughout every part of the cultivation system.

The temperature in the cultivation device may be in a range of 20.0° C. to 40.0° C.; in a range of 20.5° C. to 40.0° C.; in a range of 21.0° C. to 40.0° C.; in a range of 21.5° C. to 40.0° C.; in a range of 22.0° C. to 40.0° C.; in a range of 22.5° C. to 40.0° C.; in a range of 23.0° C. to 40.0° C.; in a range of 23.5° C. to 40.0° C.; in a range of 24.0° C. to 40.0° C.; in a range of 24.5° C. to 40.0° C.; in a range of 25.0° C. to 40.0° C.; in a range of 25.5° C. to 40.0° C.; in a range of 26.0° C. to 40.0° C.; in a range of 26.5° C. to 40.0° C.; in a range of 27.0° C. to 40.0° C.; in a range of 27.5° C. to 40.0° C.; in a range of 28.0° C. to 40.0° C.; in a range of 28.5° C. to 40.0° C.; in a range of 29.0° C. to 40.0° C.; in a range of 29.5° C. to 40.0° C.; in a range of 30.0° C. to 40.0° C.; in a range of 30.5° C. to 40.0° C.; in a range of 31.0° C. to 40.0° C.; in a range of 31.5° C. to 40.0° C.; in a range of 32.0° C. to 40.0° C.; in a range of 32.5° C. to 40.0° C.; in a range of 33.0° C. to 40.0° C.; in a range of 33.5° C. to 40.0° C.; in a range of 34.0° C. to 40.0° C.; in a range of 34.5° C. to 40.0° C.; in a range of 35.0° C. to 40.0° C.; in a range of 35.5° C. to 40.0° C.; in a range of 36.0° C. to 40.0° C.; in a range of 36.5° C. to 40.0° C.; in a range of 37.0° C. to 40.0° C.; in a range of 37.5° C. to 40.0° C.; in a range of 38.0° C. to 40.0° C.; in a range of 38.5° C. to 40.0° C.; in a range of 39.0° C. to 40.0° C.; in a range of 39.5° C. to 40.0° C.

Similarly to the temperature measurement, the pressure may also be monitored and controlled in each part of the cultivation system. The pressure may be measured using a manometer which may be positioned in a vicinity of each part of the cultivation device to ensure the proper transfer of the gaseous and liquid components. Operation of the mass flow controllers may be controlled by the control unit of the cultivation device. A plurality of the mass flow controllers may be positioned between the gas sparging system, the gas recycling system and the cultivation device.

The cultivation device may be able to withstand an internal pressure of at least 0.1 kPa compared to atmospheric pressure. The cultivation device may be able to withstand a ratio of internal pressure and atmospheric pressure in a range of 0.00001 to 10, wherein the ratio may be defined as the ratio between the internal pressure and atmospheric pressure.

In one aspect of the invention, the liquid level may be monitored and controlled in each part of the cultivation system. The liquid level may be measured using a pressure transmitter, ultrasonic sensor, conductivity sensor, float sensor, ultrasonic or radar sensor, capacitance sensor, weight sensor and/or others. The liquid level may be constant throughout the whole cultivation or it could change.

The control unit may be coupled with any component within the cultivation system. The control unit may control and/or regulate every process taking place within the cultivation system.

The control unit may be operated using at least one PCB and/or microprocessor with software capable of controlling the cultivation device, regardless of the extensions and scale of the system. The PCB unit may be connected to at least one central data storage. The cultivation system may comprise one or more subcontrol units.

In another aspect of the invention, in order to increase the efficiency of the cultivation system as previously mentioned, nutrients may be continuously loaded into the cultivation device within the culture medium according to refractometry, conductometry, spectrophotometry and/or HPLC measurement of nutrients in the culture medium. The dynamic loading of the nutrients to the culture medium may be regulated according to the real time measurement and the state of the cultivation process, which is beneficial and highly efficient as the culture medium consumption is reduced by providing only needed nutrients to the culture medium. In another aspect of the invention, the regulation of the cultivation may be provided by the cultivation system, for example by the control unit. The regulation may comprise collection of at least one input parameter from at least one sensor, measuring device and/or probe. The regulation may further comprise assessment of the input parameter with a predetermined value. The regulation may further comprise providing the nutrients in the culture medium, optimizing the aeration in the cultivation device, optimizing the temperature and pressure and/or stopping the cultivation. The input parameter may comprise data from at least one measurement from the group of spectrophotometry, refractometry, conductometry and/or HPLC. The predetermined value may be set by the control unit according to the type of the cells, type of the culture medium, type of the cultivation device and/or other aspects of the cultivation system.

Spectrophotometry may be used to measure the turbidity and/or optical density. The spectrophotometer may be positioned within the cultivation device or may be positioned within the cultivation system. The turbidity and/or optical density depends on the length of the light path between the emitter and the sensor, the size of the cells and the cell culture density. Therefore, the spectrophotometer may be calibrated for each size of the cell, calibrated to fresh culture medium and/or calibrated to water used for the preparation of the culture medium or any combination thereof. The obtained data may be used as one of input parameters for the dynamic culture medium loading.

The cultivation process may be controlled using refractometry methods. The refractometer may be positioned inside or outside the cultivation device. The refractometry sample may be obtained from the sampling port if the refractometer is positioned outside. The refractometer may be calibrated to fresh culture medium or purified water. The data obtained from the refractometer may also be used to regulate the cultivation system according to cell density. The refractometry data may also be used to calibrate the cultivation processes according to the refractive index of the mixture during every phase of the cultivation. The refractometry measurement may be calibrated according to the glucose content of the culture medium, wherein the glucose content may correspond to a cell metabolism model, thus may be calibrated to the cell density during every phase of the cultivation.

The refractive index from the refractometer calibration data is then compared with the real refractive index of the present cultivation. The obtained data may be used as one of the input parameters for the dynamic culture medium loading.

The cell biomass may be further measured by conductometry. The conductivity of the cell biomass depends on the non-human metazoan cells, cell density and the culture medium composition. As the cultivation progresses, the nutrients solubilized in the culture medium are consumed by the cells, thus generally decreasing the conductivity due to the removal of nutrients that are charged when solubilized. The conductivity of the cell biomass may be used to calculate the cell density, whether it is determined empirically using statistical methods for each cell population cultivated or measured directly. The obtained data may be used as one of the input parameters for the dynamic culture medium loading.

The cultivation system may comprise an optical density probe, an impedance probe, a turbidimeter, a refractometer and/or a spectrophotometer to conduct previously mentioned methods of measurement. Further, the cultivation system may comprise any other sensor or probe known in the art to conduct relevant measurements (e.g. temperature sensor, pressure sensor, cell counter, mass spectrometer etc.).

The cultivation process may be controlled using liquid chromatography method HPLC. The HPLC may be used quantitatively and/or qualitatively to measure amino acids and their amounts in the culture medium before, after and/or during the cultivation.

The HPLC measurement of amino acids may be performed before the cultivation to measure the amino acid content of the source of amino acids and nutritional peptides. The HPLC measurement of amino acids may also be performed after the cultivation, which may be used for the determination of amino acids consumption by the cultivated non-human metazoan cells during the cultivation. Consumption of amino acids may be calculated by subtraction of the amino acid content of the culture medium before, after and/or during the cultivation.

The HPLC measurement of amino acids may focus on measuring the content of individual amino acids by acidic hydrolysis or basic hydrolysis of the sample derived from fresh or used culture medium. The HPLC measurement may use an absorbance detector and/or any MS detector. The obtained data may be used as one of the input parameters for the dynamic culture medium loading.

All aforementioned analysis methods may be used to determine the cell density. The cell density may be expressed as the number of cells per volume unit and/or as the mass of the cells per volume unit, i. e. the mass density.

In one aspect of the invention, in order to further increase the effectiveness of the cultivation system, the central data storage may be coupled to the controlling software using artificial intelligence and/or machine-learning algorithms. The cultivation device may comprise a Programmable Logical computer (PLC) and/or Supervisory Control and Data Acquisition (SCADA).

The abbreviation Q in the FIGS. 17, 19, 21, 23, 25, 27, 29 may represent any analytical instrument and/or sensor disclosed herein. The abbreviation T in the FIGS. 17, 19, 21, 23, 25, 27, 29 may represent the thermometer and the abbreviation P in the FIGS. 17, 19, 21, 23, 25, 27, 29 may represent the manometer. The abbreviation L in the FIGS. 17, 19, 21, 23, 25, 27, 29 may represent liquid level sensor.

For example, the predetermined temperature in the cultivation device is set for 37° C. The control unit receives a signal from the thermometer, wherein the signal indicates that the temperature inside the cultivation device is 25° C. The control unit sends the signal to the heating system of the cultivation device to heat the cultivation device to the set temperature of 37° C. After reaching the set temperature, the control unit receives another signal from the thermometer, wherein the signal indicates a reached temperature of 37° C. The control unit sends the signal to the heating system of the cultivation device to keep the set temperature.

In another example, the control unit may be coupled with the spectrophotometer. The spectrophotometer senses that the turbidity of the culture environment within the cultivation device has increased about 5% compared to the fresh culture medium, indicating that the cell density also increased about 5%. The control unit receives a signal from the spectrophotometer and sends another signal to the stirring unit of the cultivation device to decrease the rotations of the impeller, so the non-human metazoan cells are not mechanically damaged by the shear stress of the culture environment.

The harvesting device may be used to separate the cell biomass from the culture medium, i. e. to process the cell biomass. The cell mass may be harvested after at least one cultivation cycle, wherein the cultivation cycle varies according to the chosen cell population to be cultivated. The cultivation cycle may be the same as at least one portion of time needed to perform more than one cell doubling of the non-human metazoan cells, wherein the cell doubling corresponds to one cycle of the cell. The cultivation cycle may be at least 1 hour, 2 hours, 4 hours, 8 hours, 12 hours, 24 hours, 36 hours, 48 hours, 72 hours, 96 hours, 120 hours, 144 hours, 168 hours and/or 336 hours.

The harvesting device may include at least one filter, sieve, centrifuge or any other appropriate utility to process the cell biomass, where the water and other components of the culture medium may be removed. The cell biomass harvesting methods may further include membrane microfiltration, tangential-flow filtration (TFF) or crossflow filtration, flocculation, magnetic separation, acoustic separation and depth filtration, as well as specialized solutions coupling either microfiltration or centrifugation with TFF or depth filtration.

Centrifugation may be used within the processes. The technique uses the centrifugal force to separate cells from the suspension based on their density. Centrifugation may be used on a larger scale using larger centrifuges or multiple smaller centrifugation cycles. The type of centrifuge used may be, for example, batch centrifuge, decanter, tubular bowl centrifuge, disk stack centrifuge, or any other appropriate centrifuge type compatible with the cultivation system.

Filtration involves passing the cell suspension through a filter with defined pore sizes to separate cells from the liquid phase. Filtration may be scaled up by using larger filtration systems or by employing multiple parallel filtration units. The pore size of the filtration devices used in the processes according to the invention may be in the range of 0.01 μm to 5 μm, or in the range of 0.1 μm to 2 μm, or in the range of 0.5 μm to 1 μm.

Among other methods, crossflow filtration (Tangential Flow Filtration—TFF) may be used within the processes according to the invention. In TFF, the cell suspension flows tangentially across the filter membrane, allowing smaller molecules to pass through, while retaining cells on the surface. TFF may be scaled up by using larger filtration systems with appropriately sized membranes.

Another method that may be used within the processes according to the invention is flocculation. Flocculation involves the addition of chemicals that cause cells to aggregate and settle out of suspension. The scalability of flocculation methods depends on the specific chemicals used and the ability to control the flocculation process in larger volumes.

Magnetic cell separation may be applied for the purpose of harvesting non-human metazoan cells or a separation of the non-human metazoan cells. This method involves labeling cells with magnetic particles and using a magnetic field to separate the cells from the suspension. Magnetic cell separation may be scaled up by using larger magnetic separators or multiple parallel systems. Acoustic separation may be used as well. Acoustic methods use sound waves to separate cells based on their size and density. Acoustic separation may be scaled up by using larger acoustic devices or by incorporating multiple devices in parallel. Continuous perfusion systems may be used for the purpose of harvesting cells or cell separation within the processes according to the invention. In perfusion systems, fresh media is continuously added to the cell culture while waste media containing cells is removed.

Figure 15:
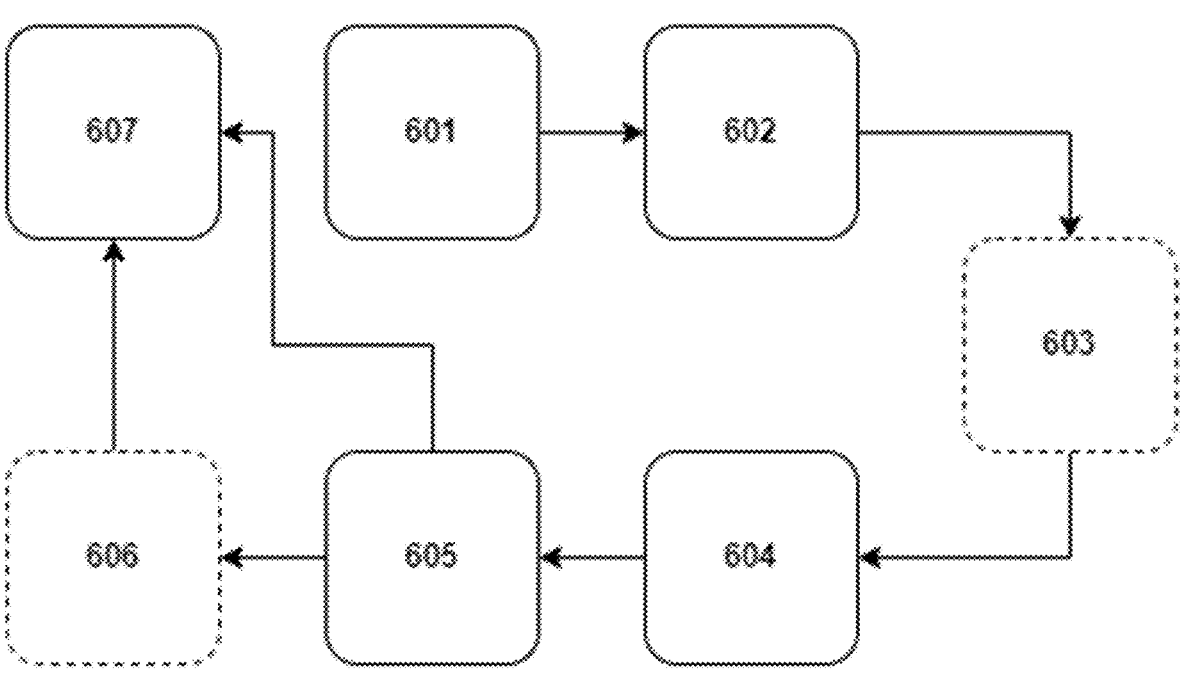

The term "cultivation methods" refers to the methods of all cultivation steps as depicted in the FIG. 15, starting from: 601 obtaining cells from metazoan tissue by biopsy and/or necropsy; and 602 isolating the non-human metazoan cells; and 603 modification of the properties of the non-human metazoan cell line, including but not limited to acclimatization, targeted or non-targeted selection of desirable mutants generated by spontaneous and induced mutagenesis, and genetic or epigenetic modification to produce a desirable loss or gain of function; and 604 inoculating the non-human metazoan cell population to the cultivation device; and 605 proliferating the non-human metazoan cell population in the cultivation device 101 and 606 differentiating the non-human metazoan cell population in the cultivation device; and 607 harvesting the non-human metazoan cell population to obtain cell biomass proper to be used as prerequisite to produce a meat-like food product suitable for human and/or animal consumption. The cultivated non-human metazoan cells may be used to produce any pharmaceutical.

The cultivation steps may not include all steps mentioned above, for example, steps 603 and 606 may be optional or may take place outside of the cultivation system. Also, steps 601, 602 and 603 may further optionally comprise cell isolation, separation, purification or any other similar appropriate processes to prepare the cell line. The scheme of the mandatory and optional cultivation steps is depicted in FIG. 15, wherein the interrupted lines represent the optional processes.

The optional modification of the properties of the non-human metazoan cells in step 603 may take place in another cultivation environment that is not a part of the present cultivation system. Similarly, the optional differentiation of the non-human metazoan cells in step 606 may take place in another cultivation environment. Cultivation may take place in a laboratory-scale environment using a cultivation device with a smaller volume than the volume of the cultivation device in the cultivation system. For example, these steps may take place in erlenmeyer flasks, T-flasks and/or multi-well plates.

The cultivation system may work under various conditions and may use various cultivation methods according to the selected non-human metazoan cells. The cells may be modified and/or adapted to proliferate, differentiate and/or mature under different conditions.

According to one aspect of the invention, the cultivation system may be able to perform anchorage-independent cultivation using suspension of single cells and/or cell aggregates. Also, the cultivation system may be able to perform anchorage-dependent cultivation using micro-carriers, macro-carriers and/or scaffolds.

The micro-carriers and/or macro-carriers may comprise a core and a coating, wherein the material used for the core and/or coating may have a polymeric character, preferably biopolymeric character. The materials that may be appropriate for the anchorage-dependent cultivation using micro-carriers and/or macro-carriers may be poly-lactic acid (PLA), polycaprolactone (PCL), poly(lactic-co-glycolic acid) (PLGA), polycaprolactone-co-lactic acid (PCLA), polyhydroxybutyrate (PHB), or protein: soy protein, pea protein, kidney bean protein, potato protein, or zein, or polysaccharide: methyl cellulose (MC), hydroxypropyl methylcellulose (HPMC), carboxymethyl cellulose (CMC), ethyl cellulose (EC), chitosan, carrageenan, xanthan gum, alginate, pectin, gellan gum, curdlan, polydextrose, pullulan, a polylysine, or any other appropriate material.

The cells may be adapted to form spheroids and/or organoids with the use of polymeric microfragments, using materials with (bio)polymeric character such as polyethylene terephthalate (PET), polycaprolactone (PCL), polytrimethylene terephthalate (PTT), polybutylene terephthalate (PBT), polyhydroxybutyrate (PHB), polyethylene naphthalate (PEN), poly(ethylene adipate) (PEA), poly(valerolactone) (PVL), poly(glycolic acid) (PGA), polyhydroxyal-kanoate (PHA), polybutylene adipate terephthalate (PBAT), polybutylene succinate (PBS), polyhydroxybutyrate (PHB), polyethylene glycol (PEG), polyvinylpyrrolidone (PVP), or any other appropriate polymer. The cells may also be adapted to form spheroids and/or organoids without the use of polymeric microfragments.

The cells may be adapted to grow on porous 3D structures known as scaffolds. The scaffolds are used to function as a template for tissue formation as they provide physical and biochemical conditions for the cells to adhere, proliferate and differentiate. The material origin for the scaffolds may be animal-derived or plant-derived, as well as synthetic materials. The scaffolds may have the characteristics of fibrous, filamentous, hydrogellic and/or 3D-printed material.

The cultivation system may perform the cultivation of non-human metazoan cells using different work modes, such as batch cultivation, fed-batch cultivation, continuous cultivation, semicontinuous cultivation and/or perfusion cultivation, or any other appropriate cultivation mode, according to the selected non-human metazoan cells to be cultivated and/or preferred cell cultivation conditions.

In the batch cultivation, all the nutrients within the culture medium are provided at the beginning and there is no further nutrient addition or waste removal during the process. In the fed-batch cultivation, part of the nutrients within the culture medium and/or culture medium volume is provided at the beginning of the cultivation and then the other part of the nutrients and/or culture medium volume is added during the cultivation in increments. In the semi-continuous cultivation, the whole culture medium and/or specific nutrients within the culture medium are periodically removed and replaced during the cultivation. In continuous cultivation, the whole culture medium and/or specific nutrients within the culture medium are continuously added and replaced. In addition to the continuous cultivation, the perfusion element may be implemented to retain at least some portion of the cultivated non-human metazoan cells that would otherwise be removed with waste medium. The waste medium may comprise residual cell mass, metabolites and/or unused nutrients.

The cultivated non-animal metazoan cells may have the characteristics and/or properties of: hepatocytes, myocytes, myoblasts, osteoblasts, fibroblasts, lipoblasts, odontoblasts, adult neuronal progenitor cells, neural stem cells, keratinocytes, multipotent stem cells from subventricular forebrain region, ependymal-derived neural stem cells, hematopoietic stem cells, liver-derived hematopoietic stem, marrow-derived stem cell, adipo-fibroblasts, adipose-derived stem cells, islet-cells producing stem cells, pancreatic-derived pluripotent islet-producing stem cells, mesenchymal stem cells, placenta cells, bone marrow stromal cells, muscle side population cells, bone marrow-derived recycling cells, blood-derived mesenchymal precursor cells, bone-marrow derived side population cells, muscle precursor cells, neural progenitor cells, multipotent adult progenitor cells, mesodermal progenitor cells, and spinal cord progenitor cells, induced pluripotent stem cells, embryonic stem cells, myofibroblasts, myosatellite cells, mixtures and any combinations thereof.

The cultivated non-human metazoan cells may be CHO, CHO-K1, CHO-DG44, MDBK, MDCK, C2C12, UMN-SAH/DF-1 or any other appropriate cell lines.

The cells may be modified to increase the efficiency of cultivation by the chosen cultivation methods, conditions and work modes described above. The methods of modification may be targeted genetic modifications or untargeted methods.

The untargeted methods of modification may comprise selecting the subpopulations of cells with desirable phenotypic characteristics from a parental cell population. Subpopulations with desirable characteristics may arise in the parental population through genetic or epigenetic changes. These may include changes in the duration of the cell cycle, average cell size, energetic and biosynthetic metabolism, signaling pathways, or any other changes which may make the cells more suitable for the production of comestible product. Such changes may be induced with non-targeted external stimuli, such as chemical mutagens, ionizing radiation, demethylating agents, or any other suitable external stimuli, or they may occur in the absence of any such stimuli. The subpopulations with desirable characteristics may be clonal (arising from a single progenitor cell) or non-clonal (arising from multiple progenitor cells). Methods of selection of desirable subpopulations from the parental population may include: fluorescence-activated cell sorting (FACS), magnetically-activated cell sorting (MACS), replica plating, prolonged cultivation under selective pressure such that the proportion of the desirable subpopulation in the overall population spontaneously increases over time through Darwinian selection, or any other suitable method of selection. At the end of the selection process, the proportion of cells in the overall population that have the desirable phenotypic characteristic is increased, preferably to over 90%, even more preferably to 100%.

The cell population of non-human metazoan cells may also undergo various combinations of adaptation steps, which may comprise adaptation to gain ability to grow in a suspension, ability to grow on scaffolds, ability to form spheroids and/or organoids, adaptation to grow in the absence of at least one of L-proline or L-glutamine, adaptation to cryopreservation, adaptation to grow in a relatively higher cell density, adaptation to a low-oxygen conditions, adaptation to serum-free medium, adaptation to protein-free medium, adaptation to low-protein medium, adaptation to mechanical stress and/or other adaptation processes leading to a beneficial gain of function in order to further increase the efficiency of the cultivation system.

The genetic modifications may comprise any gain and/or loss of function that may be hardly feasible using GM-free methods, e. g. cell lines adaptation. The genetic modifications may be used to prepare a stable cell line with desired characteristics. The characteristics may comprise the capability of continuous homogenous growth, reduced G1 phase of cell cycle in their proliferation phase, cell cycle around 24 hours in general, less than 24 hours in proliferation phase, no structural genomic changes during lifetime of population, minimal impact of epigenetic changes, consistent expression profile of cells correlating with their cell type, keeping differentiation potential and ability of induced differentiation, reduced requirements for media composition in terms of need of signaling factors, reduced requirements for media composition in terms of need of nutrition components, for example, amino acids, or maintaining their endogenous signalization, or any other desired and appropriate characteristics.

In one aspect of the invention, a model cellular metabolism and cell growth characteristics may be measured, analyzed and/or determined for each cell line. The model cellular metabolism and cell growth characteristics may be measured, analyzed and/or determined during proliferation and/or differentiation phases for its own designed media composition and the cultivation system regarding selected cultivation methods, work modes and/or conditions.

Figure 17:
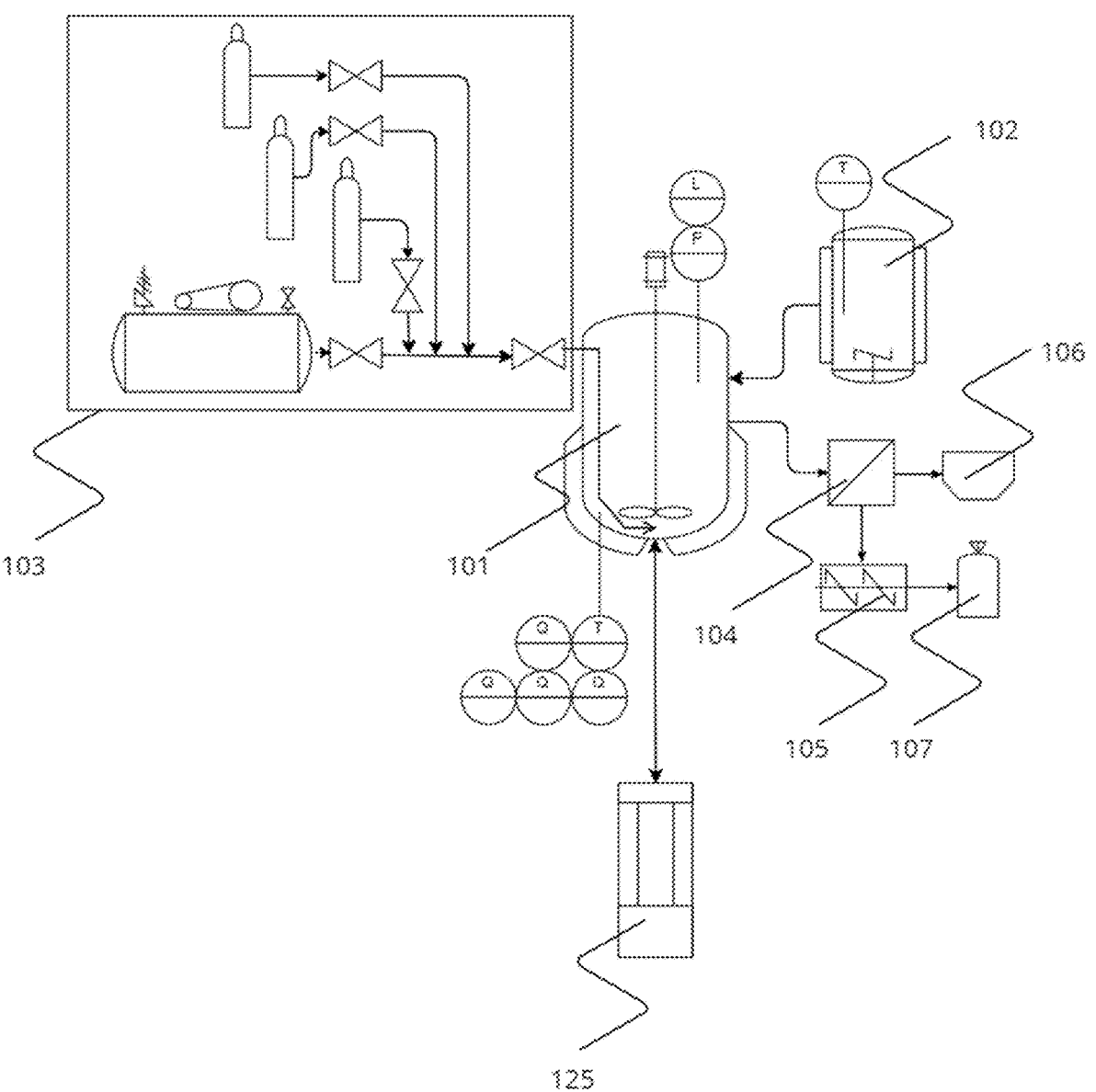
FIG. 17—illustrates the exemplary aspect of the invention illustrated in the FIG. 16.

In one aspect of the invention as depicted in FIG. 17, at least one cultivation device 101 may be coupled with the gas sparging system 103. The cultivation device 101 may be further coupled with at least one culture medium tank 127 and the cultivation device 101 may be further also coupled with at least one harvesting device 104. The cell biomass harvested by the harvesting device 104 may then be processed by the product processing device 105. The cultivation system may be communicatively and operatively coupled with the control unit 125.

Figure 16:
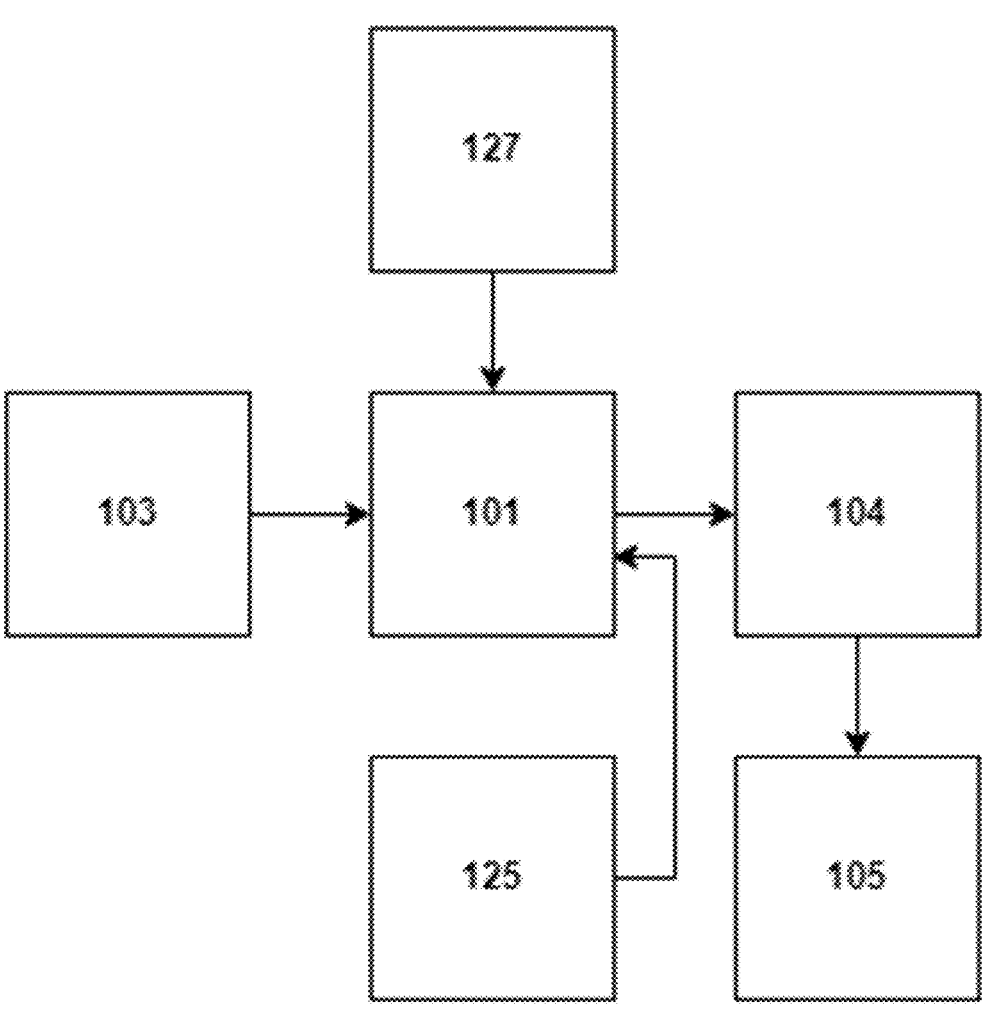

The components in FIG. 16:
101—The cultivation device
127—The culture medium tank
103—The gas sparging system
104—The harvesting device
105—The product processing device
125—The control unit The exemplary aspect of the invention as depicted in FIG. 17 is a particular variant of the present aspect of the invention as depicted in FIG. 16. The cultivation system according to the exemplary aspect depicted in FIG. 17 may have the following components:

a culture medium source, wherein the culture medium source is stored in a storage tank 102 connected to the cultivation device 101; and wherein the cultivation device 101 is connected to a gas sparging system 103 comprising a plurality of gas tanks coupled with a plurality of mass flow controllers and/or rotameters; and wherein the cultivation device 101 comprises a thermometer, conductometer, refractometer, manometer, pH meter, liquid level sensor and/or at least one gas concentration measurement instrument; and at least one stirring unit; and wherein the cultivation device 101 is connected to at least one harvesting device 104 selected from the group of centrifuge unit and/or filtration unit;

wherein the harvesting device 104 may be configured to provide a comestible product 107 and a waste medium 106;

wherein the comestible product 107 may be processed by a product processing device 105 into a food product, e.g. pet food product and/or food product for human consumption; and a control unit 125 operatively and communicatively coupled with the cultivation device 101 and/or other components within the cultivation system;

wherein the control unit 125 may control and/or regulate the cultivation system.

Figure 18:
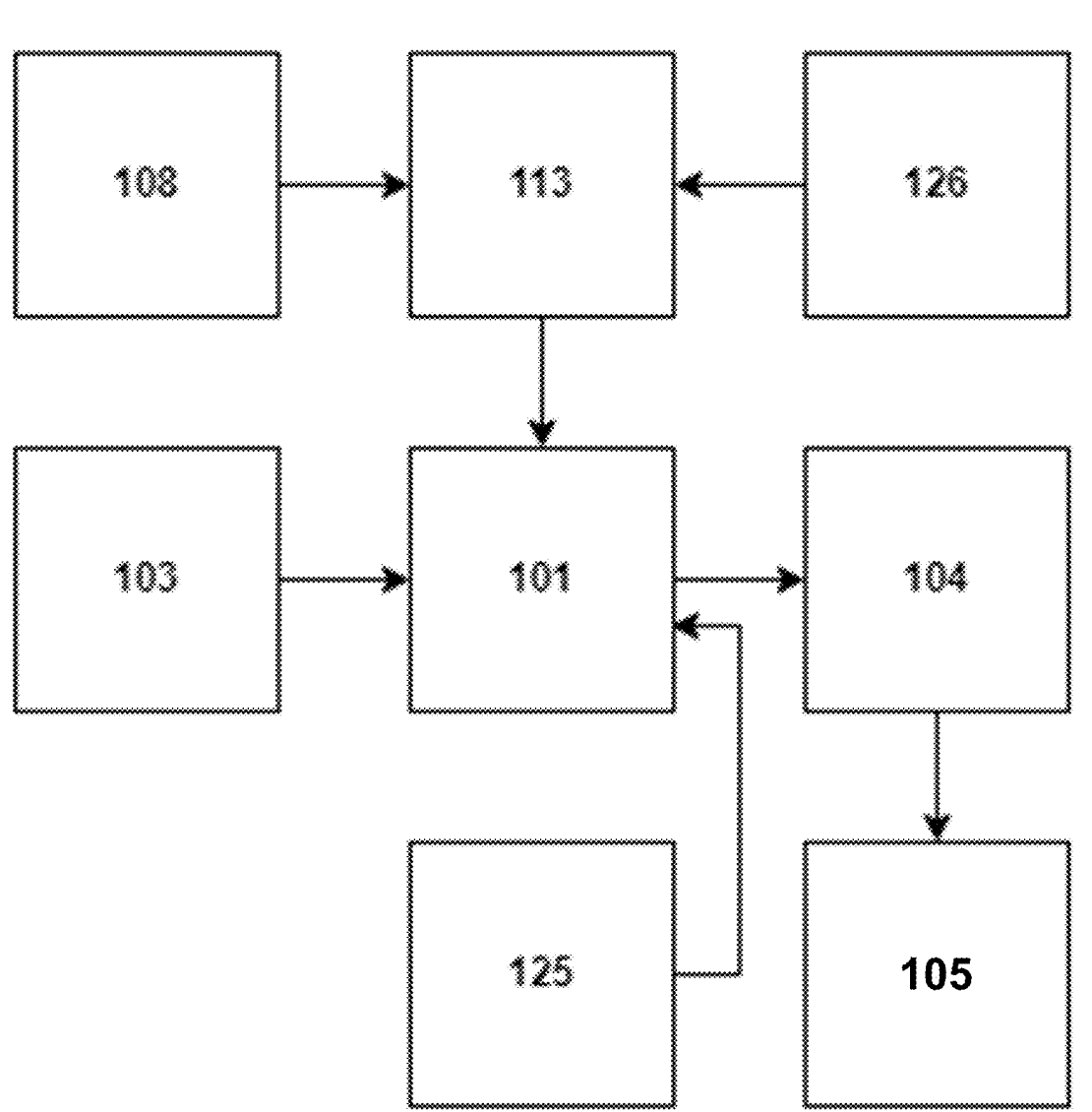
FIG. 18—illustrates one aspect of the invention comprising a tanks for the culture medium preparation.

In one aspect of the invention as depicted in FIG. 18, in order to increase the efficiency of the cultivation system depicted in FIG. 16, a water source 108 may be used to prepare the culture medium without the need to acquire a commercial culture medium. The water source 108 may be tap water or any other appropriate water source. The water from the water source may be mixed with the source of amino acids and nutritional peptides and premix of sugars, salts, proteins, vitamins, and/or other ingredients in a mixing tank 113. All aforementioned ingredients may be loaded into a mixing tank 113 from a loading tank 126. The culture medium is transported into a cultivation device 101 from the mixing tank 113. The cultivation device 101 is further coupled with a gas sparging system 103 and at least one harvesting device 104. The cell biomass harvested by the harvesting device 104 may then be processed by the product processing device 105 to the final comestible product. The cultivation system may be communicatively and operatively coupled with the control unit 125.

Figure 19:
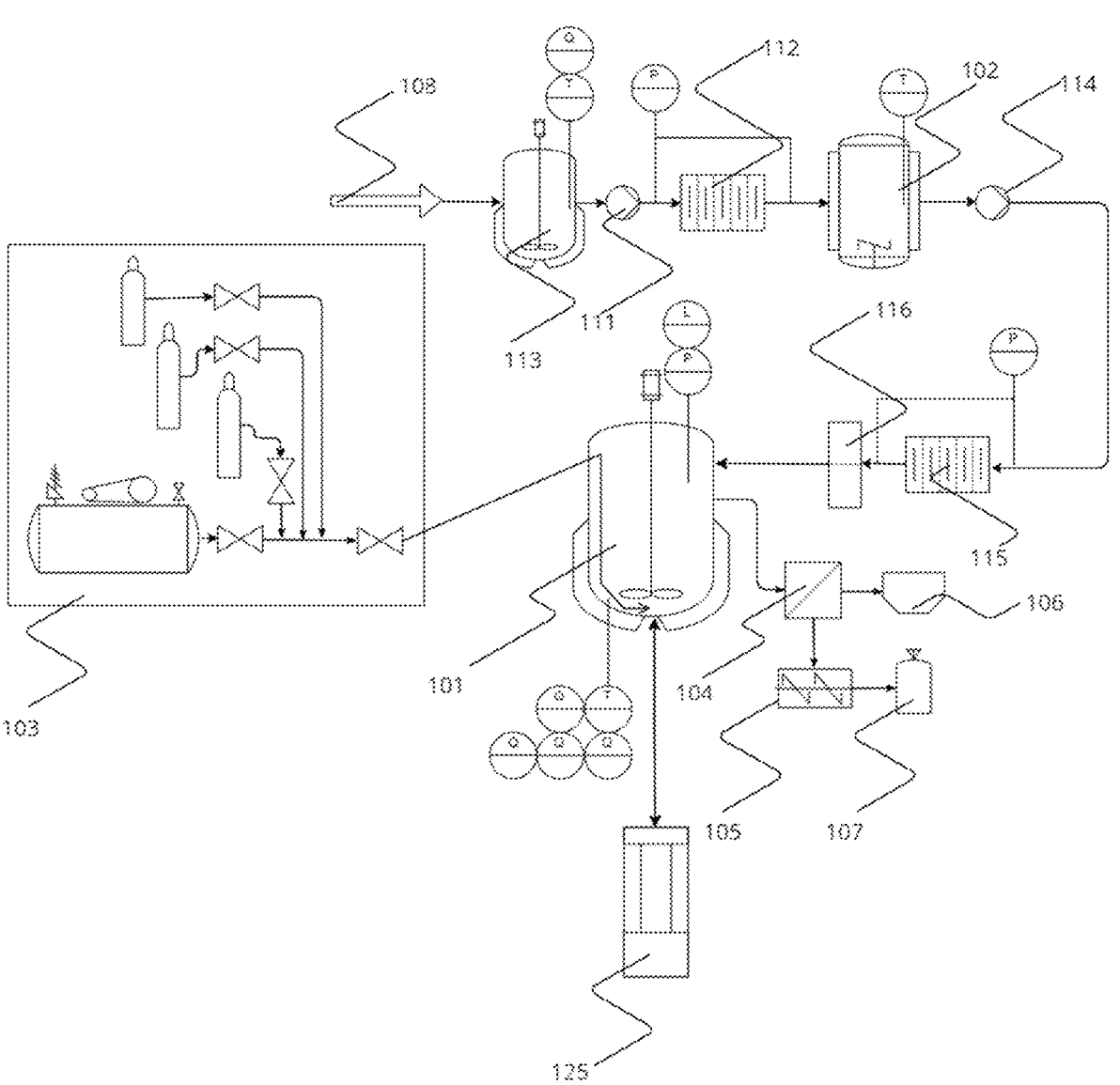
FIG. 19—illustrates an exemplary aspect of the aspect illustrated in the FIG. 18.

The components in FIG. 18:
101—The cultivation device
113—The mixing tank
103—The gas sparging system
104—The harvesting device
105—The product processing device
108—The water source
126—The loading tank
125—The control unit The exemplary aspect of the invention as depicted in FIG. 19 is a particular variant of the aspect of the invention as depicted in FIG. 18. The cultivation system according to the exemplary aspect depicted in FIG. 19 may comprise the following components:

a water source 108 may be connected to at least one mixing tank 113, wherein the mixing tank 113 may comprise a thermometer and/or conductometer, the mixing tank 113 may further comprise at least one shaft for loading the dry ingredients and at least one stirring unit; and wherein the mixing tank may be connected to a first filtration unit 112 by a first pump 111, wherein the first filtration unit 112 may comprise a manometer capable of measuring the pressure difference between the input and output of the first filtration unit 112; and wherein the first filtration unit 112 may be connected to at least one storage tank 102, wherein the storage tank 102 may comprise the thermometer; and wherein the storage tank 102 may be connected to a second filtration unit 115 by a second pump 114, wherein the second filtration unit 115 may comprise a manometer capable of measuring the difference between the input and output of the second filtration unit 115; and wherein the second filtration unit 115 may be connected to a cultivation device 101 by at least one sterile barrier 116; wherein the cultivation device 101 may comprise one or more of a thermometer, conductometer, refractometer, manometer, pH meter, liquid level sensor and/or at least one gas concentration measurement instrument;

wherein the cultivation device 101 may comprise at least one stirring unit; and wherein the cultivation device 101 may be connected to a gas sparging system 103 comprising one or more gas tanks coupled with a plurality of mass flow controllers; and wherein the cultivation device 101 may be connected to at least one harvesting device 104 selected from the group of centrifuge unit and/or filtration unit;

wherein the harvesting device 104 may be configured to provide a comestible product and a waste medium 106; and wherein the comestible product may be processed by a product processing device 105 into a food product 107, e.g. pet food product and/or food product for human consumption; and a control unit 125 operatively and communicatively coupled with the cultivation device 101 and/or other components within the cultivation system;

wherein the control unit 125 may control and/or regulate the cultivation system.

Figure 20:
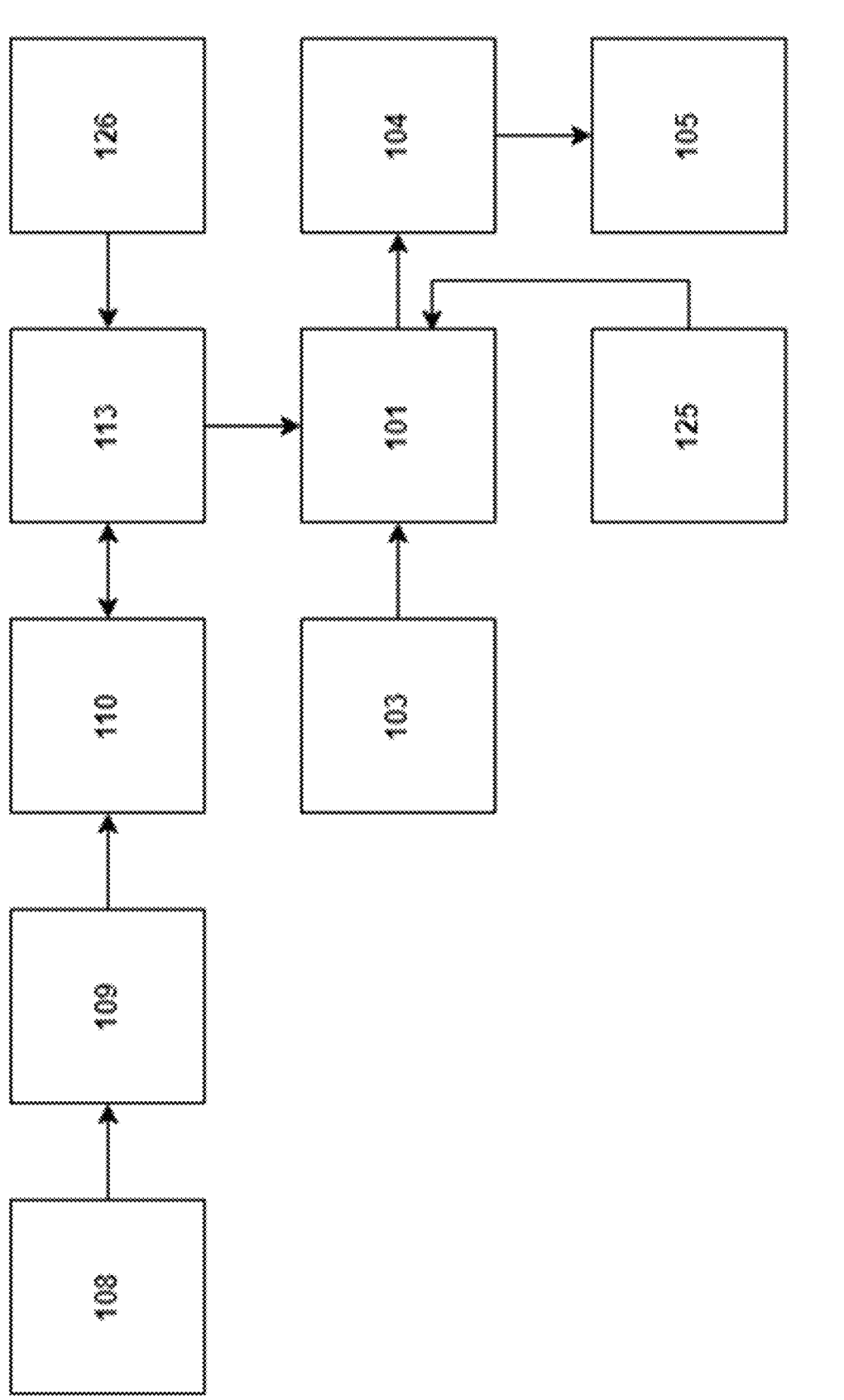
FIG. 20—illustrates one aspect of the invention comprising a water purification unit and hydrolysis tank.

In one aspect of the invention as depicted in FIG. 20, in order to further increase the efficiency of the cultivation system as depicted in FIG. 18, the water from the water source 108 may be purified, wherein the purification of the water comprises the processes and methods of removing the ions from the water, i. e. deionizing and/or demineralizing the water by at least one method selected from the group of deionization, electrodeionization, electrodialysis, reverse osmosis and/or distillation. The water may also be initially analyzed to measure the ion concentrations before the purification. The water may also be analyzed after purification. The purification methods mentioned above may be used to devoid the water of:

inorganic ions such as $Ca^{2+}$, $Mg^{2+}$, $Na^+$, $K^+$, $Cl^-$, $SO_4^{2-}$, $NO_{3-}$, $PO_4^{3-}$, $CO_3^{2-}$, $HCO^{3-}$, $F^-$, $SiO_3^{2-}$, $Fe^{2+}$, $Fe^{3+}$, $Al^{3+}$ and/or other ions; other elements in the non-charged state, such as Cu, Zn, Pb, Co and/or Mn;

organic compounds and their derivatives, such as humic substances, pesticides, herbicides, pharmaceuticals, disinfectants and other industrial chemicals;

microorganisms such as bacteria and viruses; or fungi; or any other substance or microorganisms potentially contained in the water.

Deionization (DI) is a chemical process using ion-exchange resins, where hydrogen and hydroxide ions exchange for dissolved minerals and then recombine to form water. Electrodeionization is a continuous electrochemical process that combines ion-exchange resins and an applied electrical field to remove ions from the water. Reverse osmosis uses a semipermeable membrane to separate impurities from the water by applying pressure to force water molecules through the membrane, leaving contaminants behind. Distillation is a separation process involving heating the water above boiling point of the water to vaporize and then condense the water vapor to obtain purified water. Electrodialysis is a separation process involving selective membranes and an electrical field to force ions through the membranes, thus effectively removing the ions from the water.

The flow rate of the purified water to the culture medium tank per liters of its working volume may be in the range of 0.001 L/min to 5 L/min; or in the range of 0.005 L/min to 5 L/min; or in the range of 0.01 L/min to 5 L/min; or in the range of 0.1 L/min to 5 L/min; or in the range of 1 L/min to 5 L/min; or in the range of 1 L/min. to 4 L/min.; or in the range of 2 L/min. to 3 L/min.

The water treated by the purification process described above may have the conductivity lower than lower than 1.00 µS/cm; or lower than 2.00 µS/cm; or lower than 5.00 µS/cm; or lower than 10 µS/cm; or lower than 20 µS/cm; or lower than 50 µS/cm; or lower than 100 µS/cm; or lower than 200 µS/cm; or lower than 300 µS/cm; or lower than 400 µS/cm; or lower than 500 µS/cm; or lower than 600 ρS/cm.

The water treated by the purification process described above may have the conductivity in a range of 1 µS/cm to 600 µS/cm, in a range of 5 µS/cm to 500 µS/cm, in a range of 15 µS/cm to 400 µS/cm, in a range of 30 µS/cm to 300 µS/cm or in a range of 50 µS/cm to 200 µS/cm or in a range of 60 µS/cm to 100 µS/cm.

Purified water with a low conductivity and/or high resistivity is then used to prepare the culture medium. The purified water may be mixed with the source of amino acids and nutritional peptides and a premix of saccharides, salts, proteins, vitamins and/or other dry ingredients.

In order to further increase the efficiency of the cultivation system depicted in FIG. 18, the source of amino acids and nutritional peptides may be a suitable protein source originated from plants, fungi, microorganisms, animal byproducts, their derivatives and/or any combination thereof. The protein source may enter the process of hydrolysis in its crude form, or it may be pre-processed to improve properties such as purity and solubility. Pre-processing of the protein source may include crushing, milling, baking, washing with acids, washing with alcohols, washing with non-polar solvents and/or any other suitable pre-processing methods. Suitable protein sources may comprise soy flakes, soy flour, defatted soy flour, soy protein concentrate, soy protein isolate, yeast, yeast protein isolate, whey, whey protein isolate, or any other suitable protein source treated by proteases to provide the protein hydrolysate. The hydrolysis process may take place in at least one hydrolysis tank 110 using purified water from the water purification unit 108. The protein hydrolysate comprises purified water, amino acids, nutritional peptides and a premix of sugars, salts, proteins, vitamins and/or other dry ingredients from the loading tank 126. All aforementioned ingredients may be mixed together in the mixing tank 113 and transported into the cultivation device 101. The cultivation system may be communicatively and operatively coupled with the control unit 125.

Other suitable protein sources may be originated from pea, rice, wheat, wheat gluten, corn, fava beans, alfalfa, hemp, chickpea, potato, pumpkin, rapeseed, red lentil, rice, duckweed, *spirulina, chlorella*, sunflower, water lentil, mung bean or any another suitable protein source.

For example, the culture medium may have the following composition:

the source of amino acids and nutritional peptides of the culture medium may be originated from the rice hydrolysate;

wherein the rice hydrolysate may be produced by hydrolysis of the rice protein concentrate with the mix of a proteases, peptidases and subtilases;

a mix of minerals may comprise the following ions: $Ca^{2+}$, $Cu^{2+}$, $Fe^{3+}$, $Fe^{2+}$, $Mg^{2+}$, $K^+$, $Na^+$, $Zn^{2+}$, $Cl^-$, $SO_4^{2-}$, $NO_{3-}$, $HCO_{3-}$, $HPO_4^{2-}$, $H_2PO_{4-}$, wherein the ions may be provided in the form of salts;

a mix of vitamins comprising biotin, choline chloride, D-calcium pantothenate, folic acid, niacinamide, pyridoxine hydrochloride, riboflavin, thiamine hydrochloride, vitamin B12, i-inositol; and a mix of organic amines and amino acids comprising ethanolamine, putrescine, cysteine, methionine; and a glucose;

and purified water.

The present way of preparing the culture medium results in consistent quality and quantity of the purified water and consistent source of amino acids and nutritional peptides originating from the protein hydrolysate. In addition, there are minimal energy requirements for these processes, thus contributing to increasing the effectiveness of the cultivation process.

The components in FIG. 20:

101—The cultivation device

113—The mixing tank

103—The gas sparging system

104—The harvesting device

105—The product processing device

108—The water source

126—The loading tank

110—The hydrolysis tank

109—The water purification unit

125—The control unit

Figure 21:
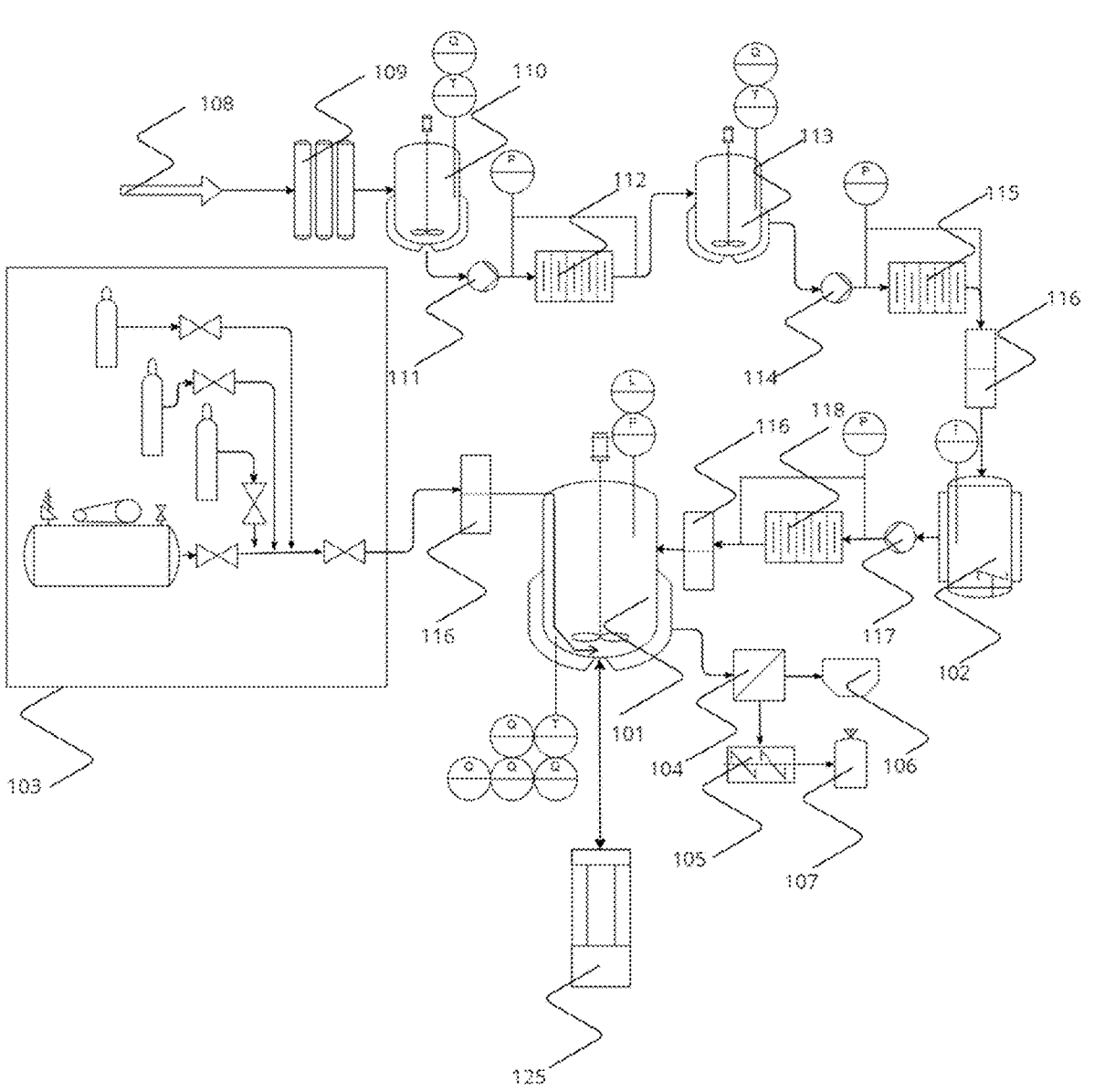
FIG. 21—illustrates an exemplary aspect of the aspect illustrated in the FIG. 20.

The exemplary aspect of the invention as depicted in FIG. 21 is a particular variant of the present aspect of the invention as depicted in FIG. 20. The cultivation system according to the exemplary aspect depicted in FIG. 21 may have the following components:

a water source 108 may be connected to the water purification unit 109, wherein the water purification unit 109 may provide at least one selected from the group of reverse osmosis, deionization, electrodeionization, electrodialysis and distillation; and wherein the water purification unit 109 may be connected to a hydrolysis tank 110, wherein the hydrolysis tank 110 may comprise a thermometer and/or conductometer and at least one shaft for loading the source of amino acid and/or nutritional peptides, wherein the source of amino acid and/or nutritional peptides may be selected from the group of protein concentrate and protein isolate;

the hydrolysis tank 110 may further include at least one stirring unit; and wherein the hydrolysis tank 110 may be connected to a first filtration unit 112 by a first pump 111, wherein the first filtration unit 112 may comprise a manometer capable of measuring the difference between the input and output of the first filtration unit 112; and wherein the first filtration unit 112 may be connected to a mixing tank 113, wherein the mixing tank 113 may comprise the thermometer and/or conductometer, at least one shaft for loading the premix of other compounds and at least one stirring unit; and wherein the mixing tank 113 may be connected to a second filtration unit 115 by a second pump 114, wherein the second filtration unit 115 may comprise the manometer capable of measuring the difference between the input and output of the second filtration unit 115; and wherein the second filtration unit 115 may be connected to a storage tank 102 by at least one sterile barrier 116, wherein the storage tank 102 comprises a thermometer; and wherein the storage tank 102 may be connected to a third filtration unit 118 by a third pump 117, wherein the third filtration unit 118 may comprise a manometer capable of measuring the difference between the input and output of the third filtration unit 118; and wherein the third filtration unit 118 may be connected to a cultivation device 101 by at least one sterile barrier 116, wherein the cultivation device 101 may comprise a thermometer, conductometer, refractometer, manometer, pH meter, liquid level sensor and/or at least one gas concentration measurement instrument; and at least one stirring unit; and wherein the cultivation device 101 may be connected to a gas sparging system 103;

wherein the gas sparging system 103 may comprise one or more gas tanks coupled with a plurality of mass flow controllers and/or rotameters;

wherein the cultivation device 101 may be connected to at least one harvesting device 104 selected from the group of centrifuge unit and/or filtration unit;

wherein the harvesting device 104 may be configured to provide a comestible product and a waste medium 106; and wherein the comestible product may be processed by a product processing device 105 into a food product 107, e.g. pet food product and/or food product for human consumption; and a control unit 125 operatively and communicatively coupled with the cultivation device 101 and/or other components within the cultivation system;

wherein the control unit 125 may control and/or regulate the cultivation system.

Figure 22:
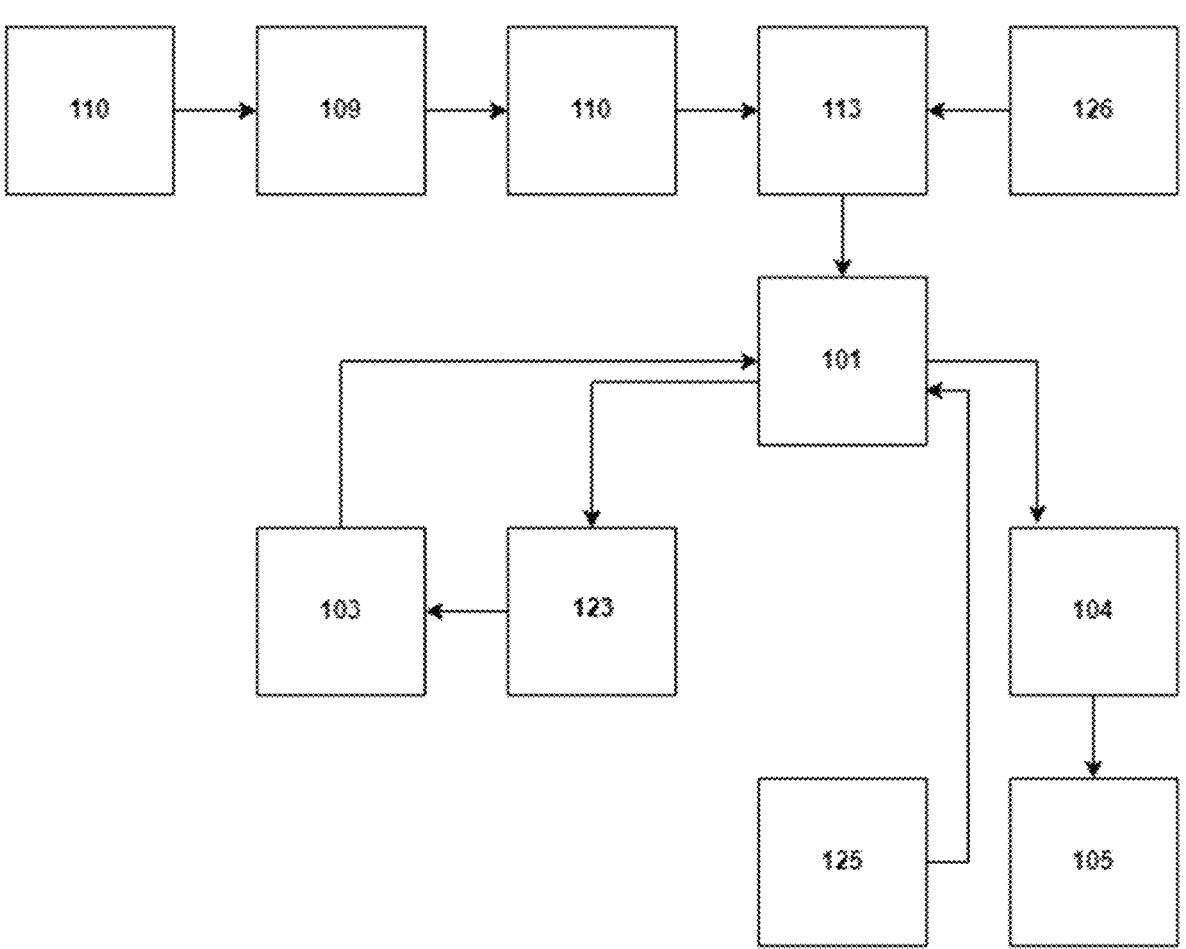
FIG. 22—illustrates one aspect of the invention comprising a gas recycling system.

In one aspect of the invention as depicted in FIG. 22, in order to further increase the efficiency of the cultivation system depicted in FIG. 20, the exhaust gas from the cultivation device 101 may be recycled using a gas recycling system 123. The cultivation system may comprise a gas recycling system 123, at least one cultivation device 101 and/or gas sparging system 103.

In one aspect of the invention, the exhaust gas from the non-working volume in the cultivation device 101 is used. The "non-working volume" refers to the gaseous phase above the liquid phase in the cultivation device 101 in the upper part of the cultivation device 101. The exhaust gas from the non-working volume is moved to the gas recycling system 103, which is connected to the gas sparging system 103. The gas sparging system 103 is then connected to the cultivation device 101, which ensures the circulating of the exhaust gas through the cultivation device 101. The gas recycling system 123 may be also used for rejuvenating the exhaust gas in case the exhaust gas is not suitable for further use. The rejuvenating of the exhaust gas comprises providing fresh gasses from the gas tanks to the exhaust gas and/or partially or completely removing specific fractions of the exhaust gas (this may include for example removing $CO_2$ from the exhaust gas, for example by pressure swing adsorption, amine scrubbing, or any other suitable method of $CO_2$ removal).

In another aspect of the invention, the gas may be delivered to the cells using a culture medium enriched by dissolving the gas from the gaseous phase in the liquid phase of the culture medium. The method for dissolving the gas in the medium comprises increasing the total pressure of the culture medium and injecting the gas into the culture medium. This process may take place in a pressure chamber. The maximum solubility of the gasses in the water is limited by the combination of the liquid and gas to be dissolved. The dissolved gasses may be oxygen, nitrogen, hydrogen, carbon dioxide and air. The maximum solubility of the gasses is also limited by the partial pressure of the gasses mentioned above and the temperature of both the liquid and gaseous phase. The cultivation system may be communicatively and operatively coupled with the control unit 125.

Figure 23:
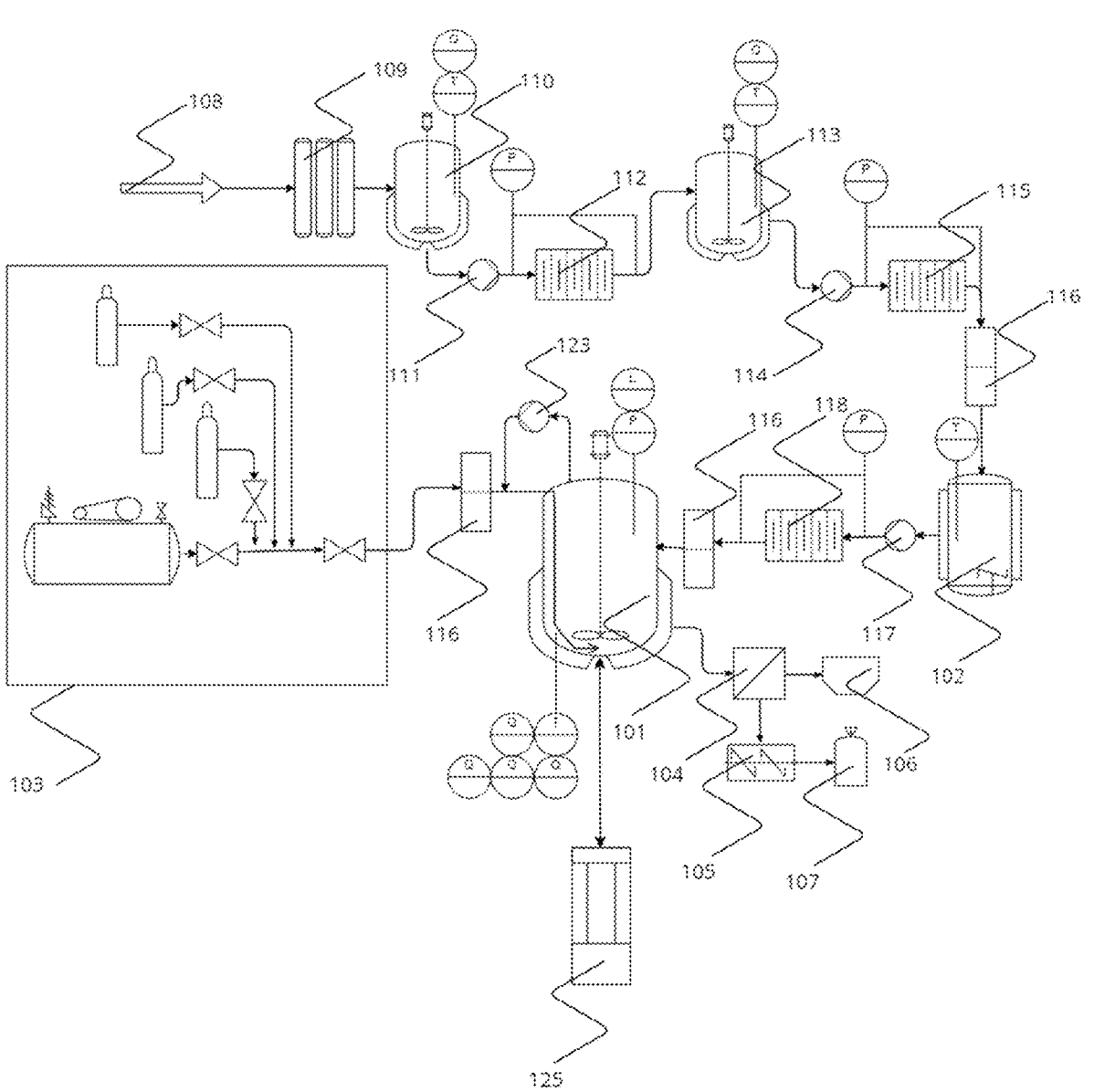
FIG. 23—illustrates an exemplary aspect of the aspect illustrated in the FIG. 22.

The components in FIG. 22:

101—The cultivation device
113—The mixing tank
103—The gas sparging system
104—The harvesting device
105—The product processing device
108—The water source
126—The loading tank
110—The hydrolysis tank
109—The water purification unit
123—The gas recycling system
125—The control unit The exemplary aspect of the invention as depicted in FIG. 23 is a particular variant of the present aspect of the invention as depicted in FIG. 22. The cultivation system according to the exemplary aspect depicted in FIG. 23 may have the following components:

a water source 108 may be connected to the water purification unit 109, wherein the water purification unit 109 may provide at least one selected from the group of reverse osmosis, deionization, electrodeionization, electrodialysis and distillation; and wherein the water purification unit 109 may be connected to a hydrolysis tank 110, wherein the hydrolysis tank 110 may comprise a thermometer and/or conductometer and at least one shaft for loading the source of amino acid and/or nutritional peptides, wherein the source of amino acid and/or nutritional peptides may be selected from the group of protein concentrate and protein isolate;

the hydrolysis tank 110 may further include at least one stirring unit; and wherein the hydrolysis tank 110 may be connected to a first filtration unit 112 by a first pump 111, wherein the first filtration unit 112 may comprise a manometer capable of measuring the difference between the input and output of the first filtration unit 112; and wherein the first filtration unit 112 may be connected to a mixing tank 113, wherein the mixing tank 113 may comprise the thermometer and/or conductometer, at least one shaft for loading the premix of other compounds and at least one stirring unit; and wherein the mixing tank 113 may be connected to a second filtration unit 115 by a second pump 114, wherein the second filtration unit 115 may comprise the manometer capable of measuring the difference between the input and output of the second filtration unit 115; and wherein the second filtration unit 115 may be connected to a storage tank 102 by at least one sterile barrier 116, wherein the storage tank 102 may comprise the thermometer; and wherein the storage tank 102 may be connected to a third filtration unit 118 by a third pump 117, wherein the third filtration unit 118 may comprise a manometer capable of measuring the difference between the input and output of the third filtration unit 118; and wherein the third filtration unit 118 may be connected to a cultivation device 101 by at least one sterile barrier 116, wherein the cultivation device 101 comprises a thermometer, conductometer, refractometer, manometer, pH meter, liquid level sensor and/or at least one gas concentration measurement instrument; and at least one stirring unit; and wherein the cultivation device 101 may be connected to a gas sparging system 103;

wherein the gas sparging system 103 may comprise one or more gas tanks coupled with a plurality of mass flow controllers and/or rotameters;

wherein the cultivation device 101 may be connected to a gas recycling system 123;

wherein the gas recycling system 123 may be configured to recycle and/or rejuvenate the exhaust gas from the non-working volume of the cultivation device 101; and wherein the cultivation device 101 may be connected to at least one harvesting device 104 selected from the group of centrifuge unit and/or filtration unit;

wherein the harvesting device 104 may be configured to provide a comestible product and a waste medium 106;

wherein the comestible product may be processed by a product processing device 105 into a food product 107, e.g. pet food product and/or food product for human consumption; and a control unit 125 operatively and communicatively coupled with the cultivation device 101 and/or other components within the cultivation system;

wherein the control unit 125 may control and/or regulate the cultivation system.

Figure 24:
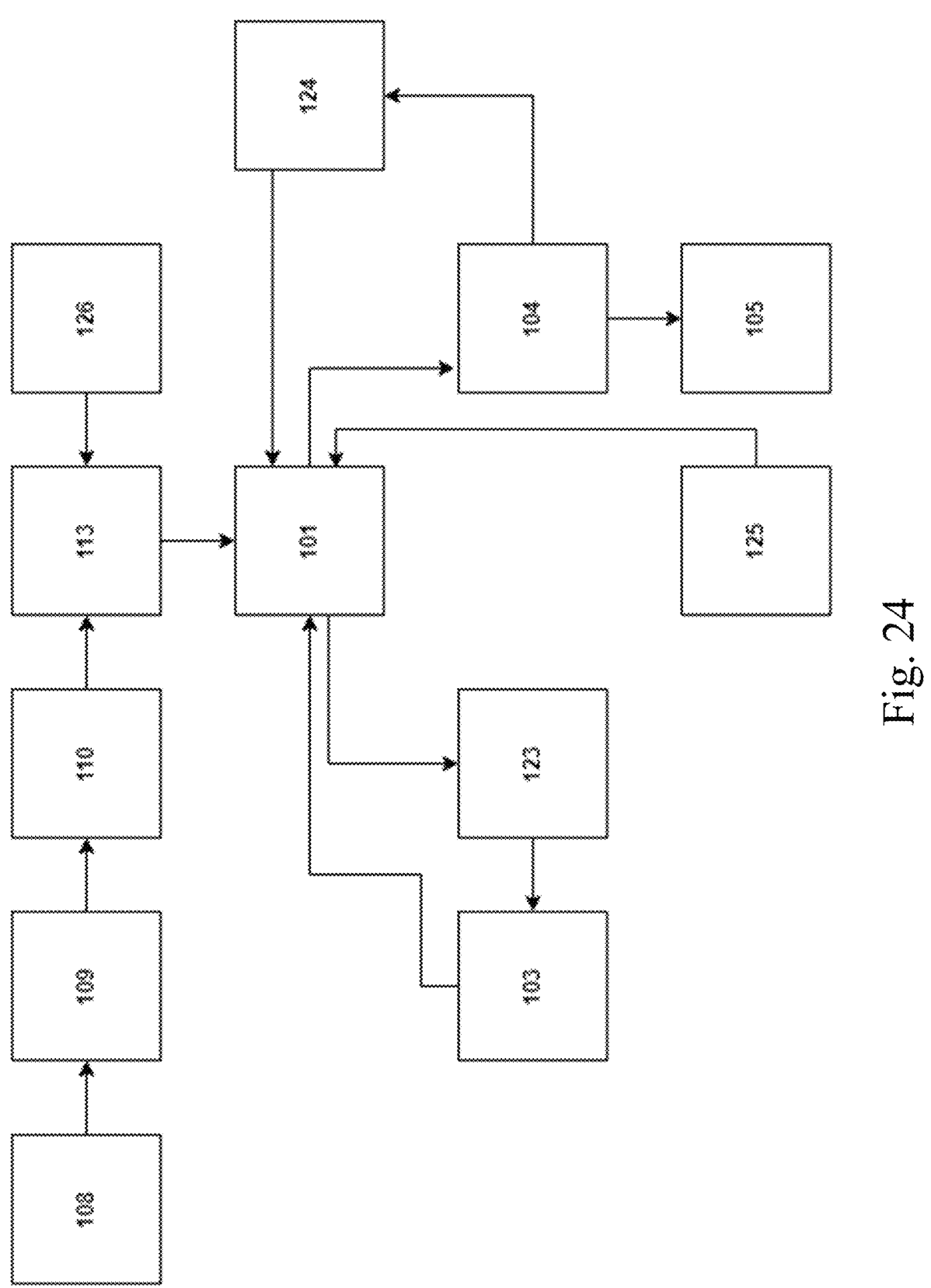
FIG. 24—illustrates one aspect of the invention comprising a medium recycling system.

In one aspect of the invention as depicted in FIG. 24, in order to further increase the efficiency of the cultivation system depicted in FIG. 22, the waste medium from the cultivation device 101 may be recycled. The cell biomass may be processed in the harvesting device 104 to separate the cultivated non-human metazoan cells from the waste medium. The liquid cell-free waste medium may comprise nutrients and metabolites and may be stored in a waste medium tank and connected to a medium recycling system 124 or may be directly transported to a medium recycling system 124 from the cultivation device 101 after the cultivation. The medium recycling system 124 may comprise at least one reverse osmosis unit and/or at least one filtration unit.

Accordingly, the filtration units may be used to separate the water from other compounds, preferably ultrafiltration units and/or reverse osmosis units. Ultrafiltration and reverse osmosis units use permeable membranes and may use pressure to separate substances, but they differ in the size of the particles they filter. Ultrafiltration primarily separates based on size, allowing small molecules to pass through while blocking larger ones. Reverse osmosis separates compounds based on both size and solubility, allowing only solvent molecules to pass through while blocking solutes.

The aforementioned processes may be repeated at least once to obtain desired concentration of the nutrients. The result of the filtration units is a concentrate, wherein the concentrate comprises mostly the metabolites and nutrients from the cultivation process and the rest is mostly water. Concentrate may be processed and used again to increase the efficiency of the process, as mentioned above.

As depicted in the FIG. 24, the medium recycling system 124 may be connected to the harvesting device 104 and the cultivation device 101. The medium recycling system 124 may be connected to the waste medium tank, the harvesting device 104 and the cultivation device 101. The cultivation system may be communicatively and operatively coupled with the control unit 125.

Figure 25:
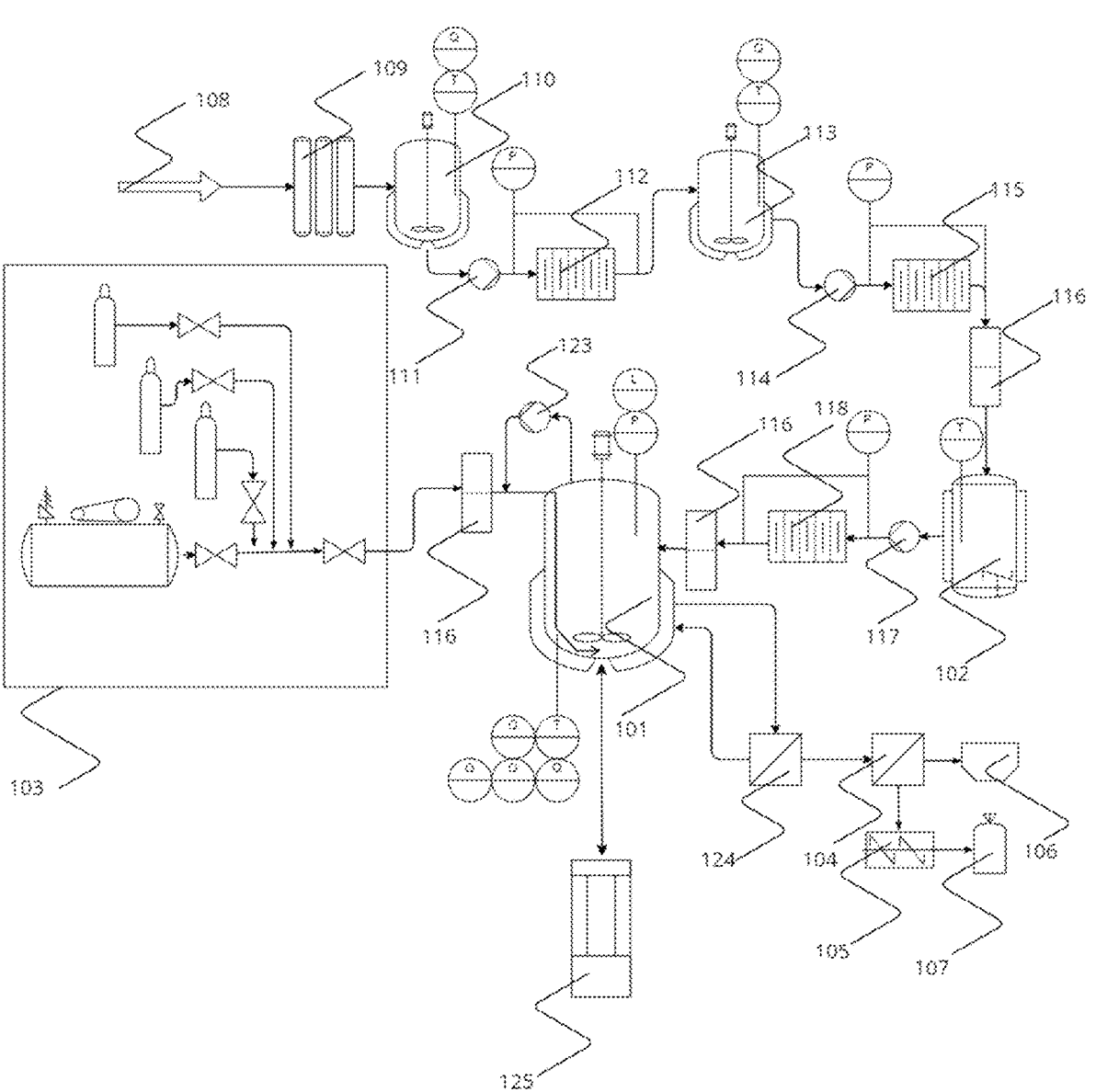
FIG. 25—illustrates an exemplary aspect of the aspect illustrated in the FIG. 24.

The components in FIG. 24:

101—The cultivation device
113—The mixing tank
103—The gas sparging system
104—The harvesting device
105—The product processing device
108—The water source
126—The loading tank
110—The hydrolysis tank
109—The water purification unit
123—The gas recycling system
124—The medium recycling system
125—The control unit The exemplary aspect of the invention as depicted in FIG. 25 is a particular variant of the present aspect of the invention as depicted in FIG. 24. The cultivation system according to the exemplary aspect depicted in FIG. 25 may have the following components:

a water source 108 may be connected to the water purification unit 109, wherein the water purification unit 109 may provide at least one selected from the group of reverse osmosis, deionization, electrodeionization, electrodialysis and distillation; and wherein the water purification unit 109 may be connected to a hydrolysis tank 110, wherein the hydrolysis tank 110 may comprise a thermometer and/or conductometer and at least one shaft for loading the source of amino acid and/or nutritional peptides, wherein the source of amino acid and/or nutritional peptides may be selected from the group of protein concentrate and protein isolate;

the hydrolysis tank 110 may further include at least one stirring unit; and wherein the hydrolysis tank 110 may be connected to a first filtration unit 112 by a first pump 111, wherein the first filtration unit 112 may comprise a manometer capable of measuring the difference between the input and output of the filtration unit; and wherein the first filtration unit 112 may be connected to a mixing tank 113, wherein the mixing tank 113 may comprise the thermometer and/or conductometer, at least one shaft for loading the premix of other compounds and at least one stirring unit; and wherein the mixing tank 113 may be connected to a second filtration unit 115 by a second pump 114 wherein the second filtration unit 115 may comprise the manometer capable of measuring the difference between the input and output of the second filtration unit 115; and wherein the second filtration unit 115 may be connected to a storage tank 102 by at least one sterile barrier 116, wherein the storage tank 102 may comprise the thermometer; and wherein the storage tank 102 may be connected to a third filtration unit 118 by a third pump 117, wherein the third filtration unit 118 may comprise a manometer capable of measuring the difference between the input and output of the third filtration unit 118; and wherein the third filtration unit 118 may be connected to a cultivation device 101 by at least one sterile barrier 116, wherein the cultivation device 101 comprises a thermometer, conductometer, refractometer, manometer, pH meter, liquid level sensor and/or at least one gas concentration measurement instrument; and at least one stirring unit; and wherein the cultivation device 101 may be connected to a gas sparging system 103;

wherein the gas sparging system 103 may comprise one or more gas tanks coupled with a plurality of mass flow controllers and/or rotameters;

wherein the cultivation device 101 may be connected to a gas recycling system 123;

wherein the gas recycling system 123 may be configured to recycle and/or rejuvenate the exhaust gas from the non-working volume of the cultivation device 101; and a medium recycling system 124, which may be connected to the cultivation device 101;

wherein the medium recycling system 124 may be configured to recycle and/or rejuvenate the culture medium; and wherein the medium recycling system 124 may be connected to at least one harvesting device 104 selected from the group of centrifuge unit and/or filtration unit;

wherein the harvesting device 104 may be connected to the medium recycling system 124 and may be configured to provide a comestible product 107 and a waste medium 106;

wherein the comestible product 107 may be processed by a product processing device 105 into a food product, e.g. pet food product and/or food product for human consumption; and a control unit 125 operatively and communicatively coupled with the cultivation device 101 and/or other components within the cultivation system;

wherein the control unit 125 may control and/or regulate the cultivation system.

Figure 26:
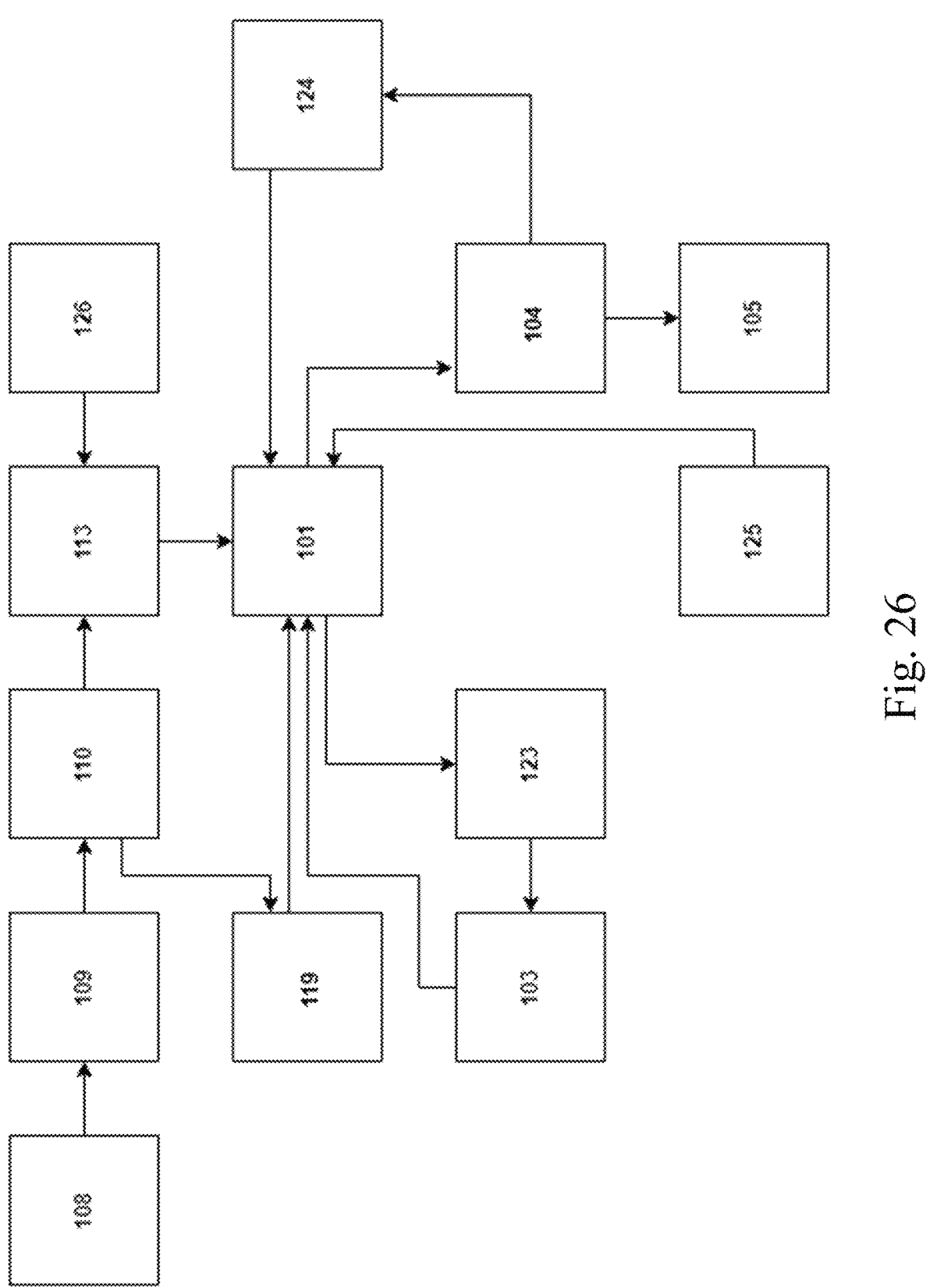
FIG. 26—illustrates one aspect of the invention comprising a heat exchange system.

In one aspect of the invention as depicted in FIG. 26, in order to further increase the efficiency of the cultivation system depicted in FIG. 24, a heat exchange system 119 may be applied. The cultivation system may comprise at least one culture medium tank where the heat is used. The heat exchange system 119 may be connected to at least one hydrolysis tank 110. The heat from at least one hydrolysis tank 110 may be transported to the cultivation device 101 using a heat exchange system 119. The cultivation system may be communicatively and operatively coupled with the control unit 125.

Figure 27:
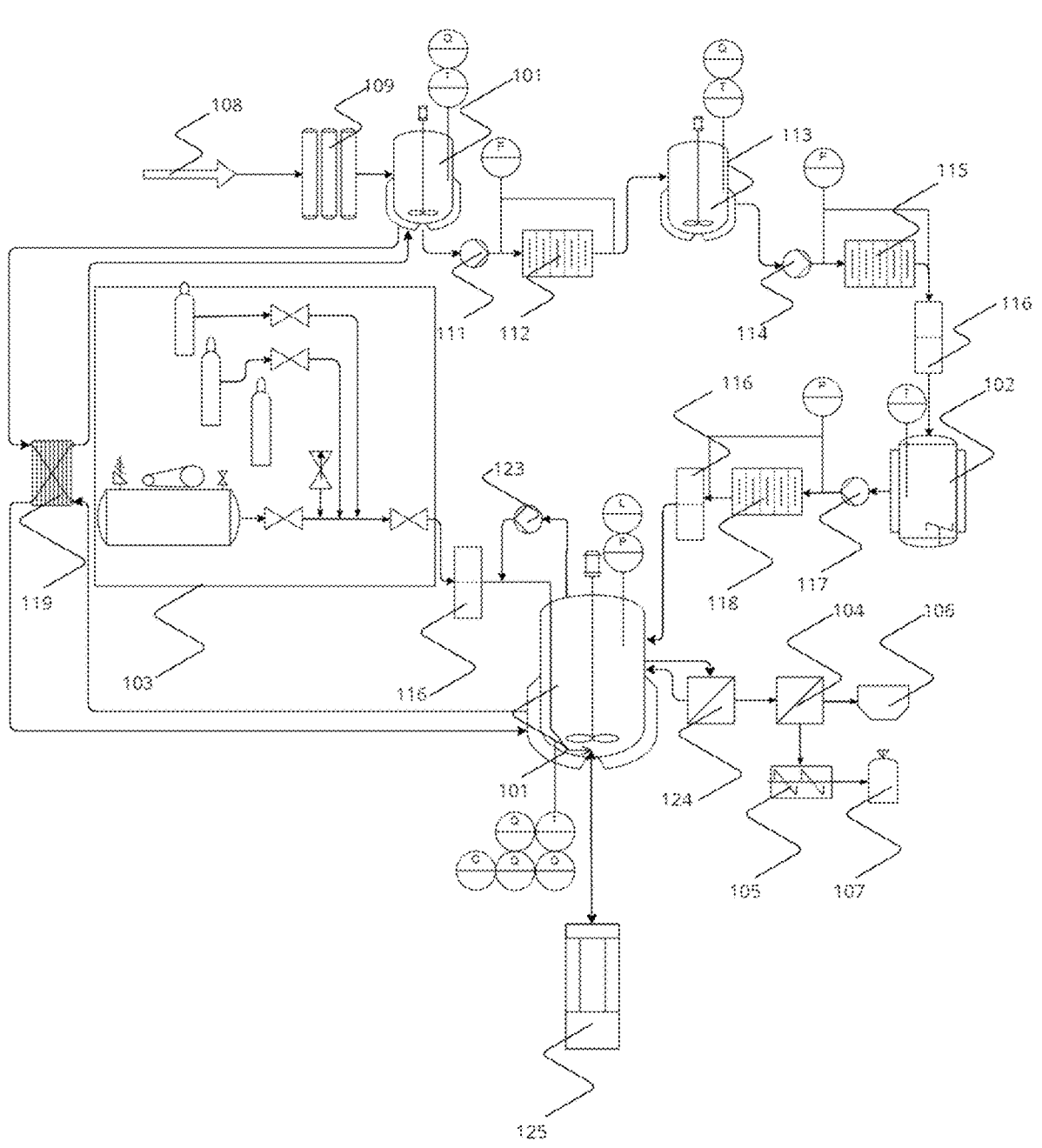
FIG. 27—illustrates an exemplary aspect of the aspect illustrated in the FIG. 26.

The components in FIG. 26:
101—The cultivation device
113—The mixing tank
103—The gas sparging system
104—The harvesting device
105—The product processing device
108—The water source
126—The loading tank
110—The hydrolysis tank
109—The water purification unit
123—The gas recycling system
124—The medium recycling system
119—The heat exchange system
125—The control unit The exemplary aspect of the invention as depicted in FIG. 27 is a particular variant of the present aspect of the invention as depicted in FIG. 26. The cultivation system according to the exemplary aspect depicted in FIG. 27 may have the following components:

a water source 108 may be connected to the water purification unit 109, wherein the water purification unit 109 may provide at least one selected from the group of reverse osmosis, deionization, electrodeionization, electrodialysis and distillation; and wherein the water purification unit 109 may be connected to a hydrolysis tank 110, wherein the hydrolysis tank 110 may comprise a thermometer and/or conductometer and at least one shaft for loading the source of amino acid and/or nutritional peptides, wherein the source of amino acid and/or nutritional peptides may be selected from the group of protein concentrate and protein isolate;

the hydrolysis tank 110 may further include at least one stirring unit; and wherein the hydrolysis tank 110 may be connected to a first filtration unit 112 by a first pump 111, wherein the first filtration unit 112 may comprise a manometer capable of measuring the difference between the input and output of the filtration unit; and wherein the first filtration unit 112 may be connected to a mixing tank 113, wherein the mixing tank 113 may comprise the thermometer and/or conductometer, at least one shaft for loading the premix of other compounds and at least one stirring unit; and wherein the mixing tank 113 may be connected to a second filtration unit 115 by a second pump 114, wherein the second filtration unit 115 may comprise the manometer capable of measuring the difference between the input and output of the second filtration unit 115; and wherein the second filtration unit 115 may be connected to a storage tank 102 by at least one sterile barrier 116, wherein the storage tank 102 may comprise the thermometer; and wherein the storage tank 102 may be connected to a third filtration unit 118 by a third pump 117, wherein the third filtration unit 118 may comprise a manometer capable of measuring the difference between the input and output of the third filtration unit 118; and wherein the third filtration unit 118 may be connected to a cultivation device 101 by at least one sterile barrier 116, wherein the cultivation device 101 comprises a thermometer, conductometer, refractometer, manometer, pH meter, liquid level sensor and/or at least one gas concentration measurement instrument; and at least one stirring unit; and wherein the cultivation device 101 may be connected to a gas sparging system 103;

wherein the gas sparging system 103 may comprise one or more gas tanks coupled with a plurality of mass flow controllers and/or rotameters;

wherein the cultivation device 101 may be connected to a gas recycling system 123;

wherein the gas recycling system 123 may be configured to recycle and/or rejuvenate the exhaust gas from the non-working volume of the cultivation device; and a medium recycling system 124 which may be connected to the cultivation device 101;

wherein the medium recycling system 124 may be configured to recycle and/or rejuvenate the culture medium; and wherein the medium recycling system 124 may be connected to at least one harvesting device 104 selected from the group of centrifuge unit and/or filtration unit;

wherein the harvesting device 104 may be connected to the medium recycling system 124 and may be configured to provide a comestible product and a waste medium 106;

wherein the comestible product may be processed by a product processing device 105 into a food product 107, e.g. pet food product and/or food product for human consumption; and a heat exchange system 119 configured to exchange the heat between the hydrolysis tank 110 and the cultivation device 101;

wherein the heat exchange system 119 may be connected to the cultivation device 101 and to the hydrolysis tank 110; and a control unit 125 operatively and communicatively coupled with the cultivation device 101 and/or other components within the cultivation system;

wherein the control unit 125 may control and/or regulate the cultivation system.

Figure 28:
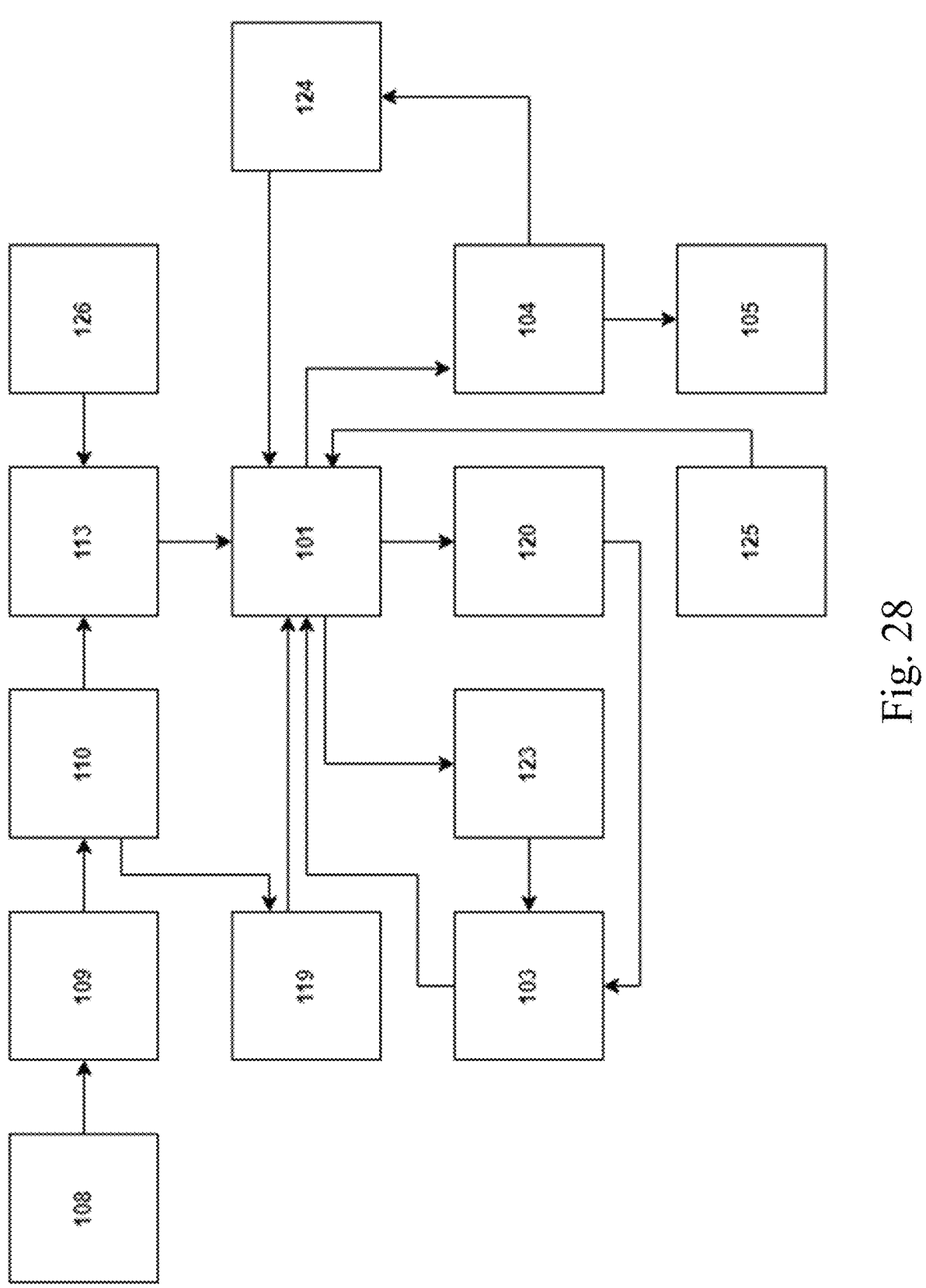
FIG. 28—illustrates one aspect of the invention comprising a collateral cultivation device.

In one aspect of the invention as depicted in FIG. 28, in order to further increase the efficiency of the cultivation system depicted in FIG. 26, the collateral cultivation device 120 may be applied and coupled with the gas recycling system 123. The collateral cultivation device 120 may be used to produce the protein-rich component, which may be subsequently used as a source of amino acids and nutritional peptides for the preparation of the culture medium.

As depicted in the FIG. 28, the protein production alongside non-human metazoan cell cultivation takes place in a collateral cultivation device 120. The collateral cultivation device 120 may comprise cultivation of the converting organisms selected from the group of bacteria, algae and/or microalgae. The collateral cultivation device 120 may further comprise at least one light source if the cultivated organisms are phototrophic. The organisms cultivated in the collateral cultivation device 120 may comprise recombinant protein, single cell protein or any other protein that may be used as a source of amino acids for the cultivation of the non-human metazoan cells. The cultivation system may be communicatively and operatively coupled with the control unit 125.

Figure 29:
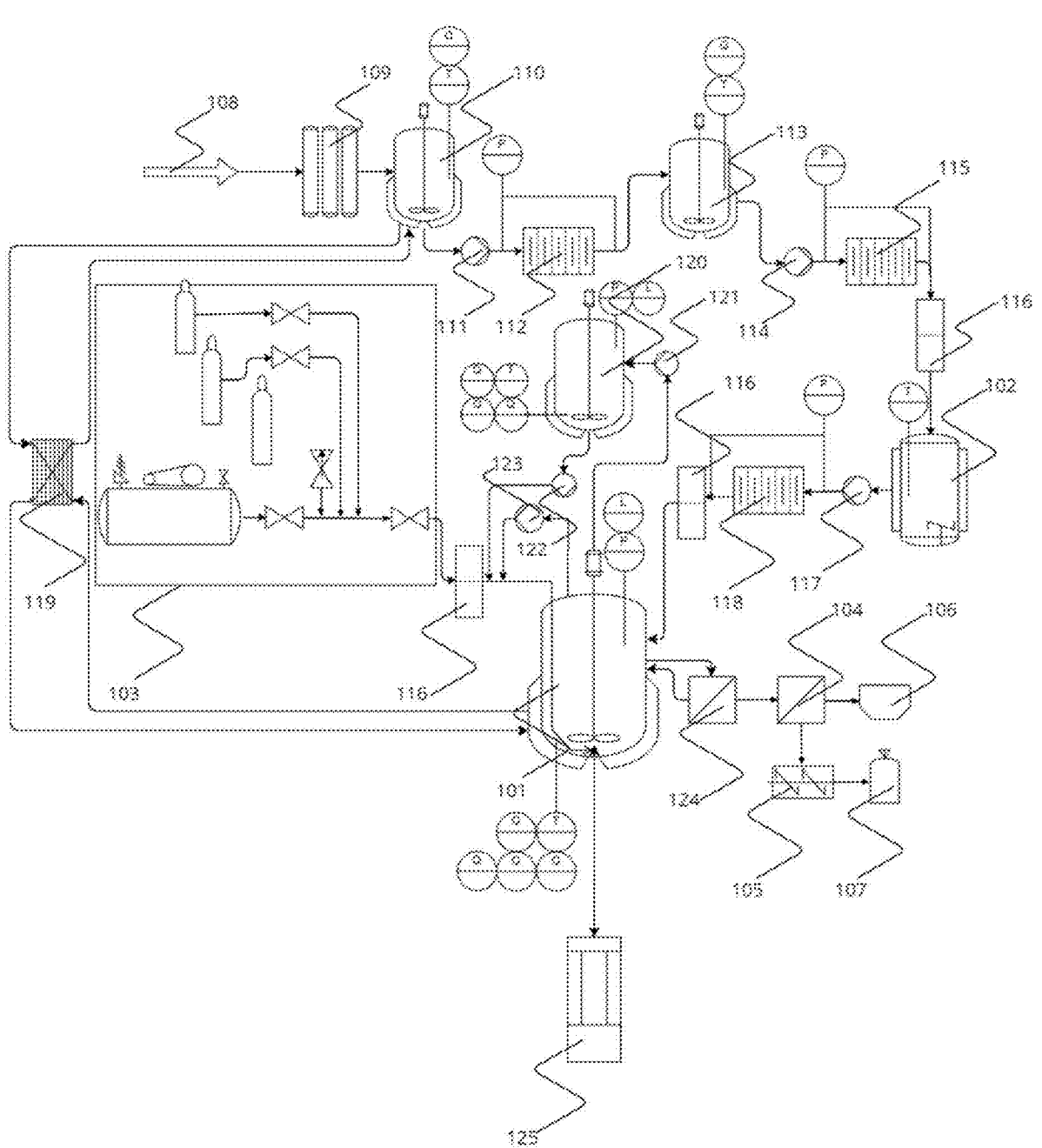
FIG. 29—illustrates an exemplary aspect of the aspect illustrated in the FIG. 28.

The components in FIG. 28:
101—The cultivation device
113—The mixing tank
103—The gas sparging system
104—The harvesting device
105—The product processing device
108—The water source
126—The loading tank
110—The hydrolysis tank
108—The water purification unit
123—The gas recycling system
124—The medium recycling system
119—The heat exchange system
120—The collateral cultivation device
125—The control unit The exemplary aspect of the invention as depicted in FIG. 29 is a particular variant of the present aspect of the invention as depicted in FIG. 28. The cultivation system according to the exemplary aspect of the invention as depicted in FIG. 29 may have the following components:

a water source 108 may be connected to the water purification unit 109, wherein the water purification unit 109 may provide at least one selected from the group of reverse osmosis, deionization, electrodeionization, electrodialysis and distillation; and wherein the water purification unit 109 may be connected to a hydrolysis tank 110, wherein the hydrolysis tank 110 may comprise a thermometer and/or conductometer and at least one shaft for loading the source of amino acid and/or nutritional peptides, wherein the source of amino acid and/or nutritional peptides may be selected from the group of protein concentrate and protein isolate;

the hydrolysis tank 110 may further include at least one stirring unit; and wherein the hydrolysis tank 110 may be connected to a first filtration unit 112 by a first pump 111, wherein the first filtration unit 112 may comprise a manometer capable of measuring the difference between the input and output of the filtration unit; and wherein the first filtration unit 112 may be connected to a mixing tank 113, wherein the mixing tank 113 may comprise the thermometer and/or conductometer, at least one shaft for loading the premix of other compounds and at least one stirring unit; and wherein the mixing tank 113 may be connected to a second filtration unit 115 by a second pump 114, wherein the second filtration unit 115 may comprise the manometer capable of measuring the difference between the input and output of the second filtration unit 115; and wherein the second filtration unit 115 may be connected to a storage tank 102 by at least one sterile barrier 116, wherein the storage tank 102 may comprise the thermometer; and wherein the storage tank 102 may be connected to a third filtration unit 118 by a third pump 117, wherein the third filtration unit 118 may comprise a manometer capable of measuring the difference between the input and output of the third filtration unit 118; and wherein the third filtration unit 118 may be connected to a cultivation device 101 by at least one sterile barrier 116, wherein the cultivation device 101 comprises a thermometer, conductometer, refractometer, manometer, pH meter, liquid level sensor and/or at least one gas concentration measurement instrument; and at least one stirring unit; and wherein the cultivation device 101 may be connected to a gas sparging system 103;

wherein the gas sparging system 103 may comprise one or more gas tanks coupled with a plurality of mass flow controllers and/or rotameters;

wherein the cultivation device 101 may be connected to a gas recycling system 123;

wherein the gas recycling system 123 may be configured to recycle and/or rejuvenate the exhaust gas from the non-working volume of the cultivation device 101; and wherein the gas recycling system 123 may be connected to a collateral cultivation device 120 by a fourth pump 121;

wherein the collateral cultivation device 120 may be configured to cultivate the converting organisms using the exhaust gas;

wherein the collateral cultivation device 120 may be connected to the cultivation device 101 by a fifth pump 122; and a medium recycling system 124, which may be connected to the cultivation device 101;

wherein the medium recycling system 124 may be configured to recycle and/or rejuvenate the culture medium; and wherein the medium recycling system 124 may be connected to at least one harvesting device 104 selected from the group of centrifuge unit and/or filtration unit;

wherein the harvesting device 104 may be connected to the medium recycling system 124 and may be configured to provide a comestible product and a waste medium 106;

wherein the comestible product may be processed by a product processing device 105 into a food product 107, e.g. pet food product and/or food product for human consumption; and a heat exchange system 119 configured to exchange the heat between the hydrolysis tank 110 and the cultivation device 101;

wherein the heat exchange system 119 may be connected to the cultivation device 101 and to the hydrolysis tank 110; and a control unit 125 operatively and communicatively coupled with the cultivation device 101 and/or other components within the cultivation system;

wherein the control unit 125 may control and/or regulate the cultivation system.

In the description of FIG. 16 to FIG. 29, the word "connected" may have meaning of "operatively coupled".

The non-human metazoan cells may be cultivated in the cultivation system. The cultivation takes place in a cultivation environment of culture medium. The cultivation may comprise all cultivation processes that take place in the cultivation device starting from the inoculation of the cells into a cultivation device and ending with the harvesting of the cell biomass. The cultivation processes may comprise phases such as growth, maintenance, differentiation and/or proliferation of the non-human metazoan cells The cultivation system may comprise at least one culture medium tank for the preparation of the culture medium and a cultivation device for the cell cultivation and features to produce a cell biomass. The cultivation device may comprise at least one culture vessel.

The cultivation system may further comprise at least one of the following features: at least one filtration unit; a plurality of sterile barriers; a plurality of pumps; a plurality of analytical instruments and sensors; a gas sparging system comprising a plurality of gas tanks; a gas recycling system;

at least one culture medium tank comprising a hydrolysis tank, a mixing tank, a loading tank, a storage tank and a waste medium tank; a water purification unit; a medium recycling system; a heat exchange system; a collateral cultivation device; at least one harvesting device; a control unit (the term "control unit" and "control device" may be interchangeable); an external physical stimulation mechanisms; and a product processing device.

The cultivation system may comprise at least one harvesting device. The harvesting device may be used to separate the cell biomass from the culture medium. The cell biomass may be harvested after at least one cultivation cycle, wherein the cultivation cycle varies according to the chosen cell line to be cultivated. The cultivation cycle may be at least as long as the length of time needed to perform more than one cell doubling of the non-human metazoan cells, wherein the cell doubling corresponds to one cycle of the cell. The cultivation cycle may be in a range of 1 hour to 336 hours, in a range of 4 hours to 168 hours, in a range of 12 hours to 168 hours, in a range of 24 hours to 144 hours, in a range of 36 hours to 120 hours, in a range of 36 hours to 96 hours or in a range of 48 hours to 72 hours.

The cultivation device may comprise at least one culture vessel made from food-grade stainless steel, stainless steel, glass, or any other suitable material that is not toxic to said metazoan cells and at the same time is inert to the culture medium, cell metabolites and other substances considered. The culture vessel may be cylindrical, cubic, rounded cubic, round-bottom cylindrical, or another suitable shape, and may comprise a stirred tank, bubble column tank, airlift tank, packed bed tank, rotating-wall tank, wheel-tank, fixed-bed tank, perfusion tank or hollow fiber tank.

The inner volume of a culture vessel in a cultivation device may be in a range of 1 l to 100,000 l, or in a range of 10 l to 10 000 l, or in the range of 100 l to 1000 l. The maximum working volume of the culture vessel may be in a range of ½ to ¹⁹⁄₂₀ of the whole volume of the culture vessel. For example, the culture vessel dimensions ratio of height to width may be in a range of 20:1 to 1:20, for example 1:1, 1:2, 1:3. The culture vessel may be able to withstand an internal pressure of at least 0.1 kPa compared to atmospheric pressure. The culture vessel may be able to withstand a ratio of internal pressure atmospheric pressure in a range of 0.01 to 5, wherein the ratio may be defined as the ratio between the internal pressure and atmospheric pressure. The internal pressure may be determined and/or measured by a pressure sensor positioned within or proximate to the cultivation device. The culture vessel may further comprise a plurality of gas and fluid inlets/outlets to keep an optimal environment; the gas inlets may be formed by spargers, which are used to sparge a gas mixture in order to deliver $O_2$ into the culture vessel, which may be designed as a membrane, sinter, ring, tube, mesh or any other similar design compatible with the cultivation device and gas outlets, which release gas from the culture vessel in order to dispose of $CO2$ from the cultivation environment; the exchange of gasses with the culture medium can occur inside or outside of the cell culture vessel.

Optionally, at least one impeller and/or at least one baffle may be located inside the culture vessel of preferred shape to obtain optimal aeration of the mixture.

The cultivation device may further comprise a plurality of sensors and analytical instruments located inside or outside the culture vessel to provide real-time data about the metazoan cell processes and the parameters, such as pH, total pressure in the culture vessel, concentrations, or partial pressures of important gasses such as $O_2$ and $CO_2$, temperature, nutrient concentration, and cell density.

Optionally, an external stimulation device stimulating the cell population may be positioned inside the culture vessel and/or proximate to the culture vessel, configured to provide radiofrequency, optical, magnetic or microwave radiation. The stimulation device may be positioned inside or outside the culture vessel to increase the effectiveness of metazoan cell processes.

The cultivation device may further comprise a control device, preferably a PC unit with a specifically designed software, which can be operated by a skilled operator to ensure total control of all processes.

In one aspect of the invention, the cultivation device may have a gas recycling system, which ensures that the overhead gas from the culture vessel may be controllably exhausted or returned to the gas inlets; optionally, the gas composition may be changed, for example by removing $CO_2$ or moisture or adding $O_2$, before it is returned to the gas inlet.

In one aspect of the invention, the culture vessel may be sterilized using chemical agents, thermal sterilization or UV-radiation.

In one aspect of the invention, the parameters in the culture vessel may be measured by these analytical methods: the temperature of the culture medium and culture vessel may be measured in real time using thermometers or thermal cameras; the nutrient and metabolite concentrations in the culture medium may be measured in real time by probes inserted directly into the culture vessel, or off-line via a sample taken from the culture vessel; preferably, measurements may be performed by electrochemical probes (for example glucose or ammonia probes), UV-Vis spectroscopy, mass spectrometry or polarimetry or other suitable methods; optionally, extraction and/or separation methods may be employed before the analysis, such as capillary electrophoresis or HPLC; cell density may be measured in real time using optical methods, such as turbidimetry, electromagnetic methods, such as the measurement of permittivity, or it may be inferred indirectly from parameters such as $O_2$ consumption, glucose consumption or $CO_2$ production.

Figure 30:
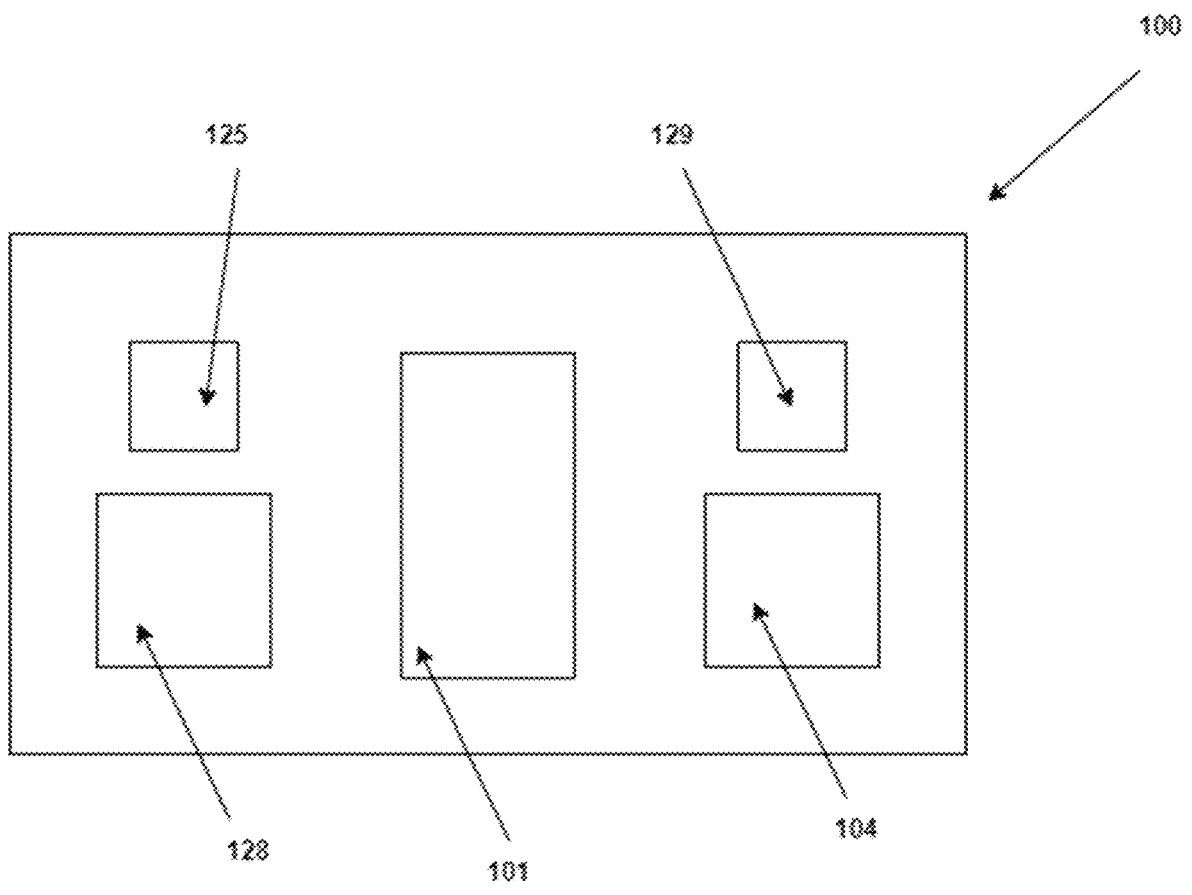
FIG. 30—illustrates the cultivation system according to the invention.

FIG. 30 depicts the cultivation system 100 according to the invention. In this aspect of the invention, the cultivation system 100 may comprise a seeding tank 128, a cultivation device 101, a harvesting device 104, a control unit 125, and sensors and analytical instruments 129. Optionally, the cultivation system 100 may further comprise a device 105 for preparing food products (not depicted in FIG. 30) that may be formed, for example, by mixer, heat dryer, extruder, heat extruder, spray dryer, freeze dryer, freezer, vacuum sealer, tissue incubator, sterilizer, cooker, cooler, or their combination.

The harvesting device 104, that serves to harvest cells, may comprise a filtration device, a centrifugation device, a sieving device, or any other appropriate device for harvesting of cells.

The device 105 for preparing food product may be able to perform at least one of the following processes: receiving, storage, grinding, mixing, conveying, extrusion, cooking, drying, cooling, pumping, coating, dividing, or packaging, or any other requested processes. The device 105 for preparing food product may be formed for example by an extruder. The extruder may comprise for example a bin, a feeder, a preconditioner, an extrusion cooker, die/knife assembly or any other appropriate components. The operating conditions may be adjusted to vary the characteristics of the finished product as requested.

Figure 31:
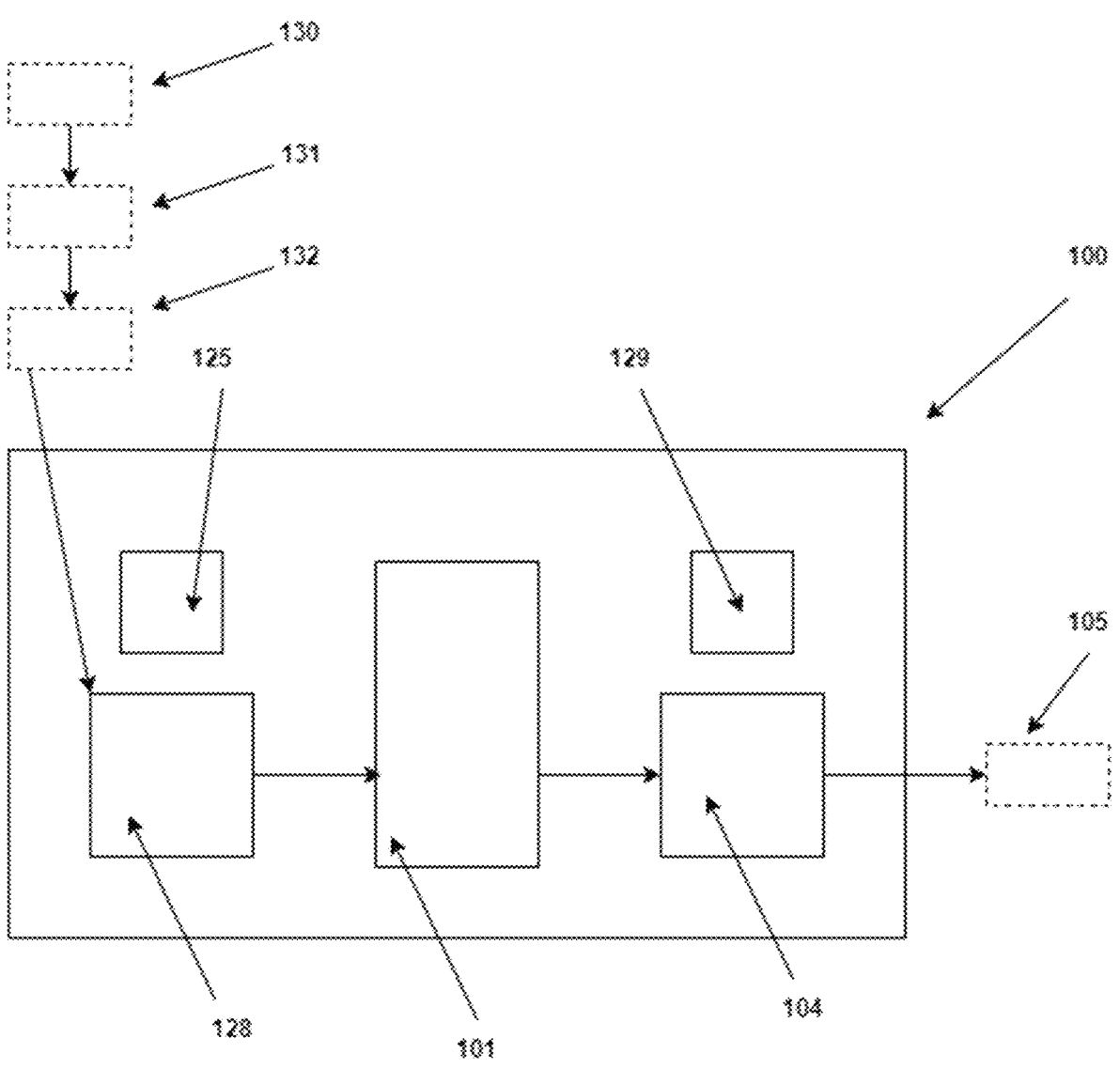
FIG. 31—illustrates the cultivation system according to the invention further comprising a primary cell bank, a production cell bank and a harvesting device.

In other aspects of the invention, the cultivation system 100 may be as depicted in FIG. 31. In this aspect of the invention, the isolated metazoan cells 130 may be deposited in the primary cell bank 131. The cells may be modified and may obtain a gain of function. These cells or cells from primary cell bank 131 may be used in the production cell bank 132. The cells from the production cell bank 9 may be used for cultivation and may be inoculated into the cultivation device 101 for cell cultivation. Optionally, the seeding tank 128 may be used in order to multiply cells before their inoculation into the cultivation device 101. After cultivation of cells is finished, the cells may be harvested using a cell harvesting device 104. All processes may be monitored and controlled by at least one of a control unit 125, or sensors and analytical instruments 129.

The control unit 125 may be coupled with any component within the cell cultivation system 100. The control unit 125 may control and/or regulate every process taking place within the cultivation system 100. The control unit 125 may be operated using at least one printed circuit board (PCB) and/or microprocessor with software capable of controlling the cultivation device 101, regardless of the extensions and scale of the system. The control unit 125 may be connected to at least one central data storage. The cultivation system 100 may comprise one or more subcontrol units.

Optionally, the cultivation system 100 may further comprise at least one of a sterilization unit, sterile barrier, reverse osmosis device, filtering device, microfiltration device, or any other device for providing a sterile environment and/or for filtration purposes. The cultivation system 100 may further comprise at least one device or vessel serving as source of cells for cultivation or production components, for example culture medium, pumps, vessels, for example pressure cylinders, with gas needed for cultivation, such as for example oxygen, carbon dioxide, nitrogen or air, tubings and valves for connection of parts of the cultivation system 100, or any other appropriate device or vessel. The cell cultivation system 100 may comprise a device for recycling of culture medium and/or purification of spent culture medium or other components involved in the cultivation process.

Optionally, the cultivation system 100 may comprise a device 105 for preparing food product. The device 105 for preparing food product may be formed by a simple vessel or bioreactor for mixing cultivated cell biomass with additional compounds, or may comprise other appropriate device for other processes for preparing the food product. The device 105 for preparing food product may be formed for example by extruder.

Figure 32:
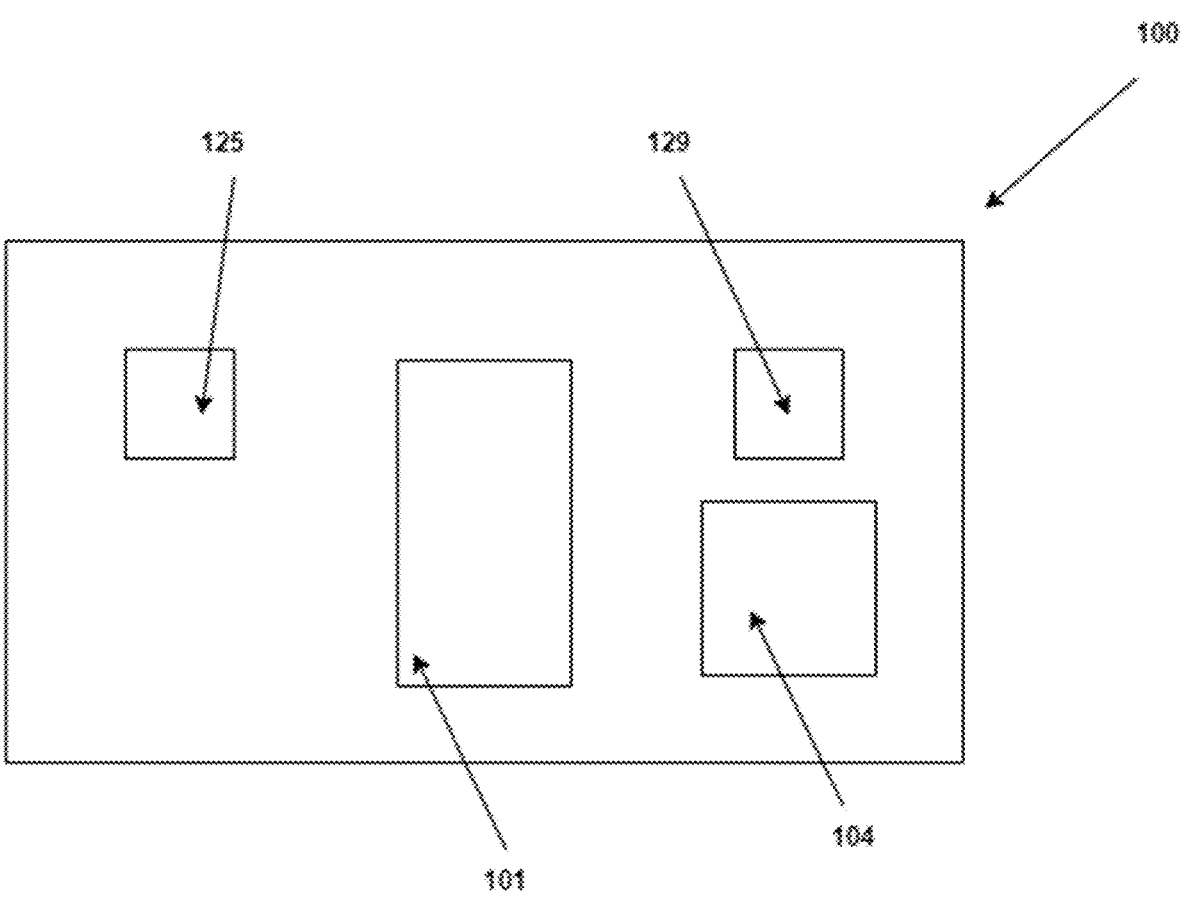
FIG. 32—illustrates the cultivation system according to the invention, wherein the seeding tank is not applied.

In yet another aspect of the invention, the cultivation system 100 may be as depicted in FIG. 32, wherein the seeding tank 128 is not applied. The cultivation system 100 may comprise the cultivation device 101, the harvesting device 104, the control unit 125, and the sensors and analytical instruments 129. The appropriate metazoan cells may be inoculated directly into the cultivation device 101.

Figure 33:
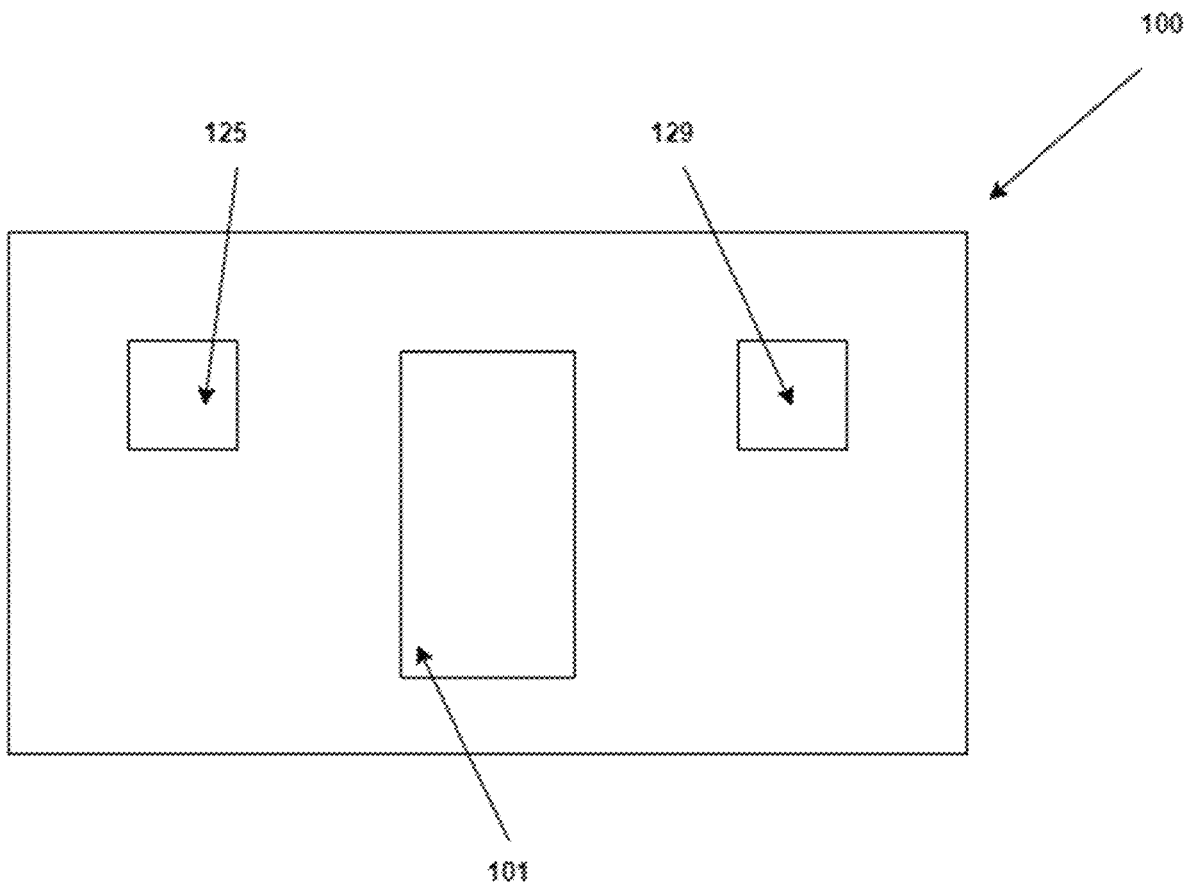
FIG. 33—illustrates the cultivation system according to the invention, wherein the process of harvesting of cells is carried out in the cultivation device.

In one aspect of the invention the cell cultivation system 100 may comprise the cultivation device 101, the control unit 125, and the sensors and analytical instruments 129. In this aspect the cultivation device 101 may serve also as the harvesting device 104, wherein the processes of harvesting of cells are carried out in the cultivation device 101. The cultivation device 101 may be equipped for cell harvesting, for example may be equipped with a component or a device for filtering or sieving out the cells or for harvesting cells based on centrifugation principle, or with any other appropriate device for harvesting the cells. The cell cultivation system 100 according to this aspect of the invention is depicted in FIG. 33.

The cultivation device 101 may be formed by the bioreactor. The cultivation device 101 may comprise at least one culture vessel made from for example food-grade stainless steel, stainless steel, glass, or any other suitable material, that is not toxic to said metazoan cells and at the same time is inert to culture medium, cell metabolites and other substances used within the cultivation processes and can withstand sterilization processes. The culture vessel may have cylindrical, cubic, rounded cubic, round-bottom cylindrical, or another suitable shape. The cultivation vessel may have the construction solution of a stirred tank, bubble column tank, airlift tank, packed bed tank, rotating-wall tank, wheeltank, fixed-bed tank, perfusion tank or hollow fiber tank or any other suitable construction.

The culture vessel may have the inner volume of culture vessel in a range of 1 liters to 1,000 000 liters, or in a range of 10 liters to 50,000 liters, or in a range of 20 liters to 30 000 liters, or in the range of 100 liters to 5000 liters, or in the range of 1000 liters to 4000 liters, or in the range of 1500 liters to 3500 liters, or in the range of 2000 liters to 3000 liters.

The culture vessel of the cultivation device 101 may be able to withstand an internal pressure of at least 0.1 kPa compared to atmospheric pressure. The culture vessel may be able to withstand a ratio of internal pressure atmospheric pressure in a range of 0.01 to 5, wherein the ratio may be defined as the ratio between the internal pressure and atmospheric pressure. The internal pressure may be determined and/or measured by a pressure sensor positioned within or proximate to the cultivation device 101.

The cultivation device 101 may further comprise at least one gas or fluid inlet and at least one gas or fluid outlet.

The gas inlet may be formed by sparger, which is used to sparge reaction mixture with a gas or a mixture of gasses. The sparger may provide delivery of oxygen into the cultivation device 101. The sparger may comprise a membrane, sinter, ring, tube, mesh or any other similar component, which may release gas, for example oxygen, into the cultivation device, or may remove gas from the cultivation device 101, for example carbon dioxide.

The exchange of gasses with the culture medium may occur inside or outside of the cultivation device 101.

The cultivation device 101 may comprise at least one impeller and/or at least one baffle located inside the cultivation device 101 for the purpose of mixing or aeration of cultivation mixture.

The cultivation device 101 may comprise at least one sensor, as a part of the sensors and analytical instruments 129, providing data in respect of the metazoan cell processes and the parameters, such as for example pH and pressure in the cultivation device 101, concentrations or partial pressures of important gasses such as oxygen and carbon dioxide in culture medium, temperature, nutrient concentration, conductivity, cell density or any other parameters.

Optionally, the cultivation device 101 may comprise an external stimulation device stimulating the cell population inside the cultivation device 101 using for example ultrasound, radiofrequency, electrical energy, laser, pulsed electromagnetic field, optical, magnetic or microwave radiation, or any other energy source. The external stimulation device may be placed inside or outside the cultivation device 101 in order to increase the effectiveness of metazoan cell processes.

The cultivation system 100 according to the invention may comprise a control device, for example the control unit 125 that may comprise a software, to control cultivation processes.

In one aspect of the invention, the cultivation system 101 may comprise a gas recycling system, which ensures that the overhead gas from the cultivation device 101 may be controllably exhausted or returned to the gas inlets; optionally, the gas composition may be changed, for example by removing carbon dioxide, removing moisture or adding oxygen, before it is returned to the gas inlet.

The cultivation device 101 may be sterilized using chemical agents, or by physical methods, for example by thermal sterilization or UV-radiation, or by any other appropriate sterilization method.

The parameters of processes in the cultivation device 101 may be measured by appropriate analytical or monitoring methods. For example the temperature of the culture medium and temperature in different parts of the cultivation device 101 may be monitored, for example in real time, using thermometers, thermal cameras or other thermal sensors. The pressure sensors, pH sensors, or any other appropriate sensors may be used.

The nutrient and metabolite concentrations in the culture medium may be measured, for example in real time, by probes inserted directly into the cultivation device 101, or in a sample taken from the cultivation device 101. The measurements may be performed by electrochemical probes, for example by glucose or ammonia probes, UV-Vis spectroscopy, mass spectrometry or polarimetry or other suitable methods. Also the extraction or separation methods may be employed before the analysis, such as capillary electrophoresis or HPLC. The cell density may be measured, for example in real time, using optical methods, such as turbidimetry, electromagnetic or any other methods, such as the measurement of permittivity, or it may be inferred indirectly from parameters such as oxygen consumption, glucose consumption or carbon dioxide production. Other physical and chemical conditions of the cultivation device 101 may be measured, for example pH, conductivity, refractive index, osmolality or pressure.

The cell cultivation system 100 according to the invention may comprise at least one seeding tank 128. The seeding tank 128 with a volume in the range of 1 l to 25 m³, or in the range of 10 l to 15 m³, or in the range of 100 l to 10 m³ may be used. Then the cells may be moved to an intermediate bioreactor, for example in the range of 150 l-15000 l, or straight into a large production bioreactor. It is possible to seed from one seeding tank 128 one or more cultivation devices 101.

The cell cultivation processes may be running in batch, fed-batch, continuous or perfusion regime, or in a combination of these regimes.

The cell biomass may be harvested using the harvesting device 104.

The wet cell biomass may be processed, for example by sieving, filtering or centrifugation, or by other appropriate processes. The residual water and other components of the cultivation solution may be removed.

In one aspect of the invention, a plurality of cultivation devices 101 may be connected together within cell cultivation processes according to the invention. The cultivation devices 101 may be formed, for example, by bioreactors. In one aspect of the invention, at least two cultivation devices 101 connected together may be used. The cultivation devices 101 may be connected together in parallel, in series, in circuit, or in combination of these types of connection. At least two cultivation devices 101 may be connected to at least one source 133 of cells and at least one source of production components 134, such as a culture media.

The source of cells 133 may comprise, for example, at least one of a seed tank 128, primary cell bank 131, production cell bank 132, or any other appropriate source of cells 133.

The part of the cultivation mixture may be left in the cultivation device 101 after the cultivation process is finished and may be used as inoculum for further cultivation process in the cultivation device 101.

In one aspect of the invention, four cultivation devices 101, for example, bioreactors, may be connected together in circuit. Each pair of cultivation devices 101 may be supplied from separate sources of production components 134, for example, from culture media storing devices, such as storage tanks. The source of cells 133, for example, a seed tank 128, may be connected to all the production cultivation devices 101. The part of the cultivation mixture after cultivation may be used as inoculum in the following cultivation device 101 for further cultivation process. The amount of part of the cultivation mixture after cultivation used as inoculum may be in the range of 1% to 40%, in the range of 2% to 30%, or in the range of 5% to 20%.

Figure 34:
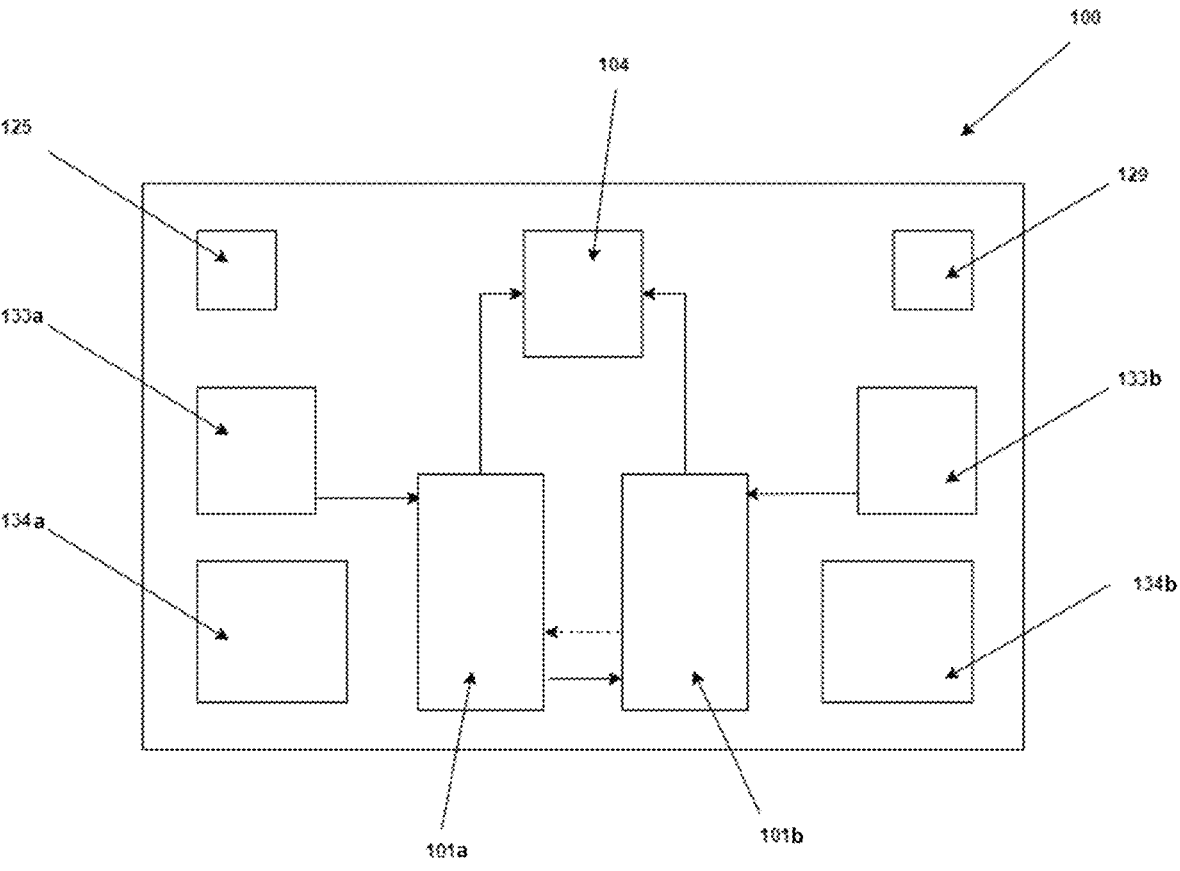
FIG. 34—illustrates the cultivation system according to the invention comprising two cultivation devices connected together.

In other aspects of the invention, the cultivation system 100 may be as depicted on FIG. 34. In this aspect, the cultivation system 100 may comprise two cultivation devices 101 that may be connected together. The cultivation system 100 may further comprise a source of cells 133 for cultivation and a source of production components 134, such as, for example, a culture medium. The cultivation system 100 in this aspect may further comprise the harvesting device 104, sensors and analytical instruments 129 for sensing important parameters of cultivation processes, and the control unit 125 for controlling the processes. Optionally, the cultivation system 100 may further comprise a device 105 for preparing food product (not depicted on FIG. 34).

The cultivation system 100 according to this aspect may comprise two sources of cells 133 and two sources of production components 134. The first cultivation device 101*a* may be connected to the first source of cells 133*a* and the first source of production components 134*a*. The second cultivation device 101*b* may be connected to the second source of cells 133*b* and the second source of production components 134*b*. The cells may be inoculated in the first cultivation device 101 and in the second cultivation device 101 at the same time, wherein the cultivation processes may run in both cultivation devices 101 simultaneously, or the cells may be inoculated into the second cultivation device 101*b* with some delay after inoculation to the first cultivation device 101*a*. The cells may be also inoculated only into the first cultivation device 101*a* and a part of the cultivation mixture, after the cultivation process is finished, may be used as inoculum into the second cultivation device 101*b*.

The cells may be cultivated in a cultivation device 101 formed, for example, by a bioreactor, in the presence of a culture media.

Cultivation may be performed in a production bioreactor with a volume in the range of 1 l to 25 m³, in the range of 10 l to 15 m³, or in the range of 100 l to 10 m³.

The cell harvesting methods may further include membrane microfiltration, tangential-flow filtration (TFF) or crossflow filtration, flocculation, magnetic separation, acoustic separation and depth filtration, as well as specialized solutions coupling either microfiltration or centrifugation with TFF or depth filtration.

Centrifugation may be used within the processes according to the invention. The technique uses the force of gravity to separate cells from the suspension based on their density. Centrifugation may be used on a larger scale using larger centrifuges or multiple smaller centrifugation cycles. The type of used centrifuge may be for example batch centrifuge, decanter, tubular bowl centrifuge, disk stack centrifuge, or any other appropriate centrifuge type.

Filtration involves passing the cell suspension through a filter with defined pore sizes to separate cells from the liquid phase. Filtration may be scaled up by using larger filtration systems or by employing multiple parallel filtration units. The pore size of the filtration devices used in the processes according to the invention may be in the range of 0.01 μm to 10 μm, or in the range of 0.1 μm to 5 μm, or in the range of 0.5 to 1 μm.

Among other methods, used within the processes according to the invention, may be crossflow filtration (Tangential Flow Filtration—TFF). In TFF, the cell suspension flows tangentially across the filter membrane, allowing smaller molecules to pass through, while retaining cells on the surface. TFF may be scaled up by using larger filtration systems with appropriately sized membranes.

Another method that may be used within the processes according to the invention, is flocculation. Flocculation involves the addition of chemicals that cause cells to aggregate and settle out of suspension. The scalability of flocculation methods depends on the specific chemicals used and the ability to control the flocculation process in larger volumes.

For the purpose of harvesting cells or cell separation, magnetic cell separation may be applied. This method involves labeling cells with magnetic particles and using a magnetic field to separate the cells from the suspension. Magnetic cell separation may be scaled up by using larger magnetic separators or multiple parallel systems.

Acoustic separation may be used as well. Acoustic methods use sound waves to separate cells based on their size and density. Acoustic separation may be scaled up by using larger acoustic devices or by incorporating multiple devices in parallel.

Continuous perfusion systems may be used for the purpose of harvesting cells or cell separation within the processes according to the invention. In perfusion systems, fresh media is continuously added to the cell culture while spent media containing cells is removed.

In one aspect of the invention, the waste medium may be used for the subsequent cultivation of converting microorganisms, such as bacteria, yeast, fungi, algae, microalgae and/or any other appropriate organism capable of metabolizing waste medium as it contains amino acids, peptides, various ions, organic amines, saccharides, fats, vitamins and/or any other compounds rich in carbon, nitrogen, oxygen, sulphur and/or hydrogen. The converting microorganisms and/or any other appropriate organism capable of metabolizing waste medium may produce components that may be used for the preparation of culture media for the non-human metazoan cells.

In one aspect of the invention, converting microorganisms may be used for the production of proteins and peptides that may be used as an amino acid source for the cultivation of the non-human metazoan cells.

Converting microorganisms may be cultivated in the collateral cultivation device that may be a part of the cultivation system. The collateral cultivation device may be coupled with the gas recycling system to use exhaust gas from the cultivation device or may be coupled with the medium recycling system to use waste medium for the cultivation. In another aspect of the invention, the converting organisms may be cultivated in the collateral cultivation device that is not part of the cultivation system and may be cultivated using a designated culture medium for the specific converting organism that was selected as compatible with the cultivation system.

In another aspect of the invention, the collateral cultivation device may be configured for the cultivation of methanogenic bacteria. Such converting organisms may use waste medium as a substrate for the cultivation of the converting organisms. The waste medium may be inoculated with at least one bacteria strain capable of producing biogas. The biogas may comprise methane, carbon dioxide, hydrogen sulfide, nitrogen, oxygen, ammonia, hydrogen, water, trace amounts of other simple organic compounds and/or simple inorganic compounds. The biogas may be further used, for example, as a fuel, heating, electricity generation and/or may be used for any other appropriate application.

In one aspect of the invention, the collateral cultivation device may be configured for the cultivation of knallgas bacteria using the waste medium or any other appropriate medium. The knallgas bacteria, also known as hydrogen-oxidizing bacteria, may be cultivated to provide a cell biomass. The cell biomass of knallgas bacteria may comprise protein-rich components that may be further used as a source of amino acids for the cultivation of non-human metazoan cells or may be further used as a component for producing edible products, such as pet food products or products for human consumption. The examples of such knallgas bacteria may comprise *Cupriavidus necator, Xanthobacter autotrophicus, Ralstonia eutropha*, and/or *Alcaligenes eutrophus*. The knallgas bacteria may be further lysed to disrupt the cell wall of said bacteria to release protein and/or peptides in the cells of the bacteria. The cell biomass that has been lysed may be further processed to obtain concentrated proteinous mass, which may be subsequently used as amino acid source in the culture medium for the cultivation of the non-human metazoan cells. In addition, the knallgas bacteria may use exhaust gas comprising $CO_2$ from the cultivation device and/or from the gas recycling system. The collateral cultivation device may be coupled with the gas recycling system. The gas recycling system may transfer $CO_2$ to the collateral cultivation device to provide $CO_2$ for the knallgas bacteria cultivation.

In one aspect of the invention, the collateral cultivation device may be configured for the cultivation of algae and/or microalgae using the waste medium or any other appropriate medium. The algae and/or microalgae may be cultivated to provide an amino acid source for the culture medium designed to cultivate non-human metazoan cells. The algae and/or microalgae may be further used as an edible component and/or as the fuel for biogas, biochar or bio-oil production. The algae and/or microalgae may comprise organisms such as Arthrospira spp., *Chlorella* spp., Dunaliela *salina, Pophyra* spp. *Laminaria* spp., *Chlorella vulgaris, Scenedesmus* spp., *Gracilaria* spp., *Nannochloropsis* spp., *Sargassum* spp. and/or any other algae and/or microalgae capable of sequestering carbon in the form of $CO_2$. Analogically, the cultivation of the algae and/or microalgae may also use exhaust gas from the gas recycling system and/or from the cultivation device.

In one aspect of the invention, the collateral cultivation device may be configured for the cultivation of yeast using the waste medium or any other appropriate medium. The yeast may be cultivated to provide an amino acid source for the culture medium designed to cultivate non-human metazoan cells. The yeast may be further used as an edible component for the production of edible products. The yeast may comprise organisms such as *Saccharomyces cerevisiae, Saccharomyces pastorianus, Saccharomyces bayanus*, or any other suitable yeast strains known for their applications known to ordinary skilled person in biotechnology, food production, or bioengineering.

The methods for sterilization of the cultivation device may comprise hot steam sterilization, UV sterilization, chemical sterilization, irradiation or any combination thereof.

In one aspect of the invention, hot steam sterilization may be used for the sterilization of the cultivation device. The hot steam sterilization may comprise a steam generator, wherein the hot steam sterilization may be coupled with a water source and with the cultivation device. The steam generator may comprise a main body comprising cylindrical housing, rectangular housing and/or any other suitable shape of housing made from material capable of withstanding temperatures higher than 150° C., such as stainless steel, PTFE and/or any other appropriate material. The steam generator may be insulated to prevent any heat loss and to ensure safety during operation of the steam generator. The steam generator may be connected with the cultivation device by at least one high-pressure pipe and/or tube to at least one port, wherein the port may be located on the top, bottom or side wall of the cultivation device. According to the present aspect of the invention, the cultivation device further comprises an outlet for the hot steam to pass through the bioreactor after performing sterilization. The hot steam may further condense into water, which may be collected and/or returned to the steam generator.

In one aspect of the invention, chemical sterilization may be used for the sterilization of the cultivation device. The chemical sterilization may comprise use of chemical agents in solid, liquid and/or gaseous state. The chemical sterilization may comprise at least one chemical agent capable of killing at least one of gram-negative bacteria, gram-positive bacteria, viruses, fungi and/or any other contamination source. Such chemical agents may comprise ethanol, isopropanol, hydrogen peroxide, ethylene oxide, ozone and/or chlorine dioxide.

In case of using liquid chemical agents, the configuration of the sterilization device may comprise at least one sterilization tank connected to the cultivation device, wherein the sterilization tank may be anti-corrosive and/or resistant to any used chemical agent. The sterilization tank may be configured to load chemical agents into the cultivation device and may be also configured to unload the chemical agent. The unloading of the chemical agent may be performed by at least one pump connected to the sterilization tank and/or the cultivation device, wherein the chemical agent may be recycled at least once.

In case of using gaseous chemical agent, the configuration of the sterilization tank may comprise at least one gas tank coupled with the cultivation device. The gas tanks may comprise at least one gas selected from the group of ethylene oxide, chlorine dioxide, hydrogen peroxide vapor, ozone and/or any other appropriate gas capable of sterilizing the cultivation device.

In one aspect of the invention, the means of sterilization described in the previous paragraphs may be combined. Such combinations may comprise combination of UV sterilization with hot steam sterilization, hot steam sterilization with gas sterilization and/or UV sterilization with gas sterilization, wherein the previously mentioned combinations are not limiting to the present invention and all present means of sterilization may be combined.

In one aspect of the invention, the cultivation device may comprise a membrane impeller configured as a part of the gas sparging system. The membrane impeller may be configured to have relatively higher surface area compared to common impeller to deliver gas inside the culture vessel without forming any bubbles inside the culture medium that may burst. The impeller may comprise a plurality of membranes having defined size of the pores to form fine and smaller bubbles relatively to bursting bubbles. Such fine bubbles may be immediately dissolved in the culture medium if the fine bubbles are formed by $O_2$ or if the fine bubbles are made from a gaseous mixture rich in $O_2$. The membranes may have high gas permeability so that direct gas transfer through the membrane into the medium may be performed without the need for any pores in the membrane. The impeller may have the shape of capillaries, plates, lamellae, discs, or perforated tubes. These shapes can be configured and/or optimized to maximize the surface area for gas delivery rate, enhancing the oxygen transfer efficiency in the cultivation device. Additionally, the impeller may feature helical or spiral designs to increase turbulence and improve the distribution of fine bubbles throughout the culture medium. Each of these configurations aims to enhance the aeration process, ensuring more efficient oxygenation and more efficient and homogenous mixing within the bioreactor.

In one aspect of the invention, the cultivation device may comprise magnetically driven aerators, impellers or any other means performing efficient mixing and oxygen delivery. Magnetic drive of the means performing efficient mixing may comprise transferring mechanical energy through the interaction of at least 2 pairs of magnetic rotors. The magnetic rotors may be positioned inside and outside of the hermetically sealed culture vessel in the form of a sealed housing. Within the sealed housing, for example, a stainless steel shaft, coupled with a gearbox and an electric motor may be fitted with inner rotors that may comprise permanent magnets. These magnets may directly receive the mechanical power of the motor. On the inside of the housing, inner rotors with impeller blades may be equipped with driven magnets. The mechanical power may be further transferred from the outer rotors to the inner rotors through magnetic interaction. As the outer rotors turn, the inner rotors rotate in sync, leading to efficient mixing.

The perfusion element may comprise cartridges configured to retain at least some portion of the cultivation non-human metazoan cells, wherein such cartridges may comprise a plurality of membranes having defined pore size capable of retaining at least some portion of the cell biomass. The perfusion cartridge may be a part of the medium recycling system.

The cooling system of the cultivation system may be configured to decrease the temperature in the cultivation device by an active cooling or inactive cooling. The inactive cooling may cool the cultivation device normally by a thermal convection to the outer environment of the cultivation device. The active cooling may cool the cultivation device by at least one of the previously mentioned means such as cooling with air, cooling with cold water or cooling by a chiller or their combination thereof, including normal inactive cooling.

According to some aspects of the invention, the terms "shaft" and "funnel" may be interchangeable when referring to the means for transporting gasses, liquids, solids and/or any other materials within the cultivation system.

In order to ensure sterility of the gas sparged by the gas sparging system, more than one filtration unit and/or sterile barrier may be employed. Employing more than one filtration unit and/or sterile barrier may result in enhanced sterility of the sparged gas. In one aspect of the invention, one or more filtration units and/or sterile barriers may be employed, each with filters of varying sizes, designed to capture different types of contaminants, thereby ensuring the sterility of the gas. Such contaminants may comprise bacteria, viruses, fungi and/or any other contaminant.

The cultivation system may comprise at least one sterile barrier configured to maintain the sterility of the cultivation device inner environment. The sterile barrier may be positioned between the cultivation device and the storage tank, as well as between the cultivation device and the gas sparging system. The sterile barrier may comprise any suitable means for preventing contamination and ensuring sterility of the inputs into the cultivation device. These means may comprise, but are not limited to, filters, membranes, valve systems, or other physical or chemical barriers known in the present field of the invention. The sterile barrier may be configured to allow the controlled passage of sterile gasses, liquids, or other materials necessary for the cultivation process while effectively preventing the ingress of contaminants. The barrier may also include features such as automatic or manual integrity testing systems to verify its functionality and ensure that sterility is maintained throughout the cultivation process. Additionally, the sterile barrier may be constructed from materials that are compatible with the process conditions, such as high temperatures, pressures, and the specific chemicals or biological agents involved in the cultivation of mammalian cells.

In one aspect of the invention, the culture medium may conventionally be sterilized using ultra-high-temperature (UHT) pasteurization to inactivate viruses, bacteria or any appropriate microorganisms using the sterile barrier. The UHT pasteurization may be performed at target temperatures in a range of 120° C. to 180° C., in a range of 130° C. to 170° C., or in a range of 140° C. to 160° C.

During the process of UHT pasteurization, the culture medium may be kept at the target temperature for a portion of time in a range of 0.5 seconds to 60 seconds, in a range of 1 second to 30 seconds and/or in a range of 2 seconds to 20 seconds.

After the UHT pasteurization, the culture medium may be allowed to rest for a time, which may be in a range of 24 hours to 48 hours, in a range of 32 hours to 44 hours, or in a range of 36 hours to 40 hours within a storage tank. During this period of time the culture medium may be subjected to the measuring of the contamination by optical density at 600 nm, flow cytometry, colony forming units calculation, pH measurement, oxygen concentration measurement, or any other appropriate methods for measuring bacterial contamination.

The ultra-high temperature pasteurization may be performed by a sterilization device capable of providing sterile culture medium.

In one aspect of the invention, the sterile barrier of the cultivation system may be designed to sterilize liquids may comprise a filter, preferably a 0.2 μm rated filter and/or a 0.1 μm rated filter, and/or a sterilization device performing UHT pasteurization.

In one aspect of the invention, the sterile barrier of the cultivation system designed to sterilize gasses may comprise a filter, preferably a 0.2 μm rated filter and/or a 0.1 μm rated filter, and/or a flow-through chamber where the sterilizing effect may be achieved through radiation, preferably UV radiation, and/or by heat.

In one aspect of the invention, the sterile barrier of the cultivation system may comprise UV sterilization, sterilization by irradiation, ozone sterilization and/or any other compatible means of sterilization.

In one aspect of the invention, at least one filtration unit may be located between the hydrolysis tank and mixing tank; and/or between the mixing tank and storage tank; and/or between the storage tank and the cultivation device.

In one aspect of the invention, the hydrolysis tank may be connected with a centrifuge unit to remove solid parts of the protein hydrolysate and/or modified protein hydrolysate to provide purified protein hydrolysate. In another aspect of the invention, in order to further increase the effectivity of the removal of solids, the hydrolysis tank may be connected with a centrifuge unit and the filtration unit together, to provide purified protein hydrolysate where removal of solid residues is more complete compared to using only a centrifuge unit. In another aspect of the invention, at least one centrifuge unit may be used.

In one aspect of the invention, the by-products from the culture medium preparation, specifically preparation of protein hydrolysate, specifically the solid residue from hydrolysis, may be used as a component for the production of pet food products.

In one aspect of the invention, the cultivation device may comprise at least one inoculation port. The inoculation port may be used to inoculate at least one non-human metazoan cell line (i. e. at least one non-human metazoan cell population) dispersed in the culture medium wherein the volume of the inoculum may be at least 3% of the inner volume of the culture vessel. The inoculation port may be equipped with a set of two 3-way valves to allow cleaning and sterilization independently from the culture vessel. The inoculation port may further comprise means for ensuring sterility of the inoculation process, such as steam sterilization, or any other appropriate means of sterilization.

In one aspect of the invention, the water purification unit may be connected with the mixing tank to provide purified water for the culture medium production.

In one aspect of the invention, the loading tank may comprise a semi-automatic weighing scale and may be operated by an operator, wherein the semi-automatic weighing scale may be configured to load all the components to the mixing tank, to the hydrolysis tank and/or to the cultivation device. In another aspect of the invention, the loading tank may comprise an automatic weighing machine, wherein the automatic weighing scale is configured to automatically weigh all components that may be added and may be also configured to load all the components to the mixing tank, to the hydrolysis tank and/or to the cultivation device. In yet another aspect of the invention, the loading tank may comprise at least one automatic dispenser for each component that may be added as a part of the culture medium.

In one aspect of the invention, the harvesting device may comprise an additional container that may be filled with the cell biomass. The cell biomass may be transferred from the cultivation device to the additional container and subsequently transferred to be processed, i. e. to be harvested, or in other words, the cell biomass may be separated into waste medium and harvested cell biomass.

Figure 35:
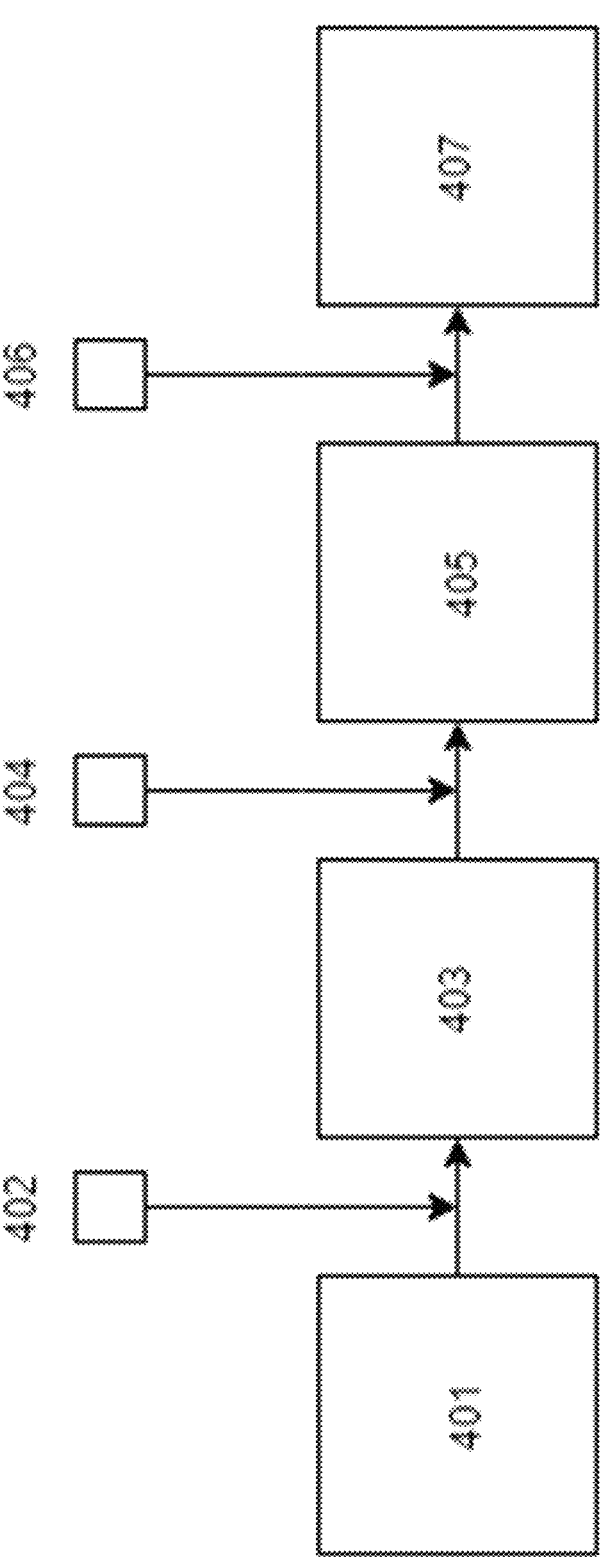
FIG. 35—illustrates scheme diagram of protein hydrolysate processing.

The protein hydrolysate processing depicted in FIG. 35 may comprise the following steps:

proteolysis of source of protein 401 by proteolytic enzymes 402 to result in formation of protein hydrolysate 403;

removal of inositol hexaphosphate and/or its derivatives from protein hydrolysate 403 by addition of enzymes having phytase activity and/or precipitating agent 404 to result in formation of modified protein hydrolysate 405.

removal of solid residues 406 from modified protein hydrolysate to result in formation of purified protein hydrolysate 407.

Disclosed herein are the methods for the production of a culture medium designed for the cultivation of non-human metazoan cells. The culture medium may comprise a source of protein with a nutritional function for the cells, signaling molecules, minerals, organic amines, saccharides, shear protectants, antifoaming agents, and vitamins. The source of protein, also referred to as substrate or source of amino acids, may comprise protein hydrolysate prepared from soy, pea, rice, wheat, wheat gluten, corn, *faba* beans, alfalfa, hemp, chickpea, potato, pumpkin, rapeseed, red lentil, *Spirulina, Chlorella*, sunflower, water lentil, mung beans, flax, baker's yeast, brewer spent grain, distillers spent grain (DDGS), tomato pomace, in form of powder, lysate, concentrate, isolate, liquid, solid or any other appropriate form. The plant sources of protein from mentioned examples often contain phytin, phytic acid, or phytate and/or any related form of those compounds, which will be referred to as inositol hexaphosphate and its derivatives in this document.

According to some aspects of the invention, the terms "source of amino acids", "substrate", "proteinous substrate", "source of protein" may be interchangeable when referring to a component for the production of protein hydrolysate and/or the culture medium.

The term "derivatives" refers to molecules derived from inositol hexaphosphate, including inositol pentaphosphate, inositol tetraphosphate, inositol triphosphate, inositol diphosphate, inositol monophosphate intermediates, inositol or a combination thereof, as well as their combination with other substances, including ions or any other compounds with which these derivatives may commonly react.

Inositol phosphates may react with cations and form precipitates, which may lead to the blockage of filters within the cultivation process. Additionally, such precipitation may result in an imbalanced ionic concentration, thereby disrupting the optimal conditions necessary for cell growth.

The cultivation system may comprise at least one of: culture medium tanks for the preparation of the culture medium, representing a system for culture medium production; and cultivation device for the cell cultivation and other additional features. The system for culture medium production may comprise at least one of the following features: at least one water source, at least one filtration unit; a plurality of sterile barriers; a plurality of pumps; a plurality of analytical instruments and sensors; and at least one culture medium tank selected from a hydrolysis tank, a mixing tank, a loading tank and/or a storage tank.

The cell biomass production system may comprise at least one gas sparging system, heat exchange system, waste medium tank, cultured medium recycling system, a heat exchange system, a cultivation device, at least one harvesting device, a control unit (the term "control unit" and "control device" may be interchangeable), an external physical stimulation mechanisms; and a product processing device.

The culture medium and/or protein hydrolysate may be subjected for removal of solid residues during the production of the culture medium. Solid residues may be removed by centrifugation, filtration or other suitable methods. The filters may comprise at least one filter selected from the group of membrane filters, depth filters, mesh filters, activated carbon filters, ceramic filters, centrifugal filters, ultrafiltration filters, nanofiltration filters, ion exchange filters, crossflow (tangential flow) filters, adsorption filters or fiber filters. The filters may comprise at least one material selected from the group of cellulose, glass fiber, polyethersulfone (PES), polyvinylidene fluoride (PVDF), surfactant-free cellulose acetate (SFCA), nylon, polypropylene, polyethylene terephthalate (PET), polytetrafluoroethylene (PTFE), polyacrylonitrile (PAN), polyvinyl chloride (PVC), stainless steel, silica, alumina, silicon carbide, titanium dioxide, titanium carbide, silicon carbide, zeolites, or synthetic polymers. The filters may vary in porosity, wherein the pore size of the filters may be in a range of 0.05 µm to 1 µm, in a range of 0.1 µm to 0.45 µm, or in a range of 0.15 µm to 0.3 µm, in a range of 0.2 µm to 0.25 µm for effective removal of solid residues while maintaining the integrity of the desired components in the culture medium.

The patent application discloses three aspects for removing inositol hexaphosphate and its derivatives from protein hydrolysate. The first aspect uses enzymes with phytase activity to degrade inositol hexaphosphate and its derivatives. The second aspect employs precipitating agents to form precipitates that can be separated from the culture medium. The third aspects combines both enzymatic removal and precipitation.

The source of protein for hydrolysis may be selected from an industrially scalable source of protein. Industrially scalable sources of amino acids include phototrophic organisms, such as land plants, green algae, red algae, brown algae, or other phototrophic eukaryotes, phototrophic prokaryotes such as cyanobacteria, or cultivated heterotrophic prokaryotes or eukaryotes, such as bacteria or yeast, or cultivated chemoautotrophic prokaryotes, such as hydrogen-oxidizing bacteria. The organism used as a source of protein may be able to synthesize all proteinogenic amino acids from inorganic nitrogen sources, such as ammonia ions, nitrate ions or molecular nitrogen. The hydrolysis may be performed, for example, in a hydrolysis tank, or in any other suitable device.

The hydrolysis may be performed on a protein isolate or concentrate or protein flour or protein meal or seed or grain from the source of protein, or on the whole biomass of the source of protein. The source of protein may be physically, mechanically or chemically pretreated, or steeped in water to induce germination, or subjected to methods such as soaking, blanching, removal of hull, husk or any other outer layer of the source of protein, milling, heat treatment or any other appropriate method to enhance the speed and efficiency of the hydrolysis process and to reduce the presence of antinutritional compounds. Saccharides, fats or other compounds may be removed from the biomass of the source of protein to facilitate easier processing. Examples of suitable industrially scalable sources of amino acids may include soy, pea, rice, wheat, wheat gluten, corn, *faba* beans, alfalfa, hemp, chickpea, potato, pumpkin, rapeseed, red lentil, *Spirulina, Chlorella,* sunflower, water lentil, mung beans, flax, brewer spent grain, distillers spent grain (DDGS), tomato pomace, in form of powder, lysate, concentrate, isolate, liquid, solid or any other appropriate form. The present invention is not limited to the listed exemplary sources of amino acids.

In one aspect of the invention, the incubation of the source of proteins in water to induce germination, or its pretreatment with soaking, blanching, milling, heat treatment or any other appropriate method may be performed in specific incubation time, wherein the incubation time may differ according to used technique.

The process of hydrolysis entails cleaving the original protein molecule into shorter peptide chains and/or single amino acids. As used herein, the term "protein hydrolysate" is understood to be a mix of amino acids, peptides and other molecules prepared from a suitable source of protein by any suitable method, including acidic, basic, or enzymatic hydrolysis, autolysis, thermal hydrolysis, or lysis by fermentation with a suitable microorganism which is able to break down the protein. The "protein hydrolysate" according to the present disclosure may be, for example, plant protein enzymatic hydrolysates, various types of yeast extracts or lysates (such as whole yeast autolysate), or algae acidic hydrolysate.

Methods of protein hydrolysis may include acidic hydrolysis, basic hydrolysis, enzymatic hydrolysis, thermal hydrolysis or autolysis. Acidic hydrolysis subjects the source of protein to a very low pH, usually at an elevated temperature. The duration of reaction may be in a range of 1 hour to 96 hours, in a range of 2 hours to 72 hours, in a range of 4 hours to 48 hours, in a range of 4 hours to 36 hours, in a range of 4 hours to 24 hours or in a range of 4 hours to 12 hours. Acidic hydrolysis unfortunately leads to significant degradation of several amino acids, most notably tryptophan, which would then have to be sourced separately at significant costs. Significant degradation of some amino acids also occurs during basic hydrolysis, which subjects the source of protein to a very high pH, usually at an elevated temperature. Additionally, the acid or base used for the hydrolysis would have to be removed from the protein hydrolysate before it could be used to cultivate cells, presenting further complications. For example, when acidic hydrolysis is performed using hydrochloric acid, the acid may be removed by neutralization or evaporation. However, both processes are economically unfavorable because: i) neutralization process results in unfavorably high concentration of salts, which also need to be removed, and ii) evaporation is energy-intensive and the resulting HCl vapors pose a health and environmental hazard that would need to be solved. Thermal hydrolysis subjects the source of protein to very high temperatures at which the peptide bonds in the protein will break. However, at these temperatures, undesirable chemical reactions may occur—for example, some amino acids may break down or react with other compounds in the hydrolysate, for example through Maillard reactions with saccharides; additionally, thermal degradation of the reaction substrate may produce compounds harmful to the cultivated cells. The process of autolysis relies on the activity of the endogenous enzymes of the source organism to break down the source of protein, and this process is usually not very efficient and does not generally result in sufficient hydrolysis of the source protein. Additionally, proteins can be broken down by fermentation with organisms such as *Bacillus licheniformis* or *Aspergillus oryzae,* which produce a large amount of proteolytic enzymes. However, with this approach, some of the amino acids from the source protein may be consumed by the organism that was used to break down the protein during the process of fermentation. Also, metabolic waste products and other compounds from the fermenting organism may contaminate the resulting lysate and adversely affect its properties in respect to mammalian cell cultivation.

The protein hydrolysate according to the invention may be obtained by enzymatic hydrolysis of a suitable source of protein. An industrially scalable source of protein is advantageous. In one aspect of the invention, soy protein isolate may be used as the source of protein for enzymatic hydrolysis. Advantageously, soy protein isolate has a favorable ratio of most amino acids for the purpose of mammalian cell cultivation. However, to achieve optimal levels of certain amino acids that may be present in lower concentrations, these amino acids may need to be supplemented separately in the culture media.

The source of protein for hydrolysis in solvent may be subjected to an initial thermal pretreatment to improve solubility and susceptibility to hydrolysis. The temperature during the thermal pretreatment may be in the range of 75° C. to 95° C., or in the range of 80° C. to 92.5° C., or in the range of 85° C. to 90° C. for a time in the range of 5 minutes to 120 minutes, in the range of 15 minutes to 60 minutes or in the range of 30 minutes to 45 minutes.

The hydrolysis by-products, including the sediment obtained from filtration, may be further utilized as components in subsequent applications. These by-products may be processed or refined to extract useful materials, which can serve as raw ingredients or additives in other industrial or biochemical processes, thereby enhancing the overall efficiency and sustainability of the production system. In one aspect of the invention, the sediment may be used for the production of edible products used for animal or human consumption.

The term "sediment" or "solid residues" refers to solid particles larger than 0.2 μm derived from the source of protein, from the enzymes or from other components entering the hydrolysis tank. In another aspect of the invention, the solid particles that may be subjected to filtration are not limited to the source of protein, enzymes or to another components entering the hydrolysis tank, but may also comprise solid particles formed in the process of preparing culture medium. It is also noted that, as an incidental effect of the solid residue removal process, particles smaller than 0.2 μm may be also removed.

In one aspect of the invention, total amino acid composition of the sediment may comprise:

alanine in a range of 0.5 wt. % to 12 wt. %, in a range of 1 wt. % to 10 wt. %, or in a range of 2 wt. % to 8 wt. % of dry mass weight;

arginine in a range of 1 wt. % to 14 wt. %, in a range of 1.5 wt. % to 12 wt. %, or in a range of 2.5 wt. % to 10 wt. % of dry mass weight;

glycine in a range of 0.5 wt. % to 10 wt. %, in a range of 1 wt. % to 8 wt. %, or in a range of 1.5 wt. % to 6 wt. % of dry mass weight;

isoleucine in a range of 0.5 wt. % to 12 wt. %, in a range of 1 wt. % to 10 wt. %, or in a range of 2 wt. % to 8 wt. % of dry mass weight;

lysine in a range of 0.5 wt. % to 11 wt. %, in a range of 1 wt. % to 9 wt. %, or in a range of 1.5 wt. % to 7 wt. % of dry mass weight;

phenylalanine in a range of 1 wt. % to 13 wt. %, in a range of 1.5 wt. % to 11 wt. %, or in a range of 2.5 wt. % to 9 wt. % of dry mass weight;

proline in a range of 0.5 wt. % to 10 wt. %, in a range of 1 wt. % to 8 wt. %, or in a range of 1.5 wt. % to 6 wt. % of dry mass weight;

serine in a range of 0.5 wt. % to 12 wt. %, in a range of 1 wt. % to 10 wt. %, or in a range of 2 wt. % to 8 wt. % of dry mass weight;

threonine in a range of 0.5 wt. % to 10 wt. %, in a range of 1 wt. % to 8 wt. %, or in a range of 1.5 wt. % to 6 wt. % of dry mass weight;

tyrosine in a range of 0.5 wt. % to 10 wt. %, in a range of 1 wt. % to 8 wt. %, or in a range of 1.5 wt. % to 6 wt. % of dry mass weight;

valine in a range of 1.5 wt. % to 14 wt. %, in a range of 2 wt. % to 12 wt. %, or in a range of 2.5 wt. % to 10 wt. % of dry mass weight;

aspartic acid in a range of 1 wt. % to 16 wt. %, in a range of 2 wt. % to 14 wt. %, or in a range of 3 wt. % to 12 wt. % of dry mass weight;

glutamic acid in a range of 1 wt. % to 18 wt. %, in a range of 3 wt. % to 16 wt. %, or in a range of 3.5 wt. % to 14 wt. % of dry mass weight;

leucine in a range of 1 wt. % to 18 wt. %, in a range of 3 wt. % to 16 wt. %, or in a range of 3.5 wt. % to 14 wt. % of dry mass weight;

histidine in a range of 0.15 wt. % to 8 wt. %, in a range of 0.5 wt. % to 6 wt. %, or in a range of 1 wt. % to 4 wt. % of dry mass weight;

In one aspect of the invention, the concentration of saccharides in the sediment may be in a range of 15 wt. % to 80 wt. %, in a range of 18 wt. % to 75 wt. %, or in a range of 20 wt. % to 70 wt. % of dry mass weight.

The method of enzymatic hydrolysis may use proteolytic enzymes in order to achieve protein hydrolysis at much milder conditions than acidic or basic hydrolysis, therefore preserving the amino acids of the original protein.

The term "proteolytic enzymes" refers to enzymes from the group of proteases, peptidases, esterases and/or any other enzyme that is capable of cleaving of peptide bonds between amino acids and/or is capable of addition of water molecule to an ester to produce alcohol or an acid.

Proteolytic enzymes may be derived from plants, animals, microorganisms, or any other appropriate source separately or in the combination thereof.

Exemplary enzymes that may be used to catalyze the breakdown of peptide bonds are ALCALASE® serine endopeptidase enzyme (protease from *Bacillus licheniformis*), Subtilisin Carlsberg (protease from *Bacillus licheniformis*), FLAVOURZYME® proteolytic enzyme blend (protease from *Aspergillus oryzae*), PROTAMEX® enzyme preparation, NOVOPRO® D protease enzyme, PROTANA® Prime, THERMOASE® PC10FNA protease, Protease AN Amano 100SD, Protease A Amano 2SD, Protease M Amano SD, Protease P Amano 6SD, ProteAX, Peptidase R, Alkaline Protease, COROLASE®C 7089 enzyme preparation, COROLASE® 2TSN enzyme preparation, COROLASE® 8000 enzyme preparation, MAXIPRO® TNP protease, MAXIPRO® FPC protease, Papain, Bromelain, SUMIZYME® BNP-L enzyme, SUMIZYME® AP-L enzyme, SUMIZYME® LP-G enzyme, SUMIZYME® FP-G enzyme, SUMIZYME® FL-G enzyme or any other appropriate proteolytic enzyme, or the combination thereof.

Proteolytic enzymes may be used either alone or in combination thereof. The number of proteolytic enzymes or enzyme mixes may be in a range of 1 to 6, or in a range of 2 to 5, or in a range of 2 to 4.

In one aspect of the invention, at least one enzyme and/or enzyme mix may be used for the catalysis of the breakdown of peptide bonds in the source of protein.

The duration of the treatment by proteolytic enzymes may differ according to the source of protein used. Proteolytic enzymes may be used for a portion of time in a range of 4 hours to 40 hours, in a range of 6 hours to 35 hours, in a range of 7 hours to 30 hours, or in a range of 10 hours to 25 hours. In one aspect of the invention, the proteolytic enzymes may be used for a portion of time of at least 2 hours, at least 2.5 hours, at least 3 hours, at least 3.5 hours, at least 4 hours, at least 4.5 hours, at least 5 hours or at least 10 hours.

The temperature during the proteolysis treatment may depend on the temperature optimum of the selected proteolytic enzyme. This enzyme and/or enzymes may be used in a range of 25° C. to 80° C., in a range of 30° C. to 70° C., or in a range of 40° C. to 65° C.

Proteolytic enzymes may contain additives used to maintain pH and stability. Examples of additives include, but are not limited to water, citric acid, glycerol, potassium sorbate, sodium chloride, sorbitol, dextrin, sucrose or any other appropriate agent used for maintaining the stability and pH.

The enzymes may further comprise additives capable of maintaining stability and pH, wherein the total composition comprises additives in a range of at least 10 wt. % to 95 wt. % of total composition, 20 wt. % to 92 wt. % of total composition, 25 wt. % to 90 wt. % of total composition, or 30 wt. % to 88 wt. % of total composition.

In one aspect of the invention, the concentration of the source of protein in the reaction mixture for hydrolysis may be in the range of 1 g/l to 150 g/l, or in the range of 30 g/l to 100 g/l, or in the range of 40 g/l to 80 g/l of the reaction mixture.

The concentration of the enzyme may be in the range of 0.01% to 10% or in the range of 0.05% to 5%, or in the range of 0.1% to 1% expressed as a ratio of the concentration of enzyme to the concentration of protein in the reaction mixture. The concentration of the enzyme may be determined by the Bradford assay, BCA assay or other protein determination assays.

One of the approaches to characterize protein hydrolysates may be size-exclusion chromatography (SEC) combined with mass spectrometry (MS) or photo diode array (PDA) which allows us to separate the peptides from hydrolysate based on their molecular weights. The results may vary according to mobile phase composition, column type and its specification, flow rate, temperature, sample injection parameters, detector settings and/or any other parameter used.

In one aspect of the invention, proteolytic enzymes within a source of protein may yield peptides in purified protein hydrolysate with a molecular weights higher than 17 kDa, with a relative fraction size in a range 0% to 10% of the purified protein hydrolysate, in a range of 0% to 8% of the purified protein hydrolysate, or in a range of 0% to 6% of the purified protein hydrolysate.

In one aspect of the invention, proteolytic enzymes within a source of protein may yield peptides in purified protein hydrolysate with a molecular weights ranging from 6.7 to 17 kDa, with a relative fraction size in a range 2% to 35% of the purified protein hydrolysate, in a range of 4% to 30% of the purified protein hydrolysate, or in a range of 5% to 25% of the purified protein hydrolysate.

In one aspect of the invention, proteolytic enzymes within a source of protein may yield peptides in purified protein hydrolysate with a molecular weights ranging from 1.7 kDa to 6.7 kDa, with a relative fraction size in a range 5% to 40% of the purified protein hydrolysate, in a range of 10% to 35% of the purified protein hydrolysate, or in a range of 15% to 30% of the purified protein hydrolysate.

In one aspect of the invention, proteolytic enzymes within a source of protein may yield amino peptides in purified protein hydrolysate with a molecular weights ranging from 1 kDa to 1.7 kDa, with a relative fraction size in a range 5% to 40% of the purified protein hydrolysate, in a range of 10% to 35% of the purified protein hydrolysate, or in a range of 20% to 30% of the purified protein hydrolysate.

In one aspect of the invention, proteolytic enzymes within a source of protein may yield free amino acids and/or peptides in purified protein hydrolysate with a molecular weights less than 1 kDa, with a relative fraction size in a range 20% to 70% of the purified protein hydrolysate, in a range of 22% to 60% of the purified protein hydrolysate, or in a range of 25% to 55% of the purified protein hydrolysate.

In one aspect of the invention, proteolytic enzymes within a source of protein may yield free amino acids in purified protein hydrolysate with a relative fraction size in a range of 30% to 50% of the purified protein hydrolysate, in a range of 35% to 45% of the purified protein hydrolysate, or in a range of 38% to 42% of the purified protein hydrolysate.

In one aspect of the invention, an additional method may be used to further separate the small peptides with molecular weights ranging from 1000 Da to 6500 Da, 600 Da to 1000 Da, 300 Da to 600 Da, or molecular weights lower than 300 Da.

In one aspect of the invention, proteolytic enzymes within a source of protein may yield amino acids and/or peptides in purified protein hydrolysate with a molecular weights ranging from 1000 Da to 6500 Da, with a relative fraction size in a range of 5% to 50%, in a range of 10% to 40%, or in a range of 15% to 35% of the measured fractions.

In one aspect of the invention, proteolytic enzymes within a source of protein may yield amino acids and/or peptides in purified protein hydrolysate with a molecular weights ranging from 600 Da to 1000 Da, with a relative fraction size in a range of 10% to 70%, in a range of 15% to 60%, or in a range of 20% to 50% of the measured fractions.

In one aspect of the invention, proteolytic enzymes within a source of protein may yield amino acids and/or peptides in purified protein hydrolysate with a molecular weights ranging from 300 Da to 600 Da, with a relative fraction size in a range of 10% to 65%, in a range of 15% to 55%, or in a range of 20% to 45% of the measured fractions.

In one aspect of the invention, proteolytic enzymes within a source of protein may yield amino acids and/or peptides in purified protein hydrolysate with a molecular weights less than 300 Da, with a relative fraction size in a range of 10% to 90%, in a range of 15% to 80%, or in a range of 20% to 70% of the measured fractions.

In one aspect of the invention, the water source may comprise distilled water, demineralized water, deionized water and/or tap water. In one aspect of the invention, the water source may be characterized by conductivity in a range of 1 pS·cm⁻¹ to 600 pS·cm⁻¹, in a range of 5 pS·cm⁻¹ to 100 pS·cm⁻¹ or in a range of 10 pS·cm⁻¹ to 50 pS·cm⁻¹.

In one aspect of the invention, the proteolytic enzymes may be immobilized on a solid support. This aspect sterically prevents the molecules of the enzyme from breaking each other down and allows the enzyme to be separated from the reaction mixture after the reaction and used again. The solid support may be present in the form of solid carriers suspended in the reaction mixture, or a solid structure with a large surface area, such as a sponge or fibrous structure, through which the reaction mixture is perfused. The enzyme may also be added in soluble (free) form. After hydrolysis is complete, the resulting protein hydrolysate is separated from the solid support with immobilized enzyme by simply draining the reaction vessel (in the case of large solid structure) or removing the enzyme on solid support by filtration or sedimentation (in the case of suspended carriers). The reaction vessel may be formed, for example, by a hydrolysis tank. The filtration step may also remove any solid residues from the source protein, such as cell wall debris. Free enzymes may be removed from the protein hydrolysate by ultrafiltration or deactivated with elevated temperature when hydrolysis is complete. Ultrafiltration of the protein hydrolysate may additionally remove any larger peptide chains which were not digested by the enzyme; these relatively larger peptide chains may not be metabolized by the cells and cause harm to them and therefore their removal may be beneficial. The temperature elevation used to deactivate the enzyme may also sterilize the resulting protein hydrolysate.

The protein hydrolysate may be thermally treated at the end of hydrolysis to deactivate enzymes and kill microorganisms. In one aspect of the invention, this treatment may take place at a lower temperature settings in the range of 80° C. to 120° C., in the range of 85° C. to 100° C. or in the range of 90° C. to 95° C. for time in the range of 15 minutes to 180 minutes or in the range of 20 minutes to 120 minutes or in the range of 25 minutes to 60 minutes. In another aspect of the invention, this treatment may be performed at a high temperature in the range 80° C. to 160° C., in the range of 100° C. to 155° C., or in the range of 110° C. to 150° C. for a time in the range of 1 seconds to 600 seconds, in the range of 3 seconds to 300 seconds, or in the range of 5 seconds to 60 seconds. The low temperature method may be performed in a hydrolysis tank, wherein the both methods may be performed in a flash pasteurizer or another suitable continuous flow heating device.

If the enzyme is removed by ultrafiltration, it may retain at least partial catalytic activity and thus may be recycled for another round of hydrolysis. Ultrafiltration or thermal deactivation may also be used to remove active enzyme molecules from hydrolysates prepared by immobilized enzymes, in the event that some of the enzyme detaches from the solid support and dissolves into the reaction mixture.

The solid support may be formed by, for example, silica, epoxide resin, cellulose, chitosan, glass wool, alginate, or by other appropriate materials. The solid support may be in the form of porous or solid beads, sponge, fibers, or another suitable configuration. The solid support may have a large surface area to volume ratio to allow the binding of a large amount of enzyme. For example, beads of porous silica or any other suitable material with a diameter in the range of 1 $\mu$m to 10,000 $\mu$m, or in the range of 10 $\mu$m to 1,000 $\mu$m, or in the range of 20 $\mu$m to 500 $\mu$m, may be used as a solid support for enzyme immobilization. Immobilization may be achieved, for example, by functionalizing the silica bead surface with amino groups and using a crosslinking agent, such as glutaraldehyde, to bind the enzyme to the solid support. Other functional groups, like aldehyde or epoxy groups, may also be used for enzyme immobilization. The amino groups in this aspect of the invention are covalently bonded to glutaraldehyde, after which excess glutaraldehyde is removed and the enzyme is added. The amino groups on the surface of the enzyme then bind the remaining free aldehyde groups of the glutaraldehyde molecules on the silica bead surface. The immobilization may be performed in water or a suitable aqueous buffer. Due to the porous nature and large surface area of the silica beads, a relatively high amount of enzyme may be immobilized relative to the weight of the solid support.

Water may be used to dissolve the source of protein for hydrolysis. Some proteins may require a buffer to adjust the pH to a level where they have better solubility. The pH may be in the range of 2 to 12, or in the range of 5 to 10, or in the range of 6 to 8.5. A very dilute buffer, or no buffer at all, may be used so that the resulting protein hydrolysate may be added to the final culture media at high concentrations while minimizing its impact on media osmolality.

The buffer may include, for example, phosphate buffer, bicarbonate buffer, tris HCl buffer, borate buffer, glycine-NaOH buffer, Good's buffer or any other appropriate buffer, or a combination thereof.

In one aspect of the invention, a concentration of potassium phosphate buffer in a range of 1 mM to 100 mM, in a range of 10 mM to 40 mM or in a range of 15 mM to 35 mM may be used for pH adjustment to dissolve soy protein to a concentration in a range of 1 g/l to 150 g/l, in a range of 20 g/l to 100 g/l, in a range of 30 g/l to 80 g/l, in a range of 40 g/l to 70 g/l, in a range of 50 g/l to 65 g/l or in a range of 55 g/l to 60 g/l. In another aspect of the invention, the soy protein is dissolved in distilled water to a concentration in a range of 1 g/l to 150 g/l, in a range of 20 g/l to 100 g/l, in a range of 30 g/l to 80 g/l, in a range of 30 g/l to 80 g/l, in a range of 40 g/l to 70 g/l, in a range of 50 g/l to 65 g/l or in a range of 55 g/l to 60 g/l, where the concentration is defined as the amount of source of protein per liter of the reaction multiplied by the percentage protein content in the source of protein.

Other concentrations of the source of protein may be used, however, very high concentrations of this source lead to incomplete dissolving of the protein and formation of a highly viscous colloidal solution, presenting problems for the hydrolysis and further processing, while low concentrations of protein may limit the speed of the hydrolysis reaction. To ensure the best dissolution of the proteins in the reaction mixture a heat-treatment may be used. Below boiling temperatures may be used for extended periods of time in order to significantly increase the content of dissolved proteins and to deactivate potential inhibitors of proteases and other antinutritional compounds.

In one aspect of the invention, the source of protein may be added at a higher concentration than the maximum soluble concentration. This additional protein may be dissolved after the protein concentration in the reaction mixture is decreased due to its hydrolysis by the enzyme. This results in high concentration of available substrate during the entire process, potentially improving hydrolysis efficiency. Multiple cycles of substrate addition into the same reaction mixture may be performed. In one aspect of the invention a base or a suitable buffer may be added to counteract changes in pH and keep the enzyme in its pH optimum or a pH stat may be used.

A parameter by which the conversion of source of protein into bioavailable products for animal cells may be evaluated, is the degree of hydrolysis (DH), defined as the percentage of peptide bonds in the source of protein that are hydrolyzed during the reaction. DH can be determined as the difference of amino nitrogen (AN) of hydrolysed substrate and amino nitrogen of substrate before hydrolysis (ANO) multiplied by factor (F) and divided by total nitrogen (TN). AN may be determined by formol titration of the hydrolysate sample, ANO may be determined by formol titration of the substrate solution before the process of hydrolysis, TN may be determined by Kjeldahl method. Factor F is a value calculated from empirical data based on amino acids composition of the particular source of protein and it represents the ratio of total nitrogen to alpha amino nitrogen in the sample. A higher degree of hydrolysis corresponds to a larger percentage of the source protein converted into free amino acids or short peptides, which are usable by mammalian cells as nutrition. Mammalian cells are generally incapable of absorbing and digesting proteins and longer peptides. Peptides longer than four amino acids, or in other words heavier than approximately 500 Daltons, have poor absorption by mammalian cells. In various aspects of the invention, the amount of the source of protein in the range of 20% to 100%, in the range of 30% to 75%, in the range of 35% to 70% or in the range of 40% to 65% may be converted into free amino acids, expressed as mass concentration of amino acids to mass concentration of protein. The degree of hydrolysis, meaning the percentage of peptide bonds that undergo hydrolysis out of the total amount of peptide bonds present in the substrate at the start of the reaction, may be in the range of 10% to 70%, in the range 20% to 60% or in the range of 25% to 50%.

Proteolytic enzymes are classified according to the basis of amino acid group present on the active site as serine proteases (subtilisin, trypsin), cysteine proteases (papain-like, trypsin-like), aspartic proteases (pepsin, cathepsin D), glutamic proteases (eqolisin), threonine proteases (ornithine, acetyltransferase) and metalloproteases (Myxobacter I and II). Another classification divides enzymes according to their enzymatic function into exoproteases and endoproteases. Exoproteases cleave the protein or peptide chains at the N or C terminal ends, whereas endoproteases can cleave peptide bonds in the middle of the protein or peptide chain. Exoproteases are classified according to the mechanism of action on aminopeptidases that act on the N terminal end and carboxypeptidases that act on the C terminal end. The present examples of proteases acting on the active side of related amino acids are not limited to the listed exemplary proteases.

In one aspect of the invention, a combination of endoproteases and exoproteases may be used, since endoproteases may create more free ends of peptide chains, increasing the efficiency of exoproteases, and exoproteases are more efficient in hydrolyzing the protein to single amino acids.

In one aspect of the invention, endoproteases and exoproteases may be used sequentially in this order to maximize hydrolysis efficiency.

In one aspect of the invention, additional enzymes may be added to the reaction mixture after the beginning of hydrolysis. This may be done with the same enzyme, mainly in order to counteract the gradual decrease in its enzymatic activity due to degradation of the enzyme molecule. In one aspect of the invention, enzymes with a higher pH optimum may be added at the start of the hydrolysis, when pH is higher, and enzymes with a lower pH optimum may be added later, when the pH is lower, thus maximizing the efficiency of the respective enzymes. The pH tends to decrease naturally during hydrolysis due to the increase in the number of carboxylic groups.

In another aspect of the invention, additional sources of protein may be added to the reaction mixture after the beginning of hydrolysis. The advantages of this aspect may be, for example, easier dispersion and dissolution of additional sources of protein when the previous amount of source of protein is at least partially hydrolyzed.

The addition of enzyme or substrate after the beginning of the hydrolysis process may be performed in a fed-batch (wherein additional reagents are added to the reaction mixture, and subsequently the whole reaction batch is harvested) or semi-continuous (wherein a portion of the reaction mixture, or certain additional reagents within the reaction mixture, is periodically removed and replaced with fresh components) or in continuous (wherein addition to and harvesting from the reaction mixture are both done continuously) reaction mode.

Regardless of whether immobilized or free enzyme is used, sufficient mixing of the reaction mixture is important to achieve high efficiency. In the case of immobilized enzymes, this applies to both the enzyme immobilization and protein hydrolysis steps. In one aspect of the invention, in the case of immobilized enzymes, mixing methods that minimize mechanical damage to the solid carriers should be used. These may include roller mixing, shaking, or low-shear impellers such as hydrofoil or elephant ear impellers. In the case of enzymes immobilized to a large solid support, sufficient perfusion of the support with the reaction mixture must be assured.

The mixing of the source of protein, e.g. protein isolate, with water, dissolving the source of protein and the process of hydrolysis itself may be performed in the hydrolysis tank 110 at a laboratory or industrial scale.

In one aspect of the invention, the hydrolysis tank 110 may be configured to provide an environment for the hydrolysis reaction. The hydrolysis tank may comprise a main body constructed from at least one material selected from stainless steel, glass-lined steel, titanium, polyethylene, polypropylene, polytetrafluoroethylene or any other suitable materials. The main body may comprise various shapes, such as cylindrical or rectangular or any other suitable geometries. The hydrolysis tank may comprise insulation configured as an outer jacket of the hydrolysis tank, wherein the space between the outer jacket and the wall of the hydrolysis tank may be filled with an appropriate insulation material or medium. The hydrolysis tank may further comprise at least one input and at least one output for loading and unloading the ingredients. The input of the hydrolysis tank may be configured as a shaft or funnel, wherein the shaft or funnel may be used for loading the ingredients. The hydrolysis tank may further comprise a heating system configured to heat the inner environment of the hydrolysis tank. The hydrolysis tank may comprise mixing mechanisms comprising at least one stirrer, paddle or any other instrument capable of mixing the protein hydrolysate. The sealing mechanisms of the hydrolysis tank may comprise materials such as silicone, ethylene propylene diene monomer, and polytetrafluoroethylene. The hydrolysis tank may be configured to withstand a maximum temperature of at least 80° C., at least 90° C., at least 100° C., at least 105° C., at least 110° C., at least 120° C., or at least 150° C. The hydrolysis tank may further comprise auxiliary components selected from the group of pumps, pressure sensors, flow meters, valves and means for monitoring the hydrolysis reaction.

The volume of the hydrolysis tank 110 may be in the range of 0.1 l to 100,000 l, or in the range of 0.3 l to 15,000 l, or in the range of 1 l to 5,000 l.

In one aspect of the invention, the hydrolysis tank may be equipped with different types of sensors, for example, thermal sensor, pH probe, conductometer, or any other type of appropriate sensor according to the needs of the process of hydrolysis. The pH may be measured by various methods and devices comprising potentiometry, colorimetry, spectrophotometry, ion-selective electrodes, conductometry or any other measuring technique and/or device. The temperature in the reaction vessel may be measured by various devices comprising resistance temperature detector, thermocouple, digital thermometer with insertion probe, infrared thermometer with fiber optic probe or any other appropriate device.

A sampling system may be used for precise monitoring of the degree of hydrolysis a sampling system may be used. The degree of hydrolysis may be monitored by titration and/or by absorbance measurement, for example at a wavelength in a range of 190 nm to 350 nm, or in a range 190 nm to 230 nm.

Water may enter the hydrolysis tank through a water purification unit. In one aspect of the invention, a water purification unit may provide at least one selected purification process from the group of reverse osmosis, deionization, electrodeionization, electrodialysis and distillation.

The mixing may be provided by the appropriate stirring unit that may comprise, for example, a paddle impeller. In some aspects, an elephant-ear impeller may be used. The outer diameter of the stirrer or impeller may be in the range of $\frac{1}{10}$ to $\frac{9}{10}$ of the inner reactor diameter, or in the range of $\frac{3}{10}$ to $\frac{8}{10}$ of the inner reactor diameter, or in the range of $\frac{4}{10}$ to $\frac{7}{10}$ of the inner reactor diameter. As an example the outer diameter of stirrer/impeller may be $\frac{2}{3}$ of the inner reactor diameter. The stirrer or impeller may be located in the center of the hydrolysis tank or outside of the center of the hydrolysis tank.

The reaction components may be added to the hydrolysis tank manually, or automatically by using a conveyor, loading tank or any other appropriate device used for transfer of reaction components. The source of protein may be in a liquid solution or in the form of a powder.

The term "reaction components" may comprise a source of protein, proteolytic enzymes, or any other appropriate component necessary for effective hydrolysis by proteolytic enzymes.

In one aspect of the invention, the loading tank 126 may be configured to provide proteolytic enzymes in liquid form into the hydrolysis tank. The loading tank may be configured to maintain the optimal conditions necessary for preserving the stability and activity of stored enzymes. The loading tank may comprise a main body constructed from at least one material selected from high-grade stainless steel, glass-lined steel, titanium, polyethylene, polypropylene, polytetrafluoroethylene or any other suitable materials. The main body may comprise various shapes, such as cylindrical or rectangular or any other suitable geometries. The interior surface of the loading tank may be polished to a mirror finish to minimize adhesion of enzyme residues and facilitate easy cleaning. The loading tank may be equipped with a cooling system to maintain a consistent temperature, essential for enzyme stability. The loading tank may comprise multiple temperature sensors to continuously monitor the internal temperature. The loading tank may be coupled with the hydrolysis tank, wherein the hydrolysis tank may further comprise at least one input and at least one output for loading and unloading the enzymes. The input of the loading tank may be configured as a shaft and/or funnel, wherein the shaft and/or funnel may be used for loading of the proteolytic enzymes. The sealing mechanisms of the loading tank may comprise materials such as silicone, ethylene propylene diene monomer, and polytetrafluoroethylene and/or any other appropriate material.

The loading tank 126 may be made, for example, of stainless steel or glass. The volume of the loading tank may be in the range of 100 ml to 5 m³, or in the range of 2 l to 3 m³, or in the range of 500 l to 1 m³.

In one aspect of the invention, another loading tank 126 may be configured to provide a source of protein into the hydrolysis tank with the same composition as the loading tank for the proteolytic enzymes.

Many plant sources of protein comprise inositol hexaphosphate, which is an important compound found in plants and is often a crucial part of a plant metabolism. Its salt form, phytin, is the main storage compound of phosphate in plants. The inositol hexaphosphate or its derivatives and/or any related form of those compounds comprising phosphate from plant sources may significantly influence the downstream processes of the invention as well as metazoan cell proliferation and viability of the cell. In order to regulate the content and/or concentration of such compounds, the 3 aspects are disclosed.

The first aspect disclosed herein relates to the use of enzymes having phytase activity derived from an animal, plant, or microorganism source or any other appropriate source. Enzymes having phytase activity may be used separately or in the combination thereof.

The term "enzyme having phytase activity" refers to the enzymes from the group of phytases, phosphatases and/or any other enzymes capable of cleaving phosphate ester bonds.

Activity of enzymes having phytase activity may differ according to the source of protein. Enzymes having phytase activity may have different activity at different pH and/or temperature conditions, which may be measured by various methods and devices including potentiometry, colorimetry, spectrophotometry, ion-selective electrodes, conductometry and/or any other measuring technique and/or device. Temperature of the reaction mixture may be monitored in real time by various devices including a resistance temperature detector, thermocouple, digital thermometer with insertion probe, infrared thermometer with fiber optic probe or any other appropriate device.

The enzyme kinetics of the reaction may be calculated based on the Michaelis-Menten model, which provides a foundational equation for describing the rate of enzymatic reaction to provide a product from a substrate. This model is integral for understanding of the relationship between substrate concentration and reaction velocity, and its incorporation allows for precise determination of key kinetic parameters, such as the maximum reaction velocity (Vmax) and the Michaelis constant ($K_m$).

Enzymes having phytase activity may contain additives used to maintain pH and stability. Examples of additives include, but are not limited to water, citric acid, glycerol, potassium sorbate, sodium chloride, sorbitol, dextrin, sucrose or any other appropriate agent used for maintaining the stability and pH.

Enzymes having phytase activity may be used either individually or in combination, wherein the combination may comprise use of at least 2 or more enzymes having phytase activity.

The duration of the treatment by enzymes having a phytase activity may differ according to the source of protein used. The duration of the treatment by enzymes having phytase activity may be finished at different times, which may be in a range of 5 minutes to 320 minutes, in a range of 10 minutes to 180 minutes, or in a range of 30 minutes to 120 minutes.

The temperature of the treatment by enzymes having a phytase activity may be in a range of 20° C. to 70° C., in a range of 25° C. to 65° C., or in a range of 30° C. to 60° C.

Enzymes having phytase activity may create complexes with a substrate. The substrate may comprise any inositol hexaphosphate or its derivatives that may undergo cleaving of phosphate ester bound connecting phosphate groups with inositol or its derivatives, in the presence of water. The function of enzymes having phytase activity according to this aspect of the invention is not limited to said substrates.

Enzymes having phytase activity may catalyze release of at least one organophosphate group from inositol hexaphosphate or its derivatives and may result in free inorganic phosphate and series of lower phosphoric esters as inositol pentaphosphate, inositol tetraphosphate, inositol triphosphate, inositol diphosphate, inositol monophosphate intermediates or inositol or their combination thereof.

After each cleavage of phosphate ester bond and release of inorganic phosphate and series of lower phosphoric esters as inositol pentaphosphate, inositol tetraphosphate, inositol triphosphate, inositol diphosphate, inositol monophosphate intermediates, inositol or their combination thereof, the enzyme having phytase activity may then bind to another inositol hexaphosphate or its derivatives or any related form of those compounds for further hydrolysis in the presence of water.

In another aspect of the invention, additional sources of protein may be added to the reaction mixture after the beginning of hydrolysis. The advantages of this aspect may be, for example, easier dispersion and dissolution of additional sources of amino acids when the previous amount of source of protein is at least partially hydrolyzed.

Addition of enzymes having phytase activity in a solid or liquid state or in a combination thereof, into hydrolysis tank 110 containing a source of protein and water source from loading tank 126 leads to cleavage of phosphate ester bonds and release of molecules in the specific pH and temperature.

In one aspect of the invention, the hydrolysis tank 110 may be composed of various materials and specific volumes and may be coupled with a water purification unit, loading tank 126 and may comprise stirring unit.

In one aspect of the invention, the loading tank 126 may be configured to provide a combination of enzymes having phytase activity in dry or liquid form or in combination thereof and proteolytic enzymes and/or source of protein into the hydrolysis tank.

In another aspect of the invention, the cultivation system may comprise two or more hydrolysis tanks. When using two or more hydrolysis tanks, they may be referred to, for example, as first hydrolysis tank, second hydrolysis tank and third hydrolysis tank. Notations of hydrolysis tanks may be chosen according to the selected number of hydrolysis tanks. The first hydrolysis tank may be configured for hydrolysis of the source of protein by proteolytic enzymes, and the second hydrolysis tank may be configured for the hydrolysis of inositol hexaphosphate and/or its derivatives by enzymes having phytase activity. All of the hydrolysis tanks may be coupled with a mixing tank, water purification unit, at least one loading tank, at least one pump and/or at least one filtration unit.

In one aspect of the invention, the concentration of enzymes having phytase activity may differ according to concentration of inositol hexaphosphate contained in the source of protein. The concentration of the enzymes having phytase activity may be in the range of 0.00001% to 5% or in the range of 0.0001% to 2%, or in the range of 0.0005% to 0.5% expressed as a ratio of the concentration of enzymes having phytase activity to the concentration of inositol hexaphosphate in the reaction mixture. The concentration of the enzyme may be determined by the Bradford assay, BCA assay or other protein determination assays. The concentration of inositol hexaphosphate or its derivatives may be determined by electrophoresis, liquid chromatography, enzymatic assay or any other suitable analytical method.

The efficiency of cleavage by enzymes having phytase activity may be regulated by pH or temperature change. Efficiency of cleavage may be improved by addition of a pH regulating substance to obtain pH in a range of 2 to 10, in a range of 3 to 9, in a range of 4 to 8, in a range of 5 to 9, or in a range of 6 to 7, wherein the substance can be an inorganic molecule comprising HCl, NaOH and/or $NH_4OH$ or any other appropriate pH regulating compound. Efficiency of cleavage may be improved by changing the temperature. The temperature may be in a range of 20° C. to 70° C., in a range of 25° C. to 65° C., or in a range of 30° C. to 60° C.

In one aspect of the invention, the use of enzymes having phytase activity on protein hydrolysate may result in a modified protein hydrolysate. As used herein, the term "modified protein hydrolysate" refers to protein hydrolysate comprising cleaved or precipitated inositol hexaphosphate and its derivatives or their combination thereof.

The modified protein hydrolysate may be thermally treated at the end of hydrolysis to deactivate enzymes having phytase activity and/or kill microorganisms. In one aspect of the invention, this treatment may be at low temperature in the range of 80° C. to 120° C., in the range of 85° C. to 100° C. or in the range of 90° C. to 95° C. for a time in the range of 15 minutes to 180 minutes or in the range of 20 minutes to 120 minutes or in the range of 25 minutes to 60 minutes. In another aspect of the invention, this treatment may be performed at a high temperature in the range 80° C. to 160° C., in the range of 100° C. to 155° C., or in the range of 110° C. to 150° C. for a time is in the range of 1 second to 600 seconds, in the range of 3 seconds to 300 seconds, or in the range of 5 seconds to 60 seconds. The low temperature method may be performed in a hydrolysis tank 110, wherein the both methods may be performed in the hydrolysis tank 110 configured as flash pasteurizer or another suitable continuous flow heating device.

If the enzyme is removed by ultrafiltration, it may retain at least partial catalytic activity and thus may be recycled for another round of hydrolysis. Ultrafiltration or thermal deactivation may also be used to remove active enzyme molecules from hydrolysates prepared by immobilized enzymes, in the event that some of the enzyme detaches from the solid support and dissolves into the reaction mixture.

In one aspect of the invention, the use of proteolytic enzymes and enzymes having phytase activity may be in one of two orders. In the first order, enzymes having phytase activity may be added to the hydrolyzed source of protein and water in the hydrolysis tank 110. The efficiency of cleavage of phosphate ester bonds may be regulated by pH and temperature changes. In the second order, proteolytic enzymes may be added to the source of protein, water and to previously cleaved phosphate and series of lower phosphoric esters as inositol pentaphosphate, inositol tetraphosphate, inositol triphosphate, inositol diphosphate, inositol monophosphate, inositol, intermediates of inositol derivatives or their combination thereof in the hydrolysis tank 110 to generate protein hydrolysate free of inositol hexaphosphate and its derivatives. The second order is less preferable due to the disadvantageous step of pH change especially if the enzyme used has a pH optimum in the acidic region.

In one aspect of the invention, solid residues may be removed from modified protein hydrolysate by filtration unit 112 In one aspect of the invention, the solid residues may be further used for the production of edible product, wherein the edible product may be used for human or animal consumption.

In one aspect of the invention, the hydrolysis tank 110 may be connected to the filtration unit 112 by pump 111. This pump may be used for the transfer of protein hydrolysate to the filtration unit.

In one aspect of the invention, the filtration unit 112 may comprise at least one filter selected from the group of membrane filters, depth filters, mesh filters, activated carbon filters, ceramic filters, ultrafiltration filters, nanofiltration filters, ion exchange filters, crossflow (tangential flow) filters, adsorption filters or fiber filters. The filter of the filtration unit may comprise at least one material selected from the group of cellulose, glass fiber, polyethersulfone (PES), polyvinylidene fluoride (PVDF), nylon, polypropylene, polyethylene terephthalate (PET), polytetrafluoroethylene (PTFE), polyacrylonitrile (PAN), polyvinyl chloride (PVC), stainless steel, silica, alumina, silicon carbide, titanium dioxide, titanium carbide, silicon carbide, zeolites, or synthetic polymers. The filter may be housed in a housing configured to cover the whole filter, wherein the housing may comprise at least one material selected from the group of stainless steel, polycarbonate, polyethylene, or other suitable biocompatible and sterilizable materials. If the filtration unit is composed of multiple filters or includes filters with non-uniform pore size distribution across the depth of the filter, the filters may be arranged so that the filters with largest pores and/or, in the case of filters with non-uniform pore size distribution, the side with the largest pores, may be located upstream (in the direction of the hydrolysis tank 110) and the filters with the smallest pores and/or the side with the smallest pores may be located downstream (in the direction of the mixing tank 113) within the filtration unit. In case of using multiple filters or using filters with non-uniform pore size distribution across the depth of the filter, the maximal pore size of the last filter used of the filtration unit may be in a range of in a range of 0.1 μm to 1 μm, in a range of 0.2 μm to 1 μm, in a range of 0.3 μm to 1 μm, in a range of 0.4 μm to 1 μm, in a range of 0.5 μm to 1 μm, in a range of 0.6 μm to 1 μm, in a range of 0.7 μm to 1 μm, in a range of 0.8 μm to 1 μm or in a range of 0.9 μm to 1 μm. The size of the pore may vary according to the selected type of filter and the specific requirements of the filtration. The filtration unit may further include sealing mechanisms such as O-rings, gaskets, clamps or any other sealing mechanisms capable of preventing leakage and maintaining a sterile environment. The sealing mechanisms of the filtration unit may comprise materials such as silicone, ethylene propylene diene monomer, or polytetrafluoroethylene. The filtration unit may further comprise auxiliary components selected from the group of pumps, pressure sensors, flow meters, valves and means for monitoring the filtration process.

In one aspect of the invention, the filtration unit may be configured to utilize centrifugal force to separate solid-phase particles from liquid phase. This separation process is facilitated by the implementation of centrifugal filters, which may be strategically designed and positioned within the filtration unit.

In one aspect of the invention, the removal of solid residues from the modified protein hydrolysate by the filtration unit may result in a purified protein hydrolysate derived from modified protein hydrolysate. As used herein, the term "purified protein hydrolysate" refers to protein hydrolysate substantially free from solid residues.

The second aspect disclosed herein relates to the use of precipitating agents to generate precipitates of inositol hexaphosphate and its derivatives. Precipitating agents comprise an organic or inorganic compound of 1) suitable cation with high affinity to inositol hexaphosphate and its derivatives—e.g. bivalent cation of calcium, zinc, cobalt, manganese, trivalent cation of iron or any other suitable cation, and 2) an anion corresponding to pKa, which is higher than pKa of inositol hexaphosphate and phosphoric acid—e.g. acetate, carbonate, or hydroxide or any other suitable anion, or any other combination of mentioned cations or anions.

Addition of salts or hydroxides into water results in dissolution of mentioned salts or hydroxides and its dissociation to cations and anions. Cations, especially divalent or multivalent metal cations, interact with negative inositol hexaphosphate and its derivatives by binding to its phosphate groups through ionic interactions. This binding reduces the solubility of inositol hexaphosphate in water, leading to the formation of insoluble metal-phytate complexes resulting in the creation of precipitates.

Addition of salts or hydroxides into hydrolysis tank 110 containing source of protein and water from the loading tank 126 may result in the generation of free metal ions from the before mentioned salts or hydroxides that may form metal-phytate complexes resulting in formation of precipitates in water containing the source of protein.

In one aspect of the invention, the hydrolysis tank 110 may be composed of various materials and specific volumes and may be configured with a stirring unit, water purification unit, loading tank 126 and storage tank 102.

In another aspect of the invention, the precipitation process may take place in second hydrolysis tank, wherein the second hydrolysis tank may be connected to the first hydrolysis tank 110 for the source of protein and to the mixing tank 113.

In one aspect of the invention, the concentration of precipitating agents may differ according to concentration of inositol hexaphosphate contained in the source of protein. The concentration of precipitating agents may be in the range of 150:1 to 1:1 or in the range of 90:1 to 3:1, or in the range of 60:1 to 10:1 expressed as a ratio of the molar concentration of precipitating agents to the molar concentration of inositol hexaphosphate and/or its derivatives in the reaction mixture.

In one aspect of the invention, the use of precipitating agents on protein hydrolysate may result in a modified protein hydrolysate.

In one aspect of the invention, removal of solid residues from protein hydrolysate by filtration unit 112 may be used. In one aspect of the invention, the solid residues may be further used for the production of edible product, wherein the edible product may be used for human or animal consumption.

In one aspect of the invention, the hydrolysis tank 110 may be connected to the filtration unit 112 by pump 114. This pump may be used for the transfer of protein hydrolysate to the filtration unit.

In one aspect of the invention, the filtration of the solid residues formed by using precipitation may be performed similarly as previously described.

In one aspect of the invention, the filtration of solid residues from the modified protein hydrolysate by the filtration unit may result in a purified protein hydrolysate.

The third aspect disclosed herein relates to the combination of the previously mentioned two aspects: the use of enzymes having phytase activity and precipitating agents. Combining these aspect may significantly decrease the amount of inositol hexaphosphate and its derivatives.

Activity of enzymes having phytase activity may differ according to the source of protein. Enzymes having phytase activity may have different activity at different pH and/or temperature conditions, which may be measured by various methods and devices including potentiometry, colorimetry, spectrophotometry, ion-selective electrodes, conductometry or any other measuring technique and/or device. Temperature of the reaction mixture may be monitored in real time by various devices including a resistance temperature detector, thermocouple, digital thermometer with insertion probe, infrared thermometer with fiber optic probe or any other appropriate device.

Enzymes having phytase activity may contain additives used to maintain pH and stability. Examples of additives include, but are not limited to water, citric acid, glycerol, potassium sorbate, sodium chloride, sorbitol, dextrin, sucrose or any other appropriate agent used for maintaining the stability and pH.

The duration of the treatment by enzymes having a phytase activity may differ according to the source of protein used. The duration of the treatment by enzymes having phytase activity may be finished at different times, which may be in a range of 5 minutes to 320 minutes, in a range of 10 minutes to 180 minutes, or in a range of 30 minutes to 120 minutes.

The temperature of treatment by enzymes having a phytase activity may be in a range of 20° C. to 70° C., in a range of 25° C. to 65° C., or in a range of 30° C. to 60° C.

In one aspect of the invention, addition of enzymes having phytase activity in solid or liquid state or their combination thereof into hydrolysis tank 110 containing source of protein may decrease the amount of inositol hexaphosphate and its derivatives. The addition of precipitating agents in the hydrolysis tank 110 after addition of enzymes having phytase activity results in the precipitation of the remaining inositol hexaphosphate and its derivatives. In another aspect of the invention, the enzymes with phytase activity and precipitating agents may be used in one of two orders.

In another aspect of the invention, the combination of treatment by enzymes having phytase activity and precipitation process may take place in a second hydrolysis tank, wherein the second hydrolysis tank may be connected to the hydrolysis tank 110 for the source of protein and to the mixing tank 113.

Enzymes having phytase activity may be used either individually or in combination thereof, wherein the combination may comprise use of at least 2 or more enzymes having phytase activity.

Addition of enzymes having phytase activity in solid or liquid state or in their combination thereof into hydrolysis tank 110 containing the source of protein and water source from loading tank 126 leads to cleavage of phosphate ester bonds in the specific pH and temperature.

Addition of precipitating agents into hydrolysis tank 110 containing the source of protein and water source from loading tank 126 leads to binding of precipitating agents to inositol hexaphosphate and its derivatives causing formation of precipitates.

In one aspect of the invention, the hydrolysis tank 110 may be composed of various materials and specific volumes and may be configured with a stirring unit, water purification unit, loading tank 126 and storage tank 102.

The first and second aspect may be combined, wherein inositol hexaphosphate and its derivatives may be removed by the first aspect at least 90% and by the second aspect by up to 10%, by the first aspect at least 80% and by the second aspect by up to 20%, by the first aspect at least 70% and by the second aspect by up to 30%, by the first aspect at least 60% and by the second aspect by up to 40%, by the first aspect at least 50% and by the second aspect by up to 50%, by the first aspect at least 40% and by the second aspect by up to 60%, by the first aspect at least 40% and by the second aspect by up to 60%, by the first aspect at least 30% and by the second aspect by up to 70%, by the first aspect at least 20% and by the second aspect by up to 80%, by the first aspect at least 10% and by the second aspect by up to 90%.

In one aspect of the invention, the ratio of precipitating agent to enzymes having phytase activity may be selected according to the amount of inositol hexaphosphate and its derivatives.

In one aspect of the invention, the use of enzymes having phytase activity and precipitating agents on protein hydrolysate may result in a modified protein hydrolysate. The term "modified protein hydrolysate" refers to protein hydrolysate comprising cleaved or precipitated inositol hexaphosphate and its derivatives or their combination thereof.

The modified protein hydrolysate may be thermally treated at the end of hydrolysis to deactivate enzymes having phytase activity and/or kill microorganisms. In one aspect of the invention, this treatment may be at low temperature in the range of 80° C. to 120° C., in the range of 85° C. to 100° C. or in the range of 90° C. to 95° C. for a time in the range of 15 minutes to 180 minutes or in the range of 20 minutes to 120 minutes or in the range of 25 minutes to 60 minutes. In another aspect of the invention, this treatment may be performed at high temperature in the range 80° C. to 160° C., in the range of 100° C. to 155° C., or in the range of 110° C. to 150° C. for a time compared to those with lower temperature settings, wherein the portion of time is in the range of 1 to 600 seconds, in the range of 3 seconds to 300 seconds, or in the range of 5 seconds to 60 seconds. The low temperature method may be performed in a hydrolysis tank 110, while both high and low temperature methods may be performed in the hydrolysis tank 110 configured as flash pasteurizer or another suitable continuous flow heating device.

If the enzyme is removed by ultrafiltration, it may retain at least partial catalytic activity and thus may be recycled for another round of hydrolysis. Ultrafiltration or thermal deactivation may also be used to remove active enzyme molecules from hydrolysates prepared by immobilized enzymes, in the event that some of the enzyme detaches from the solid support and dissolves into the reaction mixture.

In one aspect of the invention, solid residues may be removed from protein hydrolysate by filtration unit 112. In one aspect of the invention, the solid residues may be further used for the production of edible product, wherein the edible product may be used for human or animal consumption.

In one aspect of the invention, the hydrolysis tank 110 may be connected to the filtration unit 112 by pump 114. This pump may be used for the transfer of protein hydrolysate to the filtration unit.

In one aspect of the invention, the filtration of the solid residues formed by using precipitation may be performed similarly as previously described.

In one aspect of the invention, the filtration of solid residues from the modified protein hydrolysate by the filtration unit may result in a purified protein hydrolysate.

The purified protein hydrolysate is transferred to the mixing tank 113 where the nutritional additives, shear protectants, anti-foaming agents and/or proliferation additives may be loaded from the loading tank 126 in the preparation of culture medium. The term "Purified protein hydrolysate" refers to a hydrolysate that is free from solid residues in a range of 90% to 100%, in a range of 95% to 100%, in a range of 98% to 100%. The term "culture medium" refers to a mix of at least one of purified protein hydrolysate, nutritional additives, shear protectants and/or anti-foaming agents.

The nutritional additives may include saccharides, mineral compounds, vitamins, amino acids, peptides, organic amines, signaling compounds, oligonucleotides, fatty acids, phospholipids, organic micronutrients or any other appropriate nutritional additive according to the selected source of protein, wherein the selected source of protein may contain low concentration of particular amino acids that are present in a low concentration within the source of protein and which are essential for the cell growth and metabolism. Those particular amino acids may be added subsequently as nutritional additives from a loading tank 126.

In one aspect of the invention, the mixing tank 113 may comprise a main body constructed from at least one material selected from stainless steel, glass-lined steel, titanium, polyethylene, polypropylene, polytetrafluoroethylene or any other suitable materials. The main body may comprise various shapes, such as cylindrical or rectangular or any other suitable geometries. The input of the mixing tank may be configured as a shaft or funnel, wherein the shaft or funnel may be used for loading the nutritional additives. The mixing tank may further comprise a heating system configured to heat the inner environment of the mixing tank. The mixing tank may comprise mixing mechanisms comprising at least one stirrer, paddle or any other instrument capable of mixing the nutritional additives with the purified protein hydrolysate. The sealing mechanisms of the mixing tank may comprise materials such as silicone, ethylene propylene diene monomer, and polytetrafluoroethylene. The mixing tank may be configured to withstand a maximum temperature of at least 100° C. The mixing tank may further comprise auxiliary components selected from the group of pumps, pressure sensors, flow meters, valves and means for monitoring the hydrolysis reaction.

In one aspect of the invention, the loading tank 126 may be configured to provide nutritional additives in dry or liquid form or in the combination thereof, shear protectants, anti-foaming agents into the mixing tank.

In one aspect of the invention, the loading tank 126 for the addition of nutritional additives may be composed of various materials and specific volumes previously mentioned.

The first, the second and the third aspect may be applied to obtain purified protein hydrolysate, wherein each aspect may prevent the formation of precipitates. This ensures that the filters are not blocked by precipitates and that the provided nutrients are more effectively processed by the cells, as opposed to the unusable precipitates.

The first or the third aspect may be applied to obtain released free phosphates from the inositol hexaphosphate and its derivatives and may be used as nutrition for the cells and thus may not be added via loading tank 126 into mixing tank 113 with other nutritional additives.

In one aspect of the invention, the amount of free phosphate provided from the cleaved inositol hexaphosphate and its derivatives is in a range of 50% to 100% of total phosphate ions in the culture medium, in a range of 60% to 100% of total phosphate ions in the culture medium, in a range of 70% to 100% of total phosphate ions in the culture medium, in a range of 80% to 100% of total phosphate ions in the culture medium, in a range of 90% to 100% of total phosphate ions in the culture medium, in a range of 60% to 90% of total phosphate ions in the culture medium, or in a range of 70% to 80% of total phosphate ions in the culture medium.

In one aspect of the invention, the amount of free phosphate provided from the cleaved inositol hexaphosphate and its derivatives is in a range of 50% to 100% of total phosphate ions in the protein hydrolysate, in a range of 60% to 100% of total phosphate ions in the purified protein hydrolysate, in a range of 70% to 100% of total phosphate ions in the purified protein hydrolysate, in a range of 80% to 100% of total phosphate ions in the purified protein hydrolysate, in a range of 90% to 100% of total phosphate ions in the purified protein hydrolysate, in a range of 60% to 90% of total phosphate ions in the purified protein hydrolysate, or in a range of 70% to 80% of total phosphate ions in the purified protein hydrolysate.

In one aspect of the invention, solid residues may be removed from the culture medium by filtration unit 115. In one aspect of the invention, the solid residues may be further used for the production of edible or food product, wherein the edible or food product may be used for human or animal consumption. In another aspect of the invention, the solid residues may be removed by centrifugation. In another aspect of the invention, centrifugation and filtration may be used in sequence. Preferably, centrifugation comes before filtration to prolong the lifetime of the filter.

In one aspect of the invention, the filtration unit may be configured to utilize centrifugal force to separate solid-phase particles from liquid phase. This separation process may be facilitated by the implementation of centrifugal filters, which may be strategically designed and positioned within the filtration unit.

In one aspect of the invention, the sterile barrier 116 may comprise a heat sterilization by flash heat treatment, irradiation sterilization by UV irradiation using UV lamps or chemical agents that may be used for culture medium sterilization.

In one aspect of the invention, at least one storage tank 102 is configured for the storage of the culture medium to ensure its safety. The storage tank may comprise a main body constructed from at least one material selected from stainless steel, glass-lined steel, titanium, polyethylene, polypropylene, polytetrafluoroethylene or any other suitable materials. The main body may comprise various shapes, such as cylindrical or rectangular or any other suitable geometries. The storage tank may comprise insulation configured as an outer jacket of the hydrolysis tank, wherein the space between the outer jacket and the wall of the storage tank may be filled with an appropriate insulation material or medium. The hydrolysis tank may further comprise at least one input and at least one output for loading and unloading the ingredients. The storage tank may comprise mixing mechanisms comprising at least one stirrer, paddle or any other instrument capable of mixing the culture medium. The sealing mechanisms of the storage tank may comprise materials such as silicone, ethylene propylene diene monomer, and polytetrafluoroethylene. The storage tank may be configured to withstand a maximum temperature of at least 100° C. The storage tank may further comprise auxiliary components selected from the group of pumps, pressure sensors, flow meters, valves and means for monitoring the hydrolysis reaction.

The volume of the storage tank 102 may be in the range of 0.1 l to 100,000 l, or in the range of 0.3 l to 15,000 l, or in the range of 1 l to 5,000 l.

If the contamination in the culture medium is not detected, the culture medium may be transferred into a filtration unit 118 by pump 117 and to the sterile barrier 116 and then the culture medium may be further subjected for transfer into the cultivation device 101.

In one aspect of the invention, the composition of the culture medium may be defined in terms of the total input of medium components into the cultivation process. In this aspect of the invention, summary amounts of components introduced into the cultivation process at any time point over its entire duration are provided. Furthermore, in this aspect of the invention, the provided concentration ranges for the individual medium components describe the total amount of the given component introduced into the cultivation process at any time point during the cultivation process in relation to the volume of spent culture medium which exits the process. The spent culture medium may exit the cultivation process together with the cultivated cells (harvesting), or separately from the cultivated cells (perfusion). The cultivation process may further have the characteristics of a batch process, where all of the components are introduced into the cultivation process at a single time point and the harvest is performed at a single time point, a fed-batch process, where some components may be introduced after the start of the process and the harvest is done at a single time point, a continuous process, where components may be introduced during the whole duration of cultivation and harvesting may be performed during the whole duration of cultivation, or a combination of the described characteristics. For brevity, this aspect of the invention will be referred to herein as "total input".

In another aspect of the invention, the composition of the culture medium may be described in terms of the concentration of components which are present at a particular time point during the cell cultivation process in the culture medium. In this aspect of the invention, the provided concentration ranges for the individual medium components describe the concentrations present in the culture medium in the cultivation device at any time point during the cultivation process. For brevity, this aspect of the invention will be referred to herein as "momentary composition".

The total inputs into the culture medium according to the invention may comprise an optimized ratio of essential amino acids, which may be sourced from a protein hydrolysate, in combination with at least one type of compound selected from a group comprising: saccharides, vitamins and organic micronutrients, mineral compounds, iron supplementation compounds, organic amines, shear protectants, anti-foaming agents or a combination thereof. The media may also contain other compounds, like fatty acids, phospholipids, additional amino acids or oligonucleotides, for example. Media according to the invention with an optimized ratio of amino acids and other nutrients may facilitate efficient production of biomass and a low production of waste metabolites, such as ammonia or lactate, by the cells.

An optimized ratio of essential amino acids is such that essential amino acids may be introduced into the cultivation process in any ratio where the percentage of essential amino acids that can be converted into cellular protein is in the range of 5% to 100%, or in the range of 20% to 90%, or in the range of 30% to 80%. The term "highest possible conversion efficiency" determines what percent of the essential amino acids provided to the cells can be converted into cellular protein, assuming no loss of amino acids to catabolism, conversion to other compounds (nucleic acids, for example), or spontaneous degradation.

The highest possible conversion efficiency is determined by the essential amino acid that is the most limiting to the cells. It is calculated such as that for all individual essential amino acids added to the medium in any form at any time point during the cultivation process, the content of that particular essential amino acid in the culture media as a fraction of total essential amino acid content added in any form at any time point to the culture media is divided by the content of that individual amino acid in cellular protein as a fraction of total content of essential amino acids in the lowest obtained ratio, in other words the ratio for the essential amino acid which forms the lowest percentage of the amino acids added to the medium in comparison to the percentage of that particular amino acid in cellular biomass, is then multiplied by 100 to obtain the highest possible conversion efficiency of the provided essential amino acids into cellular protein. All percentages in the calculation of highest possible conversion efficiency are percentages by weight.

The amino acids in the culture media may be present in the form of free amino acids or peptides. Non-essential amino acids are omitted in this calculation, as they can be synthesized by the cells and thus are not limiting in terms of the highest possible conversion efficiency. An example of possible essential amino acid content in cellular protein can be seen in Table 14 below.

The above description may be summarized by the following equation:

$$H_{EAA} = \frac{\dfrac{A_{EAAM}}{\sum A_{EAAM}}}{\dfrac{A_{EAAC}}{\sum A_{EAAC}}} * 100,$$

where $H_{EAA}$ is the highest conversion efficiency for a particular amino acid, $A_{EAAM}$ is the content of that particular essential amino acid in 100 g of protein in culture medium, $\Sigma A_{EAAM}$ is the total content of all essential amino acids in 100 g of protein in culture medium, $A_{EAAC}$ is the content of that particular essential amino acid in 100 g of cellular protein and $\Sigma A_{EAAC}$ is the total content of all essential amino acids in 100 g of cellular protein.

An example calculation for the essential amino acid tryptophan would proceed as follows: assuming that the total amount of tryptophan added to the culture media over the period of cultivation was 2 g, and the total amount essential amino acids added to the media over the same time period was 100 g. Table 14 shows that in 100 g of cellular protein, out of 44.7 g of total essential amino acids, 1.6 g are tryptophan.

The calculation:

$$H_{EAA} = \frac{\dfrac{2}{100}}{\dfrac{1.6}{44.7}} * 100 = 55.875\%$$

shows that the highest conversion efficiency for tryptophan is 55.875%. Now, this process is repeated for each of the nine individual essential amino acids. The lowest of nine numbers obtained is the final highest conversion efficiency.

The amount of essential amino acids that can be converted into cellular protein is determined by how closely the total input of essential amino acids into the cultivation process matches the amino acid composition of cellular protein. Because cells cannot synthesize essential amino acids, the essential amino acid with the lowest relative total input into the cultivation process in comparison to its content in cellular protein will limit maximal cell yield and therefore the maximal percentage of essential amino acids converted to cellular protein (this can be understood as an application of Liebig's law of the minimum).

The conversion efficiency for total essential amino acids may be in the range of 5% to 100%, 20% to 100%, 30% to 100%, or 50% to 100%, calculated by the above mentioned equation.

If the essential amino acid composition of cellular protein according to the example mentioned in Table 1 is used, the resulting total inputs of each essential amino acid given as grams per 100 g of the total input of all essential amino acids may be in the ranges summarized in the Table 15.

The ranges of concentrations of amino acids in grams per 100 g of total essential amino acids introduced into the cultivation process may be according to Table 15, regardless of whether the essential amino acid composition of cellular protein is according to Table 14 or not.

It should be noted that for the purpose of this equation, it is necessary to consistently consider amino acid content either as free amino acids, or as amino acids that are part of a peptide chain (in which case the molecular weight of each amino acid must be considered lower by the weight of one water molecule, to account for the fact that water is a byproduct of a peptide bond formation). In the equation above and Tables 1-3, everything is counted as amino acids that form a peptide chain. Elsewhere in the present document, when amino acid input or concentration is discussed, these are calculated with the molecular weights of free amino acids, and when protein input or concentration is discussed, it is assumed that the amino acids are part of a peptide chain for any calculations.

TABLE 14

Example of possible essential amino
acid content in the cellular protein.

| Amino acid | content [g/100 g cellular protein] |
|---|---|
| His | 2.7 |
| Ile | 5.1 |
| Leu | 8.9 |
| Lys | 8.2 |
| Met | 2.9 |
| Phe | 4.7 |
| Thr | 4.8 |
| Trp | 1.6 |
| Val | 5.8 |
| Sum | 44.7 |

TABLE 15

Ranges of concentrations of amino acids in grams per 100 grams of total
essential amino acids introduced into the cultivation process.

| Amino acid | range 1 | range 2 | range 3 |
|---|---|---|---|
| His | 0.30 to 6.04 | 1.21 to 5.44 | 1.81 to 4.83 |
| Ile | 0.57 to 11.41 | 2.28 to 10.27 | 3.42 to 9.13 |
| Leu | 1.00 to 19.91 | 3.98 to 17.92 | 5.97 to 15.93 |
| Lys | 0.92 to 18.34 | 3.67 to 16.51 | 5.50 to 14.68 |
| Met | 0.32 to 6.49 | 1.30 to 5.84 | 1.95 to 5.19 |
| Phe | 0.53 to 10.51 | 2.10 to 9.46 | 3.15 to 8.41 |
| Thr | 0.54 to 10.74 | 2.15 to 9.66 | 3.22 to 8.59 |
| Trp | 0.18 to 3.58 | 0.72 to 3.22 | 1.07 to 2.86 |
| Val | 0.65 to 12.98 | 2.60 to 11.68 | 3.89 to 10.38 |

However, the composition of cell biomass is somewhat variable, and therefore the values for each essential amino acid in terms of weight percentage of total essential amino acids used in the media may also be in the ranges summarized in the Table 16.

TABLE 16

Ranges of weight percentage concentration of total essential
amino acids introduced into the cultivation process.

| Amino acid | range 4 | range 5 | range 6 |
|---|---|---|---|
| His | 0.2 to 7.9 | 0.8 to 7.1 | 1.2 to 6.3 |
| Ile | 0.3 to 14.9 | 1.5 to 13.4 | 2.3 to 11.9 |
| Leu | 0.7 to 25.9 | 2.7 to 23.3 | 4.1 to 20.8 |
| Lys | 0.6 to 23.9 | 2.5 to 21.5 | 3.8 to 19.1 |
| Met | 0.2 to 8.5 | 0.9 to 7.6 | 1.3 to 6.8 |
| Phe | 0.3 to 13.7 | 1.4 to 12.3 | 2.2 to 11.0 |
| Thr | 0.3 to 14.0 | 1.5 to 12.6 | 2.2 to 11.2 |
| Trp | 0.1 to 4.7 | 0.5 to 4.2 | 0.7 to 3.8 |
| Val | 0.4 to 16.9 | 1.8 to 15.2 | 2.7 to 13.5 |

Amino acids may be introduced into the cultivation process in the form of free amino acids, salts of amino acids, esters of amino acids, or any other suitable derivatives, as well as oligopeptides, for example dipeptides, tripeptides or tetrapeptides, or polypeptides.

The total input of hydrolysate (expressed as protein dry weight) introduced into the culture medium in the cultivation process may be in the range of 1 g/l to 200 g/l, or in the range of 3 g/l to 100 g/l, or in the range of 10 g/l to 60 g/l, or in the range of 8 g/l to 50 g/l.

The total input of amino acids from hydrolysate, including amino acids in the form of short peptides or suitable bioavailable derivatives, for example phosphoesters, such phosphoserine, or other derivatives, such as methylglycine, is at least 75%, 80%, 85%, 90%, or 95% by weight of the total input of all amino acids into the culture medium.

The culture medium according to the invention may comprise amino acids added separately from the hydrolysate, for example L-methionine, L-cysteine or L-ornithine. The total input of amino acids added separately from hydrolysate may be in the range of 0.02 g/l to 30 g/l, or in the range of 0.05 g/l to 15 g/l, or in the range of 0.1 g/l to 10 g/l.

The total amount of L-cysteine in the culture medium may be in the range of 0.1% to 10%, or 0.5% to 7%, or 1% to 5% by weight with respect to the total amount of hydrolysate protein in the culture medium.

The total amount of L-ornithine in the culture medium is in the range of 0% to 5%, or 0.0001% to 3%, or 0.001% to 0.5% with respect to the total amount of hydrolysate protein in the culture medium.

The total amount of L-methionine in the culture medium may be in the range of 0.05% to 6%, or 0.1% to 3%, or 0.2% to 2% with respect to the total amount of hydrolysate protein in the culture medium.

The total amount of L-tryptophan in the culture medium may be in the range of 0.05% to 6%, or 0.1% to 3%, or 0.2% to 2% with respect to the total amount of hydrolysate protein in the culture medium.

The total amount of L-histidine in the culture medium may be in the range of 0.03% to 4%, or 0.07% to 2%, or 0.15% to 1.5% with respect to the total amount of hydrolysate protein in the culture medium.

The total amount of L-threonine in the culture medium may be in the range of 0.1% to 7%, or 0.2% to 5%, or 0.3% to 3% with respect to the total amount of hydrolysate protein in the culture medium.

The total input of amino acids added to the culture medium separately from the hydrolysate may be in the range of 0.2% to 25%, or in the range of 0.5% to 15%, or in the range of 1% to 10%, expressed as a percentage of the total input of hydrolysate protein into the culture medium.

The culture medium according to the invention may comprise an inorganic source of bioavailable nitrogen, for example ammonia. The total input of inorganic nitrogen source may be in the range 0 g/l to 30 g/l, or in the range 0.5 g/l to 20 g/l, 1 g/l to 10 g/l. The total input of ammonia sourced from hydrolysate may be in the range of 10-1000 mg/L, or in the range of 20-500 mg/L, or in the range of 40-300 mg/L.

As a saccharide may be used at least one compound selected from the group: glucose, fructose, galactose, sucrose, lactose, maltose, or a combination thereof, or any other appropriate saccharide. Total input of saccharides may be in an amount in the range of 1 g/l to 350 g/l, or in the range of 2 g/l to 100 g/l, or in the range of 3 g/l to 20 g/l.

The media may contain at least one of or any combination of the following ions as a mineral compound: $Ca^{2+}$, $Cl^-$, $Cu^{2+}$, $SO_4^{2-}$, $Fe^{3+}$, $NO_3^{3-}$, $Fe^{2+}$, $Mg^{2+}$, $K^+$, $Na^+$, $CO_3^{2-}$, $HCO_3_-$, $H_2PO_4_-$, $HPO_4^{2-}$, $PO_4^{3-}$, $Zn^{2+}$, $SeO_3^{2-}$. The media may also contain trace amounts of other mineral compounds and elements, such as cobalt, iodine or manganese.

As the media is prepared by dissolving different constituent compounds in water, any appropriate chemical compound may be used as long as it dissociates to the desired ions in aqueous solution. For example, NaCl and KCl both produce a $Cl^-$ ion when dissolved. As another example, $CuSO_4$ and $MgCl_2$ or $MgSO_4$ and $CuCl_2$ may be used to produce $Cu^{2+}$, $Mg^{2+}$, $SO_4^{2-}$ and $Cl^-$ ions. Assuming equimolar amounts, the resulting aqueous solution will have the same composition for both combinations of compounds used. The total input of mineral compounds introduced into the cultivation process may be in the range of 0.1 g/l to 50 g/l, or in the range of 1 g/l to 20 g/l, or in the range of 3 g/l to 10 g/l.

The total input of $Na^+$ may be in the range of 20 mmol/l to 120 mmol/l, or in the range of 30 mmol/l to 100 mmol/l, or in the range of 40 mmol/l to 80 mmol/l.

The total input of $Ca^{2+}$ may be in the range of 0.01 to 2 mmol, or in the range of 0.05 to 1 mmol, or in the range of 0.1 to 0.6 mmol/L.

The total input of $Cl^-$ may be in the range of 25 mmol/l to 130 mmol/l, or in the range of 35 mmol/l to 110 mmol/l, or in the range of 45 mmol/l to 90 mmol/l.

The total input of $Mg^{2+}$ may be in the range of 0.3 mmol/l to 10 mmol/l, or in the range of 0.5 mmol/l to 8 mmol/l, or in the range of 1 mmol/l to 5 mmol/l.

The total input of $PO_4$ may be in the range of 0.5 mmol/l to 12 mmol/l, or in the range of 0.7 mmol/l to 10 mmol/l, or in the range of 1 mmol/l to 6 mmol/l.

The total input of $SO_4_2$ may be in the range of 0.1 mmol/l to 5 mmol/l, or in the range 0.3 mmol/l to 3 mmol/l, or in the range 0.6 mmol/l to 2 mmol/l.

The total input of $K^+$ may be in the range of 2 mmol/l to 18 mmol/l, or in the range of 4 mmol/l to 15 mmol/l, or in the range of 6 mmol/l to 12 mmol/l.

The culture media may contain at least one vitamin of: alpha-tocopherol (vitamin E), ascorbic acid (vitamin C), vitamin B12, biotin, choline, pantothenic acid, folic acid, niacinamide, pyridoxine, riboflavin, thiamine, i-inositol, or a combination thereof. Any appropriate bioactive derivatives or precursors of these compounds may be used. For example, cyanocobalamin may be used instead of vitamin B12, as it can be readily converted to bioactive vitamin B12 by the cells. As another example, thiamine hydrochloride (chloride salt form of thiamine) may be used instead of thiamine. The total input of vitamins introduced into the cultivation process, omitting the vitamins present in lysates or extracts, may be in the range of 0.1 mg/l to 1,000 mg/l, or in the range of 5 mg/l to 500 mg/l, or in the range of 20 mg/l to 300 mg/l.

The total input of choline may be in the range of 10 mg/l to 1,000 mg/l, or in the range of 20 mg/l to 500 mg/l, or in the range of 30 mg/l to 200 mg/l.

The total input of niacinamide (or another vitamer of vitamin B3) may be in the range 3 mg/l to 150 mg/l, or in the range 6 mg/l to 100 mg/l, or in the range of 10 mg/l to 80 mg/l.

As an organic amine may be used at least one compound selected from: putrescine, ethanolamine, or a combination thereof, or any other appropriate amine. Organic amines total input into the cultivation process may be in an amount in the range of 0.01 mg/l to 1,000 mg/l, or in the range of 0.1 mg/l to 100 mg/l, or in the range of 0.5 mg/l to 20 mg/l.

Vitamins and organic amines or their respective precursors or derivatives may be supplied in the form of a lysate or extract, for example autolysed yeast extract or any other appropriate lysate or extract. Extract or lysate for supplementation of micronutrients may be added to the culture media in an amount in the range of 0.01 g/l to 20 g/l, or in the range of 0.1 g/l to 10 g/l, or in the range of 0.5 g/l to 5 g/l.

Iron may be supplemented to the culture medium in compounds with oxidation state iron (III) or iron (II). Iron may be present as free ions, or it may be chelated with a suitable chelating agent to improve its solubility and bioavailability. Chelating agents may include citrate, gluconate, ammonium citrate, EDTA, their combinations, or any other suitable chelating agent. Iron may be introduced into the culture medium bound to the chelating agent (for example, in the form ferric citrate), or iron and the chelating agent may be added separately (for example, in the form of ferric chloride and sodium citrate). The relative amount (w/w) of the total input of the chelating agent to the total input of iron may be in the range of 10000:1 to 1:100, or in the range of 1000:1 to 1:10, or in the range of 10:1 to 1:1. The total input of iron may be in the amount in the range of 0.00001 g/l to 0.5 g/l, or in the range of 0.0001 g/l to 0.1 g/l, or in the range of 0.001 g/l to 0.05 g/l.

The culture medium may comprise a shear protectant to prevent cell damage from mechanical forces caused by mixing and/or sparging in the cultivation device. As a shear protectant may be used at least one of: polyethylene glycol (PEG), methyl cellulose (MC), (hydroxypropyl)methyl cellulose (HPMC), hydroxypropyl cellulose (HPC), carboxymethyl cellulose (CMC), dextran sulfate, or any other appropriate shear protectant, or their combination. Shear protectants may be present in the culture medium in a concentration in the range of 0 g/l to 50 g/l, or in the range of 0.02 g/l to 10 g/l, or in the range of 0.1 g/l to 5 g/l.

As described herein, the physicochemical parameters and composition of the culture medium may be optimized to facilitate fast biomass production, efficient use of nutrients and low production of waste metabolites.

The osmolality of the medium may be in the range of 200 mOsm/kg to 400 mOsm/kg, or range of 250 mOsm/kg to 350 mOsm/kg, or range of 280 mOsm/kg to 330 mOsm/kg. Osmolality may be adjusted before or after the culture medium is introduced into the cultivation device, or a combination of both, and it may be adjusted at a single time point or multiple timepoints. To increase osmolality, NaCl, KCl, glucose, any other appropriate osmolyte or their combination may be used. To decrease osmolality, water or any other appropriate dilute aqueous solution may be used.

The pH of the culture medium in the cultivation device may be in the range of 6 to 8, or in the range of 6.5 to 7.5, or in the range of 6.8 to 7.3. Adjustment of pH may be performed before or after the culture medium is introduced into the cultivation device, or a combination of both, and it may be adjusted at a single time point or multiple time-points. NaOH, HCl, $NaHCO_3$, or any other appropriate acid or base may be used to adjust the pH; alternatively, pH may be adjusted by changing the partial pressure of $CO_2$ in the cultivation device (higher $CO_2$ partial pressure will result in more $CO_2$ being dissolved into the culture medium, leading to lower pH). The partial pressure of $CO_2$ in the cultivation device may be adjusted by changing the percentage of $CO_2$ in the sparging gas, changing the total pressure in the cultivation device, or changing the mixing and sparging rate in the cultivation device (reducing or increasing $CO_2$ mass transfer coefficient), or any other appropriate method. The partial pressure of $CO_2$ in the cultivation device may be in the range of 0.05 kPa to 100 kPa, or in the range 2 kPa to 60 kPa, or in the range 5 kPa to 30 kPa.

The momentary concentration of saccharides in the medium may be in the range 0.005 g/l to 40 g/l, or in the range 0.1 g/l to 20 g/l, or in the range 0.5 g/l to 5 g/l.

The momentary concentration of all amino acids (taking into account both amino acids sourced from the hydrolysate and amino acids added separately and biologically available derivatives, such as esters) and peptides in the medium may be in the range of 0.005 g/l to 30 g/l, or in the range 0.1 g/l to 15 g/l, or in the range 0.5 g/l to 10 g/l.

The composition of culture media as described above may be suitable for cell lines that have been extensively adapted to conditions in vitro. However, some cell types may require additional components in the culture medium, for example protein growth factors, to survive and proliferate. In another aspect of the invention, the culture medium composition suitable for these growth factor dependent cell lines may be described as follows.

The hydrolysates of protein isolates may be used as amino acid sources in culture media according to the invention. Recombinant protein production may be used in culture medium components preparation.

The culture medium according to the invention may comprise macronutrients, micronutrients, signaling compounds and/or other components. The components may be dissolved, for example, in purified water, or in water with inorganic salts, for example phosphate buffer saline (PBS) or water or PBS with Bovine serum albumin (BSA), for example 1% BSA in total.

The signaling compounds may vary according to the specific cell type used in the cultivation in the cultivation device. Examples of those cells may be fibroblasts, myoblasts, adipocytes and their precursors or a combination thereof.

The signaling compounds may or may not induce specific change in the cell fate. Examples of these changes may be stimulation of proliferation and/or stimulation of differentiation. The signaling compounds may be used in a certain order during a certain time period. Examples of those may be the usage of a signaling compound for stimulation of proliferation which is then in the media substituted with the signaling compound for differentiation induction. The precise order of dosing of signaling compounds may or may not be correlated or cross-linked with other tools which affect the cell fate during cultivation.

Signaling compounds for various cell types aimed for stimulation of proliferation may comprise, for example, at least one of the following signaling proteins: FGF family ligands, insulin, insulin and insulin like growth factor (IGF) family ligands, TGF family ligands, or transferrin, or any other appropriate signaling compound.

Signaling compounds for various cell types aimed for myogenic differentiation may comprise at least one of FGF, insulin, TGF, transferrin, IGF, epidermal growth factor (EGF), Bone morphogenic protein (BMP), interleukin 6 (IL-6), or IL-13, or any other appropriate signaling compound.

The amino acids and their derivatives that may be supplied to the media are for example: glycine, L-alanine, L-arginine, L-asparagine L-aspartic acid, L-cystine L-glutamic acid, L-glutamine, L-histidine, L-hydroxyproline, L-ornithine, L-citrulline, L-isoleucine, L-leucine, L-lysine, L-methionine, L-phenylalanine, L-proline, L-serine, L-threonine, L-pyroglutamic acid, L-phosphoserine, L-tryptophan, L-tyrosine or L-valine. For the preparation of the culture medium, the given amino acid may be added in the pure form, or as part of a complex mixture of compounds (for example a hydrolysate), or the hydrates or salts (for example hydrochlorides or sodium salts) of amino acids may be used.

In one aspect of the invention, the culture media may comprise protein hydrolysate as a main source of amino acids. The protein hydrolysate may serve as a source of all important amino acids in culture media according to the invention for the purpose of cell cultivation, or some amino acids may be supplied to the media separately, for example L-methionine, which is found in very low concentrations in most scalable sources of protein. Other different individual amino acids may be supplied separately from a different source than a protein hydrolysate.

In one aspect of the invention, the culture medium may comprise at least one of the amino acids listed in Table 17. There is also disclosed in Table 17 the possible exemplary, but not limiting, concentration of at least one amino acid that may be used in the culture medium according to the invention.

TABLE 17

A list of amino acids and their corresponding concentration ranges used in the culture medium.

| Amino acids | Minimal concentration (mg/L) | Maximal concentration (mg/L) |
|---|---|---|
| Glycine | 0 | 937.5 |
| L-Alanine | 0 | 222.5 |
| L-Arginine•HCl | 0 | 7375 |
| L-Asparagine•$H_2O$ | 0 | 375 |
| L-Aspartic Acid | 0 | 332.5 |
| L-Cysteine•HCl•$H_2O$ | 0 | 2442.5 |
| L-Glutamic Acid | 0 | 367.5 |
| L-Glutamine | 0 | 18250 |
| L-Histidine•HCl•$H_2O$ | 0 | 1574 |
| L-Isoleucine | 0 | 2723.5 |
| L-Leucine | 0 | 2952.5 |
| L-Lysine•HCl | 0 | 4562.5 |
| L-Methionine | 0 | 862 |
| L-Phenylalanine | 0 | 1774 |
| L-Proline | 0 | 862.5 |
| L-Serine | 0 | 1312.5 |
| L-Threonine | 0 | 2672.5 |
| L-Tryptophan | 0 | 451 |
| L-Tyrosine | 0 | 2789.5 |
| L-Valine | 0 | 2642.5 |

In one aspect of the invention, the content of signaling compounds, for example content of growth factors, such as FGF, TGF beta 1, insulin or transferrin or other signaling compounds may be reduced. The concentration of TGF beta 1 may be in the range of 0 mg/l to 0.002 mg/l. The concentration of transferrin in the culture medium according to the invention may be in the range of 0 mg/l to 10 mg/l, or in the range of 0.1 mg/l to 8 mg/l, or in the range of 0.5 mg/l to 5 mg/l. In one aspect of the invention, the reduced amount of transferrin may be in the range of 0 mg/l to 0.01 mg/l The concentration of insulin in the culture medium may be in the range of 0 g/l to 2 g/l, or in the range of 0.1 mg/l to 1 g/l, or 0.5 mg to 500 mg/l. In one aspect of the invention, the reduced amount of insulin may be in the range of 0 mg/l to 0.1 mg/l The concentration of FGF-2 in the culture medium may be in the range of 0 mg/l to 1 mg/l, or in the range of 0.1 mg/l to 0.8 mg/l, or 0.2 mg/l to 0.5 mg/l. In one aspect of the invention, the reduced amount of FGF-2 may be in the range of 0 mg/l to 0.01 mg/l.

The concentration of TGF beta 1 in the culture medium may be in the range of 0 mg/l to 0.2 mg/l, or in the range of 0.01 mg/l to 0.15 mg/l, or 0.05 mg/l to 0.1 mg/l. In one aspect of the invention, the reduced amount of TGF beta 1 may be in the range of 0 mg/l to 0.001 mg/l.

In one aspect of the invention, the culture medium may be without content of any signaling compounds, for example growth factors. The culture medium according to the invention may be serum free and/or protein free.

The culture medium may comprise anti-foaming agent, for example silicone-based anti-foaming agents, polyethylene glycol (PEG), poly vinyl alcohol (PVA), polydimethylsiloxane, polysorbate 80, or vegetable oils, or any other appropriate anti-foaming agent, or the combination thereof. The concentration of the anti-foaming agent in the culture medium may be in the range of 0.001% to 5%, or in the range of 0.01% to 1%, or in the range of 0.1% to 0.5% by weight.

In one aspect of the invention, the content of culture medium components may be in the ranges according to Table 18.

TABLE 18

| Ranges of concentrations of culture medium components | | |
|---|---|---|
| Group of compounds | Minimal concentration (mg/L) | Maximal concentration (mg/L) |
| Supplement | | |
| FGF-2 | 0 | 1 |
| Insulin | 0 | 200 |
| L-ascorbic acid | 0 | 640 |
| Sodium selenite | 0 | 0.14 |
| TGF-beta | 0 | 0.02 |
| Sugars | | |
| D-Glucose | 500 | 15755 |
| Fatty acids | | |
| Linoleic Acid | 0 | 0.21 |
| Thioctic Acid (lipoic acid) | 0 | 0.525 |
| Amino acids | | |
| Glycine | 0 | 937.5 |
| L-Alanine | 0 | 222.5 |
| L-Arginine•HCl | 0 | 7375 |
| L-Asparagine•H$_2$O | 0 | 375 |
| L-Aspartic Acid | 0 | 332.5 |
| L-Cysteine•HCl•H$_2$O | 0 | 2442.5 |
| L-Glutamic Acid | 0 | 367.5 |
| L-Glutamine | 0 | 18250 |
| L-Histidine•HCl•H$_2$O | 0 | 1574 |
| L-Isoleucine | 0 | 2723.5 |
| L-Leucine | 0 | 2952.5 |
| L-Lysine•HCl | 0 | 4562.5 |
| L-Methionine | 0 | 862 |
| L-Phenylalanine | 0 | 1774 |
| L-Proline | 0 | 862.5 |
| L-Serine | 0 | 1312.5 |
| L-Threonine | 0 | 2672.5 |
| L-Tryptophan | 0 | 451 |
| L-Tyrosine | 0 | 2789.5 |
| L-Valine | 0 | 2642.5 |
| Vitamins | | |
| Choline Chloride | 0 | 44.9 |
| D-biotin | 0 | 0.0175 |
| D-Pantothenic Acid (hemicalcium) | 0 | 11.2 |
| Folic Acid | 0 | 13.25 |
| myo-Inositol | 0 | 63 |
| Niacinamide | 0 | 10.1 |
| Pyridoxine•HCl | 0 | 10.065 |
| Riboflavin | 0 | 1.095 |
| Thiamine•HCl | 0 | 10.85 |
| Vitamin B12 | 0 | 3.4 |

TABLE 18-continued

| Ranges of concentrations of culture medium components | | |
|---|---|---|
| Group of compounds | Minimal concentration (mg/L) | Maximal concentration (mg/L) |
| Inorganic Salts | | |
| Calcium Chloride | 0 | 349.8 |
| Cupric Sulfate•5H$_2$O | 0 | 0.003 |
| Ferric citrate | 0 | 200 |
| Ferrous Sulfate•7H$_2$O | 0 | 1.251 |
| Magnesium Chloride•6H$_2$O | 0 | 85.92 |
| MgSO$_4$•7H$_2$O | 0 | 146.52 |
| Potassium Chloride | 0 | 935.4 |
| Sodium Bicarbonate | 0 | 7314 |
| Sodium Chloride | 0 | 20473.002 |
| Sodium phosphate dibasic•2H$_2$O | 0 | 213.06 |
| Sodium phosphate monobasic monohydrate | 0 | 187.5 |
| Zinc Sulfate•7H$_2$O | 0 | 1.296 |
| Other compounds | | |
| Hypoxanthine•Na | 0 | 11.95 |
| Putrescine•2HCl | 0 | 0.405 |
| Pyruvic Acid•Na | 0 | 275 |
| Thymidine | 0 | 1.825 |

In one aspect of the invention, oligonucleotides may be used as constituent components of a culture medium for a cultivation of cells. Oligonucleotides may be with single or double stranded chains of nucleic acids containing 10 nucleotides to 70 nucleotides or 10 nucleotides to 120 nucleotides or 1 nucleotides to 1,000 nucleotides.

In one aspect of the invention, the oligonucleotides may be added to the culture medium in molar concentration in the range of 5 nM/l to 100 nM/l, or in the range of 5 nM/l to 500 nM/l, or in the range of 50 nM/l to 50 mM/l, or the concentration may vary during the cultivation, when a peak of higher concentration may be followed with the lower concentration. The peak of high concentration may be from 1 hour to 10 hours or 10 hours to 72 hours of the cultivation.

In one aspect of the invention oligonucleotides may be a one of the components of a cell type specific signaling compound or may be added to the culture medium independently to the other components.

Oligonucleotides may be used for regulating gene expression by binding to target genes and translation process by binding to mRNA. Examples of those target genes may be genes encoding ferroportin, myostatin, p53, miRNA140 or other genes.

Examples of oligonucleotides serving as ligand to the suitable protein (aptamers) may be oligonucleotides able to bind to the target protein from FGFR family, TGF-beta superfamily receptors, transferrin receptor family, insulin receptor and/or IGFR family or other receptor families.

As additional compound may be used at least one of hypoxanthine, putrescine, pyruvate, thymidine, ethanolamine the salts or derivatives thereof or any other appropriate additional compound.

The hypoxanthine, for example hypoxanthine sodium, may be used in the culture medium according to the invention in the concentration in the range of 0 mg/l to 239 mg/l, or in the range of 10 mg/l to 200 mg/l, or in the range of 50 mg/l to 100 mg/l.

The putrescine, for example putrescine dihydrochloride, may be used in the culture medium according to the invention in the concentration in the range of 0 mg/l to 8.1 mg/l, or in the range of 1 mg/l to 6 mg/l, or in the range of 2 mg/l to 5 mg/l.

The pyruvate, for example pyruvate sodium, may be used in the culture medium according to the invention in the concentration in the range of 0 mg/l to 5.5 g/l, or in the range of 100 mg/l to 3 g/l, or in the range of 500 mg/l to 1 g/l.

The thymidine may be used in the culture medium according to the invention in the concentration in the range of 0 mg/l to 36.5 mg/l, or in the range of 5 mg/l to 25 mg/l, or in the range of 10 mg/l to 20 mg/l.

The recombinantly prepared signaling compounds may be used in the culture medium according to the invention. The signaling compounds may be stabilized to prevent degradation, for example thermal degradation or proteolytic degradation. They may be secreted into the culture medium, or accumulated in the cellular or subcellular compartment. Then in the process of harvesting they may be or may not be collected, purified and separated or whole culture may be collected. From the whole cultivated culture, various fractions (parts) may be divided and collected in a form of pellets that are easy to handle. Those pellets may be further processed and may serve as a direct compound to be added to the culture medium. Pellets may be dissolved, lysed or reconstituted prior the application into the culture medium in an appropriate solvent.

In one aspect of the invention, a production of recombinant signaling compounds may be used as culture medium components. The recombinant protein production may comprise the following expression systems: bacterial (for example *Escherichia coli, Bacillus subtilis*), Brewer's yeast (*Saccharomyces cerevisiae*), non-conventional yeast (for example *Pichia pastoris, Hansenula polymorpha, Yarrowia lipolytica*), filamentous fungi (for example *Aspergillus* spp., *Trichoderma reesei*), plants (for example *Nicotiana tabacum, Hordeum vulgare, Zea Mays*), insect cells or mammalian cell lines (for example HEK293, CHO-K1), or any other appropriate expression systems. The recombinant protein production followed by the cellular lysis and derivation of the pellets or other recombinant protein rich derivatives may be used for example in *Streptococcus thermophilus, S. cerevisiae, P. pastoris* and various strains of species *Lactobacillus* spp. such as *Lactobacillus acidophilus, Lactobacillus plantarum*, and *Lactobacillus casei*.

In one aspect of the invention, the culture medium for cell cultivation for preparing food products may have the total input of hydrolysate expressed as dry protein weight introduced into the culture medium within the cultivation process in the range of 8 g/l to 50 g/l.

The total input of amino acids from hydrolysate, including amino acids in the form of short peptides or suitable bioavailable derivatives may be at least 75% by weight of the total input of all amino acids into the culture medium.

The source of protein for hydrolysis may be selected from at least one of: soy, pea, rice, wheat, wheat gluten, corn, *faba* beans, alfalfa, hemp, chickpea, potato, pumpkin, rapeseed, red lentil, *Spirulina, Chlorella,* sunflower, water lentil, mung beans, flax, baker's yeast, brewer spent grain, distillers spent grain (DDGS), tomato pomace or any suitable microbial protein in form of powder, lysate, concentrate, isolate, liquid, solid or any other appropriate form.

The culture medium may be used for the cultivation of one or more non-human metazoan cell lines. The cell lines used for cultivation processes in the culture media according to the invention may include, for example, Chinese hamster ovary (CHO) cells, for example CHO-K1 or CHO-DG44, C2C12, Madin-Darby bovine kidney cells (MDBKs), Madin-Darby canine kidney (MDCK) cells, UMNSAH/DF-1, or any other appropriate cell lines.

The non-human metazoan cells may have the characteristics and/or properties of: hepatocytes, myocytes, myoblasts, osteoblasts, fibroblasts, lipoblasts, odontoblasts, keratinocytes, mesenchymal stem cells, multipotent progenitor cells, embryonic stem cells, myofibroblasts, myosatellite cells and/or any combinations thereof.

The non-human metazoan cells used for cultivation processes in the culture media according to the invention may be any appropriate non-human metazoan cells. The cells for cultivation may be non-human vertebrate cells. The cells may be, for example, bovine, porcine, fish (piscine), game (*cervine*), avian, rodent (cricetine, murine), equine or any other appropriate cells. The cells for cultivation may be selected, without limitation, from at least one of the following animals: cattle (*Bos taurus*), chicken (*Gallus domesticus*), domestic pig (*Sus domesticus*), house cricket (*Acheta domesticus*), garden snail (*Helix pomatia*), common carp (*Cyprinus carpio*), horse (*Equus ferus*), edible crab (*Cancer pagurus*), marsh frog (*Pelophylax ridibundus*), common octopus (*Octopus vulgaris*), gilt-head bream (*Sparus aurata*), roe deer (*Capreolus capreolus*), common sea urchin (*Echinus esculentus*), harbor seal (*Phoca vitulina*), European stag beetle (*Lucanus cervus*), African elephant (*Loxodonta africana*), house mouse (*Mus musculus*), green sea turtle (*Chelonia mydas*), or from any other appropriate animals.

The non-human metazoan cells may be modified in various ways to improve their characteristics and/or properties. The non-human metazoan cells may be genetically modified, may be subjected to modification of their characteristics and/or properties by methods other than genetic engineering, such as adaptation to different conditions and environments.

The genetic modifications may comprise permanent and/or transient genetic modifications, wherein such genetic modifications may be gain-of-function or loss-of-function modifications. They may be in the nuclear genome, mitochondrial genome or episomal DNA. The modifications may include point substitutions, point deletions, point insertions, larger deletions or larger insertions. The nucleic acid introduced into the cells may be naturally present within the species of the target cells, may be of the origin of another species, may be a synthetic, or a combination thereof. Such genetic modifications may be performed using methods such as CRISPR/Cas9, ZFNs, TALENs and/or other tools. Other methods for genetic modification may comprise introduction by viral vectors based on adenoviruses, adeno-associated viruses, retro/lentiviruses and/or vectors derived on the above mentioned.

The non-genetic-engineering methods and/or adaptation processes may comprise selecting subpopulations with uniform common phenotypes based on specific characteristics such as doubling time, ability to grow in suspension or ability to synthesize a specific amino acid. To create cell lines with such characteristics, populations originating from a single cell or populations originating from multiple cells may be established and may be further cultivated under conditions of a continuous selection pressure. The cells may be exposed to stress treatment, wherein the stress treatment may comprise absence of growth factors, nutrient limitation, mechanical forces caused by for example stirring or sparging, absence of adhesive surfaces, accumulated waste metabolites, extreme pH or osmolality values, very high concentrations of nutrient compounds, UV radiation, gamma radiation and/or other suitable stress factors.

The result of such improvement by any modification methods previously mentioned may be a gain of function and/or a loss of function, which may comprise:

at least one modification achieved by methods other than genetic modification selected from the group of: an adaptation to grow in a suspension, adaptation to grow on scaffolds, adaptation to form spheroids, adaptation to grow in the absence of at least one of L-proline or L-glutamine, adaptation to higher cell density level, adaptation to cryopreservation, adaptation to low-oxygen conditions, adaptation to serum-free culture medium, adaptation to protein-free culture medium, adaptation to low-protein culture medium, adaptation to mechanical stress;

and/or at least one change of cell characteristics achieved by genetic modification selected from the group of: shortening G1 phase in their proliferation phase, shortening cell cycle, capability of homogenous growth, immortalization, reduced telomeres shortening and their preservation, maintaining the ability to differentiate, ability to grow in a suspension, various changes of epigenetic profile, loss of contact inhibition, maintenance of cell divisions, enhanced nutrition metabolism, enhanced sugar metabolism;

and any combination of genetic modification, non-genetic modification and/or adaptation.

The non-human metazoan cells may be modified to improve their sensory properties and flavors by increasing the production of endogenous and exogenous heme proteins. The heme proteins may comprise at least one of nonsymbiotic hemoglobin, a Hell's gate globin I, a flavohemoprotein, a leghemoglobin, a heme-dependent peroxidase, a cytochrome c peroxidase, a mammalian myoglobin, an androglobin, a cytoglobin, a globin E, a globin X, a globin Y, a hemoglobin, a myoglobin, an erythrocruorin, a beta hemoglobin, an alpha hemoglobin, a protoglobin, a cyanoglobin, a cytoglobin, a histaglobin, a neuroglobins, a chlorocruorin, a truncated hemoglobin, a hemoglobin 3, a hemopexin, a methemoglobin, a catalase, a cytochrome, a peroxidase and/or any other heme-protein.

The non-human metazoan cells may be modified to improve their nutritional properties by decreasing the production of nucleic acids. The amount of nucleic acids in the cell biomass may be decreased by a genetic modification, adaptation processes and/or any other process capable of decreasing the amount of nucleic acids within the non-human metazoan cells.

In one aspect of the invention, the non-human metazoan cells may be utilized for the endogenous expression of compounds having therapeutic effect and/or signaling compounds. Such examples of compounds having therapeutic effect may comprise polyclonal antibodies, monoclonal antibodies and/or any other compounds having this effect. Examples of signaling compounds according to this aspect of the invention may comprise insulin, transferrin, FGF family compounds, IGF family compounds and/or any other signaling compounds.

Figure 36:
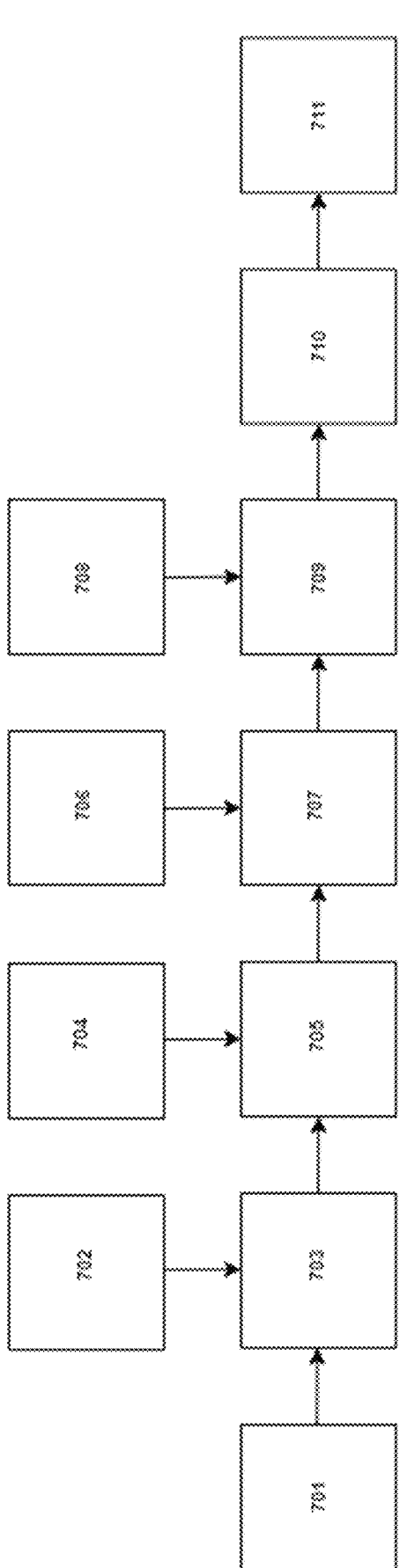
FIG. 36—illustrates scheme diagram of the culture medium preparation method process.

The scheme diagram of the method process of the cultivation system depicted in the FIG. 36 may have the following steps:

701 addition of a source of protein into the hydrolysis tank comprising the water source;

702 addition of proteolytic enzymes of the source of protein into the hydrolysis tank;

703 generation of the protein hydrolysate;

704 addition of enzymes having phytase activity or precipitating agents or combination thereof into the hydrolysis tank to cleave and/or precipitate inositol hexaphosphate or its derivatives;

705 generation of the modified protein hydrolysate;

706 addition of nutritional additives;

707 to generate culture medium;

708 used for inoculation of non-human metazoan cells;

709 and its descent cultivation of non-human metazoan cells;

710 harvest of the cell biomass;

711 use of the harvested cells for the production of compounds having therapeutic effects and/or may be used for food production.

Figure 37:
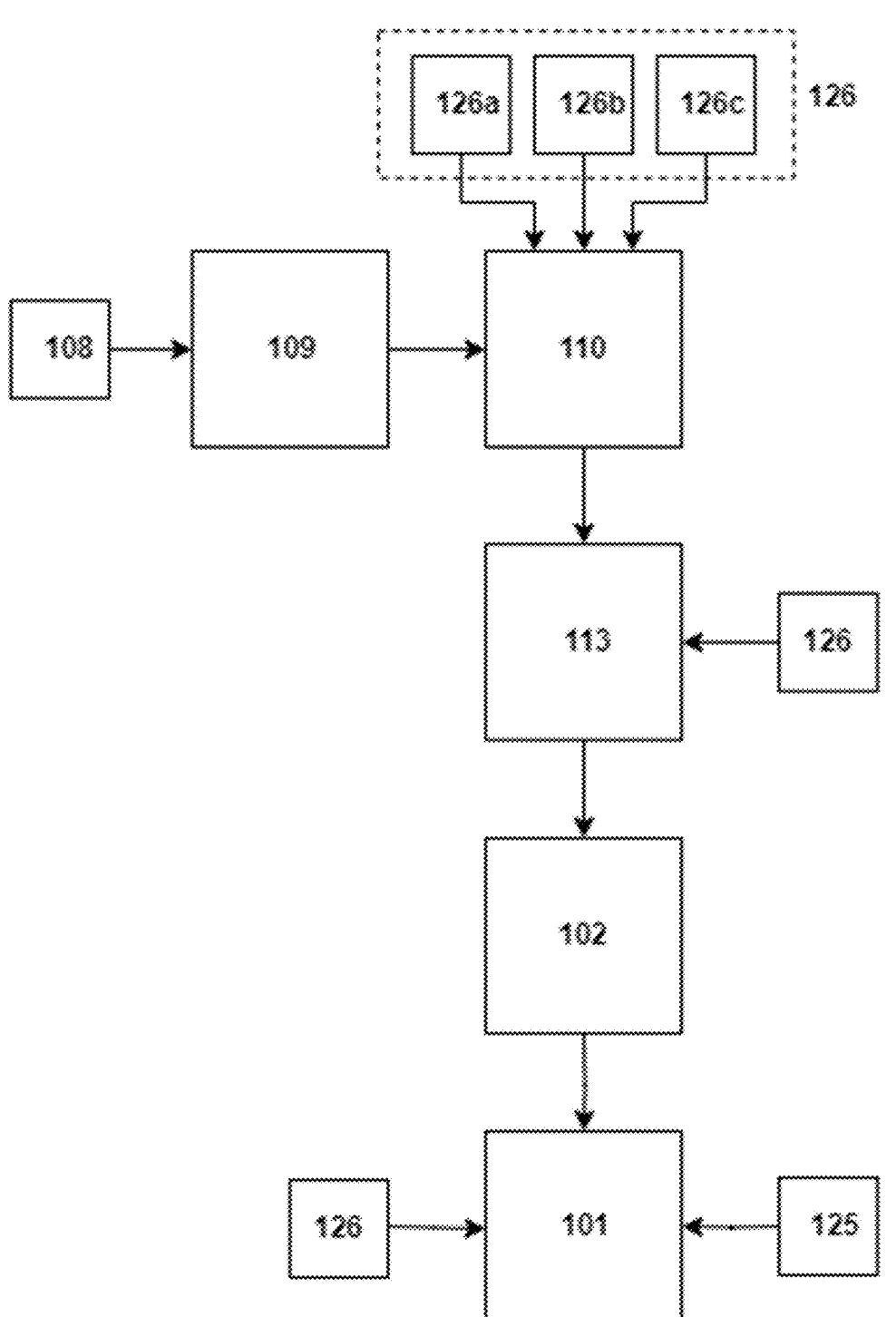
FIG. 37—illustrates scheme diagram of the cultivation system process.

The exemplary aspect of the invention as depicted in FIG. 37 is a particular variant of the scheme diagram of the method process of a cultivation system, which is depicted in the FIG. 36. The cultivation system according to the exemplary aspect of the invention as depicted in the FIG. 37 may have the following components:

water purification unit 109 utilized for the purification of a water source 108, wherein the water purification unit 109 may provide at least one selected from the group of reverse osmosis, deionization, electrodeionization, electrodialysis, and distillation;

the water purification unit 109 may be further connected to hydrolysis tank 110 configured for the preparation of protein hydrolysate and modified protein hydrolysate, wherein the hydrolysis tank 110 may comprise at least one thermometer and/or conductometer;

at least one loading tank 126 may be connected to the hydrolysis tank 110, wherein the loading tank 126 may comprise:

a loading tank 126a configured for the addition of source of protein; a loading tank 126b configured for the addition of proteolytic enzymes; a loading tank configured for the addition of enzymes having phytase activity and/or precipitating agents 126c; and/or any other loading tank configured for loading of any other component to produce modified protein hydrolysate;

the hydrolysis tank 110 may be further connected to a mixing tank 113 utilized for the mixing of purified protein hydrolysate with nutritional additives provided by loading tank 126 to generate the culture medium used for the cultivation of non-human metazoan cells;

the mixing tank 113 may be connected to a storage tank 102 utilized for the storage of the culture medium;

the storage tank 102 may be further connected to a cultivation device 101 utilized for the cultivation of non-human metazoan cells in the culture medium;

the cultivation device may be further connected to a control unit 125 and the loading tank 126 for the addition of antimicrobial agents and/or pH modifying agents.

Figure 38:
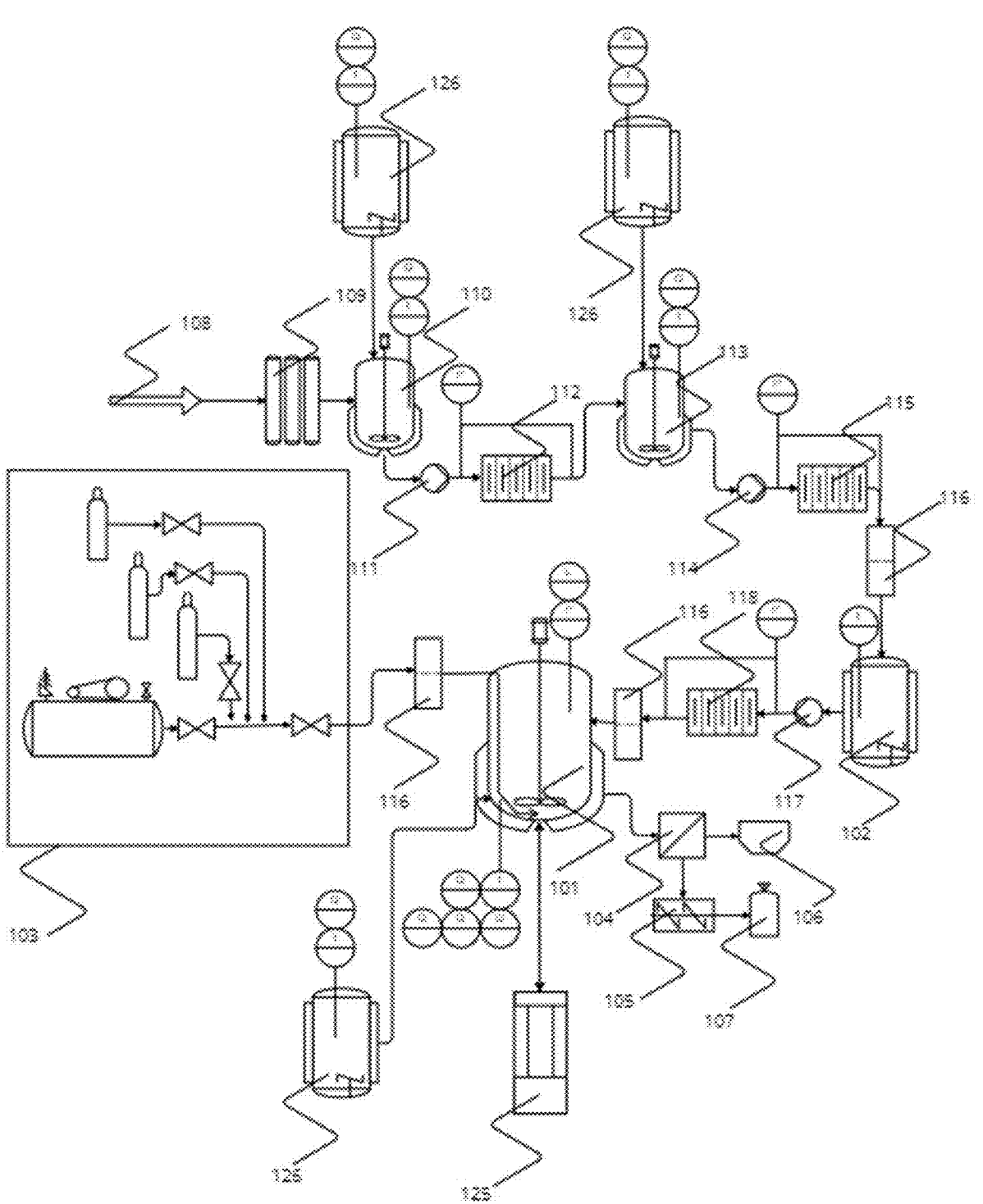
FIG. 38—illustrates scheme representation of the cultivation system.

The exemplary aspect of the invention as depicted in FIG. 38 is a scheme representation of a detailed configuration of the cultivation system. The scheme representation of the cultivation system according to the exemplary aspect depicted in FIG. 36 and FIG. 37 may have the following configuration:

a water source 108 may be connected to a water purification unit 109, wherein the water purification unit 109 may provide at least one selected from the group of reverse osmosis, deionization, electrodeionization, electrodialysis and distillation; and wherein the water purification unit 109 may be connected to a hydrolysis tank 110, wherein the hydrolysis tank 110 may comprise a thermometer and/or conductometer and at least one shaft or funnel for loading the source of amino acid and/or nutritional peptides, wherein the source of amino acid and/or nutritional peptides may be selected from the group of protein concentrate and protein isolate;

the hydrolysis tank 110 may further include at least one stirring unit and at least one loading tank 126 utilized for the addition of source of protein, proteolytic enzymes and enzymes having phytase activity; and wherein the hydrolysis tank 110 may be connected to a first filtration unit 112 by a first pump 111, wherein the first filtration unit 112 may comprise a manometer capable of measuring the difference between the input and output of the first filtration unit 112; and wherein the first filtration unit 112 may be connected to a mixing tank 113, wherein the mixing tank 113 may comprise the thermometer and/or conductometer, at least one shaft or funnel for loading the premix of other compounds and at least one stirring unit; and the mixing tank 110 may further include at least one loading tank 126 utilized for the addition of nutritional additives; and wherein the mixing tank 113 may be connected to a second filtration unit 115 by a second pump 114, wherein the second filtration unit 115 may comprise the manometer capable of measuring the difference between the input and output of the second filtration unit 115; and wherein the second filtration unit 115 may be connected to a storage tank 102 by at least one sterile barrier 116, wherein the storage tank 102 comprises a thermometer; and wherein the storage tank 102 may be connected to a third filtration unit 118 by a third pump 117, wherein the third filtration unit 118 may comprise a manometer capable of measuring the difference between the input and output of the third filtration unit 118; and wherein the third filtration unit 118 may be connected to a cultivation device 101 by at least one sterile barrier 116, wherein the cultivation device 101 may comprise a thermometer, conductometer, refractometer, manometer, pH meter, liquid level sensor and/or at least one gas concentration measurement instrument, and at least one stirring unit; and

wherein the cultivation device 101 may be connected to at least one loading tank 126 utilized for the addition of antimicrobial agents, and to a gas sparging system 103;

wherein the gas sparging system 103 may comprise one or more gas tanks coupled with a plurality of mass flow controllers and/or rotameters;

wherein the cultivation device 101 may be connected to at least one harvesting device 104 selected from the group of centrifuge unit and/or filtration unit;

wherein the harvesting device 104 may be configured to provide a comestible product and a waste medium 106; and wherein the comestible product may be processed by a product processing device 105 into a food product 107, e.g. pet food product and/or food product for human consumption; and a control unit 125 operatively and communicatively coupled with the cultivation device 101 and/or other components within the cultivation system;

wherein the control unit 125 may control and/or regulate the cultivation system.

Example 18: 1$^{st}$ Aspect (Phytase Treatment)

30 kg of soy protein isolate was added to 1000 l of water in the hydrolysis tank 110 with constant stirring, this mixture was heated to 90° C. for 30 minutes to improve dissolution and to ensure the deactivation of the protease inhibitors. After this treatment and equilibration to 60° C., 300 ml of ALCALASE® serine endopeptidase enzyme 2.4 FG from Novonesis (for 120 minutes at 60° C.), before the end of the 2 hour treatment the temperature was changed to 55° C., exactly after 2 hours 900 ml of FLAVOURZYME® proteolytic enzyme blend from Novonesis was added (for 21 hours at 55° C.) to hydrolyze the soy proteins into peptide chains and/or single amino acids, creating a protein hydrolysate. Next, amount equivalent to 40 g of protein (determined by Bradford, BCA or any other protein determination assay) of Maxamyl P, Quantum Blue, OptiPhos Plus 10 000 G or other enzymes having phytase activity from different suppliers, either alone or in combination, were added to the protein hydrolysate containing peptides and/or amino acids (for 60 minutes at 35° C.) to remove the phytic acids or their related compounds. Following the additional hydrolysis reaction with the phytases, the protein hydrolysate was centrifuged at 6000 G to separate the insoluble and soluble fractions using a filtration unit, thereby obtaining a purified protein hydrolysate. This purified protein hydrolysate was then transferred to the mixing tank 113.

The same process may be performed in the opposite direction: starting with phytase treatment followed by protease treatment.

In the mixing tank 113, 150 ml of the purified protein hydrolysate was mixed with nutritional additives, comprising 5 g of saccharides, 5 g of amino acids, 1 g of minerals, 0.5 mg of vitamins. In one aspect of the invention, after the phytase treatment, the purified protein hydrolysate contained a significant amount of phosphate groups. Therefore, the phosphate anions ($PO_4^{3-}$) were not included as part of the nutritional additives, as phosphate was already present in the purified protein hydrolysate. The combination of protein hydrolysate and nutritional additives formed a culture medium, which was then diluted with purified water to the volume of 1 l, sterilized using a sterile barrier 116 and filtered using a filtration unit 115

After the culture medium was sterilized, it was transferred into a storage tank 102 filtered, and sterilized again. The culture medium was then transferred into a cultivation device 101, where it was used for the cultivation of CHO-K1 cell lines derived from *Cricetulus griseus* (37° C., pH 7, 125 rpm, 120 hours). After the cultivation process, a portion of the grown cells, as part of the cell biomass, was transferred and processed for comestible products.

Example 19: 2$^{nd}$ Aspect (Precipitation)

70 kg of soybean meal were added to 1000 l of water in the hydrolysis tank 110 with constant stirring, this mixture was heated to 90° C. for 30 minutes to improve dissolution and to ensure the deactivation of the protease inhibitors. After this treatment and equilibration to 60° C., 400 ml of ALCALASE® serine endopeptidase enzyme 2.4 FG from Novonesis (for 120 minutes at 60° C.), before the end of the 2 hour treatment the temperature was changed to 55° C., exactly after 2 hours 1000 ml of FLAVOURZYME® proteolytic enzyme blend from Novonesis was added (for 21 hours at 55° C.) to hydrolyze the soy proteins into peptide chains and/or single amino acids, creating a protein hydrolysate. Next, 10 kg of calcium acetate was used to remove the phytic acids or their related compounds by precipitation. Following the additional precipitation process, the protein hydrolysate was centrifuged at 6000 G to separate the insoluble and soluble fractions using a filtration unit, thereby obtaining a purified protein hydrolysate. This purified protein hydrolysate was then transferred to the mixing tank.

In the mixing tank 113, 100 ml of the purified protein hydrolysate was mixed with nutritional additives, comprising 2 g of saccharides, 3 g of amino acids, 1 g of minerals, 5 mg of vitamins. The combination of protein hydrolysate and nutritional additives previously mentioned in the paragraph formed a culture medium, which was then filled up to 1 l, sterilized using a sterile barrier 116 and filtered filtration unit 115

After the culture medium was sterilized, it was transferred into a storage tank 102, filtered, and sterilized again. The culture medium was then transferred into a culture device 101, where it was used for the cultivation of CHO-K1 cell lines derived from *Cricetulus griseus* (37° C., pH 7, 300 rpm, 144 hours). After the cultivation process, a portion of the grown cells, as part of the cell biomass, was transferred and processed for comestible products.

Example 20: 3$^{rd}$ Aspect (Combination)

30 kg of *faba* bean concentrate were added to 1000 l of water in the hydrolysis tank 110 with constant stirring, this mixture was heated to 90° C. for 30 minutes to improve dissolution and to ensure the deactivation of the protease inhibitors. After this treatment and equilibration to 60° C., 300 ml of ALCALASE® serine endopeptidase enzyme 2.4 FG from Novonesis (for 120 minutes at 60° C.), before the end of the 2 hour treatment the temperature was changed to 55° C., exactly after 2 hours 900 ml of FLAVOURZYME® proteolytic enzyme blend from Novonesis was added (for 21 hours at 55° C.) to hydrolyze the soy proteins into peptide chains and/or single amino acids, creating a protein hydrolysate. Next, amount equivalent to 40 g of protein (determined by Bradford, BCA or any other protein determination assay), of Maxamyl P, Quantum Blue, OptiPhos Plus 10 000 G or other enzymes having phytase activity from different suppliers, either alone or in combination in ratio, were added to the protein hydrolysate containing peptides and/or amino acids (for 60 minutes at 35° C.) to remove the phytic acids or their related compounds. Amount of 5 kg of calcium acetate was then used to remove the phosphate ions by precipitation. Following the additional hydrolysis reaction with the phytases and precipitation process, the protein hydrolysate was centrifuged at 6000 G to separate the insoluble and soluble fractions using a filtration unit, thereby obtaining a purified protein hydrolysate. This purified protein hydrolysate was then transferred to the mixing tank 113.

The same process may be performed in the opposite direction: starting with phytase treatment along with precipitation treatment followed by protease treatment.

In the mixing tank, 200 ml of the purified protein hydrolysate was mixed with nutritional additives, comprising 10 g of saccharides, 10 g of amino acids, 3 g of minerals, 20 mg of vitamins. The combination of protein hydrolysate and nutritional additives formed a culture medium, which was then filled up to 11, sterilized using a sterile barrier 116 and filtered using a filtration unit 115.

After sterilization of the culture medium, it was transferred into a storage tank 102, filtered, and sterilized again. The culture medium was then transferred into a culture device 101, where it was used for the cultivation of CHO-K1 cell lines derived from *Cricetulus griseus* (37° C., pH 7, 125 rpm, 96 hours). After the cultivation process, a portion of the grown cells, as part of the cell biomass, was transferred and processed for comestible products.

Example 21: Culture Medium Composition

According to the previous examples (18, 19 and 20), the culture medium derived from the hydrolysed soy and free from non-beneficial residues has a composition according to Table 19.

TABLE 19

| Composition of the culture medium created by the protease and the phytase treatment. | |
| --- | --- |
| Composition of the culture medium | Concentration range (mg/l) |
| L-Alanine | 50-300 |
| L-Arginine | 200-400 |
| L-Asparagine | 150-400 |
| L-Aspartic Acid | 150-400 |
| L-Cysteine | 200-400 |
| L-Glutamic Acid | 100-350 |
| Glycine | 50-200 |
| L-Histidine | 100-350 |
| L-Isoleucine | 150-300 |
| L-Leucine | 250-500 |
| L-Lysine | 150-300 |
| L-Methionine | 20-150 |
| L-Proline | 20-150 |
| L-Threonine | 50-250 |
| L-Tryptophan | 20-80 |
| L-Tyrosine | 100-300 |
| L-Valine | 150-300 |
| L-Phenylalanine | 150-350 |
| L-Serine | 100-300 |
| Vitamin B12 | 0.1-1 |
| Biotin | 0.01-0.1 |
| D-Calcium pantothenate | 0.1-5 |
| Nicotinamide | 1-20 |
| Pyridoxine | 1-10 |
| Riboflavin | 0.1-1 |
| Thiamine | 0.5-5 |
| Folic Acid | 0.5-5 |
| Zinc(II) Sulphate | 0.1-10 |
| Copper(II) Sulphate | 0.1-1 |
| Magnesium Chloride | 100-500 |
| Potassium Chloride | 100-1000 |
| Sodium Selenite | 0.01-1 |
| Sodium Bicarbonate | 600-2000 |
| Sodium Chloride | 1000-10000 |
| Iron(III) Citrate | 10-200 |

TABLE 19-continued

| Composition of the culture medium created by the protease and the phytase treatment. | |
| --- | --- |
| Composition of the culture medium | Concentration range (mg/l) |
| Soy protein (hydrolysate) | 1000-30000 |
| Sodium hydroxide | As needed to adjust pH |
| Hydrochloric acid | As needed to adjust pH |
| Methylcellulose | 100-10000 |
| Glucose | 1000-10000 |

Example 22: Production of Transferrin by Modified CHO Cells

CHO cells were genetically engineered to express and produce transferrin under conditions optimal for the production of transferrin in the cultivation device 101.

Modified CHO cells were cultivated in 37° C. for 120 hours and after the cultivation the cells were centrifuged from the culture medium at 220 RCF.

The transferrin protein was then extracted from the cell-free medium and subsequently purified through established column chromatography.

The quality and purity of the extracted transferrin were assessed using High-Performance Liquid Chromatography (HPLC), Western blot analysis, or other suitable analytical methods.

ABBREVIATIONS

Used Abbreviations

Bcl-2 B-cell lymphoma 2 (Bcl-2)
Inhibitor of apoptosis (IAP)
Fetal Bovine Serum (FBS)
Phosphate-Buffered Saline (PBS)
embryonic stem cells (ESCs)
induced pluripotent stem cells (iPSCs)
Madin-Darby bovine kidney cells (MDBKs)
Madin-Darby canine kidney (MDCK)
Antisense oligonucleotides (AONs)
Fibroblast growth factor (FGF)
Transforming growth factor (TGF)
lipid nanoparticles (LNPs)
Genetic modifications (GM)
transcription activator-like effector nucleases (TALEN)
nucleic acid (NA)
deoxyribonucleic acid (DNA)
ribonucleic acid (RNA)
bovine telomerase reverse transcriptase (bTERT)
untranslated region (UTR)
adeno-associated virus integration site 1 (AAVS1)
C-C motif chemokine receptor 5 (CCR5)
glyceraldehyde-3-phosphate dehydrogenase (GAPDH)
Engorgement factor aplha (EFα)
myosine heavy chain (MYH9)
Phosphodiesterase 4D (PDE4D)
Cyklin-dependent kinase 4 (CDK4)
Transferrin receptor (TFRC)
Transforming growth factor receptor beta (TGFBR)
Insulin (INS)
Myoblast determination protein (MyoD)
Pair box protein 7 (Pax7)
Sterol regulatory element binding protein (SREBP)

Peroxisome proliferator-activated receptor gamma (PPARγ)

Protein kinase B (PKB)

Myristoylation signal-attached Akt (myr-Akt)

Elongation factor 1 α (EF1a)

Phosphoglycerate kinase 1 (PGK1)

Growth hormone polyadenylation signal (bGH-PolyA)

Endogenous retroviruses (ERVs)

Transmissible spongiform encephalopathies (TSE)

Cluster of differentiation 230 (CD230)

Solute carrier family 40 member 1 (SLC40A1)

Clustered regularly interspaced short palindromic repeats (CRISPR)

Caspase 9 (Cas9)

sodium leak channel (NALCN)

Focal adhesion kinase (FAK)

Cluster of differentiation 2 (CD2)

Myogenin (MyoG)

Green fluorescent protein (GFP)

mFruits family of monomeric red fluorescent proteins (mRFPs)

Yellow fluorescent protein (YFP)

puromycin N-acetyltransferase (PAC)

beta lactamase (BLA)

fluorescence activated cell sorting (FACS)

dimethylsulfoxide (DMSO)

Dulbecco's Modified Eagle Medium (DMEM)

polyethylen glycol (PEG)

methylcellulose (MC)

Relative Centrifugal Force (RCF)

poly-lactic acid (PLA)

polycaprolactone (PCL)

poly(lactic-co-glycolic acid) (PLGA)

polycaprolactone-co-lactic acid (PCLA)

polyhydroxybutyrate (PHB)

methyl cellulose (MC)

hydroxypropyl methylcellulose (HPMC)

carboxymethyl cellulose (CMC)

ethyl cellulose (EC)

polyethylene terephthalate (PET)

polycaprolactone (PCL)

polytrimethylene terephthalate (PTT)

polybutylene terephthalate (PBT)

polyhydroxybutyrate (PHB)

polyethylene naphthalate (PEN)

poly(ethylene adipate) (PEA)

poly(valerolactone) (PVL)

poly(glycolic acid) (PGA)

polyhydroxyalkanoate (PHA)

polybutylene adipate terephthalate (PBAT)

polybutylene succinate (PBS)

polyhydroxybutyrate (PHB)

polyethylene glycol (PEG)

polyvinylpyrrolidone (PVP)

Insuline like growth factor 1 (IGF-1)

Epidermal growth factor (EGF)

Bone morphogenic protein (BMP)

Interleukin 6 (IL-6)

amino acid (AA)

tangential-flow filtration (TFF)

coding sequence (CDS)

INDUSTRIAL APPLICABILITY

The cell cultivation processes according to the invention may be suitable, for example, for the production of food products for human consumption or pet food products. The food products provided by said processes and a cell cultivation system are also provided.

FEATURES LISTING

101—The cultivation device

101a—The first cultivation device

101b—The second cultivation device

102—The storage tank

103—The gas sparging system

104—The harvesting device

105—The product processing device

106—The waste medium

107—The food product

108—The water source

109—The water purification unit

110—The hydrolysis tank

111—First pump

112—First filtration unit

113—The mixing tank

114—The second pump

115—Second filtration unit

116—The sterile barrier

117—Third pump

118—Third filtration unit

119—The heat exchange system

120—The collateral cultivation device

121—Fourth pump

122—Fifth pump

123—The gas recycling system

124—The medium recycling system

125—The control unit

126—The loading tank

126a—The loading tank configured for the addition of source of protein

126b—The loading tank configured for the addition of proteolytic enzymes

126c—The loading tank configured for the addition of enzymes having phytase activity and/or precipitating agents 127—The culture medium tank 128—Seeding tank 129—Sensors and analytical instruments 130—The isolated metazoan cells 131—Primary cell bank 132—Production cell bank 133—Source of cells 133a—The first source of cells 133b—The second source of cells 134—The production components 134a—The first source of production components 134b—The second source of production components 201—The process of obtaining non-human metazoan cells 202—The process of inoculation in the culture vessel within the cultivation device 203—The process of cultivating the non-human metazoan cells in the culture vessel within the cultivation device 204—The process of harvesting the non-human metazoan cells from the culture vessel within the cultivation device 205—The process of providing primary component 206—The process of providing secondary component 207—The process of providing tertiary component 208—Processing the pet food composition 209—Processed pet food composition 301—The primary component 302—The secondary component
303—The tertiary component
304—The mixer unit
305—The extruder
306—The die
307—The cutter
308—The drying unit
309—The cooler
310—The finishing station
311—The packaging station
312—The conveyor
313—The cold-press
314—The filling station
315—The sterilizing unit
319—The feeder
401—The proteolytic enzymes
402—The process of formation of protein hydrolysate
403—The protein hydrolysate
404—The process of addition of enzymes having phytase activity and/or precipitating agents
405—The modified protein hydrolysate
406—The process of removal of solid residues
407—The purified protein hydrolysate
501—The process of preparing a non-human metazoan cell line
502—The process of cultivating the non-human metazoan cells in a cultivation system to obtain cell biomass
503—Processing cell biomass to obtain a primary component
504—The process of combining primary component with at least one component from the secondary component and the tertiary
component
505—Processing the combined components
506—The process of packaging and sterilizing the pet food product
601—The process of obtaining cells from metazoan tissue by biopsy and/or necropsy 602—The process of isolating the non-human metazoan cells
603—The process of modification of the properties of the non-human metazoan cell line
604—The process of inoculating the non-human metazoan cell population to the cultivation device
605—The process of proliferating the non-human metazoan cell population in the cultivation device
606—The process of differentiating the non-human metazoan cell population in the cultivation device
607—The process of harvesting the non-human metazoan cell population to obtain cell biomass
701—The process of addition of a source of protein into the hydrolysis tank comprising the water source
702—The process of addition of proteolytic enzymes of the source of protein into the hydrolysis tank
703—The process of generation of the protein hydrolysate
704—The process of addition of enzymes having phytase activity or precipitating agents or combination thereof into the hydrolysis
tank to cleave and/or precipitate inositol hexaphosphate or its derivatives;
705—The process of generation of the modified protein hydrolysate
706—The process of addition of nutritional additives
707—The process of generating the culture medium
708—The process used for inoculation of non-human metazoan cells
709—The process of cultivation of non-human metazoan cells
710—The process of harvesting of the cell biomass
711—The process of using the harvested cell biomass for the production of compounds having therapeutic effects and/or may be used for food production

SEQUENCE LISTING

```
SEQ ID NO: 1
>bTERT protein sequence (1125 aa)
MPRAPRCRAVRALLRASYRQVLPLAAFVRRLRPQGHRLVRRGDPAAFRALVAQCLVCVPWDAQPPPAAPSFRQVSCLKELVARVVQ
RLCERGARNVLAFGFTLLAGARGGPPVAFTTSVRSYLPNTVTDTLRGSGAWGLLLHRVGDDVLTHLLSRCALYLLVPPTCAYQVCGPP
LYDLRAAAAAARRPTRQVGGTRAGFGLPRPASSNGGHGEAEGLLEARAQGARRRRSSARGRLPPAKRPRRGLEPGRDLEGQVARS
PPRVVTPTRDAAEAKSRKGDVPGPCRLFPGGERGVGSASWRLSPSEGEPGAGACAETKRFLYCSGGGEQLRRSFLLCSLPPSLAGA
RTLVETIFLDSKPGPPGAPRRPRRLPARYWQMRPLFRKLLGNHARSPYGALLRAHCPLPASAPRAGPDHQKCPGVGGCPSERPAAAP
EGEANSGRLVQLLRQHSSPWQVYGLLRACLRRLVPAGLWGSRHNERRFLRNVKKLLSLGKHGRLSQQELTWKMKVQDCAWLRASP
GARCVPAAEHRQREAVLGRFLHWLMGAYVVELLRSFFYVTETTFQKNRLFFFRKRIWSQLQRLGVRQHLDRVRLRELSEAEVRQHQE
ARPALLTSRLRFVPKPGGLRPIVNVGCVEGAPAPPRDKKVQHLSSRVKTLFAVLNYERARRPGLLGASVLGMDDIHRAWRAFVLPLRA
RGPAPPLYFVKVDWVGAYDALPQDKLAEVIANVLQPQENTYCVRHCAMVRTARGRMRKSFKRHVSTFSDFQPYLRQLVEHLQAMGSL
RDAVVIEQSCSLNEPGSSLFNLFLHLVRSHVIRIGGRSYIQCQGIPQGSILSTLLCSFCYGDMENKLFPGVQQDGVLLRLVDDFLLVTPHL
TRARDFLRTLVRGVPEYGCQVNLRKTVVNFPVEPGALGGAAPLQLPAHCLFPWCGLLLDTRTLEVHGDHSSYARTSIRASLTFTQGFK
PGRNMRRKLLAVLQLKCHGLFLDLQVNSLQTVFTNVYKIFLLQAYRFHACVLQLPFSQPVRSSPAFFLQVIADTASRGYALLKARNAGA
SLGARGAAGLFPSEAAQWLCLHAFLLKLARHRVTYSRLLGALRTARARLHRQLPGPTRAALEAAADPALTADFKTILD SEQ ID NO: 2
>bTERT CDS (3375 bp)
ATGCCGCGCGCGCCCAGGTGCCGGGCCGTGCGCGCCCTTCTGCGGGCCAGCTACCGGCAGGTGCTGCCCCTGGCCGCCTTC
GTACGGCGCCTGCGGCCCCAGGGCCACCGGCTTGTGCGGCGCGGGGACCCGGCGGCCTTCCGCGGCGCTGGTGGCTCAGTGC
TTGGTGTGCGTGCCCTGGGACGCGCAGCCGCCCCCTGCCGCCCCGTCCTTCCGCCAGGTGTCCTGCCTGAAGGAGCTGGTGG
CCAGAGTCGTGCAGAGGCTCTGCGAGCGCGGCGCGAGGAACGTGCTGGCCTTCGGCTTCACGCTGCTGGCCGGGGCCCGCG
GCGGGCCGCCCGTGGCCTTCACGACCAGCGTACGCAGCTACCTGCCCAACACGGTAACCGACACGCTGCGCGGCAGCGGCGC
CTGGGGGCTGCTGCTGCACCGCGTGGGCGACGACGTGCTCACCCACCTGCTGTCGCGCTGCGCGCTCTACCTGCTGGTGCCC
CCGACCTGCGCCTACCAGGTGTGTGGGCCGCCGCTCTATGACCTCCGCGCCGCCGCCGCCGCCGCTCGTCGGCCCACGCGGC
AAGTGGGCGGGACCCGGGGGGGCTTCGGACTCCCGCGCCCGGCCTCGTCGAACGGCGGCCACGGGGAGGCCGAAGGACTCC
TGGAGGCGCGGGCCCAGGGCGCGAGGCGGCGTCGCAGTAGCGCGCGGGGACGACTGCCTCCAGCCAAGAGGCCCAGGCGC
GGCCTGGAGCCCGGGGGGGGATCTCGAAGGGCAGGTGGCCCGCAGCCCGCCCCGCGTGGTGACACCTACCCGAGACGCTGCG
GAAGCCAAGTCTCGGAAGGGCGACGTGCCCGGGCCCTGCCGCCTCTTCCCGGGGGGCGAGCGGGGTGTCGGCTCCGCGTCCT
GGCGGCTGTCACCCTCGGAGGGCGAGCCGGGTGCCGGAGCTTGCGCTGAGACCAAGAGGTTCCTTTACTGCTCCGGCGGTGG
CGAACAGCTGCGCCGCTCCTTCCTGCTCTGCTCCCTGCCTCCCAGCCTGGCCGGGGCGCGGACACTCGTGGAAACCATCTTTC
TGGACTCGAAGCCCGGGCCGCCAGGGGCTCCCCGCCGGCCGCGCCGCCTGCCCGCGCGCTACTGGCAGATGCGGCCCCTGT
TCCGGAAACTGCTTGGGAACCACGCGCGGAGCCCCTATGGCGCGCTGCTCAGGGCGCACTGCCCGCTGCCGGCCTCTGCGCC
```

```
CCGGGGGGGGCCAGACCATCAGAAGTGCCCTGGTGTTGGGGGCTGCCCCTCTGAGAGGCCGGCCGCTGCCCCCGAGGGCGA
GGCGAACTCAGGGCGCCTGGTCCAGCTGCTCCGCCAGCACAGCAGCCCCTGGCAGGTGTACGGGCTCCTGCGGGCCTGTCTT
CGCCGCCTGGTGCCCGCCGGCCTCTGGGGCTCCCGGCACAACGAGCGGCGCTTCCTGCGGAACGTGAAGAAGCTCCTCTCCC
TGGGGAAGCACGGCAGGCTCTCGCAGCAGGAGCTCACGTGGAAGATGAAGGTGCAGGACTGCGCCTGGCTGCGCGCGAGCCC
AGGGGCTCGCTGCGTGCCCGCCGCGGAGCACCGCCAGCGCCAGCGCCGGGCGTCCTGGGTCGCTTCCTGCACTGGCTGATGGGCGC
CTACGTGGTGGAGCTGCTCAGGAGCTTCTTCTACGTCACAGAGACCACGTTCCAGAAGAACCGGCTCTTCTTCTTCCGGAAGCG
CATCTGGAGCCAGCTGCAGCGCCTGGGCGTCAGACAACACTTAGACCGTGTGCGGCTTCGAGAACTGTCAGAAGCAGAGGTCA
GGCAGCACCAGGAGGCCAGGCCGGCTCTGCTGACATCCAGGCTCCGTTTCGTCCCCAAGCCCGGGGGGCTGCGGCCCATCGT
GAACGTGGGCGTGTTGAGGGCGCCCCGGCACCGCCCAGAGACAAGAAGGTGCAGCATCTCAGCTCACGGGTCAAGACGCTGT
TCGCGGTGCTGAACTACGAGCGAGCTCGGCGGCCTGGCCTCCTGGGGGCCTCGGTGCTGGGCATGGACGACATCCACAGGGC
CTGGCGGGCCTTCGTGCTGCCCCTGAGGGCCCGGGGCCCAGCCCCCCCGCTCTACTTCGTCAAGGTGGACGTGGTGGGGGCC
TACGATGCCCTCCCCCAGGATAAGCTGGCAGAGGTGATCGCTAACGTGCTGCAGCCGCAGGAGAATACGTACTGCGTGCGCCA
CTGCGCCATGGTCCGGACTGCGCGCGGGCGCATGCGCAAGTCCTTCAAGAGACACGTGTCCACCTTCTCGGACTTCCAGCCGT
ACCTGAGGCAGCTCGTGGAGCATCTGCAGGCGATGGGCTCCCTGAGGGACGCCGTGGTCATCGAGCAGAGCTGCTCCCTGAAC
GAGCCTGGCAGCAGCCTCTTCAACCTCTTCCTGCACCTGGTCCGCAGCCACGTCATCAGGATCGGGGGCAGGTCCTACATCCA
GTGTCAGGGGATCCCCCAGGGCTCCATCCTGTCCACCCTGCTCTGCAGCTTCTGCTATGGGGACATGGAGAACAAGCTCTTCCC
TGGAGTCCAGCAGGACGGGGTGCTTCTGCGCCTGGTGGACGACTTCCTGCTGGTCACCCCACACCTGACGCGGGCCAGAGACT
TCCTCAGGACGCTGGTGCGCGGTGTGCCTGAGTATGGCTGCCAGGTGAACCTGCGGAAGACGGTGGTGAACTTCCCCGTGGAG
CCCGGGGCCCTGGGCGGCGCGGCGCCCCTGCAGCTGCCGGCCCACTGCCTGTTCCCCTGGTGCGGCCTGCTGCTGGATACCC
GCACCCTGGAGGTGCATGGCGACCACTCCAGTTATGCCCGGACGTCCATCAGAGCGAGTCTCACCTTCACCCAGGGCTTCAAG
CCCGGGAGGAACATGCGTCGCAAGCTGTTGGCGGTCTTGCAGCTCAAGTGCCATGGGCTCTTCCTGGACCTGCAGGTGAACAG
TCTGCAGACGGTCTTCACAAACGTTTACAAGATATTCCTGCTGCAGGCCTACAGGTTCCACGCCTGCGTGCTGCAGCTGCCCTTC
AGCCAGCCGGTCAGGAGCAGCCCCGCGTTCTTTCTCCAGGTCATCGCCGACACCGCATCCCGCGGCTACGCCCTCCTGAAAGC
CAGGAACGCAGGGGCGTCACTGGGGGCCAGGGGCGCCGCCGGCCTGTTCCCGTCTGAAGCTGCGCAGTGGCTGTGTCTCCAC
GCCTTCCTGCTCAAGCTGGCTCGCCACCGTGTGCACCTACAGCCGCCTGCTGGGGGCCCTCCGGACAGCCCGAGCACGGCTGCA
CCGGCAGCTCCCGGGGCCCACACGGGCCGCCCTGGAGGGGGGGGCCGACCCCGCCCTGACCGCAGACTTCAAGACCATCTTG
GAC
```

SEQ ID NO: 3
>rbTERT protein sequence (1105 aa)
```
MPRAPRCRAVRALLRASYRQVLPLAAFVRRLRPQGHRLVRRGDPAAFRALVAQCLVCVPWDAQPPPAAPSFRQVSCLKELVARWVQ
RLCERGARNVLAFGFTLLAGARGGPPVAFTTSVRSYLPNTVTDTLRGSGAWGLLLHRVGDDVLTHLLSRCALYLLVPPTCAYQVCGPP
LYDLRAAAAAARRPTRQVGGTRAGFGLPRPASSNGGHGEAEGLLEARAQGARRRRSSARGRLPPAKRPRRGLEPGRDLEGQVARS
PPRVVTPTRDAAEAKSRKGDVPGPCRLFPGGERGVGSASWRLSPSGEGEPGAGCAETKRFLYCSGGGEQLRRSFLLCSLPPSLAGA
RTLVETIFLDSKPGPPGAPRRPRRLPARYWQMRPLFRKLLGNHARSPYGALLRAHCPLPASAPRAAPEGEANSGRLVQLLRQHSSPW
QVYGLLRACLRRLVPAGLWGSRHNERRFLRNVKKLLSLGKHGRLSQQELTWKMKVQDCAWLRASPGARCVPAAEHRQREAVLGRFL
HWLMGAYVVELLRSFFYVTETTFQKNRLFFFRKRIWSQLQRLGVRQHLDRVRLRELSEAEVRQHQEARPALLTSRLRFVPKPGGLRPI
VNVGCVEGAPAPPRDKKVQHLSSRVKTLFAVLNYERARRPGLLGASVLGMDDIHRAWRAFVLPLRARGPAPPLYFVKVDVVGAYDAL
PQDKLAEVIANVLQPQENTYCVRHCAMVRTARGRMRKSFKRHVSTFSDFQPYLRQLVEHLQAMGSLRDAVVIEQSCSLNEPGSSLFN
LFLHLVRSHVIRIGGRSYIQCQGIPQGSILSTLLCSFCYGDMENKLFPGVQQDGVLLRLVDDFLLVTPHLTRARDFLRTLVRGVPEYGCQ
VNLRKTVVNFPVEPGALGGAAPLQLPAHCLFPWCGLLLDTRTLEVHGDHSSYARTSIRASLTFTQGFKPGRNMRRKLLAVLQLKCHGL
FLDLQVNSLQTVFTNVYKIFLLQAYRFHACVLQLPFSQPVRSSPAFFLQVIADTASRGYALLKARNAGASLGARGAAGLFPSEAAQWLC
LHAFLLKLARHRVTYSRLLGALRTARARLHRQLPGPTRAALEAAADPALTADFKTILD
```

SEQ ID NO: 4
>rbTERT CDS (3315 bp)
```
ATGCCGCGCGCGCCCAGGTGCCGGGCCGTGCGCGCCCTTCTGCGGGCCAGCTACCGGCAGGTGCTGCCCCTGGCCGCCTTC
GTACGGCGCCTGCGGCCCCAGGGCCACCGGCTTGTGCGGCGCGGGGACCCGGCGGCCTTCCGCGCGCTGGTGGCTCAGTGC
TTGGTGTGCGTGCCCTGGGACGCGCAGCCGCCCCCTGCCGCCCCCGTCCTTCCGCCAGGTGTCCTGCCTGAAGGAGCTGGTGG
CCAGAGTCGTGCAGAGGCTCTGCGAGCGCGGCGCGAGGAACGTGCTGGCCTTCGGCTTCACGCTGCTGGCCGGGGCCCGCG
GCGGGCCGCCCGTGGCCTTCACGACCAGCGTACGCAGCTACCTGCCCAACACGGTAACCGACACGCTGCGCGGCAGCGGCGC
CTGGGGGCTGCTGCTGCACCGCGTGGGCGACGACGTGCTCACCCACCTGCTGTCGCGCTGCGCGCTCTACCTGCTGGTGCCC
CCGACCTGCGCCTACCAGGTGTGTGGGCCGCCGCTCTATGACCTCCGCGCCGCCGCCGCCGCCGCTCGTCGGCCCACGCGGC
AAGTGGGCGGGACCCGGGGGGGGCTTCGGACTCCCGCGCCCGGCCTCGTCGAACGGCGGCCACGGGGAGGCCGAAGGACTCC
TGGAGGCGCGGGCCCAGGGCGCGAGGCGGCGTCGCAGTAGCGCGCGGGGACGACTGCCTCCAGCCAAGAGGCCCAGGCGC
GGCCTGGAGCCCGGGCGGGATCTCGAAGGGCAGGTGGCCCGCAGCCCGCCCCGCGTGGTGACACCTACCCGAGACGCTGCG
GAAGCCAAGTCTCGGAAGGGCGACGTGCCCGGGCCCTGCCGCCTCTTCCCGGGGGGCGAGCGGGGTGTCGGCTCCGCGTCCT
GGCGGCTGTCACCCTCGGAGGGCGAGCCGGGTGCCGGAGCTTGCGCTGAGACCAAGAGGTTCCTTTACTGCTCCGGCGGTGG
CGAACAGCTGCGCCGCTCCTTCCTGCTCTGCTCCCTGCCTCCCAGCCTGGCCGGGGCGCGGACACTCGTGGGAAACCATCTTTC
TGGACTCGAAGCCCGGGCCGCCAGGGGCTCCCGCCGGCCGCGCCGCTGCCCGCGCGCTACTGGCAGATGCGGCCCCTGT
TCCGGAAACTGCTTGGGAACCACGCGCGGAGCCCCTATGGCGCGCTGCTCAGGGCGCACTGCCCCGCTGCCGGCCTCTGCGCC
CCGGGCTGCCCCCGAGGGCGAGGCGAACTCAGGGCGCCTGGTCCAGCTGCTCCGCCAGCACAGCAGCCCCTGGCAGGTGTAC
GGGCTCCTGCGGGCCTGTCTTCGCCGCCTGGTGCCCGCCGGCCTCTGGGGCTCCCGGCACAACGAGCGGCGCTTCCTGCGGA
ACGTGAAGAAGCTCCTCTCCCTGGGGAAGCACGGCAGGCTCTCGCAGCAGGAGCTCACGTGGAAGATGAAGGTGCAGGACTGC
GCCTGGCTGCGCGCGAGCCCAGGGGCTCGCTGCGTGCCCGCCGCGGAGCACCGCCAGCGCGAGGCCGTCCTGGGTCGCTTC
CTGCACTGGCTGATGGGCGCCTACGTGGTGGAGCTGCTCAGGAGCTTCTTCTACGTCACAGAGACCACGTTCCAGAAGAACCG
GCTCTTCTTCTTCCGGAAGCGCATCTGGAGCCAGCTGCAGCGCCTGGGCGTCAGACAACACTTAGACCGTGTGCGGCTTCGAGA
ACTGTCAGAAGCAGAGGTCAGGCAGCACCAGGAGGCCAGGCCGGCTCTGCTGACATCCAGGCTCCGTTTCGTCCCCAAGCCCG
GCGGGCTGCGGCCCATCGTGAACGTGGGCGTGTTGAGGGCGCCCCGGCACCGCCCAGAGACAAGAAGGTGCAGCATCTCAG
CTCACGGGTCAAGACGCTGTTCGCGGTGCTGAACTACGAGCGAGCTCGGCGGCCTGGCCTCCTGGGGGCCTCGGTGCTGGGC
ATGGACGACATCCACAGGGCCTGGCGGGCCTTCGTGCTGCCCCTGAGGGCCCGGGGCCCAGCCCCCCCGCTCTACTTCGTCA
AGGTGGACGTGGTGGGGGCCTACGATGCCCTCCCCCAGGATAAGCTGGCAGAGGTGATCGCTAACGTGCTGCAGCCGCAGGA
GAATACGTACTGCGTGCGCCACTGCGCCATGGTCCGGACTGCGCGCGGGCGCATGCGCAAGTCCTTCAAGAGACACGTGTCCA
CCTTCTCGGACTTCCAGCCGTACCTGAGGCAGCTCGTGGAGCATCTGCAGGCGATGGGCTCCCTGAGGGACGCCGTGGTCATC
GAGCAGAGCTGCTCCCTGAACGAGCCTGGCAGCAGCCTCTTCAACCTCTTCCTGCACCTGGTCCGCAGCCACGTCATCAGGATC
GGGGGCAGGTCCTACATCCAGTGTCAGGGGATCCCCCAGGGCTCCATCCTGTCCACCCTGCTCTGCAGCTTCTGCTATGGGGA
CATGGAGAACAAGCTCTTCCCTGGAGTCCAGCAGGACGGGGTGCTTCTGCGCCTGGTGGACGACTTCCTGCTGGTCACCCCAC
ACCTGACGCGGGCCAGAGACTTCCTCAGGACGCTGGTGCGCGGTGTGCCTGAGTATGGCTGCCAGGTGAACCTGCGGAAGAC
GGTGGTGAACTTCCCCGTGGAGCCCGGGGCCCTGGGCGGCGCGGCGCCCCTGCAGCTGCCGGCCCACTGCCTGTTCCCCTGG
```

```
TGCGGCCTGCTGCTGGATACCCGCACCCTGGAGGTGCATGGCGACCACTCCAGTTATGCCCGGACGTCCATCAGAGCGAGTCT
CACCTTCACCCAGGGCTTCAAGCCCGGGAGGAACATGCGTCGCAAGCTGTTGGCGGTCTTGCAGCTCAAGTGCCATGGGCTCTT
CCTGGACCTGCAGGTGAACAGTCTGCAGACGGTCTTCACAAACGTTTACAAGATATTCCTGCTGCAGGCCTACAGGTTCCACGC
CTGCGTGCTGCAGCTGCCCTTCAGCCAGCCGGTCAGGAGCAGCCCCGCGTTCTTTCTCCAGGTCATCGCCGACACCGCATCCC
GCGGCTACGCCCTCCTGAAAGCCAGGAACGCAGGGGCGTCACTGGGGGCCAGGGGCGCCGCCGGCCTGTTCCCGTCTGAAGC
TGCGCAGTGGCTGTGTCTCCACGCCTTCCTGCTCAAGCTGGCTCGCCACCGTGTCACCTACAGCCGCCTGCTGGGGGCCCTCC
GGACAGCCCGAGCACGGCTGCACCGGCAGCTCCCGGGGCCCACACGGGCCGCCCTGGAGGCGGCGGCCGACCCCGCCCTGA
CCGCAGACTTCAAGACCATCTTGGAC

SEQ ID NO: 5
>bPGK1 promoter sequence (511 bp)
TTCATTTGCATCTATCCTGAATAGGGTTGCCGGGAATTCCATGGGATGTGGGGTGACGTTTTCCCCGAGGCTGCCATGGGTTTGC
GGGGCTCTGCAGCTGCCTCCGGTGCGGCCGCAGGAACCCGAGCCGTGTCCGCCCCTCGGCGCCAACTGGCTCCAGATCCCGC
CGCCGCTTAGTCCGGCGGCACCGCCTCCTGCCTCTAGTCACGAAAGTTCCCAGCCGCTCGCTGCGTGCTGGACGTGACTGGCG
GCAGCTGCACGTCCCACAATCGCGCTCGCTGACTGACAGCGCCTCGGTGCAATGGCAGCCAGCGGGCGCCTTCGGGCCGCGT
TCTAGAGCGGCCACTGGGCGCCGAGAGCCGGGCGCGGCGGCCGGAAAGGGGGGGGGGGGGAGGAGTGGCGACCCAGCCCG
TGAGGTGCTAGGCATTTTCCACGCGTTCGGACCCTGAGTCGGTCTCAGTCTCTGCCGCTGTCTCATCCCCTGGCCTCTCGCTGC
AGCTGAATTGCCAAG SEQ ID NO: 6
>bEF1a promoter sequence (1191 bp)
GGCGCCCAGCGCTCGTCAGTGGGCTGAGCGTACATCGCCCACGGTCCCCGAGACGTGGGGGGAGGGGACGGAGATTGAACTG
GTGCCTGGTGGAGGCGGCGCGGGGTAATCTGGGAAAGTGGTGTCGTGTGCTGGCTCCGCCCTTTTCCCCGAGGGTGGGGGGA
GAACCGTATATAAGTGCCGTAGTCTCCGTGAACGTTCTTTTTCGCAACGGGTTTGCCGCCGGGACACAGGTGAGTGCCGGGTGT
GGCTTCGGTGGGCCCAGCCTCCGCCGACGGCCGCGGCCTTCGCGTGCGTGTATCTCCCGCCGCGCCCGTGGGCATTTTCACC
ATGTTCTTCACCGGAATTTCGGGGTGTGAGAGGGTGGGGGGTGGGGAGAGTTCAGGGACCTTGCGCTTTTCTCACAGTCCCTTC
GCCTCGTGCTTGGGTTGAGGCTGGGCTGTGGCACCGTGGCCGCTGCGTGTGGATCCTGCCGCGCTTTGCCGCTCTGTTCCCC
CCACCCCGCCGCCACACACACACTATTGAACAACTCCACACAGCCGCGGGTTTTTCGGCCGGGGCGGTTCATCCGGGGCCGGC
CGGGGGCTGACAGGCTGGGCTTCTCGGCGCTCGTCGGGATTCGGGGTAGGGGGGGGCCGCGAGGCGCAGAGAGCGCGGGCC
TGCTTCCCCGGCGACATGCCATAGCGGCCTCGCTGGGCCGAGGCGGGGGGGGAGAGCCGTGGCAGCCCGGGCGAGCAGAGC
GCCGCCCGCCCGGCACCAGTTGCGTGCGCGGAAAGATGGCCGCTCCCCGGCCCCTCTGCACGGCTTCAAAATGGAGGACGC
GGCGGCCCGGGAGGGGAGCGGCCGGTGAGTCACCCGCACAAAGGGCCCGGGCCCGTCCCTGCCTGGCGCCGCTTCCTTGGG
ACACCCCCCCGCCCCCCGCGGCGGACCGGGTGCCGTCCTGGCCCCTCGATGCCTCGTGGTTCCAGAGCGACACATGGGGTGG
GGGAGGGGAATCTGGACGGTGGAGCTTATGGGTGGAGACTTGAGTTGGGCCAGCTTGGCGCTAGTTGTAATGCTCCTTGGAATT
TGCCCTTGGAGTTTGGATCGTAGCTTTTTCTTCAGCTTCCGGACAGTGGTTTAAAGTTTCCCACACCTCCACCCCTTTCCAATTAG
GTGTCGTGAAAACCACCGTTAAACCTAAGCCAAA SEQ ID NO: 7
>bovine transferrin receptor (bTFRC) CDS (2310 bp)
ATGATGGATCAAGCCAGATCAGCATTCTCTAACTTGTTTGGTGGAGAACCATTGTCATATACCAGGTTTAGTCTGGCTCGGCAAGT
AGATGGTGATAACAGTCATGTGGAGATGAAATTAGCTGCAGATGAAGAAGAAATGTTGACAGTAACATGAGGGGCAACCAAACC
AGTATCGCAAAACCGAAAAGGTTAAATGGATATGTCTGCTACGGGATCATTGCTGTAATCGTCTTTTTCTTGATTGGATTTATGATT
GGCTACTTGGGCTATTGTAGACGTGTGGAATCACAAGATTGTGGGAAAGAGGCAGGAACACAGCGTTCGTGCCCAGAGGAGACA
GAAACTTTCGAATCAGAAGAGCAACTCCCTGGAGTACCTCGCATATTCTGGGCAGACCTCAAATCAACGTTGTCAGGAAACTGG
ATGCCGTAGACTTTGCCAGGGCCATCAAGATGCTGAATGAAAATTCTTATGTCCCACGTGAAGCTGGATCTGAAAAAGATACCAG
TTTGGCTTTTTTCATTGAAAATCAATTACAGGACTGTAAACTCGGCAAAGTCTGGCATGATGAACATTTTATTAAGATTCAGGTCAA
AGGCAGTTCTCAAAACTCGGTGTCTATAGTGAGTACAAGCGGTAACGGCAGTCAGGCATACCCAGTGGAGAGTCCTGAGGGTTA
CGTGGCATATAGTAAGGCTGCGACCGTTACTGGCAAACTGGTCCATGCTAATTTTGGCACTAAACAAGACTTTGAGGATTTAAATA
TGCCTGTAAATGGATCTTTAGTGATTGTAAGAGCTGGAAAAATCAGTTTTGCTGAAAAGGTGGCAAATGCTGAAAGTTTAAATGCA
ATTGGTGTCTTGATATACATGGACTACAGTAAATATCCCATTGTTAATGCAAATCTTCCAGTTTTTGGACATGCTCATCTGGGAACA
GGTGACCCTTACACACCTGGATTCCCTTCTTTAATCACACTCAATTTCCACCATCTCAGTCATCAGGATTGCCCAACATACCTGT
CCAAACAATTACCAGAGCCGGTGCAGAAAAGCTATTTCAAAATATGGAAGGAGACTGTCCTCGTATTTGGGGAACAGACTCTTCA
TGTAAGCTGGTATCCTCACAGGATAAGAATGTGAAACTTAGCGTGAACAATGTGCTGAAGGAGATAAGAATTCTTAACGTCTTTGG
AGTTATTAAGGGCTTTGAAGAACCAGATCGCTATGTTATAGTAGGGGCCCAGAGGGATGCCTGGGGTCCTGGAGCTGCAAAGTC
CAGTGTAGGAACAAGTCTGCTATTGACACTTGCCCGGATACTTTCCGATATGGTCTTAAAAGGTCAGTTTAAAACCCAGCAGAAGC
ATTGTCTTTGCCAGCTGGAGTGGTGGAGACTTTGGAGCCGTTGGTGCCACTGAATGGCTAGAGGGATACCTTTCCTCATTGCATT
TAAAGGCTTTCACTTACATTAATCTGGATAAAGCTGTTGTTGGTACTACCAATTTCAAAGTTTCTGCCAGCCCACTGTTGTATTCAC
TTATTGAGAAAATCATGAAAGATGTGAAGCATCCACTTAATGGGCTGTCTCTGTATCGGGACAGCAACTGGATCAGCAAAGTGCA
AAAACTTTCTTTGGATAATGCTGCTTTCCCTTTCCTTGCATATTCTGGAATCCCAGCGGTCTCTTTCTGTTTTTGTGAGGACACAGA
TTACCCTTATTTAGGCACTCCCATGGACACCTATGAGACACTGAACAGAGAAGTTCCTCAGTTGAACAGAGTGGCACGTGCAGCA
GCAGAAGTGGCCGGTCAGCTTGTGATTAAACTTACCCATGGGGTTGAGCTGAACCTGAACTACGAGATGTATAATGACGAAATAC
TTCGGTTTGTGAAGGAAATGAACCTATTCAGAGCAGACATAAGGGATATGGGTCTGAATATGCAGTGGCTGTATTCTGCTCGTGG
AGACTTCTTCCGTGCTACGTCTAGACTAACTACGGATTATAAGAATGCTGAGAAAACAGACAGATCTGTGATGAGGGAAATCAATG
ACCGTATCATGAAAGTGGAATATCACCTCCTCTCACCCTATGTATCTCCAAGAGAGTTTCCTTTCCGACACATCTTCTGGGGCTCT
GGCTCTCACACTCTGTCAGCTTTACTGGAGCACTTGAAGCTGCGTAAGAAAAATAACGGTGCTTTTAATCAAACACTGTTGGAAAA
CCAGTTGGCTCTGGCAACTTGGACTATTCAGGGAGCCGCAAATGCCCTCTCTGGGGACATTTGGGACATTGACAACGAATTTTAA SEQ ID NO: 8
>bInsulin CDS (318 bp)
ATGGCCCTGTGGACACGCCTGCGGCCCCTGCTGGCCCTGCTGGCGCTCTGGCCCCCCCCCCCCGGCCCGCGCCTTCGTCAACC
AGCATCTGTGTGGCTCCCACCTGGTGGAGGCGCTGTACCTGGTGTGCGGAGAGCGCGGCTTCTTCTACACGCCCAAGGCCCGC
CGGGAGGTGGAGGGCCCGCAGGTGGGGGCGCTGGAGCTGGCCGGAGGCCCGGGGGGGGGGGGGCCTGGAGGGGCCCCCGC
AGAAGCGTGGCATCGTGGAGCAGTGCTGTGCCAGCGTCTGCTCGCTCTACCAGCTGGAGAACTACTGTAACTAG SEQ ID NO: 9
>bInsulin protein sequence (105 aa)
MALWTRLRPLLALLALWPPPPARAFVNQHLCGSHLVEALYLVCGERGFFYTPKARREVEGPQVGALELAGGPGAGGLEGPPQKRGIV
EQCCASVCSLYQLENYCN
```

SEQ ID NO: 10
>optimized bFGF2 CDS (465 bp)
ATGGCTGCTGGTTCCATCACTACACTGCCGGCCCTCCCAGAAGACGGCGGTAGCGGTGCTTTTCCTCCTGGACATTTTAAAGATC
CAAAACGGTTGTATTGCAAAAACGGGGGCTTTTTTCTCAGAATCCATCCCGATGGCCGAGTTGACGGGGTTCGAGAGAAGTCCG
ATCCGCACATTAAGCTGCAACTGCAAGCTGAGGAGCGAGGAGTTGTCAGTATAAAGGGCGTCTGTGCTAATAGATACCTTGCCAT
GAAGGAAGATGGTAGGTTGTTGGCGAGCAAATGCGTTACGGACGAATGCTTTTTCTTCGAAAGACTCGAATCCAACAATTACAAC
ACATATCGGTCCAGGAAATATAGTTCATGGTACGTGGCCTTGAAACGGACGGGGCAGTATAAACTCGGTCCGAAAACTGGTCCG
GGTCAGAAGGCAATCCTGTTTCTGCCAATGTCCGCTAAGAGC SEQ ID NO: 11
>bFGF2 protein sequence (155 aa)
MAAGSITTLPALPEDGGSGAFPPGHFKDPKRLYCKNGGFFLRIHPDGRVDGVREKSDPHIKLQLQAEERGVVSIKGVCANRYLAMKED
GRLLASKCVTDECFFFERLESNNYNTYRSRKYSSWYVALKRTGQYKLGPKTGPGQKAILFLPMSAKS SEQ ID NO: 12
>bTFRC protein sequence (769 aa)
MMDQARSAFSNLFGGEPLSYTRFSLARQVDGDNSHVEMKLAADEEENVDSNMRGNQTSIAKPKRLNGYVCYGIIAVIVFFLIGFMIGYL
GYCRRVESQDCGKEAGTQPSCPEETETFESEEQLPGVPRIFWADLKSTLSGKLDAVDFARAIKMLNENSYVPREAGSEKDTSLAFFIE
NQLQDCKLGKVWHDEHFIKIQVKGSSQNSVSIVSTSGNGSQAYPVESPEGYVAYSKAATVTGKLVHANFGTKQDFEDLNMPVNGSLVI
VRAGKISFAEKVANAESLNAIGVLIYMDYSKYPIVNANLPVFGHAHLGTGDPYTPGFPSFNHTQFPPSQSSGLPNIPVQTITRAGAEKLF
QNMEGDCPRIWGTDSSCKLVSSQDKNVKLSVNNVLKEIRILNVFGVIKGFEEPDRYVIVGAQRDAWGPGAAKSSVGTSLLLTLARILSD
MVLKGQFKPSRSIVFASWSGGDFGAVGATEWLEGYLSSLHLKAFTYINLDKAWGTTNFKVSASPLLYSLIEKIMKDVKHPLNGLSLYRD
SNWISKVQKLSLDNAAFPFLAYSGIPAVSFCFCEDTDYPYLGTPMDTYETLNREVPQLNRVARAAAEVAGQLVIKLTHGVELNLNYEMY
NDEILRFVKEMNLFRADIRDMGLNMQWLYSARGDFFRATSRLTTDYKNAEKTDRSVMREINDRIMKVEYHLLSPYVSPREFPFRHIFWG
SGSHTLSALLEHLKLRKKNNGAFNQTLLENQLALATWTIQGAANALSGDIWDIDNEF SEQ ID NO: 13
>bTGFBR1 CDS (1500 bp)
ATGGAGGCAGCGGCCGCTACTCCGCGTCCCCGGCTGTTCCTCCTCATGCTGGGGGGGGCGGCCACGCTGGTCCCGGAGGCAA
CGCCATTACAGTGTTTCTGCCACCTTTGTACAAAAGACAATTTTACTTGTGTCACAGATGGGCTTTGCTTTGTCTCTGTCACAGAG
ACCACAGACAAAGTTATACATAATAGCATGTGTATAGCTGAAATTGACCTAATTCCACGAGACAGGCCATTTGTATGTGCACCATC
TTCAAAAACTGGGTCTATAACTACAACATATTGCTGCAACCAGGACCACTGCAATAAAATGACTTCCAACTGTTGGAAAGCCAT
CATCTGGCCTTGGTCCTGTTGAACTGGCAGCTGTCATTGCTGGACCAGTCTGCTTTGTCTGTATCTCACTCATGTTGATGGTCTAT
ATTTGCCATAACCGCACTGTCATTCACCATCGAGTGCCAAATGAAGAGGATCCCTCGTTAGATCGCCCTTTTATTTCAGAGGGTAC
AACGTTAAAAGATTTAATTTACGACATGACAACATCAGGTTCTGGATCAGGTTTACCATTGCTTGTTCAGAGAACAATTGCGAGAA
CTATTGTGTTACAAGAAAGTATTGGCAAAGGTCGTTTTGGAGAAGTTTGGCGAGGAAAATGGAGAGGAGAAGAAGTTGCTGTTAA
AATATTCTCCTCTAGAGAAGAACGTTCATGGTTCCGTGAAGCAGAGATTTACTGACTGTCATGTTACGTCACGAAAACATCTTGG
GATTTATAGCAGCAGACAATAAAGACAATGGCACATGGACTCAGCTCTGGTTGGTGTCAGATTATCATGAGCACGGATCCCTTTTT
GATTATTTGAACAGATACACAGTTACTGTGGAAGGAATGATAAAACTTGCTCTGTCCACAGCAAGTGGACTTGCCCATCTTCACAT
GGAGATAGTTGGTACCCAAGGAAAACCAGCCATAGCTCATAGGGATTTGAAATCAAAGAATATCTTGGTAAAGAAGAATGGAACT
TGCTGTATTGCAGACTTAGGATTGGCAGTAAGGCATGATTCGGCCACGGATACAATTGACATTGCTCCAAACCACAGAGTGGGAA
CAAAAAAGGTACATGGCCCCTGAAGTTCTAGATGATTCCATAAATATGAAACACTTTGAATCCTTCAAACGTGCTGACATCTATGCA
ATGGGACTAGTATTCTGGGAAGTAGCTCGACGATGTTCCATTGGTGGAATACATGGGAATTACCAGCTGCCTTATTATGATCTTGT
ACCTTCCGATCCATCAGTTGAAGAAATGAGAAAAGTTGTTTGTGAACAGAAGTTAAGGCCAAATATTCCAAACAGATGGCAGAGCT
GTGAAGCCTTGAGAGTAATGGCTAAAATTATGAGAGAATGTTGGTATGCCAATGGAGCAGCTAGGCTTACAGCTTTGCGGATTAA
GAAAACATTGTCACAACTCAGTCAGCAGGAAGGCATCAAAATGTAA SEQ ID NO: 14
>bTGFBR1 protein sequence (499 aa)
MEAAAATPRPRLFLLMLAAAATLVPEATPLQCFCHLCTKDNFTCVTDGLCFVSVTETTDKVIHNSMCIAEIDLIPRDRPFVCAPSSKTGSI
TTTYCCNQDHCNKIELPTVGKPSSGLGPVELAAVIAGPVCFVCISLMLMVYICHNRTVIHHRVPNEEDPSLDRPFISEGTTLKDLIYDMTT
SGSGSGLPLLVQRTIARTIVLQESIGKGRFGEVWRGKWRGEEVAVKIFSSREERSWFREAEIYQTVMLRHENILGFIAADNKDNGTWTQ
LWLVSDYHEHGSLFDYLNRYTVTVEGMIKLALSTASGLAHLHMEIVGTQGKPAIAHRDLKSKNILVKKNGTCCIADLGLAVRHDSATDTID
IAPNHRVGTKRYMAPEVLDDSINMKHFESFKRADIYAMGLVFWEVARRCSIGGIHEDYQLPYYDLVPSDPSVEEMRKVVCEQKLRPNIP
NRWQSCEALRVMAKIMRECWYANGAARLTALRIKKTLSQLSQQEGIKM SEQ ID NO: 15
>G3N1U2_BOVIN
MTEYKLVWVGAGGVGKSALTIQLIQNHFVDEYDPTIEDSYRKQWIDGETCLLDILDTAGQEEYSAMRDQYMRTGEGFLCVFAINHVKSF
EDIHQYREQIKRVKDSDDVPMVLVGNKCDLAARTVESRQAQDLARSYGIPYIETSAKTRQGSRSGSGSSSGTLWDPPGPP SEQ ID NO: 16
>G3N1U2_BOVIN Q61L
MTEYKLVWVGAGGVGKSALTIQLIQNHFVDEYDPTIEDSYRKQWIDGETCLLDILDTAGLEEYSAMRDQYMRTGEGFLCVFAINHVKSF
EDIHQYREQIKRVKDSDDVPMVLVGNKCDLAARTVESRQAQDLARSYGIPYIETSAKTRQGSRSGSGSSSGTLWDPPGPP SEQ ID NO: 17
>HRAS-201 cds:protein_coding ENSBTAT00000063375.2
ATGACGGAGTATAAGCTCGTGTGGTGGGCGCCGGTGGCGTGGGGAAGAGCGCCCTGACTATCCAGCTCATTCAGAATCACTT
CGTGGACGAGTACGACCCCACCATCGAGGACTCCTACCGGAAGCAAGTGGTCATCGATGGGGAGACGTGCCTGCTGGACATCC
TGGACACAGCGGGCCAGGAGGAATACAGCGCCATGCGAGACCAGTACATGCGCACCGGGGAGGGCTTTCTCTGCGTGTTTGCT
ATCAACCACGTCAAGTCCTTCGAGGACATCCACCAGTACCGGGAGCAGATCAAGCGGGTGAAGGACTCGGATGACGTGCCCAT
GGTGTTGGTGGGGAACAAGTGCGACCTGGCCGCGCGCACCGTGGAGTCTCGGCAGGCCCAGGACCTCGCCCGCAGCTACGGC
ATCCCGTACATCGAGACCTCCGCCAAGACCCGCCAGGGCGTGGAGGATGCTTTCTACACCCTGGTGCGCGAGATCCGGCAGCA
CAAGGTGCGCAAGCTGAGCCCGCCGGACGAGGGGGGCCCCCGGCTGCCTGAGCTGCAGGTGCCTGCTCTCCTGA SEQ ID NO: 18
>HRAS-201 cds:protein_coding (modified)
ATGACGGAGTATAAGCTCGTGGTGGTGGGCGCCGGTGGCGTGGGGAAGAGCGCCCTGACTATCCAGCTCATTCAGAATCACTT
CGTGGACGAGTACGACCCCACCATCGAGGACTCCTACCGGAAGCAAGTGGTCATCGATGGGGAGACGTGCCTGCTGGACATCC
TGGACACAGCGGGCCTGGAGGAATACAGCGCCATGCGAGACCAGTACATGCGCACCGGGGAGGGCTTTCTCTGCGTGTTTGCT
ATCAACCACGTCAAGTCCTTCGAGGACATCCACCAGTACCGGGAGCAGATCAAGCGGGTGAAGGACTCGGATGACGTGCCCAT
GGTGTTGGTTGGGAACAAGTGCGACCTGGCCGCGCGCACCGTGGAGTCTCGGCAGGCCCAGGACCTCGCCCGCAGCTACGGC
ATCCCGTACATCGAGACCTCCGCCAAGACCCGCCAGGGCGTGGAGGATGCTTTCTACACCCTGGTGCGCGAGATCCGGCAGCA
CAAGGTGCGCAAGCTGAGCCCGCCGGACGAGGGGGGCCCCGGCTGCCTGAGCTGCAGGTGCCTGCTCTCCTGA

SEQ ID NO: 19
>HBD3
GIINTLQKYYCRVRGGRCAVLSCLPKEEQIGKCSTRGRKCCRRKK

SEQ ID NO: 20
>HD5
ATCYCRHGRCATRESLSGVCEISGRLYRLCCR

SEQ ID NO: 21
>DEFB1_BOVIN
DFASCHTNGGICLPNRCPGHMIQIGICFRPRVKCCRSW

SEQ ID NO: 22
>DEFB2_BOVIN
VRNHVTCRINRGFCVPIRCPGRTRQIGTCFGPRIKCCRSW

SEQ ID NO: 23
>DEFB3_BOVIN
LALLFLVLSAGSGFTQGVRNHVTCRINRGFCVPIRCPGRTRQIGTCFGPRIKCCRSW

SEQ ID NO: 24
>DEFB4_BOVIN
MRLHHLLLAVLFLVLSAGSGFTQRVRNPQSCRWNMGVCIPFLCRVGMRQIGTCFGPRVPCCRR

SEQ ID NO: 25
>DEFB5_BOVIN
MRLHHLLLVLLFLVLSAGSGFTQVVRNPQSCRWNMGVCIPISCPGNMRQIGTCFGPRVPCCRRW

SEQ ID NO: 26
>DEFB6_BOVIN
QGVRNHVTCRIYGGFCVPIRCPGRTRQIGTCFGRPVKCCRRW

SEQ ID NO: 27
>DEFB7_BOVIN
MRLHHLLLALLFLVLSAGSGFTQGVRNFVTCRINRGFCVPIRCPGHRRQIGTCLGPRIKCCR

SEQ ID NO: 28
>DEFB8_BOVIN
VRNFVTCRINRGFCVPIRCPGHRRQIGTCLGPQIKCCR

SEQ ID NO: 29
>DEFB9_BOVIN
LALLFLVLSAGSGFTQGVRNFVTCRINRGFCVPIRCPGHRRQIGTCLAPQIKCCR

SEQ ID NO: 30
>DFB10_BOVIN
MRLHHLLLLLLLVVLSSGSGFTQGVRSYLSCWGNRGICLLNRCPGRMRQIGTCLAPRVKCCR

SEQ ID NO: 31
>DFB11_BOVIN
MRLHHLLLALLFLVLSAGSGISGPLSCRRNGGVCIPIRCPGPMRQIGTCFGRPVKCCRSW

SEQ ID NO: 32
>DFB12_BOVIN
GPLSCGRNGGVCIPIRCPVPMRQIGTCFGRPVKCCRSW

---

The invention claimed is:

1. A genetically modified non-human metazoan cell line comprising:

a. a gene encoding modified telomerase reverse transcriptase (TERT) or an allelic variant thereof resulting in cell immortalization, wherein the TERT gene is located at a safe harbor site within the genome of the cell; and b. a genetic modification that alters the level of expression of at least one gene selected from genes encoding fibroblast growth factor (FGF) molecules, resulting in reduced growth factor requirements for the cultivation of non-human metazoan cells compared to wild-type cell lines, wherein the FGF molecule is regulated by a promoter; and c. adaptation of the cell line to grow in a culture medium comprising a protein hydrolysate at a concentration, expressed as dry protein weight, in a range from 8 g/L to 50 g/L.

2. The genetically modified non-human metazoan cell line according to claim 1, wherein the genetically modified non-human metazoan cell line further comprises a transferrin receptor 1 (TFRC) gene encoding a protein having a sequence with at least 80% sequence identity to SEQ ID NO: 12.

3. The genetically modified non-human metazoan cell line according to claim 1, wherein the genetically modified non-human metazoan cell line further comprises a transforming growth factor beta receptor 1 (TGFBR1) gene encoding a protein having a sequence with at least 80% sequence identity to SEQ ID NO: 14.

4. The genetically modified non-human metazoan cell line according to claim 1, wherein the genetically modified non-human metazoan cell line further comprises a gene encoding an insulin protein having a sequence with at least 80% sequence identity to SEQ ID NO: 9.

5. The genetically modified non-human metazoan cell line according to claim 1, wherein the genetically modified non-human metazoan cell line comprises a FGF2 gene encoding a protein having a sequence with at least 80% sequence identity to SEQ ID NO: 11.

6. The genetically modified non-human metazoan cell line according to claim 1, wherein the FGF molecule is selected from FGF-2, FGF-5, FGF-1, and FGF-8, and wherein the FGF molecule is regulated by single-stranded DNA or RNA oligonucleotide sequences complementary to a target sequence of mRNA.

7. The genetically modified non-human metazoan cell line according to claim 1, wherein the gene encoding the FGF molecule is selected from FGF-2,-FGF-5, FGF-1, and FGF-8, and is regulated by the promoter.

8. The genetically modified non-human metazoan cell line according to claim 7, wherein the promoter is at least one selected from glyceraldehyde-3-phosphate dehydrogenase, eukaryotic translation elongation factor 1α, and phosphoglycerate kinase 1.

9. The genetically modified non-human metazoan cell line according to claim 8, wherein the promoter of eukaryotic translation elongation factor 1α comprises a sequence of SEQ ID NO: 6.

10. The genetically modified non-human metazoan cell line according to claim 1, wherein the genetically modified non-human metazoan cell line has reduced growth factor requirements compared to the wild-type cell line and is adapted for cultivation in a protein-free culture medium.

11. The genetically modified non-human metazoan cell line according to claim 1, wherein the genetically modified non-human metazoan cell line further comprises a fusion protein of myr-Akt to reduce growth factor requirements in the culture medium.

12. The genetically modified non-human metazoan cell line according to claim 1, wherein the non-human metazoan cell line comprises bovine, avian, porcine, equine, piscine, *cervine*, or cricetine cell lines.

13. The genetically modified non-human metazoan cell line according to claim 1, wherein the protein hydrolysate is prepared from soy, pea, rice, wheat, wheat gluten, corn, *faba* beans, alfalfa, hemp, chickpea, potato, pumpkin, rapeseed, red lentil, *Spirulina, Chlorella*, sunflower, water lentil, mung beans, flax, brewer spent grain, distillers spent grain (DDGS), or tomato pomace.

14. The genetically modified non-human metazoan cell line according to claim 1, wherein a total input of amino acids from the protein hydrolysate is at least 75% by weight of a total input of all amino acids in the culture medium.

15. The genetically modified non-human metazoan cell line according to claim 14, wherein the culture medium further comprises one or more amino acids added separately, wherein a total input of said separately added amino acids is in a range of 0.02 g/l to 30 g/l.

16. A genetically modified non-human metazoan cell line comprising:

a. a gene encoding modified telomerase reverse transcriptase (TERT) or an allelic variant thereof, wherein the TERT gene is located at a safe harbor site within the genome of the cell; and b. adaptation of the cell line to grow in a culture medium comprising protein hydrolysate as a main source of amino acids, wherein the total input of supplemental amino acids added separately to the culture medium comprising the protein hydrolysate is in the range of 0.2% to 25%.

17. The genetically modified non-human metazoan cell line according to claim 16, wherein the genetically modified non-human metazoan cell line has a TERT gene located in a safe harbor locus within the bovine phosphodiesterase 4D (bPDE4D) gene on chromosome 20 of the non-human metazoan cell line.

18. The genetically modified non-human metazoan cell line according to claim 17, wherein the genetically modified non-human metazoan cell line has a TERT gene located in a safe harbor locus within the bovine phosphodiesterase 4D (bPDE4D) gene on chromosome 20 of the non-human metazoan cell line at position 19533000.

19. The genetically modified non-human metazoan cell line according to claim 18, wherein the safe harbor locus within the bovine phosphodiesterase 4D (bPDE4D) gene on chromosome 20 of the non-human metazoan cell line at position 19533000 is in the range of 100,000 bp in both directions from position 19533000 of chromosome 20.

20. The genetically modified non-human metazoan cell line according to claim 16, wherein the safe harbor locus is PGRandom site.

21. The genetically modified non-human metazoan cell line according to claim 16, wherein the genetically modified non-human metazoan cell line comprises a bovine truncated telomerase reverse transcriptase (rbTERT) gene having a sequence with at least 80% sequence identity to SEQ ID NO: 4.

22. The genetically modified non-human metazoan cell line according to claim 16, wherein the genetically modified non-human metazoan cell line comprises a bovine telomerase reverse transcriptase (bTERT) gene encoding a protein having a sequence with at least 80% sequence identity to SEQ ID NO: 1.

23. The genetically modified non-human metazoan cell line according to claim 16, wherein the genetically modified non-human metazoan cell line comprises a bovine telomerase reverse transcriptase (bTERT) gene having a sequence with at least 80% sequence identity to SEQ ID NO: 2.

24. The genetically modified non-human metazoan cell line according to claim 16, wherein the genetically modified non-human metazoan cell line comprises a bovine truncated telomerase reverse transcriptase (rbTERT) gene encoding a protein having a sequence with at least 80% sequence identity to SEQ ID NO: 3.

25. The genetically modified non-human metazoan cell line according to claim 16, wherein an immortalization cassette comprises the gene encoding TERT, which is removed from the cell at the time of inoculation into a cultivation device.

26. A food product composition comprising genetically modified non-human metazoan cells, wherein the genetically modified non-human metazoan cells comprise:

a. a gene encoding modified telomerase reverse transcriptase (TERT) or an allelic variant thereof resulting in cell immortalization wherein the TERT gene is located at a safe harbor site within the genome of the cell; and b. adaptation of the cell line to grow in a culture medium comprising protein hydrolysate as a main source of amino acids, wherein at least 75% by weight of the total amino acid input in the culture medium is derived from the protein hydrolysate.

27. The food product composition according to claim 26, wherein the genetically modified non-human metazoan cell line comprises a modified Harvey rat sarcoma viral oncogene homolog (HRas) gene comprising SEQ ID NO: 18, wherein the modified HRas gene encodes a modified HRas protein with a Q61L substitution comprising SEQ ID NO: 16.

28. The food product composition according to claim 26, wherein the food product is intended for human consumption or as a pet food.

29. The food product composition according to claim 26, further comprising at least one additional component selected from saccharides, fats, vitamins, minerals, binders, palatants, antioxidants, colorants and preservatives.

30. The food product composition according to claim 26, wherein the composition comprises a cell biomass, wherein the cell biomass has a mass density in a range of 900 kg·m$^{-3}$ to 1200 kg·m$^{-3}$.

\* \* \* \* \*

SEQUENCE LISTING

Sequence total quantity: 32
SEQ ID NO: 1      moltype = AA   length = 1125
FEATURE      Location/Qualifiers
source      1..1125
     mol_type = protein
     organism = synthetic construct -continued

```
SEQUENCE: 1
MPRAPRCRAV RALLRASYRQ VLPLAAFVRR LRPQGHRLVR RGDPAAFRAL VAQCLVCVPW   60
DAQPPPAAPS FRQVSCLKEL VARVVQRLCE RGARNVLAFG FTLLAGARGG PPVAFTTSVR  120
SYLPNTVTDT LRGSGAWGLL LHRVGDDVLT HLLSRCALYL LVPPTCAYQV CGPPLYDLRA  180
AAAAARRPTR QVGGTRAGFG LPRPASSNGG HGEAEGLLEA RQAGARRRRS SARGRLPPAK  240
RPRRGLEPGR DLEGQVARSP PRVVTPTRDA AEAKSRKGDV PGPCRLFPGG ERGVGSASWR  300
LSPSEGEPGA GACAETKRFL YCSGGGEQLR RSFLLCSLPP SLAGARTLVE TIFLDSKPGP  360
PGAPRRPRRL PARYWQMRPL FRKLLGNHAR SPYGALLRAH CPLPASAPRA GPDHQKCPGV  420
GGCPSERPAA APEGEANSGR LVQLLRQHSS PWQVYGLLRA CLRRLVPAGL WGSRHNERRF  480
LRNVKKLLSL GKHGRLSQQE LTWKMKVQDC AWLRASPGAR CVPAAEHRQR EAVLGRFLHW  540
LMGAYVVELL RSFFYVTETT FQKNRLFFFR KRIWSQLQRL GVRQHLDRVR LRELSEAEVR  600
QHQEARPALL TSRLRFVPKP GGLRPIVNVG CVEGAPAPPR DKKVQHLSSR VKTLFAVLNY  660
ERARRPGLLG ASVLGMDDIH RAWRAFVLPL RARGPAPPLY FVKVDVVGAY DALPQDKLAE  720
VIANVLQPQE NTYCVRHCAM VRTARGRMRK SFKRHVSTFS DFQPYLRQLV EHLQAMGSLR  780
DAVVIEQSCS LNEPGSSLFN LFLHLVRSHV IRIGGRSYIQ CQGIPQGSIL STLLCSFCYG  840
DMENKLFPGV QQDGVLLRLV DDFLLVTPHL TRARDFLRTL VRGVPEYGCQ VNLRKTVVNF  900
PVEPGALGGA APLQLPAHCL FPWCGLLLDT RTLEVHGDHS SYARTSIRAS LTFTQGFKPG  960
RNMRRKLLAV LQLKCHGLFL DLQVNSLQTV FTNVYKIFLL QAYRFHACVL QLPFSQPVRS 1020
SPAFFLQVIA DTASRGYALL KARNAGASLG ARGAAGLFPS EAAQWLCLHA FLLKLARHRV 1080
TYSRLLGALR TARARLHRQL PGPTRAALEA AADPALTADF KTILD             1125

SEQ ID NO: 2              moltype = DNA   length = 3375
FEATURE                   Location/Qualifiers
source                    1..3375
                          mol_type = other DNA
                          organism = synthetic construct
SEQUENCE: 2
atgccgcgcg cgcccaggtg ccgggccgtg cgcgcccttc tgcgggccag ctaccggcag   60
gtgctgcccc tggccgcctt cgtacggcgc ctgcggcccc agggccaccg gcttgtgcgg  120
cgcgggacc cggcggcctt ccgcgcgctg gtggctcagt gcttggtgtg cgtgccctgg  180
gacgcgcagc cgcccctgc cgccccgtcc ttccgccagg tgtcctgcct gaaggagctg  240
gtggccagag tcgtgcagag gctgctgcgag cgcggcgcga ggaacgtgct ggccttcggc  300
ttcacgctgc tggccggggc ccgcggcggg ccgcccgtgg ccttcacgac cagcgtacgc  360
agctacctgc ccaacacggt aaccgacacg ctgcgcggca gcggcgcctg ggggctgctg  420
ctgcaccgcg tgggcgacga cgtgctcacc cacctgctgt cgcgctgcgc gctctacctg  480
ctggtgcccc cgacctgcgc ctaccaggtg tgtgggccgc cgctctatga cctccgcgcc  540
gccgccgccg ccgctcgtcg gcccacgcgg caagtgggcg ggacccgggc gggcttcgga  600
ctcccgcgcc cggcctcgtc gaacggcggc cacggggagg ccgaaggact cctggaggcg  660
cgggcccagg gcgcgaggcg gcgtcgcagt agcgcgcggg gacgactgcc tccagccagg  720
aggcccaggc gcggcctgga gcccgggcgg gatctcgaag ggcaggtggc ccgcagcccg  780
ccccgcgtgg tgacacctac ccgagacgct gcggaagcca agtctcggaa gggcgacgtg  840
cccgggcct gccgcctctt cccgggcggc gagcggggtg tcggctccgc gtcctggcgg  900
ctgtcaccct cggaggggcga gcgggtgcc ggagcttgcg gtgagaccaa gaggttcctt  960
tactgctccg gcggtggcga acagctgcgc cgctccttcc tgctctgctc cctgcctccc 1020
agcctggccg gggcgcggac actcgtggaa accatctttc tggactcgaa gcccgggccg 1080
ccagggctc cccgccggcc gcgccgcctg cccgcgcgct actggcagat gcggcccctg 1140
ttccggaaac tgcttgggaa ccacggcggg agcccctatg gcgctgct cagggcgcac 1200
tgcccgctgc cggcctctgc gccccgggcg gggccagacc atcagaagtg ccctggtgtt 1260
gggggctgcc cctctgagag gccggccgct gcccccgagg gcgaggcgaa ctcagggcgc 1320
ctggtccagc tgctccgcca gcacagcagc ccctggcagg tgtacgggct cctgcgggcc 1380
tgtcttcgcc gcctggtgcc cgccggcctc tggggctcac gcacaacgga gcggcgcttc 1440
ctgcggaacg tgaagaagct cctctccctg gggaagcacg gcaggctctc gcagcaggag 1500
ctcacgtgga agatgaaggt gcaggactgc gcctggctgc gcgcgagccc aggggctcgc 1560
tgcgtgcccg ccgcggagca ccgccagcgc gaggccgtcc tgggtcgctt cctgcactgg 1620
ctgatgggcg cctacgtggt ggagctgctc aggagcttct tctacgtcac agagaccacg 1680
ttccagaaga accggctctt cttcttccgg aagcgcatct ggagccagct gcagcgcctg 1740
ggcgtcagac aacacttaga ccgtgtgcgg cttcgagaac tgtcagaagc agaggtcagg 1800
cagcaccagg aggccaggcc ggctctgctg acatccaggc tccgtttcgt ccccaagccc 1860
ggcgggctgc ggcccatcgt gaacgtgggc tgtgttgagg gcgccccggc accgcccaga 1920
gacaagaagg tgcagcatct cagctcacgg gtcaagacgc tgttcgcggt gctgaactac 1980
gagcgagctc ggcggcctgg cctcctgggg gcctcggtgc tgggcatgga cgacatccac 2040
agggcctggc gggccttcgt gctgcccctg agggcccggg gcccagcccc ccgctctac 2100
ttcgtcaagg tggacgtggt ggggggcctac gatgccctcc cccaggataa gctggcagag 2160
gtgatcgcta acgtgctgca gccgcaggag aatacgtact gcgtgcgcca ctgcgccatg 2220
gtccggactg cgcgcgggcg catgcgcaag tccttcaaga gacacgtgtc caccttctcg 2280
gacttccagc cgtacctgag gcagctcgtg gagcatctgc aggcgatggg ctccctgagg 2340
gacgccgtg tcatcgagca gagctgctcc ctgaacgagc ctggcagcag cctcttcaac 2400
ctcttcctgc acctggtccg cagccacgtc atcaggatcg ggggcaggtc ctacatccag 2460
tgtcagggga tcccccaggg ctccatcctg tccaccctgc tctgcagctt ctgctatgag 2520
gacatggaga acaagctctt ccctggagtc cagcaggacg gggtgcttct gcgcctggtg 2580
gacgacttcc tgctggtcac cccacacctg acgcgggcca gagacttcct caggacgctg 2640
gtgcgcggtg tgcctgagta tggctgccag gtgaacctgc ggaagacggt ggtgaacttc 2700
cccgtggagc ccggggccct gggcggcgcg gcgcccctgc agctgccggc ccactgcctg 2760
ttccctggt gcgggctgct gctggatacc cgcaccctgg aggtgcatgg cgaccactcc 2820
agttatgccc ggacgtccat cagagcgagt ctcaccttca cccagggctt caagcccggg 2880
aggaacatgc gtcgcaagct gttggcggtc ttgcagctca agtggcatgg gctcttcctg 2940
gacctgcagg tgaacagtct gcagacggtc ttcacaaacg tttacaagat attcctgctg 3000
caggcctaca ggttccacgc ctgcgtgctg cagctgcct tcagccagcc ggtcaggagc 3060
agccccgcgt tctttctcca ggtcatcgcc gacaccgcat cccgcggcta cgccctcctg 3120
```

```
aaagccagga acgcaggggc gtcactgggg gccagggggcg ccgccggcct gttcccgtct   3180
gaagctgcgc agtggctgtg tctccacgcc ttcctgctca agctggctcg ccaccgtgtc   3240
acctacagcc gcctgctggg ggccctccgg acagcccgag cacggctgca ccggcagctc   3300
ccggggccca cacgggccgc cctgaggcg gcggccgacc ccgccctgac cgcagacttc   3360
aagaccatct tggac                                                    3375

SEQ ID NO: 3              moltype = AA   length = 1105
FEATURE                   Location/Qualifiers
source                    1..1105
                          mol_type = protein
                          organism = synthetic construct
SEQUENCE: 3
MPRAPRCRAV RALLRASYRQ VLPLAAFVRR LRPQGHRLVR RGDPAAFRAL VAQCLVCVPW   60
DAQPPPAAPS FRQVSCLKEL VARVVQRLCE RGARNVLAFG FTLLAGARGG PPVAFTTSVR   120
SYLPNTVTDT LRGSGAWGLL LHRVGDDVLT HLLSRCALYL LVPPTCAYQV CGPPLYDLRA   180
AAAAARRPTR QVGGTRAGFG LPRPASSNGG HGEAEGLLEA RAQGARRRRS SARGRLPPAK   240
RPRRGLEPGR DLEGQVARSP PRVVTPTRDA AEAKSRKGDV PGPCRLFPGG ERGVGSASWR   300
LSPSEGEPGA GACAETKRFL YCSGGGEQLR RSFLLCSLPP SLAGARTLVE TIFLDSKPGP   360
PGAPRRPRRL PARYWQMRPL FRKLLGNHAR SPYGALLRAH CPLPASAPRA APEGEANSGR   420
LVQLLRQHSS PWQVYGLLRA CLRRLVPAGL WGSRHNERRF LRNVKKLLSL GKHGRLSQQE   480
LTWKMKVQDC AWLRASPGAR CVPAAEHRQR EAVLGRFLHW LMGAYVVELL RSFFYVTETT   540
FQKNRLFFFR KRIWSQLQRL GVRQHLDRVR LRELSEAEVR QHQEARPALL TSRLRFVPKP   600
GGLRPIVNVG CVEGAPAPPR DKKVQHLSSR VKTLFAVLNY ERARRPGLLG ASVLGMDDIH   660
RAWRAFVLPL RARGPAPPLY FVKVDVVGAY DALPQDKLAE VIANVLQPQE NTYCVRHCAM   720
VRTARGRMRK SFKRHVSTFS DFQPYLRQLV EHLQAMGSLR DAVVIEQSCS LNEPGSSLFN   780
LPFLHLVRSHV IRIGGRSYIQ CQGIPQGSIL STLLCSFCYG DMENKLFPGV QQDGVLLRLV   840
DDFLLVTPHL TRARDFLRTL VRGVPEYGCQ VNLRKTVVNF PVEPGALGGA APLQLPAHCL   900
FPWCGLLLDT RTLEVHGDHS SYARTSIRAS LTFTQGFKPG RNMRRKLLAV LQLKCHGLFL   960
DLQVNSLQTV FTNVYKIFLL QAYRFHACVL QLPFSQPVRS SPAFFLQVIA DTASRGYALL   1020
KARNAGASLG ARGAAGLFPS EAAQWLCLHA FLLKLARHRV TYSRLLGALR TARARLHRQL   1080
PGPTRAALEA AADPALTADF KTILD                                         1105

SEQ ID NO: 4              moltype = DNA   length = 3315
FEATURE                   Location/Qualifiers
source                    1..3315
                          mol_type = other DNA
                          organism = synthetic construct
SEQUENCE: 4
atgccgcgcg cgcccaggtg ccgggccgtg cgcgcccttc tgcgggccag ctaccggcag   60
gtgctgcccc tggccgcctt cgtacggcgc ctgcggcccc agggccaccg gcttgtgcgg   120
cgcggggacc cggcggcctt ccgcgcgctg gtggctcagt gcttggtgtg cgtgccctgg   180
gacgcgcagc cgcccctgc cgcccgtcc ttcgccagg tgtcctgcct gaaggagctg   240
gtggccagag tcgtgcagag gctctgcgag cgcggccgga ggaacgtgct ggccttcggc   300
ttcacgctgc tggccggggc ccgcggcggg ccgcccgtgg ccttcacgac cagcgtacgc   360
agctacctgc ccaacacggt aaccgacacg ctgcgcggca gcggcgcctg ggggctgctg   420
ctgcaccgcg tgggcgacga cgtgctcacc cacctgctgt cgcgctgcgc gctctacctg   480
ctggtgcccc cgacctgcgc ctaccaggtg tgtgggcgc cgctctatga cctccgcgcc   540
gccgccgccg ccgctcgtcg gcccacgcgg caagtgggcg ggacccgggc gggcttcgga   600
ctcccgcgcc cggcctcgtc gaacggcggc cacggggagg ccgaaggact cctgaggcg   660
cgggcccagg gcgcgaggcg gcgtcgcagt agcgcgcggg gacgactgcc tccagccaag   720
aggcccaggc gcggcctgga gcccggggcgg gatctcgaag ggcaggtggc ccgcagcccg   780
cccccgcgtgg tgacacctac ccgagacgct gcggaagcca agtctcggaa gggcgacgtg   840
cccgggccct gccgcctctt cccgggcggc gagcggggtg tcggctccgc gtcctggcgg   900
ctgtcaccct cggagggcga gccgggtgcc ggagcttgcg ctgagaccaa gaggttcctt   960
tactgctccg gcggtggcga acagctgcgc cgctccttcc tgctctgctc cctgcctccc   1020
agcctggccg gggcgcggac actcgtggaa accatctttc tggactcgaa gcccgggccg   1080
ccaggggctc ccgccggcc gcgccgcctg cccgcgcgct actggcagat gcggcccctg   1140
ttccggaaac tgcttgggaa ccacgcgcgg agccccatg gcgcgctgct cagggcgcac   1200
tgcccgctgc cggcctctgc gcccccgggct gcccccgagg gcgagcgaa ctcagggcgc   1260
ctggtccagc tgctccgcca gcacagcagc cctggcagg tgtacgggct cctgcgggcc   1320
tgtcttcgcc gcctggtgcc cgccggcctc tggggctccc ggcacaacga gcggcgcttc   1380
ctgcggaacg tgaagaagct cctctccctg gggaagcacg gcaggctctc gcagcaggag   1440
ctcacgtgga agatgaaggt gcaggactgc gcctggctgc gcgcgagccc aggggctcgc   1500
tgcgtgcccg ccgcggagca ccgccagcgc gaggccgtgc tgggtcgctt cctgcactgg   1560
ctgatgggcg cctacgtggt ggagctgctc aggagcttct tctacgtcac agagaccacg   1620
ttccagaaga accggctctt cttcttccgg aagcgcatct ggagccagct gcagcgcctg   1680
ggcgtcagac aacacttaga ccgtgtgcgg cttcgagaac tgtcagaagc agaggtcagg   1740
cagcaccagg aggccaggcc ggctctgctg acatccaggc tccgtttcgt ccccaagccg   1800
ggcggggctgc ggcccatcgt gaacgtgggc tgtgttgagg gcgccccggc accgccaga   1860
gacaagaagg tgcagcatct cagctcacgg gtcaagacgc tgttcgcggt gctgaactac   1920
gagcgagctc ggcggcctgg cctcctgggg gcctcggtgc tgggcatgga cgacatccac   1980
agggcctggc gggccttcgt gctgcccctg agggcccggg gcccagcccc ccgctctac   2040
ttcgtcaagg tggacgtggt ggggggcctac gatgccctcc cccaggataa gctggcagag   2100
gtgatcgcta acgtgctgca gccgcaggag aatacgtact gctgtcgcca ctgcgccatg   2160
gtccggactg cgcgcgggcg catgcgcaag tccttcaaga gacacgtgtc caccttctcg   2220
gacttccagc cgtacctgag gcagctcgtg gagcatctgc aggcgatggg ctccctgagg   2280
gacgccgtgg tcatcgagca gagctgctcc ctgaacgagc ctggcagcag cctcttcaac   2340
ctcttcctgc acctggtccg cagccacgtc atcaggatcg ggggcaggtc ctacatccag   2400
tgtcagggga tcccccaggg ctccatcctg tccaccctgc tctgcagctt ctgctatggg   2460
```

```
gacatggaga acaagctctt ccctggagtc cagcaggacg gggtgcttct gcgcctggtg   2520
gacgacttcc tgctggtcac cccacacctg acgcgggcca gagacttcct caggacgctg   2580
gtgcgcggtg tgcctgagta tggctgccag gtgaacctgc ggaagacggt ggtgaacttc   2640
cccgtggagc ccgggccct gggcggcgcg gcgccctgc agctgccggc ccactgcctg    2700
ttccctggt gcggcctgct gctggatacc cgcaccctgg aggtgcatgg cgaccactcc    2760
agttatgccc ggacgtccat cagagcgagt ctcaccttca cccagggctt caagcccggg   2820
aggaacatgc gtcgcaagct gttggcggtc ttgcagctca agtgcatgg gctcttcctg    2880
gacctgcagg tgaacagtct gcagacggtc ttcacaaacg tttacaagat attcctgctg   2940
caggcctaca ggttccacgc ctgcgtgctg cagctgccct tcagccagcc ggtcaggagc   3000
agccccgcgt tctttctcca ggtcatcgcc gacaccgcat cccgcggcta cgccctcctg   3060
aaagccagga acgcaggggc gtcactgggg gccaggggcg ccgccggcct gttcccgtct   3120
gaagctgcgc agtggctgtg tctccacgcc ttcctgctca agctggctcg ccaccgtgtc   3180
acctacagcc gcctgctggg ggccctccgg acagcccgag cacggctgca ccggcagctc   3240
ccggggccca cacgggccgc cctggaggcg gcggccgacc ccgccctgac cgcagacttc   3300
aagaccatct tggac                                                     3315

SEQ ID NO: 5               moltype = DNA   length = 511
FEATURE                    Location/Qualifiers
source                     1..511
                           mol_type = other DNA
                           organism = synthetic construct
SEQUENCE: 5
ttcatttgca tctatcctga atagggttgc cgggaattcc atgggatgtg gggtgacgtt   60
ttccccgagg ctgccatggg tttgcggggc tctgcagctg cctccggtgc ggccgcagga   120
acccgagccg tgtccgcccc tcggcgccaa ctggctccag atcccgccgc cgcttagtcc   180
ggcggcaccg cctcctgcct ctagtcacga aagttcccag ccgctcgctg cgtgctggac   240
gtgactggcg gcagctgcac gtcccacaat cgcgctcgct gactgacagc gcctcggtgc   300
aatggcagcc agcgggcgcc ttcgggccgc gttctagagc ggccactggg cgccgagagc   360
cgggcgcggc ggccggaaag gggcggggcg ggaggagtgg cgacccagcc cgtgaggtgc   420
taggcatttt ccacgcgttc ggaccctgag tcggtctcag tctctgccgc tgtctcatcc   480
cctggcctct cgctgcagct gaattgccaa g                                   511

SEQ ID NO: 6               moltype = DNA   length = 1191
FEATURE                    Location/Qualifiers
source                     1..1191
                           mol_type = other DNA
                           organism = synthetic construct
SEQUENCE: 6
ggcgcccagc gctcgtcagt gggctgagcg tacatcgccc acggtccccg agacgtgggg   60
ggaggggacg gagattgaac tggtgcctgg tggaggcggc gcggggtaat ctgggaaagt   120
ggtgtcgtgt gctggctccg cccttttccc cgagggtggg gggagaaccg tatataagtg   180
ccgtagtctc cgtgaacgtt cttttcgca acgggtttgc cgccgggaca caggtgagtg    240
ccgggtgtgg cttcggtggg cccagcctcc gccgacggcc gcggccttcg cgtgcgtgta   300
tctcccgccg cgcccgtggg cattttcacc atgttcttca ccggaatttc ggggtgtgag   360
agggtggggg ggtggggaga gttcgaggcc ttgcgctttt ctcacagtcc cttcgcctcg   420
tgcttgggtt gaggcctggg ctgtggcacc gtggccgctg cgtgtggatc ctgccgcgct   480
ttgccgctct gttccccca ccccgccgcc acacacacac tattgaacaa ctccacacag   540
ccgcgggttt ttcggccggg gcggttcatc cggggccggc cggggggctga caggctgggc   600
ttctcggcgc tcgtcgggat tcggggtagg gggcggccgc gaggcgcaga gagcgcgggc   660
ctgcttcccc ggcgcacatg ccatagcggc ctcgctgggc cgaggcgggg cgggagagcc   720
gtggcggccg ggcgagcaga gcgccgcccc gcccggcacc agttgcgtgc gcggaaagat   780
ggccgctccc cggcccctct gcacggcttc aaaatggagg acgcggcggc ccgggagggg   840
agcggccggt gagtcacccg cacaaagggc ccgggcccgt ccctgcctgg cgccgcttcc   900
ttgggacacc cccccgcccc ccgcggcgga ccgggtgccg tcctggcccc tcgatgcctc   960
gtggttccag agcgacacat gggggtgggg aggggaatct ggacggtgga gcttatgggt   1020
ggagacttga gttgggccag cttggcgcta gttgtaatgc tccttggaat ttgcccttgg   1080
agtttggatc gtagctttt cttcagcttc cggacagtgg tttaaagttt cccacacctc   1140
cacccctttc caattaggtg tcgtgaaaac caccgttaaa cctaagccaa a             1191

SEQ ID NO: 7               moltype = DNA   length = 2310
FEATURE                    Location/Qualifiers
source                     1..2310
                           mol_type = other DNA
                           organism = synthetic construct
SEQUENCE: 7
atgatggatc aagccagatc agcattctct aacttgtttg gtggagaacc attgtcatat   60
accaggttta gtctggctcg gcaagtagat ggtgataaca gtcatgtgga gatgaaatta   120
gctgcagatg aagaagaaaa tgttgacagt aacatgaggg gcaaccaaac cagtatcgca   180
aaaccgaaaa ggttaaatgg atatgtctgc tacgggatca ttgctgtaat cgtctttttc   240
ttgattggat ttatgattgg ctacttgggc tattgtagac gtgtggaatc acaagattgt   300
gggaaagagg caggaacaca gccttcgtgc ccagaggaga cagaaactt cgaatcagaa   360
gagcaactcc ctgagtacc tcgcatattc tgggcagacc tcaaatcaac gttgtcagga   420
aaactggatg ccgtagactt tgccaggc atcaagatgc tgaatgaaaa ttcttatgtc   480
ccacgtgaag ctggatctga aaaagatacc agtttggctt ttttcattga aaatcaatta   540
caggactgta aactcggcaa agtctggcat gatgaacatt ttattaagat tcaggtcaaa   600
ggcagttctc aaaactcggt gtctatagtg agtacaagcg gtaacggcag tcaggcatac   660
ccagtggaga gtcctgaggg ttacgtggca tatagtaagg ctgcgaccgt tactggcaaa   720
ctggtccatg ctaattttgg cactaaacaa gactttgagg atttaaatat gcctgtaaat   780
ggatcttag tgattgtaag agctggaaaa atcagttttg ctgaaaaggt ggcaaatgct   840
```

```
gaaagtttaa atgcaattgg tgtcttgata tacatggact acagtaaata tcccattgtt    900
aatgcaaatc ttccagtttt tggacatgct catctgggaa caggtgaccc ttacacacct    960
ggattccctt cttttaatca cactcaattt ccaccatctc agtcatcagg attgcccaac    1020
atacctgtcc aaacaattac cagagccggt gcagaaaagc tatttcaaaa tatggaagga    1080
gactgtcctc gtatttgggg aacagactct tcatgtaactg tggtatcctc acaggataag    1140
aatgtgaaac ttagcgtgaa caatgtgctg aaggagataa gaattcttaa cgtctttgga    1200
gttattaagg gctttgaaga accagatcgc tatgttatag taggggccca gagggatgcc    1260
tggggtcctg gagctgcaaa gtccagtgta ggaacaagtc tgctattgac acttgcccgg    1320
atactttccg atatggtctt aaaaggtcag tttaaaccca gcagaagcat tgtctttgac    1380
agctggagtg gtggagactt tgggaccgtt ggtgccactg aatggctaga gggatacctt    1440
tcctcattgc atttaaaggc tttcacttac attaatctgg ataaagctgt tgttggtact    1500
accaatttca aagtttctgc cagcccactg ttgtattcac ttattgagaa aatcatgaaa    1560
gatgtgaagc atccacttaa tgggctgtct ctgtatcggg acagcaactg gatcagcaaa    1620
gtgcaaaaac tttctttgga taatgctgct ttccctttcc ttgcatattc tggaatccca    1680
gcggtctctt tctgtttttg tgaggacaca gattaccctt atttaggcac tcccatggac    1740
acctatgaga cactgaacag agaagttcct cagttgaaca gagtggcacg tgcagcagca    1800
gaagtggccg gtcagcttgt gattaaactt acccatgggg ttgagctgaa cctgaactac    1860
gagatgtata atgacgaaat acttcggttt gtgaaggaaa tgaacctatt cagagcagac    1920
ataagggata tgggtctgaa tatgcagtgg ctgtattctg ctcgtggaga cttcttccgt    1980
gctacgtcta gactaactac ggattataag aatgctgaga aaacagacag atctgtgatg    2040
agggaaatca atgaccgtat catgaaagtg gaatatcacc tcctctcacc ctatgtatct    2100
ccaagagagt ttcctttccg acacatcttc tggggctctg gctctcacac tctgtcagct    2160
ttactggagc acttgaagct gcgtaagaaa aataacggtg cttttaatca aacactgttg    2220
gaaaaccagt tggctctggc aacttggact attcagggag ccgcaaatgc cctctctggg    2280
gacatttggg acattgacaa cgaatttttaa                                    2310
```

```
SEQ ID NO: 8            moltype = DNA   length = 318
FEATURE                 Location/Qualifiers
source                  1..318
                        mol_type = other DNA
                        organism = synthetic construct
SEQUENCE: 8
atggccctgt ggacacgcct gcggcccctg ctggccctgc tggcgctctg gcccccccc     60
ccggcccgcg ccttcgtcaa ccagcatctg tgtggctccc acctggtgga ggcgctgtac    120
ctggtgtgcg gagagcgcgg cttcttctac acgcccaagg ccgcgcggga ggtggagggc    180
ccgcaggtgg gggcgctgga gctggccgga ggccccgggcg cgggcggcct ggaggggccc    240
ccgcagaagc gtggcatcgt ggagcagtgc tgtgccagcg tctgctcgct ctaccagctg    300
gagaactact gtaactag                                                  318
```

```
SEQ ID NO: 9            moltype = AA   length = 105
FEATURE                 Location/Qualifiers
source                  1..105
                        mol_type = protein
                        organism = synthetic construct
SEQUENCE: 9
MALWTRLRPL LALLALWPPP PARAFVNQHL CGSHLVEALY LVCGERGFFY TPKARREVEG     60
PQVGALELAG GPGAGGLEGP PQKRGIVEQC CASVCSLYQL ENYCN                    105
```

```
SEQ ID NO: 10           moltype = DNA   length = 465
FEATURE                 Location/Qualifiers
source                  1..465
                        mol_type = other DNA
                        organism = synthetic construct
SEQUENCE: 10
atggctgctg gttccatcac tacactgccg gccctccag aagacggcgg tagcggtgct      60
tttcctcctg gacattttaa agatccaaaa cggttgtatt gcaaaaacgg gggctttttt    120
ctcagaatcc atcccgatgg ccgagttgac ggggttcgag agaagtccga tccgcacatt    180
aagctgcaac tgcaagctga ggagcgagga gttgtcagta taaagggcgt ctgtgctaat    240
agataccttg ccatgaagga agatggtagg ttgttggcga gcaaatgcgt tacggacgaa    300
tgctttttct tcgaaagact cgaatccaac aattacaaca catatcggtc caggaaatat    360
agttcatggt acgtggcctt gaaacggacg gggcagtata aactcggtcc gaaaactggt    420
ccgggtcaga aggcaatcct gtttctgcca atgtccgcta agagc                    465
```

```
SEQ ID NO: 11           moltype = AA   length = 155
FEATURE                 Location/Qualifiers
source                  1..155
                        mol_type = protein
                        organism = synthetic construct
SEQUENCE: 11
MAAGSITTLP ALPEDGGSGA FPPGHFKDPK RLYCKNGGFF LRIHPDGRVD GVREKSDPHI     60
KLQLQAEERG VVSIKGVCAN RYLAMKEDGR LLASKCVTDE CFFFERLESN NYNTYRSRKY    120
SSWYVALKRT GQYKLGPKTG PGQKAILFLP MSAKS                              155
```

```
SEQ ID NO: 12           moltype = AA   length = 769
FEATURE                 Location/Qualifiers
source                  1..769
                        mol_type = protein
                        organism = synthetic construct
SEQUENCE: 12
```

```
MMDQARSAFS NLFGGEPLSY TRFSLARQVD GDNSHVEMKL AADEEENVDS NMRGNQTSIA   60
KPKRLNGYVC YGIIAVIVFF LIGFMIGYLG YCRRVESQDC GKEAGTQPSC PEETETFESE   120
EQLPGVPRIF WADLKSTLSG KLDAVDFARA IKMLNENSYV PREAGSEKDT SLAFFIENQL   180
QDCKLGKVWH DEHFIKIQVK GSSQNSVSIV STSGNGSQAY PVESPEGYVA YSKAATVTGK   240
LVHANFGTKQ DFEDLNMPVN GSLVIVRAGK ISFAEKVANA ESLNAIGVLI YMDYSKYPIV   300
NANLPVFGHA HLGTGDPYTP GFPSFNHTQF PPSQSSGLPN IPVQTITRAG AEKLFQNMEG   360
DCPRIWGTDS SCKLVSSQDK NVKLSVNNVL KEIRILNVFG VIKGFEEPDR YVIVGAQRDA   420
WGPGAAKSSV GTSLLLTLAR ILSDMVLKGQ FKPSRSIVFA SWSGGDFGAV GATEWLEGYL   480
SSLHLKAFTY INLDKAVVGT TNFKVSASPL LYSLIEKIMK DVKHPLNGLS LYRDSNWISK   540
VQKLSLDNAA FPFLAYSGIP AVSFCFCEDT DYPYLGTPMD TYETLNREVP QLNRVARAAA   600
EVAGQLVIKL THGVELNLNY EMYNDEILRF VKEMNLFRAD IRDMGLNMQW LYSARGDFFR   660
ATSRLTTDYK NAEKTDRSVM REINDRIMKV EYHLLSPYVS PREFPFRHIF WGSGSHTLSA   720
LLEHLKLRKK NNGAFNQTLL ENQLALATWT IQGAANALSG DIWDIDNEF              769
```

```
SEQ ID NO: 13          moltype = DNA  length = 1500
FEATURE                Location/Qualifiers
source                 1..1500
                       mol_type = other DNA
                       organism = synthetic construct
SEQUENCE: 13
atggaggcag cggccgctac tccgcgtccc cggctgttcc tcctcatgct ggcggcggcg   60
gccacgctgg tcccggaggc aacgccatta cagtgtttct gccacctttg tacaaaagac   120
aattttactt gtgtcacaga tgggctttgc tttgtctctg tcacagagac cacagacaaa   180
gttatacata atagcatgtg tatagctgaa attgacctaa ttccacgaga caggccattt   240
gtatgtgcac catcttcaaa aactgggtct ataactacaa catattgctg caaccaggac   300
cactgcaata aaatagaact tccaactgtt ggaaagccat catctggcct tggtcctgtt   360
gaactggcag ctgtcattgc tggaccagtc tgctttgtct gtatctcact catgttgatg   420
gtctatattt gccataaccg cactgtcatt caccatcgag tgccaaatga gaggatccc    480
tcgttagatc gccctttat ttcagagggt acaacgttaa aagatttaat ttacgacatg    540
acaacatcag gttctggatc aggtttacca ttgcttgttc agagaacaat tgcgagaact   600
attgtgttac aagaaagtat tggcaaaggt cgttttggag aagtttggcg aggaaaatgg   660
agaggagaag aagttgctgt taaaatattc tcctctagag aagaacgttc atggttccgt   720
gaagcagaga tttatcagac tgtcatgtta cgtcacgaaa acatcttggg atttatagca   780
gcagcaaata aagacaatgg cacatggact cagctctggt tggtgtcaga ttatcatgag   840
cacggatccc ttttttgatta tttgaacaga tacacagtta ctgtggaagg aatgataaaa   900
cttgctctgt ccacagcaag tggacttgcc catcttcaca tggagatagt tggtacccaa   960
ggaaaaccag ccatagctca tagggatttg aaatcaaaga atatcttggt aaagaagaat   1020
ggaacttgct gtattgcaga cttaggattg gcagtaaggc atgattcggc cacggataca   1080
attgacattg ctccaaacca cagagtggga acaaaaaggt acatggcccc tgaagttcta   1140
gatgattcca taaatatgaa acactttgaa tccttcaaac gtgctgacat ctatgcaatg   1200
ggactagtat tctgggaagt agctcgacga tgttccattg gtggaataca tgaagattac   1260
cagctgcctt attatgatct tgtaccttcc gatccatcag ttgaagaaat gagaaaagtt   1320
gtttgtgaac agaagttaag gccaaatatt ccaaacagat ggcagagctg tgaagcctg    1380
agagtaatgg ctaaaattat gagagaatgt tggtatgcca atgagcagc taggcttaca    1440
gctttgcgga ttaagaaaac attgtcacaa ctcagtcagc aggaaggcat caaaatgtaa   1500
```

```
SEQ ID NO: 14          moltype = AA  length = 499
FEATURE                Location/Qualifiers
source                 1..499
                       mol_type = protein
                       organism = synthetic construct
SEQUENCE: 14
MEAAAATPRP RLFLLMLAAA ATLVPEATPL QCFCHLCTKD NFTCVTDGLC FVSVTETTDK   60
VIHNSMCIAE IDLIPRDRPF VCAPSSKTGS ITTTYCCNQD HCNKIELPTV GKPSSGLGPV   120
ELAAVIAGPV CFVCISLMLM VYICHNRTVI HHRVPNEEDP SLDRPFISEG TTLKDLIYDM   180
TTSGSGSGLP LLVQRTIART IVLQESIGKG RFGEVWRGKW RGEEVAVKIF SSREERSWFR   240
EAEIYQTVML RHENILGFIA ADNKDNGTWT QLWLVSDYHE HGSLFDYLNR YTVTVEGMIK   300
LALSTASGLA HLHMEIVGTQ GKPAIAHRDL KSKNILVKKN GTCCIADLGL AVRHDSATDT   360
IDIAPNHRVG TKRYMAPEVL DDSINMKHFE SFKRADIYAM GLVFWEVARR CSIGGIHEDY   420
QLPYYDLVPS DPSVEEMRKV VCEQKLRPNI PNRWQSCEAL RVMAKIMREC WYANGAARLT   480
ALRIKKTLSQ LSQQEGIKM                                              499
```

```
SEQ ID NO: 15          moltype = AA  length = 170
FEATURE                Location/Qualifiers
source                 1..170
                       mol_type = protein
                       organism = synthetic construct
SEQUENCE: 15
MTEYKLVVVG AGGVGKSALT IQLIQNHFVD EYDPTIEDSY RKQVVIDGET CLLDILDTAG   60
QEEYSAMRDQ YMRTGEGFLC VFAINHVKSF EDIHQYREQI KRVKDSDDVP MVLVGNKCDL   120
AARTVESRQA QDLARSYGIP YIETSAKTRQ GSRSGSGSSS GTLWDPPGPP            170
```

```
SEQ ID NO: 16          moltype = AA  length = 170
FEATURE                Location/Qualifiers
source                 1..170
                       mol_type = protein
                       organism = synthetic construct
SEQUENCE: 16
MTEYKLVVVG AGGVGKSALT IQLIQNHFVD EYDPTIEDSY RKQVVIDGET CLLDILDTAG   60
```

-continued

```
LEEYSAMRDQ YMRTGEGFLC VFAINHVKSF EDIHQYREQI KRVKDSDDVP MVLVGNKCDL   120
AARTVESRQA QDLARSYGIP YIETSAKTRQ GSRSGSGSSS GTLWDPPGPP                170

SEQ ID NO: 17          moltype = DNA  length = 570
FEATURE                Location/Qualifiers
source                 1..570
                       mol_type = other DNA
                       organism = synthetic construct
SEQUENCE: 17
atgacggagt ataagctcgt ggtggtgggc gccggtggcg tggggaagag cgccctgact   60
atccagctca ttcagaatca cttcgtggac gagtacgacc ccaccatcga ggactcctac   120
cggaagcaag tggtcatcga tggggagacg tgcctgctgg acatcctgga cacagcgggc   180
caggaggaat acagcgccat gcgagaccag tacatgcgca ccggggaggg ctttctctgc   240
gtgtttgcta tcaaccacgt caagtccttc gaggacatcc accagtaccg ggagcagatc   300
aagcgggtga aggactcgga tgacgtgccc atggtgttgg ttgggaacaa gtgcgacctg   360
gccgcgcgca ccgtggagtc tcggcaggcc caggacctcg cccgcagcta cggcatcccg   420
tacatcgaga cctccgccaa gacccgccag ggcgtggagg atgctttcta caccctggtg   480
cgcgagatcc ggcagcacaa ggtgcgcaag ctgagcccgc cggacgaggg cggccccggc   540
tgcctgagct gcaggtgcct gctctcctga                                      570

SEQ ID NO: 18          moltype = DNA  length = 570
FEATURE                Location/Qualifiers
source                 1..570
                       mol_type = other DNA
                       organism = synthetic construct
SEQUENCE: 18
atgacggagt ataagctcgt ggtggtgggc gccggtggcg tggggaagag cgccctgact   60
atccagctca ttcagaatca cttcgtggac gagtacgacc ccaccatcga ggactcctac   120
cggaagcaag tggtcatcga tggggagacg tgcctgctgg acatcctgga cacagcgggc   180
ctggaggaat acagcgccat gcgagaccag tacatgcgca ccggggaggg ctttctctgc   240
gtgtttgcta tcaaccacgt caagtccttc gaggacatcc accagtaccg ggagcagatc   300
aagcgggtga aggactcgga tgacgtgccc atggtgttgg ttgggaacaa gtgcgacctg   360
gccgcgcgca ccgtggagtc tcggcaggcc caggacctcg cccgcagcta cggcatcccg   420
tacatcgaga cctccgccaa gacccgccag ggcgtggagg atgctttcta caccctggtg   480
cgcgagatcc ggcagcacaa ggtgcgcaag ctgagcccgc cggacgaggg cggccccggc   540
tgcctgagct gcaggtgcct gctctcctga                                      570

SEQ ID NO: 19          moltype = AA  length = 45
FEATURE                Location/Qualifiers
source                 1..45
                       mol_type = protein
                       organism = synthetic construct
SEQUENCE: 19
GIINTLQKYY CRVRGGRCAV LSCLPKEEQI GKCSTRGRKC CRRKK                      45

SEQ ID NO: 20          moltype = AA  length = 32
FEATURE                Location/Qualifiers
source                 1..32
                       mol_type = protein
                       organism = synthetic construct
SEQUENCE: 20
ATCYCRHGRC ATRESLSGVC EISGRLYRLC CR                                    32

SEQ ID NO: 21          moltype = AA  length = 38
FEATURE                Location/Qualifiers
source                 1..38
                       mol_type = protein
                       organism = synthetic construct
SEQUENCE: 21
DFASCHTNGG ICLPNRCPGH MIQIGICFRP RVKCCRSW                              38

SEQ ID NO: 22          moltype = AA  length = 40
FEATURE                Location/Qualifiers
source                 1..40
                       mol_type = protein
                       organism = synthetic construct
SEQUENCE: 22
VRNHVTCRIN RGFCVPIRCP GRTRQIGTCF GPRIKCCRSW                            40

SEQ ID NO: 23          moltype = AA  length = 57
FEATURE                Location/Qualifiers
source                 1..57
                       mol_type = protein
                       organism = synthetic construct
SEQUENCE: 23
LALLFLVLSA GSGFTQGVRN HVTCRINRGF CVPIRCPGRT RQIGTCFGPR IKCCRSW         57

SEQ ID NO: 24          moltype = AA  length = 63
FEATURE                Location/Qualifiers
```

-continued

```
source                  1..63
                        mol_type = protein
                        organism = synthetic construct
SEQUENCE: 24
MRLHHLLLAV LFLVLSAGSG FTQRVRNPQS CRWNMGVCIP FLCRVGMRQI GTCFGPRVPC  60
CRR                                                                63

SEQ ID NO: 25           moltype = AA   length = 64
FEATURE                 Location/Qualifiers
source                  1..64
                        mol_type = protein
                        organism = synthetic construct
SEQUENCE: 25
MRLHHLLLVL LFLVLSAGSG FTQVVRNPQS CRWNMGVCIP ISCPGNMRQI GTCFGPRVPC  60
CRRW                                                               64

SEQ ID NO: 26           moltype = AA   length = 42
FEATURE                 Location/Qualifiers
source                  1..42
                        mol_type = protein
                        organism = synthetic construct
SEQUENCE: 26
QGVRNHVTCR IYGGFCVPIR CPGRTRQIGT CFGRPVKCCR RW                      42

SEQ ID NO: 27           moltype = AA   length = 62
FEATURE                 Location/Qualifiers
source                  1..62
                        mol_type = protein
                        organism = synthetic construct
SEQUENCE: 27
MRLHHLLLAL LFLVLSAGSG FTQGVRNFVT CRINRGFCVP IRCPGHRRQI GTCLGPRIKC  60
CR                                                                 62

SEQ ID NO: 28           moltype = AA   length = 38
FEATURE                 Location/Qualifiers
source                  1..38
                        mol_type = protein
                        organism = synthetic construct
SEQUENCE: 28
VRNFVTCRIN RGFCVPIRCP GHRRQIGTCL GPQIKCCR                           38

SEQ ID NO: 29           moltype = AA   length = 55
FEATURE                 Location/Qualifiers
source                  1..55
                        mol_type = protein
                        organism = synthetic construct
SEQUENCE: 29
LALLFLVLSA GSGFTQGVRN FVTCRINRGF CVPIRCPGHR RQIGTCLAPQ IKCCR        55

SEQ ID NO: 30           moltype = AA   length = 62
FEATURE                 Location/Qualifiers
source                  1..62
                        mol_type = protein
                        organism = synthetic construct
SEQUENCE: 30
MRLHHLLLLL LLVVLSSGSG FTQGVRSYLS CWGNRGICLL NRCPGRMRQI GTCLAPRVKC  60
CR                                                                 62

SEQ ID NO: 31           moltype = AA   length = 60
FEATURE                 Location/Qualifiers
source                  1..60
                        mol_type = protein
                        organism = synthetic construct
SEQUENCE: 31
MRLHHLLLAL LFLVLSAGSG ISGPLSCRRN GGVCIPIRCP GPMRQIGTCF GRPVKCCRSW  60

SEQ ID NO: 32           moltype = AA   length = 38
FEATURE                 Location/Qualifiers
source                  1..38
                        mol_type = protein
                        organism = synthetic construct
SEQUENCE: 32
GPLSCGRNGG VCIPIRCPVP MRQIGTCFGR PVKCCRSW                           38
```